US012692254B2

(12) United States Patent
Ngu

(10) Patent No.: US 12,692,254 B2
(45) **Date of Patent: *Jul. 28, 2026**

(54) BENZIMIDAZOLE INHIBITORS OF PAD ENZYMES

(71) Applicant: BRISTOL-MYERS SQUIBB COMPANY, Princeton, NJ (US)

(72) Inventor: Khehyong Ngu, Pennington, NJ (US)

( * ) Notice: Subject to any disclaimer, the term of this patent is extended or adjusted under 35 U.S.C. 154(b) by 740 days.

This patent is subject to a terminal disclaimer.

(21) Appl. No.: 17/265,840

(22) PCT Filed: Aug. 7, 2019

(86) PCT No.: PCT/US2019/045459

§ 371 (c)(1),
(2) Date: Feb. 4, 2021

(87) PCT Pub. No.: WO2020/033514

PCT Pub. Date: Feb. 13, 2020

(65) Prior Publication Data

US 2022/0348562 A1 Nov. 3, 2022

Related U.S. Application Data

(60) Provisional application No. 62/715,845, filed on Aug. 8, 2018.

(51) Int. Cl.

| | |
|---|---|
| ***C07D 403/14*** | (2006.01) |
| ***A61K 31/4184*** | (2006.01) |
| ***A61K 31/4192*** | (2006.01) |
| ***A61K 31/4196*** | (2006.01) |
| ***A61K 31/422*** | (2006.01) |
| ***A61K 31/427*** | (2006.01) |
| ***A61K 31/437*** | (2006.01) |
| ***A61K 31/438*** | (2006.01) |
| ***A61K 31/4439*** | (2006.01) |
| ***A61K 31/497*** | (2006.01) |
| ***A61K 31/506*** | (2006.01) |
| ***C07D 401/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |

(52) U.S. Cl.

CPC ........ *C07D 403/14* (2013.01); *A61K 31/4184* (2013.01); *A61K 31/4192* (2013.01); *A61K 31/4196* (2013.01); *A61K 31/422* (2013.01); *A61K 31/427* (2013.01); *A61K 31/437* (2013.01); *A61K 31/438* (2013.01); *A61K 31/4439* (2013.01); *A61K 31/497* (2013.01); *A61K 31/506* (2013.01); *C07D 401/14* (2013.01); *C07D 409/14* (2013.01); *C07D 413/14* (2013.01); *C07D 417/14* (2013.01); *C07D 471/04* (2013.01)

(58) Field of Classification Search

CPC .. C07D 403/14; C07D 401/14; C07D 409/14; C07D 413/14; C07D 417/14; C07D 471/04; C07D 401/04; A61K 31/4184; A61K 31/4192; A61K 31/4196; A61K 31/422; A61K 31/427; A61K 31/437; A61K 31/438; A61K 31/4439; A61K 31/497; A61K 31/506; A61P 35/00; A61P 19/02; A61P 25/00; A61P 29/00; A61P 35/02

USPC .......................................................... 514/210

See application file for complete search history.

(56) References Cited

U.S. PATENT DOCUMENTS

| | | | | |
|---|---|---|---|---|
| 9,765,093 B2 * | 9/2017 | Devraj | .................... | A61P 31/06 |
| 9,963,448 B2 * | 5/2018 | Devraj | .................... | A61P 17/00 |
| 10,703,741 B2 * | 7/2020 | Beaumont | ............... | A61P 33/10 |
| 11,198,681 B2 * | 12/2021 | Devraj | .................... | A61P 29/02 |
| 2018/0161316 A1 * | 6/2018 | Atkinson | ................ | A61P 35/00 |
| 2019/0276440 A1 | 9/2019 | Zhao | | |

FOREIGN PATENT DOCUMENTS

| | | |
|---|---|---|
| CN | 107311933 A | 11/2017 |
| WO | 2001021634 A1 | 3/2001 |
| WO | 2010051245 A1 | 5/2010 |

(Continued)

OTHER PUBLICATIONS

Patani et al. Chemical Reviews, 1996, vol. 96, No. 8, p. 3147-3176, Bioisosterism: A Rational Approach in Drug Design. (Year: 1996).*

Guo, et al., Synthesis of reversible PAD4 inhibitors via copper-catalyzed C—H arylation of benzimidazole; Science China Chemistry; The Frontiers of Chemicalbiology and Synthesis, vol. 62, No. 5, pp. 592-596, 2019.

(Continued)

*Primary Examiner* — Jared Barsky
*Assistant Examiner* — Liyuan Mou
(74) *Attorney, Agent, or Firm* — Hong Liu

(57) ABSTRACT

The present invention provides compounds of Formula (I): or a pharmaceutically acceptable salt thereof, useful as inhibitors of PAD4, compositions thereof, and methods of treating PAD4-related disorders. Variables rings A, B, $R_1$, $R_3$, $R_8$, and other variables are as defined herein.

(I)

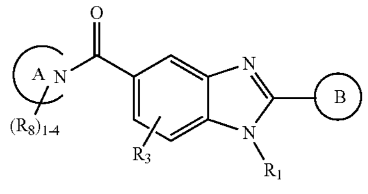

3 Claims, No Drawings

(56) References Cited

FOREIGN PATENT DOCUMENTS

| | | | |
|---|---|---|---|
| WO | 2014015905 | A1 | 1/2014 |
| WO | 2016185279 | A1 | 11/2016 |
| WO | 2017/100601 | A1 | 6/2017 |
| WO | 2017108282 | A1 | 6/2017 |
| WO | 2017/100594 | A1 | 7/2017 |
| WO | 2017147102 | A1 | 8/2017 |
| WO | 2018022897 | A1 | 2/2018 |
| WO | 2018049296 | A1 | 3/2018 |
| WO | 2019077631 | A1 | 4/2019 |
| WO | 2020033488 | A1 | 2/2020 |
| WO | 2020033490 | A1 | 2/2020 |
| WO | 2020033514 | A1 | 2/2020 |
| WO | 2020033520 | A1 | 2/2020 |

OTHER PUBLICATIONS

Lange et al., "Peptidylarginine Deiminases as Mediators ofMicrovesicular Release—Novel Therapeutic Interventions" 2017.

Goker, et al. "Synthesis of some new benzimidazolecarboxamides and evaluation of their antimicrobial activity", II Fannaco vol. 53, pp. 415-420 (1998).

Rios et al.; "Identification of novel benzimidazole derivatives as anti-Trypanosoma cruzi agents: solid-phase synthesis, structure-activity relationships and molecular docking studies", Future Med. Chem. vol. 5(15). pp. 1-14, (2013).

* cited by examiner

BENZIMIDAZOLE INHIBITORS OF PAD ENZYMES

CROSS REFERENCE TO RELATED APPLICATIONS

This application is a national phase application under 35 U.S.C. § 371 of International Patent Application No. PCT/US2019/045459 filed on Aug. 7, 2019, which is entitled to priority pursuant to 35 U.S.C. § 119€ to U.S. provisional patent application No. 62/715,845, filed Aug. 8, 2018, which is incorporated herein in its entirety.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, *Curr. Opin. Drug Discov. Devel.*, 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an auto-immune disease affecting approximately 1% of the population (Wegner N. et al, *Immunol. Rev.*, 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. el al, *Ann. Rheum. Dis.*, 70, (2011), 512-5/5). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrullination and is deficient in PAD4 knockout mice (Neeli I. et al, *J. Immunol.*, 180, (2008), 1895-1902 and Li P. et al, *J. Exp. Med.*, 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, *Nat. Med.*, 15(6), (2009), 623-625), systemic lupus erythematosus (Hakkim A. et al, *Proc. Natl. Acad. Sci. USA*, 107(21), (2010), 9813-9818 and Villanueva E. et al, *J. Immunol.*, 187(1), (2011), 538-52), ulcerative colitis (Savchenko A. et al, *Pathol. Int.*, 61(5), (2011), 290-7), cystic fibrosis, asthma (Dworski R. et al, *J. Allergy Clin. Immunol.*, 127(5), (2011), 1260-6), deep vein thrombosis (Fuchs T. et al, *Proc. Natl. Acad. Sci. USA*, 107(36), (2010), 15880-5), periodontitis (Vitkov L. et al, *Ultrastructural Pathol.*, 34(1), (2010), 25-30), sepsis (Clark S. R. et al, *Nat. Med.*, 13(4), (2007), 463-9), appendicitis (Brinkmann V. et al, *Science*, 303, (2004), 1532-5), and stroke. In addition, there is evidence that NETs may contribute to pathology in diseases affecting the skin, e.g., in cutaneous lupus erythematosus (Villanueva E. et al, *J. Immunol.*, 187(1), (2011), 538-52) and psoriasis (Lin A. M. et al., *J. Immunol.*, 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis VC. et al, *J. Immunol.*, 186(7), (2011), 4396-4404), dextran sulfate sodium (DSS)-induced experimental colitis (Chumanevich A. A. et al. *Am. J. Physiol. Gastrointest. Liver Physiol.*, 300(6), (2011), G9294G938), spinal cord repair (Lange S. et al, *Dev. Biol.*, 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack J. L. et al. *Cell. Mol. Life Sci.*, 68(4), (2011), 709-720). Over-expression of PAD4 has been demonstrated in numerous cancers (Chang X. et al, BAC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, *Mol. Cell Biol.*, 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formula (I) are useful as inhibitors of PAD4:

(I)

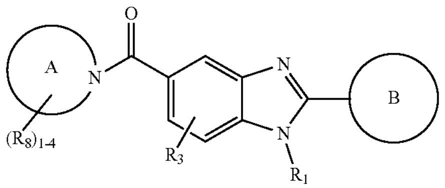

or a pharmaceutically acceptable salt thereof, wherein each of Rings A and B, $R_1$, $R_3$, $R_8$, and other variables is as defined herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosus, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of formula (I):

(I)

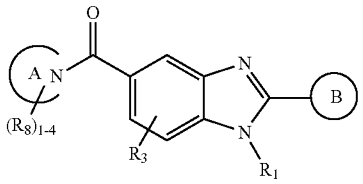

or a pharmaceutically acceptable salt thereof, wherein:

Ring A is 4- to 15-membered heterocyclyl substituted with 1-4 $R_8$;

Ring B is selected from

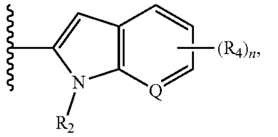

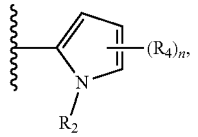

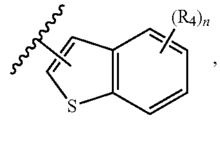

, and

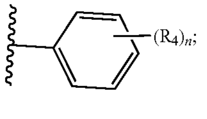

Q is selected from N and $CR_4$;

$R_1$ is selected from $-(CH_2)_{2-4}R_{5a}$, $-(CH_2)_{1-4}-C_{3-6}$cycloalkyl substituted with 1-5 $R_5$, $-(CH_2)_{1-4}-(O)_{0-1}$-aryl substituted with 1-5 $R_5$, and $-(CH_2)_r$-4-6-membered heterocyclyl comprising carbon atoms and 1-4 heteroatoms selected from N, $NR_6$ O, and $S(O)_p$ and substituted with 1-5 $R_5$;

$R_2$, at each occurrence, is independently selected from H and $C_{1-3}$ alkyl optionally substituted with $C_{3-6}$cycloalkyl;

$R_3$ is selected from H, F, Cl, Br, $C_{1-3}$ alkyl, and $-OR_b$;

$R_4$, at each occurrence, is independently selected from H, F, Cl, Br, CN, $C_{1-3}$ alkyl substituted with 0-1 OH and $OC_{1-3}$alkyl, and $-OR_b$;

$R_5$, at each occurrence, is independently selected from H, F, Cl, Br, CN, $=O$, $C_{1-3}$ alkyl, $C(=O)NR_aR_a$, $NR_aR_a$, $NR_aC(=O)R_b$, $NR_aC(=O)OR_b$, $NR_aS(=O)_pR_c$, and aryl substituted with 1-5 $R_7$;

$R_{5a}$, at each occurrence, is independently selected from $C(=O)NR_aR_a$, $NR_aR_a$, $NRC(=O)R_b$, $NR_aC(=O)OR_b$, and $NR_aS(=O)_pR_c$;

$R_6$ is selected from H, $C_{1-3}$ alkyl substituted with 1-5 $R_7$, $-S(O)_pR_c$, $-C(=O)R_b$, $-C(=O)OR_b$, $-C(=O)(CH_2)_rNR_aR_a$, $-S(O)_pNR_aR_a$, $-(CH_2)_r-C_{3-6}$cycloalkyl substituted with 1-5 $R_7$, $-(CH_2)_r$-aryl substituted with 1-5 $R_7$, $-(CH_2)_r$-heterocyclyl substituted with 1-5 $R_7$, $-C(=O)-(CH_2)_r-C_{3-6}$cycloalkyl substituted with 1-5 $R_7$, $-C(=O)-(CH_2)_r$-aryl substituted with 1-5 $R_7$, $-C(=O)-(CH_2)_r$-heterocyclyl substituted with 1-5 $R_7$; $-S(=O)_2-(CH_2)_r-C_{3-6}$cycloalkyl substituted with 1-5 $R_7$, $-S(=O)_2-(CH_2)_r$-aryl substituted with 1-5 $R_7$, $-S(=O)_2-(CH_2)_r$-heterocyclyl substituted with 1-5 $R_7$, $-C(=O)NR_a$-aryl substituted with 1-5 $R_7$, and $-C(=O)NR_a$-heterocyclyl substituted with 1-5 $R_7$; wherein said heterocyclyl comprises carbon atoms and 1-4 heteroatoms selected from N, $NR_{7a}$, O, and S;

$R_7$, at each occurrence, is independently selected from H, F, Cl, Br, $C_{1-4}$alkyl substituted with 0-4 $R_e$, $C_{2-4}$alkenyl substituted with 0-4 $R_e$, $C_{2-4}$alkynyl substituted with 0-4 $R_e$, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_a\ C(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl substituted with 0-5 $R_e$, $-(CHR_d)_r$-aryl substituted with 0-5 $R_e$, and $-(CHR_d)_r$-heterocyclyl substituted with 0-5 $R_e$;

$R_{7a}$ at each occurrence, is independently selected from H and $C_{1-4}$alkyl substituted with 0-4 $R_e$;

$R_8$, at each occurrence, is independently selected from H, F, Cl, CN, $C_{1-3}$ alkyl, $=N-OR_b$, $-(CH_2)OR_b$, $-(CH_2)_rNR_aR_a$, $-NR_aC(=NH)C_{1-3}$alkyl, $-NRC(=O)OR_b$, a carbocyle, and a heterocycle; alternatively, two $R_8$ groups are taken together to form a carbocycle or heterocyle;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_d$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, —$(CH_2)_d$$OR_f$, C(=O)$OR_f$, S(=O)$_p$$R_f$, C(=O)$NR_fR_f$, S(=O)$_p$$NR_fR_f$, and —$(CH_2)_r$$NR_fR_f$, $C_{1-6}$ alkyl substituted with 1-5 $R_f$, $C_{2-6}$ alkenyl substituted with 1-5 $R_f$, $C_{2-6}$ alkynyl substituted with 1-5 $R_f$, —$(CH_2)_r$—$C_{3-6}$ cycloalkyl substituted with 1-5 $R_f$, —$(CH_2)_r$-aryl substituted with 1-5 $R_f$, and —$(CH_2)_r$-heterocyclyl substituted with 1-5 $R_f$;

$R_f$, at each occurrence, is independently selected from H, F, Cl, Br, CN, OH, $C_{1-5}$ alkyl optionally substituted with OH, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from zero, 1, 2, 3, and 4;

p, at each occurrence, is independently selected from zero, 1, and 2; and r, at each occurrence, is independently selected from zero, 1, 2, 3, and 4:

provided that when Ring B is

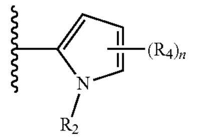

$R_1$ is —$(CH_2)_{1-3}$-4-6-membered heterocyclyl comprising carbon atoms and $NR_6$.

2. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary,* 15th Edition, John Wiley & Sons, Inc., New York (2007). "$C_{6-10}$ aryl" refers to phenyl and naphthyl.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium ($Na^+$), potassium ($K^+$), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis*, Biology, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl, (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988);
e) Kakeya, N. et al., *Chem. Pharm. Bull.,* 32:692 (1984); and
f) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-4}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism, Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, CA (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "S" for delta, "s" for singlet, "d" for doublet, "t" for triplet, "q" for quartet, "i" for multiplet, "br" for broad, "Hz" for hertz, and "α", "β", "R", "S", "E", "Z" and "ee" are stereochemical designations familiar to one skilled in the art. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

AcOH or HOAc acetic acid
ACN acetonitrile
Alk Alkyl
$AlMe_3$ Trimethylaluminum
$BBr_3$ boron tribromide
Bn benzyl
Boc tert-butyloxycarbonyl
BOP reagent benzotriazol-1-yloxytris(dimethylamino) phosphonium hexafluorophosphate
Bu butyl
i-Bu isobutyl
t-Bu tert-butyl
t-BuOH tert-butanol
Cbz cadbobenzyloxy
$CDCl_3$ deutero-chloroform
$CD_3OD$ deutero-methanol
$CH_2Cl_2$ dichloromethane
$CH_3CN$ acetonitrile
$CHCl_3$ chloroform
DCM dichloromethane
DIEA, DIPEA or diisopropylethylamine
Hunig's base
DMF dimethyl formamide
DMSO dimethyl sulfoxide
Et ethyl
$Et_3N$ or TEA triethylamine
$Et_2O$ diethyl ether
EtOAc ethyl acetate
EtOH ethanol
HCl hydrochloric acid
HPLC high-performance liquid chromatography
$K_2CO_3$ potassium carbonate
$K_2HPO_4$ potassium hydrogenphosphate
LCMS liquid chromatography mass spectrometry
LiHMDS lithium bis(trimethylsilyl)amide
LG leaving group
Me methyl
MeOH methanol
$MgSO_4$ magnesium sulfate
MsOH or MSA methylsulfonic acid
NaCl sodium chloride
$Na_2CO_3$ sodium carbonate
$NaHCO_3$ sodium bicarbonate
NaOH sodium hydroxide
$Na_2SO_4$ sodium sulfate
$NH_3$ ammonia
$NH_4C_1$ ammonium chloride
$NH_4OAc$ ammonium acetate
$Pd(OAc)_2$ palladium(II) acetate
$Pd(dppf)Cl_2$ [1,1'-Bis(diphenylphosphino)ferrocene]palladium(II)
$Pd(PPh_3)_4$ tetrakis(triphenylphosphine)palladium(0)
PG protecting group
Ph phenyl
Pr propyl
i-Pr isopropyl
i-PrOH or IPA isopropanol
Rt retention time
$SiO_2$ silica oxide
SFC supercritical fluid chromatography
TBAI Tetrabutylammonium iodide
TEA triethylamine
TFA trifluoroacetic acid
TFAA Trifluoroacetic anhydride
THF tetrahydrofuran
$TiCl_4$ titanium tetrachloride
T3P 1-propanephosphonic acid cyclic anhydride

3. Description of Exemplary Compounds

In a first aspect, the present invention provides a compound of formula (I):

(I)

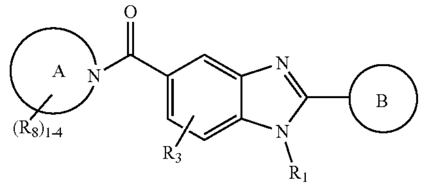

or a pharmaceutically acceptable salt thereof, wherein:

Ring A is 4- to 15-membered heterocyclyl substituted with 1-4 $R_8$;

Ring B is selected from

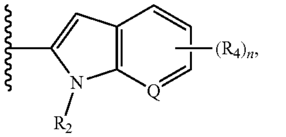

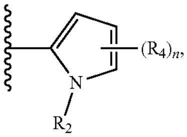

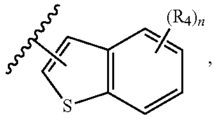

, and

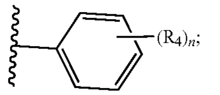

Q is selected from N and CH;

$R_j$ is selected from $-(CH_2)_{2-4}R_{5a}$, $-(CH_2)_{0-4}-C_{3-6}$cycloalkyl substituted with 1-2 $R_{5a}$, $-(CH_2)_{1-4}-(O)_{0-1}$-aryl substituted with 1-5 $R_5$, and $-(CH_2)_r$-4-6-membered heterocyclyl comprising carbon atoms and 1-4 heteroatoms selected from N, $NR_6$ O, and S(O), and substituted with 1-5 $R_5$;

$R_2$, at each occurrence, is independently selected from H and $C_{1-3}$ alkyl optionally substituted with $C_{3-6}$cycloalkyl;

$R_3$ is selected from H, F, Cl, Br, and $-OR_b$;

$R_4$, at each occurrence, is independently selected from H, F, Cl, Br, CN, $C_{1-3}$ alkyl, and $-OR_b$;

$R_5$, at each occurrence, is independently selected from H, F, Cl, Br, CN, $NR_aR_a$, =O, and $C_{1-3}$ alkyl;

$R_{5a}$, at each occurrence, is independently selected from $C(=O)NR_aR_a$, $NR_aR_a$, $NR_aC(=O)R_b$, $NR_aC(=O)OR_b$, and $NR_aS(=O)_pR_c$;

$R_6$ is selected from H, $C_{1-3}$ alkyl substituted with 1-5 $R_7$, $-S(O)_pR_c$, $-C(=O)R_b$, $-C(=O)OR_b$, $-C(=O)(CH_2)_rNR_aR_a$, $-S(O)_pNR_aR_a$, $-(CH_2)_r-C_{3-6}$cycloalkyl substituted with 1-5 $R_7$, $-(CH_2)_r$-aryl substituted with 1-5 $R_7$, $-(CH_2)_r$-heterocyclyl substituted with 1-5 $R_7$, $-C(=O)-(CH_2)_r-C_{3-6}$cycloalkyl substituted with 1-5 $R_7$, $-C(=O)-(CH_2)_r$-aryl substituted with 1-5 $R_7$, $-C(=O)-(CH_2)_r$-heterocyclyl substituted with 1-5 $R_7$; $-S(=O)_2-(CH_2)_r-C_{3-6}$cycloalkyl substituted with 1-5 $R_7$, $-S(=O)_2-(CH_2)_r$-aryl substituted with 1-5 $R_7$, and $-S(=O)_2-(CH_2)_r$-heterocyclyl substituted with 1-5 $R_7$;

$R_7$, at each occurrence, is independently selected from H, F, Cl, Br, $C_{1-4}$alkyl substituted with 0-4 $R_e$, $C_{2-4}$alkenyl substituted with 0-4 $R_7$, $C_{2-4}$alkynyl substituted with 0-4 R, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_a C(=O)NR_aR_a$, $-(CHR_d)_rC(=O)OR_b$, $-(CHR_d)_rC(=O)R_b$, $-(CHR_d)_rOC(=O)R_b$, $-(CHR_d)_rC(=O)NR_aR_a$, $-(CHR_d)_r$-cycloalkyl substituted with 0-5 $R_e$, $-(CHR_d)_r$-aryl substituted with 0-5 $R_e$, and $-(CHR_d)_r$-heterocyclyl, substituted with 0-5 $R_e$;

$R_8$, at each occurrence, is independently selected from H, F, Cl, CN, $C_{1-3}$ alkyl, $=N-OR_b$, $-(CH_2)OR_b$, $-(CH_2)_rNR_aR_a$, $-NR_aC(=NH)C_{1-3}$alkyl, $-NR_aC(=O)OR_b$, carbocyle, and heterocycle; alternatively, two $R_8$ groups are taken together to form a carbocycle or heterocyle;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $-(CH_2)_r-C_{3-6}$ carbocyclyl substituted with 0-5 $R_e$, and $-(CH_2)_r$-heterocyclyl substituted with 0-5 $R_e$;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $-(CH_2)_rOR_f$, $C(=O)OR_f$, $S(=O)_pR_f$, $C(=O)NR_fR_f$, $S(=O)_pNR_fR_f$, and $-(CH_2)_rNR_fR_f$, $C_{1-6}$ alkyl substituted with 1-5 $R_f$, $C_{2-6}$ alkenyl, $C_{2-6}$ alkynyl, $-(CH_2)_r-C_{3-6}$ cycloalkyl substituted with 1-5 $R_f$, $-(CH_2)_r$-aryl substituted with 1-5 $R_f$, and $-(CH_2)_r$-heterocyclyl substituted with 1-5 $R_f$;

$R_f$, at each occurrence, is independently selected from H, F, Cl, Br, CN, OH, $C_{1-5}$ alkyl optionally substituted with OH, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from zero, 1, 2, 3, and 4;

p, at each occurrence, is independently selected from zero, 1, and 2;

r, at each occurrence, is independently selected from zero, 1, 2, 3, and 4;

provided that when Ring B is

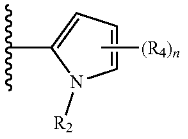

$R_1$ is $-(CH_2)_{1-3}$-4-6-membered heterocyclyl comprising carbon atoms and $NR_6$, wherein $R_6$ is $C_{3-6}$cycloalkyl substituted with 1-5 $R_7$, aryl substituted with 1-5 $R_7$, and heterocyclyl substituted with 1-5 $R_7$.

In a second aspect, the present invention provides a compound of formula (II):

(II)

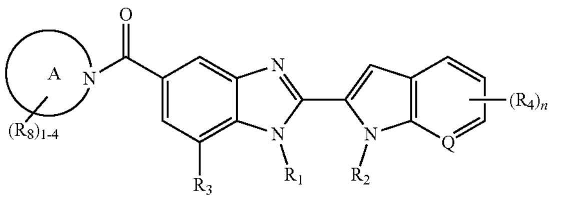

or a pharmaceutically acceptable salt thereof, within the scope of the first aspect, wherein: Ring A is selected from

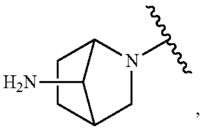
,
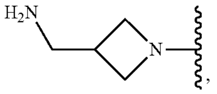
,
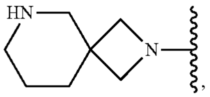
,
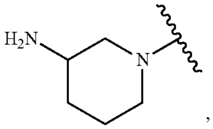
,
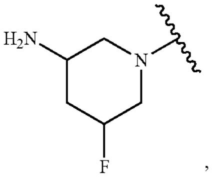
,
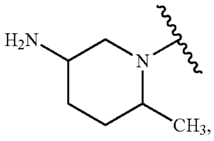
and
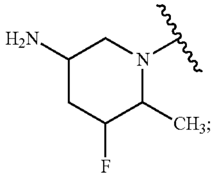
;

Q is selected from N and CH;

$R_1$ is selected from $-(CH_2)_{2-3}R_{5a}$,

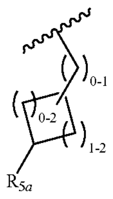
,
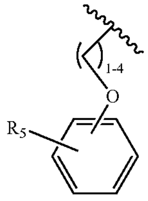
,
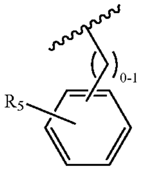
,
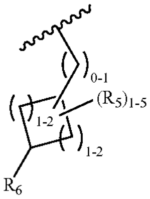
,
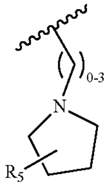
,
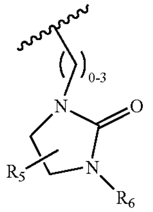
,
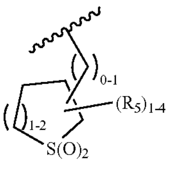
,
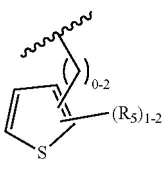
,
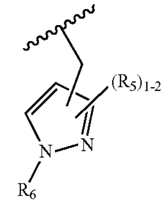
,
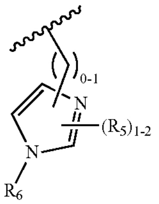
,
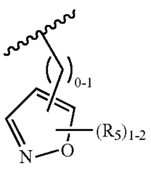
,
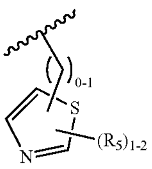
and -continued

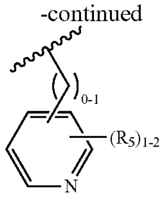
;

$R_2$ is $C_{1-2}$ alkyl optionally substituted with $C_{3-6}$cycloalkyl;

$R_3$ is selected from H, F, Cl, Br, and $-OR_b$;

$R_4$, at each occurrence, is independently selected from F, Cl, Br, CN, $C_{1-3}$ alkyl, and $-OR_b$;

$R_5$, at each occurrence, is independently selected from H, F, Cl, Br, CN, $NH_2$, $=O$, and $C_{1-3}$ alkyl;

$R_{5a}$, at each occurrence, is independently selected from $NR_aR_a$, $NR_aC(=O)R_b$, $NR_aC(=O)OR_b$, and $NR_aS(O)_pR_c$;

$R_6$, at each occurrence, is independently selected from H, $C_{1-3}$ alkyl, $-S(O)_pR_c$, $-C(=O)R_b$, $-C(=O)NR_aR_a$, $-C(=O)(CH_2)_rNR_aR_a$, $-C(=O)OR_b$, $-S(O)_pNR_aR_a$, $-(CH_2)_r$-aryl substituted with 1-5 $R_7$; and $-(CH_2)_r$-heterocyclyl, substituted with 1-5 $R_7$, $-C(=O)-(CH_2)_r$-aryl substituted with 1-5 $R_7$, $-C(=O)-(CH_2)_r$-heterocyclyl substituted with 1-5 $R_7$; $-S(=O)_2-(CH_2)_r-C_{3-6}$cycloalkyl substituted with 1-5 $R_7$, $-S(=O)_2-(CH_2)_r$-aryl substituted with 1-5 $R_7$, and $-S(=O)_2-(CH_2)_r$-heterocyclyl substituted with 1-5 $R_7$;

$R_7$, at each occurrence, is independently selected from H, F, Cl, Br, CN, $C_{1-4}$alkyl substituted with 0-4 $R_e$, $C_{2-4}$alkenyl substituted with 0-4 $R_e$, $C_{2-4}$alkynyl substituted with 0-4 $R_e$, $-S(=O)_pR_c$, $-S(=O)_pNR_aR_a$, $-NR_aS(=O)_pR_c$, $-OR_b$, $-NR_aR_a$, $-NR_aC(=O)R_b$, $-NR_aC(=O)NR_aR_a$, $-C(=O)OR_b$, $-C(=O)R_b$, $-OC(=O)R_b$, $-C(=O)NR_aR_a$, $C_{3-6}$cycloalkyl substituted with 0-4 $R_e$, heterocyclyl substituted with 0-4 $R_e$, aryl substituted with 0-4 $R_e$, and heteroaryl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $-(CH_2)_r-C_{3-6}$ carbocyclyl substituted with 0-5 $R_e$, and $-(CH_2)_r$-heterocyclyl substituted with 0-5 $R_e$;

$R_e$, at each occurrence, is independently selected from F, Cl, Br, CN, $=O$, $-(CH_2)_rOH$, $-(CH_2)_rOC_{1-4}$alkyl, $-C(=O)OH$, $-C(=O)OC_{1-4}$alkyl, $-(CH_2)_rNH_2$, $-(CH_2)_rNH(C_{1-4}$ alkyl), $-(CH_2)_rN(C_{1-4}$ alkyl$)_2$, $C_{1-6}$ alkyl substituted with 1-5 $R_f$, $C_{2-6}$ alkenyl substituted with 1-5 $R_f$, $C_{2-6}$ alkynyl substituted with 1-5 $R_f$, $-(CH_2)_r-C_{3-6}$ cycloalkyl, $-(CH_2)_r$-aryl, and $-(CH_2)_r$-heterocyclyl;

$R_f$, at each occurrence, is independently selected from H, F, Cl, Br, CN, OH, $C_{1-5}$ alkyl optionally substituted with OH, $C_{3-6}$ cycloalkyl, and phenyl;

n, at each occurrence, is independently selected from zero, 1, 2, and 3;

p, at each occurrence, is independently selected from zero, 1, and 2; and r, at each occurrence, is independently selected from zero, 1, 2, 3, and 4.

In a third aspect, the present invention provides a compound of formula (III):

(III)

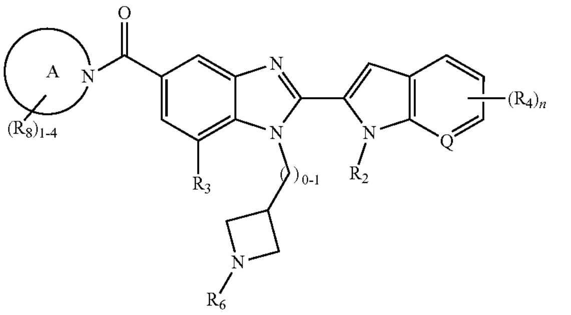

or a pharmaceutically acceptable salt thereof, wherein:

Ring A is selected from

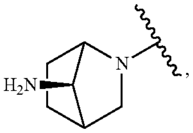,
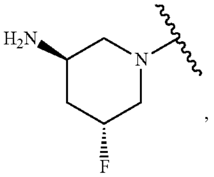,
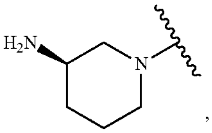,
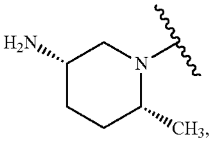, and
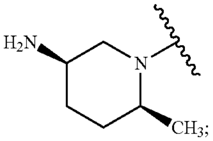;

Q is selected from N and CH;

$R_2$ is selected from methyl and —$CH_2$-cyclopropyl;

$R_3$ is selected from H, F, Cl, and —$OC_{1-4}$ alkyl;

$R_4$, at each occurrence, is selected from F, Cl, Br, and —$OC_{1-3}$ alkyl;

$R_6$, at each occurrence, is independently selected from H, $C_{1-3}$ alkyl, —S(=O)$_p$R$_c$, —C(=O)R$_b$, —C(=O)OR$_b$, —C(=O)(CH$_2$)$_r$NR$_a$R$_a$, —S(=O)$_p$NR$_a$R$_a$, —(CH$_2$)$_r$—C$_{3-6}$cycloalkyl substituted with 1-5 R$_7$, —(CH$_2$)$_r$-aryl substituted with 1-5 R$_7$, and —(CH$_2$)$_r$-heterocyclyl, substituted with 1-5 R$_7$, —C(=O)—C$_{3-6}$cycloalkyl substituted with 1-5 R$_7$, —C(=O)—(CH$_2$)$_r$-aryl substituted with 1-5 R$_7$, —C(=O)—(CH$_2$)$_r$-heterocyclyl substituted with 1-5 R$_7$; —S(=O)$_2$—(CH$_2$)$_r$C$_{3-6}$cycloalkyl, —S(=O)$_2$—(CH$_2$)$_r$-aryl, and —S(=O)$_2$—(CH$_2$)$_r$-heterocyclyl, wherein said cycloalkyl, aryl, and heterocyclyl are selected from

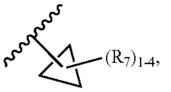
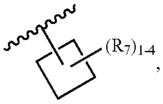,
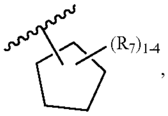,
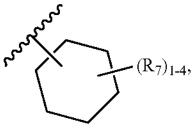
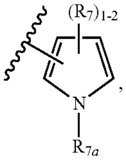,
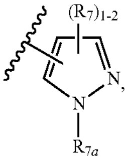
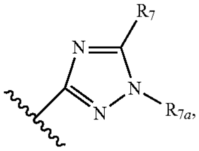
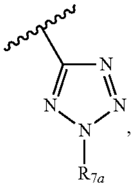,
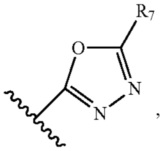,
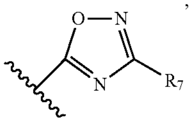,
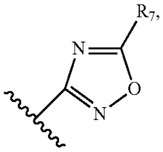
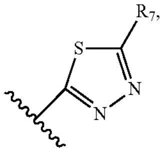
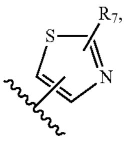
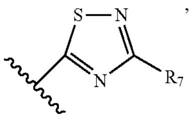,
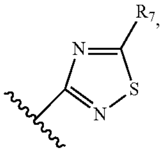
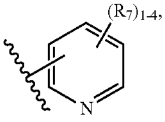
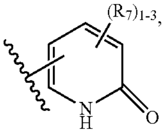
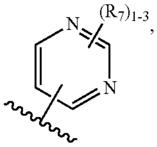
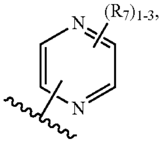
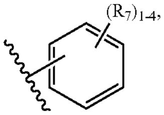 and
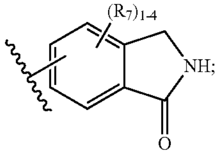

R$_7$, at each occurrence, is independently selected from H, F, Cl, Br, CN, C$_{1-4}$alkyl, C$_{2-4}$alkenyl, C$_{2-4}$alkynyl, nitro, —S(=O)$_p$R$_c$, —S(=O)$_p$NR$_a$R$_a$, —NR$_a$S(=O)$_p$R$_c$, —OR$_b$, —NR$_a$R$_a$, —NR$_a$C(=O)R$_b$, —NR$_a$C(=O)NR$_a$R$_a$, —C(=O)OR$_b$, —C(=O)R$_b$, —OC(=O)R$_b$, —C(=O)NR$_a$R$_a$, C$_{3-6}$ cycloalkyl substituted with 0-4 R$_e$, heterocyclyl substituted with 0-4 R$_e$, aryl substituted with 0-4 R$_e$, and heteroaryl substituted with 0-4 R$_e$;

R$_{7a}$, at each occurrence, is independently selected from H and C$_{1-4}$alkyl;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $-(CH_2)_r-C_{3-6}$ carbocyclyl substituted with 0-5 $R_e$, and $-(CH_2)_r$-heterocyclyl substituted with 0-5 $R_e$;

$R_e$, at each occurrence, is independently selected from F, Cl, Br, CN, =O, $-(CH_2)_rOH$, $-(CH_2)_rOC_{1-4}$alkyl, $-C(=O)OH$, $-C(=O)OC_{1-4}$alkyl, $-(CH_2)_rNH_2$, $C_{1-6}$ alkyl substituted with 1-5 $R_f$, $-(CH_2)_r-C_{3-6}$ cycloalkyl, and $-(CH_2)_r$-aryl;

$R_f$, at each occurrence, is independently selected from H, F, Cl, Br, CN, OH, $C_{1-5}$ alkyl optionally substituted with OH, $C_{3-6}$ cycloalkyl, and phenyl;

n, at each occurrence, is independently selected from zero and 1;

p, at each occurrence, is independently selected from zero, 1, and 2; and r, at each occurrence, is independently selected from zero, 1, 2, 3, and 4.

In a fourth aspect, the present invention provides a compound or a pharmaceutically acceptable salt thereof, within the scope of the third aspect, wherein:

Ring A is selected from F, and

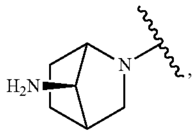,
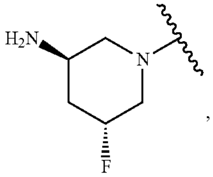,
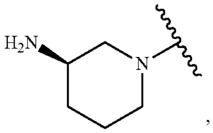, and
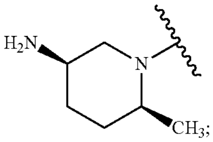

$R_2$ is selected from methyl and $-CH_2$-cyclopropyl;

$R_3$ is $-OC_{1-4}$ alkyl;

$R_4$, at each occurrence, is selected from Cl and $-OC_{1-3}$ alkyl;

$R_6$ is selected from

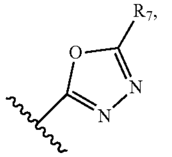
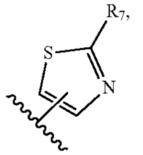
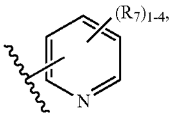
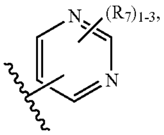
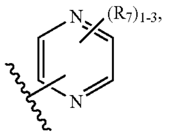
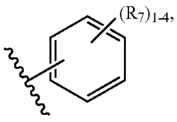 and

-continued

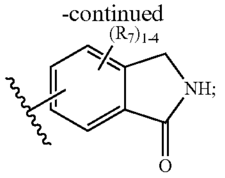

$R_7$, at each occurrence, is independently selected from H, F, Cl, Br, CN, $C_{1-4}$alkyl, $-S(=O)_pR_c$, $-S(=O)_pNR_aR_a$, $C(=O)R_b$, $C(=O)NR_aR_a$, $-NR_aS(=O)_pR_c$, $-OR_b$, and $C_{3-6}$cycloalkyl;

$R_b$, at each occurrence, is independently selected from H and $C_{1-6}$ alkyl substituted with 0-5 $R_e$;

$R_c$ is $C_{1-6}$ alkyl substituted with 0-5 $R_e$;

$R_e$, at each occurrence, is independently selected from F, Cl, Br, CN, $C_{1-6}$ alkyl, $C_{3-6}$ cycloalkyl, and aryl;

n, at each occurrence, is independently selected from zero and 1;

p, at each occurrence, is independently selected from zero, 1, and 2; and r, at each occurrence, is independently selected from zero, 1, 2, 3, and 4.

In a fifth aspect, the present invention provides a compound or a pharmaceutically acceptable salt thereof, within the scope of the third aspect, wherein:

Ring A is selected from

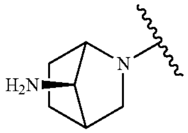 and 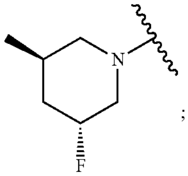;

$R_2$ is $-CH_2$-cyclopropyl;

$R_3$ is selected from H, F, Cl, and $-OC_{1-4}$ alkyl;

$R_6$ is selected from $-C(=O)R_b$, $-C(=O)OR_b$, $-C(=O)-(CH_2)_r-C_{3-6}$cycloalkyl substituted with 1-5 $R_7$, $-C(=O)-(CH_2)_r$-aryl, and $-C(=O)-(CH_2)_r$-heterocyclyl, wherein said cycloalkyl, aryl, and heterocyclyl are selected from

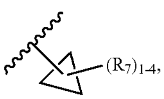
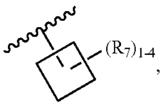,
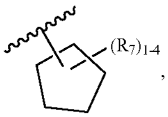,
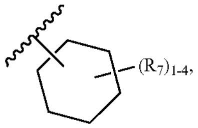
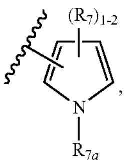,
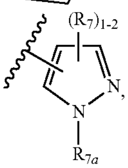
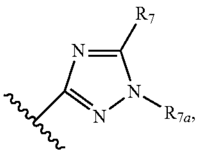
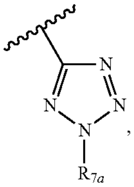,
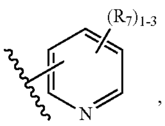, -continued

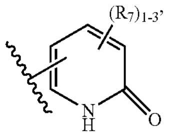

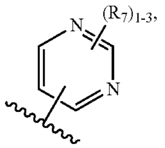

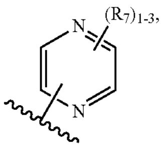

and

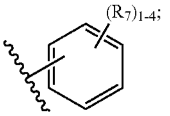

$R_7$, at each occurrence, is independently selected from H, F, Cl, Br, CN, $C_{1-4}$alkyl, $-OR_b$, $-NR_aR_a$, $-C(=O)OR_b$, $-C(=O)R_b$, $-C(=O)NR_aR_a$, $C_{3-6}$ cycloalkyl substituted with 0-4 $R_e$, heterocyclyl substituted with 0-4 $R_e$, aryl substituted with 0-4 $R_e$, and heteroaryl substituted with 0-4 $R_e$;

$R_b$ is selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$;

$R_e$, at each occurrence, is independently selected from F, Cl, Br, CN, $=O$, $-(CH_2)_rOH$, $-(CH_2)_r$ $OC_{1-4}$alkyl, $-C(=O)OH$, $-C(=O)OC_{1-4}$alkyl, $-(CH_2)_rNH_2$, $C_{1-6}$ alkyl substituted with 1-5 $R_f$, $-(CH_2)_r-C_{3-6}$ cycloalkyl, and $-(CH_2)_r$-aryl;

$R_f$, at each occurrence, is independently selected from H, F, Cl, Br, CN, OH, $C_{1-5}$ alkyl optionally substituted with OH, $C_{3-6}$ cycloalkyl, and phenyl; and n is zero.

In a sixth aspect, the present invention provides a compound or a pharmaceutically acceptable salt thereof, within the scope of the third aspect, wherein:

Ring A is selected from

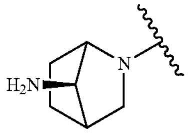

and

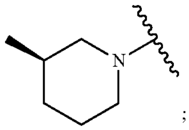

;

$R_2$ is $-CH_2$-cyclopropyl;

$R_3$ is $-OC_{1-4}$ alkyl;

$R_6$ is $-S(O)_pR_c$, $-S(=O)_2-(CH_2)_r-C_{3-6}$cycloalkyl, $-S(=O)_2-(CH_2)_r$-aryl, and $-S(=O)_2-(CH_2)_r$-heterocyclyl, wherein said cycloalkyl, aryl and heterocyclyl are selected from

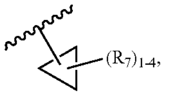

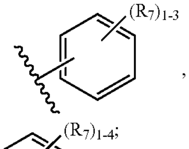

, and

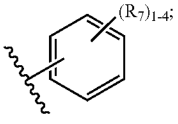

$R_7$, at each occurrence, is independently selected from H, F, Cl, Br, CN, $C_{1-4}$alkyl, and $-OH$;

$R_c$ is $C_{1-4}$ alkyl substituted with 0-5 $R_e$, $R_e$, at each occurrence, is independently selected from Ct-3 alkyl, F, Cl, Br, and CN;

n is zero; and r, at each occurrence, is independently selected from zero and 1.

In a seventh aspect, the present invention provides a compound of formula (IV):

(IV)

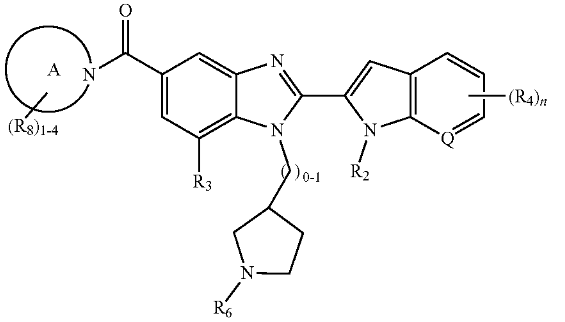

or a pharmaceutically acceptable salt thereof, within the embodiment of the second aspect, wherein:

Ring A is selected from

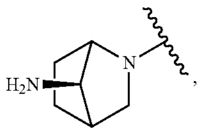 [SMILES: *N1CC2CCC1[C@@H]2N]

,

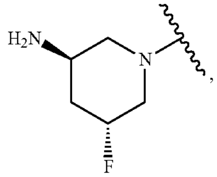

,

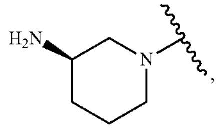

,

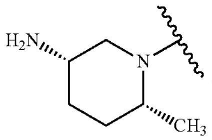

, and

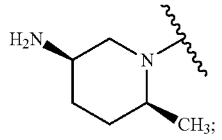

Q is selected from N and CH;

$R_2$ is selected from methyl and $-CH_2$-cyclopropyl;

$R_3$ is selected from F and $-OC_{1-4}$ alkyl;

$R_4$, at each occurrence, is selected from Cl and $-OC_{1-3}$ alkyl;

$R_e$ is selected from H, $-C(=O)R_b$, $-C(=O)OR_b$, $-C(=O)-(CH_2)_r-C_{3-6}$cycloalkyl, $-C(=O)-(CH_2)_r$-aryl, and $-C(=O)-(CH_2)_r$-heterocyclyl, wherein said cycloalkyl, aryl, and heterocyclyl are selected from

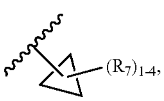

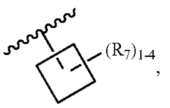

,

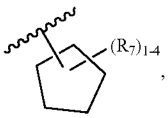

,

-continued

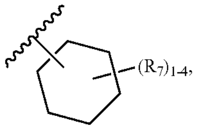 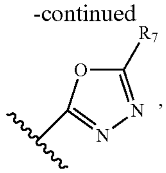 , 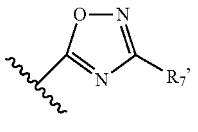

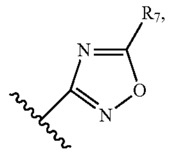 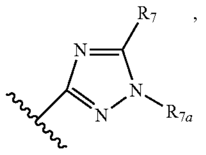 , 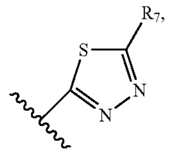

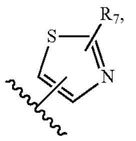 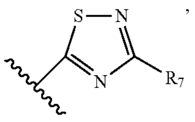 , 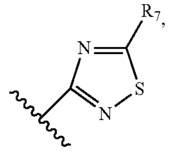

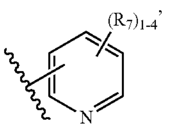 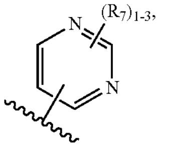 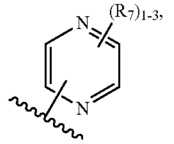

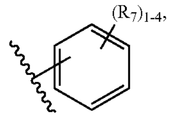 and 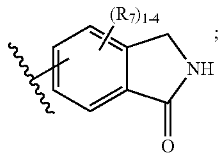 ;

$R_7$, at each occurrence, is independently selected from F, Cl, Br, CN, $C_{1-4}$alkyl, $C_{2-4}$alkenyl, $C_{2-4}$alkynyl, $—S(O)_pR_c$, $—S(O)_pNR_aR_a$, $—NR_aS(O)_pR_c$, $—OR_b$, $—NR_aR_a$, $—NR_aC(=O)R_b$, $—NR_aC(=O)NR_aR_a$, $—C(=O)OR_b$, $—C(=O)R_b$, $—OC(=O)R_b$, $—C(=O)NR_aR_a$, $C_{3-6}$ cycloalkyl, heterocyclyl, aryl, and heteroaryl, wherein said alkyl, cycloalkyl, heterocyclyl, aryl, or heteroaryl is substituted with 0-4 $R_e$;

$R_{7a}$ is selected from F, Cl, Br, $C_{1-4}$alkyl;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, phenyl substituted with 0-5 $R_f$, and $—(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $C_{3-6}$ carbocyclyl substituted with 0-5 $R_e$, and heterocyclyl substituted with 0-5 $R_e$;

$R_e$, at each occurrence, is independently selected from F, Cl, Br, CN, $NO_2$, =O, $C_{1-6}$ alkyl substituted with 1-5 $R_f$, $C_{2-6}$ alkenyl, $C_{2-6}$ alkynyl, C(=O)OH, —C(=O)$OC_{1-4}$ alkyl, $—(CH_2)_rOH$, $—(CH_2)_rOC_{1-4}$alkyl, $—(CH_2)_rC_{3-6}$ cycloalkyl, and $—(CH_2)_r$-aryl;

$R_f$, at each occurrence, is independently selected from H, F, Cl, Br, CN, OH, $C_{1-5}$ alkyl optionally substituted with OH, $C_{3-6}$ cycloalkyl, and phenyl;

n, at each occurrence, is independently selected from zero and 1;

p, at each occurrence, is independently selected from zero, 1, and 2; and r, at each occurrence, is independently selected from zero, 1, 2, 3, and 4.

In an eighth aspect, the present invention provides a compound or a pharmaceutically acceptable salt thereof, within the embodiment of the seventh aspect, wherein:

Ring A is

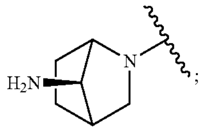 ;

$R_2$ is $—CH_2$-cyclopropyl;

$R_3$ is $—OC_{1-4}$ alkyl;

$R_6$ is selected from —C(=O)-aryl and —C(=O)-heterocyclyl wherein said aryl and heterocyclyl are selected from

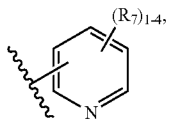 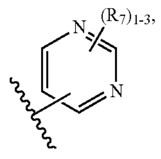 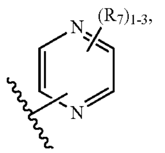 and

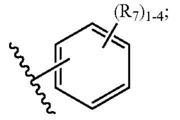 ;

$R_7$, at each occurrence, is independently selected from F, Cl, Br, $C_{1-4}$alkyl, $OR_b$, CN, $C_{3-6}$ cycloalkyl wherein said alkyl or cycloalkyl is substituted with 0-4 $R_e$;

$R_e$, at each occurrence, is independently selected from F, Cl, Br, CN, $NO_2$, =O, $C_{1-6}$ alkyl substituted with 1-5 $R_f$, $C_{2-6}$ alkenyl, $C_{1-6}$ alkynyl, C(=O)OH, —C(=O)$OC_{1-4}$alkyl, $—(CH_2)_rOH$, $—(CH_2)_rOC_{1-4}$alkyl, $—(CH_2)_r—C_{3-6}$ cycloalkyl, and $—(CH_2)_r$-aryl;

$R_f$, at each occurrence, is independently selected from H, F, Cl, Br, CN, OH, $C_{1-6}$ alkyl optionally substituted with OH, $C_{3-6}$ cycloalkyl, and phenyl;

n is zero;

p, at each occurrence, is independently selected from zero, 1, and 2; and r, at each occurrence, is independently selected from zero, 1, 2, 3, and 4.

In a ninth aspect, the present invention provides a compound of formula (V):

(V)

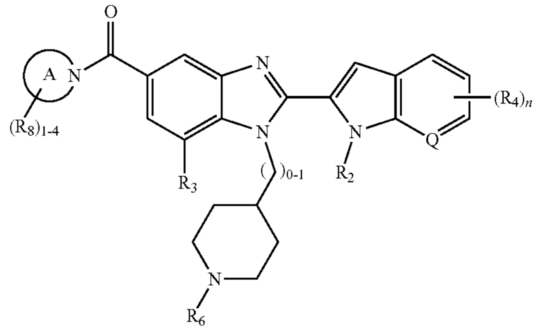

or a pharmaceutically acceptable salt thereof, within the scope of the second aspect, wherein:

Ring A is selected from

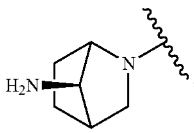,
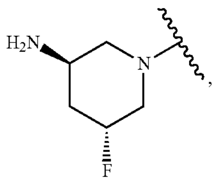,
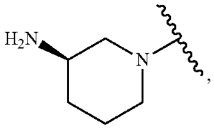,
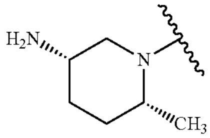, and
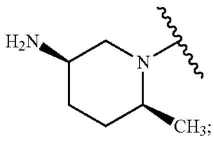

Q is selected from N and CH;

$R_2$ is selected from methyl and —$CH_2$-cyclopropyl;

$R_3$ is selected from F and —$OC_{1-4}$ alkyl;

$R_4$, at each occurrence, is selected from Cl and —$OC_{1-3}$ alkyl;

$R_6$ is selected from H, —C(═O)$R_b$, —C(═O)O$R_b$, aryl, heterocyclyl, —C(O)-aryl, and —C(═O)-heterocyclyl, wherein said aryl and heterocyclyl are selected from

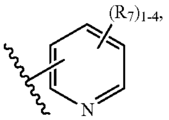
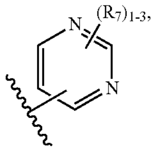
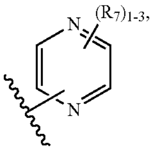 and
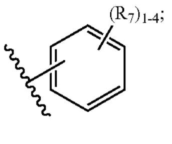

$R_7$, at each occurrence, is independently selected from F, Cl, Br, CN, $C_{1-4}$alkyl, $C_{2-4}$alkenyl, $C_{2-4}$alkynyl, nitro, —$S(O)_pR_c$, —$S(O)_pNR_aR_a$, —$NR_aS(O)_pR_c$, —$OR_v$, —$NR_aR_a$, —$NR_aC$(═O)$R_b$, —$NR_aC$(═O)$NR_aR_a$, —C(═O)$OR_b$, —C(═O)$R_b$, —OC(═O)$R_b$, —C(═O)$NR_aR_a$, $C_{3-6}$ cycloalkyl, heterocyclyl, aryl, and heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, phenyl substituted with 0-5 $R_e$, and —$(CH_2)$-heterocyclyl substituted with 0-5 $R_e$;

$R_e$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $C_{3-6}$ carbocyclyl substituted with 0-5 $R_e$, and heterocyclyl substituted with 0-5 $R_e$;

$R_e$, at each occurrence, is independently selected from F, Cl, Br, CN, $NO_2$, ═O, $C_{1-6}$ alkyl substituted with 1-5 $R_f$, $C_{2-6}$ alkenyl, $C_{2-6}$ alkynyl, C(═O)OH, —C(═O)$OC_{1-4}$alkyl, —$(CH_2)_r$OH, —$(CH_2)_rOC_{1-4}$alkyl, —$(CH_2)_r$—$C_{3-6}$ cycloalkyl, and —$(CH_2)_r$-aryl;

$R_f$, at each occurrence, is independently selected from H, F, Cl, Br, CN, OH, $C_{1-6}$ alkyl optionally substituted with OH, $C_{3-6}$ cycloalkyl, and phenyl;

n, at each occurrence, is independently selected from zero and 1;

p, at each occurrence, is independently selected from zero, 1, and 2; and r, at each occurrence, is independently selected from zero, 1, 2, 3, and 4.

In a tenth aspect, the present invention provides a compound or a pharmaceutically acceptable salt thereof, within the embodiment of the ninth aspect, wherein:

Ring A is

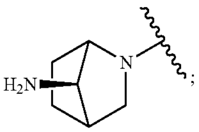

$R_2$ is —$CH_2$-cyclopropyl;

$R_3$ is —$OC_{1-4}$ alkyl;

$R_6$ is selected from —C(═O)-aryl and —C(═O)heterocyclyl wherein said aryl and heterocyclyl are selected from

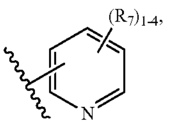
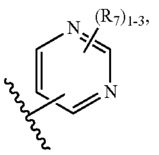
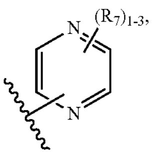 and

-continued

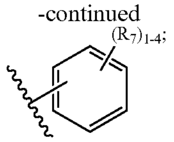

$R_7$, at each occurrence, is independently selected from F, Cl, Br, CN, $C_{1-4}$alkyl, $OR_b$, $C_{3-6}$ cycloalkyl wherein said alkyl or cycloalkyl is substituted with 0-4 $R_e$;

$R_e$, at each occurrence, is independently selected from F, Cl, Br, CN, $NO_2$, =O, $C_{1-6}$ alkyl substituted with 1-5 $R_f$, $C_{2-6}$ alkenyl, $C_{2-6}$ alkynyl, C(=O)OH, —C(=O)$OC_{1-4}$alkyl, —$(CH_2)_r$OH, —$(CH_2)_r OC_{1-4}$alkyl, —$(CH_2)_r$—$C_{3-6}$ cycloalkyl, and —$(CH_2)_r$-aryl;

$R_f$, at each occurrence, is independently selected from H, F, Cl, Br, CN, OH, $C_{1-5}$ alkyl optionally substituted with OH, $C_{3-6}$ cycloalkyl, and phenyl;

n is zero;

p, at each occurrence, is independently selected from zero, 1, and 2; and r, at each occurrence, is independently selected from zero, 1, 2, 3, and 4.

In an eleventh aspect, the present invention provides a compound of formula (VI):

(VI)

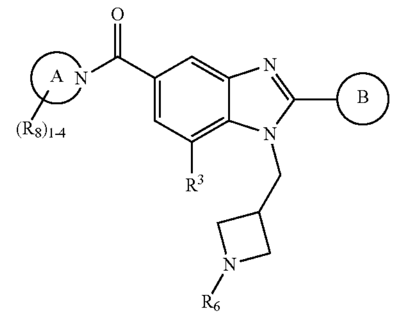

or a pharmaceutically acceptable salt thereof, within the embodiment of the first aspect, wherein:

Ring A is

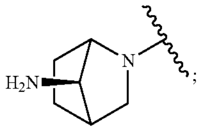

Ring B is selected from

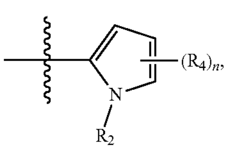

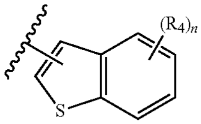

, and

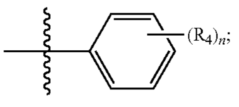

$R_2$ is selected from methyl and —$CH_2$-cyclopropyl;

$R_3$ is —$OC_{1-4}$ alkyl;

$R_4$, at each occurrence, is selected from Cl and $C_{1-3}$ alkyl;

$R_6$ is selected from —C(=O)$OR_b$e,

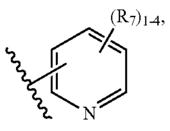

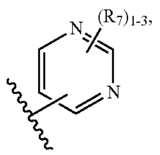

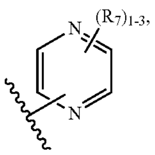

and

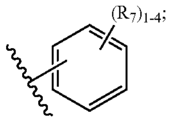

$R_7$, at each occurrence, is independently selected from H, F, Cl, Br, CN, $C_{1-4}$ alkyl, $OR_b$—C(O)$OR_b$, —C(O)$NR_aR_a$, $C_{3-6}$ cycloalkyl, heterocyclyl, aryl, and heteroaryl, wherein said alkyl, cycloalkyl, heterocyclyl, aryl, or heteroaryl is substituted with 0-4 $R_e$.

$R_a$, at each occurrence, is independently selected from H and $C_{1-6}$ alkyl substituted with 0-5 $R_e$;

$R_b$, at each occurrence, is independently selected from H, $C_{1-6}$ alkyl substituted with 0-5 $R_e$, —$(CH_2)$phenyl substituted with 0-5 $R_e$, and -heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_c$, $C_{2-6}$ alkynyl substituted with 0-5 $R_e$, $C_{3-6}$ carbocyclyl substituted with 0-5 $R_e$, and heterocyclyl substituted with 0-5 $R_e$;

$R_e$, at each occurrence, is independently selected from F, Cl, Br, CN, =O, and $C_{1-6}$ alkyl; and n, at each occurrence, is independently selected from zero and 1.

In a twelfth aspect, the present invention provides a compound or a pharmaceutically acceptable salt thereof, within the embodiment of the second aspect, wherein:

Ring A is selected from

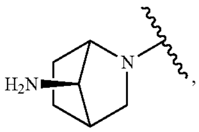 [SMILES: *N1CC2CCC1[C@@H]2N]

,

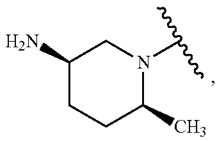

, and

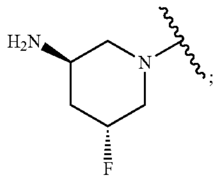

$R_1$ is selected from

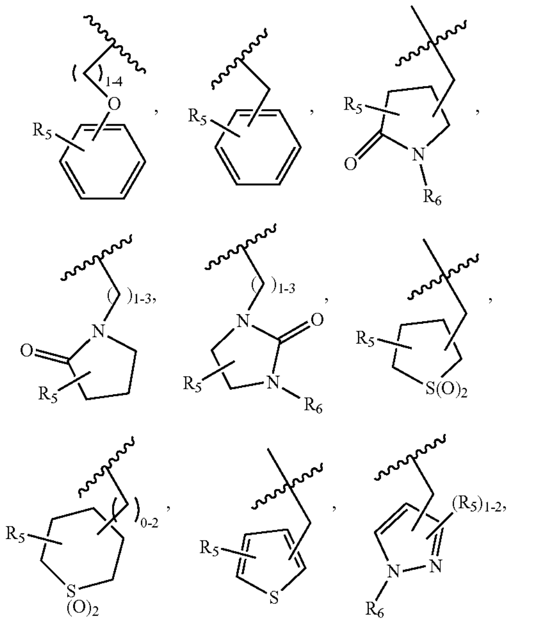

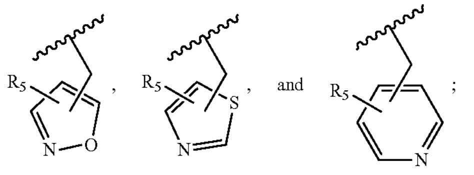

Q is selected from N and CH;

$R_2$ is selected from methyl and —$CH_2$-cyclopropyl;

$R_5$, at each occurrence, is independently selected from H, F, Cl, Br, CN, $NH_2$, =O, and $C_{1-3}$ alkyl; and $R_6$, at each occurrence, is independently selected from H, $C_{1-3}$ alkyl, and —$(CH_2)_{0-1}$-phenyl.

In a thirteenth aspect, the present invention provides a compound of formula (VII):

(VII)

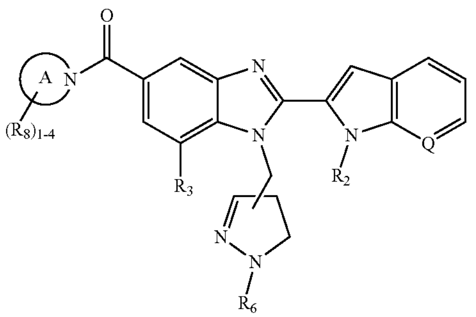

or a pharmaceutically acceptable salt thereof, within the embodiment of the twelfth aspect, wherein:

Ring A is selected from

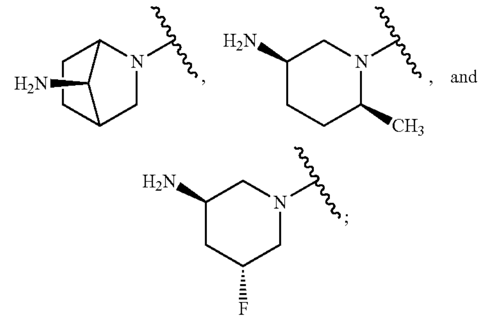

Q is selected from N and CH;

$R_2$ is selected from methyl and —$CH_2$-cyclopropyl;

$R_3$ is selected from H, F, Cl, Br, and —$OC_{1-3}$alkyl; and $R_6$, at each occurrence, is independently selected from H, $C_{1-3}$ alkyl, and —$(CH_2)_{0-1}$-phenyl.

In a fourteenth aspect, the present invention provides a compound or a pharmaceutically acceptable salt thereof, within the embodiment of the second aspect, wherein:

Ring A is

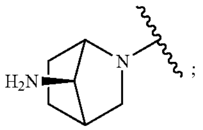 [SMILES: *N1CC2CCC1[C@@H]2N]

Q is selected from N and CH;

$R_1$ is —$(CH_2)_{2-3}R_{5a}$, $R_2$ is selected from methyl and —$CH_2$-cyclopropyl;

$R_{5a}$ is selected from $NHR_a$, $NHC(=O)R_b$, $NHC(=O)OR_b$, and $NHS(=O)_2R_c$;

$R_a$ is independently selected from H and $C_{1-4}$alkyl;

$R_b$, at each occurrence, is independently selected from H and $C_{1-4}$alkyl; and $R_c$ is $C_{1-4}$alkyl.

In a fifteenth aspect, the present invention provides a compound of Formula (VIII):

(VIII)

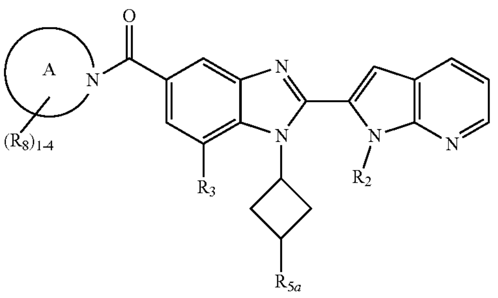

or a pharmaceutically acceptable salt thereof, within the embodiment of the second aspect, wherein:

Ring A is selected from

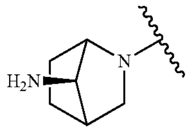 , 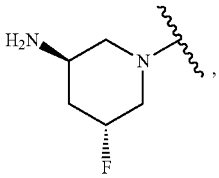 , and

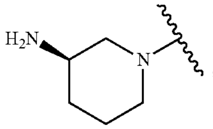 ;

$R_2$ is selected from methyl and —$CH_2$-cyclopropyl;

$R_3$ is selected from F and —$OC_{1-4}$ alkyl;

$R_{5a}$ is selected from C(═O)$NR_aR_a$, $NR_aR_a$, $NR_aC$(═O)$R_a$, $NR_aC$(═O)$OR_a$ and $NR_aS(O)_2R_c$;

$R_a$, at each occurrence, is independently selected from H and $C_{1-6}$ alkyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$ is $C_{1-4}$alkyl substituted with 0-5 $R_e$;

$R_e$, at each occurrence, is independently selected from $C_{1-6}$ alkyl, and ═O, and r, at each occurrence, is independently selected from zero, 1, 2, 3, and 4.

In a sixteenth aspect, the present invention provides a compound of Formula (I):

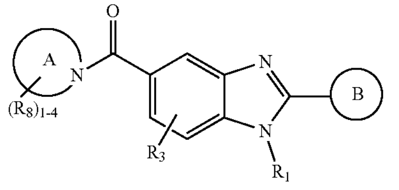

(I)

or a pharmaceutically acceptable salt thereof, wherein:

Ring A is 4- to 15-membered heterocyclyl substituted with 1-4 $R_8$;

Ring B is selected from

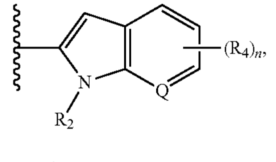 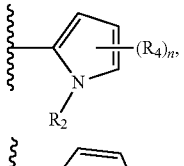

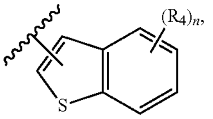 and 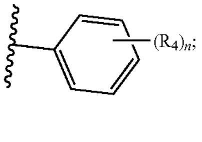 ;

Q is selected from N and $CR_4$;

$R_1$ is selected from —$(CH_2)_{2-4}R_{5a}$, $C_{3-6}$cycloalkyl substituted with 1-2 $R_{5a}$, —$(CH_2)_{1-4}$—$C_{3-6}$cycloalkyl substituted with 1-5 $R_5$, —$(CH_2)_{1-4}$—$(O)_{0-1}$-aryl substituted with 1-5 $R_5$, and —$(CH_2)_r$-4-6-membered heterocyclyl comprising carbon atoms and 1-4 heteroatoms selected from N, $NR_6$ O, and S(O), and substituted with 1-5 $R_5$;

$R_2$, at each occurrence, is independently selected from H and $C_{1-3}$ alkyl optionally substituted with F, Cl, and $C_{3-6}$ cycloalkyl;

$R_3$ is selected from H, F, Cl, Br, $C_{1-3}$ alkyl, and —$OR_a$;

$R_4$, at each occurrence, is independently selected from H, F, Cl, Br, CN, $C_{1-3}$ alkyl substituted with 0-1 OH and $OC_{1-3}$alkyl, and —$OR_b$;

$R_5$, at each occurrence, is independently selected from H, F, Cl, Br, CN, ═O, $C_{1-3}$ alkyl, C(═O)$NR_aR_a$, $NR_aR_a$, $NR_aC$(═O)$R_b$, $NR_aC$(═O)$OR_b$, $NR_aS$(═O)$_pR_c$, and aryl substituted with 1-5 $R_7$;

$R_{5a}$, at each occurrence, is independently selected from C(═O)$NR_aR_a$, $NR_aR_a$, $NR_aC$(═O)$R_b$, $NR_aC$(═O)$R_b$, and $NR_aS$(═O)$_pR_c$;

$R_6$ is selected from H, $C_{1-3}$ alkyl substituted with 1-5 $R_7$, —$S(O)_pR_c$, —C(═O)$R_b$, —C(═O)$OR_b$, —C(═O)$(CH_2)_rNR_aR_a$, —$S(O)_pNR_aR_a$, —$(CH_2)_r$—$C_{3-6}$cycloalkyl substituted with 1-5 $R_7$, —$(CH_2)$-aryl substituted with 1-5 $R_7$, —$(CH_2)_r$-heterocyclyl substituted with 1-5 $R_7$, —C(═O)—$(CH_2)_r$—$C_{3-6}$ cycloalkyl substituted with 1-5 $R_7$, —C(═O)—$(CH_2)_r$-aryl substituted with 1-5 $R_7$, —C(═O)—$(CH_2)_r$-heterocyclyl substituted with 1-5 $R_7$; —S(═O)$_2$—$(CH_2)_r$—$C_{3-6}$cycloalkyl substituted with 1-5 $R_7$, —S(═O)$_2$—$(CH_2)_r$-aryl substituted with 1-5 $R_7$, —S(═O)$_2$—$(CH_2)_r$-heterocyclyl substituted with 1-5 $R_7$, —C(═O)$NR_a$-aryl substituted with 1-5 $R_7$, and —C(═O)$NR_a$-heterocyclyl substituted with 1-5 $R_7$;

$R_7$, at each occurrence, is independently selected from H, F, Cl, Br, $C_{1-4}$alkyl substituted with 0-4 $R_e$, $C_{2-4}$alkenyl substituted with 0-4 $R_e$, $C_{2-4}$alkynyl substituted with 0-4 $R_e$, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_r$CN, —$(CHR_d)_rNR_aR_a$, —$(CHR_d)_rNR_aC$(═O)$R_b$, —$(CHR_d)_rNR_a$ C(═O)$NR_aR_a$, —$(CHR_d)_r$C(═O)$OR_b$, —$(CHR_d)_r$C(═O)$R_b$, —$(CHR_d)_r$OC(═O)$R_b$, —$(CHR_d)_r$C(═O)$NR_aR_a$, —$(CHR_d)_r$-cycloalkyl substituted with 0-5 $R_e$, —$(CHR_d)_r$-aryl substituted with 0-5 $R_e$, and —$(CHR_d)_r$-heterocyclyl, substituted with 0-5 $R_e$;

$R_8$, at each occurrence, is independently selected from H, F, Cl, CN, $C_{1-3}$ alkyl, ═N—$OR_b$, —$(CH_2)_rOR_b$, —$(CH_2)_rNR_aR_a$, —$NR_aC$(═NH)$C_{1-3}$alkyl, —$NR_aC$(═O)$OR_b$, a carbocyle, and a heterocycle; alternatively, two $R_8$ groups are taken together to form a carbocycle or heterocyle;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)$, $C_{3-6}$ carbocyclyl substituted with 0-5 $R_e$, and —$(CH_2)_r$-heterocyclyl substituted with 0-5 $R_e$;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, —$(CH_2)_r OR_f$, $C(=O)OR_f$, $S(=O)_p R_f$, $C(=O)NR_f R_f$, $S(=O)_p NR_f R_f$, and —$(CH_2)_r NR_f R_f$, $C_{1-6}$ alkyl substituted with 1-5 $R_f$, $C_{2-6}$ alkenyl substituted with 1-5 $R_f$, $C_{2-6}$ alkynyl substituted with 1-5 $R_f$, —$(CH_2)_r$—$C_{3-6}$ cycloalkyl substituted with 1-5 $R_f$, —$(CH_2)_r$-aryl substituted with 1-5 $R_f$, and —$(CH_2)_r$-heterocyclyl substituted with 1-5 $R_f$;

$R_f$, at each occurrence, is independently selected from H, F, Cl, Br, CN, OH, $C_{1-5}$ alkyl optionally substituted with OH, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from zero, 1, 2, 3, and 4;

p, at each occurrence, is independently selected from zero, 1, and 2; and r, at each occurrence, is independently selected from zero, 1, 2, 3, and 4;

provided that when Ring B is

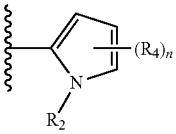

$R_1$ is —$(CH_2)_{1-3}$-4-6-membered heterocyclyl comprising carbon atoms and $NR_6$.

In a seventeenth aspect, the present invention provides a compound of Formula (II):

(II)

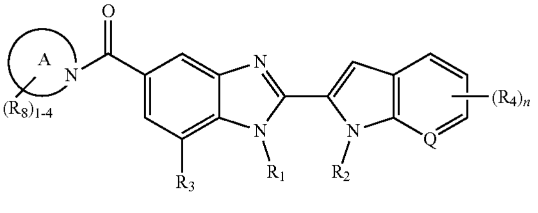

or a pharmaceutically acceptable salt thereof, within the embodiment of the sixteenth aspect, wherein:

Ring A is selected from

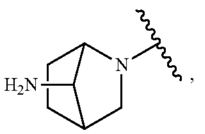,
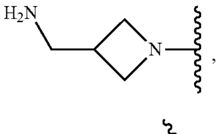,
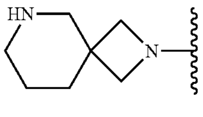,
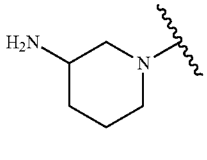,

-continued

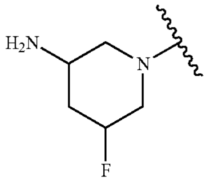,
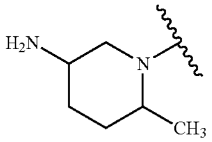, and
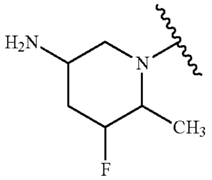;

Q is selected from N and CH;

$R_1$ is selected from —$(CH_2)_{2-3}R_{5a}$,

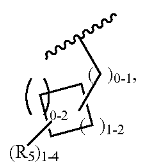
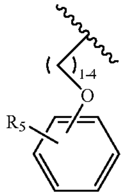,
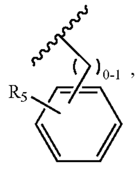
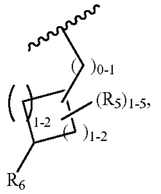
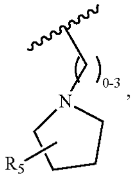
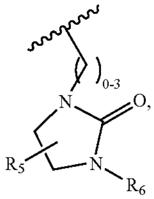
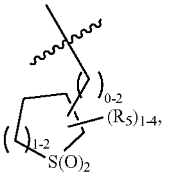
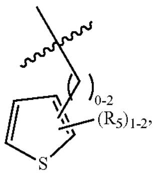
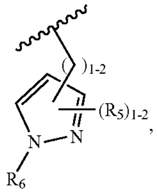
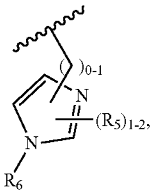
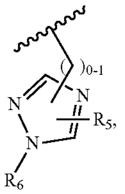
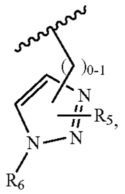
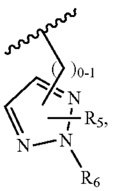
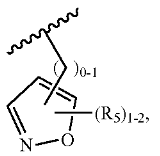
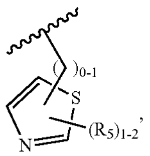, and
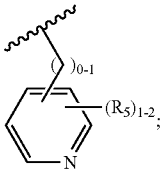

$R_2$ is $C_{1-2}$ alkyl optionally substituted with $C_{3-6}$cycloalkyl;

$R_3$ is selected from H, F, Cl, Br, $C_{1-2}$ alkyl, and —$OR_b$;

$R_4$, at each occurrence, is independently selected from H, F, Cl, Br, CN, $C_{1-3}$alkyl substituted with 0-1 OH and $OC_{1-3}$alkyl, and —$OR_b$;

$R_5$, at each occurrence, is independently selected from H, F, Cl, Br, CN, $NH_2$, =O, $C_{1-3}$ alkyl, $C(=O)NR_aR_a$, $NR_aR_a$, $NR_aC(=O)R_b$, $NR_aC(=O)OR_b$, $NR_aS(O)_pR_c$, and aryl substituted with 1-4 $R_7$;

$R_{5a}$, at each occurrence, is independently selected from $NR_aR_a$, $NR_aC(=O)R_b$, $NR_aC(=O)OR_b$, and $NR_aS(O)_pR_c$;

$R_6$, at each occurrence, is independently selected from H, $C_{1-3}$ alkyl, $-S(O)_pR_c$, $-C(=O)R_b$, $-C(=O)NR_aR_a$, $-C(=O)(CH_2)_rNR_aR_a$, $-C(=O)OR_b$, $-S(O)_pNR_aR_a$, $-(CH_2)_r$-aryl substituted with 1-5 $R_7$, and $-(CH_2)_r$-heterocyclyl, substituted with 1-5 $R_7$, $-C(=O)-(CH_2)_r$-aryl substituted with 1-5 $R_7$, $-C(=O)-(CH_2)_r$-heterocyclyl substituted with 1-5 $R_7$; $-S(=O)_2-(CH_2)_r-C_{3-6}$cycloalkyl substituted with 1-5 $R_7$, $-S(=O)_2-(CH_2)_r$-aryl substituted with 1-5 $R_7$, and $-S(=O)_2-(CH_2)_r$-heterocyclyl substituted with 1-5 $R_7$, $-C(=O)NH$-aryl substituted with 1-5 $R_7$, and $-C(=O)NH$-heterocyclyl substituted with 1-5 $R_7$;

$R_7$, at each occurrence, is independently selected from H, F, Cl, Br, CN, $C_{1-4}$alkyl substituted with 0-4 $R_e$, $C_{2-4}$alkenyl substituted with 0-4 $R_e$, $C_{2-4}$alkynyl substituted with 0-4 $R_e$, $-S(=O)_pR_c$, $-S(=O)_pNR_aR_a$, $-NR_aS(=O)_pR_c$, $-OR_b$, $-NR_aR_a$, $-NR_aC(=O)R_b$, $-NR_aC(=O)NR_aR_a$, $-C(=O)OR_b$, $-C(=O)R_b$, $-OC(=O)R_b$, $-C(=O)NR_aR_a$, $C_{3-6}$cycloalkyl substituted with 0-4 $R_e$, heterocyclyl substituted with 0-4 $R_e$, aryl substituted with 0-4 $R_e$, and heteroaryl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, $-(CH_2)_r-C_{3-6}$ carbocyclyl substituted with 0-5 $R_e$, and $-(CH_2)_r$-heterocyclyl substituted with 0-5 $R_e$;

$R_e$, at each occurrence, is independently selected from F, Cl, Br, CN, =O, $-(CH_2)_rOH$, $-(CH_2)_rOC_{1-4}$alkyl, $-C(=O)OH$, $-C(=O)OC_{1-4}$alkyl, $-(CH_2)_rNH_2$, $-(CH_2)_rNH(C_{1-4}$ alkyl), $-(CH_2)_rN(C_{1-4}$ alkyl$)_2$, $C_{1-6}$ alkyl substituted with 1-5 $R_f$, $C_{2-6}$ alkenyl substituted with 1-5 $R_f$, $C_{2-6}$ alkynyl substituted with 1-5 $R_1$, $-(CH_2)_r-C_{3-6}$ cycloalkyl, $-(CH_2)_r$-aryl, and $-(CH_2)_r$-heterocyclyl, $R_f$, at each occurrence, is independently selected from H, F, Cl, Br, CN, OH, $C_{1-5}$ alkyl optionally substituted with OH, $C_{3-6}$ cycloalkyl, and phenyl;

n, at each occurrence, is independently selected from zero, 1, 2, and 3;

p, at each occurrence, is independently selected from zero, 1, and 2; and r, at each occurrence, is independently selected from zero, 1, 2, 3, and 4.

In an eighteenth aspect, the present invention provides a compound of Formula (IX):

(IX)

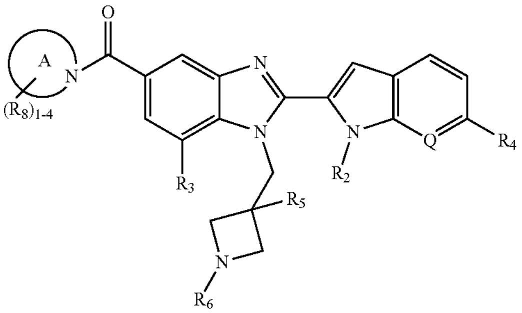

or a pharmaceutically acceptable salt thereof, within the embodiment of the seventeenth aspect, wherein:

Ring A is selected from

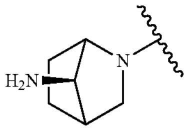 and 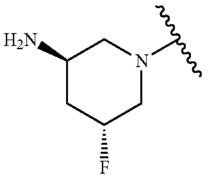 ;

Q is selected from N and CH;

$R_2$ is selected from $CH_3$ and $-CH_2$-cyclopropyl;

$R_3$ is selected from F, $CH_3$ and $-OCH_3$;

$R_4$, is selected from H, F, Cl, Br, and $C_{1-3}$ alkyl substituted with 0-1 OH and $OC_{1-3}$alkyl; $R_5$ is selected from H, F, and $C_{1-2}$ alkyl;

$R_6$, is selected from $-C(=O)$-aryl substituted with 1-5 $R_7$ and $-C(=O)$-heterocyclyl substituted with 1-5 $R_7$, $-C(=O)NH$-aryl substituted with 1-5 $R_7$, and $-C(=O)NH$-heterocyclyl substituted with 1-5 $R_7$; wherein said aryl and heterocyclyl are selected from

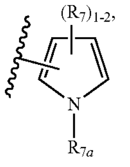 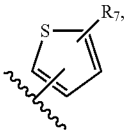 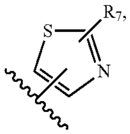

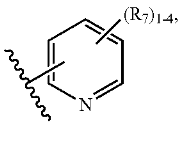 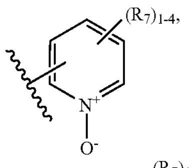

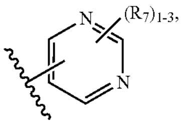 and 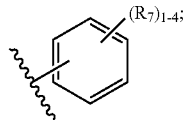

$R_7$, at each occurrence, is independently selected from H, F, Cl, Br, CN, $C_{1-4}$alkyl, and $-OH$; and $R_{7a}$, at each occurrence, is independently selected from H and $C_{1-4}$alkyl.

In a nineteenth aspect, the present invention provides a compound of Formula (X);

(X)

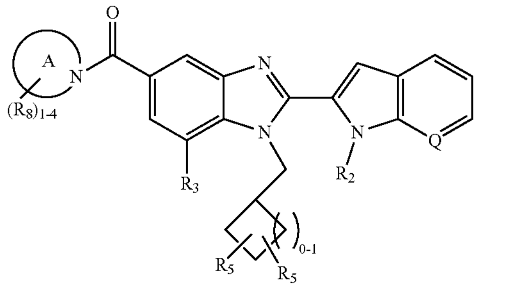

or a pharmaceutically acceptable salt thereof, within the embodiment of the seventeenth aspect, wherein:

Ring A is selected from

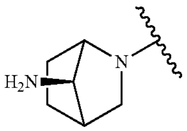 and 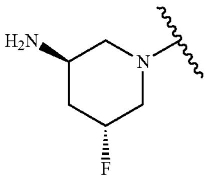 ;

$R_2$ is selected from $CH_3$ and $-CH_2$-cyclopropyl;

$R_3$ is selected from F and $-OC_{1-4}$ alkyl;

$R_5$ is selected from H, F, Cl, $C(=O)NR_aR_a$, and aryl substituted with 1-4 $R_7$;

$R_7$, at each occurrence, is independently selected from H, F, Cl, Br, CN, $C_{1-4}$alkyl, and —OH; and $R_a$, at each occurrence, is independently selected from H and $C_{1-6}$ alkyl.

In a twentieth aspect, the present invention provides a compound of Formula (XI):

(XI)

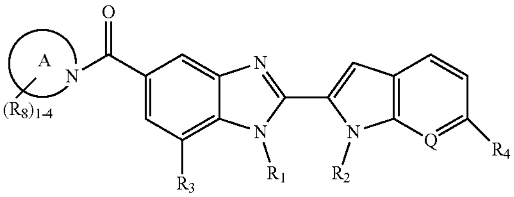

or a pharmaceutically acceptable salt thereof, within the embodiment of the seventeenth aspect, wherein:

Ring A is selected from

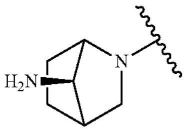 and 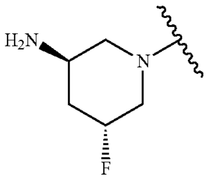 ;

Q is selected from N and CH;

$R_1$ is selected from

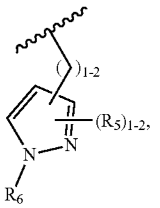 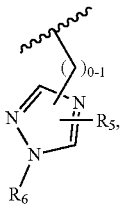 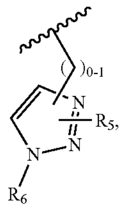 and 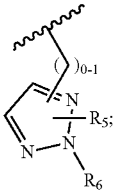

$R_2$ is selected from $CH_3$ and $-CH_2$-cyclopropyl;

$R_3$ is selected from H, F, and $-OCH_3$;

$R_4$, is selected from H, F, Cl, Br, and $C_{1-3}$ alkyl substituted with 0-1 OH and $OC_{1-3}$alkyl;

$R_5$, at each occurrence, is independently selected from H and $C_{1-2}$ alkyl; and $R_6$, at each occurrence, is independently selected from H and $C_{1-2}$ alkyl.

As defined above and described herein, each $R_R$ is $-(CH_2)_{2-3}R_{5a}$,

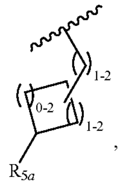 , 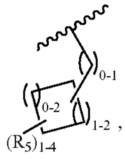 , 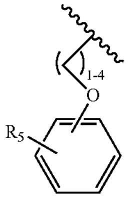 , 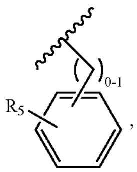 , 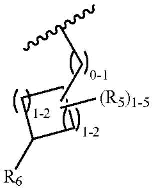 , 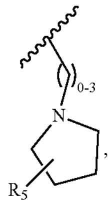 , 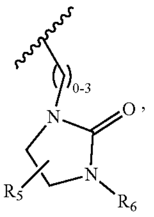 , 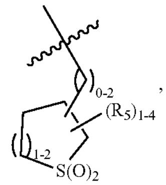 , 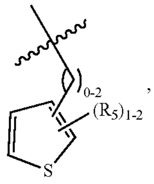 , 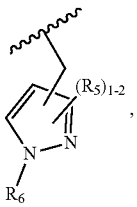 , 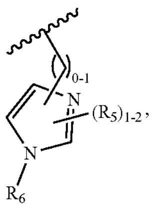 , 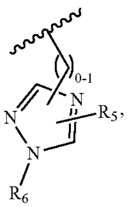

-continued
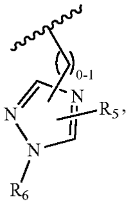
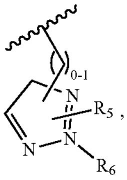
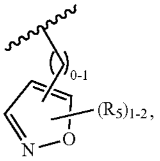
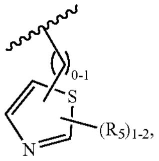
and
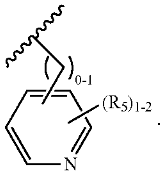
In some embodiments, $R_1$ is
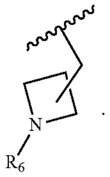
In some embodiments, $R_1$ is
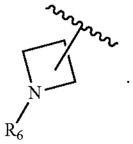
In some embodiments, $R_1$ is
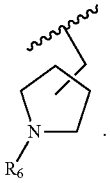
In some embodiments, $R_1$ is
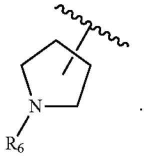
In some embodiments, $R_1$ is
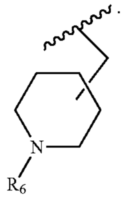
In some embodiments, $R_1$ is
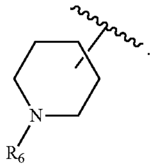
In some embodiments, $R_1$ is
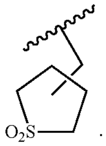
In some embodiments, $R_1$ is
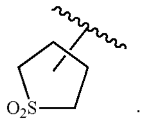
In some embodiments, $R_1$ is
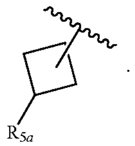
In some embodiments, $R_1$ is
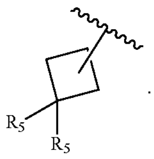
wherein each $R_5$ is F.

In some embodiments, $R_1$ is

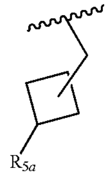

In some embodiments, $R_1$ is

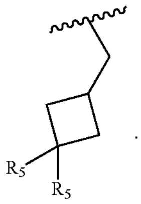

wherein each $R_5$ is F.

In some embodiments, $R_1$ is

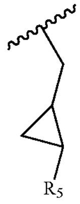

wherein each $R_5$ is H ro phenyl.

In some embodiments, $R_1$ is

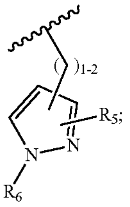

$R_5$ and $R_6$ are independently H or methyl.

In some embodiments, $R_1$ is

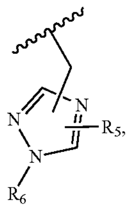

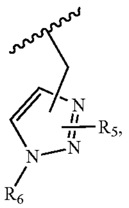

or

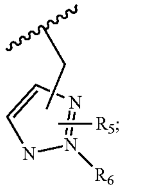

$R_5$ and $R_6$ are independently H or methyl

In some embodiments, $R_1$ is —$(CH_2)_2NHS(=O)_2$ $C_{1-4}$alkyl. In some embodiments, $R_1$ is —$(CH_2)_2NHC(=O)$ $C_{1-4}$alkyl. In certain embodiments, $R_1$ is selected from those functional groups depicted in the examples below.

As defined above and described herein, $R_2$ is hydrogen, $C_{1-3}$ alkyl substituted with 0-5 $R_e$, or $C_{3-6}$ cycloalkyl substituted with 0-5 $R_e$. In some embodiments, $R_2$ is hydrogen. In some embodiments, $R_2$ is $C_{1-2}$ alkyl substituted with $C_{3-6}$ cycloalkyl. In some embodiments, $R_2$ is $C_{3-6}$ cycloalkyl. In some embodiments, $R_2$ is methyl. In some embodiments, $R_2$ is ethyl. In some embodiments, $R_2$ is cyclopropyl. In some embodiments, $R_2$ is cyclobutyl. In some embodiments, $R_2$ is cyclopentyl. In some embodiments, $R_2$ is cyclohexyl. In some embodiments, $R_2$ is cyclopropylmethyl. In some embodiments, $R_2$ is cyclobutylmethyl. In some embodiments, $R_2$ is cyclopentylmethyl. In some embodiments, $R_2$ is cyclohexylmethyl. In some embodiments, $R_2$ is cyclopropylethyl. In some embodiments, $R_2$ is cyclobutylethyl. In some embodiments, $R_2$ is cyclopentylethyl. In some embodiments, $R_2$ is cyclohexylethyl. In some embodiments, $R_2$ is —$CH_2$-cyclopropyl or —$CH_2$-cyclobutyl. In some embodiments, $R_2$ is —$CH_2$-cyclobutyl optionally substituted with methyl and —OH. In certain embodiments, $R_2$ is selected from those functional groups depicted in the examples below.

As defined above and described herein, Q is N or CH. In some embodiments, Q is N. In some embodiments. Q is CH. In certain embodiments, Q is selected from those functional groups depicted in the examples below.

As defined above and described herein, each $R_3$ is H, F, Cl, Br, —$OR_b$, or $C_{1-3}$ alkyl substituted with 0-5 $R_e$. In some embodiments, $R_3$ is H. In some embodiments, $R_3$ is F, Cl, and Br. In some embodiments, $R_3$ is F. In some embodiments, $R_3$ is $C_{1-3}$ alkyl. In some embodiments, $R_3$ is methyl. In some embodiments, $R_3$ is ethyl. In some embodiments, $R_3$ is propyl. In some embodiments, $R_3$ is $OR_b$. In some embodiments, $R_3$ is —$OCH_3$. In some embodiments, $R_3$ is —$OCH_2CH_3$. In some embodiments, $R_3$ is —$OCH_2CH_2CH_3$. In some embodiments, $R_3$ is —$OCH(F)_2$. In certain embodiments, $R_3$ is selected from those functional groups depicted in the examples below.

As defined above and described herein, each $R_4$ is F, Cl, Br, CN, $C_{1-3}$ alkyl substituted with 0-1 OH and $OC_{1-4}$ alkyl, or —$OR_b$. In some embodiments, $R_4$ is Cl. In some embodiments, $R_4$ is absent when n is zero. In some embodiments, $R_4$ is $OC_{1-4}$ alkyl. In certain embodiments, $R_4$ is at the 6-position of the indole and is selected from F, Cl, Br, methyl, ethyl, or ethane-1-ol.

As defined above and described herein, each $R_5$ is H, $C_{1-4}$ alkyl, or =O. In some embodiments, $R_5$ is H. In some embodiments, $R_5$ is =O. In some embodiments, $R_5$ is $C_{1-4}$ alkyl. In certain embodiments, $R_5$ is selected from those functional groups depicted in the examples below.

As defined above and described herein, in some embodiments, each $R_6$ is

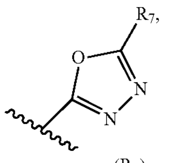

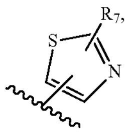

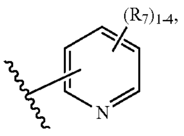

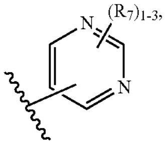

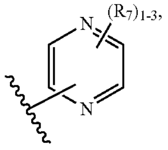

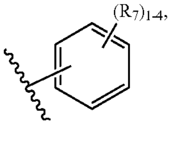

-continued or 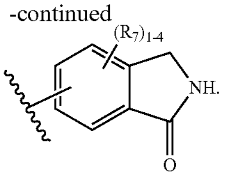

In some embodiments, $R_6$ is —C(=O)$R_b$, —C(=O)O$R_b$, —C(=O)—$(CH_2)_r$$C_{3-6}$cycloalkyl, —C(=O)—$(CH_2)_r$-aryl, or —C(=O)—$(CH_2)_r$-heterocyclyl, wherein said cycloalkyl, aryl, and heterocyclyl are selected from

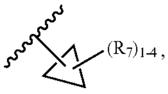 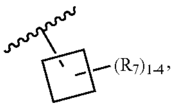 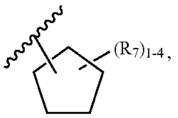

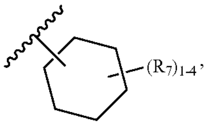 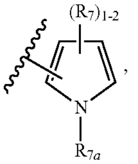 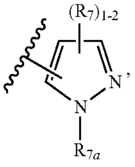

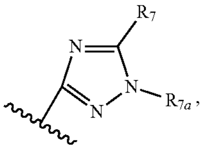 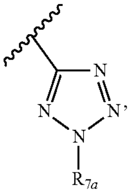

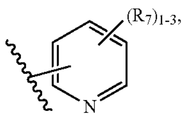 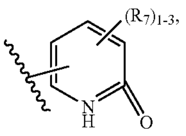 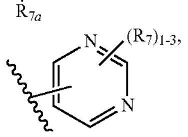

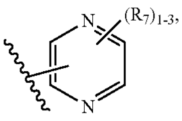 and 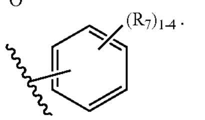

In some embodiments, $R_6$ is —C(=O)-aryl, or —C(=O)-heterocyclyl, wherein said aryl and heterocyclyl are selected from

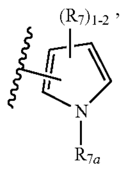 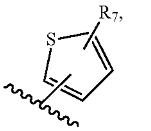 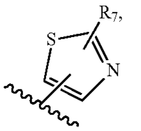

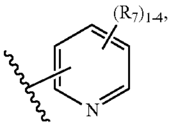 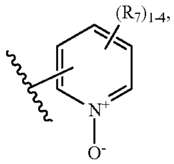 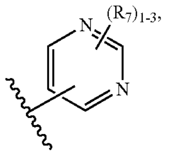

and 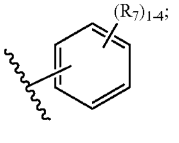

In some embodiments, $R_6$ is —S(O)$_p$$R_c$, —S(=O)$_2$—$(CH_2)_r$$C_{3-6}$cycloalkyl, —S(=O)$_2$—$(CH_2)_r$-aryl, or —S(=O)$_2$—$(CH_2)_r$-heterocyclyl, wherein said cycloalkyl aryl and heterocyclyl are selected from

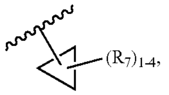 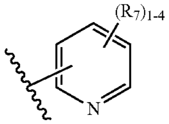 , and

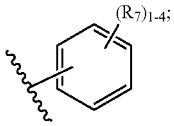

In certain embodiments, $R_6$ is selected from those functional groups depicted in the examples below.

As defined above and described herein, each $R_7$ is F, Cl, Br, CN, $C_{1-4}$alkyl, —S(O)$_p$$R_c$, —O$R_b$, —N$R_a$$R_a$, —C(=O)O$R_b$, —C(=O)$R_b$, C(=O)N$R_a$$R_a$, —$(CH_2)_{0-1}$-cycloalkyl substituted with 0-5 $R_e$, —$(CH_2)_{0-1}$-aryl substituted with 0-5 $R_e$, and —$(CH_2)_{0-1}$-heterocyclyl, substituted with 0-5 $R_e$.

In some embodiments, $R_7$ is F, Cl, or Br. In some embodiments, $R_7$ is CN. In some embodiments, $R_7$ is methyl or ethyl. In some embodiments, $R_7$ is OH In some embodiments, $R_7$ is NH$R_a$, wherein $R_a$ is $C_{1-4}$ alkyl substituted with OH. In some embodiments, $R_7$ is —C(=O)OH, —C(=O)O$C_{1-4}$ alkyl or —C(=O)$C_{1-4}$ alkyl. In some embodiments, $R_7$ is —C(=O)$NH_2$. In some embodiments, $R_7$ is phenyl. In some embodiments, $R_7$ is cyclopropyl. In certain embodiments, $R_7$ is selected from those functional groups depicted in the examples below.

As defined above and described herein, each $R_5$ is H, F, Cl, $C_{1-3}$alkyl, —N$R_a$$R_a$, or —N$R_a$C(=O)O$R_b$. In some embodiments, $R_7$ is $NH_2$. In some embodiments, $R_7$ is F. In certain embodiments, $R_8$ is selected from those functional groups depicted in the examples below.

As defined above, Ring A is

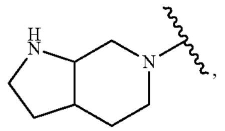 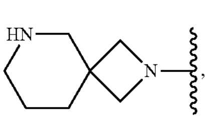

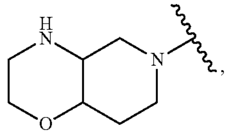 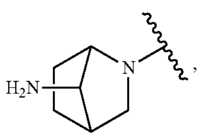

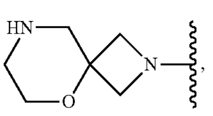 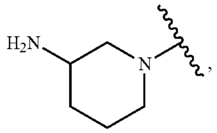

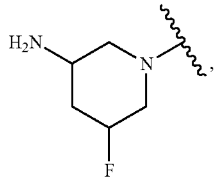 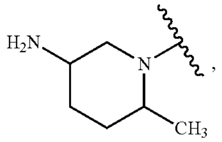

-continued
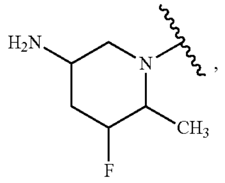
or
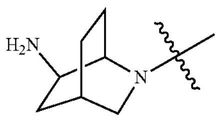
wherein Ring A is optionally substituted with 1-4 groups selected from fluorine or $C_{1-6}$ alky optionally substituted with 1-3 fluorine atoms.
In some embodiments, Ring A is
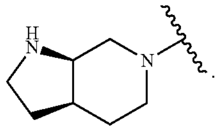 [SMILES: *N1CC[C@H]2CCN[C@H]2C1]
In some embodiments, Ring A is
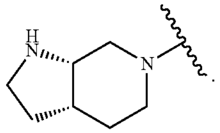 [SMILES: *N1CC[C@@H]2CCN[C@@H]2C1]
In some embodiments, Ring A is
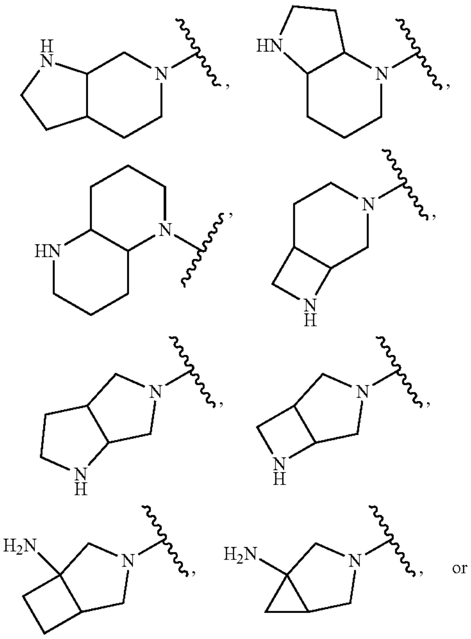
or
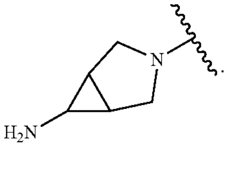
In some embodiments, Ring A is
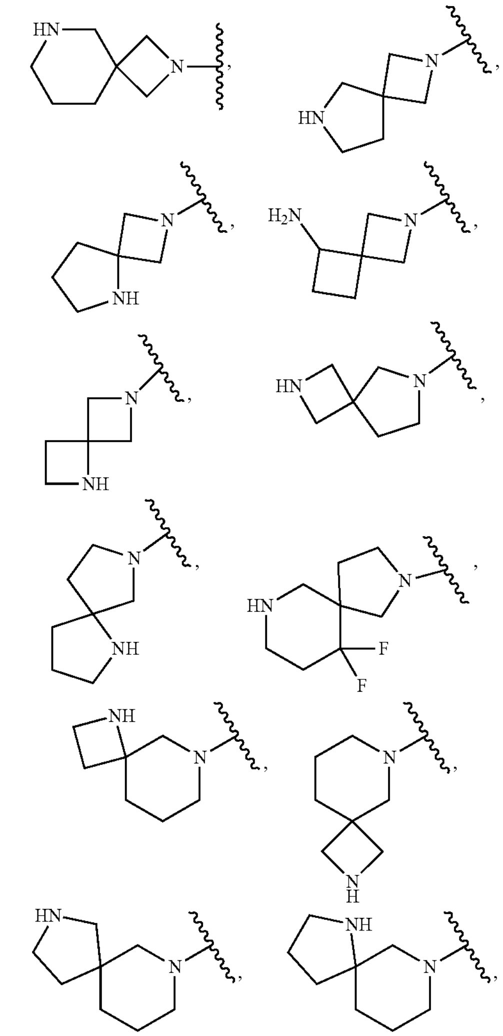
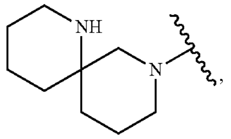
or
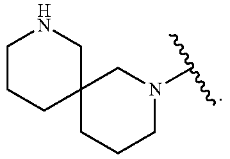
In some embodiments, Ring A is
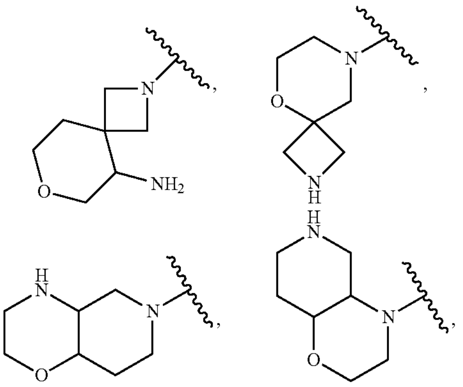

-continued
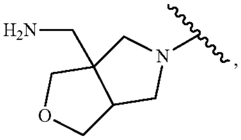
or
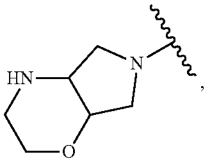
In some embodiments, Ring A is
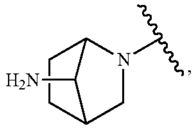
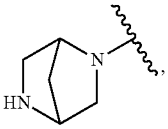
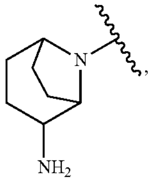
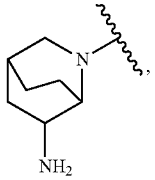
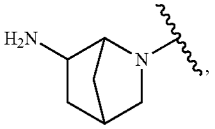
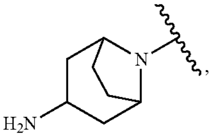
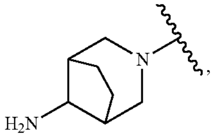
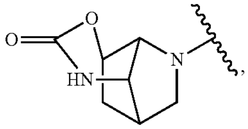
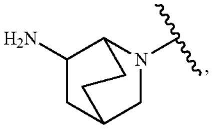
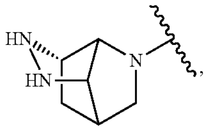
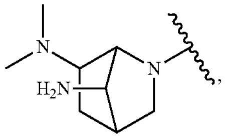
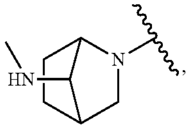
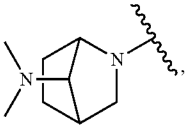
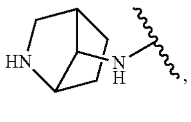
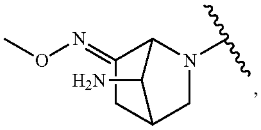
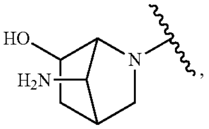
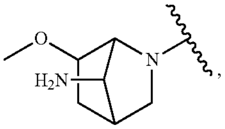
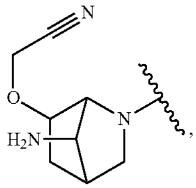
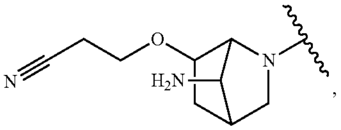
-continued
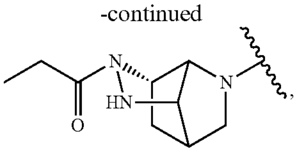
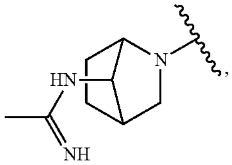
or
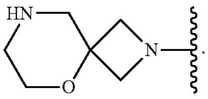
In some embodiments, Ring A is
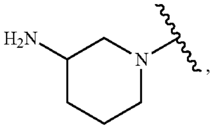
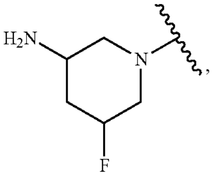
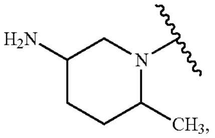
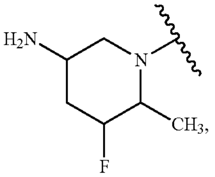
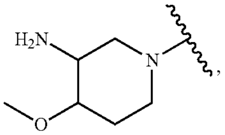
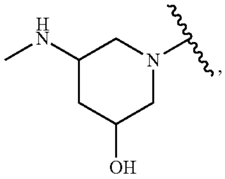
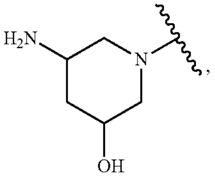
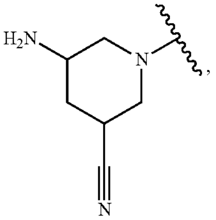
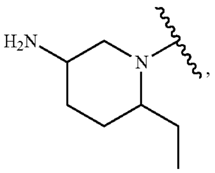
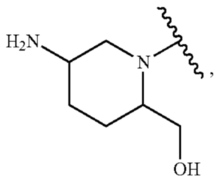
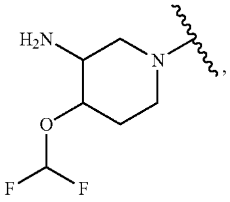
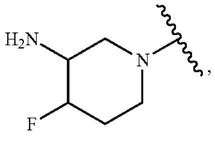
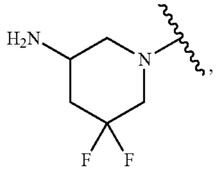
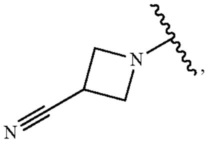

-continued
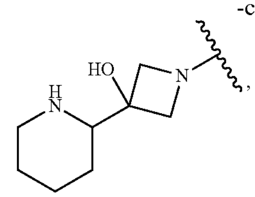
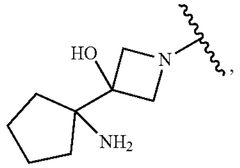
or
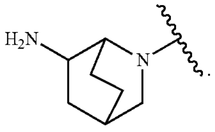
In some embodiments, Ring A is
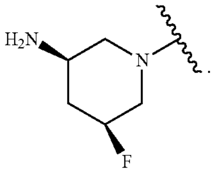 [SMILES: *N1C[C@H](N)C[C@H](F)C1]
In some embodiments, Ring A is
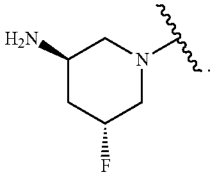 [SMILES: *N1C[C@H](N)C[C@@H](F)C1]
In some embodiments, Ring A is
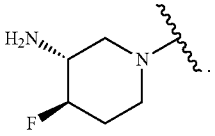 [SMILES: *N1CC[C@@H](F)[C@H](N)C1]
In some embodiments, Ring A is
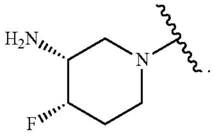 [SMILES: *N1CC[C@H](F)[C@H](N)C1]
In some embodiments, Ring A is
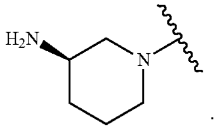 [SMILES: *N1CCC[C@@H](N)C1]
In some embodiments, Ring A is
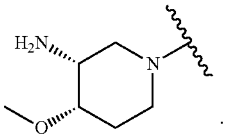 [SMILES: *N1CC[C@H](OC)[C@H](N)C1]
In some embodiments, Ring A is
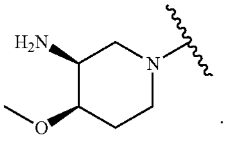 [SMILES: *N1CC[C@@H](OC)[C@@H](N)C1]
In some embodiments, Ring A is
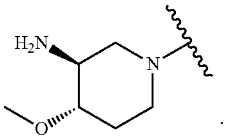 [SMILES: *N1CC[C@H](OC)[C@@H](N)C1]
In some embodiments. Ring A is
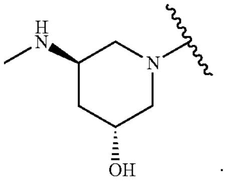 [SMILES: *N1C[C@H](O)C[C@@H](NC)C1]
In some embodiments, Ring A is
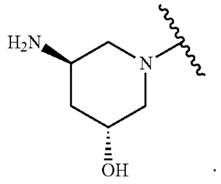 [SMILES: *N1C[C@H](N)C[C@@H](O)C1]
In some embodiments, Ring A is
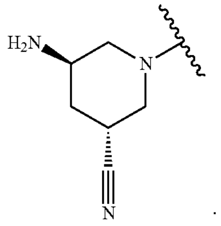 [SMILES: *N1C[C@H](N)C[C@@H](C#N)C1]

In some embodiments, Ring A is
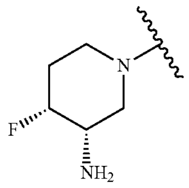
.
In some embodiments. Ring A is
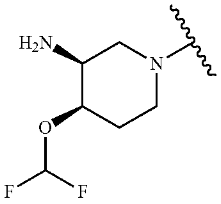
.
In some embodiments, Ring A is
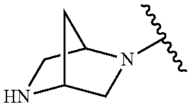
.
In some embodiments, Ring A is
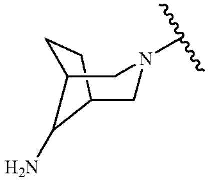
.
In some embodiments, Ring A is
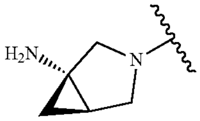
.
In some embodiments, Ring A is
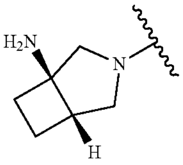
.
In some embodiments, Ring A is
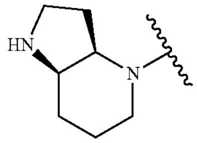
.
In some embodiments, Ring A is
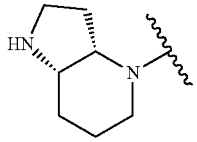
.
In some embodiments, Ring A is
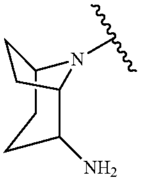
.
In some embodiments, Ring A is
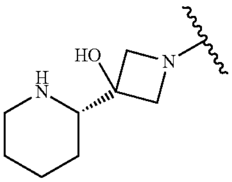
.
In some embodiments, Ring A is
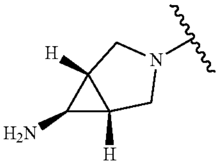
.
In some embodiments. Ring A is
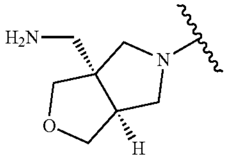
.

In some embodiments. Ring A is

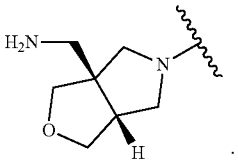

In some embodiments, Ring A is

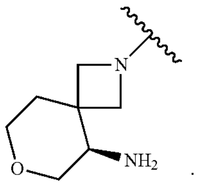 [SMILES: *N1CC2(CCOC[C@@H]2N)C1]

In some embodiments, Ring A is

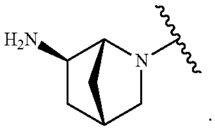

In some embodiments, Ring A is

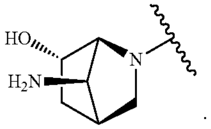 [SMILES: *N1C[C@H]2C[C@H](O)[C@@H]1[C@@H]2N]

In some embodiments, Ring A is

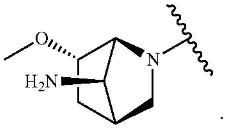 [SMILES: *N1C[C@H]2C[C@H](OC)[C@@H]1[C@@H]2N]

In some embodiments, Ring A is

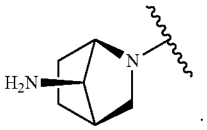

In some embodiments, Ring A is

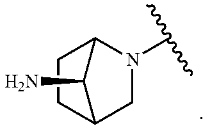

In some embodiments, Ring A is

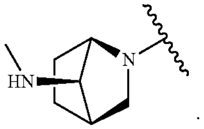 [SMILES: *N1C[C@H]2CC[C@@H]1[C@@H]2NC]

In some embodiments, Ring A is

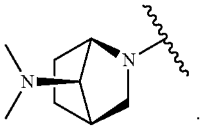 [SMILES: *N1C[C@H]2CC[C@@H]1[C@@H]2N(C)C]

In some embodiments, Ring A is

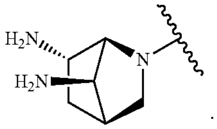 [SMILES: *N1C[C@H]2C[C@H](N)[C@@H]1[C@@H]2N]

In some embodiments, Ring A is

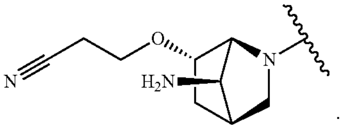 [SMILES: *N1C[C@H]2C[C@H](OCCC#N)[C@@H]1[C@@H]2N]

In some embodiments, Ring A is

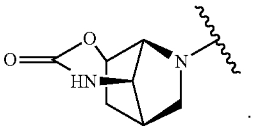 [SMILES: *N1C[C@H]2CC3OC(=O)N[C@H]2[C@@H]31]

In some embodiments, Ring A is

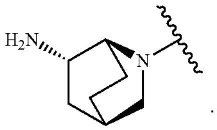 [SMILES: *N1C[C@@H]2CC[C@H]1[C@@H](N)C2]

In some embodiments, Ring A is

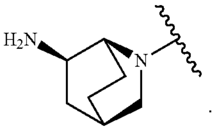 [SMILES: *N1C[C@@H]2CC[C@H]1[C@H](N)C2]

In some embodiments, Ring A is

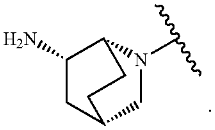

In some embodiments, Ring A is

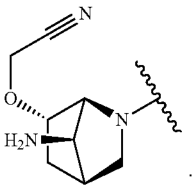 [SMILES: *N1C[C@H]2C[C@H](OCC#N)[C@@H]1[C@@H]2N]

In some embodiments, Ring A is

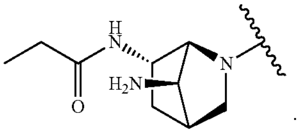 [SMILES: *N1C[C@H]2C[C@H](NC(=O)CC)[C@@H]1[C@@H]2N]

In some embodiments, Ring A is

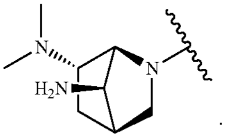 [SMILES: *N1C[C@H]2C[C@H](N(C)C)[C@@H]1[C@@H]2N]

In some embodiments. Ring A is

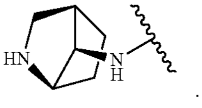 [SMILES: *N[C@@H]1[C@@H]2CC[C@H]1NC2]

In some embodiments, Ring A is

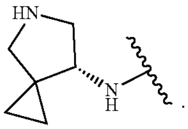 [SMILES: *N[C@H]1CNCC12CC2]

In some embodiments, Ring A is

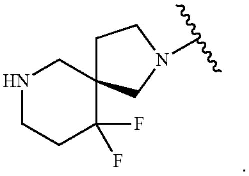 [SMILES: *N1CC[C@]2(CNCCC2(F)F)C1 ; "."]

In some embodiments, Ring A is

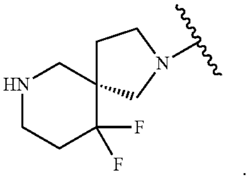 [SMILES: *N1CC[C@@]2(CNCCC2(F)F)C1 ; "."]

In some embodiments, Ring A is

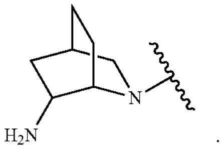

In some embodiments, Ring A is

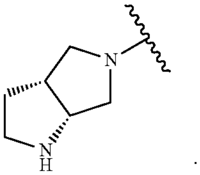 [SMILES: *N1C[C@H]2CCN[C@H]2C1]

In some embodiments, Ring A is

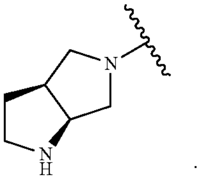 [SMILES: *N1C[C@@H]2CCN[C@@H]2C1]

In some embodiments, Ring A is

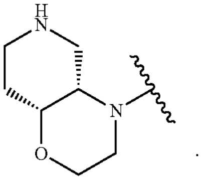 [SMILES: *N1CCO[C@@H]2CCNC[C@@H]21]

In some embodiments, Ring A is

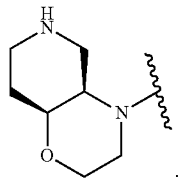 [SMILES: *N1CCO[C@H]2CCNC[C@H]21].

In some embodiments, Ring A is

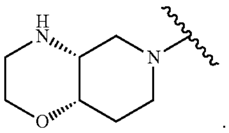 [SMILES: *N1CC[C@@H]2OCCN[C@@H]2C1].

In some embodiments, Ring A is

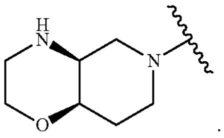 [SMILES: *N1CC[C@H]2OCCN[C@H]2C1].

In some embodiments, Ring A is

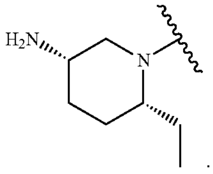.

In some embodiments, Ring A is

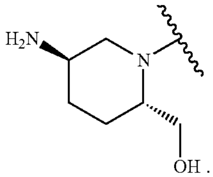 [SMILES: *N1C[C@H](N)CC[C@H]1CO].

In some embodiments, Ring A is

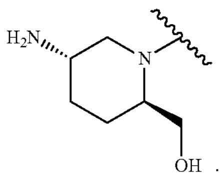 [SMILES: *N1C[C@@H](N)CC[C@@H]1CO].

In some embodiments, Ring A is

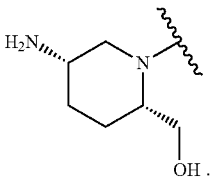.

In some embodiments, Ring A is

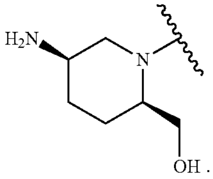 [SMILES: *N1C[C@H](N)CC[C@@H]1CO].

In some embodiments. Ring A is

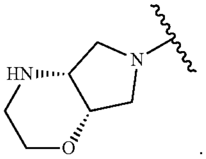 [SMILES: *N1C[C@@H]2OCCN[C@@H]2C1].

In some embodiments, Ring A is

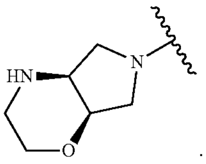 [SMILES: *N1C[C@@H]2NCCO[C@@H]2C1].

In certain embodiments. Ring A is selected from those functional groups depicted in the examples below.

As defined above and described herein. Ring B is

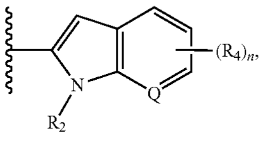, 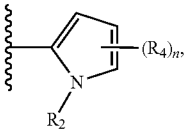,

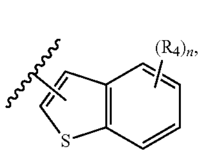 or 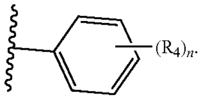.

In some embodiments, Ring B is

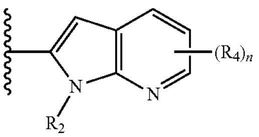

or

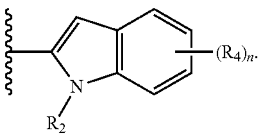

In some embodiments, Ring B is

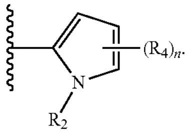

In some embodiments, Ring B is

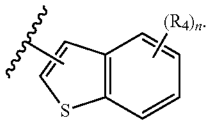

In some embodiments, Ring B is

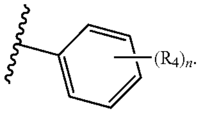

As defined above and described herein, n is 0-4. In some embodiments, n is 0. In some embodiments, n is 1. In some embodiments, n is 2. In some embodiments, n is 3. In some embodiments, n is 4.

As defined above and described herein, r is 0-4. In some embodiments, r is 0. In some embodiments, r is 1. In some embodiments, r is 2. In some embodiments, r is 3. In some embodiments, r is 4.

In some embodiments, Ring A is

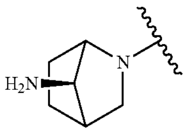

or

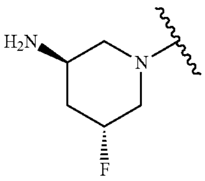

;

Ring B is

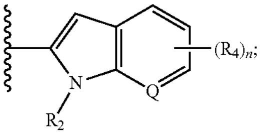

-continued $R_1$ is

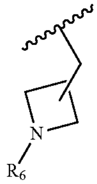

or

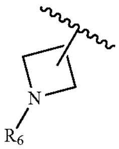

;

$R_2$ is cyclopropylmethyl; Q is N or CH; $R_3$ is H, F, or $—OCH_3$, $R_4$ is methoxy or Cl; $R_6$ is

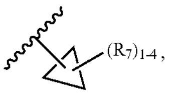

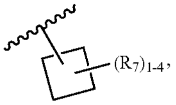

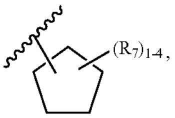

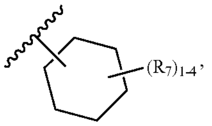

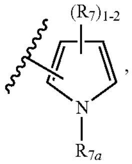

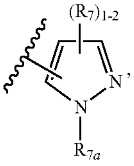

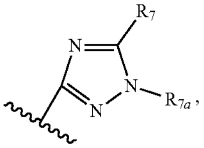

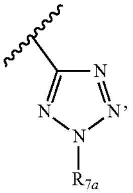

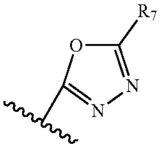

,

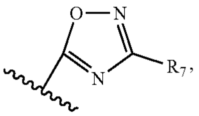

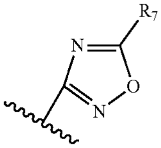

,

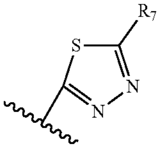

,

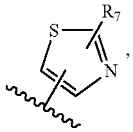

,

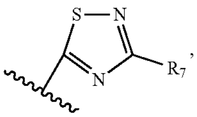

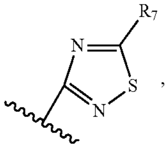

,

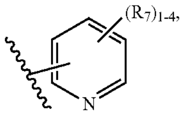

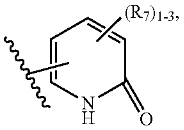

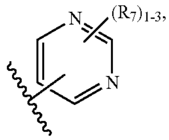

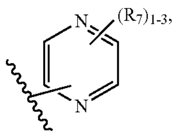

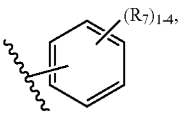

or

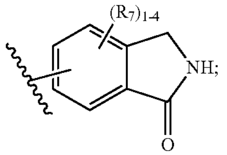

$R_7$ is F, Cl, Br, CN, $C_{1-4}$ alkyl, $—S(O)_pR_c$, $—OR_b$, $—NR_aR_a$, $—C(=O)OR_b$, $—C(=O)R_b$, $C(=O)NR_aR_a$, $—(CH_2)_{0-1}$-cycloalkyl substituted with 0-5 $R_e$, $—(CH_2)_{0-1}$-aryl substituted with 0-5 $R_e$, and $—(CH_2)_{0-1}$-heterocyclyl, substituted with 0-5 $R_e$; n is zero or 1.

In some embodiments, Ring A is

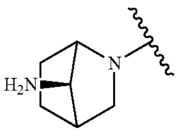

or

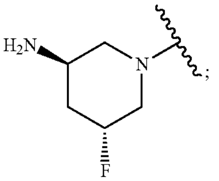

Ring B is

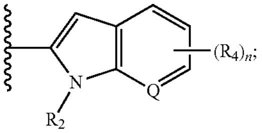

; $R_1$ is

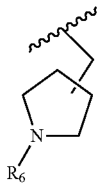

or

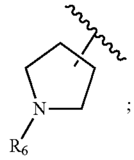

;

$R_2$ is cyclopropylmethyl; Q is N or CH; $R_3$ is H, F, or $—OCH_3$, $R_4$ is methoxy or Cl; $R_6$ is

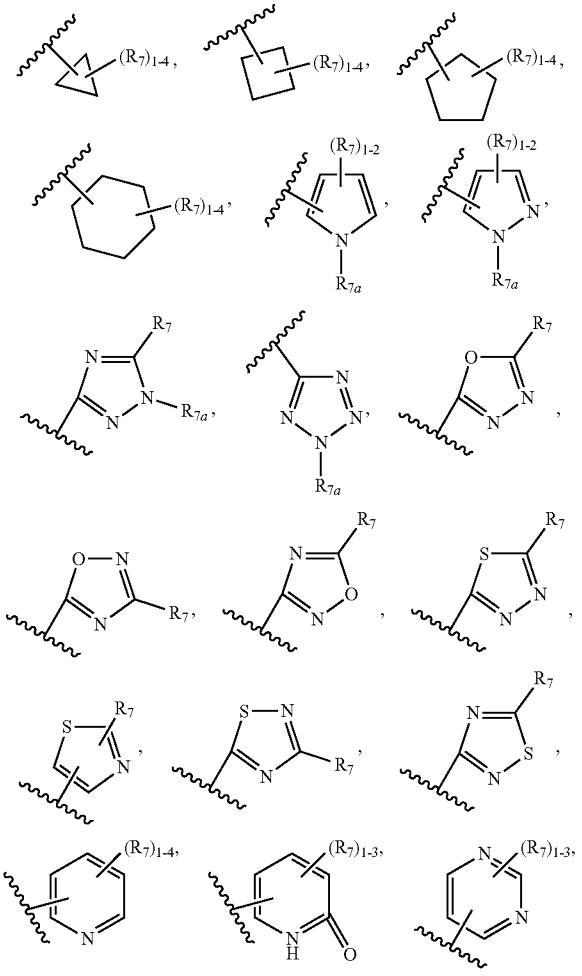

-continued

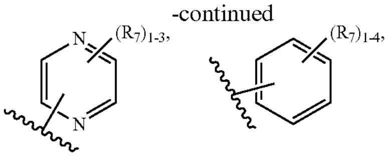

or

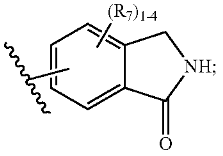

$R_7$ is F, Cl, Br, CN, $C_{1-4}$alkyl, $—S(O)_pR_c$, $—OR_b$, $—NR_aR_a$, $—C(=O)OR_b$, $—C(=O)R_b$, $C(=O)NR_aR_a$, $—(CH_2)_{0-1}$-cycloalkyl substituted with 0-5 $R_e$, $—(CH_2)_{0-1}$-aryl substituted with 0-5 $R_e$, and $—(CH_2)_{0-1}$-heterocyclyl, substituted with 0-5 $R_e$; n is zero or 1.

In some embodiments, Ring A is

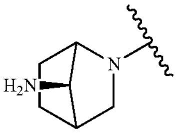

or

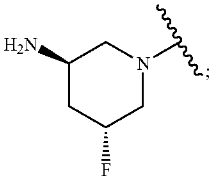

Ring B is

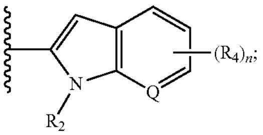

; $R_1$ is

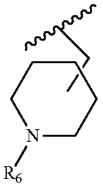

or

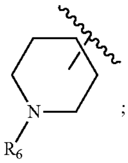

;

$R_2$ is cyclopropylmethyl; Q is N or CH; $R_3$ is H, F, or $—OCH_3$, $R_4$ is methoxy or Cl; $R_6$ is

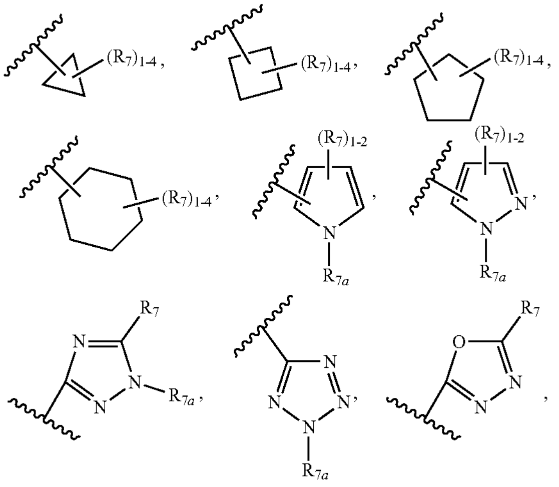

-continued

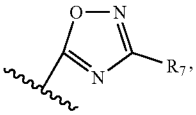 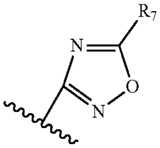 , 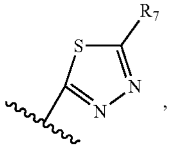 ,

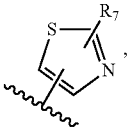 , 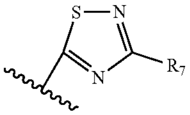 , 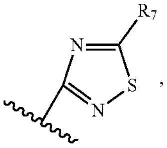 ,

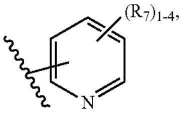 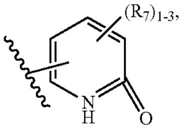 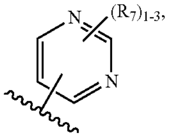

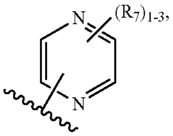 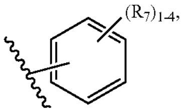 or

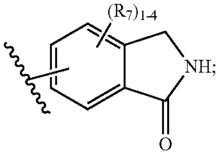

$R_7$ is F, Cl, Br, CN, $C_{1-4}$alkyl, $—S(O)_pR_c$, $—OR_b$, $—NR_aR_a$, $—C(=O)OR_b$, $—C(=O)R_b$, $C(=O)NR_aR_a$, $—(CH_2)_{0-1}$-cycloalkyl substituted with 0-5 $R_e$, $—(CH_2)_{0-1}$-aryl substituted with 0-5 $R_e$, and $—(CH_2)_{0-1}$-heterocyclyl, substituted with 0-5 $R_e$; n is zero or 1.

In some embodiments. Ring A is

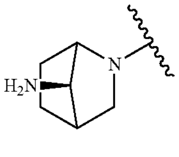 or 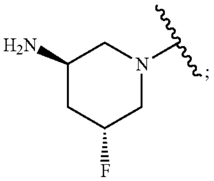

Ring B is

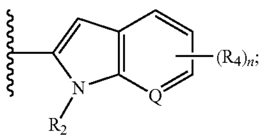 $R_1$ is 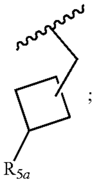 ;

$R_2$ is cyclopropylmethyl; Q is N or CH; $R_3$ is H, F, or $—OCH_3$, $R_4$ is methoxy or Cl, $R_{5a}$ is $C(=O)NHR_a$, $NH_2$, $NHC(=O)C_{1-3}$ alkyl, $NHC(=O)$-pyridone, $NR_aC(=O)OC_{1-3}$ alkyl, or $NHS(=O)_2C_{1-3}$ alkyl; n is zero or 1.

In some embodiments, Ring A is

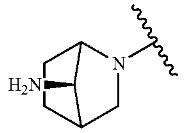 or 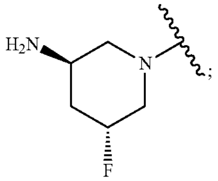

Ring B is

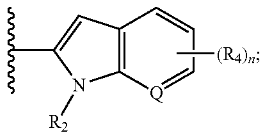

$R_1$ is $—(CH_2)_{2-3}R_{5a}$; $R_2$ is cyclopropylmethyl; Q is N or CH; $R_3$ is H. F, or $—OCH_3$, $R_4$ is methoxy or Cl, $R_{5a}$ is $C(=O)NHR_a$, $NH_2$, $NHC(=O)C_{1-3}$ alkyl, $NHC(=O)$-pyridone, $NR_aC(=O)OC_{1-3}$ alkyl, or $NHS(=O)_2C_{1-3}$ alkyl; n is zero or 1.

In some embodiments, Ring A is

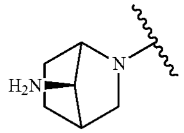 or 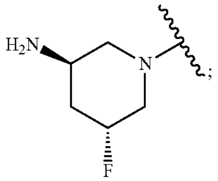

Ring B is

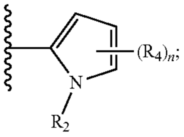 $R_1$ is 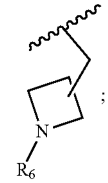 ;

$R_2$ is cyclopropylmethyl; $R_6$ is

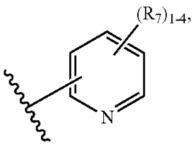 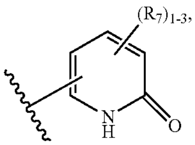 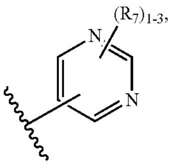

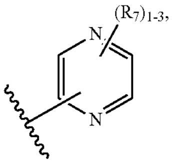 or 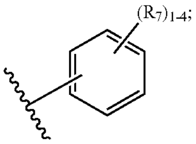

$R_7$ is F, Cl, Br, CN, and $C_{1-4}$alkyl; n is zero or 1.

In some embodiments. Ring A is

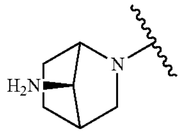

or

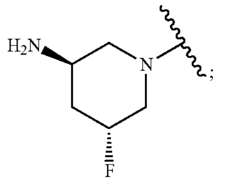

;

Ring B is

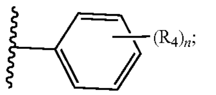

$R_1$ is

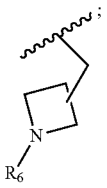

_$R_2$ is cyclopropylmethyl; $R_4$ is $C_{1-4}$ alkyl; $R_6$ is

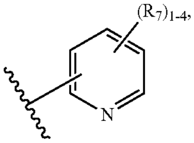

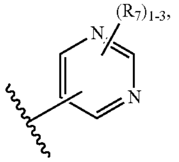

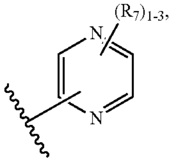

or

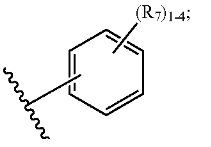

$R_7$ is F, Cl, Br, or CN; n is zero or 1.

In some embodiments. Ring A is

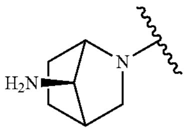

or

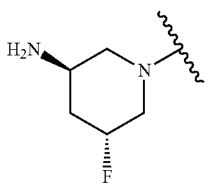

;

Ring B is

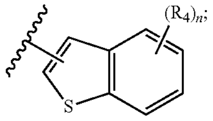

$R_1$ is

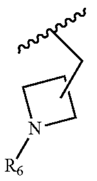

;

$R_2$ is cyclopropylmethyl; $R_4$ is F or Cl; $C_{1-4}$ alkyl; $R_6$ is

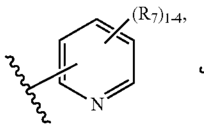

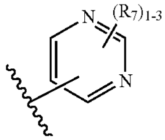

or ,

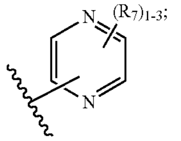

$R_7$ is F, Cl, Br, or CN; n is zero or 1.

In some embodiments, the compound of formula (I) is selected from examples depicted below. In certain embodiments, the present invention provides any compound described above and herein, or a pharmaceutically acceptable salt thereof. In some embodiments, the present invention provides any compound described above and herein in isolated form.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, bucally, vaginally or via an implanted reservoir. The term, "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringers solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation, Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration.

Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drags (NSAIDs) such as ibuprofen, celecoxib and rofecoxib; steroids such as prednisone or dexamethasone, antiviral agents such as abacavir; antiproliferative agents such as methotrexate, leflunomide, FK506 (tacrolimus, Prograf); cytotoxic drugs such as azathiprine and cyclophosphamide; TNF-□ inhibitors such as tenidap, anti-TNF antibodies or soluble TNF receptor, and rapamycin (sirolimus or Rapamune) or derivatives thereof. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part, of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosus, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosus. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosus, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosus, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Behcet's disease, Behcet's syndrome, Bells Palsy, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, Crohn's disease, cryopyrin-associated periodic syndromes, cyrptococc-osis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinaemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonary fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid haemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjögren's syndrome, antineutrophil cytoplasmic antibody (ANCA)-associated vasculitis, antiphospholipid antibody syndrome, sepsis, deep vein thrombosis, fibrosis, Alzheimer's, scleroderma and CREST syndrome.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosus. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof in the manufacture of a medicament for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosus. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosus, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosus comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Certain compounds of the present invention were prepared according to Schemes described below.

Scheme 1

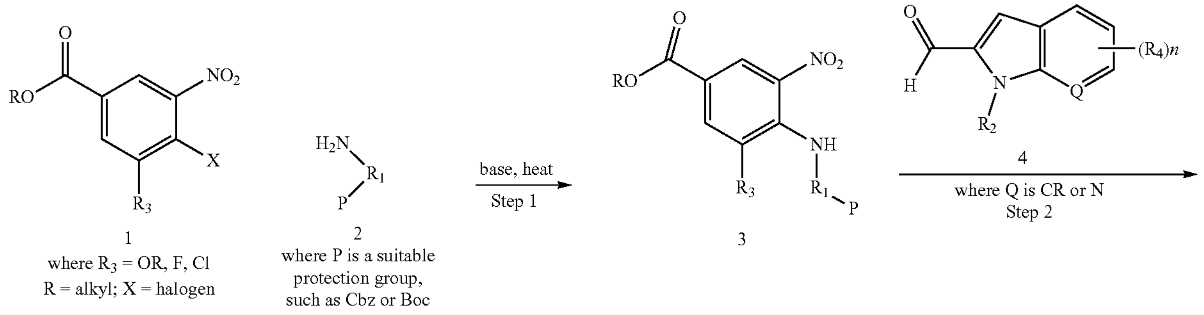

-continued
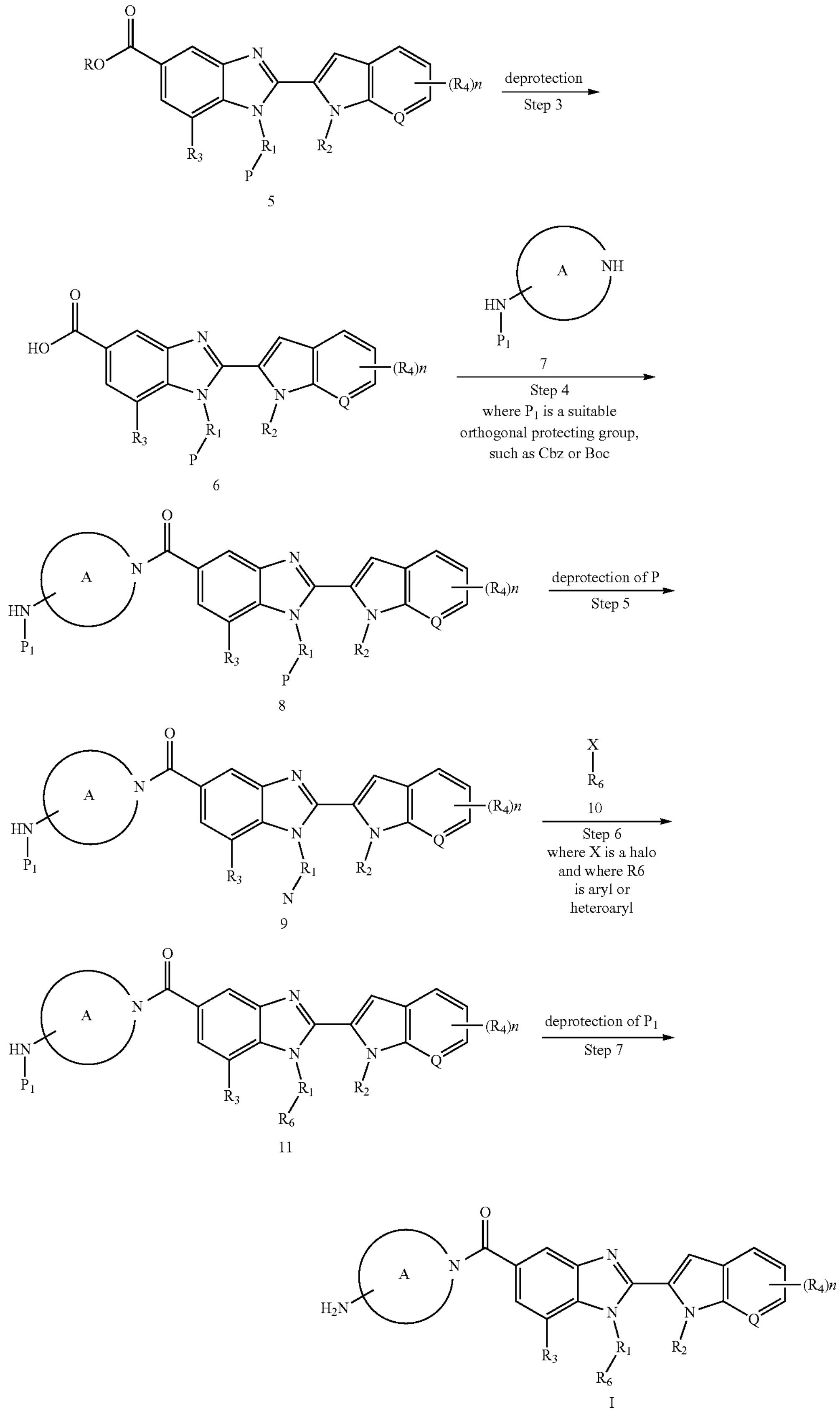

Step 1 describes the preparation of amino nitro compounds 3 from suitably activated nitro ester 1 and protected amines 2 (prepared by methods known to those skilled in the art) by heating in the presence of a base, such as potassium carbonate.

Step 2 describes the preparation of benzimidazoles 5 from compounds 3 and the aldehyde 4 (prepared by methods as shown in the patent application WO2017100594 as well as similar patent family members) by heating the mixture with a reducing agent, such as sodium dithionite.

Step 3 describes the deprotection of the ester 5 to the acid 6 by either a base such as sodium or lithium hydroxide for R equals methyl or ethyl, or acid (TFA) when R is tert-butyl.

Step 4 describes the amide coupling of 6 with an orthogonally protected diamine 7 (prepared by methods as shown in the patent application WO2017100594 as well as similar patent family members) using standard conditions, such as BOP or HATU and base, to give amide 8.

Step 5 describes the deprotection of the protecting group P using the appropriate conditions, such as acid for a Boc group or hydrogenolysis with palladium and hydrogen for a Cbz group, to give amines 9.

Step 6 describes the coupling of aromatic halides 10 (either commercially available or prepared under conditions known to those skilled in the art) with 9 to give compounds 11. The compounds 11, can be prepared using Buchwald coupling conditions, with a palladium source, such as a $Pd_2(dba)_3$, a ligand (BINAP) and a base such as cesium carbonate. Other coupling conditions are well known in the art.

Step 7 describes the preparation of compounds of Formula (I) by deprotecting the $P_1$ group, such as acidic conditions for a Boc group.

Scheme 2

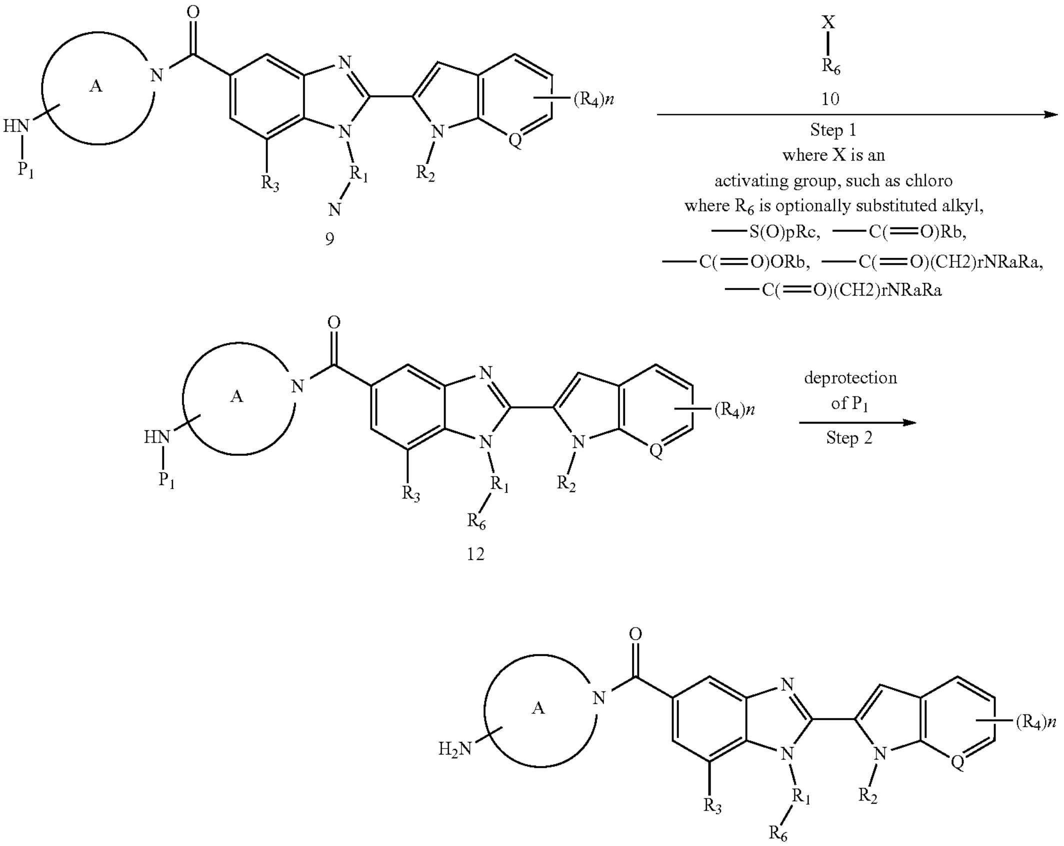

Alternatively

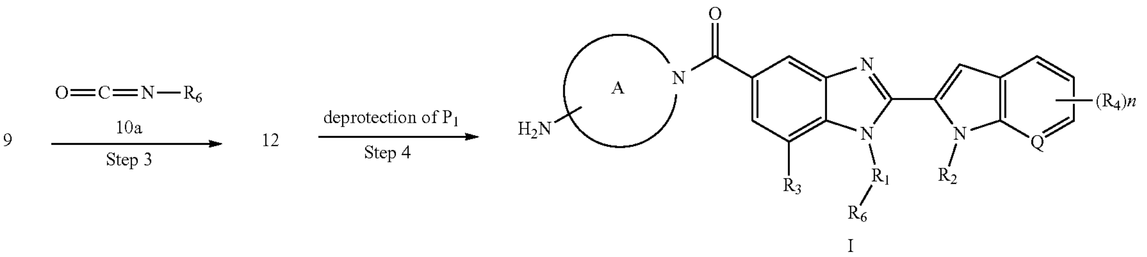

Step 1 describes the preparation of compounds 12 by reacting amines 9 with activated compounds 10. Compounds 12 that are substituted alkyls, sulfonamides, amides, or carbamates can be formed using conditions known in the art.

Step 2 describes the preparation of compounds of Formula (I) by deprotecting the $P_1$ group on compounds 12, such as acidic conditions for a Boc group.

Alternatively, Step 3 describes reacting amines 9 with isocyanates 10a to give compounds 12 that are ureas. Step 4 describes preparation of compounds of Formula (I) by deprotecting the $P_1$ group on compounds 12, such as acidic conditions for a Boc group.

Step 1 describes the preparation of amino nitro compounds 13 from suitably activated nitro ester 1 and amines 2 by heating in the presence of a base, such as potassium carbonate.

Step 2 describes the preparation of benzimidazoles H from compounds 13 and the aldehyde 4 by heating the mixture with a reducing agent, such as sodium dithionite.

Step 3 describes the deprotection of the ester 14 to the acid 15 by a base such as sodium or lithium hydroxide for R equals methyl or ethyl.

Step 4 describes the amide coupling of 15 with a suitably protected diamine 7 using standard conditions, such as BOP or HATU and base, to give amide 16.

Scheme 3

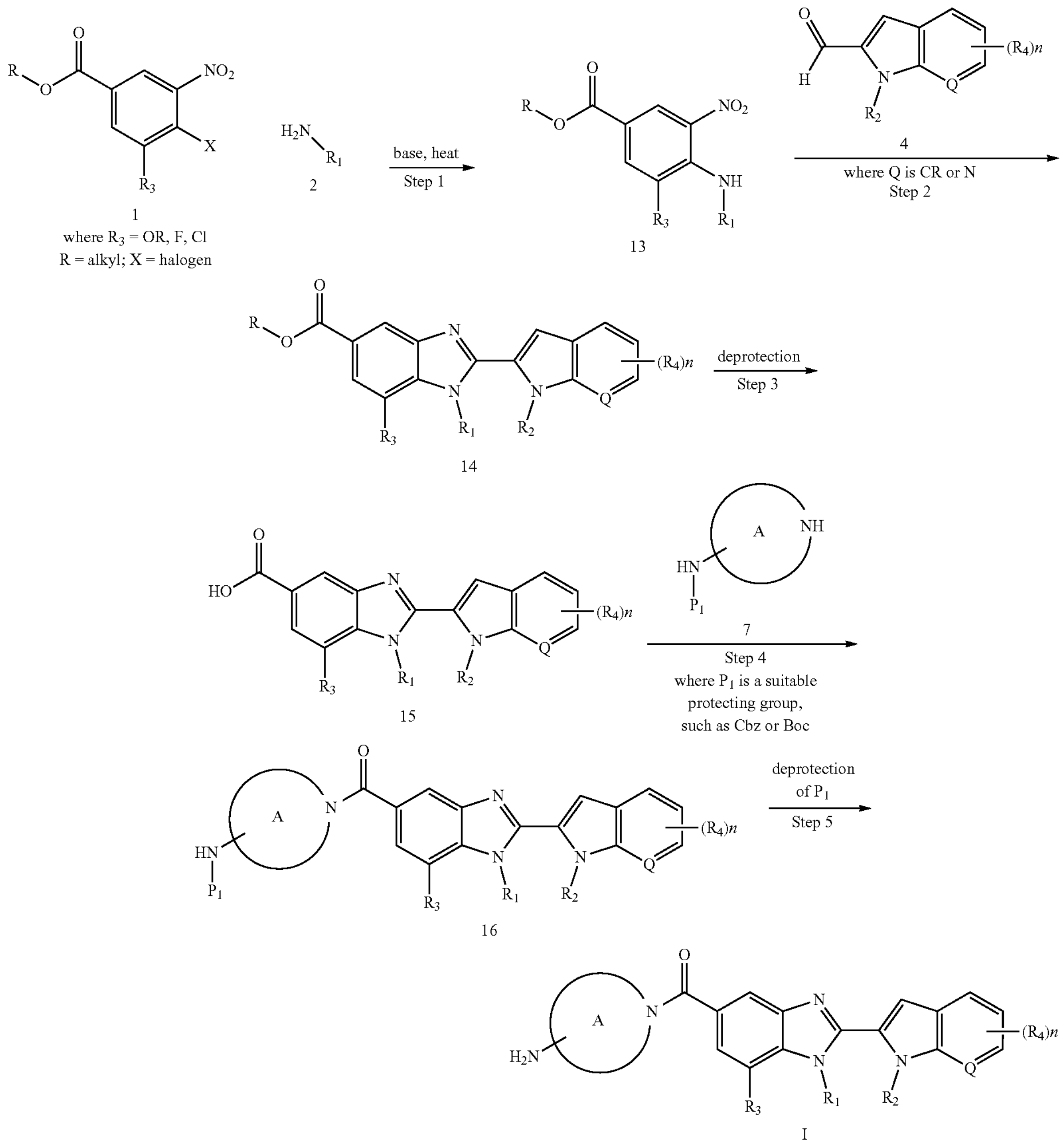

Step 5 describes the preparation of compounds of Formula (I) by deprotecting the $P_1$ group, such as acidic conditions for a Boc group, Scheme 4

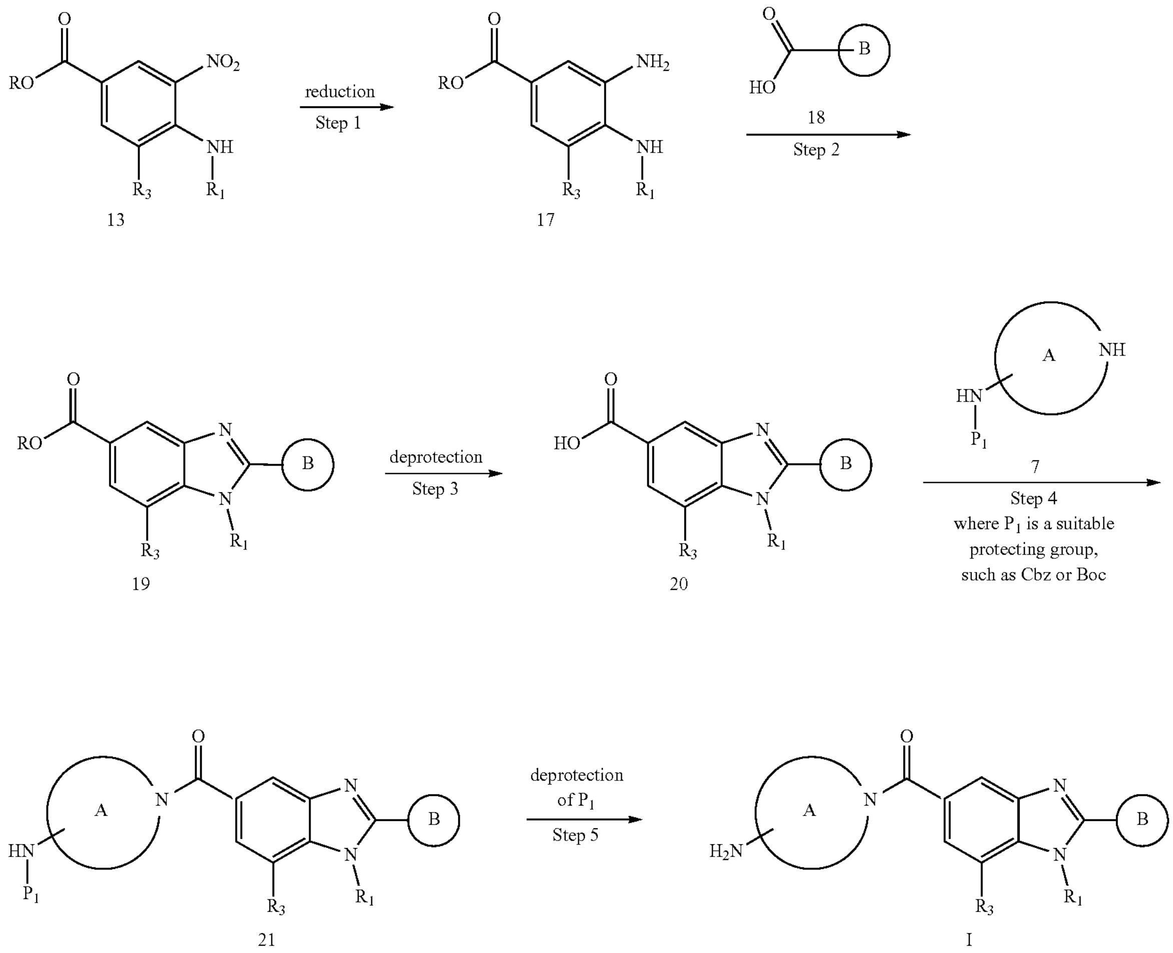

Alternatively

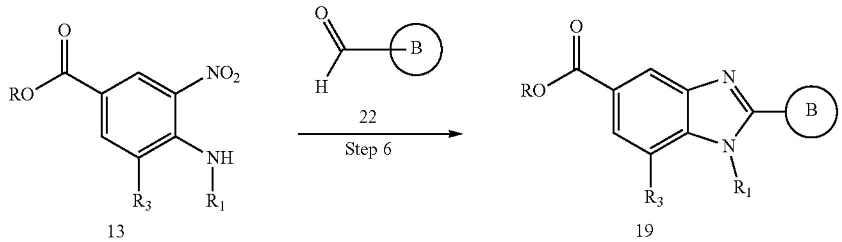

Step 1 describes the preparation of di-amino compounds 17 by reducing nitro ester 13 using methods known in the art, such as hydrogenation or metal assisted reductions (with zinc or tin, for example).

Step 2 describes the preparation of benzimidazoles 19 from compounds 17 and the acid 18 through an amide coupling, using standard conditions, such as BOP or HATU and base, then heating the mixture with acid, such as acetic acid. The amide intermediate can also be isolated before acid treatment to give 19.

Step 3 describes the deprotection of the ester 19 to the acid 20 by a base such as sodium or lithium hydroxide for R equals methyl or ethyl.

Step 4 describes the amide coupling of 20 with a suitably protected diamine 7 using standard conditions, such as BOP or HATU and base, to give amide 21.

Step 5 describes the preparation of compounds of Formula (I) by deprotecting the $P_1$ group of 21, such as acidic conditions for a Boc group.

Alternatively, Step 6 describes the preparation of benzimidazoles 19 from compounds 13 and the aldehyde 22 by heating the mixture with a reducing agent, such as sodium dithionite.

Description of Analytical LCMS Methods:

Method 1: Column: Waters XBridge C18, 2.1 mm×50 mm, 1.7 μm particles; Mobile Phase A: 5:95 acetonitrile: water with 10 mM ammonium acetate, Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Method 2: Column: Waters XBridge C18, 2.1 mm×50 mm, 1.7 μm particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B, Flow: 1 mL/min; Detection: MS and UV (220 nm).

Method 3: Waters Acquity UPLC BEH C18, 2.1×50 mm, 1.7 μm particles, Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).

Method 4: Shimadzu UPLC C18, 2.1×50 mm, 1.9 μm particles; Mobile Phase A: 5:95 ACN:water with 0.05% TFA; Mobile Phase B: 95:5 ACN:water with 0.05% TFA; Temperature: 50° C.; Gradient: 0-100% B over 1.5 minutes, then a 0.30 minute hold at 100% B; Flow: 0.60 mL/min; Detection: UV at 254 nm.

The final products were all treated with a resin to remove trace metals as follows. The purified material was diluted with DMF, treated with Si-Pyridine and shaken for a minimum of 2 h. The resulting mixture was filtered and dried, usually by centrifugal evaporation.

The structures drawn in the current application generically as A and B below (FIG. 1) are meant as a representation of the fully chiral structures C or D, with the chiral azabicycloheptane moiety named as ((1R,4R,7R)-7-amino-2-azabicyclo[2.2.1]heptan-2-yl).

Figure 1

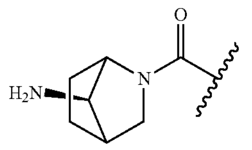

A

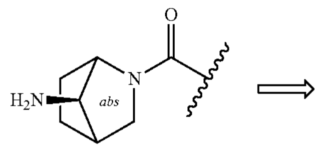

B

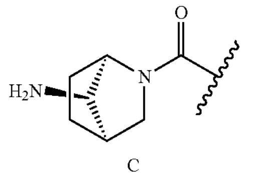

C

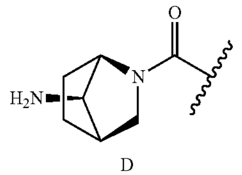

D

Example 1

4-(3-((5-((1R,4R,7R)-7-amino-2-azabicyclo[2.2.1]heptane-2-carbonyl)-2-(1-(cyclopropylmethyl)-1H-indol-2-yl)-7-methoxy-1H-benzo[d]imidazol-1-yl)methyl)azetidin-1-yl)pyrimidine-2-carbonitrile

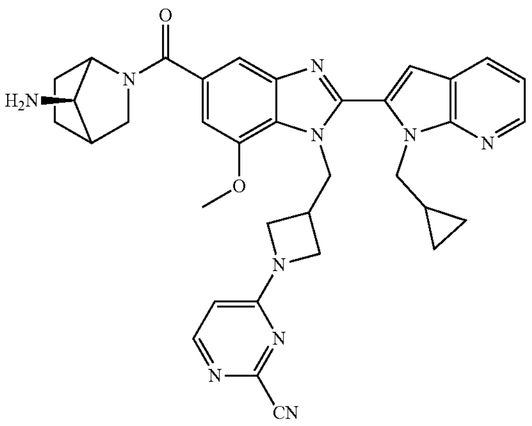 [SMILES: COc1cc(C(=O)N2CC3CCC2[C@@H]3N)cc2nc(-c3cc4cccnc4n3CC3CC3)n(CC3CN(c4ccnc(C#N)n4)C3)c12]

Intermediate 1A: Benzyl 3-(((2-methoxy-4-(methoxycarbonyl)-6-nitrophenyl)amino)methyl)azetidine-1-carboxylate

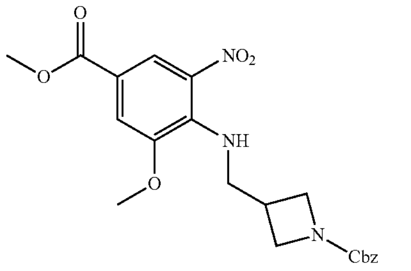 [SMILES: COC(=O)c1cc(OC)c(NCC2CN(C(=O)OCc3ccccc3)C2)c([N+](=O)[O-])c1]

A mixture of methyl 4-chloro-3-methoxy-5-nitrobenzoate (2.79 g, 11.35 mmol), benzyl 3-(aminomethyl)azetidine-1-carboxylate (2.5 g, 11.35 mmol) and potassium carbonate (4.71 g, 34.0 mmol) in DMF (20 mL) was stirred at 60° C. for 18 hours. The mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-EtOAc 100:0 to 0:100 gradient) to yield benzyl 3-(((2-methoxy-4-(methoxycarbonyl)-6-nitrophenyl)amino)methyl)azetidine-1-carboxylate (3.755 g, 8.31 mmol, 73.2% yield) as red gum, LC/MS (M+H): 430, LC retention time: 1.07 min (analytical HPLC Method 3). $^{1}H$ NMR (499 MHz, CHLOROFORM-d) δ 8.51 (d, J=1.9 Hz, 1H), 8.21-8.13 (m, 1H), 7.57-7.51 (m, 1H), 7.41-7.31 (m, 5H), 5.15-5.05 (m, 2H), 4.22-4.11 (m, 2H), 3.99-3.86 (m, 8H), 3.82-3.73 (m, 2H), 2.94-2.79 (m, 1H)

Intermediate 1B: 1-(cyclopropylmethyl)-1H-indole-2-carbaldehyde

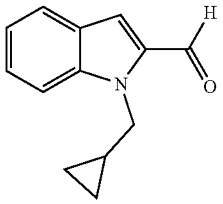 [SMILES: O=Cc1cc2ccccc2n1CC1CC1]

To a suspension of sodium hydride (0.854 g, 21.36 mmol) in anhydrous DMF (50 mL) was added a solution of 1H-indole-2-carbaldehyde (3.10 g, 21.36 mmol) in DMF (20 mL) under nitrogen, and the mixture was stirred at RT for 45 min. (Bromomethyl)cyclopropane (2.88 g, 21.36 mmol) was added to the mixture and the reaction was stirred at RT for 18 hours. The mixture was diluted with EtOAc (45 mL) and was washed with a solution of aqueous saturated sodium bicarbonate (3×45 mL). The organic layer was dried over sodium sulfate and concentrated. The crude product was subjected to ISCO flash chromatography (silica gel/hexane-EtOAc 100:0 to 50:50 gradient) to yield 1-(cyclopropylmethyl)-1H-indole-2-carbaldehyde (3.41 g, 16.26 mmol, 76% yield) as clear oil. LC/MS (M+H): 200; LC retention time: 0.99 min (analytical HPLC Method 3). $^1$H NMR (499 MHz, CHLOROFORM-d) δ 9.90 (s, 1H), 7.82-7.70 (m, 1H), 7.51-7.39 (m, 2H), 7.32-7.26 (m, 1H), 7.24-7.14 (m, 1H), 4.53 (d, J=6.9 Hz, 2H), 1.48-1.18 (m, 1H), 0.58-0.35 (m, 4H).

Intermediate 1C: Methyl 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylate

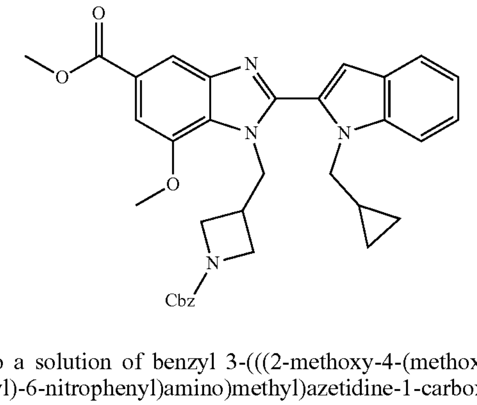

To a solution of benzyl 3-(((2-methoxy-4-(methoxycarbonyl)-6-nitrophenyl)amino)methyl)azetidine-1-carboxylate (840 mg, 1.956 mmol) and 1-(cyclopropylmethyl)-1H-indole-2-carbaldehyde (390 mg, 1.956 mmol) in EtOH (10 mL) was added a solution of sodium dithionite (1022 mg, 5.87 mmol) in water (5.00 mL), and the mixture was stirred at 80° C. for 4 hours. The mixture was diluted with EtOAc (10 mL) and was washed with a solution of aqueous saturated sodium chloride (2×10 mL). The ethyl acetate layer was dried over sodium sulfate and concentrated. The crude product was subjected to ISCO flash chromatography (silica gel/hexane-EtOAc 100:0 to 0:100 gradient) to give methyl 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylate (780 mg, 1.281 mmol, 65.5% yield) as off-white foam, LC/MS (M+H): 579, LC retention time: 1.17 min (analytical HPLC Method 3); $^1$H NMR (400 MHz, METHANOL-$d_4$) δ 8.07 (d, J=1.3 Hz, 1H), 7.70 (d, J=7.9 Hz, 1H), 7.60 (d, J=8.6 Hz, 1H), 7.56 (s, 1H), 7.38-7.16 (m, 7H), 7.02 (s, 1H), 4.99-4.88 (m, 4H), 4.29-3.90 (m, 10H), 3.65 (dd, J=8.8, 5.3 Hz, 2H), 3.09-2.98 (m, 1H), 1.05-0.95 (m, 1H), 0.42-0.30 (m, 2H), 0.10--0.02 (m, 2H).

Intermediate 1D: Benzyl 3-((5-(1R,4R,7R)-7-((tert-butoxycarbonyl)amino)-2-azabicyclo[2.2.1]heptane-2-carbonyl)-2-(1-(cyclopropylmethyl)-1H-indol-2-yl)-7-methoxy-1H-benzo[d]imidazol-1-yl)methyl) azetidine-1-carboxylate

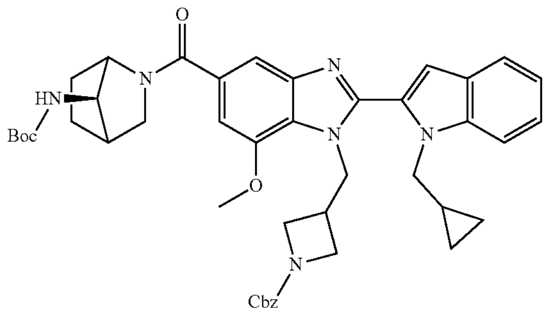 [SMILES: COc1cc(C(=O)N2CC3CCC2[C@@H]3NC(=O)OC(C)(C)C)cc2nc(-c3cc4ccccc4n3CC3CC3)n(CC3CN(C(=O)OCc4ccccc4)C3)c12]

A mixture of sodium hydroxide (5.18 mL, 5.18 mmol) and tert-butyl ((7R)-2-azabicyclo[2.2.1]heptan-7-yl)carbamate (220 mg, 1.037 mmol) in THF (7.0 mL) was stirred at 50° C. for 2 days. The mixture was cooled to RT, a solution of 1.0 N aqueous HCl (3.90 mL) was added and the mixture was concentrated. The resulting mixture was extracted with EtOAc (2×15 mL), the organic layer was dried over sodium sulfate and concentrated to give 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylic acid. LC/MS (M+H): 565; LC retention time: 1.03 min (analytical HPLC Method 3). The material was used as is in the next reaction.

A mixture of 1-((1-((benzyloxy)carbonyl)azetidin-3-yl) methyl)-2-(1-(cyclopropylmethyl)-1H-indol-2-yl)-7-methoxy-1H-benzo[d]imidazole-5-carboxylic acid, tert-butyl ((1R,4R,7R)-2-azabicyclo[2.2.1]heptan-7-yl) carbamate (220 mg, 1.037 mmol), BOP (459 mg, 1.037 mmol) and TEA (0.723 mL, 5.18 mmol) in DMF (10 mL) was stirred at RT for 2 hours. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-((5-((1R,4R,7R)-7-((tert-butoxycarbonyl) amino)-2-azabicyclo[2.2.1]heptane-2-carbonyl)-2-(1-(cyclopropylmethyl)-1H-indol-2-yl)-7-methoxy-1H-benzo[d] imidazol-1-yl)methyl)azetidine-1-carboxylate (659 mg, 0.825 mmol, 80% yield) as white solid. LC/MS (M+H); 759; LC retention time: 1.08 min (analytical HPLC Method 3).

Intermediate 1E: Tert-butyl ((1R,4R,7R)-2-(1-(azetidin-3-ylmethyl)-2-)-1-(cyclopropylmethyl)-1H-indol-2-yl)-7-methoxy-1H-benzo[d]imidazole-5-carbonyl)-2-azabicyclo[2.2.1]heptan-7-yl)carbamate

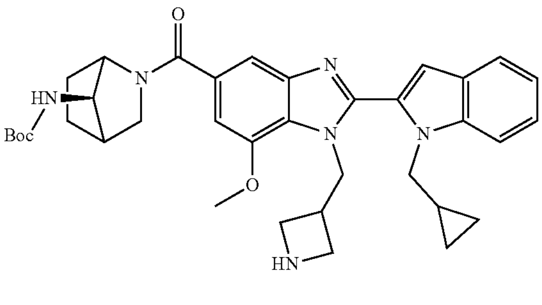 [SMILES: COc1cc(C(=O)N2CC3CCC2[C@@H]3NC(=O)OC(C)(C)C)cc2nc(-c3cc4ccccc4n3CC3CC3)n(CC3CNC3)c12]

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-indol-2-yl)-7-methoxy-1H-benzo[d]imidazol-1-yl)methyl)azetidine-1-carboxylate (659 mg, 0.868 mmol) and 10% palladium on carbon (92 mg, 0.087 mmol) in MeOH (15 mL) was hydrogenated under 1 atm of hydrogen for 18 hours. Pd/C was filtered off and the filtrate was concentrated to give a crude yield of tert-butyl ((1R,4R,7R)-2-(1-(azetidin-3-ylmethyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate (518 mg, 0.788 mmol, 91% yield) as white solid. LC/MS (M+H): 625; LC retention time: 0.86 min (analytical HPLC Method 3).

Example 1: 4-(3-((5-((1R,4R,7R)-7-amino-2-azabicyclo[2.2.1]heptane-2-carbonyl)-2-(1-(cyclopropylmethyl)-1H-indol-2-yl)-7-methoxy-1H-benzo[d]imidazol-1-yl)methyl)azetidin-1-yl)pyrimidine-2-carbonitrile A mixture of tert-butyl ((1R,4R,7R)-2-(1-(azetidin-3-ylmethyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate (15 mg, 0.024 mmol), 4-bromopyrimidine-2-carbonitrile (4.42 mg, 0.024 mmol), cesium carbonate (15.64 mg, 0.048 mmol), BINAP (0.747 mg, 1.200 μmol) and Pd2(dba)3 (1.099 mg, 1.200 μmol) in degassed dioxane (1.0 mL) under nitrogen in a sealed vial was stirred at 80° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-((1-(2-cyanopyrimidin-4-yl)azetidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(2-cyanopyrimidin-4-yl)azetidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid, Mobile Phase B: 95:5 acetonitrile:water with 0.1% trifluoroacetic acid; Gradient: a 0-minute hold at 18% B, 18-58% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyrimidine-2-carbonitrile (12.2 mg, 19.4 μmol, 81%) was isolated. LC/MS (M+H): 627; LC retention time: 1.81 min (analytical HPLC Method 1). $^{1}$H NMR (500 MHz, DMSO-$d_6$) δ 8.03 (br d, 0.7=5.8 Hz, 1H), 7.60-7.51 (m, 2H), 7.47-7.28 (m, 1H), 7.22-7.12 (m, 1H), 7.07-6.99 (m, 1H), 6.97-6.83 (m, 2H), 6.45-6.33 (m, 1H), 4.87-4.70 (m, 2H), 4.46-4.07 (m, 3H), 4.00-3.88 (m, 2H), 3.85 (br s, 3H), 3.71-3.30 (m, 4H), 3.13-2.94 (m, 2H), 2.60-2.46 (m, 1H), 1.94-1.72 (m, 3H), 1.61-1.47 (m, 1H), 1.19-1.04 (m, 1H), 0.96-0.69 (m, 1H), 0.29-0.16 (m, 2H), 0.06--0.06 (m, 2H)

Example 2

4-(3-((5-((1R,4R,7R)-7-amino-2-azabicyclo[2.2.1]heptane-2-carbonyl)-2-(1-(cyclopropylmethyl)-6-methoxy-1H-pyrrolo[2,3-b]pyridin-2-yl)-7-methoxy-1H-benzo[d]imidazol-1-yl)methyl)azetidin-1-yl)pyrimidine-2-carbonitrile

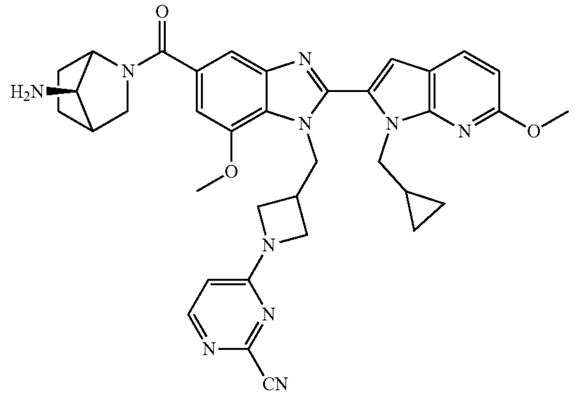 [SMILES: COc1ccc2cc(-c3nc4cc(C(=O)N5CC6CCC5[C@@H]6N)cc(OC)c4n3CC3CN(c4ccnc(C#N)n4)C3)n(CC3CC3)c2n1]

Intermediate 2A: Tert-butyl 3-(((2-amino-6-methoxy-4-(methoxycarbonyl)phenyl)amino)methyl)azetidine-1-carboxylate

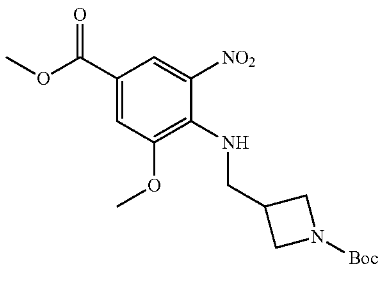 [SMILES: COC(=O)c1cc(OC)c(NCC2CN(C(=O)OC(C)(C)C)C2)c([N+](=O)[O-])c1]

A mixture of 1-boc-3-(aminomethyl)azetidine (227 mg, 1.221 mmol), methyl 4-chloro-3-methoxy-5-nitrobenzoate (300 mg, 1.221 mmol) and potassium carbonate (506 mg, 3.66 mmol) in DMF (5.0 mL) was stirred at 80° C. for 5 hour. The mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-EtOAc 100:0 to 0:100 gradient) to yield tert-butyl 3-(((2-methoxy-4-(methoxycarbonyl)-6-nitrophenyl)amino)methyl)azetidine-1-carboxylate (360 mg, 0.865 mmol, 70.8% yield) as orange gum, LC/MS (2M+H): 791, LC retention time: 1.08 min (analytical HPLC Method 3).

A mixture of tert-butyl 3-(((2-methoxy-4-(methoxycarbonyl)-6-nitrophenyl)amino)methyl)azetidine-1-carboxylate and 10% palladium on carbon (130 mg, 0.122 mmol) in MeOH (10 mL) was hydrogenated under 1 atm of hydrogen for 4 hour. Pd/C was filtered off and the filtrate was concentrated to give a crude yield of tert-butyl 3-(((2-amino-6-methoxy-4-(methoxycarbonyl)phenyl)amino)methyl)azetidine-1-carboxylate (330 mg, 0,858 mmol, 70.2% yield) as white foam. LC/MS (M+H): 366; LC retention time: 0.80 min (analytical HPLC Method 3).

Intermediate 2B: Methyl 1-((1-(tert-butoxycarbonyl)azetidin-3-yl)methyl)-2-(1-(cyclopropylmethyl)-6-methoxy-1H-pyrrolo[2,3-b]pyridin-2-yl)-7-methoxy-1H-benzo[d]imidazole-5-carboxylate

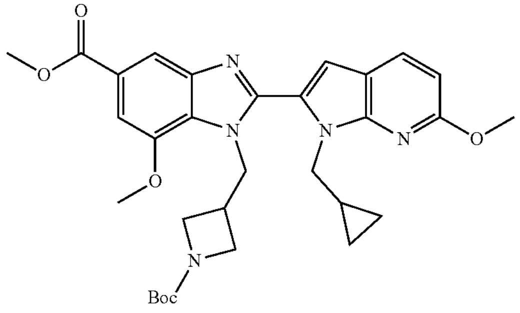

To a solution of tert-butyl 3-(((2-amino-6-methoxy-4-(methoxycarbonyl)phenyl)amino)methyl)azetidine-1-carboxylate (860 mg, 2.353 mmol), 1-(cyclopropylmethyl)-6-methoxy-pyrrolo[2,3-b]pyridine-2-carboxylic acid (638 mg, 2.59 mmol) and TEA (0.984 mL, 7.06 mmol) in DMF (20 mL) was added HATU (984 mg, 2.59 mmol), the mixture was stirred at RT for 18 hour. The mixture was diluted with EtOAc (15 mL) and was washed with a solution of aqueous saturated sodium bicarbonate (2×15 mL). The organic layer was dried over sodium sulfate and concentrated to give crude tert-butyl 3-(((2-(1-(cyclopropylmethyl)-6-methoxy-1H-pyrrolo[2,3-b]pyridine-2-carboxamido)-6-methoxy-4-(methoxycarbonyl)phenyl)amino)methyl)azetidine-1-carboxylate. LC/MS (M+H): 594; LC retention time: 1.18 min (analytical HPLC Method 3). Material used as is in next reaction.

A solution of tert-butyl 3-(((2-(1-(cyclopropylmethyl)-6-methoxy-1H-pyrrolo[2,3-b]pyridine-2-carboxamido)-6-methoxy-4-(methoxycarbonyl)phenyl)amino)methyl)azetidine-1-carboxylate in HOAc (20 mL) was stirred at 80° C. for 18 hour. The mixture was concentrated. The mixture was diluted with EtOAc (25 mL) and was washed with a solution of aqueous saturated sodium bicarbonate (2×25 mL). The organic layer was dried over sodium sulfate and concentrated. The crude product was subjected to ISCO flash chromatography (silica gel/hexane-EtOAc 100:0 to 0:100 gradient) to yield methyl 1-((1-(tert-butoxycarbonyl)azetidin-3-yl)methyl)-2-(1-(cyclopropylmethyl)-6-methoxy-1H-pyrrolo[2,3-b]pyridin-2-yl)-7-methoxy-1H-benzo[d]imidazole-5-carboxylate (120 mg, 0.188 mmol, 7.97% yield). LC/MS (M+H): 576; LC retention time: 1.16 min (analytical HPLC Method 3).

Intermediate 2C: Benzyl 3-((5-((1R,4R,7R)-7-((tert-butoxycarbonyl)amino)-2-azabicyclo[2.2.1]heptane-2-carbonyl)-2-(1-(cyclopropylmethyl)-6-methoxy-1H-pyrrolo[2,3-b]pyridin-2-yl)-7-methoxy-1H-benzo[d]imidazol-1-yl)methyl)azetidine-1-carboxylate

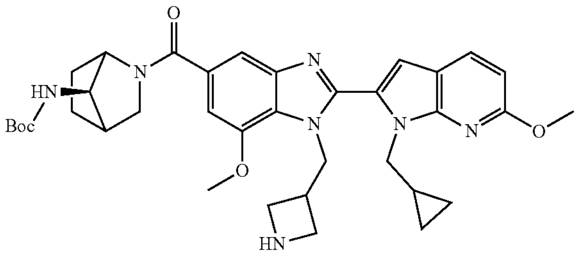 [SMILES: COc1ccc2cc(-c3nc4cc(C(=O)N5CC6CCC5[C@@H]6NC(=O)OC(C)(C)C)cc(OC)c4n3CC3CNC3)n(CC3CC3)c2n1]

A mixture of methyl 1-((1-(tert-butoxycarbonyl)azetidin-3-yl)methyl)-2-(1-(cyclopropylmethyl)-6-methoxy-1H-pyrrolo[2,3-b]pyridin-2-yl)-7-methoxy-1H-benzo[d]imidazole-5-carboxylate (120 mg, 0.208 mmol) and 1.0 M aqueous sodium hydroxide (1.042 mL, 1.042 mmol) in THF (4.0 mL) was stirred at 50° C. for 18 hour. The mixture was cooled to RT. A solution of 1.0 M aqueous HCl (1.10 mL) was added and the mixture was concentrated. The mixture was diluted with EtOAc (5 mL) and the organic layer was dried over sodium sulfate and concentrated to give crude 1-((1-(tert-butoxycarbonyl)azetidin-3-yl)methyl)-2-(1-(cyclopropylmethyl)-6-methoxy-1H-pyrrolo[2,3-b]pyridin-2-yl)-7-methoxy-1H-benzo[d]imidazole-5-carboxylic acid. LC/MS (M+H): 562; LC retention time: 1.08 min (analytical HPLC Method 3). Material was used as is in next reaction.

A mixture of 1-((1-(tert-butoxycarbonyl)azetidin-3-yl)methyl)-2-(1-(cyclopropylmethyl)-6-methoxy-1H-pyrrolo[2,3-b]pyridin-2-yl)-7-methoxy-1H-benzo[d]imidazole-5-carboxylic acid in DCM (1.0 mL) and TFA (1.0 mL) was stirred at RT for 30 min. The mixture was concentrated to give crude amino acid. LC/MS (M+H): 462; LC retention time: 0.77 min (analytical HPLC Method 3), Material was used as is in next reaction.

To a mixture of the crude amino acid and TEA (0.291 mL, 2,085 mmol) in DMF (3.0 mL) was added benzyl (2,5-dioxopyrrolidin-1-yl) carbonate (57.1 mg, 0.229 mmol), and the resulting mixture was stirred at RT for 2 hour. tert-Butyl ((7R)-2-azabicyclo[2.2.1]heptan-7-yl)carbamate (53.1 mg, 0.250 mmol) and BOP (101 mg, 0.229 mmol) was then added to the mixture, and stirring continued at RT for 2 hour. The mixture was diluted with EtOAc (5 mL) and was washed with a solution of aqueous saturated sodium bicarbonate (2×5 mL). The organic layer was dried over sodium sulfate and concentrated. The crude product was subjected to ISCO flash chromatography (silica gel/hexane-10% MeOH/EtOAc 100:0 to 0:100 gradient) to give benzyl 3-((5-((1R,4R,7R)-7-((tert-butoxycarbonyl)amino)-2-azabicyclo[2.2.1]heptane-2-carbonyl)-2-(1-(cyclopropylmethyl)-6-methoxy- 1H-pyrrolo[2,3-b]pyridin-2-yl)-7-methoxy-1H-benzo[d]imidazol-1-yl)methyl)azetidine-1-carboxylate (110 mg, 0.139 mmol, 66.8% yield) as light, brown gum. LC/MS (M+H): 790; LC retention time: 1.06 min (analytical HPLC Method 3).

Intermediate 2D: Tert-butyl ((1R,4R,7R)-2-(1-(azetidin-3-ylmethyl)-2-(1-(cyclopropylmethyl)-6-methoxy-1H-pyrrolo[2,3-b]pyridin-2-yl)-7-methoxy-1H-benzo[d]imidazole-5-carbonyl)-2-azabicyclo[2.2.1]heptan-7-yl)carbamate

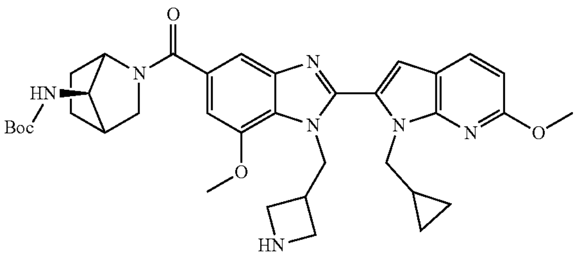 [SMILES: COc1ccc2cc(-c3nc4cc(C(=O)N5CC6CCC5[C@@H]6NC(=O)OC(C)(C)C)cc(OC)c4n3CC3CNC3)n(CC3CC3)c2n1]

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-6-methoxy-1H-pyrrolo[2,3-b]pyridin-2-yl)-7-methoxy-1H-benzo[d]imidazol-1-yl)methyl)azetidine-1-carboxylate (110 mg, 0.139 mmol) and 10% palladium on carbon (148 mg, 0.139 mmol) in MeOH (10 mL) was hydrogenated under 1 atm of hydrogen for 8 hour. Pd/C was filtered off and the filtrate was concentrated to give a crude yield of tert-butyl ((1R,4R,7R)-2-(1-(azetidin-3-ylmethyl)-2-(1-(cyclopropylmethyl)-6-methoxy-1H-pyrrolo[2,3-b]pyridin-2-yl)-7-methoxy-1H-benzo[d]imidazole-5-carbonyl)-2-azabicyclo[2.2.1]heptan-7-yl)carbamate (81 mg, 0.111 mmol, 80% yield) as brown foam. LC/MS (M+H): 656, LC retention time: 0.84 min (analytical HPLC Method 3).

Example 2: 4-(3-((5-((1R,4R,7R)-7-amino-2-azabicyclo[2.2.1]heptane-2-carbonyl)-2-(1-(cyclopropylmethyl)-6-methoxy-1H-pyrrolo[2,3-b]pyridin-2-yl)-7-methoxy-1H-benzo[d]imidazol-1-yl)methyl)azetidin-1-yl)pyrimidine-2-carbonitrile A mixture of tert-butyl ((1R,4R,7R)-2-(1-(azetidin-3-ylmethyl)-2-(1-(cyclopropylmethyl)-6-methoxy-1H-pyrrolo[2,3-b]pyridin-2-yl)-7-methoxy-1H-benzo[d]imidazole-5-carbonyl)-2-azabicyclo[2.2.1]heptan-7-yl)carbamate (15 mg, 0,023 mmol), 4-bromopyrimidine-2-carbonitrile (4.21 mg, 0.023 mmol), cesium carbonate (14.90 mg, 0.046 mmol), BINAP (0.712 mg, 1.144 μmol) and Pd2(dba)3 (1.047 mg, 1.144 μmol) in degassed dioxane (1.0 mL) under nitrogen in a seal vial was stirred at 100° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-((1-(2-cyanopyrimidin-4-yl)azetidin-3-yl)methyl)-2-(1-(cyclopropylmethyl)-6-methoxy-1H-pyrrolo[2,3-b]pyri din-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(2-cyanopyrimidin-4-yl)azetidin-3-yl)methyl)-2-(1-(cyclopropylmethyl)-6-methoxy-1H-pyrrolo[2,3-b]pyri din-2-yl)-7-methoxy-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 19% B, 19-59% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. 4-[3-({5-[(1R,4R,7R)-7-amino-2-azabicyclo[2.2.1]heptane-2-carbonyl]-2-[1-(cyclopropylmethyl)-6-methoxy-1H-pyrrolo[2,3-b]pyridin-2-yl]-7-methoxy-1H-1,3-benzodiazol-1-yl}methyl)azetidin-1-yl]pyrimidine-2-carbonitrile (7.3 mg, 11.1 μmol, 48.2%) was isolated. LC/MS (M+H): 659; LC retention time: 1.77 min (analytical HPLC Method 1). $^1$H NMR (500 MHz, DMSO-$d_6$) δ 7.95-7.83 (m, 1H), 7.77-7.70 (m, 1H), 7.38-7.15 (m, 1H), 6.84-6.75 (m, 2H), 6.52-6.38 (m, 1H), 6.32-6.18 (m, 1H), 4.81-4.57 (m, 2H), 4.38-3.94 (m, 3H), 3.89-3.67 (m, 4H), 3.50-3.18 (m, 2H), 3.08-2.83 (m, 3H), 2.74-2.37 (m, 4H), 1.89-1.37 (m, 4H), 1.27-0.49 (m, 3H), 0.21-0.07 (m, 2H), 0.05--0.05 (m, 2H).

Example 3

6-(3-((5-(1R,4R,7R)-7-amino-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)azetidin-1-yl)pyrazine-2-carbonitrile

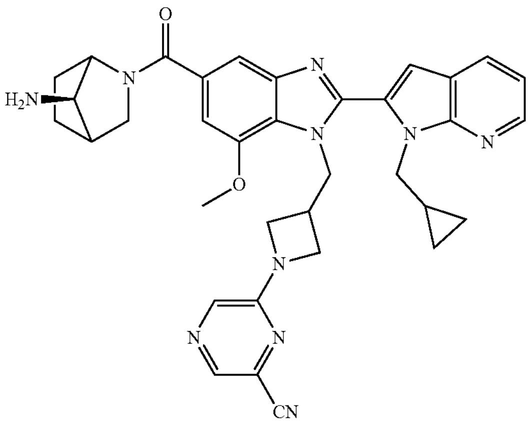 [SMILES: COc1cc(C(=O)N2CC3CCC2[C@@H]3N)cc2nc(-c3cc4cccnc4n3CC3CC3)n(CC3CN(c4cncc(C#N)n4)C3)c12]

Intermediate 3A: 1-(cyclopropylmethyl)-1H-pyrrolo[2,3-b]pyridine-2-carbaldehyde

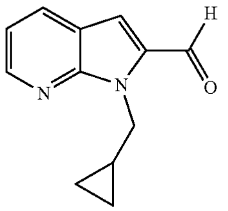 [SMILES: O=Cc1cc2cccnc2n1CC1CC1]

To a suspension of sodium hydride (0,739 g, 18.47 mmol) in anhydrous DMF (50 mL) was added a solution of 1H-pyrrolo[2,3-b]pyridine-2-carbaldehyde (2.70 g, 18.47 mmol) in DMF (20 mL) under nitrogen, and the mixture was stirred at RT for 45 min. (Bromomethyl)cyclopropane (2.494 g, 18.47 mmol) was added to the mixture and the reaction was stirred at RT for 18 hours. The mixture was diluted with EtOAc (45 mL) and was washed with a solution of aqueous saturated sodium bicarbonate (3×45 mL). The organic layer was dried over sodium sulfate and concentrated. The crude product was subjected to ISCO flash chromatography (silica gel/hexane-EtOAc 100:0 to 50:50 gradient) to yield 1-(cyclopropylmethyl)-1H-pyrrolo[2,3-b]pyridine-2-carbaldehyde (2.93 g, 13.90 mmol, 75% yield) as clear oil. LC/MS (M+H): 201; LC retention time: 0.86 min (analytical HPLC Method 3). $^1$H NMR (499 MHz, CHLOROFORM-d) δ 10.01-9.91 (m, 1H), 8.60-8.47 (m, 1H), 8.13-8.04 (m, 1H), 7.26-7.23 (m, 1H), 7.20-7.13 (m, 1H), 4.69-4.53 (m, 2H), 1.49-1.35 (m, 1H), 0.54-0.38 (m, 4H).

Intermediate 3B: Methyl 1-((1-((benzyloxy)carbonyl)azetidin-3-yl)methyl)-2-(1-(cyclopropylmethyl)-1H-pyrrolo[2,3-b]pyridin-2-yl)-7-methoxy-1H-benzo[d]imidazole-5-carboxylate

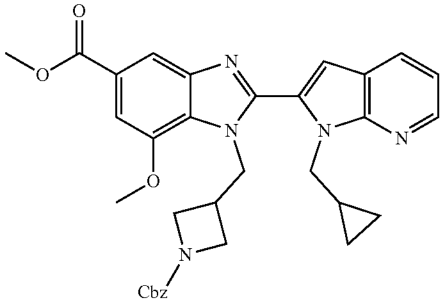 [SMILES: COC(=O)c1cc(OC)c2c(c1)nc(-c1cc3cccnc3n1CC1CC1)n2CC1CN(C(=O)OCc2ccccc2)C1]

To a solution of benzyl 3-(((2-methoxy-4-(methoxycarbonyl)-6-nitrophenyl)amino)methyl)azetidine-1-carboxylate, intermediate 1A (815 mg, 1,898 mmol) and 1-(cyclopropylmethyl)-1H-pyrrolo[2,3-b]pyridine-2-carbaldehyde (380 mg, 1.898 mmol) in EtOH (10 mL) was added a solution of sodium dithionite (991 mg, 5.69 mmol) in water (5.00 mL), the mixture was stirred at 80° C. for 4 hours. The mixture was diluted with EtOAc (10 mL) and was washed with a solution of aqueous saturated sodium chloride (2×10 mL). The organic layer was dried over sodium sulfate and concentrated. The crude product was subjected to ISCO flash chromatography (silica gel/hexane-EtOAc 100:0 to 0:100 gradient) to yield methyl 1-((1-((benzyloxy)carbonyl)azetidin-3-yl)methyl)-2-(1-(cyclopropylmethyl)-1H-pyrrolo[2,3-b]pyridin-2-yl)-7-methoxy-1H-benzo[d]imidazole-5-carboxylate (818 mg, 1.341 mmol, 70.6% yield) as white foam. LC/MS (M+H): 580; LC retention time: 1.13 min (analytical HPLC Method 3).

Intermediate 3C: Benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl-7-methoxy-1H-benzo[d]imidazol-1-yl)methyl)azetidine-1-carboxylate

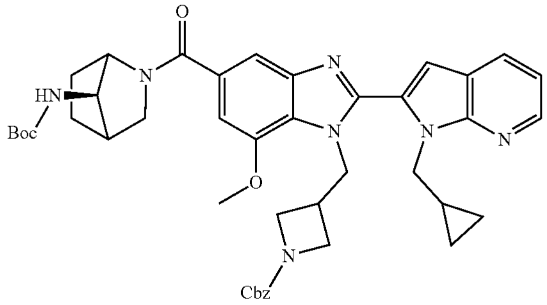 [SMILES: COc1cc(C(=O)N2CC3CCC2[C@@H]3NC(=O)OC(C)(C)C)cc2nc(-c3cc4cccnc4n3CC3CC3)n(CC3CN(C(=O)OCc4ccccc4)C3)c12]

A mixture of methyl 1-((1-((benzyl oxy)carbonyl)azetidin-3-yl)methyl)-2-(1-(cyclopropylmethyl)-1H-pyrrolo[2,3-b]pyridin-2-yl)-7-methoxy-1H-benzo[d]imidazole-5-carboxylate (1.66 g, 2.86 mmol) and 1.0 M aqueous sodium hydroxide (14.32 mL, 14.32 mmol) in THF (20 mL) was stirred at 50° C. for 18 hour. The mixture was cooled to RT. A solution of 1.0 M aqueous HCl (5.5 mL) was added to the mixture and THF was removed. The resulting mixture was extracted with EtOAc (45 mL) and the organic layer was dried over sodium sulfate and concentrated to give a crude yield of 1-((1-((benzyloxy)carbonyl)azetidin-3-yl)methyl)-2-(1-(cyclopropylmethyl)-1H-pyrrolo[2,3-b]pyridin-2-yl)-7-methoxy-1H-benzo[d]imidazole-5-carboxylic acid. LC/MS (M+H): 566; LC retention time: 0.89 min (analytical HPLC Method 3), Material was used as is in next reaction.

A mixture of 1-((1-((benzyloxy)carbonyl)azetidin-3-yl)methyl)-2-(1-(cyclopropylmethyl)-1H-pyrrolo[2,3-b]pyridin-2-yl)-7-methoxy-1H-benzo[d]imidazole-5-carboxylic acid, tert-butyl ((1R,4R,7R)-2-azabicyclo[2.2.1]heptan-7-yl)carbamate (0.608 g, 2.86 mmol), BOP (1.267 g, 2.86 mmol) and TEA (1.996 mL, 14.32 mmol) in DMF (30 mL) was stirred at RT for 2 hour. The mixture was diluted with EtOAc (45 mL) and was washed with a solution of aqueous saturated sodium bicarbonate (2×45 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7- methoxy-1H-benzo[d]imidazol-1-yl)methyl)azetidine-1-carboxylate (1.85 g, 2,313 mmol, 81% yield). LC/MS (M+H): 760; LC retention time: 0.98 min (analytical HPLC Method 3).

Intermediate 3D: Tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate

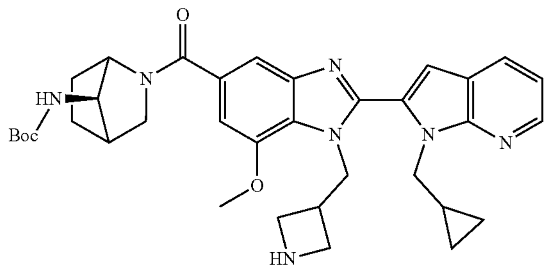 [SMILES: COc1cc(C(=O)N2CC3CCC2[C@@H]3NC(=O)OC(C)(C)C)cc2nc(-c3cc4cccnc4n3CC3CC3)n(CC3CNC3)c12]

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)azetidine-1-carboxylate (1.80 g, 2,369 mmol) and 10% palladium on carbon (0.252 g, 0.237 mmol) in MeOH (60 mL) was hydrogenated under 1 atm of hydrogen for 18 hour. Pd/C was filtered and the filtrate was concentrated to give a crude yield of tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate (1.42 g, 2.156 mmol, 91% yield), LC/MS (M+H): 626, LC retention time: 0.81 min (analytical HPLC Method 3).

Example 3: 6-(3-((5-((1R,4R,7R)-7-amino-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)azetidin-1-yl)pyrazine-2-carbonitrile A mixture of tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate (15 mg, 0.024 mmol), 6-chloropyrazine-2-carbonitrile (3.34 mg, 0,024 mmol), cesium carbonate (15.62 mg, 0.048 mmol), BINAP (0.746 mg, 1.199 μmol) and Pd2(dba)3 (1.098 mg, 1.199 μmol) in degassed dioxane (1.0 mL) under nitrogen in a seal vial was stirred at 90° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate (15 mg, 0.024 mmol). Material was used as is in next reaction.

A mixture of tert-butyl ((1R,4R,7R)-2-(1-((1-(6-cyanopyrazin-2-yl)azetidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 12% B, 12-52% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. 6-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrazine-2-carbonitrile (13.5 mg, 21.5 μmol, 89.5%) was isolated. LC/MS (M+H): 629; LC retention time: 1.33 min (analytical HPLC Method 2). $^1H$ NMR (500 MHz, DMSO-$d_6$) δ 8.28-8.23 (m, 1H), 8.09-8.04 (m, 1H), 8.00-7.93 (m, 1H), 7.90-7.85 (m, 1H), 7.45-7.28 (m, 1H), 7.10-7.04 (m, 1H), 7.00-6.94 (m, 1H), 6.93-6.83 (m, 1H), 4.89-4.72 (m, 2H), 4.43-4.03 (m, 3H), 3.94-3.77 (m, 4H), 3.67-3.40 (m, 2H), 3.10-2.94 (m, 2H), 2.86-2.71 (m, 2H), 2.57-2.42 (m, 1H), 1.93-1.65 (m, 4H), 1.57-1.44 (m, 1H), 1.15-1.05 (m, 1H), 0.93-0.64 (m, 2H), 0.21-0.11 (m, 2H), 0.04--0.04 (m, 2H).

Example 4

4-(3-((5-((3R,5R)-3-amino-5-fluoropiperidine-1-carbonyl)-2-(1-(cyclopropylmethyl)-1H-indol-2-yl)-7-methoxy-1H-benzo[d]imidazol-1-yl)methyl)azetidin-1-yl)pyrimidine-2-carbonitrile

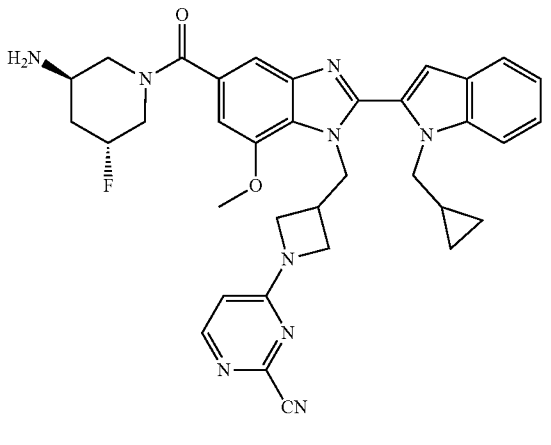 [SMILES: COc1cc(C(=O)N2C[C@H](N)C[C@@H](F)C2)cc2nc(-c3cc4ccccc4n3CC3CC3)n(CC3CN(c4ccnc(C#N)n4)C3)c12]

Intermediate 4A: Benzyl 3-((5-((3R,5R)-3-((tert-butoxycarbonyl)amino)-5-fluoropiperidine-1-carbonyl)-2-(1-(cyclopropylmethyl)-1H-indol-2-yl)-7-methoxy-1H-benzo[d]imidazol-1-yl)methyl) azetidine-1-carboxylate

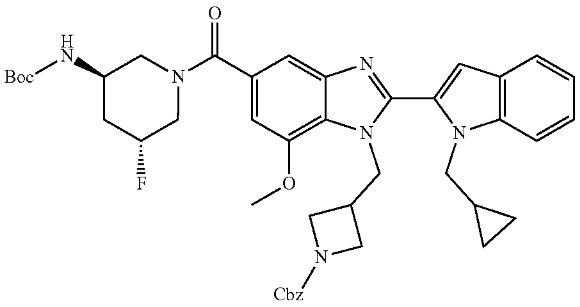 [SMILES: COc1cc(C(=O)N2C[C@H](F)C[C@@H](NC(=O)OC(C)(C)C)C2)cc2nc(-c3cc4ccccc4n3CC3CC3)n(CC3CN(C(=O)OCc4ccccc4)C3)c12]

A mixture of methyl 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylate intermediate 1C (187 mg, 0.323 mmol) and 1.0 M aqueous sodium hydroxide (1.616 mL, 1.616 mmol) in THF (4.0 mL) was stirred at 50° C. for 18 hour. A solution of 1.0 M aqueous HQ (1.62 mL) was added and the mixture was concentrated to give crude 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylic acid. LC/MS (M+H): 565; LC retention time: 0.98 min (analytical HPLC Method 3). Material was used as is in next reaction.

A mixture of 1-((1-((benzyloxy)carbonyl)azetidin-3-yl)methyl)-2-(1-(cyclopropylmethyl)-1H-indol-2-yl)-7-methoxy-1H-benzo[d]imidazole-5-carboxylic acid, tert-butyl ((3R,5R)-5-fluoropiperidin-3-yl)carbamate (70.5 mg, 0.323 mmol), BOP (143 mg, 0.323 mmol) and TEA (0.225 mL, 1.616 mmol) in DMF (5.0 mL) was stirred at RT for 2 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-((5-((3R,5R)-3-((tert-butoxycarbonyl)amino)-5-fluoropiperidine-1-carbonyl)-2-(1-(cyclopropylmethyl)-1H-indol-2-yl)-7-methoxy-1H-benzo[d]imidazol-1-yl)methyl)azetidine-1-carboxylate (195 mg, 0.242 mmol, 74.9% yield) as clear gum. LC/MS (M+H): 765, LC retention time: 1.01 min (analytical HPLC Method 3).

Intermediate 4B: Tert-butyl ((3R,5R)-1-(1-(azetidin-3-ylmethyl)-2-(1-(cyclopropylmethyl)-1H-indol-2-yl)-7-methoxy-1H-benzo[d]imidazole-5-carbonyl-5-fluoropiperidin-3-yl)carbamate

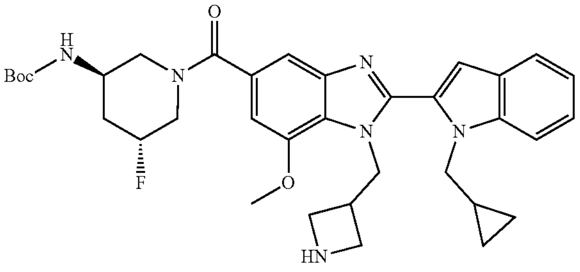 [SMILES: COc1cc(C(=O)N2C[C@H](F)C[C@@H](NC(=O)OC(C)(C)C)C2)cc2nc(-c3cc4ccccc4n3CC3CC3)n(CC3CNC3)c12]

A mixture of benzyl 3-((5-((3R,5R)-3-((tert-butoxycarbonyl)amino)-5-fluoropiperidine-1-carbonyl)-2-(1-(cyclopropylmethyl)-1H-indol-2-yl)-7-methoxy-1H-benzo[d]imidazol-1-yl)methyl)azetidine-1-carboxylate (195 mg, 0,255 mmol) and 10% palladium on carbon (27.1 mg, 0.025 mmol) in MeOH (15 mL) was hydrogenated under 1 atm of hydrogen for 6 hours. Pd/C was filtered off and the filtrate was concentrated to give a crude yield of tert-butyl ((3R,5R)-1-(1-(azetidin-3-ylmethyl)-2-(1-(cyclopropylmethyl)-1H-indol-2-yl)-7-methoxy-1H-benzo[d]imidazole-5-carbonyl)-5-fluoropiperidin-3-yl)carbamate (148 mg, 0.223 mmol, 87% yield) as white solid. LC/MS (M+H): 631; LC retention time: 0.78 min (analytical HPLC Method 3).

Example 4: 4-(3-((5-((3R,5R)-3-amino-5-fluoropiperidine-1-carbonyl)-2-(1-(cyclopropylmethyl)-1H-indol-2-yl)-7-methoxy-1H-benzo[d]imidazol-1-yl)methyl)azetidin-1-yl)pyrimidine-2-carbonitrile A mixture of tert-butyl ((3R,5R)-1-(1-(azetidin-3-ylmethyl)-2-(1-(cyclopropylmethyl)-1H-indol-2-yl)-7-methoxy-1H-benzo[d]imidazole-5-carbonyl)-5-fluoropiperidin-3-yl)carbamate (15 mg, 0.024 mmol), 4-bromopyrimidine-2-carbonitrile (4.38 mg, 0,024 mmol), cesium carbonate (15.50 mg, 0.048 mmol), BINAP (0.740 mg, 1.189 μmol) and $Pd_2(dba)_3$ (1.089 mg, 1.189 μmol) in degassed dioxane (1.0 mL) under nitrogen in a seal vial was stirred at 80° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((3R,5R)-1-(1-((1-(2-cyanopyrimidin-4-yl)azetidin-3-yl)methyl)-2-(1-(cyclopropylmethyl)-1H-indol-2-yl)-7-methoxy-1H-benzo[d]imidazole-5-carbonyl)-5-fluoropiperidin-3-yl)carbamate. Material was used as is in next reaction.

A mixture of tert-butyl ((3R,5R)-1-(1-((1-(2-cyanopyrimidin-4-yl)azetidin-3-yl)methyl)-2-(1-(cyclopropylmethyl)-1H-indol-2-yl)-7-methoxy-1H-benzo[d]imidazole-5-carbonyl)-5-fluoropiperidin-3-yl)carbamate in DCM (1.0 mL) and TEA (1.0 mL) was stirred at RT for 30 min. The mixture was concentrated. The crude material was purified via preparative LC/MS with the following conditions: Column: XBridge CIS, 200 mm×19 mm, 5-Åμm particles, Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 6-minute hold at 100% B; Flow Rate: 20 mL/min; Column Temperature: 25 C. Fraction collection was triggered by MS signals. Fractions containing the desired product were combined and dried via centrifugal evaporation. 4-[3-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)azetidin-1-yl]pyrimidine-2-carbonitrile (8.4 mg, 13.3 μmol, 55.2%) was isolated. LC/MS (M+H): 634; LC retention time: 1.66 min (analytical HPLC Method 1). $^1$H NMR (500 MHz, DMSO-$d_6$) δ 8.00 (br d, J=6.1 Hz, 1H), 7.54 (br d, J=7.6 Hz, 2H), 7.27-7.08 (m, 2H), 7.00 (br t, J=7.3 Hz, 1H), 6.91 (s, 1H), 6.77 (s, 1H), 6.38 (br d, J=6.1 Hz, 1H), 4.77 (br d, J=6.4 Hz, 2H), 4.21 (br s, 2H), 3.98-3.85 (m, 2H), 3.59 (br d, J=8.5 Hz, 2H), 3.09-2.47 (m, 3H), 2.30-1.81 (m, 3H), 1.76 (s, 2H), 1.50-0.63 (m, 5H), 0.21 (br d, J=7.0 Hz, 2H), 0.05--0.05 (m, 2H).

Example 5

4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-2-carbonitrile

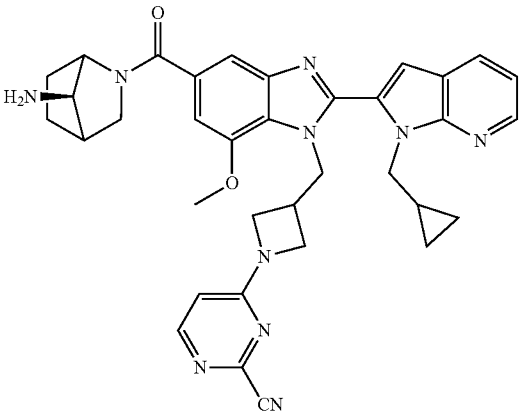 [SMILES: COc1cc(C(=O)N2CC3CCC2[C@@H]3N)cc2nc(-c3cc4cccnc4n3CC3CC3)n(CC3CN(c4ccnc(C#N)n4)C3)c12]

A mixture of tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate intermediate 3D (20 mg, 0.032 mmol), 4-bromopyrimidine-2-carbonitrile (5.88 mg, 0.032 mmol), cesium carbonate (20.83 mg, 0.064 mmol), BINAP (0.995 mg, 1.598 μmol) and $Pd_2(dba)_3$ (1.463 mg, 1.598 μmol) in degassed dioxane (1.0 mL) under nitrogen in a seal vial was stirred at 100° C. for 18 hour. The mixture was diluted with EtOAc (15 mL) and was washed with a solution of aqueous saturated sodium bicarbonate (15 mL). The organic layer was dried over sodium sulfate and concentrated to give crude tert-butyl ((1R,4R,7R)-2-(1-((1-(2-cyanopyrimidin-4-yl)azetidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate, Material was used as is in next reaction.

A mixture of tert-butyl ((1R,4R,7R)-2-(1-((1-(2-cyanopyrimidin-4-yl)azetidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude product was purified by prep-HPLC (Phenomenex, Luna 5 micron 30×250 mm, flow rate=30 ml/min., gradient=20% A to 100% B in 30 min., A=H2O/ACN/TFA (90:10:0.1), B=H2O/ACN/TF A (10:90:0.1)). The semi pure product was purified via preparative LC/MS with the following conditions: Column: XBridge C18, 19×200 mm, 5-nm particles; Mobile Phase A: 5:95 acetonitrile:water with 0.1% trifluoroacetic acid; Mobile Phase B: 95:5 acetonitrile: water with 0.1% trifluoroacetic acid; Gradient: 10-50% B over 20 minutes, then a 4-minute hold at 100% B; Flow: 20 mL/min. Fractions containing the desired product were combined and dried via centrifugal evaporation, 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-2-carbonitrile (8.8 mg, 14 μmol, 43.7%) was isolated. LC/MS (M+H): 629; LC retention time: 1.44 min (analytical HPLC Method 1). $^1$H NMR (499 MHz, DMSO-$d_6$) δ 8.48-8.37 (m, 1H), 8.21-8.08 (m, 2H), 7.67-7.41 (m, 1H), 7.27-7.18 (m, 1H), 7.13-7.10 (m, 1H), 7.09-7.00 (m, 1H), 6.59-6.46 (m, 1H), 5.02-4.88 (m, 2H), 4.61-4.18 (m, 3H), 4.13-3.92 (m, 5H), 3.83-3.49 (m, 4H), 3.25-3.07 (m, 2H), 2.72-2.57 (m, 2H), 2.47-2.31 (m, 1H), 2.10-1.82 (m, 3H), 1.77-1.58 (m, 1H), 1.33-1.19 (m, 1H), 1.12-0.96 (m, 1H), 0.39-0.29 (m, 2H), 0.24-0.15 (m, 2H).

Example 6

((1R,4R,7R)-7-amino-2-azabicyclo[2.2.1]heptan-2-yl)(7-methoxy-2-(1-methyl-1H-indol-2-yl)-1-((1-(2-methyl pyrimidin-4-yl)azetidin-3-yl)methyl)-1H-benzo[d]imidazol-5-yl)methanone

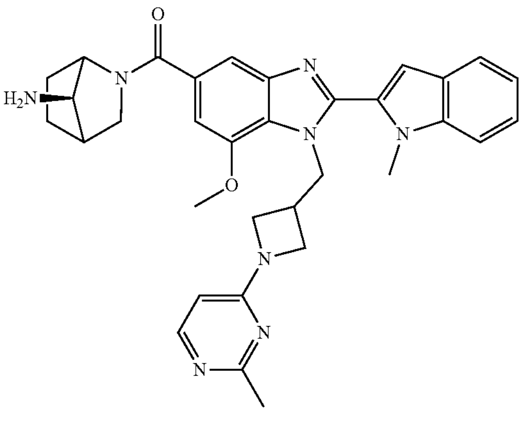 [SMILES: COc1cc(C(=O)N2CC3CCC2[C@@H]3N)cc2nc(-c3cc4ccccc4n3C)n(CC3CN(c4ccnc(C)n4)C3)c12]

Intermediate 6A: Benzyl 3-(((4-((1R,4R,7R)-7-((tert-butoxycarbonyl)amino)-2-azabicyclo[2.2.1]heptane-2-carbonyl)-2-methoxy-6-nitrophenyl)amino)methyl)azetidine-1-carboxylate

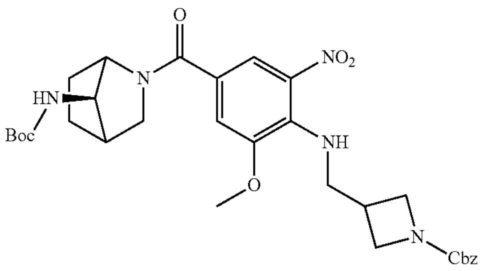 [SMILES: COc1cc(C(=O)N2CC3CCC2[C@@H]3NC(=O)OC(C)(C)C)cc([N+](=O)[O-])c1NCC1CN(C(=O)OCc2ccccc2)C1]

A mixture of benzyl 3-(((2-methoxy-4-(methoxycarbonyl)-6-nitrophenyl)amino)methyl)azetidine-1-carboxylate, intermediate 1A (0.98 g, 2.282 mmol) and 1.0 M aqueous sodium hydroxide (11.41 mL, 11.41 mmol) in THF (30 mL) was stirred at 50° C. for 18 hour. A solution of 1.0 M aqueous HCl (12 mL) was added to the mixture and it was then concentrated to give crude 4-(((1-((benzyloxy)carbonyl)azetidin-3-yl)methyl)amino)-3-methoxy-5-nitrobenzoic acid. LC/MS (M+H): 416, LC retention time: 0.92 min (analytical HPLC Method 3). Material was used as is in next reaction.

A mixture of 4-(((1-((benzyloxy)carbonyl)azetidin-3-yl)methyl)amino)-3-methoxy-5-nitrobenzoic acid, tert-butyl ((1R,4R,7R)-2-azabicyclo[2.2.1]heptan-7-yl)carbamate (0.484 g, 2.282 mmol), BOP (1.009 g, 2.282 mmol) and TEA (1.590 mL, 11.41 mmol) in DMF (20 mL) was stirred at RT for 2 hour. The mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-(((4-((1R,4R,7R)-7-((tert-butoxycarbonyl)amino)-2-azabicyclo[2.2.1]heptane-2-carbonyl)-2-methoxy-6-nitrophenyl)amino)methyl)azetidine-1-carboxylate (1.010 g, 1.574 mmol, 69.0% yield) as orange foam. LC/MS (M+H): 610; LC retention time: 1.07 min (analytical HPLC Method 3).

Intermediate 6B: Tert-butyl ((1R,4R,7R)-2-(1-(azetidin-3-ylmethyl)-7-methoxy-2-(1-methyl-1H-indol-2-yl)-1H-benzo[d]imidazole-5-carbonyl)-2-azabicyclo[2.2.1]heptan-7-yl)carbamate

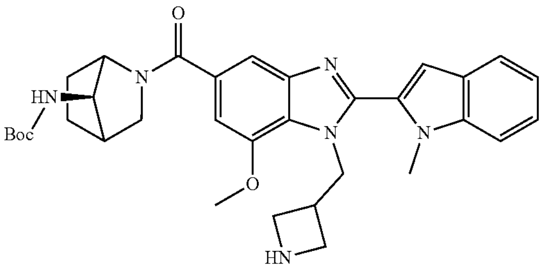 [SMILES: COc1cc(C(=O)N2CC3CCC2[C@@H]3NC(=O)OC(C)(C)C)cc2nc(-c3cc4ccccc4n3C)n(CC3CNC3)c12]

To a solution of benzyl 3-(((4-((1R,4R,7R)-7-((tert-butoxycarbonyl)amino)-2-azabicyclo[2.2.1]heptane-2-carbonyl)-2-methoxy-6-nitrophenyl)amino)methyl)azetidine-1-carboxylate (150 mg, 0.246 mmol) and 6-chloro-1-methyl-1H-indole-2-carbaldehyde (47.6 mg, 0.246 mmol) in EtOH (0.80 mL) was added a solution of sodium dithionite (128 mg, 0.738 mmol) in water (0.40 mL) at RT under nitrogen. The mixture was stirred at 80° C. for 18 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-((5-((1R,4R,7R)-7-((tert-butoxycarbonyl)amino)-2-azabicyclo[2.2.1]heptane-2-carbonyl)-2-(6-chloro-1-methyl-1H-indol-2-yl)-7-methoxy-1H-benzo[d]imidazol-1-yl)methyl)azetidine-1-carboxylate (105 mg, 0.132 mmol, 53.8% yield) as white solid. LC/MS (M+H): 753; LC retention time: 1.05 min (analytical HPLC Method 3). Material was used as is in next reaction.

A mixture of benzyl 3-((5-((1R,4R,7R)-7-((tert-butoxycarbonyl)amino)-2-azabicyclo[2.2.1]heptane-2-carbonyl)-2-(6-chloro-1-methyl-1H-indol-2-yl)-7-methoxy-1H-benzo[d]imidazol-1-yl)methyl)azetidine-1-carboxylate (105 mg, 0.132 mmol) and 10% palladium on carbon (26.2 mg, 0.025 mmol) in MeOH (10 mL) was hydrogenated under 1 atm of hydrogen for 4 hour. Pd/C was filtered off and the filtrate was concentrated to give a crude yield of tert-butyl ((1R,4R,7R)-2-(1-(azetidin-3-ylmethyl)-7-methoxy-2-(1-methyl-1H-indol-2-yl)-1H-benzo[d]imidazole-5-carbonyl)-2-azabicyclo[2.2.1]heptan-7-yl)carbamate (76 mg, 0.123 mmol, 50.2% yield) as white solid. LC/MS (M+H): 585; LC retention time: 0.72 min (analytical HPLC Method 3).

Example 6: ((1R,4R,7R)-7-amino-2-azabicyclo[2.2.1]heptan-2-yl)(7-methoxy-2-(1-methyl-1H-indol-2-yl)-1-((1-(2-methylpyrimidin-4-yl)azetidin-3-yl)methyl)-1H-benzo[d]imidazol-5-yl)methanone A mixture of tert-butyl ((1R,4R,7R)-2-(1-(azetidin-3-ylmethyl)-7-methoxy-2-(1-methyl-1H-indol-2-yl)-1H-benzo[d]imidazole-5-carbonyl)-2-azabicyclo[2.2.1]heptan-7-yl)carbamate (15 mg, 0.026 mmol), 4-bromo-2-methylpyrimidine (4.44 mg, 0.026 mmol), cesium carbonate (16.72 mg, 0.051 mmol), BINAP (0.799 mg, 1.283 µmol) and $Pd_2(dba)_3$ (1.175 mg, 1.283 µmol) in degassed dioxane (1.0 mL) under nitrogen in a seal vial was stirred at 80° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(7-methoxy-2-(1-methyl-1H-indol-2-yl)-1-((1-(2-methylpyrimidin-4-yl)azetidin-3-yl)methyl)-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(7-methoxy-2-(1-methyl-1H-indol-2-yl)-1-((1-(2-methylpyrimidin-4-yl)azetidin-3-yl)methyl)-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 12% B, 12-52% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. (1R,4R,7R)-2-[7-methoxy-2-(1-methyl-1H-indol-2-yl)-1-{[1-(2-methylpyrimidin-4-yl)azetidin-3-yl]methyl}-1H-1,3-benzodiazole-5-carbonyl]-2-azabicyclo[2.2.1]heptan-7-amine (5.6 mg, 9.7 μmol, 37.3%) was isolated, LC/MS (M+H): 577; LC retention time: 0.94 min (analytical HPLC Method 2). $^1H$ NMR (500 MHz, DMSO-$d_6$) δ 7.93 (d, J=5.8 Hz, 1H), 7.66 (br d, J=8.0 Hz, 1H), 7.58 (br d, J=8.2 Hz, 1H), 7.41 (br s, 1H), 7.31 (br t, J=7.6 Hz, 1H), 7.15 (br t, J=7.4 Hz, 1H), 6.98 (s, 2H), 6.01 (d, 7=5.9 Hz, 1H), 4.85 (br d, 7=7.1 Hz, 2H), 4.03-3.87 (m, 4H), 3.67-3.36 (m, 7H), 3.27-2.95 (m, 3H), 2.34-2.16 (m, 3H), 2.09-1.68 (m, 6H), 1.56-1.32 (m, 1H), 1.11-0.73 (m, 1H).

Example 7 to Example 87 in Table 1 were prepared as described by the general procedure given for Examples 1-6.

TABLE 1

| Ex # | Structure | Name | LC/MS Rt (min) | LC/MS Method | M + H (obs ion) |
|---|---|---|---|---|---|
| 7 | 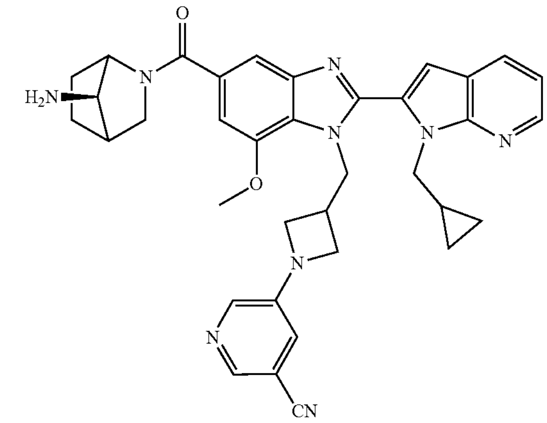 [SMILES: COc1cc(C(=O)N2CC3CCC2[C@@H]3N)cc2nc(-c3cc4cccnc4n3CC3CC3)n(CC3CN(c4cncc(C#N)c4)C3)c12] | 5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyridine-3-carbonitrile | 1.45 | 1 | 628 |
| 8 | 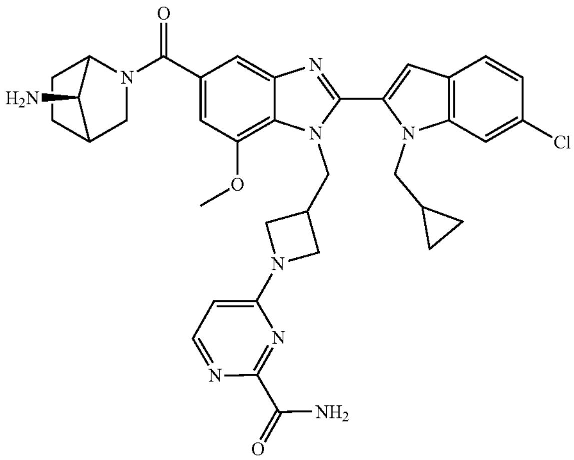 [SMILES: COc1cc(C(=O)N2CC3CCC2[C@@H]3N)cc2nc(-c3cc4ccc(Cl)cc4n3CC3CC3)n(CC3CN(c4ccnc(C(N)=O)n4)C3)c12] | 4-[3-({5-[(1R,4R,7R)-7-amino-2-azabicyclo[2.2.1]heptane-2-carbonyl]-2-[6-chloro-1-(cyclopropylmethyl)-1H-indol-2-yl]-7-methoxy-1H-1,3-benzodiazol-1-yl}methyl)azetidin-1-yl]pyrimidine-2-carboxamide | 1.59 | 1 | 680 |
| 9 | 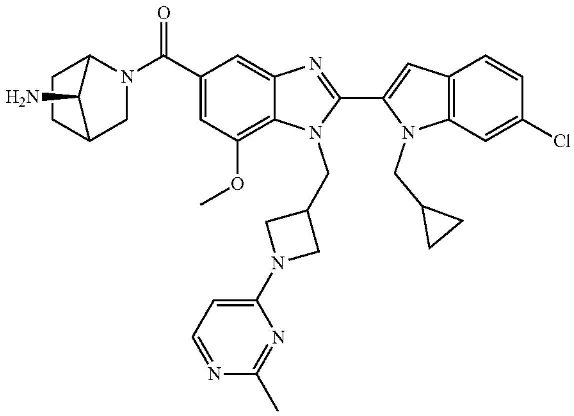 [SMILES: COc1cc(C(=O)N2CC3CCC2[C@@H]3N)cc2nc(-c3cc4ccc(Cl)cc4n3CC3CC3)n(CC3CN(c4ccnc(C)n4)C3)c12] | (1R,4R,7R)-2-{2-[6-chloro-1-(cyclopropylmethyl)-1H-indol-2-yl]-7-methoxy-1-{[1-(2-methylpyrimidin-4-yl)azetidin-3-yl]methyl}-1H-1,3-benzodiazole-5-carbonyl}-2-azabicyclo[2.2.1]heptan-7-amine | 1.62 | 1 | 651 |

TABLE 1-continued

| Ex # | Structure | Name | LC/MS Rt (min) | LC/MS Method | M + H (obs ion) |
|---|---|---|---|---|---|
| 10 | 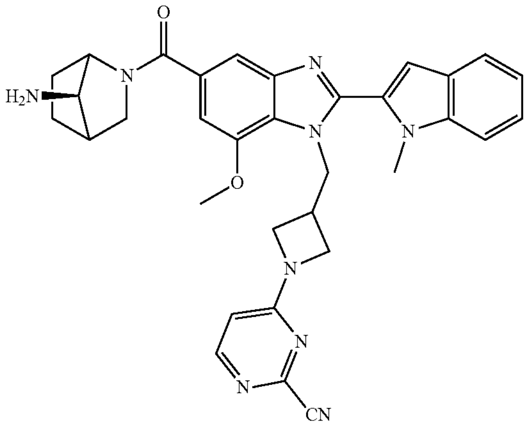 [SMILES: COc1cc(C(=O)N2CC3CCC2[C@@H]3N)cc2nc(-c3cc4ccccc4n3C)n(CC3CN(c4ccnc(C#N)n4)C3)c12] | 4-[3-({5-[(1R,4R,7R)-7-amino-2-azabicyclo[2.2.1]heptane-2-carbonyl]-7-methoxy-2-(1-methyl-1H-indol-2-yl)-1H-1,3-benzodiazol-1-yl}methyl)azetidin-1-yl]pyrimidine-2-carbonitrile | 1.44 | 2 | 588 |
| 11 | 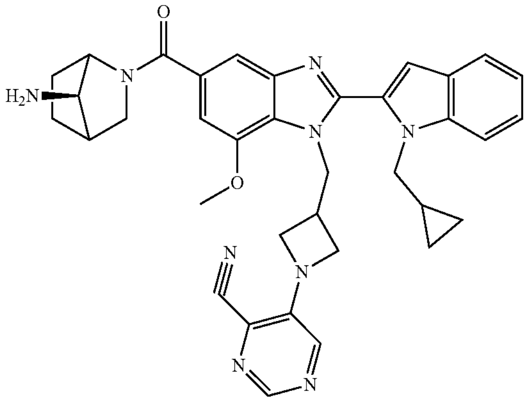 [SMILES: COc1cc(C(=O)N2CC3CCC2[C@@H]3N)cc2nc(-c3cc4ccccc4n3CC3CC3)n(CC3CN(c4cncnc4C#N)C3)c12] | 5-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyrimidine-4-carbonitrile | 1.64 | 2 | 628 |
| 12 | 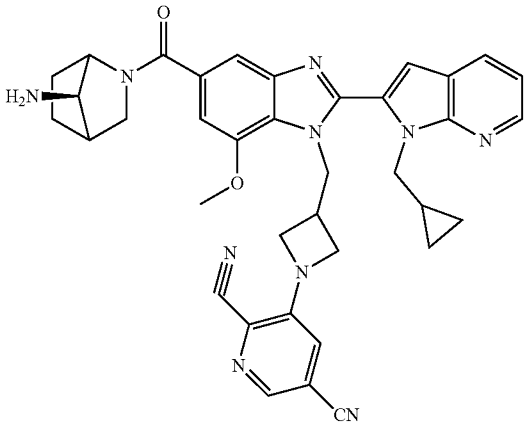 [SMILES: COc1cc(C(=O)N2CC3CCC2[C@@H]3N)cc2nc(-c3cc4cccnc4n3CC3CC3)n(CC3CN(c4cc(C#N)cnc4C#N)C3)c12] | 3-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyridine-2,5-dicarbonitrile | 0.82 | 3 | 653 |

TABLE 1-continued

| Ex # | Structure | Name | LC/MS Rt (min) | LC/MS Method | M + H (obs ion) |
|---|---|---|---|---|---|
| 13 | 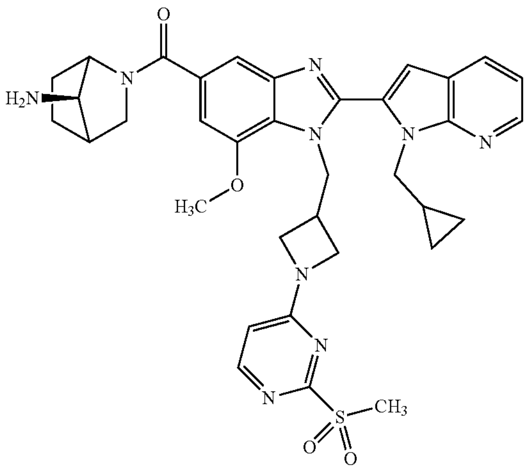 [SMILES: COc1cc(C(=O)N2CC3CCC2[C@@H]3N)cc2nc(-c3cc4cccnc4n3CC3CC3)n(CC3CN(c4ccnc(S(C)(=O)=O)n4)C3)c12] | (1R,4R,7R)-2-{2-[1-(cyclopropylmethyl)-1H-pyrrolo[2,3-b]pyridin-2-yl]-1-{[1-(2-methanesulfonylpyrimidin-4-yl)azetidin-3-yl]methyl}-7-methoxy-1H-1,3-benzodiazole-5-carbonyl}-2-azabicyclo[2.2.1]heptan-7-amine | 1.36 | 1 | 682 |
| 14 | 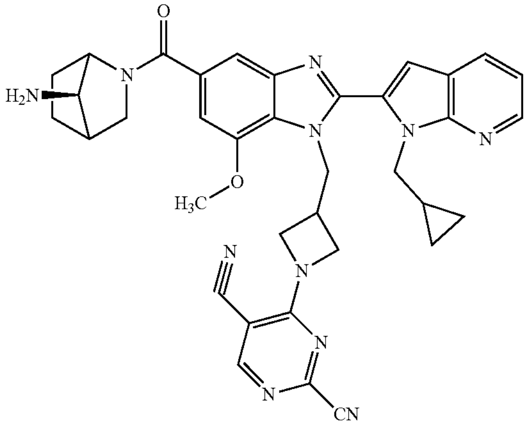 [SMILES: COc1cc(C(=O)N2CC3CCC2[C@@H]3N)cc2nc(-c3cc4cccnc4n3CC3CC3)n(CC3CN(c4nc(C#N)ncc4C#N)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-2,5-dicarbonitrile | 1.33 | 2 | 628 |
| 15 | 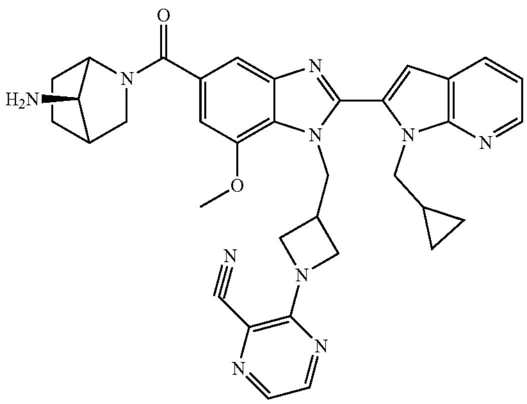 [SMILES: COc1cc(C(=O)N2CC3CCC2[C@@H]3N)cc2nc(-c3cc4cccnc4n3CC3CC3)n(CC3CN(c4nccnc4C#N)C3)c12] | 3-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrazine-2-carbonitrile | 1.46 | 2 | 628 |

TABLE 1-continued

| Ex # | Structure | Name | LC/MS Rt (min) | LC/MS Method | M + H (obs ion) |
|---|---|---|---|---|---|
| 16 | 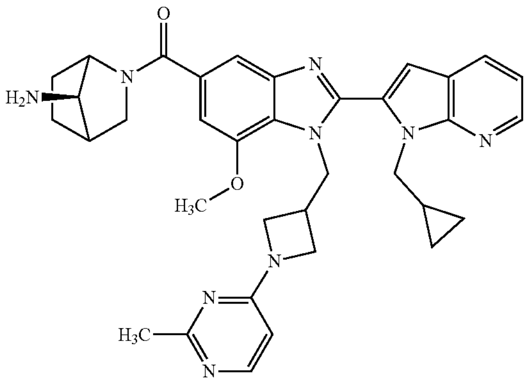 [SMILES: COc1cc(C(=O)N2CC3CCC2[C@@H]3N)cc2nc(-c3cc4cccnc4n3CC3CC3)n(CC3CN(c4ccnc(C)n4)C3)c12] | (1R,4R,7R)-2-{2-[1-(cyclopropylmethyl)-1H-pyrrolo[2,3-b]pyridin-2-yl]-7-methoxy-1-{[1-(2-methylpyrimidin-4-yl)azetidin-3-yl]methyl}-1H-1,3-benzodiazole-5-carbonyl}-2-azabicyclo[2.2.1]heptan-7-amine | 1.14 | 1 | 618 |
| 17 | 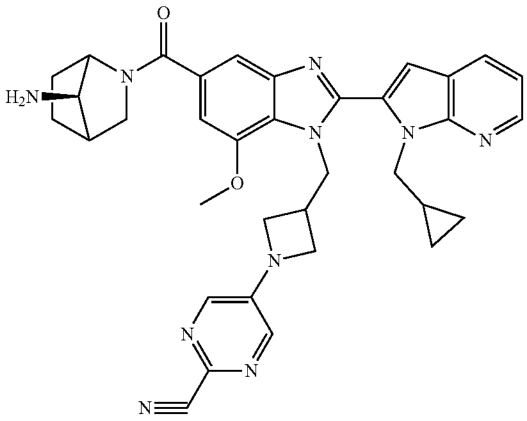 [SMILES: COc1cc(C(=O)N2CC3CCC2[C@@H]3N)cc2nc(-c3cc4cccnc4n3CC3CC3)n(CC3CN(c4cnc(C#N)nc4)C3)c12] | 5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-2-carbonitrile | 1.39 | 1 | 629 |
| 18 | 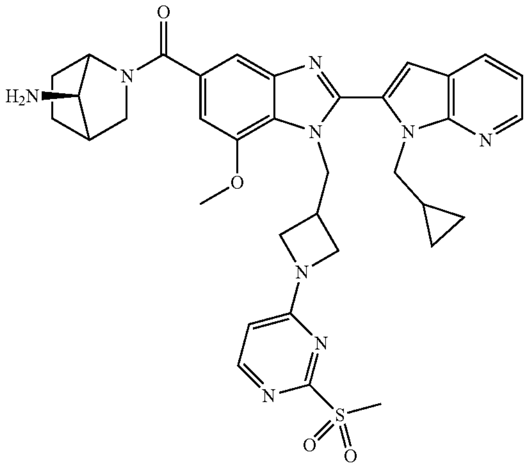 [SMILES: COc1cc(C(=O)N2CC3CCC2[C@@H]3N)cc2nc(-c3cc4cccnc4n3CC3CC3)n(CC3CN(c4ccnc(S(C)(=O)=O)n4)C3)c12] | (1R,4R,7R)-2-{2-[1-(cyclopropylmethyl)-1H-pyrrolo[2,3-b]pyridin-2-yl]-1-{[1-(2-methanesulfonylpyrimidin-4-yl)azetidin-3-yl]methyl}-7-methoxy-1H-1,3-benzodiazole-5-carbonyl}-2-azabicyclo[2.2.1]heptan-7-amine | 1.14 | 2 | 682 |

TABLE 1-continued

| Ex # | Structure | Name | LC/MS Rt (min) | LC/MS Method | M + H (obs ion) |
|---|---|---|---|---|---|
| 19 | 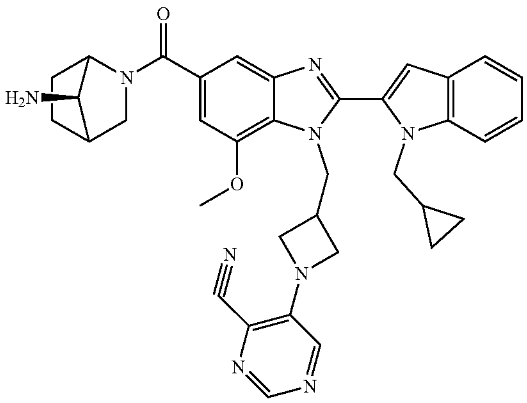 [SMILES: COc1cc(C(=O)N2CC3CCC2[C@@H]3N)cc2nc(-c3cc4ccccc4n3CC3CC3)n(CC3CN(c4cncnc4C#N)C3)c12] | 5-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyrimidine-4-carbonitrile | 1.45 | 2 | 628 |
| 20 | 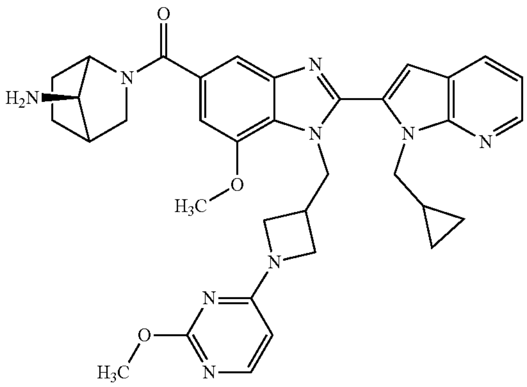 [SMILES: COc1nccc(N2CC(Cn3c(-c4cc5cccnc5n4CC4CC4)nc4cc(C(=O)N5CC6CCC5[C@@H]6N)cc(OC)c43)C2)n1] | (1R,4R,7R)-2-{2-[1-(cyclopropylmethyl)-1H-pyrrolo[2,3-b]pyridin-2-yl]-7-methoxy-1-{[1-(2-methoxypyrimidin-4-yl)azetidin-3-yl]methyl}-1H-1,3-benzodiazole-5-carbonyl}-2-azabicyclo[2.2.1]heptan-7-amine | 1.04 | 2 | 634 |
| 21 | 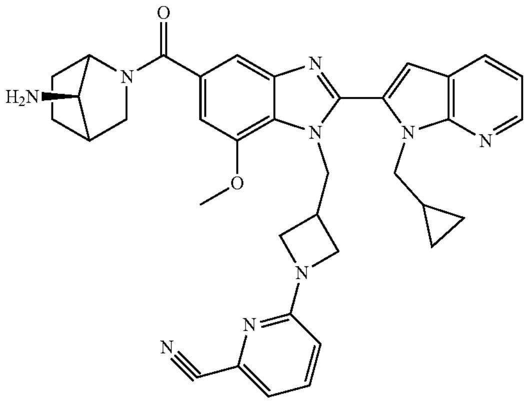 [SMILES: COc1cc(C(=O)N2CC3CCC2[C@@H]3N)cc2nc(-c3cc4cccnc4n3CC3CC3)n(CC3CN(c4cccc(C#N)n4)C3)c12] | 6-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyridine-2-carbonitrile | 1.53 | 2 | 628 |

TABLE 1-continued

| Ex # | Structure | Name | LC/MS Rt (min) | LC/MS Method | M + H (obs ion) |
|---|---|---|---|---|---|
| 22 | 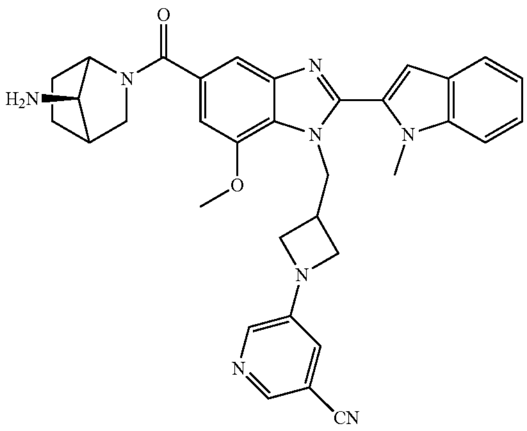 [SMILES: COc1cc(C(=O)N2CC3CCC2[C@@H]3N)cc2nc(-c3cc4ccccc4n3C)n(CC3CN(c4cncc(C#N)c4)C3)c12] | 5-[3-({5-[(1R,4R,7R)-7-amino-2-azabicyclo[2.2.1]heptane-2-carbonyl]-7-methoxy-2-(1-methyl-1H-indol-2-yl)-1H-1,3-benzodiazol-1-yl}methyl)azetidin-1-yl]pyridine-3-carbonitrile | 1.38 | 2 | 587 |
| 23 | 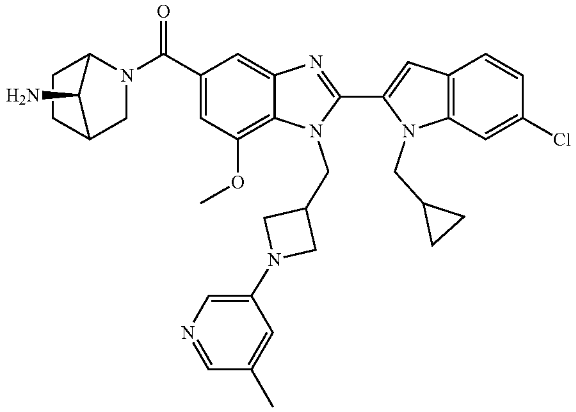 [SMILES: COc1cc(C(=O)N2CC3CCC2[C@@H]3N)cc2nc(-c3cc4ccc(Cl)cc4n3CC3CC3)n(CC3CN(c4cncc(C)c4)C3)c12] | (1R,4R,7R)-2-{2-[6-chloro-1-(cyclopropylmethyl)-1H-indol-2-yl]-7-methoxy-1-{[1-(5-methylpyridin-3-yl)azetidin-3-yl]methyl}-1H-1,3-benzodiazole-5-carbonyl}-2-azabicyclo[2.2.1]heptan-7-amine | 1.89 | 1 | 650 |
| 24 | 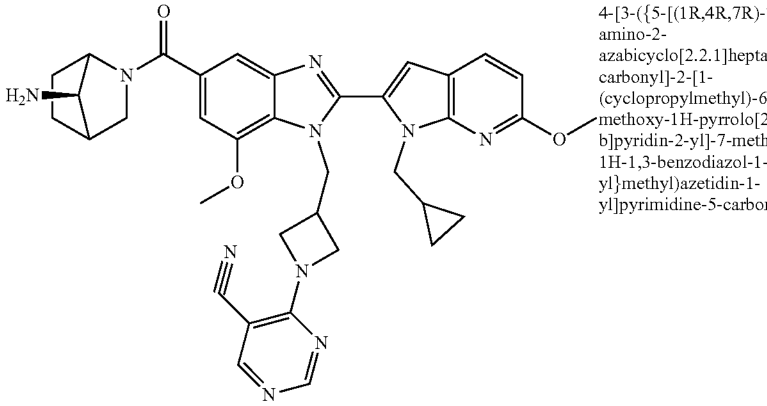 | 4-[3-({5-[(1R,4R,7R)-7-amino-2-azabicyclo[2.2.1]heptane-2-carbonyl]-2-[1-(cyclopropylmethyl)-6-methoxy-1H-pyrrolo[2,3-b]pyridin-2-yl]-7-methoxy-1H-1,3-benzodiazol-1-yl}methyl)azetidin-1-yl]pyrimidine-5-carbonitrile | 1.25 | 2 | 659 |

TABLE 1-continued

| Ex # | Structure | Name | LC/MS Rt (min) | LC/MS Method | M + H (obs ion) |
|---|---|---|---|---|---|
| 25 | 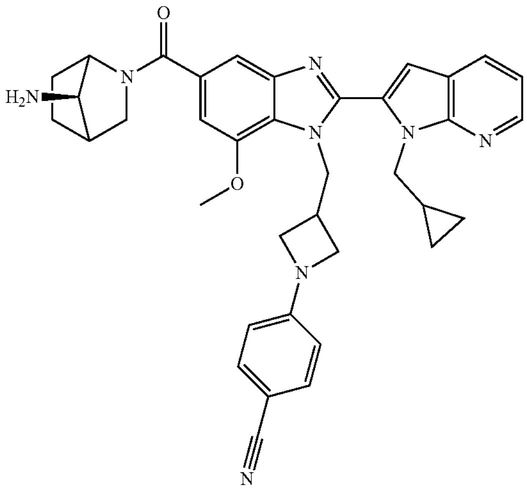 [SMILES: COc1cc(C(=O)N2CC3CCC2[C@@H]3N)cc2nc(-c3cc4cccnc4n3CC3CC3)n(CC3CN(c4ccc(C#N)cc4)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]benzonitrile | 1.69 | 1 | 627 |
| 26 | 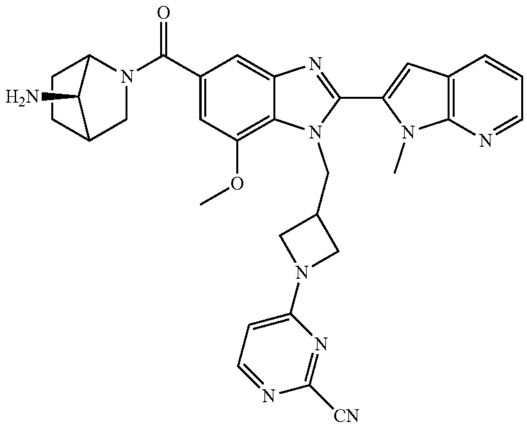 [SMILES: COc1cc(C(=O)N2CC3CCC2[C@@H]3N)cc2nc(-c3cc4cccnc4n3C)n(CC3CN(c4ccnc(C#N)n4)C3)c12] | 4-[3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)azetidin-1-yl]pyrimidine-2-carbonitrile | 1.39 | 1 | 588 |
| 27 | 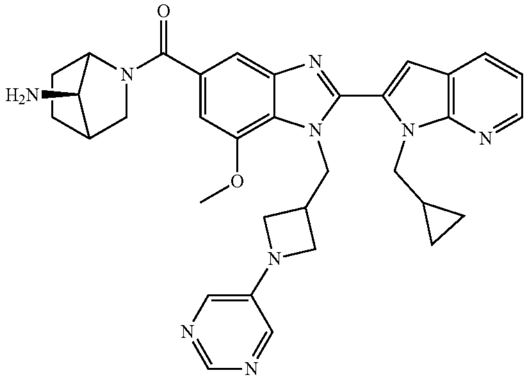 [SMILES: COc1cc(C(=O)N2CC3CCC2[C@@H]3N)cc2nc(-c3cc4cccnc4n3CC3CC3)n(CC3CN(c4cncnc4)C3)c12] | (1R,4R,7R)-2-{2-[1-(cyclopropylmethyl)-1H-pyrrolo[2,3-b]pyridin-2-yl]-7-methoxy-1-{[1-(pyrimidin-5-yl)azetidin-3-yl]methyl}-1H-1,3-benzodiazole-5-carbonyl}-2-azabicyclo[2.2.1]heptan-7-amine | 1.14 | 2 | 604 |

TABLE 1-continued

| Ex # | Structure | Name | LC/MS Rt (min) | LC/MS Method | M + H (obs ion) |
|---|---|---|---|---|---|
| 28 | 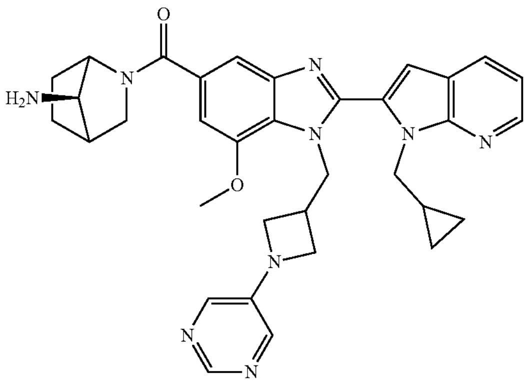 [SMILES: COc1cc(C(=O)N2CC3CCC2[C@@H]3N)cc2nc(-c3cc4cccnc4n3CC3CC3)n(CC3CN(c4cncnc4)C3)c12] | (1R,4R,7R)-2-{2-[1-(cyclopropylmethyl)-1H-pyrrolo[2,3-b]pyridin-2-yl]-7-methoxy-1-{[1-(pyrimidin-4-yl)azetidin-3-yl]methyl}-1H-1,3-benzodiazole-5-carbonyl}-2-azabicyclo[2.2.1]heptan-7-amine | 0.88 | 2 | 604 |
| 29 | 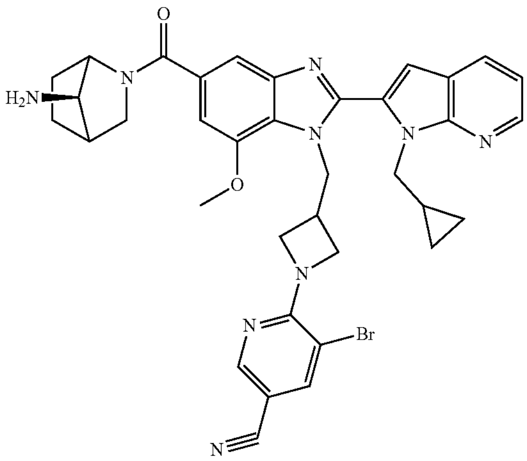 [SMILES: COc1cc(C(=O)N2CC3CCC2[C@@H]3N)cc2nc(-c3cc4cccnc4n3CC3CC3)n(CC3CN(c4ncc(C#N)cc4Br)C3)c12] | 6-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-5-bromopyridine-3-carbonitrile | 1.7 | 1 | 706 |
| 30 | 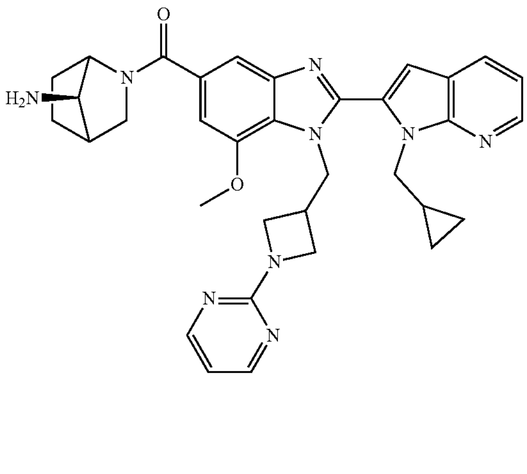 [SMILES: COc1cc(C(=O)N2CC3CCC2[C@@H]3N)cc2nc(-c3cc4cccnc4n3CC3CC3)n(CC3CN(c4ncccn4)C3)c12] | (1R,4R,7R)-2-{2-[1-(cyclopropylmethyl)-1H-pyrrolo[2,3-b]pyridin-2-yl]-7-methoxy-1-{[1-(pyrimidin-2-yl)azetidin-3-yl]methyl}-1H-1,3-benzodiazole-5-carbonyl}-2-azabicyclo[2.2.1]heptan-7-amine | 1.35 | 1 | 604 |

TABLE 1-continued

| Ex # | Structure | Name | LC/MS Rt (min) | LC/MS Method | M + H (obs ion) |
|---|---|---|---|---|---|
| 31 | 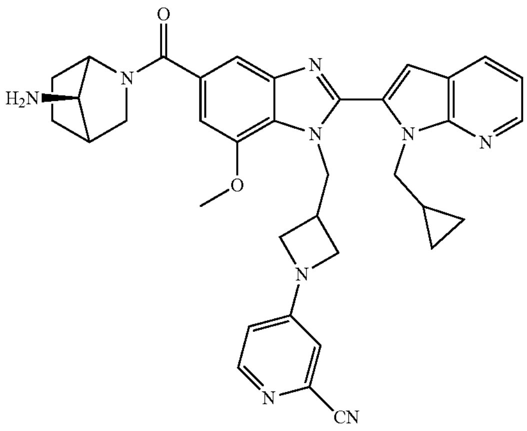 [SMILES: COc1cc(C(=O)N2CC3CCC2[C@@H]3N)cc2nc(-c3cc4cccnc4n3CC3CC3)n(CC3CN(c4ccnc(C#N)c4)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyridine-2-carbonitrile | 1.42 | 1 | 628 |
| 32 | 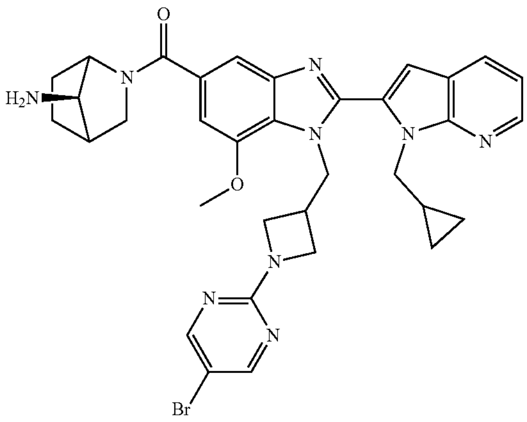 [SMILES: COc1cc(C(=O)N2CC3CCC2[C@@H]3N)cc2nc(-c3cc4cccnc4n3CC3CC3)n(CC3CN(c4ncc(Br)cn4)C3)c12] | (1R,4R,7R)-2-(1-{[1-(5-bromopyrimidin-2-yl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.46 | 2 | 682 |
| 33 | 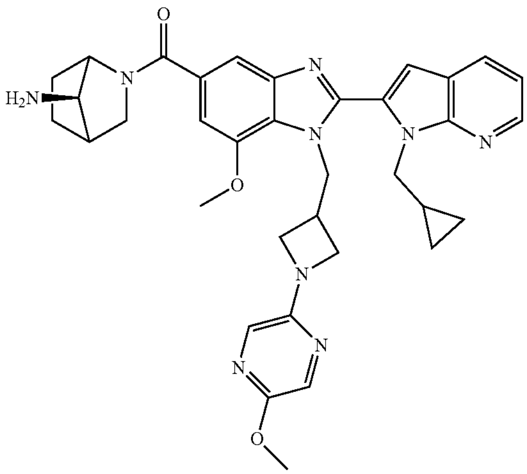 [SMILES: COc1cnc(N2CC(Cn3c(-c4cc5cccnc5n4CC4CC4)nc4cc(C(=O)N5CC6CCC5[C@@H]6N)cc(OC)c43)C2)cn1] | (1R,4R,7R)-2-{2-[1-(cyclopropylmethyl)-1H-pyrrolo[2,3-b]pyridin-2-yl]-7-methoxy-1-{[1-(5-methoxypyrazin-2-yl)azetidin-3-yl]methyl}-1H-1,3-benzodiazole-5-carbonyl}-2-azabicyclo[2.2.1]heptan-7-amine | 1.55 | 1 | 634 |

TABLE 1-continued

| Ex # | Structure | Name | LC/MS Rt (min) | LC/MS Method | M + H (obs ion) |
|---|---|---|---|---|---|
| 34 | 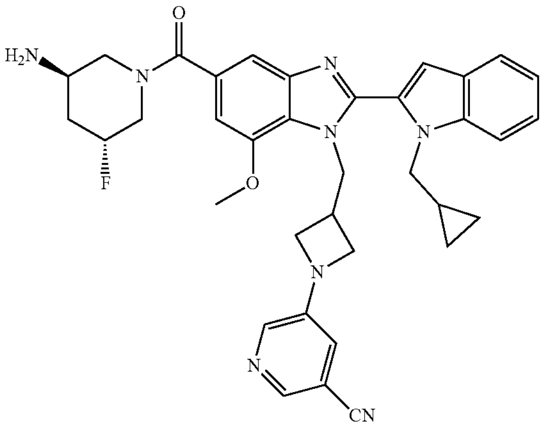 [SMILES: COc1cc(C(=O)N2C[C@H](N)C[C@@H](F)C2)cc2nc(-c3cc4ccccc4n3CC3CC3)n(CC3CN(c4cncc(C#N)c4)C3)c12] | 5-[3-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)azetidin-1-yl]pyridine-3-carbonitrile | 1.69 | 1 | 633 |
| 35 | 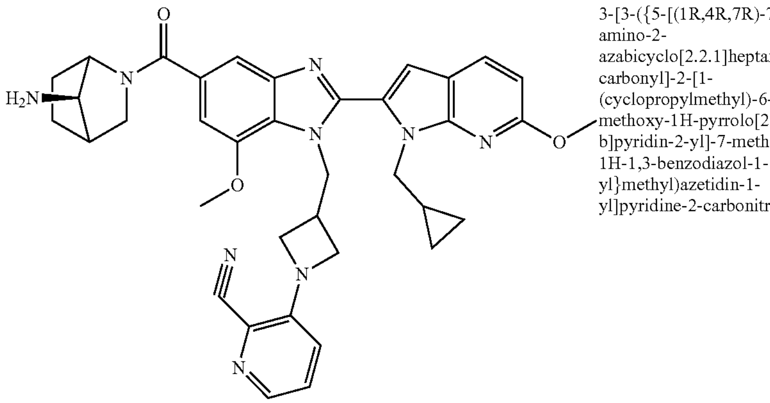 | 3-[3-({5-[(1R,4R,7R)-7-amino-2-azabicyclo[2.2.1]heptane-2-carbonyl]-2-[1-(cyclopropylmethyl)-6-methoxy-1H-pyrrolo[2,3-b]pyridin-2-yl]-7-methoxy-1H-1,3-benzodiazol-1-yl}methyl)azetidin-1-yl]pyridine-2-carbonitrile | 1.81 | 1 | 658 |
| 36 | 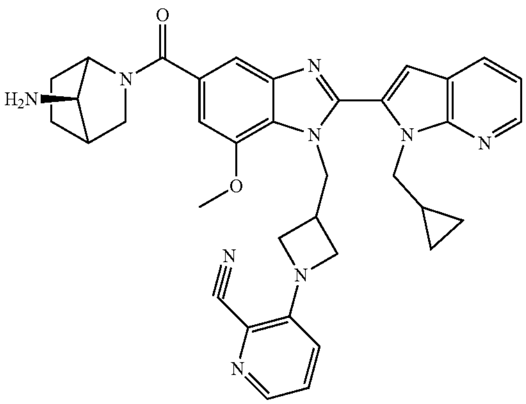 | 3-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyridine-2-carbonitrile | 1.28 | 2 | 628 |

TABLE 1-continued

| Ex # | Structure | Name | LC/MS Rt (min) | LC/MS Method | M + H (obs ion) |
|---|---|---|---|---|---|
| 37 | 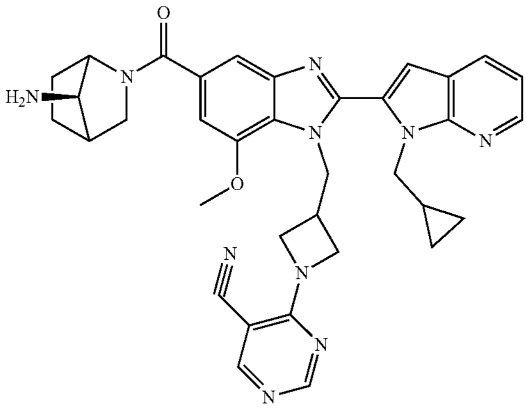 [SMILES: COc1cc(C(=O)N2CC3CCC2[C@@H]3N)cc2nc(-c3cc4cccnc4n3CC3CC3)n(CC3CN(c4ncncc4C#N)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-5-carbonitrile | 1.43 | 1 | 629 |
| 38 | 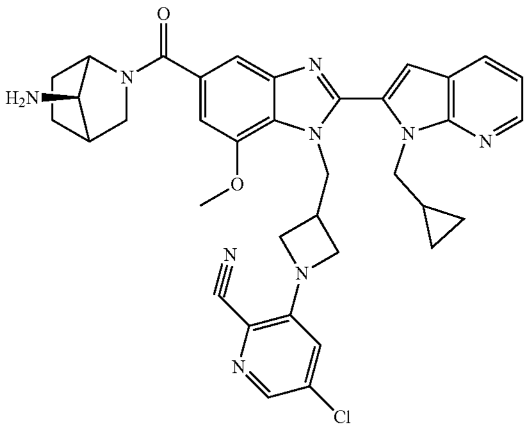 [SMILES: COc1cc(C(=O)N2CC3CCC2[C@@H]3N)cc2nc(-c3cc4cccnc4n3CC3CC3)n(CC3CN(c4cc(Cl)cnc4C#N)C3)c12] | 3-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-l-yl}methyl)azetidin-1-yl]-5-chloropyridine-2-carbonitrile | 1.64 | 2 | 662 |
| 39 | 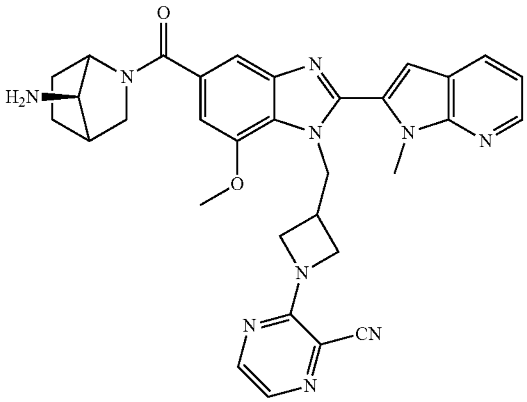 [SMILES: COc1cc(C(=O)N2CC3CCC2[C@@H]3N)cc2nc(-c3cc4cccnc4n3C)n(CC3CN(c4nccnc4C#N)C3)c12] | 3-[3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)azetidin-1-yl]pyrazine-2-carbonitrile | 1.08 | 2 | 589 |

TABLE 1-continued

| Ex # | Structure | Name | LC/MS Rt (min) | LC/MS Method | M + H (obs ion) |
|---|---|---|---|---|---|
| 40 | 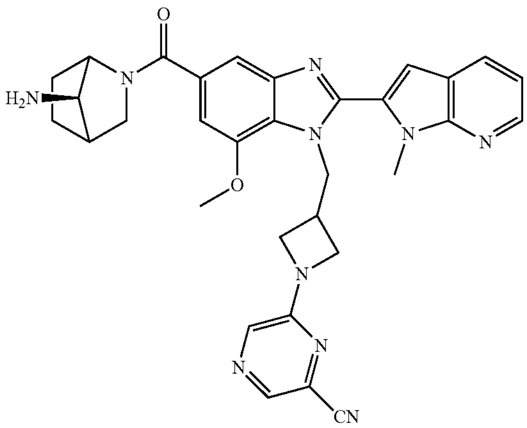 [SMILES: COc1cc(C(=O)N2CC3CCC2[C@@H]3N)cc2nc(-c3cc4cccnc4n3C)n(CC3CN(c4cncc(C#N)n4)C3)c12] | 6-[3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)azetidin-1-yl]pyrazine-2-carbonitrile | 1.32 | 1 | 589 |
| 41 | 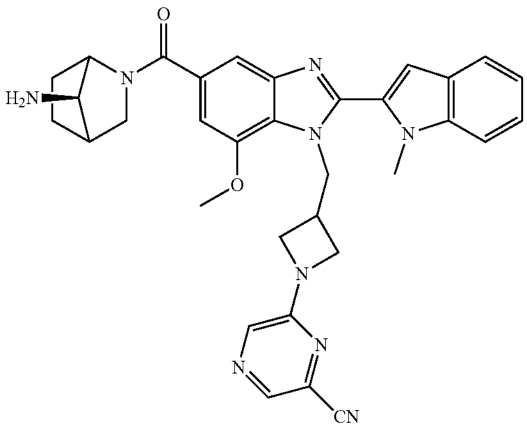 [SMILES: COc1cc(C(=O)N2CC3CCC2[C@@H]3N)cc2nc(-c3cc4ccccc4n3C)n(CC3CN(c4cncc(C#N)n4)C3)c12] | 6-[3-({5-[(1R,4R,7R)-7-amino-2-azabicyclo[2.2.1]heptane-2-carbonyl]-7-methoxy-2-(1-methyl-1H-indol-2-yl)-1H-1,3-benzodiazol-1-yl}methyl)azetidin-1-yl]pyrazine-2-carbonitrile | 1.59 | 1 | 588 |
| 42 | 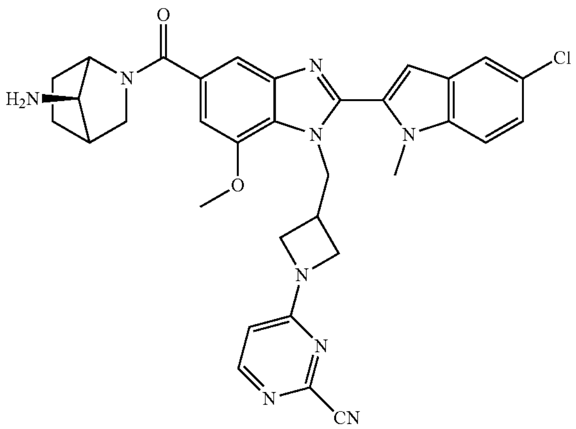 [SMILES: COc1cc(C(=O)N2CC3CCC2[C@@H]3N)cc2nc(-c3cc4cc(Cl)ccc4n3C)n(CC3CN(c4ccnc(C#N)n4)C3)c12] | 4-[3-({5-[(1R,4R,7R)-7-amino-2-azabicyclo[2.2.1]heptane-2-carbonyl]-2-(5-chloro-1-methyl-1H-indol-2-yl)-7-methoxy-1H-1,3-benzodiazol-1-yl}methyl)azetidin-1-yl]pyrimidine-2-carbonitrile | 1.69 | 1 | 622 |

TABLE 1-continued

| Ex # | Structure | Name | LC/MS Rt (min) | LC/MS Method | M + H (obs ion) |
|---|---|---|---|---|---|
| 43 | 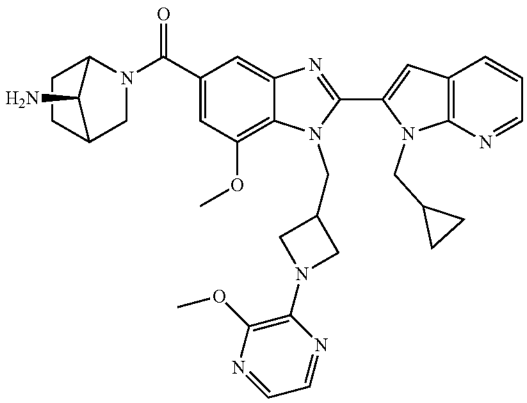 [SMILES: COc1nccnc1N1CC(Cn2c(-c3cc4cccnc4n3CC3CC3)nc3cc(C(=O)N4CC5CCC4[C@@H]5N)cc(OC)c32)C1] | (1R,4R,7R)-2-{2-[1-(cyclopropylmethyl)-1H-pyrrolo[2,3-b]pyridin-2-yl]-7-methoxy-1-{[1-(3-methoxypyrazin-2-yl)azetidin-3-yl]methyl}-1H-1,3-benzodiazole-5-carbonyl}-2-azabicyclo[2.2.1]heptan-7-amine | 1.24 | 2 | 634 |
| 44 | 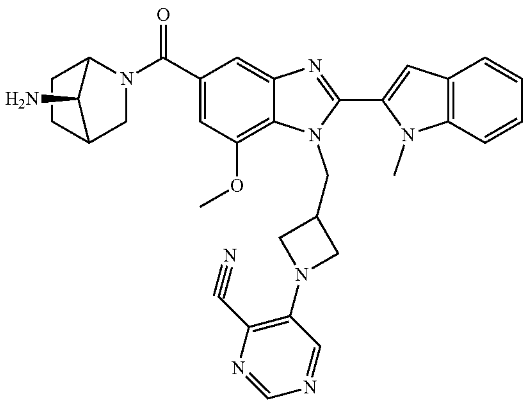 [SMILES: COc1cc(C(=O)N2CC3CCC2[C@@H]3N)cc2nc(-c3cc4ccccc4n3C)n(CC3CN(c4cncnc4C#N)C3)c12] | 5-[3-({5-[(1R,4R,7R)-7-amino-2-azabicyclo[2.2.1]heptane-2-carbonyl]-7-methoxy-2-(1-methyl-1H-indol-2-yl)-1H-1,3-benzodiazol-1-yl}methyl)azetidin-1-yl]pyrimidine-4-carbonitrile | 1.37 | 1 | 588 |
| 45 | 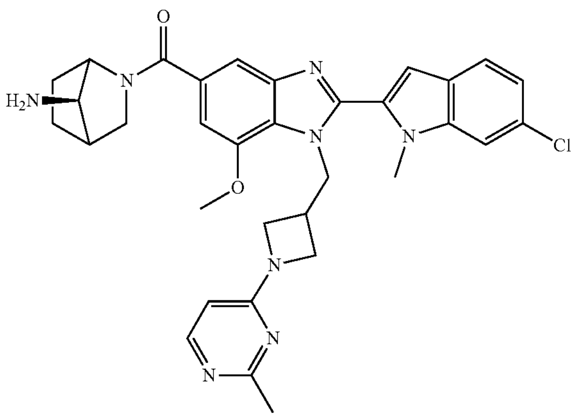 [SMILES: COc1cc(C(=O)N2CC3CCC2[C@@H]3N)cc2nc(-c3cc4ccc(Cl)cc4n3C)n(CC3CN(c4ccnc(C)n4)C3)c12] | (1R,4R,7R)-2-[2-(6-chloro-1-methyl-1H-indol-2-yl)-7-methoxy-1-{[1-(2-methylpyrimidin-4-yl)azetidin-3-yl]methyl}-1H-1,3-benzodiazole-5-carbonyl]-2-azabicyclo[2.2.1]heptan-7-amine | 1.27 | 1 | 611 |

TABLE 1-continued

| Ex # | Structure | Name | LC/MS Rt (min) | LC/MS Method | M + H (obs ion) |
|---|---|---|---|---|---|
| 46 | 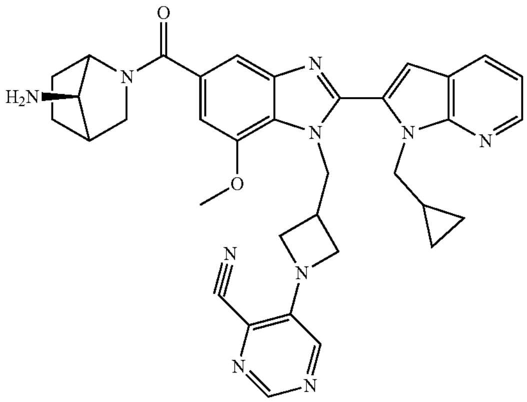 [SMILES: COc1cc(C(=O)N2CC3CCC2[C@@H]3N)cc2nc(-c3cc4cccnc4n3CC3CC3)n(CC3CN(c4cncnc4C#N)C3)c12] | 5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-4-carbonitrile | 1.23 | 2 | 629 |
| 47 | 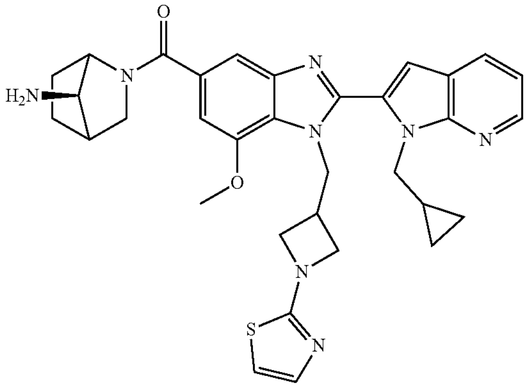 [SMILES: COc1cc(C(=O)N2CC3CCC2[C@@H]3N)cc2nc(-c3cc4cccnc4n3CC3CC3)n(CC3CN(c4nccs4)C3)c12] | (1R,4R,7R)-2-{2-[1-(cyclopropylmethyl)-1H-pyrrolo[2,3-b]pyridin-2-yl]-7-methoxy-1-{[1-(1,3-thiazol-2-yl)azetidin-3-yl]methyl}-1H-1,3-benzodiazole-5-carbonyl}-2-azabicyclo[2.2.1]heptan-7-amine | 1.45 | 1 | 609 |
| 48 | 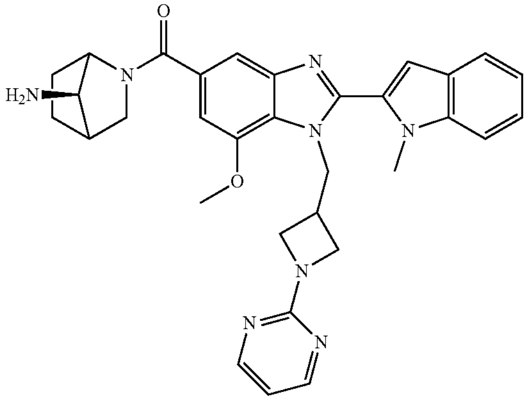 [SMILES: COc1cc(C(=O)N2CC3CCC2[C@@H]3N)cc2nc(-c3cc4ccccc4n3C)n(CC3CN(c4ncccn4)C3)c12] | (1R,4R,7R)-2-[7-methoxy-2-(1-methyl-1H-indol-2-yl)-1-{[1-(pyrimidin-2-yl)azetidin-3-yl]methyl}-1H-1,3-benzodiazole-5-carbonyl]-2-azabicyclo[2.2.1]heptan-7-amine | 1.52 | 1 | 562 |

TABLE 1-continued

| Ex # | Structure | Name | LC/MS Rt (min) | LC/MS Method | M + H (obs ion) |
|---|---|---|---|---|---|
| 49 | 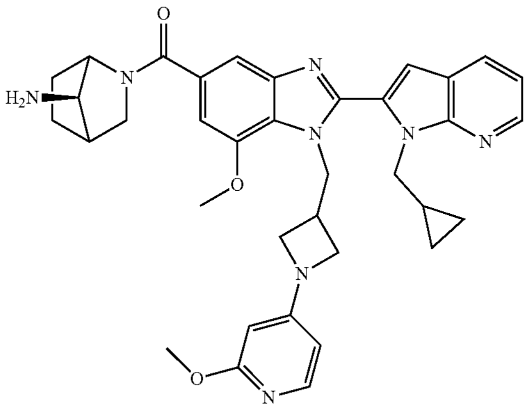 [SMILES: COc1cc(N2CC(Cn3c(-c4cc5cccnc5n4CC4CC4)nc4cc(C(=O)N5CC6CCC5[C@@H]6N)cc(OC)c43)C2)ccn1] | (1R,4R,7R)-2-{2-[1-(cyclopropylmethyl)-1H-pyrrolo[2,3-b]pyridin-2-yl]-7-methoxy-1-{[1-(2-methoxypyridin-4-yl)azetidin-3-yl]methyl}-1H-1,3-benzodiazole-5-carbonyl}-2-azabicyclo[2.2.1]heptan-7-amine | 1.06 | 2 | 633 |
| 50 | 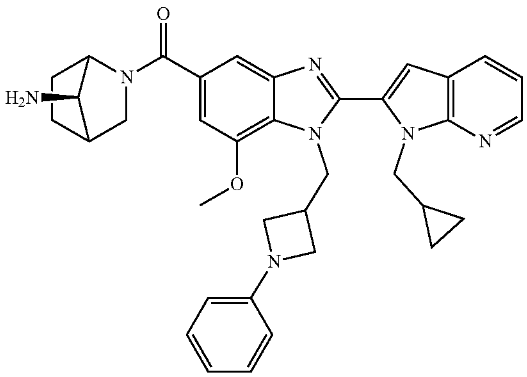 [SMILES: COc1cc(C(=O)N2CC3CCC2[C@@H]3N)cc2nc(-c3cc4cccnc4n3CC3CC3)n(CC3CN(c4ccccc4)C3)c12] | (1R,4R,7R)-2-{2-[1-(cyclopropylmethyl)-1H-pyrrolo[2,3-b]pyridin-2-yl]-7-methoxy-1-[(1-phenylazetidin-3-yl)methyl]-1H-1,3-benzodiazole-5-carbonyl}-2-azabicyclo[2.2.1]heptan-7-amine | 1.66 | 2 | 602 |
| 51 | 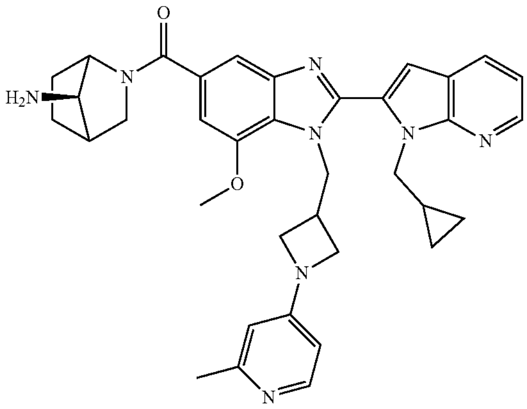 [SMILES: COc1cc(C(=O)N2CC3CCC2[C@@H]3N)cc2nc(-c3cc4cccnc4n3CC3CC3)n(CC3CN(c4ccnc(C)c4)C3)c12] | (1R,4R,7R)-2-{2-[1-(cyclopropylmethyl)-1H-pyrrolo[2,3-b]pyridin-2-yl]-7-methoxy-1-{[1-(2-methylpyridin-4-yl)azetidin-3-yl]methyl}-1H-1,3-benzodiazole-5-carbonyl}-2-azabicyclo[2.2.1]heptan-7-amine | 1.19 | 1 | 617 |

TABLE 1-continued

| Ex # | Structure | Name | LC/MS Rt (min) | LC/MS Method | M + H (obs ion) |
|---|---|---|---|---|---|
| 52 | 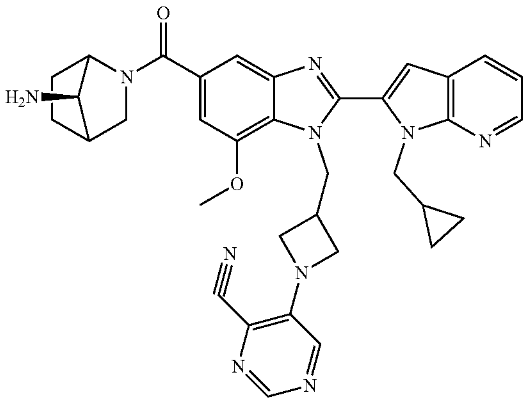 [SMILES: COc1cc(C(=O)N2CC3CCC2[C@@H]3N)cc2nc(-c3cc4cccnc4n3CC3CC3)n(CC3CN(c4cncnc4C#N)C3)c12] | 5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pyrimidine-4-carbonitrile | 1.39 | 1 | 629 |
| 53 | 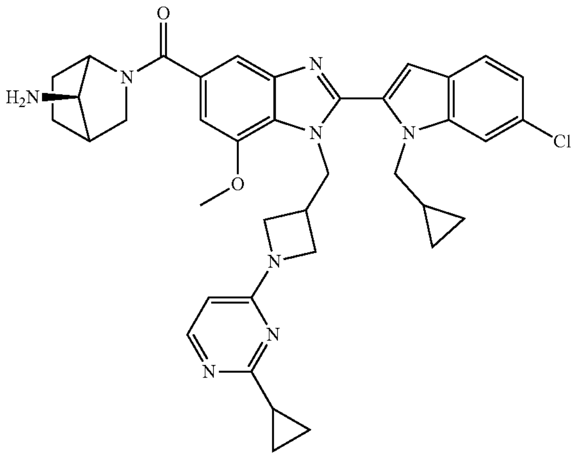 [SMILES: COc1cc(C(=O)N2CC3CCC2[C@@H]3N)cc2nc(-c3cc4ccc(Cl)cc4n3CC3CC3)n(CC3CN(c4ccnc(C5CC5)n4)C3)c12] | (1R,4R,7R)-2-{2-[6-chloro-1-(cyclopropylmethyl)-1H-indol-2-yl]-1-{[1-(2-cyclopropylpyrimidin-4-yl)azetidin-3-yl]methyl}-7-methoxy-1H-1,3-benzodiazole-5-carbonyl}-2-azabicyclo[2.2.1]heptan-7-amine | 1.52 | 2 | 677 |
| 54 | 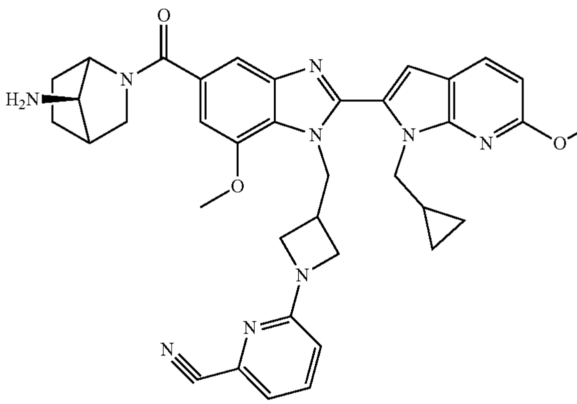 | 6-[3-({5-[(1R,4R,7R)-7-amino-2-azabicyclo[2.2.1]heptane-2-carbonyl]-2-[1-(cyclopropylmethyl)-6-methoxy-1H-pyrrolo[2,3-b]pyridin-2-yl]-7-methoxy-1H-1,3-benzodiazol-1-yl}methyl)azetidin-1-yl]pyridine-2-carbonitrile | 1.93 | 1 | 658 |

TABLE 1-continued

| Ex # | Structure | Name | LC/MS Rt (min) | LC/MS Method | M + H (obs ion) |
|---|---|---|---|---|---|
| 55 | 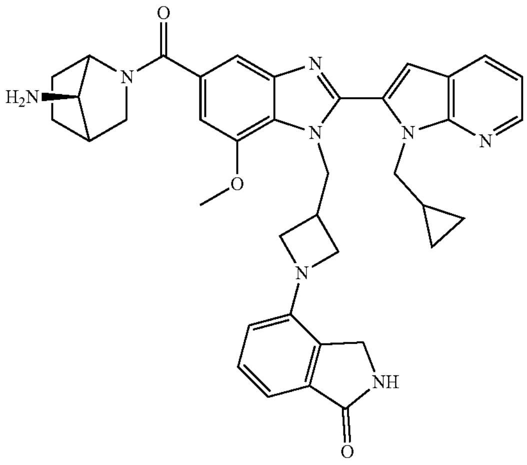 [SMILES: COc1cc(C(=O)N2CC3CCC2[C@@H]3N)cc2nc(-c3cc4cccnc4n3CC3CC3)n(CC3CN(c4cccc5c4CNC5=O)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-2,3-dihydro-1H-isoindol-1-one | 1.19 | 2 | 657 |
| 56 | 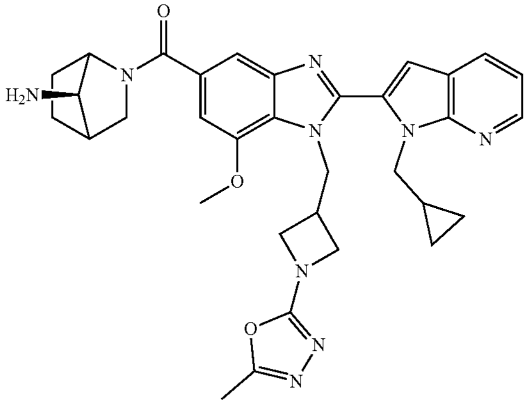 [SMILES: COc1cc(C(=O)N2CC3CCC2[C@@H]3N)cc2nc(-c3cc4cccnc4n3CC3CC3)n(CC3CN(c4nnc(C)o4)C3)c12] | (1R,4R,7R)-2-{2-[1-(cyclopropylmethyl)-1H-pyrrolo[2,3-b]pyridin-2-yl]-7-methoxy-1-{[1-(5-methyl-1,3,4-oxadiazol-2-yl)azetidin-3-yl]methyl}-1H-1,3-benzodiazole-5-carbonyl}-2-azabicyclo[2.2.1]heptan-7-amine | 1.18 | 1 | 608 |
| 57 | 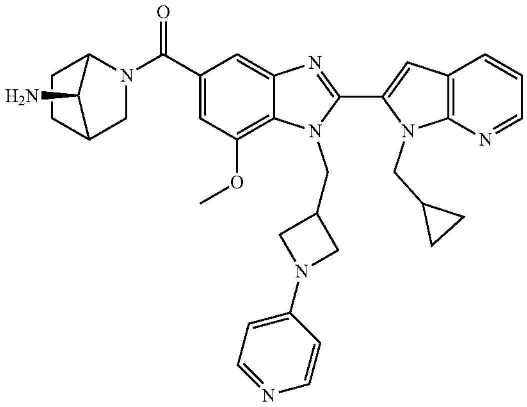 [SMILES: COc1cc(C(=O)N2CC3CCC2[C@@H]3N)cc2nc(-c3cc4cccnc4n3CC3CC3)n(CC3CN(c4ccncc4)C3)c12] | (1R,4R,7R)-2-{2-[1-(cyclopropylmethyl)-1H-pyrrolo[2,3-b]pyridin-2-yl]-7-methoxy-1-{[1-(pyridin-4-yl)azetidin-3-yl]methyl}-1H-1,3-benzodiazole-5-carbonyl}-2-azabicyclo[2.2.1]heptan-7-amine | 0.99 | 1 | 603 |

TABLE 1-continued

| Ex # | Structure | Name | LC/MS Rt (min) | LC/MS Method | M + H (obs ion) |
|---|---|---|---|---|---|
| 58 | 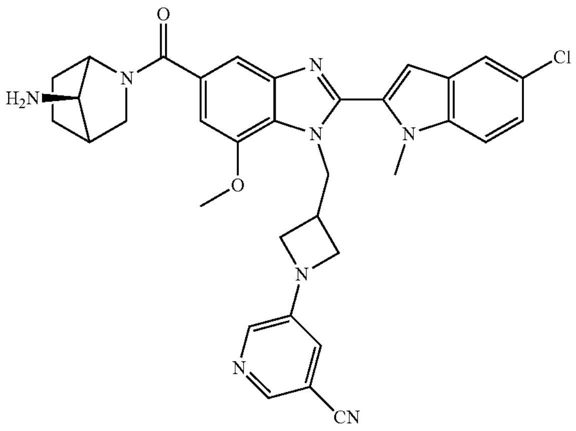 [SMILES: COc1cc(C(=O)N2CC3CCC2[C@@H]3N)cc2nc(-c3cc4cc(Cl)ccc4n3C)n(CC3CN(c4cncc(C#N)c4)C3)c12] | 5-[3-({5-[(1R,4R,7R)-7-amino-2-azabicyclo[2.2.1]heptane-2-carbonyl]-2-(5-chloro-1-methyl-1H-indol-2-yl)-7-methoxy-1H-1,3-benzodiazol-1-yl}methyl)azetidin-1-yl]pyridine-3-carbonitrile | 1.69 | 1 | 621 |
| 59 | 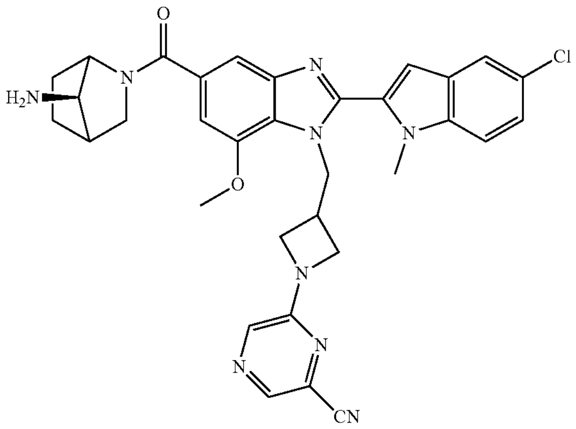 | 6-[3-({5-[(1R,4R,7R)-7-amino-2-azabicyclo[2.2.1]heptane-2-carbonyl]-2-(5-chloro-1-methyl-1H-indol-2-yl)-7-methoxy-1H-1,3-benzodiazol-1-yl}methyl)azetidin-1-yl]pyrazine-2-carbonitrile | 1.65 | 1 | 622 |
| 60 | 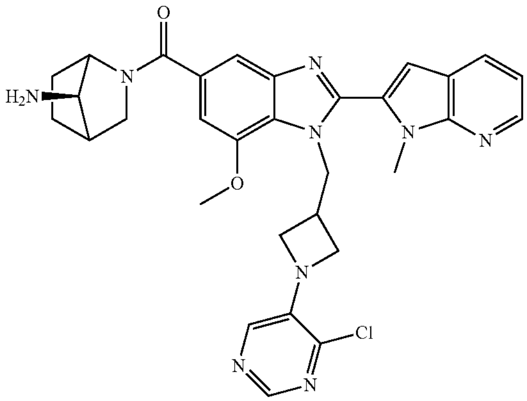 [SMILES: COc1cc(C(=O)N2CC3CCC2[C@@H]3N)cc2nc(-c3cc4cccnc4n3C)n(CC3CN(c4cncnc4Cl)C3)c12] | 5-[3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)azetidin-1-yl]pyrimidine-4-carbonitrile | 1.04 | 2 | 589 |

TABLE 1-continued

| Ex # | Structure | Name | LC/MS Rt (min) | LC/MS Method | M + H (obs ion) |
|---|---|---|---|---|---|
| 61 | 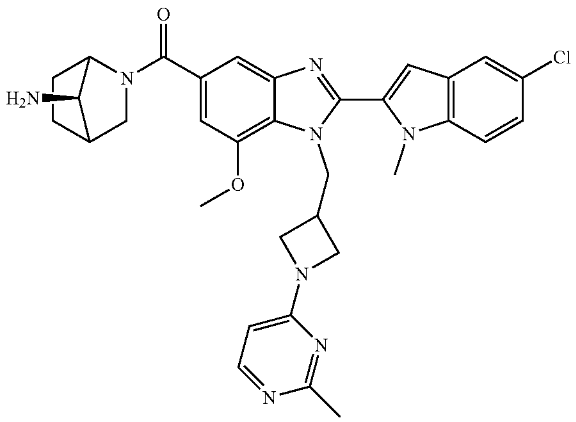 [SMILES: COc1cc(C(=O)N2CC3CCC2[C@@H]3N)cc2nc(-c3cc4cc(Cl)ccc4n3C)n(CC3CN(c4ccnc(C)n4)C3)c12] | (1R,4R,7R)-2-[2-(5-chloro-1-methyl-1H-indol-2-yl)-7-methoxy-1-{[1-(2-methylpyrimidin-4-yl)azetidin-3-yl]methyl}-1H-1,3-benzodiazole-5-carbonyl]-2-azabicyclo[2.2.1]heptan-7-amine | 1.42 | 1 | 611 |
| 62 | 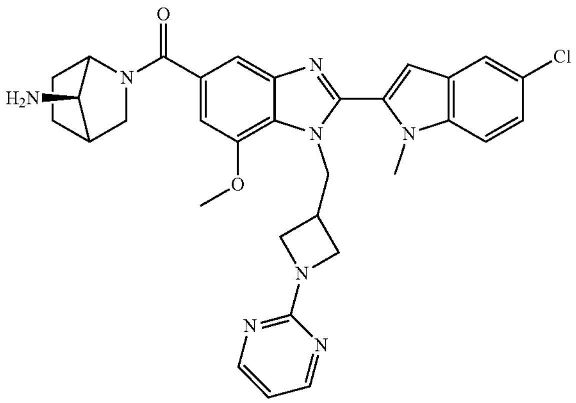 [SMILES: COc1cc(C(=O)N2CC3CCC2[C@@H]3N)cc2nc(-c3cc4cc(Cl)ccc4n3C)n(CC3CN(c4ncccn4)C3)c12] | (1R,4R,7R)-2-[2-(5-chloro-1-methyl-1H-indol-2-yl)-7-methoxy-1-{[1-(pyrimidin-2-yl)azetidin-3-yl]methyl}-1H-1,3-benzodiazole-5-carbonyl]-2-azabicyclo[2.2.1]heptan-7-amine | 1.54 | 1 | 597 |
| 63 | 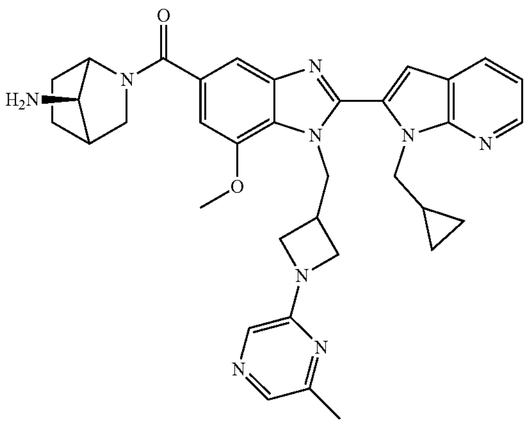 [SMILES: COc1cc(C(=O)N2CC3CCC2[C@@H]3N)cc2nc(-c3cc4cccnc4n3CC3CC3)n(CC3CN(c4cncc(C)n4)C3)c12] | (1R,4R,7R)-2-{2-[1-(cyclopropylmethyl)-1H-pyrrolo[2,3-b]pyridin-2-yl]-7-methoxy-1-{[1-(6-methylpyrazin-2-yl)azetidin-3-yl]methyl}-1H-1,3-benzodiazole-5-carbonyl}-2-azabicyclo[2.2.1]heptan-7-amine | 1.41 | 1 | 618 |

TABLE 1-continued

| Ex # | Structure | Name | LC/MS Rt (min) | LC/MS Method | M + H (obs ion) |
|---|---|---|---|---|---|
| 64 | 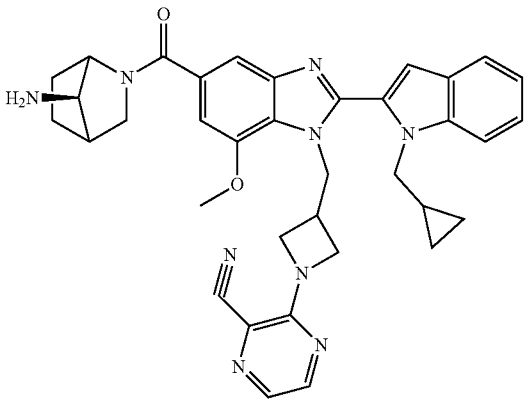 [SMILES: COc1cc(C(=O)N2CC3CCC2[C@@H]3N)cc2nc(-c3cc4ccccc4n3CC3CC3)n(CC3CN(c4nccnc4C#N)C3)c12] | 3-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyrazine-2-carbonitrile | 1.67 | 2 | 628 |
| 65 | 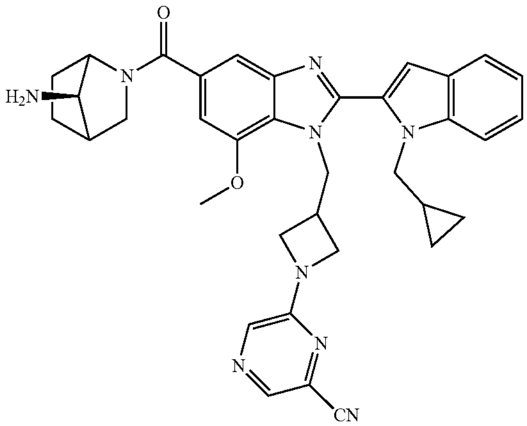 | 6-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyrazine-2-carbonitrile | 1.67 | 2 | 628 |
| 66 | 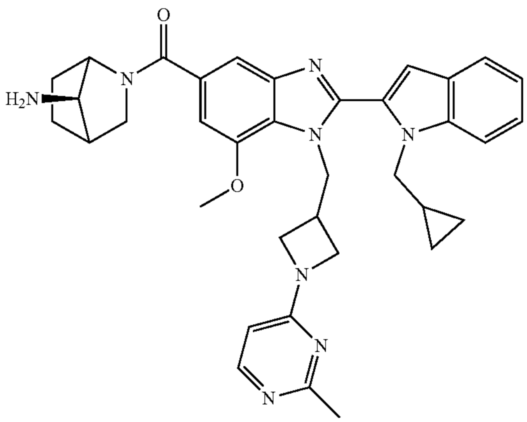 | (1R,4R,7R)-2-{2-[1-(cyclopropylmethyl)-1H-indol-2-yl]-7-methoxy-1-{[1-(2-methylpyrimidin-4-yl)azetidin-3-yl]methyl}-1H-1,3-benzodiazole-5-carbonyl}-2-azabicyclo[2.2.1]heptan-7-amine | 1.63 | 1 | 617 |

TABLE 1-continued

| Ex # | Structure | Name | LC/MS Rt (min) | LC/MS Method | M + H (obs ion) |
|---|---|---|---|---|---|
| 67 | 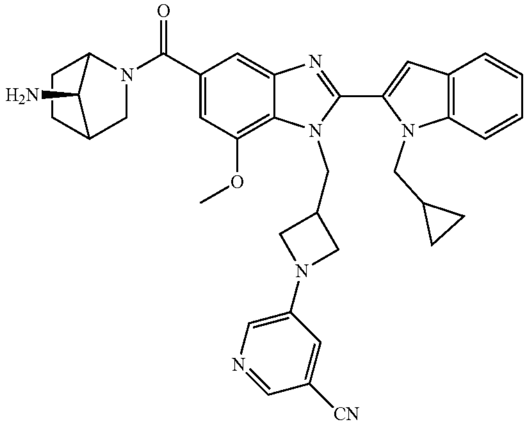 [SMILES: COc1cc(C(=O)N2CC3CCC2[C@@H]3N)cc2nc(-c3cc4ccccc4n3CC3CC3)n(CC3CN(c4cncc(C#N)n4)C3)c12] | 5-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidin-1-yl]pyridine-3-carbonitrile | 1.75 | 1 | 627 |
| 68 | 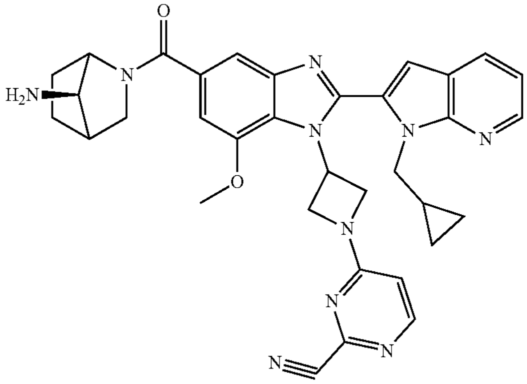 [SMILES: COc1cc(C(=O)N2CC3CCC2[C@@H]3N)cc2nc(-c3cc4cccnc4n3CC3CC3)n(C3CN(c4ccnc(C#N)n4)C3)c12] | 4-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyrimidine-2-carbonitrile | 1.33 | 2 | 615 |
| 69 | 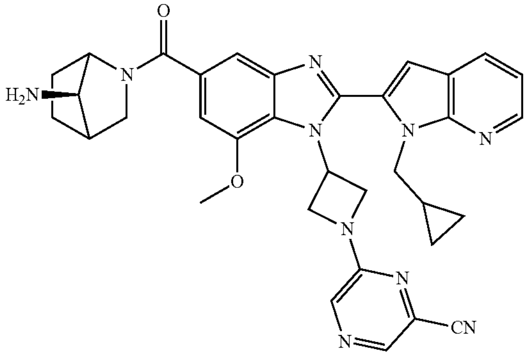 [SMILES: COc1cc(C(=O)N2CC3CCC2[C@@H]3N)cc2nc(-c3cc4cccnc4n3CC3CC3)n(C3CN(c4cncc(C#N)n4)C3)c12] | 6-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyrazine-2-carbonitrile | 1.54 | 1 | 615 |
| 70 | 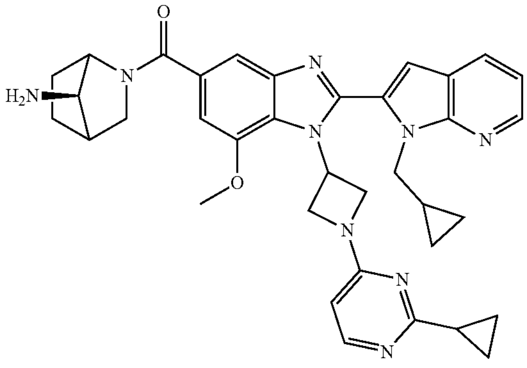 [SMILES: COc1cc(C(=O)N2CC3CCC2[C@@H]3N)cc2nc(-c3cc4cccnc4n3CC3CC3)n(C3CN(c4ccnc(C5CC5)n4)C3)c12] | (1R,4R,7R)-2-{2-[1-(cyclopropylmethyl)-1H-pyrrolo[2,3-b]pyridin-2-yl]-1-[1-(2-cyclopropylpyrimidin-4-yl)azetidin-3-yl]-7-methoxy-1H-1,3-benzodiazole-5-carbonyl}-2-azabicyclo[2.2.1]heptan-7-amine | 1.23 | 2 | 630 |

TABLE 1-continued

| Ex # | Structure | Name | LC/MS Rt (min) | LC/MS Method | M + H (obs ion) |
|---|---|---|---|---|---|
| 71 | 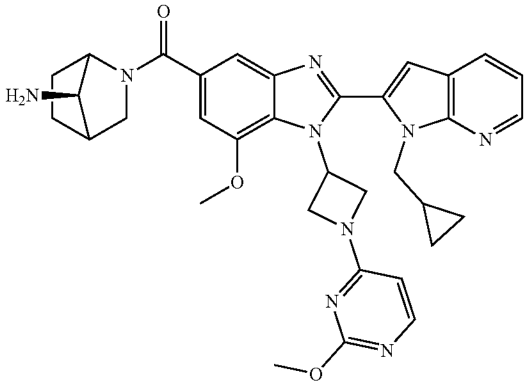 [SMILES: COc1nccc(N2CC(n3c(-c4cc5cccnc5n4CC4CC4)nc4cc(C(=O)N5CC6CCC5[C@@H]6N)cc(OC)c43)C2)n1] | (1R,4R,7R)-2-{2-[1-(cyclopropylmethyl)-1H-pyrrolo[2,3-b]pyridin-2-yl]-7-methoxy-1-[1-(2-methoxypyrimidin-4-yl)azetidin-3-yl]-1H-1,3-benzodiazole-5-carbonyl}-2-azabicyclo[2.2.1]heptan-7-amine | 1.55 | 1 | 620 |
| 72 | 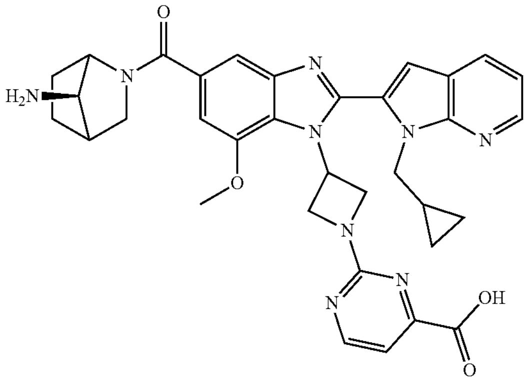 [SMILES: COc1cc(C(=O)N2CC3CCC2[C@@H]3N)cc2nc(-c3cc4cccnc4n3CC3CC3)n(C3CN(c4nccc(C(=O)O)n4)C3)c12] | 2-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyrimidine-4-carboxylic acid | 1.18 | 2 | 634 |
| 73 | 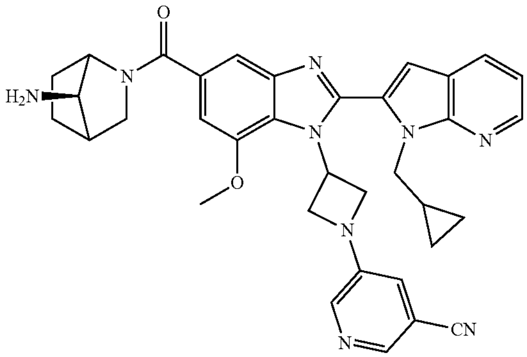 [SMILES: COc1cc(C(=O)N2CC3CCC2[C@@H]3N)cc2nc(-c3cc4cccnc4n3CC3CC3)n(C3CN(c4cncc(C#N)c4)C3)c12] | 5-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyridine-3-carbonitrile | 1.33 | 2 | 614 |
| 74 | 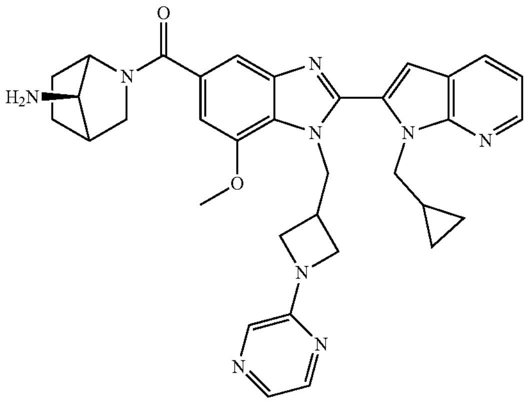 [SMILES: COc1cc(C(=O)N2CC3CCC2[C@@H]3N)cc2nc(-c3cc4cccnc4n3CC3CC3)n(CC3CN(c4cnccn4)C3)c12] | (1R,4R,7R)-2-{2-[1-(cyclopropylmethyl)-1H-pyrrolo[2,3-b]pyridin-2-yl]-7-methoxy-1-{[1-(pyrazin-2-yl)azetidin-3-yl]methyl}-1H-1,3-benzodiazole-5-carbonyl}-2-azabicyclo[2.2.1]heptan-7-amine | 1.43 | 1 | 604 |

TABLE 1-continued

| Ex # | Structure | Name | LC/MS Rt (min) | LC/MS Method | M + H (obs ion) |
|---|---|---|---|---|---|
| 75 | 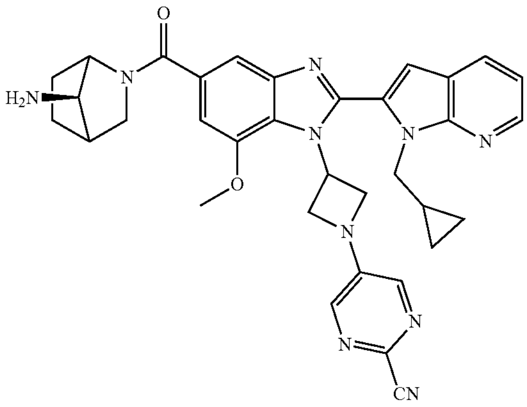 [SMILES: COc1cc(C(=O)N2CC3CCC2[C@@H]3N)cc2nc(-c3cc4cccnc4n3CC3CC3)n(C3CN(c4cnc(C#N)nc4)C3)c12] | 5-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyrimidine-2-carbonitrile | 1.43 | 1 | 615 |
| 76 | 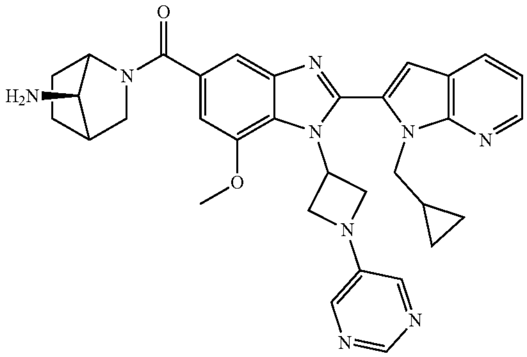 [SMILES: COc1cc(C(=O)N2CC3CCC2[C@@H]3N)cc2nc(-c3cc4cccnc4n3CC3CC3)n(C3CN(c4cncnc4)C3)c12] | (1R,4R,7R)-2-{2-[1-(cyclopropylmethyl)-1H-pyrrolo[2,3-b]pyridin-2-yl]-7-methoxy-1-[1-(pyrimidin-5-yl)azetidin-3-yl]-1H-1,3-benzodiazole-5-carbonyl}-2-azabicyclo[2.2.1]heptan-7-amine | 1.17 | 2 | 590 |
| 77 | 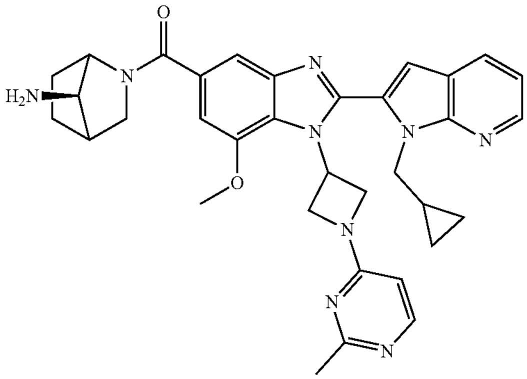 [SMILES: COc1cc(C(=O)N2CC3CCC2[C@@H]3N)cc2nc(-c3cc4cccnc4n3CC3CC3)n(C3CN(c4ccnc(C)n4)C3)c12] | (1R,4R,7R)-2-{2-[1-(cyclopropylmethyl)-1H-pyrrolo[2,3-b]pyridin-2-yl]-7-methoxy-1-[1-(2-methylpyrimidin-4-yl)azetidin-3-yl]-1H-1,3-benzodiazole-5-carbonyl}-2-azabicyclo[2.2.1]heptan-7-amine | 1.26 | 1 | 604 |
| 78 | 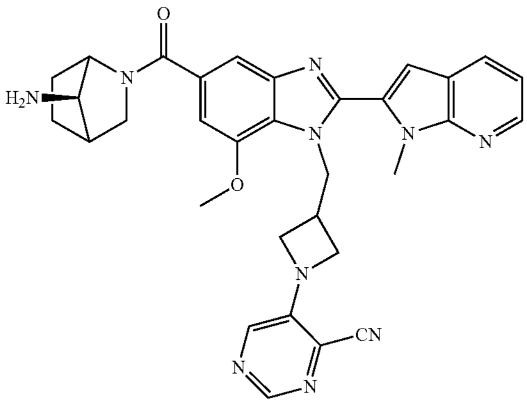 [SMILES: COc1cc(C(=O)N2CC3CCC2[C@@H]3N)cc2nc(-c3cc4cccnc4n3C)n(CC3CN(c4cncnc4C#N)C3)c12] | 5-[3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)azetidin-1-yl]pyrimidine-4-carbonitrile | 1.13 | 1 | 589 |

TABLE 1-continued

| Ex # | Structure | Name | LC/MS Rt (min) | LC/MS Method | M + H (obs ion) |
|---|---|---|---|---|---|
| 79 | 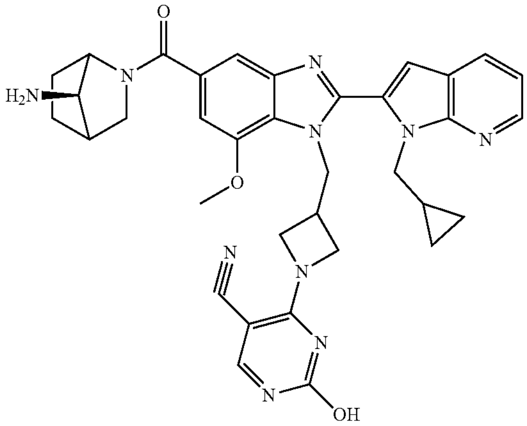 [SMILES: COc1cc(C(=O)N2CC3CCC2[C@@H]3N)cc2nc(-c3cc4cccnc4n3CC3CC3)n(CC3CN(c4nc(O)ncc4C#N)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-2-hydroxypyrimidine-5-carbonitrile | 1.09 | 1 | 645 |
| 80 | 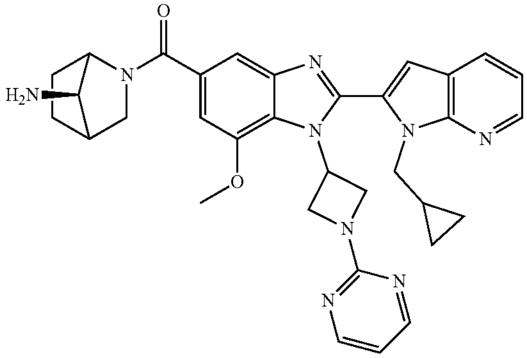 [SMILES: COc1cc(C(=O)N2CC3CCC2[C@@H]3N)cc2nc(-c3cc4cccnc4n3CC3CC3)n(C3CN(c4ncccn4)C3)c12] | (1R,4R,7R)-2-{2-[1-(cyclopropylmethyl)-1H-pyrrolo[2,3-b]pyridin-2-yl]-7-methoxy-1-[1-(pyrimidin-2-yl)azetidin-3-yl]-1H-1,3-benzodiazole-5-carbonyl}-2-azabicyclo[2.2.1]heptan-7-amine | 1.27 | 1 | 590 |
| 81 | 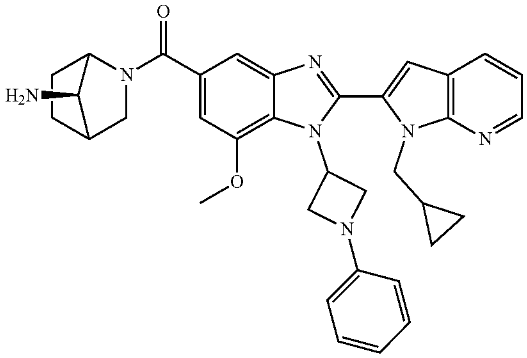 [SMILES: COc1cc(C(=O)N2CC3CCC2[C@@H]3N)cc2nc(-c3cc4cccnc4n3CC3CC3)n(C3CN(c4ccccc4)C3)c12] | (1R,4R,7R)-2-{2-[1-(cyclopropylmethyl)-1H-pyrrolo[2,3-b]pyridin-2-yl]-7-methoxy-1-(1-phenylazetidin-3-yl)-1H-1,3-benzodiazole-5-carbonyl}-2-azabicyclo[2.2.1]heptan-7-amine | 1.72 | 2 | 588 |
| 82 | 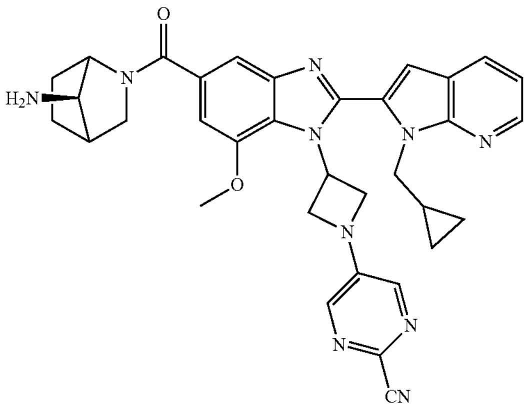 [SMILES: COc1cc(C(=O)N2CC3CCC2[C@@H]3N)cc2nc(-c3cc4cccnc4n3CC3CC3)n(C3CN(c4cnc(C#N)nc4)C3)c12] | 5-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)pyrimidine-2-carbonitrile | 1.32 | 2 | 615 |

TABLE 1-continued

| Ex # | Structure | Name | LC/MS Rt (min) | LC/MS Method | M + H (obs ion) |
|---|---|---|---|---|---|
| 83 | 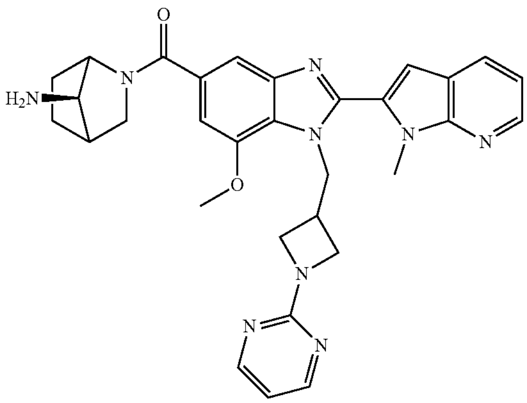 [SMILES: COc1cc(C(=O)N2CC3CCC2[C@@H]3N)cc2nc(-c3cc4cccnc4n3C)n(CC3CN(c4ncccn4)C3)c12] | (1R,4R,7R)-2-(7-methoxy-2-{1-methyl-1H-pyrrolo[2,3-b]pyridin-2-yl}-1-{[1-(pyrimidin-2-yl)azetidin-3-yl]methyl}-1H-1,3-benzodiazole-5-carbonyl)-2-azabicyclo[2.2.1]heptan-7-amine | 1.12 | 1 | 564 |
| 84 | 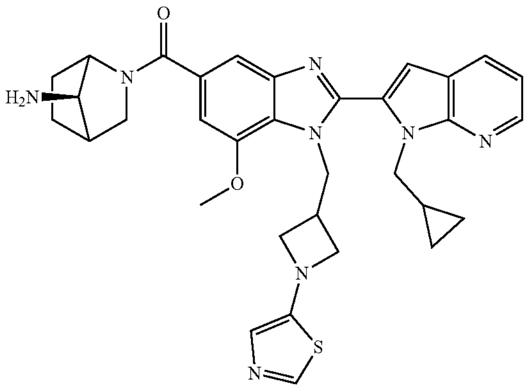 [SMILES: COc1cc(C(=O)N2CC3CCC2[C@@H]3N)cc2nc(-c3cc4cccnc4n3CC3CC3)n(CC3CN(c4cncs4)C3)c12] | (1R,4R,7R)-2-{2-[1-(cyclopropylmethyl)-1H-pyrrolo[2,3-b]pyridin-2-yl]-7-methoxy-1-{[1-(1,3-thiazol-5-yl)azetidin-3-yl]methyl}-1H-1,3-benzodiazole-5-carbonyl}-2-azabicyclo[2.2.1]heptan-7-amine | 1.49 | 1 | 609 |
| 85 | 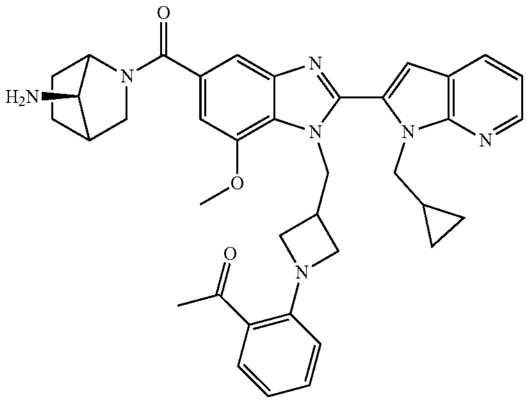 [SMILES: COc1cc(C(=O)N2CC3CCC2[C@@H]3N)cc2nc(-c3cc4cccnc4n3CC3CC3)n(CC3CN(c4ccccc4C(C)=O)C3)c12] | 1-{2-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]phenyl}ethan-1-one | 1.38 | 2 | 644 |

TABLE 1-continued

| Ex # | Structure | Name | LC/MS Rt (min) | LC/MS Method | M + H (obs ion) |
|---|---|---|---|---|---|
| 86 | 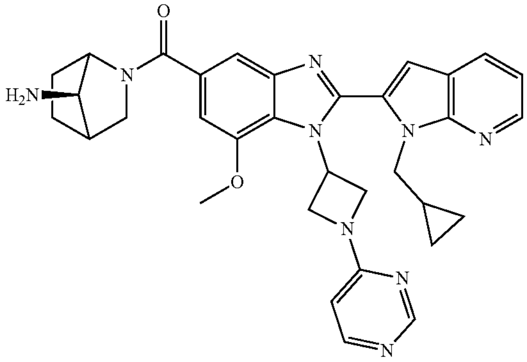 [SMILES: COc1cc(C(=O)N2CC3CCC2[C@@H]3N)cc2nc(-c3cc4cccnc4n3CC3CC3)n(C3CN(c4ccncn4)C3)c12] | (1R,4R,7R)-2-{2-[1-(cyclopropylmethyl)-1H-pyrrolo[2,3-b]pyridin-2-yl]-7-methoxy-1-[1-(pyrimidin-4-yl)azetidin-3-yl]-1H-1,3-benzodiazole-5-carbonyl}-2-azabicyclo[2.2.1]heptan-7-amine | 0.97 | 2 | 590 |
| 87 | 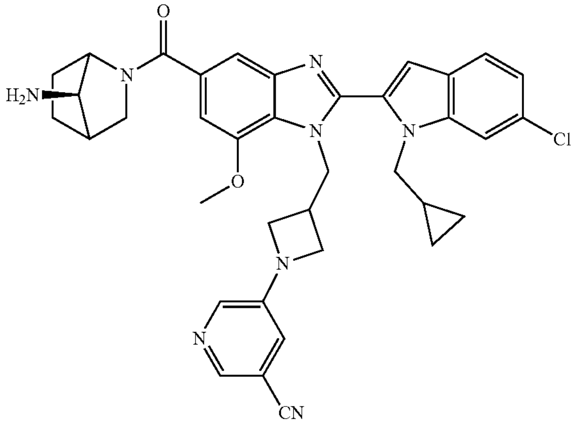 [SMILES: COc1cc(C(=O)N2CC3CCC2[C@@H]3N)cc2nc(-c3cc4ccc(Cl)cc4n3CC3CC3)n(CC3CN(c4cncc(C#N)c4)C3)c12] | 5-[3-({5-[(1R,4R,7R)-7-amino-2-azabicyclo[2.2.1]heptane-2-carbonyl]-2-[6-chloro-1-(cyclopropylmethyl)-1H-indol-2-yl]-7-methoxy-1H-1,3-benzodiazol-1-yl}methyl)azetidin-1-yl]pyridine-3-carbonitrile | 2.04 | 1 | 660 |

Example 88

(1R,4R,7R)-2-{1-[(1-benzoylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine

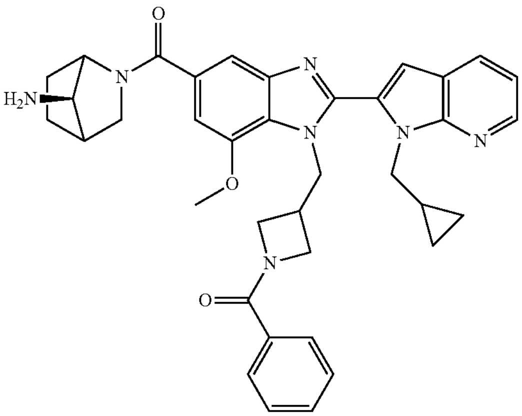 [SMILES: COc1cc(C(=O)N2CC3CCC2[C@@H]3N)cc2nc(-c3cc4cccnc4n3CC3CC3)n(CC3CN(C(=O)c4ccccc4)C3)c12]

To a solution tert-butyl ((1R,4R,7R)-2-(1-(azetidin-3-ylmethyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate, intermediate 3D (10 mg, 0.016 mmol) and TEA (0.011 mL, 0.080 mmol) in DCM (1.0 mL) at 0° C. was added a solution of benzoyl chloride (2.246 mg, 0.016 mmol) in DCM (0.1 mL), the mixture was stirred at 0° C. for 30 min. The mixture was concentrated to give crude tert-butyl ((1R,4R,7R)-2-(1-((1-benzoylazetidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-benzoylazetidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate in DCM (1.0 mL) and TFA (1.0 mL), the mixture was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 12% B, 12-52% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. (1R,4R,7R)-2-{1-[(1-benzoylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine (6.7 mg, 10.6 μmol, 66.5%) was isolated.

LC/MS (2M+H): 630; LC retention time: 1.45 min (analytical HPLC Method 2). $^1$H NMR (499 MHz, methanol-$d_4$) δ 8.47-8.40 (m, 1H), 8.19-8.12 (m, 1H), 7.55-7.44 (m, 2H), 7.41-7.31 (m, 4H), 7.29-7.23 (m, 1H), 7.12-7.04 (m, 2H), 5.06-4.95 (m, 2H), 4.51-4.42 (m, 2H), 4.40-4.33 (m, 1H), 4.32-4.23 (m, 1H), 4.20-4.11 (m, 1H), 4.08-4.03 (m, 3H), 3.99-3.93 (m, 1H), 3.93-3.80 (m, 2H), 3.79-3.63 (m, 1H), 3.52-3.39 (m, 1H), 3.31-3.07 (m, 3H), 2.45-2.24 (m, 1H), 2.16-1.87 (m, 3H), 1.72-1.45 (m, 1H), 0.97-0.83 (m, 1H), 0.34-0.23 (m, 2H), 0.17--0.03 (m, 2H).

Example 89

(3-((5-((1R,4R,7R)-7-amino-2-azabicyclo[2.2.1]heptane-2-carbonyl)-7-chloro-2-(1-(cyclopropylmethyl)-1H-pyrrolo[2,3-b]pyridin-2-yl)-1H-benzo[d]imidazol-1-yl)methyl)azetidin-1-yl)phenyl)methanone

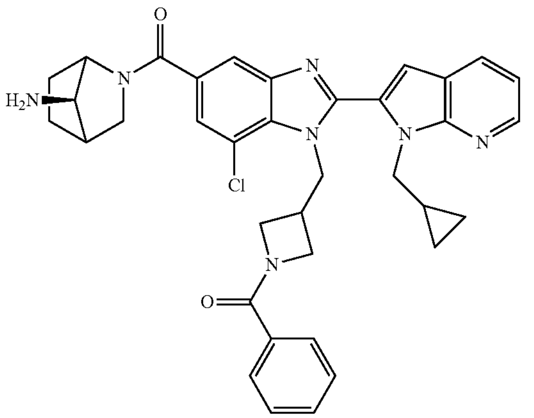 [SMILES: N[C@@H]1C2CCC1N(C(=O)c1cc(Cl)c3c(c1)nc(-c1cc4cccnc4n1CC1CC1)n3CC1CN(C(=O)c3ccccc3)C1)C2]

Intermediate 89A: Tert-butyl 3-(((2-chloro-4-(methoxycarbonyl)-6-nitrophenyl)amino)methyl)azetidine-1-carboxylate

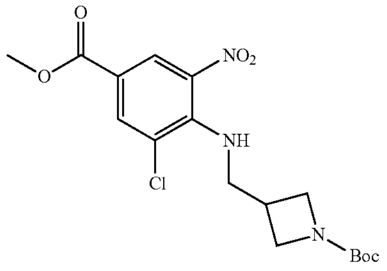 [SMILES: COC(=O)c1cc(Cl)c(NCC2CN(C(=O)OC(C)(C)C)C2)c([N+](=O)[O-])c1]

A mixture of methyl 3,4-dichloro-5-nitrobenzoate (430 mg, 1.720 mmol), tert-butyl 3-(aminomethyl)azetidine-1-carboxylate (320 mg, 1.720 mmol) and potassium carbonate (713 mg, 5.16 mmol) in DMF (10 mL) was stirred at RT for 18 hours. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient) to yield tert-butyl 3-(((2-chloro-4-(methoxycarbonyl)-6-nitrophenyl)amino)methyl)azetidine-1-carboxylate (481 mg, 1.143 mmol, 66.5% yield) as light brown gum. LC/MS (2M+H): 799; LC retention time: 1.06 min (analytical HPLC Method 3). $^1$H NMR (499 MHz, chloroform-d) δ 8.66 (d, J=2.1 Hz, 1H), 8.16 (d, J=2.0 Hz, 1H), 4.12-4.06 (m, 2H), 3.98-3.88 (m, 3H), 3.81 (dd, J=7.3, 5.5 Hz, 2H), 3.68 (dd, J=8.9, 5.0 Hz, 2H), 2.83 (quint, J=7.7, 5.0 Hz, 1H), 1.49-1.40 (m, 9H).

Intermediate 89B: Methyl 1-((1-(tert-butoxycarbonyl)azetidin-3-yl)methyl)-7-chloro-2-(1-(cyclopropylmethyl)-1H-pyrrolo[2,3-b]pyridin-2-yl)-1H-benzo[d]imidazole-5-carboxylate

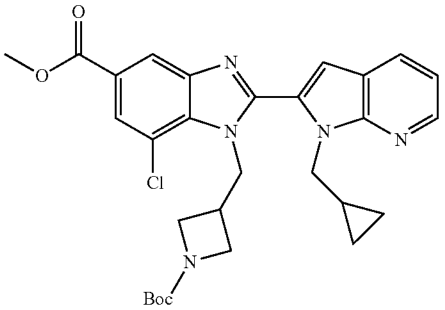 [SMILES: COC(=O)c1cc(Cl)c2c(c1)nc(-c1cc3cccnc3n1CC1CC1)n2CC1CN(C(=O)OC(C)(C)C)C1]

To a solution of tert-butyl 3-(((2-chloro-4-(methoxycarbonyl)-6-nitrophenyl)amino)methyl)azetidine-1-carboxylate (733 mg, 1.833 mmol) and 1-(cyclopropylmethyl)-1H-pyrrolo[2,3-b]pyridine-2-carbaldehyde (367 mg, 1.833 mmol) in EtOH (6.0 mL) was added a solution of sodium dithionite (958 mg, 5.50 mmol) in water (3.00 mL), the mixture was stirred at 80° C. for 18 hours. The mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient) to yield methyl 1-((1-(tert-butoxycarbonyl)azetidin-3-yl)methyl)-7-chloro-2-(1-(cyclopropylmethyl)-1H-pyrrolo[2,3-b]pyridin-2-yl)-1H-benzo[d]imidazole-5-carboxylate (718 mg, 1.240 mmol, 67.6% yield) as off-white foam. LC/MS (2M+H): 550; LC retention time: 1.14 mm (analytical HPLC Method 3). $^1$H NMR (499 MHz, CHLOROFORM-d) δ 8.50 (d, 0.7=4.9 Hz, 1H), 8.48 (s, 1H), 8.08 (s, 1H), 8.05 (d, J 7.8 Hz, 1H), 7.20 (dd, J=7.9, 4.6 Hz, 1H), 6.88 (s, 1H), 5.06 (d, 0.7=7.3 Hz, 2H), 4.56 (br d, 0.7=6.1 Hz, 2H), 4.03-3.97 (m, 3H), 3.94-3.80 (m, 2H), 3.51 (br s, 2H), 3.06-2.98 (m, 1H), 1.31 (s, 9H), 1.13-1.05 (m, 1H), 0.41-0.34 (m, 2H), 0.29-0.23 (m, 2H).

Intermediate 89C: 1-((1-(tert-butoxycarbonyl)azetidin-3-yl)methyl)-7-chloro-2-(1-(cyclopropylmethyl)-1H-pyrrolo[2,3-b]pyridin-2-yl)-1H-benzo[d]imidazole-5-carboxylic acid

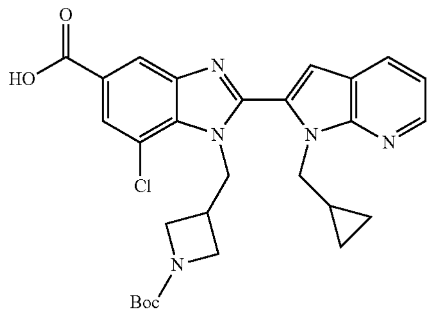 [SMILES: CC(C)(C)OC(=O)N1CC(Cn2c(-c3cc4cccnc4n3CC3CC3)nc3cc(C(=O)O)cc(Cl)c32)C1]

A mixture of methyl 1-((1-(tert-butoxycarbonyl)azetidin-3-yl)methyl)-7-chloro-2-(1-(cyclopropylmethyl)-1H-pyrrolo[2,3-b]pyridin-2-yl)-1H-benzo[d]imidazole-5-carboxylate (85 mg, 0.154 mmol) and 1.0 M aqueous sodium hydroxide (0.825 mL, 0.825 mmol) in THF (5.0 mL) was stirred at 50° C. for 18 hours. A solution of 1.0 N aqueous HCl (0.83 mL) was added and the mixture was concentrated. The mixture was extracted with EtOAc (15 mL) and the organic layer was dried over sodium sulfate and concentrated to give a crude yield of 1-((1-(tert-butoxycarbonyl) azetidin-3-yl)methyl)-7-chloro-2-(1-(cyclopropylmethyl)-1H-pyrrolo[2,3-b]pyridin-2-yl)-1H-benzo[d]imidazole-5-carboxylic acid (78 mg, 0.131 mmol, 79% yield) as white solid. LC/MS (2M+H): 536; LC retention time: 0.96 min (analytical HPLC Method 3).

Example 89: (3-((5-((1R,4R,7R)-7-amino-2-azabicyclo[2.2.1]heptane-2-carbonyl)-7-chloro-2-(1-(cyclopropylmethyl)-1H-pyrrolo[2,3-b]pyridin-2-yl)-1H-benzo[d]imidazol-1-yl)methyl)azetidin-1-yl)(phenyl)methanone A mixture of 1-((1-(tert-butoxycarbonyl)azetidin-3-yl) methyl)-7-chloro-2-(1-(cyclopropylmethyl)-1H-pyrrolo[2,3-b]pyridin-2-yl)-1H-benzo[d]imidazole-5-carboxylic acid (15 mg, 0.028 mmol) in DCM (1.0 mL) and TFA (1.0 mL) was stirred at RT for 30 min. The mixture was concentrated to give crude 1-(azetidin-3-ylmethyl)-7-chloro-2-(1-(cyclopropylmethyl)-1H-pyrrolo[2,3-b]pyridin-2-yl)-1H-benzo[d] imidazole-5-carboxylic acid. Material was used as is in next reaction.

To a solution of 1-(azetidin-3-ylmethyl)-7-chloro-2-(1-(cyclopropylmethyl)-1H-pyrrolo[2,3-b]pyridin-2-yl)-1H-benzo[d]imidazole-5-carboxylic acid and TEA (0.023 mL, 0.168 mmol) in DCM (1.0 mL) was added a solution of benzoyl chloride (3.93 mg, 0.028 mmol) in DCM (0.10 mL), and the mixture was stirred at RT for 1 hour. The resulting mixture was concentrated to give crude 1-((1-benzoylazetidin-3-yl)methyl)-7-chloro-2-(1-(cyclopropylmethyl)-1H-pyrrolo[2,3-b]pyridin-2-yl)-1H-benzo[d]imidazole-5-carboxylic acid. Material was used as is in next reaction.

A mixture of 1-((1-benzoylazetidin-3-yl)methyl)-7-chloro-2-(1-(cyclopropylmethyl)-1H-pyrrolo[2,3-b]pyridin-2-yl)-1H-benzo[d]imidazole-5-carboxylic acid, tert-butyl ((1R,4R,7R)-2-azabicyclo[2.2.1]heptan-7-yl)carbamate (5.94 mg, 0.028 mmol), BOP (12.38 mg, 0.028 mmol) and TEA (0.023 mL, 0.168 mmol) in DMF (3.0 mL) was stirred at RT for 2 hours. The mixture was diluted with EtOAc (5 mL) and was washed with a solution of aqueous saturated sodium bicarbonate (2×5 mL). The organic layer was dried over sodium sulfate and concentrated to give crude tert-butyl ((1R,4R,7R)-2-(1-((1-benzoylazetidin-3-yl)methyl)-7-chloro-2-(1-(cyclopropylmethyl)-1H-pyrrolo[2,3-b]pyridin-2-yl)-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-benzoylazetidin-3-yl)methyl)-7-chloro-2-(1-(cyclopropylmethyl)-1H-pyrrolo[2,3-b]pyridin-2-yl)-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 13% B, 13-53% B over 20 minutes, then a 6-minute hold at 100% B; Flow Rate: 20 mL/mm; Column Temperature: 25 C. Fraction collection was triggered by MS signals. Fractions containing the desired product were combined and dried via centrifugal evaporation. (1R,4R,7R)-2-{1-[(1-benzoylazetidin-3-yl)methyl]-7-chloro-2-[1-(cyclopropylmethyl)-1H-pyrrolo[2,3-b]pyridin-2-yl]-1H-1,3-benzodiazole-5-carbonyl}-2-azabicyclo[2.2.1]heptan-7-amine (10.4 mg, 16.4 µmol, 58.6%) was isolated. LC/MS (M+H): 634; LC retention time: 1.61 min (analytical HPLC Method 1). $^1$H NMR (500 MHz, DMSO-$d_6$) δ 8.35 (d, J=4.0 Hz, 1H), 8.06 (d, J=7.8 Hz, 1H), 7.90-7.77 (m, 1H), 7.69 (s, 1H), 7.46-7.35 (m, 1H), 7.31 (t, J=7.6 Hz, 1H), 7.19-7.05 (m, 5H), 5.00 (br d, J=6.6 Hz, 2H), 4.43-4.23 (m, 2H), 4.12-3.85 (m, 2H), 3.76-3.55 (m, 2H), 3.28-2.84 (m, 2H), 2.83-2.74 (m, 2H), 2.67-2.59 (m, 2H), 2.19-2.01 (m, 1H), 1.95-1.51 (m, 2H), 1.42-1.07 (m, 1H), 0.92-0.71 (m, 1H), 0.23--0.11 (m, 4H).

Example 90

4-[3-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)azetidine-1-carbonyl]benzonitrile

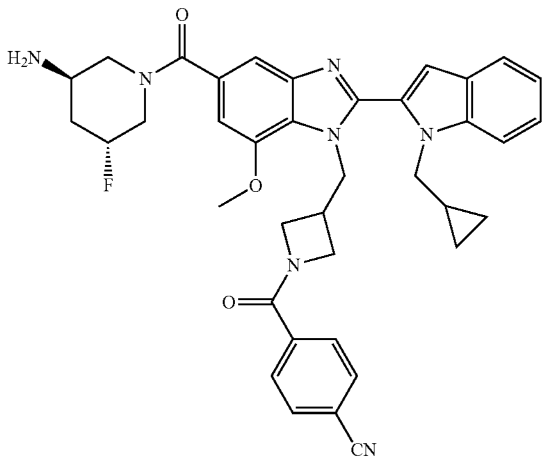 [SMILES: COc1cc(C(=O)N2C[C@H](N)C[C@@H](F)C2)cc2nc(-c3cc4ccccc4n3CC3CC3)n(CC3CN(C(=O)c4ccc(C#N)cc4)C3)c12]

To a solution of tert-butyl ((3R,5R)-1-(1-(azetidin-3-ylmethyl)-2-(1-(cyclopropylmethyl)-1H-indol-2-yl)-7-methoxy-1H-benzo[d]imidazole-5-carbonyl)-5-fluoropiperidin-3-yl)carbamate, intermediate 4B (10 mg, 0.016 mmol) and TEA (6.63 µl, 0.048 mmol) in DCM (1.0 mL) was added 4-cyanobenzoyl chloride (2.63 mg, 0.016 mmol), and the mixture was stirred at RT for 60 min. The mixture was concentrated to give crude tert-butyl ((3R,5R)-1-(1-((1-(4-cyanobenzoyl)azetidin-3-yl)methyl)-2-(1-(cyclopropylmethyl)-1H-indol-2-yl)-7-methoxy-1H-benzo[d]imidazole-5-carbonyl)-5-fluoropiperidin-3-yl)carbamate. Material was used as is in next reaction.

A mixture of tert-butyl ((3R,5R)-1-(1-((1-(4-cyanobenzoyl)azetidin-3-yl)methyl)-2-(1-(cyclopropylmethyl)-1H-indol-2-yl)-7-methoxy-1H-benzo[d]imidazole-5-carbonyl)-5-fluoropiperidin-3-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 4-minute hold at 0.100% B; Flow Rate: 20 mL/min; Column Temperature: 25 C. Fraction collection was triggered by MS and UV signals. Fractions containing the desired product were combined and dried via centrifugal evaporation, 4-[3-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)azetidine-1-carbonyl]benzonitrile (6.7 mg, 10.2 µmol, 63.5%) was isolated. LC/MS (M+H): 660; LC retention time: 1.60 min (analytical HPLC Method 1). $^1$H NMR (500 MHz, DMSO-$d_6$) δ 7.90-7.52 (m, 1H), 7.39 (br d, J=7.9 Hz, 2H), 7.29-7.17 (m, 2H), 7.07 (br t, J=7.3 Hz, 1H), 6.97 (s, 1H), 6.80 (s, 1H), 4.82 (br d, J=6.7 Hz, 2H), 4.52-3.72 (m, 7H), 3.67-3.52 (m, 1H), 3.00-2.74 (m, 3H), 2.69-2.57 (m, 1H), 2.15-1.99 (m, 1H), 1.88-1.73 (m, 2H), 1.60-0.50 (m, 4H), 0.28-−0.13 (m, 4H).

To a solution tert-butyl ((1R,4R,7R)-2-(1-(azetidin-3-ylmethyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate (10 mg, 0.016 mmol) and TEA (0.011 mL, 0.080 mmol) in DCM (1.0 mL) at 0° C. was added a solution of 4-cyanobenzoic acid (2.355 mg, 0.016 mmol) in DCM (0.1 mL), and the mixture was stirred at 0° C. for 30 min. The resulting mixture was concentrated to give crude tert-butyl ((1R,4R,7R)-2-(1-((1-(4-cyanobenzoyl)azetidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(4-cyanobenzoyl)azetidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate in DCM (1.0 mL) and IT A (1.0 mL) was stirred at RT for 30 min. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 17% B, 17-57% B over 20 minutes, then a 6-minute hold at 100% B; Flow Rate: 20 mL/min; Column Temperature: 25 C. Fraction collection was triggered by MS signals. Fractions containing the desired product were combined and dried via centrifugal evaporation. 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzonitrile (7.9 mg, 12.1 µmol, 75.5%) was isolated. LC/MS (2M+H): 654; LC retention time: 1.06 min (analytical HPLC Method 2). $^1$H NMR (500 MHz, DMSO-$d_6$) δ 7.88-7.50 (m, 4H), 7.44-7.17 (m, 4H), 7.09-7.01 (m, 1H), 6.98-6.79 (m, 2H), 4.80 (br s, 2H), 4.35-3.75 (m, 6H), 3.73-3.36 (m, 2H), 3.13-2.73 (m, 4H), 2.67-2.57 (m, 2H), 2.20-1.51 (m, 3H), 1.43-0.66 (m, 3H), 0.27-0.09 (m, 2H), 0.06-−0.13 (m, 2H).

Example 91

4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzonitrile

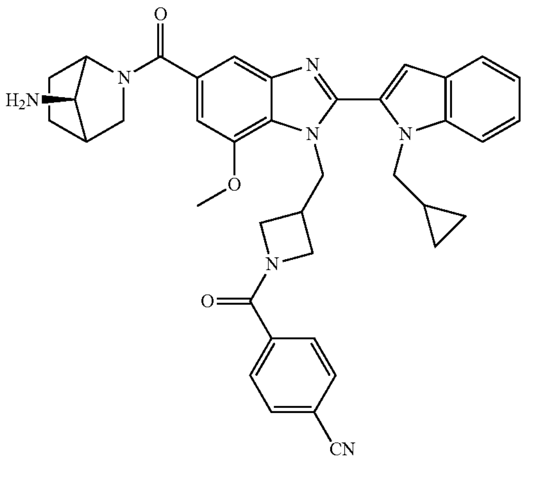 [SMILES: COc1cc(C(=O)N2CC3CCC2[C@@H]3N)cc2nc(-c3cc4ccccc4n3CC3CC3)n(CC3CN(C(=O)c4ccc(C#N)cc4)C3)c12]

Example 92

4-(3-((5-((1R,4R,7R)-7-amino-2-azabicyclo[2.2.1]heptane-2-carbonyl)-2-(1-(cyclopropylmethyl)-1H-indol-2-yl)-7-fluoro-1H-benzo[d]imidazol-1-yl)methyl)azetidine-1-carbonyl)benzonitrile

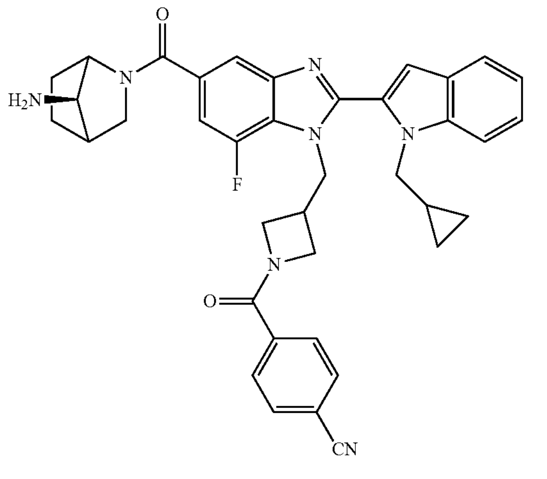 [SMILES: N#Cc1ccc(C(=O)N2CC(Cn3c(-c4cc5ccccc5n4CC4CC4)nc4cc(C(=O)N5CC6CCC5[C@@H]6N)cc(F)c43)C2)cc1]

Intermediate 92A: Benzyl 3-(((2-fluoro-4-(methoxycarbonyl)-6-nitrophenyl)amino)methyl)azetidine-1-carboxylate

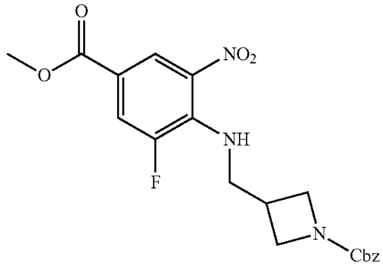 [SMILES: COC(=O)c1cc(F)c(NCC2CN(C(=O)OCc3ccccc3)C2)c([N+](=O)[O-])c1]

A mixture of methyl 4-chloro-3-fluoro-5-nitrobenzoate (600 mg, 2.57 mmol), benzyl 3-(aminomethyl)azetidine-1-carboxylate (566 mg, 2.57 mmol) and potassium carbonate (1065 mg, 7.71 mmol) in DMF (10 mL) was stirred at RT for 3 days. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient) to yield benzyl 3-(((2-fluoro-4-(methoxycarbonyl)-6-nitrophenyl)amino)methyl)azetidine-1-carboxylate (1.02 mg, 2.322 μmol, 0.090% yield) as light brown gum. LC/MS (M+H): 418; LC retention time: 1.00 min (analytical HPLC Method 3).

Intermediate 92B: 1-((1-((benzyloxy)carbonyl)azetidin-3-yl)methyl)-2-(1-(cyclopropylmethyl)-1H-indol-2-yl)-7-fluoro-1H-benzo[d]imidazole-5-carboxylic acid

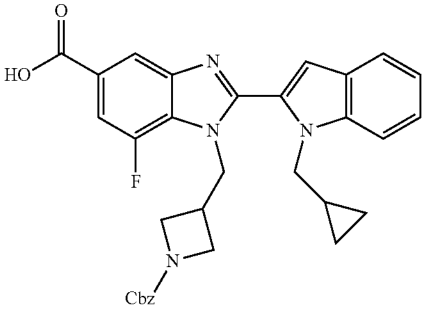 [SMILES: O=C(O)c1cc(F)c2c(c1)nc(-c1cc3ccccc3n1CC1CC1)n2CC1CN(C(=O)OCc2ccccc2)C1]

To a solution of benzyl 3-(((2-fluoro-4-(methoxycarbonyl)-6-nitrophenyl)amino)methyl)azetidine-1-carboxylate (60 mg, 0.144 mmol) and 1-(cyclopropylmethyl)-1H-indole-2-carbaldehyde (28.6 mg, 0.144 mmol) in EtOH (3.0 mL) was added a solution of sodium dithionite (75 mg, 0.431 mmol) in water (1.5 mL), and the mixture was stirred at 80° C. for 18 hours. The mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient) to yield methyl 1-((1-((benzyloxy)carbonyl)azetidin-3-yl)methyl)-2-(1-(cyclopropylmethyl)-1H-indol-2-yl)-7-fluoro-1H-benzo[d]imidazole-5-carboxylate as white solid. LC/MS (M+H): 567; LC retention time: 1.12 min (analytical HPLC Method 3). Material was used as is in next reaction.

A mixture of methyl 1-((1-((benzyloxy)carbonyl)azetidin-3-yl)methyl)-2-(1-(cyclopropylmethyl)-1H-indol-2-yl)-7-fluoro-1H-benzo[d]imidazole-5-carboxylate and 1.0 M aqueous sodium hydroxide (0.719 mL, 0.719 mmol) in THE (5.0 mL) was stirred at 50° C. for 18 hours. A solution of 1.0 N aqueous HCl (0.72 mL) was added and the mixture was concentrated. The mixture was extracted with EtOAc (15 mL) and the organic layer was dried over sodium sulfate and concentrated to give a crude yield of 1-((1-((benzyloxy)carbonyl)azetidin-3-yl)methyl)-2-(1-(cyclopropylmethyl)-1H-indol-2-yl)-7-fluoro-1H-benzo[d]imidazole-5-carboxylic acid (66 mg, 0.107 mmol, 74.8% yield) as white solid. LC/MS (M+H): 553; LC retention time: 1.59 min (analytical HPLC Method 4).

Intermediate 92C: Tert-butyl ((1R,4R,7R)-2-(1-(azetidin-3-ylmethyl)-2-(1-(cyclopropylmethyl)-1H-indol-2-yl)-7-fluoro-1H-benzo[d]imidazole-5-carbonyl)-2-azabicyclo[2.2.1]heptan-7-yl) carbamate

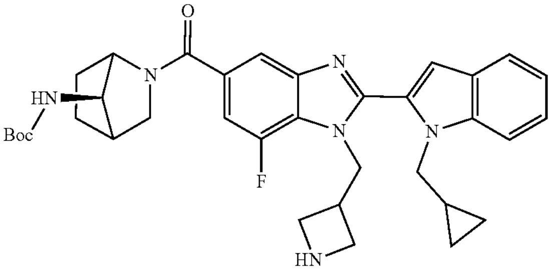 [SMILES: CC(C)(C)OC(=O)N[C@@H]1C2CCC1N(C(=O)c1cc(F)c3c(c1)nc(-c1cc4ccccc4n1CC1CC1)n3CC1CNC1)C2]

A mixture of 1-((1-((benzyloxy)carbonyl)azetidin-3-yl)methyl)-2-(1-(cyclopropylmethyl)-1H-indol-2-yl)-7-fluoro-1H-benzo[d]imidazole-5-carboxylic acid (66 mg, 0.119 mmol), tert-butyl ((7R)-2-azabicyclo[2.2.1]heptan-7-yl)carbamate (25.4 mg, 0.119 mmol), BOP (52.8 mg, 0.119 mmol) and TEA (0.083 mL, 0.597 mmol) in DMF (3.0 mL) was stirred at RT for 2 hours. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to give benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-indol-2-yl)-7-fluoro-1H-benzo[d]imidazol-1-yl)methyl)azetidine-1-carboxylate. LC/MS (M+H): 747; LC retention time: 1.08 min (analytical HPLC Method 3). Material was used as is in next reaction.

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-indol-2-yl)-7-fluoro-1H-benzo[d]imidazol-1-yl)methyl)azetidine-1-carboxylate and 10% palladium on carbon (12.71 mg, 0.012 mmol) in MeOH (5.0 mL) was hydrogenated under 1 atm of hydrogen for 18 hours. Pd/C was filtered off and the filtrate was concentrated to give a crude yield of tert-butyl ((1R,4R,7R)-2-(1-(azetidin-3-ylmethyl)-2-(1-(cyclopropylmethyl)-1H-indol-2-yl)-7-fluoro-1H-benzo[d]imidazole-5-carbonyl)-2-azabicyclo[2.2.1]heptan-7-yl)carbamate (60 mg, 0.088 mmol, 73.8% yield) as white solid. LC/MS (M+H): 613; LC retention time: 0.77 min (analytical HPLC Method 3).

Example 92: 4-(3-((5-((1R,4R,7R)-7-amino-2-azabicyclo[2.2.1]heptane-2-carbonyl)-2-(1-(cyclopropylmethyl)-1H-indol-2-yl)-7-fluoro-1H-benzo[d]imidazol-1-yl)methyl)azetidine-1-carbonyl)benzonitrile To a solution of tert-butyl ((1R,4R,7R)-2-(1-(azetidin-3-ylmethyl)-2-(1-(cyclopropylmethyl)-1H-indol-2-yl)-7-fluoro-1H-benzo[d]imidazole-5-carbonyl)-2-azabicyclo[2.2.1]heptan-7-yl)carbamate (10 mg, 0.016 mmol) and TEA (0.011 mg, 0.082 mmol) in DCM (1.0 mL) was added a solution of 4-cyanobenzoyl chloride (2.70 mg, 0.016 mmol) in DCM (0.10 mL), and the mixture was stirred at RT for 30 min. The mixture was concentrated to give crude tert-butyl ((1R,4R,7R)-2-(1-((1-(4-cyanobenzoyl)azetidin-3-yl)methyl)-2-(1-(cyclopropylmethyl)-1H-indol-2-yl)-7-fluoro-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(4-cyanobenzoyl)azetidin-3-yl)methyl)-2-(1-(cyclopropylmethyl)-1H-indol-2-yl)-7-fluoro-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 10-μM ammonium acetate; Mobile Phase B: 95:5 acetonitrile:water with 10-mM ammonium acetate; Gradient: a 0-minute hold at 19% B, 19-59% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. 4-[3-({5-[(1R,4R,7R)-7-amino-2-azabicyclo[2.2.1]heptane-2-carbonyl]-2-[1-(cyclopropylmethyl)-1H-indol-2-yl]-7-fluoro-1H-1,3-benzodiazol-1-yl}methyl)azetidine-1-carbonyl]benzonitrile (6 mg, 9.3 μmol, 58.4%) was isolated. LC/MS (2M+H): 642; LC retention time: 1.59 min (analytical HPLC Method 1). $^1$H NMR (500 MHz, DMSO-$d_6$) δ 7.84-7.45 (m, 5H), 7.34-7.25 (m, 2H), 7.23-7.09 (m, 2H), 7.06-6.94 (m, 2H), 4.87-4.58 (m, 2H), 4.36-3.83 (m, 4H), 3.63-3.27 (m, 2H), 3.11-2.82 (m, 2H), 2.79-2.69 (m, 1H), 2.64-2.53 (m, 1H), 2.14-1.44 (m, 4H), 1.37-0.61 (m, 3H), 0.22-0.21 (m, 4H).

Example 93

(3-((5-((1R,4R,7R)-7-amino-2-azabicyclo[2.2.1]heptane-2-carbonyl)-7-chloro-2-(1-(cyclopropylmethyl)-1H-indol-2-yl)-1H-benzo[d]imidazol-1-yl)methyl)azetidin-1-yl)pyridin-4-yl)methanone

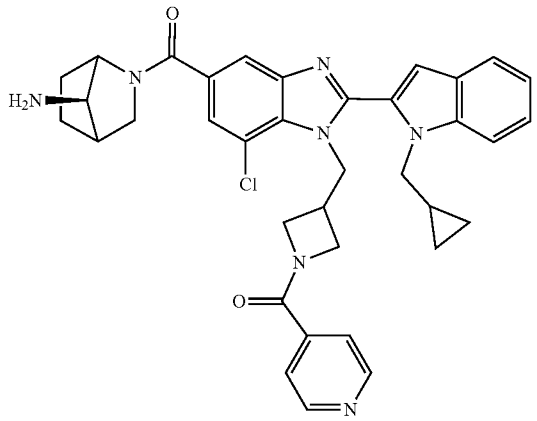 [SMILES: N[C@@H]1C2CCC1N(C(=O)c1cc(Cl)c3c(c1)nc(-c1cc4ccccc4n1CC1CC1)n3CC1CN(C(=O)c3ccncc3)C1)C2]

Intermediate 93A: Methyl 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylate

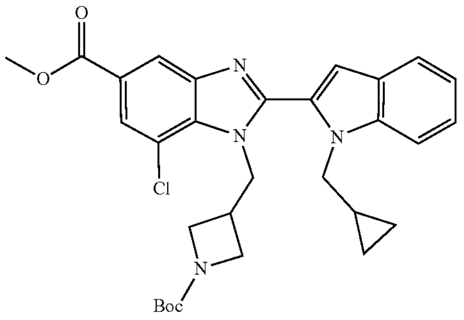 [SMILES: COC(=O)c1cc(Cl)c2c(c1)nc(-c1cc3ccccc3n1CC1CC1)n2CC1CN(C(=O)OC(C)(C)C)C1]

To a solution of tert-butyl 3-(((2-chloro-4-(methoxycarbonyl)-6-nitrophenyl)amino)methyl)azetidine-1-carboxylate (50 mg, 0.125 mmol) and 1-(cyclopropylmethyl)-1H-indole-2-carbaldehyde (24.92 mg, 0.125 mmol) in EtOH (3.0 mL) was added a solution of sodium dithionite (65.3 mg, 0.375 mmol) in water (1,500 mL), and the mixture was stirred at 80° C. for 18 hours. The resulting mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient) to yield methyl 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylate as white solid. LC/MS (M+H): 549; LC retention time: 1.17 mm (analytical HPLC Method 3).

Intermediate 93B: 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylic acid

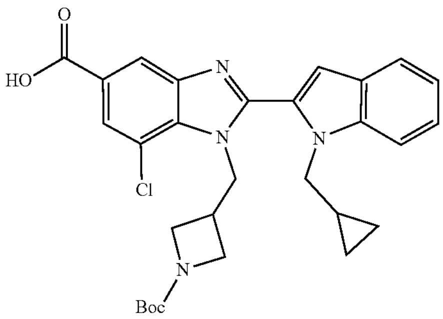

A mixture of methyl 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylate and 1.0 M aqueous sodium hydroxide (0.625 mL, 0.625 mmol) in THF (5.0 mL) was stirred at 50° C. for 18 hours. A solution of 1.0 N aqueous HCl (0.63 mL) was added and the mixture was concentrated. The mixture was extracted with EtOAc (15 mL) and the organic layer was dried over sodium sulfate and concentrated to give a crude yield of 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylic acid (50 mg, 0.084 mmol, 67.3% yield) as white solid. LC/MS (M+H): 535; LC retention time: 1.64 min (analytical HPLC Method 4).

Example 93: (3-((5-((1R,4R,7R)-7-amino-2-azabicyclo[2.2.1]heptane-2-carbonyl)-7-chloro-2-(1-(cyclopropylmethyl)-1H-indol-2-yl)-1H-benzo[d]imidazol-1-yl)methyl)azetidin-1-yl)(pyridin-4-yl)methanone A mixture of 1-((1-(tert-butoxycarbonyl)azetidin-3-yl)methyl)-7-chloro-2-(1-(cyclopropylmethyl)-1H-indol-2-yl)-1H-benzo[d]imidazole-5-carboxylic acid (16 mg, 0.030 mmol) in DCM (1.0 mL) and TEA (1.0 mL) was stirred at RT for 30 min. The mixture was concentrated to give crude 1-(azetidin-3-ylmethyl)-7-chloro-2-(1-(cyclopropylmethyl)-1H-indol-2-yl)-1H-benzo[d]imidazole-5-carboxylic acid. Material was used as is in next reaction.

To a solution of 1-(azetidin-3-ylmethyl)-7-chloro-2-(1-(cyclopropylmethyl)-1H-indol-2-yl)-1H-benzo[d]imidazole-5-carboxylic acid and TEA (0.025 mL, 0.179 mmol) in DCM (1.0 mL) was added a solution of isonicotinoyl chloride (4.23 mg, 0.030 mmol) in DCM (0.10 mL), and the mixture was stirred at RT for 1 hour. The mixture was concentrated to give crude 7-chloro-2-(1-(cyclopropylmethyl)-1H-indol-2-yl)-1-((1-isonicotinoylazetidin-3-yl)methyl)-1H-benzo[d]imidazole-5-carboxylic acid. Material was used as is in next reaction.

A mixture of 7-chloro-2-(1-(cyclopropylmethyl)-1H-indol-2-yl)-1-((1-isonicotinoylazetidin-3-yl)methyl)-1H-benzo[d]imidazole-5-carboxylic acid, tert-butyl ((1R,4R,7R)-2-azabicyclo[2.2.1]heptan-7-yl)carbamate (6.35 mg, 0.030 mmol), BOP (13.23 mg, 0.030 mmol) and TEA (0.025 mL, 0.179 mmol) in DMF (3.0 mL) was stirred at RT for 2 hours. The mixture was diluted with EtOAc (5 mL) and was washed with a solution of aqueous saturated sodium bicarbonate (2×5 mL). The organic layer was dried over sodium sulfate and concentrated to give crude tert-butyl ((1R,4R,7R)-2-(7-chloro-2-(1-(cyclopropylmethyl)-1H-indol-2-yl)-1-((1-isonicotinoylazetidin-3-yl)methyl)-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(7-chloro-2-(1-(cyclopropylmethyl)-1H-indol-2-yl)-1-((1-isonicotinoylazetidin-3-yl)methyl)-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge CIS, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 22% B, 22-44% B over 25 minutes, then a 2-minute hold at 100% B; Flow Rate: 20 mL/min; Column Temperature: 25 C, Fraction collection was triggered by MS signals. Fractions containing the desired product were combined and dried via centrifugal evaporation. (1R,4R,7R)-2-{7-chloro-2-[1-(cyclopropylmethyl)-1H-indol-2-yl]-1-{[1-(pyridine-4-carbonyl)azetidin-3-yl]methyl}-1H-1,3-benzodiazole-5-carbonyl}-2-azabicyclo[2.2.1]heptan-7-amine (8.9 mg, 14 μmol, 46.8%) was isolated. LC/MS (M+H): 634; LC retention time: 1.39 min (analytical HPLC Method 1). $^{1}H$ NMR (500 MHz, DMSO-$d_6$) δ 8.37-8.28 (m, 2H), 7.82-7.49 (m, 4H), 7.38-7.14 (m, 2H), 7.06-6.91 (m, 3H), 4.98-4.78 (m, 2H), 4.28-3.80 (m, 4H), 3.59-3.29 (m, 2H), 3.08-2.81 (m, 2H), 2.76-2.68 (m, 2H), 2.62-2.51 (m, 2H), 2.09-1.43 (m, 4H), 1.35-0.62 (m, 3H), 0.22--0.18 (m, 4H).

Examples 94 to 193 in Table 2 were prepared as described in the general procedures given for Example 88 to 93.

TABLE 2

| Ex # | Structure | Name | LC/MS Rt (min) | LC/MS Method | M + H (obs ion) |
|---|---|---|---|---|---|
| 94 | 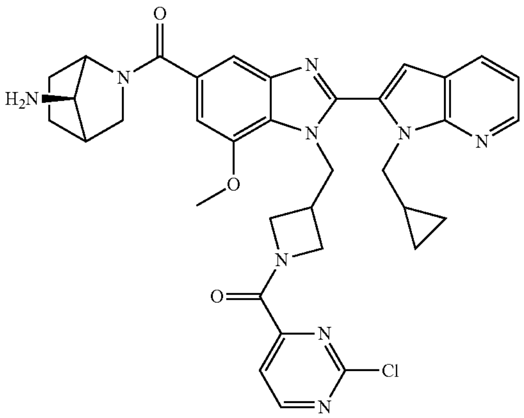 [SMILES: COc1cc(C(=O)N2CC3CCC2[C@@H]3N)cc2nc(-c3cc4cccnc4n3CC3CC3)n(CC3CN(C(=O)c4ccnc(Cl)n4)C3)c12] | (1R,4R,7R)-2-{1-[1-(2-chloropyrimidine-4-carbonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.28 | 2 | 652 |
| 95 | 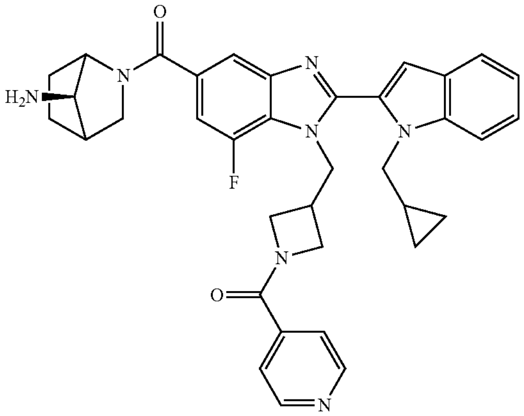 [SMILES: N[C@@H]1C2CCC1N(C(=O)c1cc(F)c3c(c1)nc(-c1cc4ccccc4n1CC1CC1)n3CC1CN(C(=O)c3ccncc3)C1)C2] | (1R,4R,7R)-2-{2-[1-(cyclopropylmethyl)-1H-indol-2-yl]-7-fluoro-1-{[1-(pyridine-4-carbonyl)azetidin-3-yl]methyl}-1H-1,3-benzodiazole-5-carbonyl}-2-azabicyclo[2.2.1]heptan-7-amine | 1.08 | 2 | 618 |
| 96 | 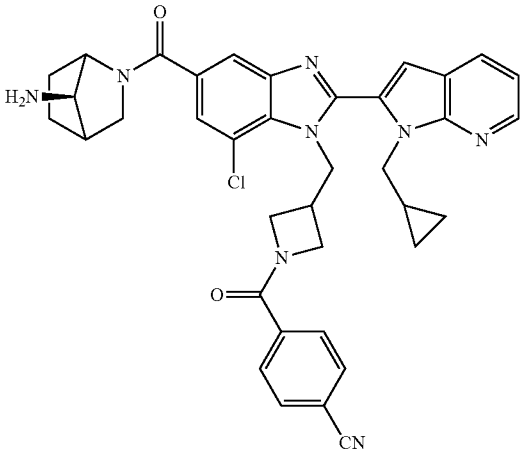 | 4-[3-({5-[(1R,4R,7R)-7-amino-2-azabicyclo[2.2.1]heptane-2-carbonyl]-7-chloro-2-[1-(cyclopropylmethyl)-1H-pyrrolo[2,3-b]pyridin-2-yl]-1H-1,3-benzodiazol-1-yl}methyl)azetidine-1-carbonyl]benzonitrile | 1.35 | 2 | 659 |

TABLE 2-continued

| Ex # | Structure | Name | LC/MS Rt (min) | LC/MS Method | M + H (obs ion) |
| --- | --- | --- | --- | --- | --- |
| 97 | 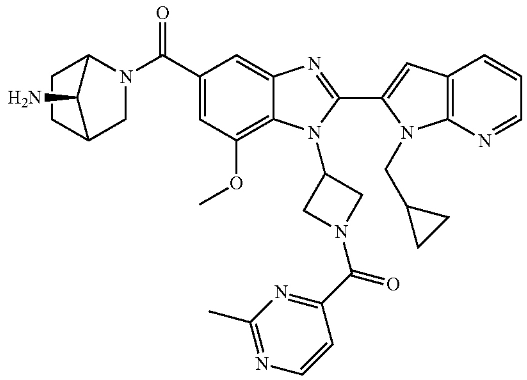 [SMILES: COc1cc(C(=O)N2CC3CCC2[C@@H]3N)cc2nc(-c3cc4cccnc4n3CC3CC3)n(C3CN(C(=O)c4ccnc(C)n4)C3)c12] | (1R,4R,7R)-2-{2-[1-(cyclopropylmethyl)-1H-pyrrolo[2,3-b]pyridin-2-yl]-7-methoxy-1-[1-(2-methylpyrimidine-4-carbonyl)azetidin-3-yl]-1H-1,3-benzodiazole-5-carbonyl}-2-azabicyclo[2.2.1]heptan-7-amine | 1.29 | 1 | 632 |
| 98 | 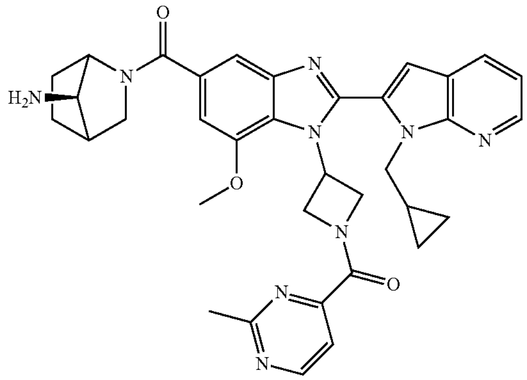 [SMILES: COc1cc(C(=O)N2CC3CCC2[C@@H]3N)cc2nc(-c3cc4cccnc4n3CC3CC3)n(C3CN(C(=O)c4ccnc(C)n4)C3)c12] | (1R,4R,7R)-2-{1-[1-(2-chloropyridine-4-carbonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.35 | 1 | 651 |
| 99 | 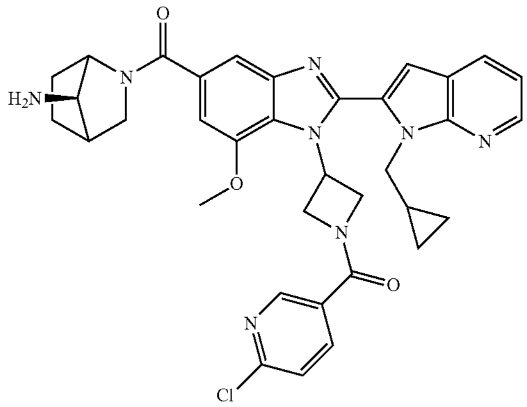 [SMILES: COc1cc(C(=O)N2CC3CCC2[C@@H]3N)cc2nc(-c3cc4cccnc4n3CC3CC3)n(C3CN(C(=O)c4ccc(Cl)nc4)C3)c12] | (1R,4R,7R)-2-{1-[1-(6-chloropyridine-3-carbonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.41 | 1 | 651 |
| 100 | 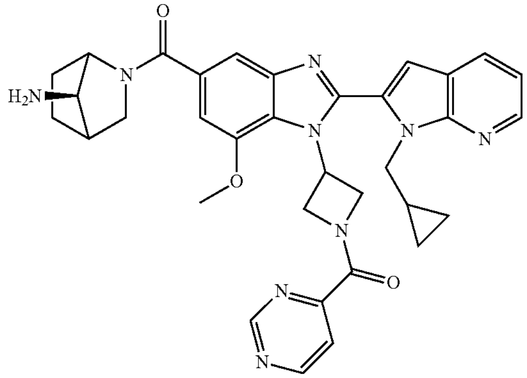 [SMILES: COc1cc(C(=O)N2CC3CCC2[C@@H]3N)cc2nc(-c3cc4cccnc4n3CC3CC3)n(C3CN(C(=O)c4ccncn4)C3)c12] | (1R,4R,7R)-2-{2-[1-(cyclopropylmethyl)-1H-pyrrolo[2,3-b]pyridin-2-yl]-7-methoxy-1-[1-(pyrimidine-4-carbonyl)azetidin-3-yl]-1H-1,3-benzodiazole-5-carbonyl}-2-azabicyclo[2.2.1]heptan-7-amine | 1.09 | 2 | 618 |

TABLE 2-continued

| Ex # | Structure | Name | LC/MS Rt (min) | LC/MS Method | M + H (obs ion) |
|---|---|---|---|---|---|
| 101 | 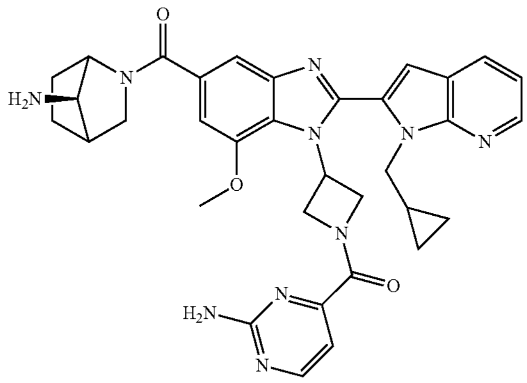 [SMILES: COc1cc(C(=O)N2CC3CCC2[C@@H]3N)cc2nc(-c3cc4cccnc4n3CC3CC3)n(C3CN(C(=O)c4ccnc(N)n4)C3)c12] | (1R,4R,7R)-2-{1-[1-(2-aminopyrimidine-4-carbonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.18 | 1 | 633 |
| 102 | 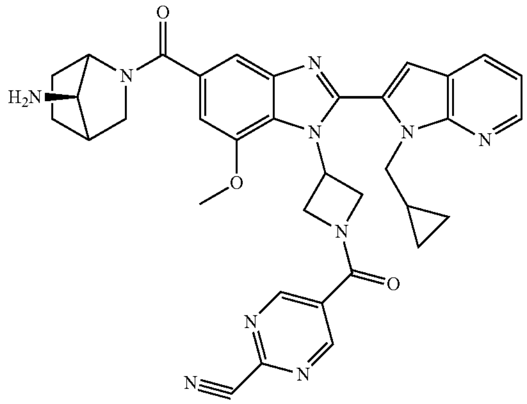 [SMILES: COc1cc(C(=O)N2CC3CCC2[C@@H]3N)cc2nc(-c3cc4cccnc4n3CC3CC3)n(C3CN(C(=O)c4cnc(C#N)nc4)C3)c12] | 5-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidine-1-carbonyl)pyrimidine-2-carbonitrile | 1.24 | 2 | 643 |
| 103 | 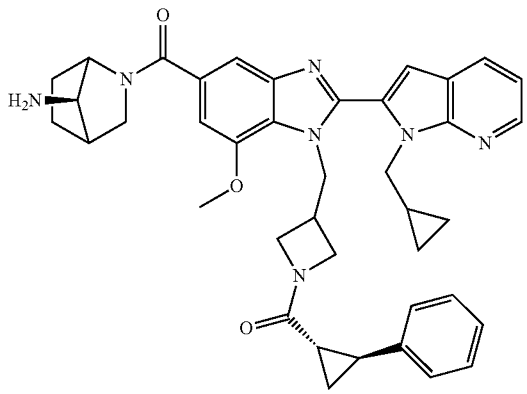 [SMILES: COc1cc(C(=O)N2CC3CCC2[C@@H]3N)cc2nc(-c3cc4cccnc4n3CC3CC3)n(CC3CN(C(=O)[C@H]4C[C@@H]4c4ccccc4)C3)c12] | (1R,4R,7R)-2-{2-[1-(cyclopropylmethyl)-1H-pyrrolo[2,3-b]pyridin-2-yl]-7-methoxy-1-({1-[(1S,2S)-2-phenylcyclopropanecarbonyl]azetidin-3-yl}-methyl)-1H-1,3-benzodiazole-5-carbonyl}-2-azabicyclo[2.2.1]heptan-7-amine | 1.44 | 2 | 670 |

TABLE 2-continued

| Ex # | Structure | Name | LC/MS Rt (min) | LC/MS Method | M + H (obs ion) |
|---|---|---|---|---|---|
| 104 | 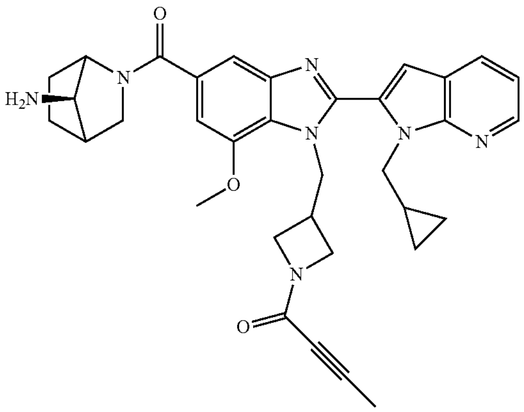 [SMILES: CC#CC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]but-2-yn-1-one | 1.52 | 1 | 592 |
| 105 | 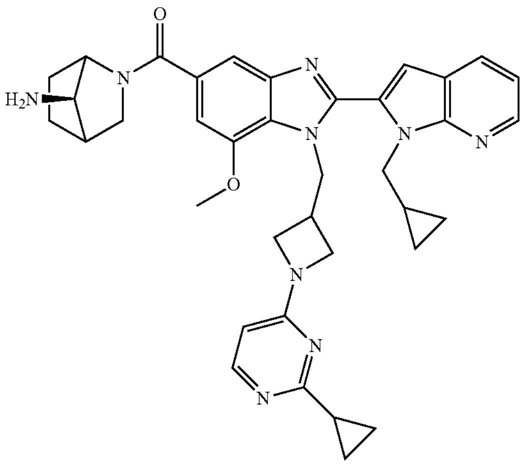 [SMILES: COc1cc(C(=O)N2CC3CCC2[C@@H]3N)cc2nc(-c3cc4cccnc4n3CC3CC3)n(CC3CN(c4ccnc(C5CC5)n4)C3)c12] | (1R,4R,7R)-2-{2-[1-(cyclopropylmethyl)-1H-pyrrolo[2,3-b]pyridin-2-yl]-1-{[1-(2-cyclopropylpyrimidin-4-yl)azetidin-3-yl]methyl}-7-methoxy-1H-1,3-benzodiazole-5-carbonyl}-2-azabicyclo[2.2.1]heptan-7-amine | 1.45 | 1 | 644 |
| 106 | 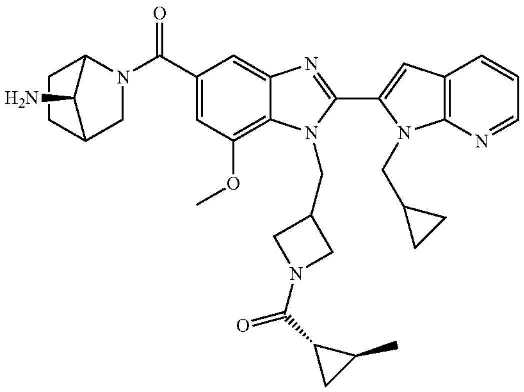 [SMILES: COc1cc(C(=O)N2CC3CCC2[C@@H]3N)cc2nc(-c3cc4cccnc4n3CC3CC3)n(CC3CN(C(=O)[C@H]4C[C@@H]4C)C3)c12] | (1R,4R,7R)-2-{2-[1-(cyclopropylmethyl)-1H-pyrrolo[2,3-b]pyridin-2-yl]-7-methoxy-1-({1-[(1S,2S)-2-methylcyclopropanecarbonyl]azetidin-3-yl}methyl)-1H-1,3-benzodiazole-5-carbonyl}-2-azabicyclo[2.2.1]heptan-7-amine | 1.37 | 2 | 608 |

TABLE 2-continued

| Ex # | Structure | Name | LC/MS Rt (min) | LC/MS Method | M + H (obs ion) |
|---|---|---|---|---|---|
| 107 | 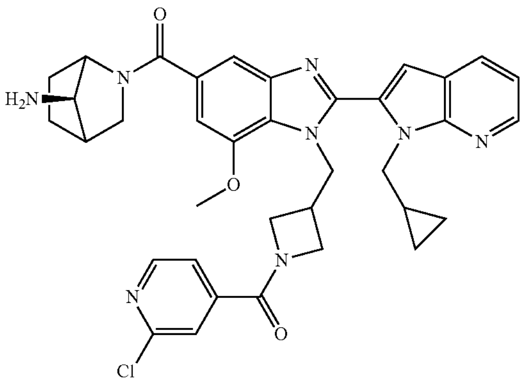 [SMILES: COc1cc(C(=O)N2CC3CCC2[C@@H]3N)cc2nc(-c3cc4cccnc4n3CC3CC3)n(CC3CN(C(=O)c4ccnc(Cl)c4)C3)c12] | (1R,4R,7R)-2-(1-{[1-(2-chloropyridine-4-carbonyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.38 | 1 | 665 |
| 108 | 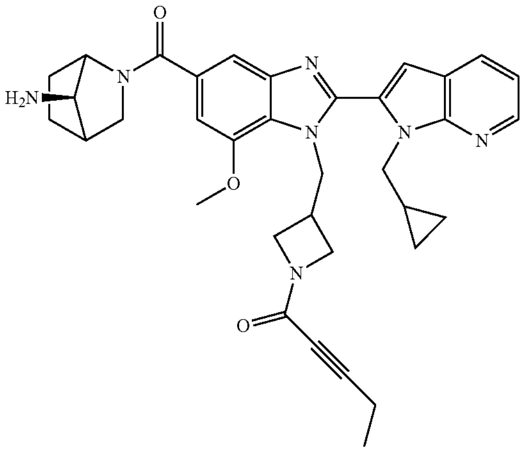 [SMILES: CCC#CC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]pent-2-yn-1-one | 1.48 | 1 | 606 |
| 109 | 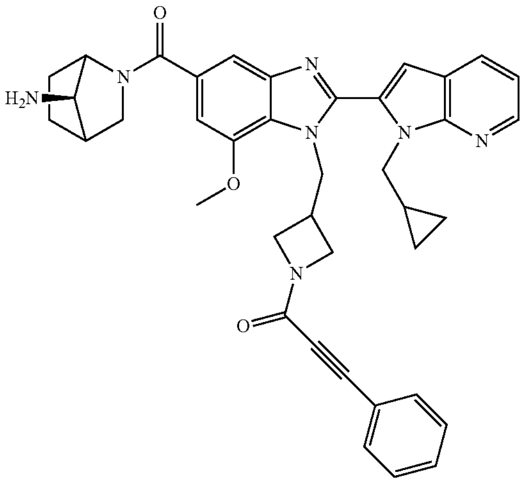 [SMILES: COc1cc(C(=O)N2CC3CCC2[C@@H]3N)cc2nc(-c3cc4cccnc4n3CC3CC3)n(CC3CN(C(=O)C#Cc4ccccc4)C3)c12] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-3-phenylprop-2-yn-1-one | 1.63 | 2 | 654 |

TABLE 2-continued

| Ex # | Structure | Name | LC/MS Rt (min) | LC/MS Method | M + H (obs ion) |
|---|---|---|---|---|---|
| 110 | 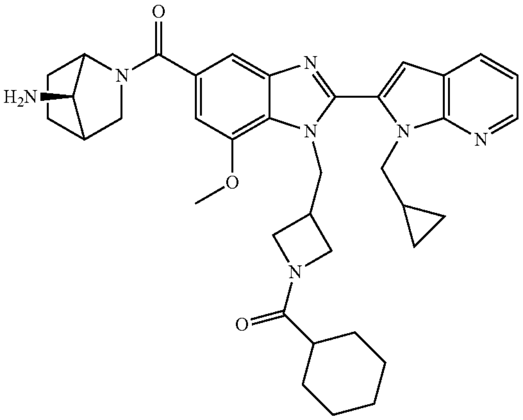 [SMILES: COc1cc(C(=O)N2CC3CCC2[C@@H]3N)cc2nc(-c3cc4cccnc4n3CC3CC3)n(CC3CN(C(=O)C4CCCCC4)C3)c12] | (1R,4R,7R)-2-{1-[(1-cyclohexanecarbonylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.41 | 2 | 636 |
| 111 | 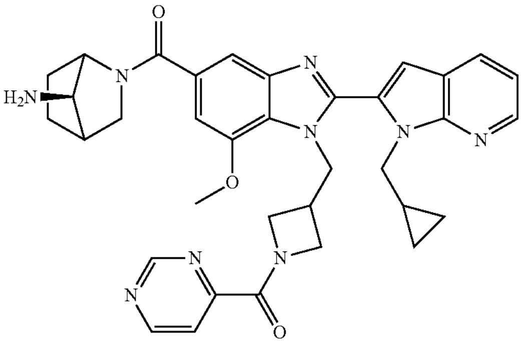 [SMILES: COc1cc(C(=O)N2CC3CCC2[C@@H]3N)cc2nc(-c3cc4cccnc4n3CC3CC3)n(CC3CN(C(=O)c4ccncn4)C3)c12] | (1R,4R,7R)-2-{2-[1-(cyclopropylmethyl)-1H-pyrrolo[2,3-b]pyridin-2-yl]-7-methoxy-1-{[1-(pyrimidine-4-carbonyl)azetidin-3-yl]methyl}-1H-1,3-benzodiazole-5-carbonyl}-2-azabicyclo[2.2.1]heptan-7-amine | 1.15 | 1 | 632 |
| 112 | 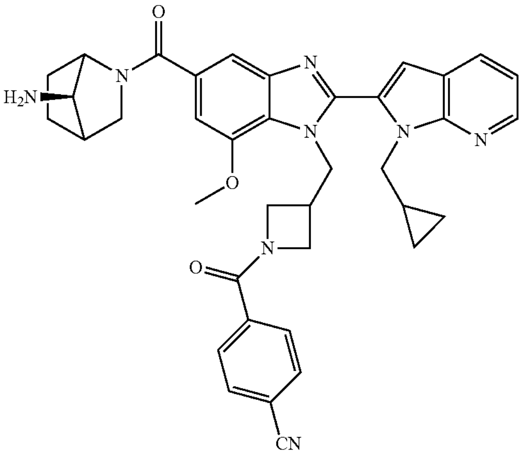 [SMILES: COc1cc(C(=O)N2CC3CCC2[C@@H]3N)cc2nc(-c3cc4cccnc4n3CC3CC3)n(CC3CN(C(=O)c4ccc(C#N)cc4)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]benzonitrile | 1.48 | 1 | 655 |

TABLE 2-continued

| Ex # | Structure | Name | LC/MS Rt (min) | LC/MS Method | M + H (obs ion) |
|---|---|---|---|---|---|
| 113 | 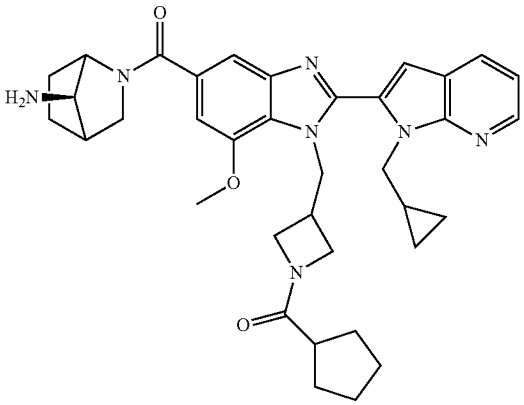 [SMILES: COc1cc(C(=O)N2CC3CCC2[C@@H]3N)cc2nc(-c3cc4cccnc4n3CC3CC3)n(CC3CN(C(=O)C4CCCC4)C3)c12] | (1R,4R,7R)-2-{1-[(1-cyclopentanecarbonylazetidin-3-yl)methyl]-2-[1-(cyclopropylmethyl)-1H-pyrrolo[2,3-b]pyridin-2-yl]-7-methoxy-1H-1,3-benzodiazole-5-carbonyl]-2-azabicyclo[2.2.1]heptan-7-amine | 1.55 | 1 | 644 |
| 114 | 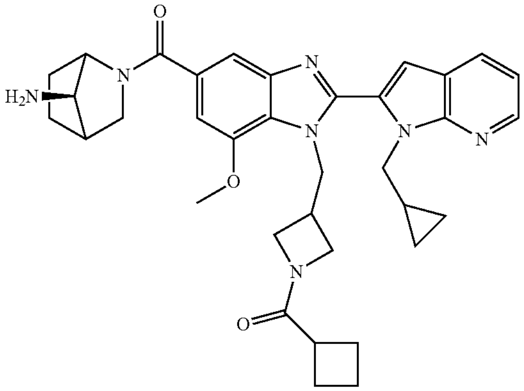 [SMILES: COc1cc(C(=O)N2CC3CCC2[C@@H]3N)cc2nc(-c3cc4cccnc4n3CC3CC3)n(CC3CN(C(=O)C4CCC4)C3)c12] | (1R,4R,7R)-2-{1-[(1-cyclobutanecarbonylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.47 | 1 | 608 |
| 115 | 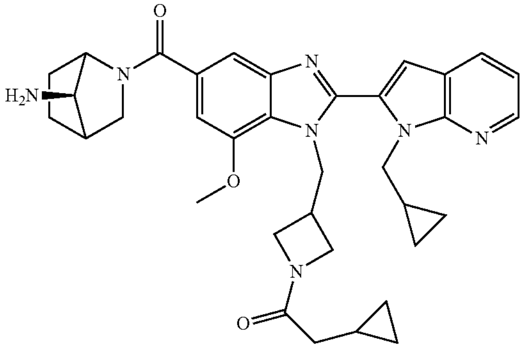 [SMILES: COc1cc(C(=O)N2CC3CCC2[C@@H]3N)cc2nc(-c3cc4cccnc4n3CC3CC3)n(CC3CN(C(=O)CC4CC4)C3)c12] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-2-cyclopropylethan-1-one | 1.43 | 1 | 608 |
| 116 | 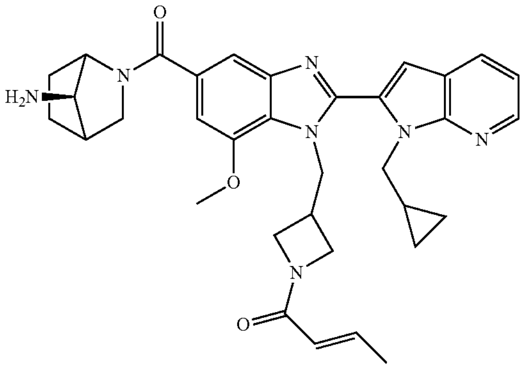 [SMILES: C/C=C/C(=O)N1CC(Cn2c(-c3cc4cccnc4n3CC3CC3)nc3cc(C(=O)N4CC5CCC4[C@@H]5N)cc(OC)c32)C1] | (2E)-1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]but-2-en-1-one | 1.36 | 2 | 594 |

TABLE 2-continued

| Ex # | Structure | Name | LC/MS Rt (min) | LC/MS Method | M + H (obs ion) |
| --- | --- | --- | --- | --- | --- |
| 117 | 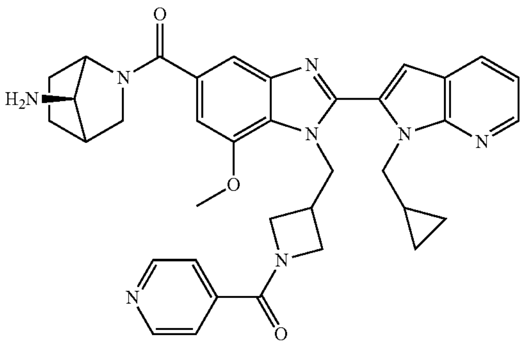 [SMILES: COc1cc(C(=O)N2CC3CCC2[C@@H]3N)cc2nc(-c3cc4cccnc4n3CC3CC3)n(CC3CN(C(=O)c4ccncc4)C3)c12] | (1R,4R,7R)-2-{2-[1-(cyclopropylmethyl)-1H-pyrrolo[2,3-b]pyridin-2-yl]-7-methoxy-1-{[1-(pyridine-4-carbonyl)azetidin-3-yl]methyl}-1H-1,3-benzodiazole-5-carbonyl}-2-azabicyclo[2.2.1]heptan-7-amine | 0.9 | 2 | 631 |
| 118 | 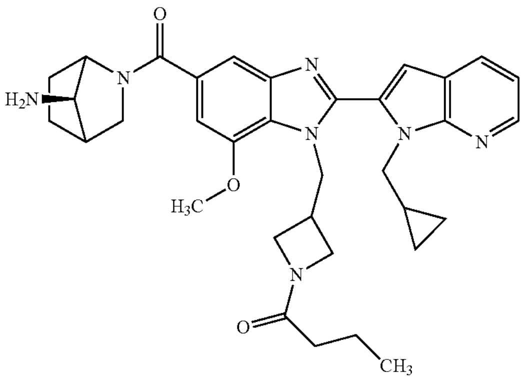 [SMILES: CCCC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]butan-1-one | 1.27 | 1 | 596 |
| 119 | 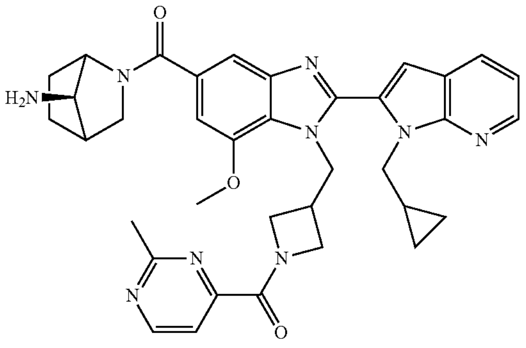 [SMILES: COc1cc(C(=O)N2CC3CCC2[C@@H]3N)cc2nc(-c3cc4cccnc4n3CC3CC3)n(CC3CN(C(=O)c4ccnc(C)n4)C3)c12] | (1R,4R,7R)-2-{2-[1-(cyclopropylmethyl)-1H-pyrrolo[2,3-b]pyridin-2-yl]-7-methoxy-1-{[1-(2-methylpyrimidine-4-carbonyl)azetidin-3-yl]methyl}-1H-1,3-benzodiazole-5-carbonyl}-2-azabicyclo[2.2.1]heptan-7-amine | 1.26 | 1 | 646 |
| 120 | 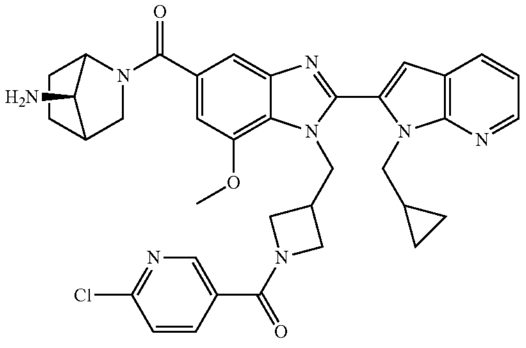 [SMILES: COc1cc(C(=O)N2CC3CCC2[C@@H]3N)cc2nc(-c3cc4cccnc4n3CC3CC3)n(CC3CN(C(=O)c4ccc(Cl)nc4)C3)c12] | (1R,4R,7R)-2-(1-{[1-(6-chloropyridine-3-carbonyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.37 | 1 | 664 |

TABLE 2-continued

| Ex # | Structure | Name | LC/MS Rt (min) | LC/MS Method | M + H (obs ion) |
|---|---|---|---|---|---|
| 121 | 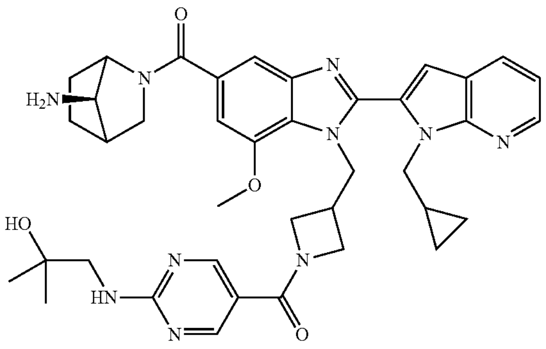 [SMILES: COc1cc(C(=O)N2CC3CCC2[C@@H]3N)cc2nc(-c3cc4cccnc4n3CC3CC3)n(CC3CN(C(=O)c4cnc(NCC(C)(C)O)nc4)C3)c12] | 1-({5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]pyrimidin-2-yl}amino)-2-methylpropan-2-ol | 1.04 | 2 | 719 |
| 122 | 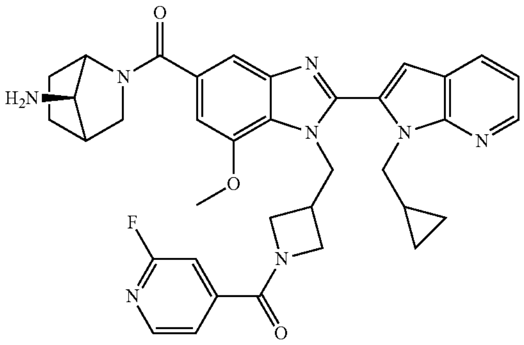 [SMILES: COc1cc(C(=O)N2CC3CCC2[C@@H]3N)cc2nc(-c3cc4cccnc4n3CC3CC3)n(CC3CN(C(=O)c4ccnc(F)c4)C3)c12] | (1R,4R,7R)-2-{2-[1-(cyclopropylmethyl)-1H-pyrrolo[2,3-b]pyridin-2-yl]-1-{[1-(2-fluoropyridine-4-carbonyl)azetidin-3-yl]methyl}-7-methoxy-1H-1,3-benzodiazole-5-carbonyl}-2-azabicyclo[2.2.1]heptan-7-amine | 1.14 | 2 | 649 |
| 123 | 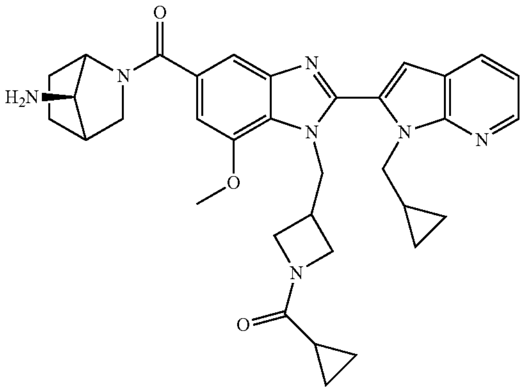 [SMILES: COc1cc(C(=O)N2CC3CCC2[C@@H]3N)cc2nc(-c3cc4cccnc4n3CC3CC3)n(CC3CN(C(=O)C4CC4)C3)c12] | (1R,4R,7R)-2-{1-[(1-cyclopropanecarbonylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.38 | 1 | 594 |
| 124 | 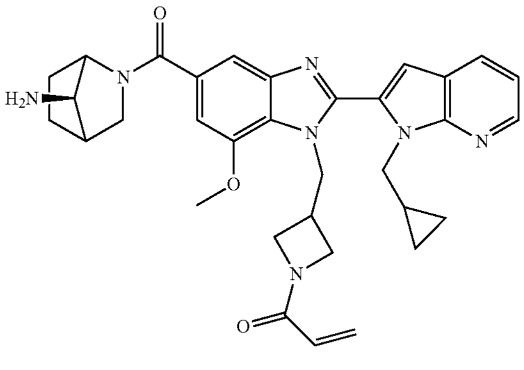 [SMILES: C=CC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]prop-2-en-1-one | 1.28 | 1 | 580 |

TABLE 2-continued

| Ex # | Structure | Name | LC/MS Rt (min) | LC/MS Method | M + H (obs ion) |
|---|---|---|---|---|---|
| 125 | 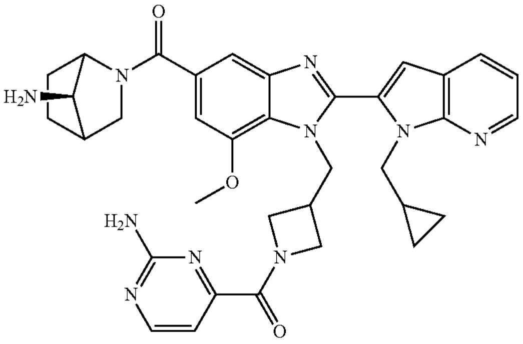 [SMILES: COc1cc(C(=O)N2CC3CCC2[C@@H]3N)cc2nc(-c3cc4cccnc4n3CC3CC3)n(CC3CN(C(=O)c4ccnc(N)n4)C3)c12] | (1R,4R,7R)-2-(1-{[1-(2-aminopyrimidine-4-carbonyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 0.95 | 2 | 647 |
| 126 | 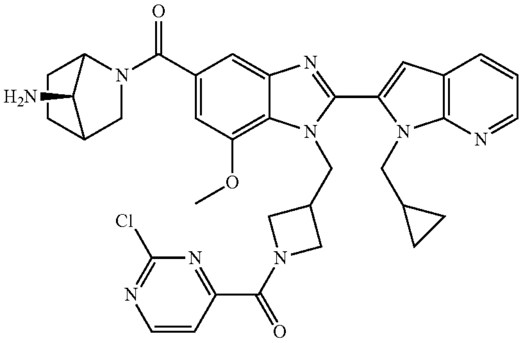 [SMILES: COc1cc(C(=O)N2CC3CCC2[C@@H]3N)cc2nc(-c3cc4cccnc4n3CC3CC3)n(CC3CN(C(=O)c4ccnc(Cl)n4)C3)c12] | (1R,4R,7R)-2-(1-{[1-(2-chloropyrimidine-4-carbonyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.24 | 2 | 666 |
| 127 | 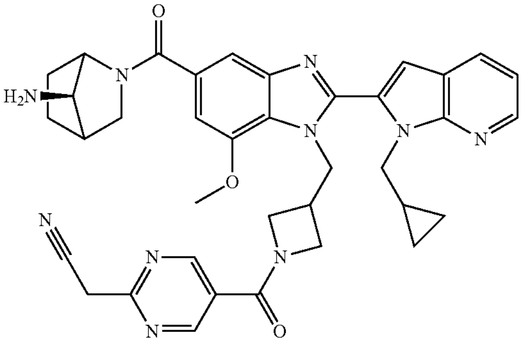 [SMILES: COc1cc(C(=O)N2CC3CCC2[C@@H]3N)cc2nc(-c3cc4cccnc4n3CC3CC3)n(CC3CN(C(=O)c4cnc(CC#N)nc4)C3)c12] | 5-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]pyrimidine-2-carbonitrile | 1.19 | 2 | 657 |
| 128 | 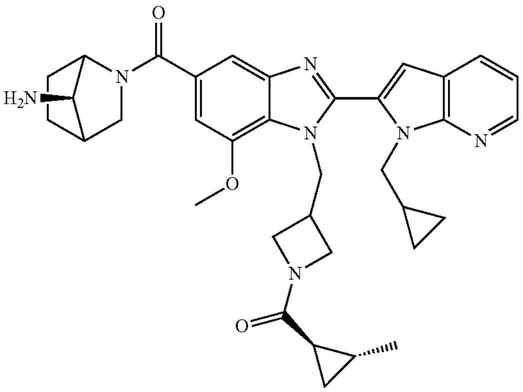 [SMILES: COc1cc(C(=O)N2CC3CCC2[C@@H]3N)cc2nc(-c3cc4cccnc4n3CC3CC3)n(CC3CN(C(=O)[C@@H]4C[C@H]4C)C3)c12] | (1R,4R,7R)-2-{2-[1-(cyclopropylmethyl)-1H-pyrrolo[2,3-b]pyridin-2-yl]-7-methoxy-1-({1-[(1R,2R)-2-methylcyclopropanecarbonyl]azetidin-3-yl}methyl)-1H-1,3-benzodiazole-5-carbonyl}-2-azabicyclo[2.2.1]heptan-7-amine | 1.48 | 1 | 608 |

TABLE 2-continued

| Ex # | Structure | Name | LC/MS Rt (min) | LC/MS Method | M + H (obs ion) |
|---|---|---|---|---|---|
| 129 | 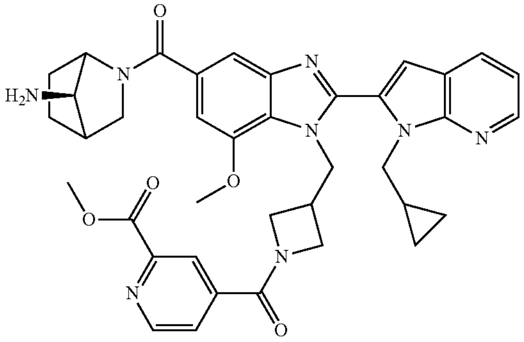 [SMILES: COC(=O)c1cc(C(=O)N2CC(Cn3c(-c4cc5cccnc5n4CC4CC4)nc4cc(C(=O)N5CC6CCC5[C@@H]6N)cc(OC)c43)C2)ccn1] | methyl 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]pyridine-2-carboxylate | 1.12 | 1 | 689 |
| 130 | 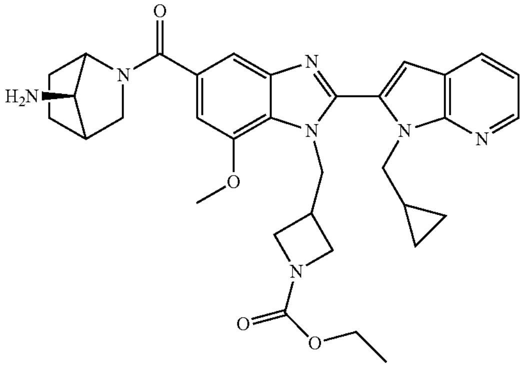 [SMILES: CCOC(=O)N1CC(Cn2c(-c3cc4cccnc4n3CC3CC3)nc3cc(C(=O)N4CC5CCC4[C@@H]5N)cc(OC)c32)C1] | ethyl 3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carboxylate | 1.37 | 1 | 598 |
| 131 | 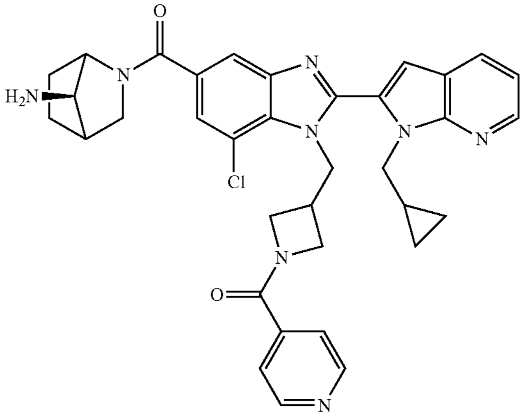 [SMILES: N[C@@H]1C2CCC1N(C(=O)c1cc(Cl)c3c(c1)nc(-c1cc4cccnc4n1CC1CC1)n3CC1CN(C(=O)c3ccncc3)C1)C2] | (1R,4R,7R)-2-{7-chloro-2-[1-(cyclopropylmethyl)-1H-pyrrolo[2,3-b]pyridin-2-yl]-1-{[1-(pyridine-4-carbonyl)azetidin-3-yl]methyl}-1H-1,3-benzodiazole-5-carbonyl}-2-azabicyclo[2.2.1]heptan-7-amine | 1.07 | 2 | 635 |
| 132 | 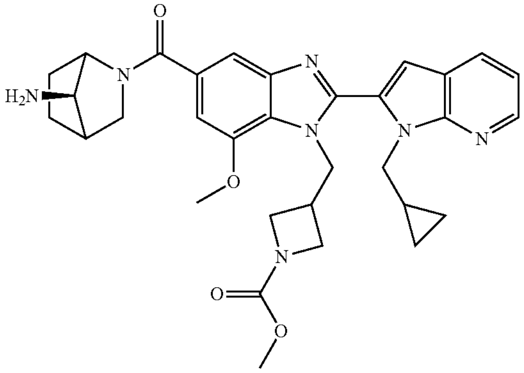 [SMILES: COC(=O)N1CC(Cn2c(-c3cc4cccnc4n3CC3CC3)nc3cc(C(=O)N4CC5CCC4[C@@H]5N)cc(OC)c32)C1] | methyl 3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carboxylate | 1.39 | 1 | 584 |

TABLE 2-continued

| Ex # | Structure | Name | LC/MS Rt (min) | LC/MS Method | M + H (obs ion) |
|---|---|---|---|---|---|
| 133 | 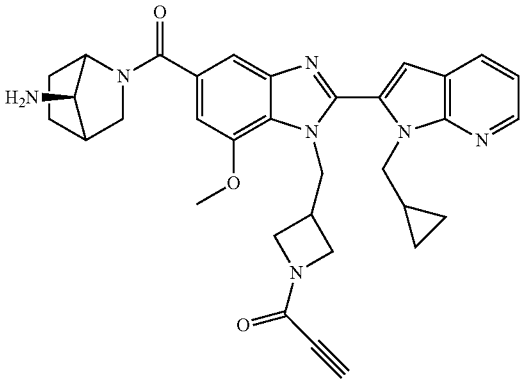 [SMILES: C#CC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]prop-2-yl-1-one | 1.25 | 1 | 578 |
| 134 | 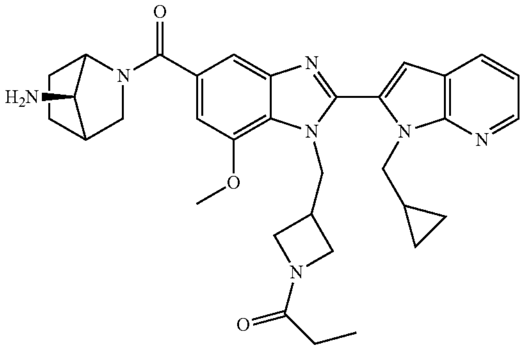 [SMILES: CCC(=O)N1CC(Cn2c(-c3cc4cccnc4n3CC3CC3)nc3cc(C(=O)N4CC5CCC4[C@@H]5N)cc(OC)c32)C1] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]propan-1-one | 1.17 | 1 | 582 |
| 135 | 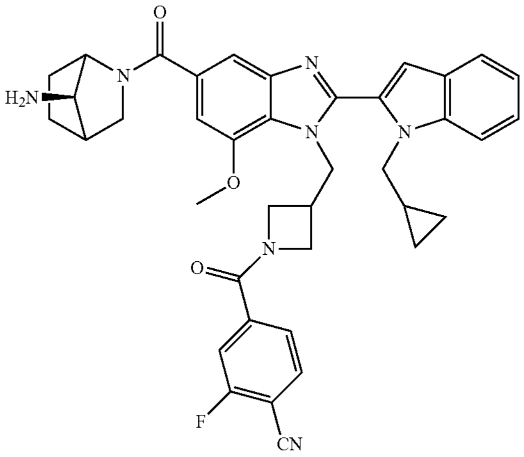 [SMILES: COc1cc(C(=O)N2CC3CCC2[C@@H]3N)cc2nc(-c3cc4ccccc4n3CC3CC3)n(CC3CN(C(=O)c4ccc(C#N)c(F)c4)C3)c12] | 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-2-fluorobenzonitrile | 1.72 | 1 | 672 |

TABLE 2-continued

| Ex # | Structure | Name | LC/MS Rt (min) | LC/MS Method | M + H (obs ion) |
| --- | --- | --- | --- | --- | --- |
| 136 | 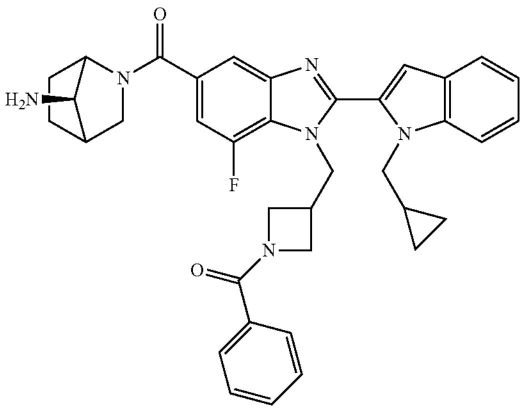 [SMILES: N[C@@H]1C2CCC1N(C(=O)c1cc(F)c3c(c1)nc(-c1cc4ccccc4n1CC1CC1)n3CC1CN(C(=O)c3ccccc3)C1)C2] | (1R,4R,7R)-2-{1-[(1-benozylazetidin-3-yl)methyl]-2-[1-(cyclopropylmethyl)-1H-indol-2-yl]-7-fluoro-1H-1,3-benzodiazole-5-carbonyl}-2-azabicyclo[2.2.1]heptan-7-amine | 1.7 | 1 | 617 |
| 137 | 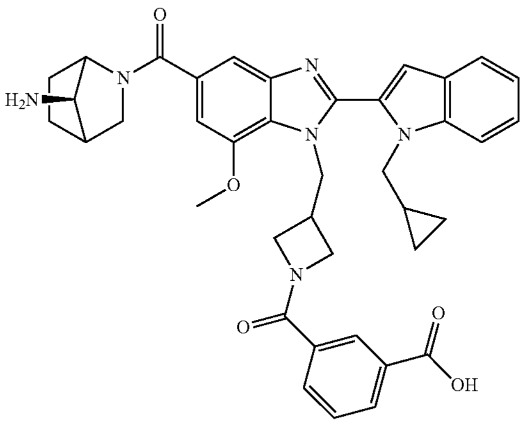 [SMILES: COc1cc(C(=O)N2CC3CCC2[C@@H]3N)cc2nc(-c3cc4ccccc4n3CC3CC3)n(CC3CN(C(=O)c4cccc(C(=O)O)c4)C3)c12] | 3-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzoic acid | 1.22 | 1 | 673 |
| 138 | 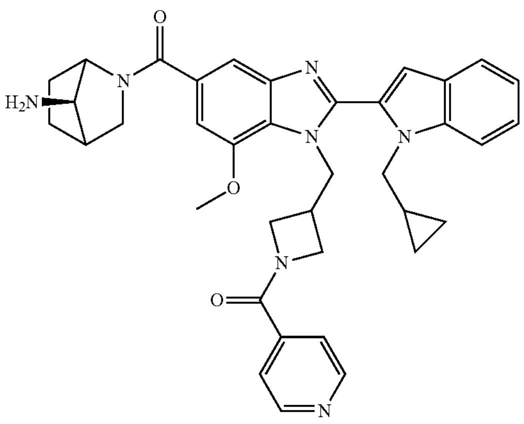 [SMILES: COc1cc(C(=O)N2CC3CCC2[C@@H]3N)cc2nc(-c3cc4ccccc4n3CC3CC3)n(CC3CN(C(=O)c4ccncc4)C3)c12] | (1R,4R,7R)-2-{2-[1-(cyclopropylmethyl)-1H-indol-2-yl]-7-methoxy-1-{[1-(pyridine-4-carbonyl)azetidin-3-yl]methyl}-1H-1,3-benzodiazole-5-carbonyl}-2-azabicyclo[2.2.1]heptan-7-amine | 1.46 | 1 | 630 |

TABLE 2-continued

| Ex # | Structure | Name | LC/MS Rt (min) | LC/MS Method | M + H (obs ion) |
| --- | --- | --- | --- | --- | --- |
| 139 | 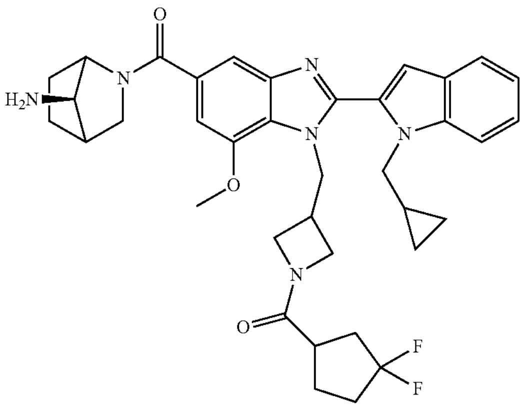 [SMILES: COc1cc(C(=O)N2CC3CCC2[C@@H]3N)cc2nc(-c3cc4ccccc4n3CC3CC3)n(CC3CN(C(=O)C4CCC(F)(F)C4)C3)c12] | (1R,4R,7R)-2-{2-[1-(cyclopropylmethyl)-1H-indol-2-yl]-1-{[1-(3,3-difluorocyclopentanecarbonyl)azetidin-3-yl]methyl}-7-methoxy-1H-1,3-benzodiazole-5-carbonyl}-2-azabicyclo[2.2.1]heptan-7-amine | 1.8 | 1 | 657 |
| 140 | 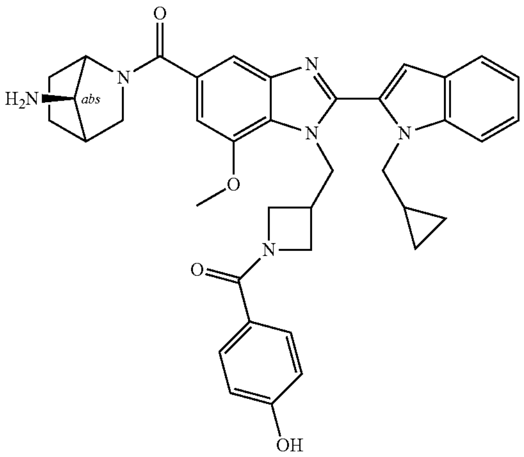 [SMILES: COc1cc(C(=O)N2CC3CCC2[C@@H]3N)cc2nc(-c3cc4ccccc4n3CC3CC3)n(CC3CN(C(=O)c4ccc(O)cc4)C3)c12] | 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]phenol | 1.5 | 1 | 645 |
| 141 | 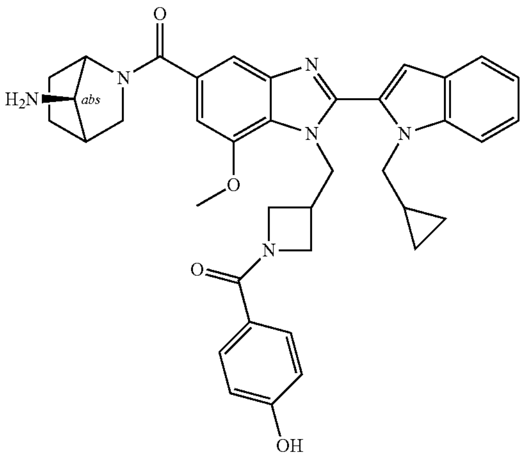 [SMILES: COc1cc(C(=O)N2CC3CCC2[C@@H]3N)cc2nc(-c3cc4ccccc4n3CC3CC3)n(CC3CN(C(=O)c4ccc(O)cc4)C3)c12] | 3-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzonitrile | 1.56 | 1 | 654 |

TABLE 2-continued

| Ex # | Structure | Name | LC/MS Rt (min) | LC/MS Method | M + H (obs ion) |
|---|---|---|---|---|---|
| 142 | 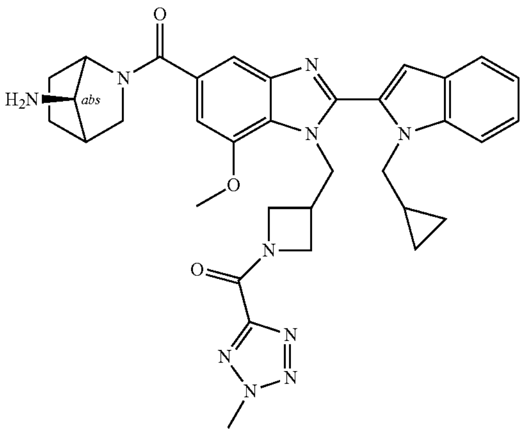 [SMILES: COc1cc(C(=O)N2CC3CCC2[C@@H]3N)cc2nc(-c3cc4ccccc4n3CC3CC3)n(CC3CN(C(=O)c4nnn(C)n4)C3)c12] | (1R,4R,7R)-2-{2-[1-(cyclopropylmethyl)-1H-indol-2-yl]-7-methoxy-1-{[1-(2-methyl-2H-1,2,3,4-tetrazole-5-carbonyl)azetidin-3-yl]methyl}-1H-1,3-benzodiazole-5-carbonyl}-2-azabicyclo[2.2.1]heptan-7-amine | 1.47 | 1 | 635 |
| 143 | 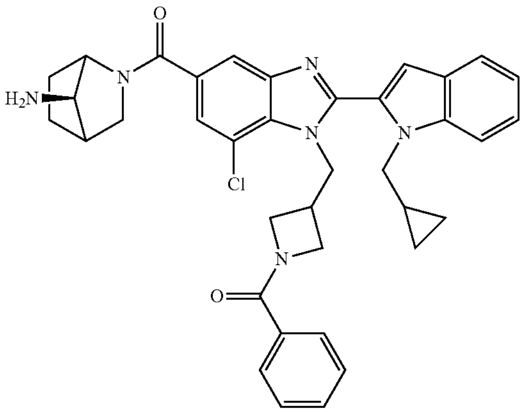 [SMILES: N[C@@H]1C2CCC1N(C(=O)c1cc(Cl)c3c(c1)nc(-c1cc4ccccc4n1CC1CC1)n3CC1CN(C(=O)c3ccccc3)C1)C2] | (1R,4R,7R)-2-{1-[(1-benozylazetidin-3-yl)methyl]-7-chloro-2-[1-(cyclopropylmethyl)-1H-indol-2-yl]-1H-1,3-benzodiazole-5-carbonyl}-2-azabicyclo[2.2.1]heptan-7-amine | 1.63 | 2 | 633 |
| 144 | 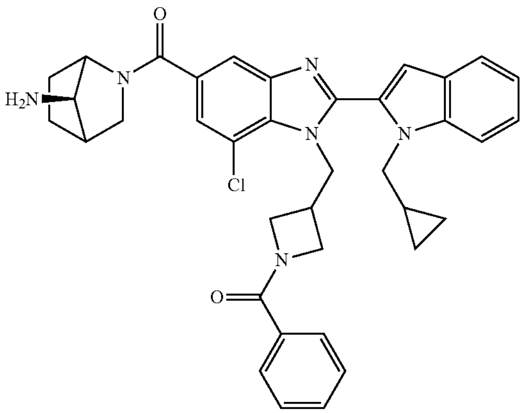 [SMILES: N[C@@H]1C2CCC1N(C(=O)c1cc(Cl)c3c(c1)nc(-c1cc4ccccc4n1CC1CC1)n3CC1CN(C(=O)c3ccccc3)C1)C2] | (1R,4R,7R)-2-{1-[(1-cyclopentanecarbonylazetidin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine | 1.64 | 1 | 621 |

TABLE 2-continued

| Ex # | Structure | Name | LC/MS Rt (min) | LC/MS Method | M + H (obs ion) |
|---|---|---|---|---|---|
| 145 | 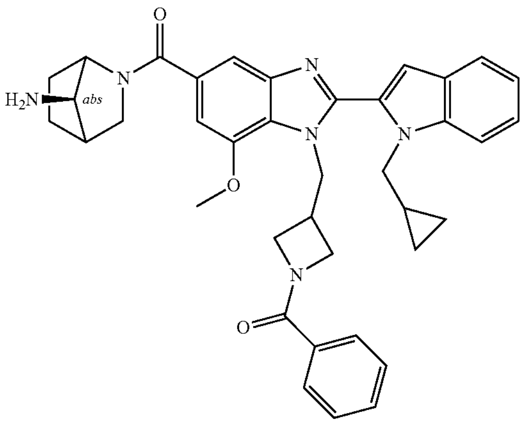 [SMILES: COc1cc(C(=O)N2CC3CCC2[C@@H]3N)cc2nc(-c3cc4ccccc4n3CC3CC3)n(CC3CN(C(=O)c4ccccc4)C3)c12] | (1R,4R,7R)-2-{1-[(1-benzoylazetidin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine | 1.57 | 2 | 629 |
| 146 | 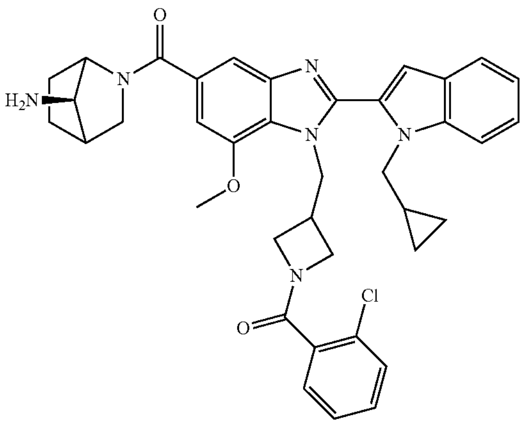 [SMILES: COc1cc(C(=O)N2CC3CCC2[C@@H]3N)cc2nc(-c3cc4ccccc4n3CC3CC3)n(CC3CN(C(=O)c4ccccc4Cl)C3)c12] | (1R,4R,7R)-2-(1-{[1-(2-chlorobenzoyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.6 | 2 | 663 |
| 147 | 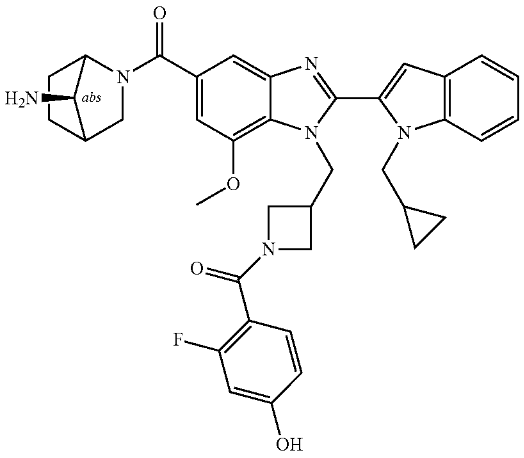 | 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-3-fluorophenol | 1.54 | 1 | 663 |

TABLE 2-continued

| Ex # | Structure | Name | LC/MS Rt (min) | LC/MS Method | M + H (obs ion) |
|---|---|---|---|---|---|
| 148 | 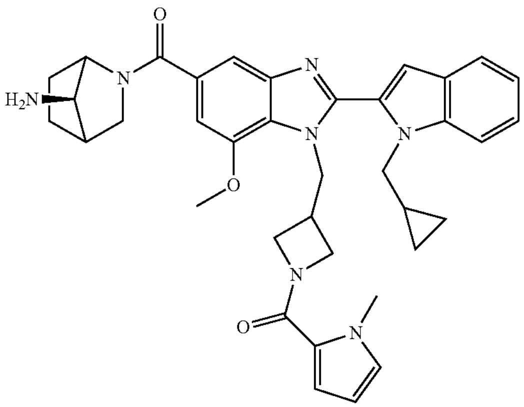 [SMILES: COc1cc(C(=O)N2CC3CCC2[C@@H]3N)cc2nc(-c3cc4ccccc4n3CC3CC3)n(CC3CN(C(=O)c4cccn4C)C3)c12] | (1R,4R,7R)-2-{2-[1-(cyclopropylmethyl)-1H-indol-2-yl]-7-methoxy-1-{[1-(1-methyl-1H-pyrrole-2-carbonyl)azetidin-3-yl]methyl}-1H-1,3-benzodiazole-5-carbonyl}-2-azabicyclo[2.2.1]heptan-7-amine | 1.64 | 1 | 632 |
| 149 | 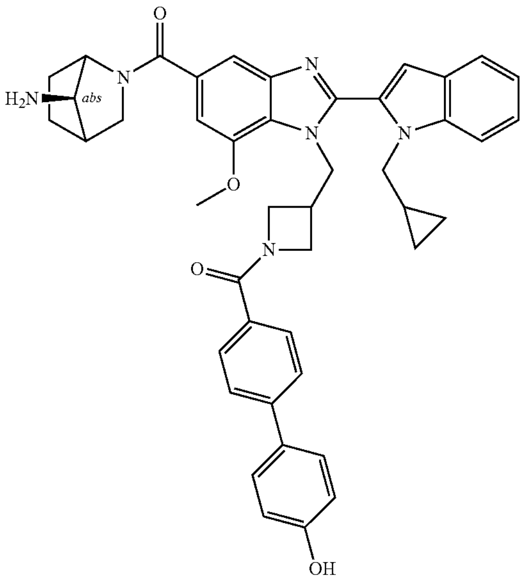 [SMILES: COc1cc(C(=O)N2CC3CCC2[C@@H]3N)cc2nc(-c3cc4ccccc4n3CC3CC3)n(CC3CN(C(=O)c4ccc(-c5ccc(O)cc5)cc4)C3)c12] | 4'-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-[1,1'-biphenyl]-4-ol | 1.73 | 1 | 721 |
| 150 | 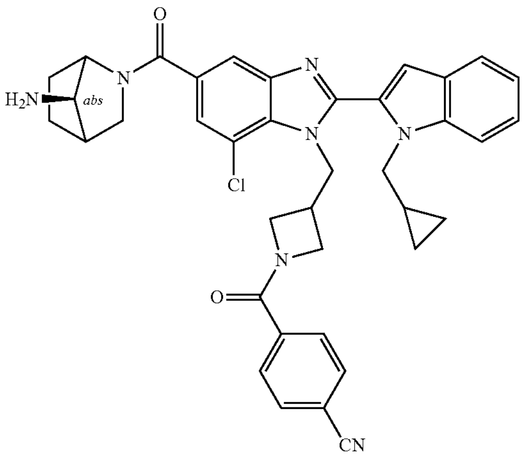 [SMILES: N#Cc1ccc(C(=O)N2CC(Cn3c(-c4cc5ccccc5n4CC4CC4)nc4cc(C(=O)N5CC6CCC5[C@@H]6N)cc(Cl)c43)C2)cc1] | 4-[3-({5-[(1R,4R,7R)-7-amino-2-azabicyclo[2.2.1]heptane-2-carbonyl]-7-chloro-2-[1-(cyclopropylmethyl)-1H-indol-2-yl]-1H-1,3-benzodiazol-1-yl}methyl)azetidine-1-carbonyl]benzonitrile | 1.63 | 1 | 658 |

TABLE 2-continued

| Ex # | Structure | Name | LC/MS Rt (min) | LC/MS Method | M + H (obs ion) |
| --- | --- | --- | --- | --- | --- |
| 151 | 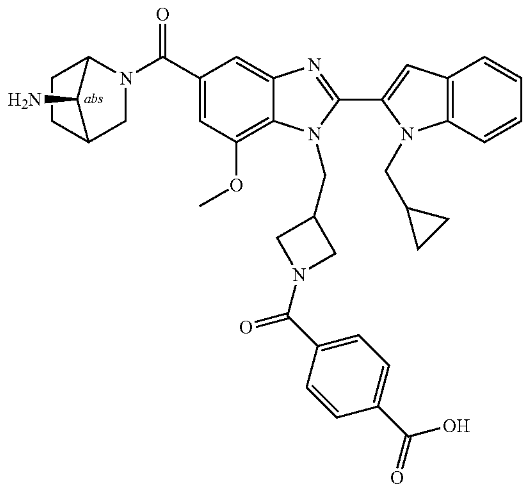 [SMILES: COc1cc(C(=O)N2CC3CCC2[C@@H]3N)cc2nc(-c3cc4ccccc4n3CC3CC3)n(CC3CN(C(=O)c4ccc(C(=O)O)cc4)C3)c12] | 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzoic acid | 1.12 | 1 | 673 |
| 152 | 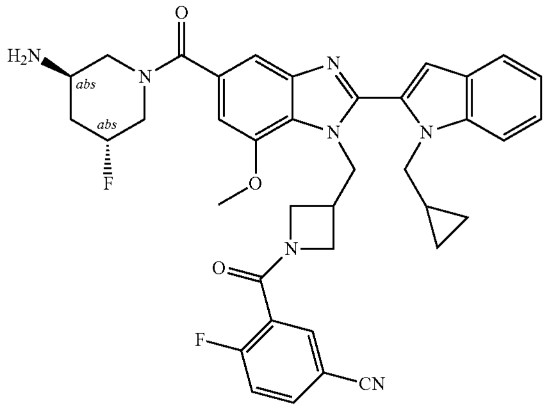 [SMILES: COc1cc(C(=O)N2C[C@H](N)C[C@@H](F)C2)cc2nc(-c3cc4ccccc4n3CC3CC3)n(CC3CN(C(=O)c4cc(C#N)ccc4F)C3)c12] | 3-[3-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)azetidine-1-carbonyl]-4-fluorobenzonitrile | 1.59 | 2 | 678 |
| 153 | 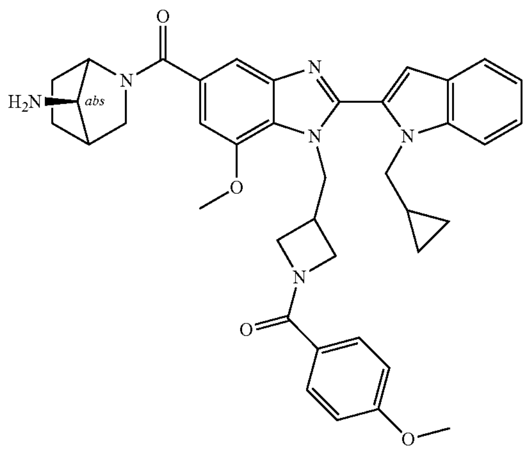 [SMILES: COc1ccc(C(=O)N2CC(Cn3c(-c4cc5ccccc5n4CC4CC4)nc4cc(C(=O)N5CC6CCC5[C@@H]6N)cc(OC)c43)C2)cc1] | (1R,4R,7R)-2-{2-[1-(cyclopropylmethyl)-1H-indol-2-yl]-7-methoxy-1-{[1-(4-methoxybenzoyl)azetidin-3-yl]methyl}-1H-1,3-benzodiazole-5-carbonyl}-2-azabicyclo[2.2.1]heptan-7-amine | 1.7 | 1 | 681 |

TABLE 2-continued

| Ex # | Structure | Name | LC/MS Rt (min) | LC/MS Method | M + H (obs ion) |
|---|---|---|---|---|---|
| 154 | 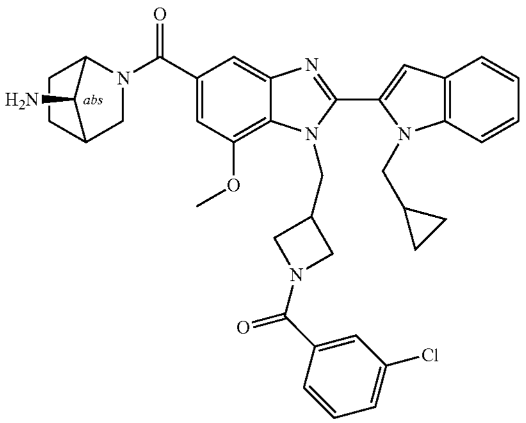 [SMILES: COc1cc(C(=O)N2CC3CCC2[C@@H]3N)cc2nc(-c3cc4ccccc4n3CC3CC3)n(CC3CN(C(=O)c4cccc(Cl)c4)C3)c12] | (1R,4R,7R)-2-(1-{[1-(3-chlorobenzoyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.7 | 2 | 663 |
| 155 | 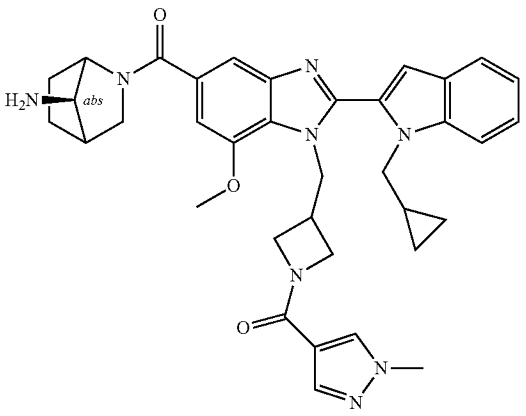 [SMILES: COc1cc(C(=O)N2CC3CCC2[C@@H]3N)cc2nc(-c3cc4ccccc4n3CC3CC3)n(CC3CN(C(=O)c4cnn(C)c4)C3)c12] | (1R,4R,7R)-2-{2-[1-(cyclopropylmethyl)-1H-indol-2-yl]-7-methoxy-1-{[1-(1-methyl-1H-pyrazole-4-carbonyl)azetidin-3-yl]methyl}-1H-1,3-benzodiazole-5-carbonyl}-2-azabicyclo[2.2.1]heptan-7-amine | 1.31 | 1 | 633 |
| 156 | 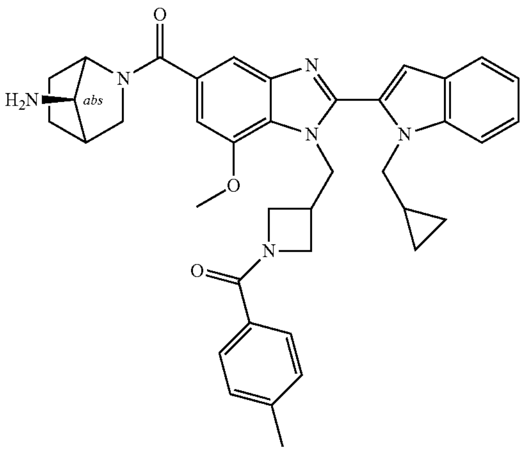 [SMILES: COc1cc(C(=O)N2CC3CCC2[C@@H]3N)cc2nc(-c3cc4ccccc4n3CC3CC3)n(CC3CN(C(=O)c4ccc(C)cc4)C3)c12] | (1R,4R,7R)-2-{2-[1-(cyclopropylmethyl)-1H-indol-2-yl]-7-methoxy-1-{[1-(4-methylbenzoyl)azetidin-3-yl]methyl}-1H-1,3-benzodiazole-5-carbonyl}-2-azabicyclo[2.2.1]heptan-7-amine | 1.65 | 2 | 643 |

TABLE 2-continued

| Ex # | Structure | Name | LC/MS Rt (min) | LC/MS Method | M + H (obs ion) |
|---|---|---|---|---|---|
| 157 | 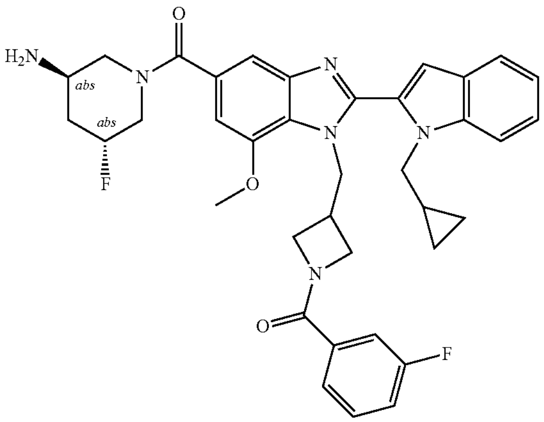 [SMILES: COc1cc(C(=O)N2C[C@H](N)C[C@@H](F)C2)cc2nc(-c3cc4ccccc4n3CC3CC3)n(CC3CN(C(=O)c4cccc(F)c4)C3)c12] | (3R,5R)-1-{2-[1-(cyclopropylmethyl)-1H-indol-2-yl]-1-{[1-(3-fluorobenzoyl)azetidin-3-yl]methyl}-7-methoxy-1H-1,3-benzodiazol-5-carbonyl}-5-fluoropiperidin-3-amine | 1.76 | 1 | 652 |
| 158 | 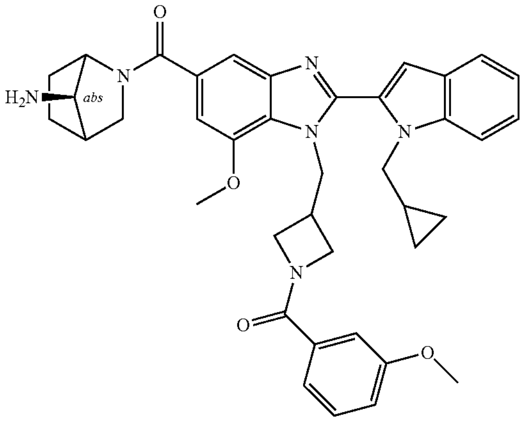 [SMILES: COc1cccc(C(=O)N2CC(Cn3c(-c4cc5ccccc5n4CC4CC4)nc4cc(C(=O)N5CC6CCC5[C@@H]6N)cc(OC)c43)C2)c1] | (1R,4R,7R)-2-{2-[1-(cyclopropylmethyl)-1H-indol-2-yl]-7-methoxy-1-{[1-(3-methoxybenzoyl)azetidin-3-yl]methyl}-1H-1,3-benzodiazole-5-carbonyl}-2-azabicyclo[2.2.1]heptan-7-amine | 1.73 | 1 | 681 |
| 159 | 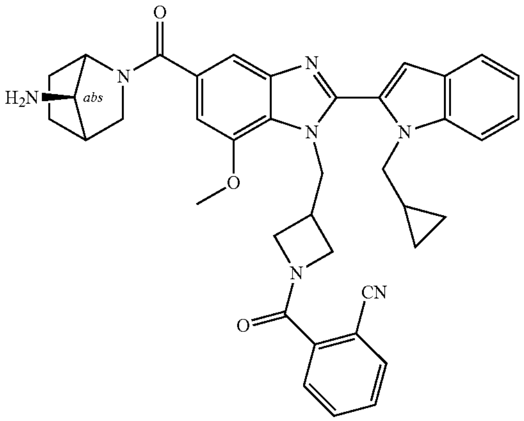 [SMILES: COc1cc(C(=O)N2CC3CCC2[C@@H]3N)cc2nc(-c3cc4ccccc4n3CC3CC3)n(CC3CN(C(=O)c4ccccc4C#N)C3)c12] | 2-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]benzonitrile | 1.55 | 1 | 654 |

TABLE 2-continued

| Ex # | Structure | Name | LC/MS Rt (min) | LC/MS Method | M + H (obs ion) |
|---|---|---|---|---|---|
| 160 | 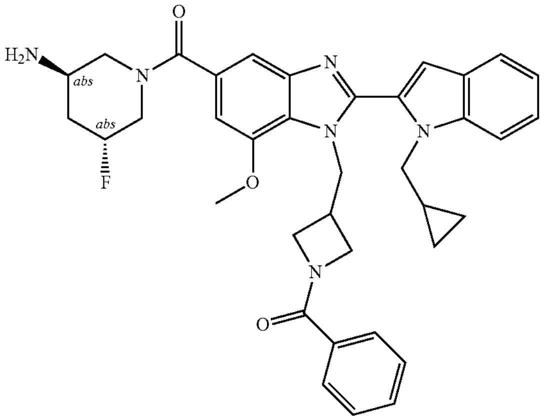 [SMILES: COc1cc(C(=O)N2C[C@H](N)C[C@@H](F)C2)cc2nc(-c3cc4ccccc4n3CC3CC3)n(CC3CN(C(=O)c4ccccc4)C3)c12] | (3R,5R)-1-{1-[(1-benzoylazetidin-3-yl)methyl]-2-[1-(cyclopropylmethyl)-1H-indol-2-yl]-7-methoxy-1H-1,3-benzodiazole-5-carbonyl}-5-fluoropiperidin-3-amine | 1.71 | 1 | 635 |
| 161 | 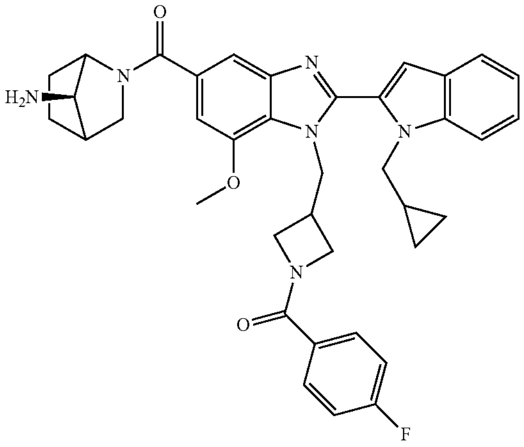 [SMILES: COc1cc(C(=O)N2CC3CCC2[C@@H]3N)cc2nc(-c3cc4ccccc4n3CC3CC3)n(CC3CN(C(=O)c4ccc(F)cc4)C3)c12] | (1R,4R,7R)-2-{2-[1-(cyclopropylmethyl)-1H-indol-2-yl]-1-{[1-(4-fluorobenzoyl)azetidin-3-yl]methyl}-7-methoxy-1H-1,3-benzodiazole-5-carbonyl}-2-azabicyclo[2.2.1]heptan-7-amine | 1.76 | 1 | 647 |
| 162 | 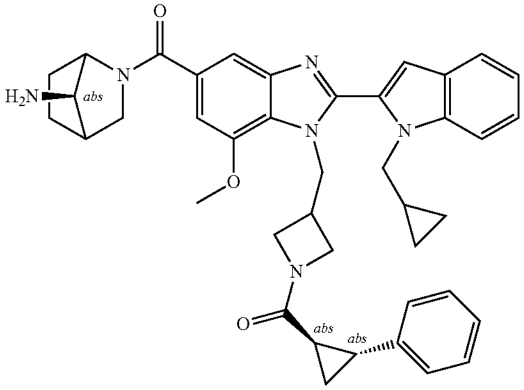 [SMILES: COc1cc(C(=O)N2CC3CCC2[C@@H]3N)cc2nc(-c3cc4ccccc4n3CC3CC3)n(CC3CN(C(=O)[C@@H]4C[C@H]4c4ccccc4)C3)c12] | (1R,4R,7R)-2-{2-[1-(cyclopropylmethyl)-1H-indol-2-yl]-7-methoxy-1-({1-[(1R,2R)-2-phenylcyclopropanecarbonyl]azetidin-3-yl}methyl)-1H-1,3-benzodiazole-5-carbonyl}-2-azabicyclo[2.2.1]heptan-7-amine | 1.95 | 1 | 669 |

TABLE 2-continued

| Ex # | Structure | Name | LC/MS Rt (min) | LC/MS Method | M + H (obs ion) |
|---|---|---|---|---|---|
| 163 | 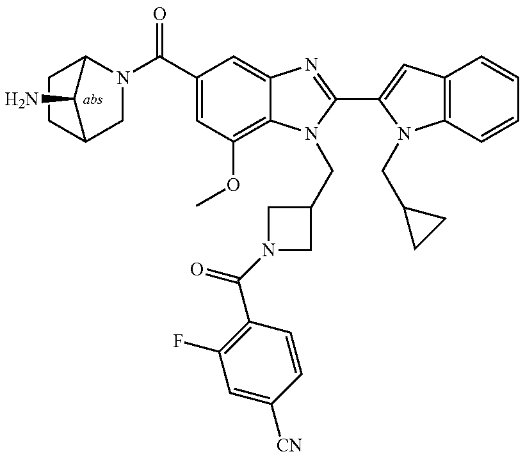 [SMILES: COc1cc(C(=O)N2CC3CCC2[C@@H]3N)cc2nc(-c3cc4ccccc4n3CC3CC3)n(CC3CN(C(=O)c4ccc(C#N)cc4F)C3)c12] | 4-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-3-fluorobenzonitrile | 1.67 | 1 | 672 |
| 164 | 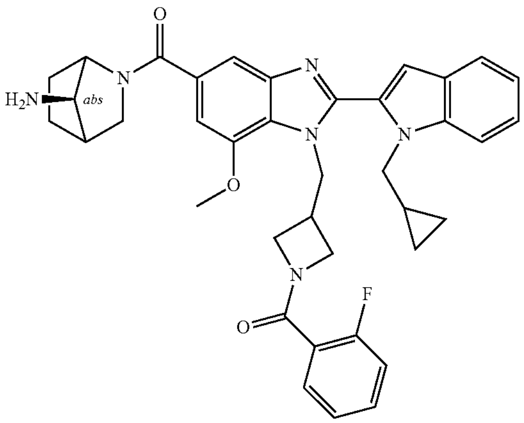 [SMILES: COc1cc(C(=O)N2CC3CCC2[C@@H]3N)cc2nc(-c3cc4ccccc4n3CC3CC3)n(CC3CN(C(=O)c4ccccc4F)C3)c12] | (1R,4R,7R)-2-{2-[1-(cyclopropylmethyl)-1H-indol-2-yl]-1-{[1-(2-fluorobenzoyl)azetidin-3-yl]methyl}-7-methoxy-1H-1,3-benzodiazole-5-carbonyl}-2-azabicyclo[2.2.1]heptan-7-amine | 1.45 | 2 | 647 |
| 165 | 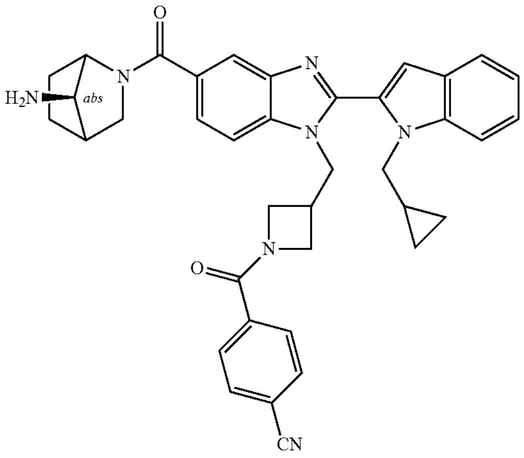 [SMILES: N#Cc1ccc(C(=O)N2CC(Cn3c(-c4cc5ccccc5n4CC4CC4)nc4cc(C(=O)N5CC6CCC5[C@@H]6N)ccc43)C2)cc1] | 4-[3-({5-[(1R,4R,7R)-7-amino-2-azabicyclo[2.2.1]heptane-2-carbonyl]-2-[1-(cyclopropylmethyl)-1H-indol-2-yl]-1H-1,3-benzodiazol-1-yl}methyl)azetidine-1-carbonyl]benzonitrile | 1.39 | 2 | 624 |

TABLE 2-continued

| Ex # | Structure | Name | LC/MS Rt (min) | LC/MS Method | M + H (obs ion) |
|---|---|---|---|---|---|
| 166 | 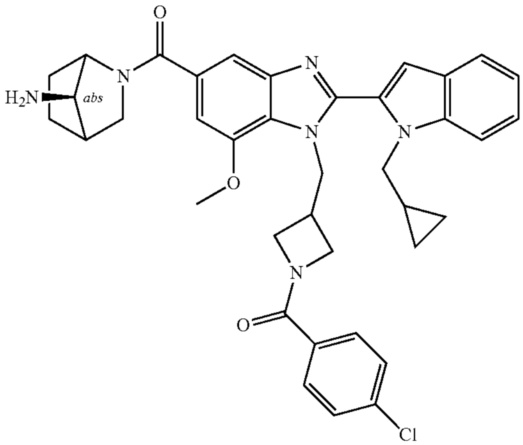 [SMILES: COc1cc(C(=O)N2CC3CCC2[C@@H]3N)cc2nc(-c3cc4ccccc4n3CC3CC3)n(CC3CN(C(=O)c4ccc(Cl)cc4)C3)c12] | (1R,4R,7R)-2-(1-{[1-(4-chlorobenzoyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.71 | 2 | 663 |
| 167 | 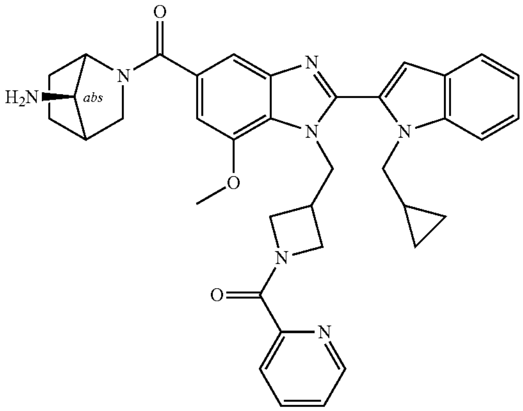 [SMILES: COc1cc(C(=O)N2CC3CCC2[C@@H]3N)cc2nc(-c3cc4ccccc4n3CC3CC3)n(CC3CN(C(=O)c4ccccn4)C3)c12] | (1R,4R,7R)-2-{2-[1-(cyclopropylmethyl)-1H-indol-2-yl]-7-methoxy-1-{[1-(pyridine-2-carbonyl)azetidin-3-yl]methyl}-1H-1,3-benzodiazole-5-carbonyl}-2-azabicyclo[2.2.1]heptan-7-amine | 1.46 | 1 | 630 |
| 168 | 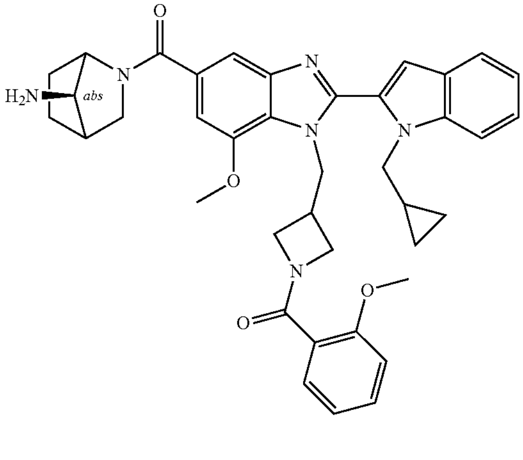 [SMILES: COc1ccccc1C(=O)N1CC(Cn2c(-c3cc4ccccc4n3CC3CC3)nc3cc(C(=O)N4CC5CCC4[C@@H]5N)cc(OC)c32)C1] | (1R,4R,7R)-2-{2-[1-(cyclopropylmethyl)-1H-indol-2-yl]-7-methoxy-1-{[1-(2-methoxybenzoyl)azetidin-3-yl]methyl}-1H-1,3-benzodiazol-5-carbonyl}-2-azabicyclo[2.2.1]heptan-7-amine | 1.44 | 2 | 659 |

TABLE 2-continued

| Ex # | Structure | Name | LC/MS Rt (min) | LC/MS Method | M + H (obs ion) |
|---|---|---|---|---|---|
| 169 | 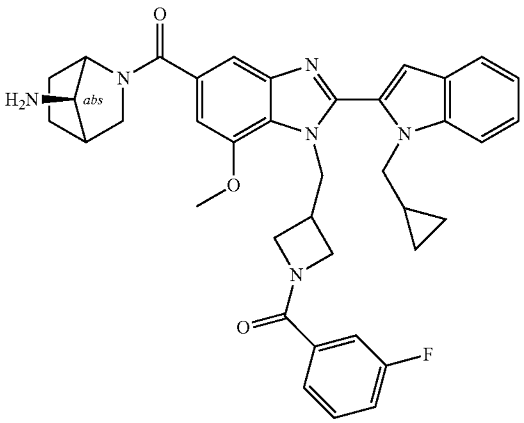 [SMILES: COc1cc(C(=O)N2CC3CCC2[C@@H]3N)cc2nc(-c3cc4ccccc4n3CC3CC3)n(CC3CN(C(=O)c4cccc(F)c4)C3)c12] | (1R,4R,7R)-2-{2-[1-(cyclopropylmethyl)-1H-indol-2-yl]-1-{[1-(3-fluorobenzoyl)azetidin-3-yl]methyl}-7-methoxy-1H-1,3-benzodiazole-5-carbonyl}-2-azabicyclo[2.2.1]heptan-7-amine | 1.62 | 2 | 647 |
| 170 | 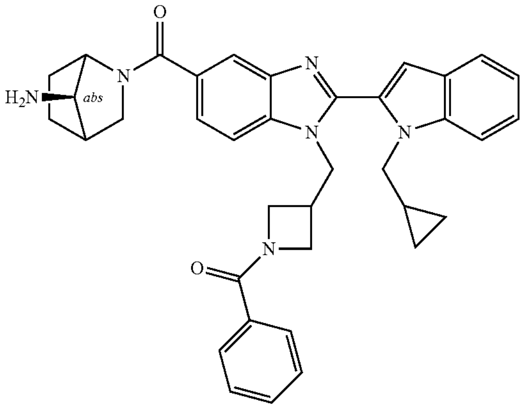 [SMILES: N[C@@H]1C2CCC1N(C(=O)c1ccc3c(c1)nc(-c1cc4ccccc4n1CC1CC1)n3CC1CN(C(=O)c3ccccc3)C1)C2] | (1R,4R,7R)-2-{1-[(1-benozylazetidin-3-yl)methyl]-2-[1-(cyclopropylmethyl)-1H-indol-2-yl]-1H-1,3-benzodiazol-5-carbonyl}-2-azabicyclo[2.2.1]heptan-7-amine | 1.58 | 1 | 599 |
| 171 | 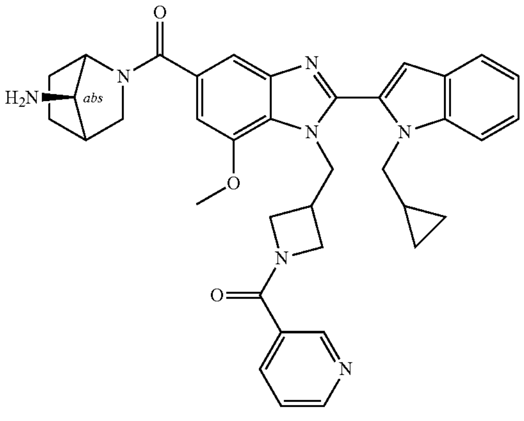 [SMILES: COc1cc(C(=O)N2CC3CCC2[C@@H]3N)cc2nc(-c3cc4ccccc4n3CC3CC3)n(CC3CN(C(=O)c4cccnc4)C3)c12] | (1R,4R,7R)-2-{2-[1-(cyclopropylmethyl)-1H-indol-2-yl]-7-methoxy-1-{[1-(pyridine-3-carbonyl)azetidin-3-yl]methyl}-1H-1,3-benzodiazole-5-carbonyl}-2-azabicyclo[2.2.1]heptan-7-amine | 1.37 | 1 | 630 |

TABLE 2-continued

| Ex # | Structure | Name | LC/MS Rt (min) | LC/MS Method | M + H (obs ion) |
|---|---|---|---|---|---|
| 172 | 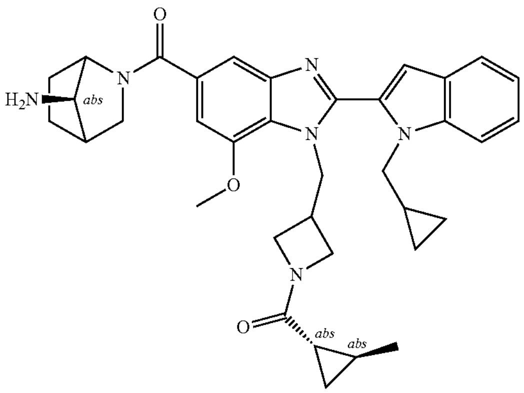 [SMILES: COc1cc(C(=O)N2CC3CCC2[C@@H]3N)cc2nc(-c3cc4ccccc4n3CC3CC3)n(CC3CN(C(=O)[C@H]4C[C@@H]4C)C3)c12] | (1R,4R,7R)-2-{2-[1-(cyclopropylmethyl)-1H-indol-2-yl]-7-methoxy-1-({1-[(1S,2S)-2-methylcyclopropanecarbonyl]azetidin-3-yl}methyl)-1H-1,3-benzodiazole-5-carbonyl}-2-azabicyclo[2.2.1]heptan-7-amine | 1.67 | 1 | 607 |
| 173 | 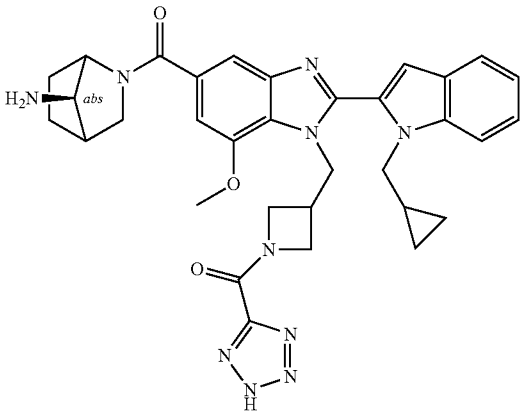 [SMILES: COc1cc(C(=O)N2CC3CCC2[C@@H]3N)cc2nc(-c3cc4ccccc4n3CC3CC3)n(CC3CN(C(=O)c4nn[nH]n4)C3)c12] | (1R,4R,7R)-2-{2-[1-(cyclopropylmethyl)-1H-indol-2-yl]-7-methoxy-1-{[1-(2H-1,2,3,4-tetrazole-5-carbonyl)azetidin-3-yl]methyl}-1H-1,3-benzodiazole-5-carbonyl}-2-azabicyclo[2.2.1]heptan-7-amine | 1.27 | 1 | 621 |
| 174 | 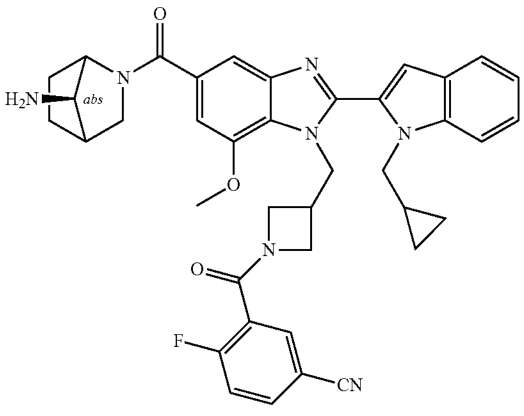 [SMILES: COc1cc(C(=O)N2CC3CCC2[C@@H]3N)cc2nc(-c3cc4ccccc4n3CC3CC3)n(CC3CN(C(=O)c4cc(C#N)ccc4F)C3)c12] | 3-[3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-4-fluorobenzonitrile | 1.55 | 2 | 672 |

TABLE 2-continued

| Ex # | Structure | Name | LC/MS Rt (min) | LC/MS Method | M + H (obs ion) |
|---|---|---|---|---|---|
| 175 | 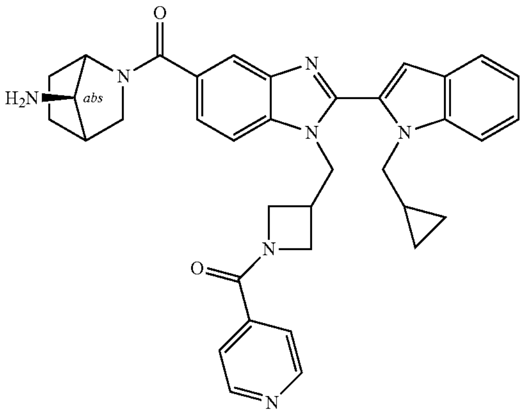 [SMILES: N[C@@H]1C2CCC1N(C(=O)c1ccc3c(c1)nc(-c1cc4ccccc4n1CC1CC1)n3CC1CN(C(=O)c3ccncc3)C1)C2] | (1R,4R,7R)-2-{2-[1-(cyclopropylmethyl)-1H-indol-2-yl]-1-{[1-(pyridine-4-carbonyl)azetidin-3-yl]methyl}-1H-1,3-benzodiazole-5-carbonyl}-2-azabicyclo[2.2.1]heptan-7-amine | 1.18 | 2 | 600 |
| 176 | 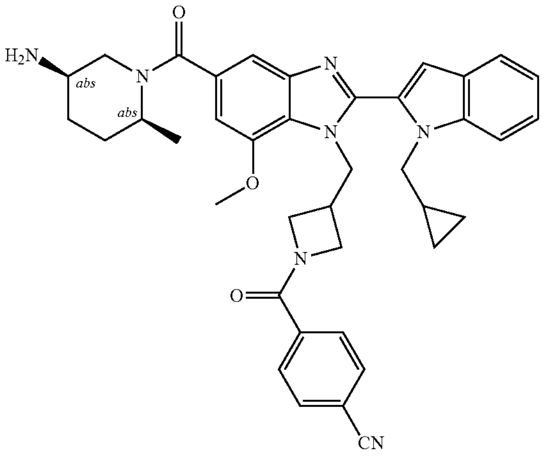 [SMILES: COc1cc(C(=O)N2C[C@H](N)CC[C@@H]2C)cc2nc(-c3cc4ccccc4n3CC3CC3)n(CC3CN(C(=O)c4ccc(C#N)cc4)C3)c12] | 4-[3-({5-[(2S,5R)-5-amino-2-methylpiperidine-1-carbonyl]-2-[1-(cyclopropylmethyl)-1H-indol-2-yl]-7-methoxy-1H-1,3-benzodiazol-1-yl}methyl)azetidine-1-carbonyl]benzonitrile | 1.66 | 1 | 656 |
| 177 | 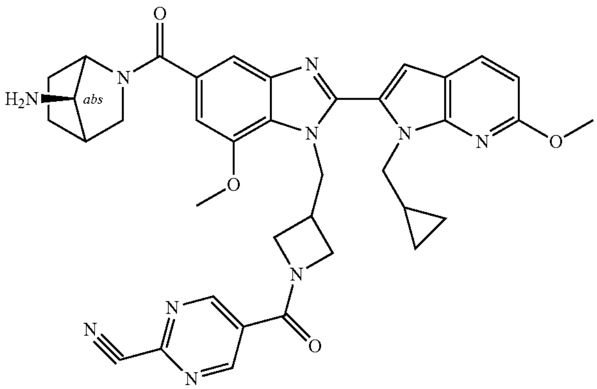 [SMILES: COc1ccc2cc(-c3nc4cc(C(=O)N5CC6CCC5[C@@H]6N)cc(OC)c4n3CC3CN(C(=O)c4cnc(C#N)nc4)C3)n(CC3CC3)c2n1] | 5-[3-({5-[(1R,4R,7R)-7-amino-2-azabicyclo[2.2.1]heptane-2-carbonyl]-2-[1-(cyclopropylmethyl)-6-methoxy-1H-pyrrolo[2,3-b]pyridin-2-yl]-7-methoxy-1H-1,3-benzodiazol-1-yl}methyl)azetidine-1-carbonyl]pyrimidine-2-carbonitrile | 1.68 | 1 | 687 |

TABLE 2-continued

| Ex # | Structure | Name | LC/MS Rt (min) | LC/MS Method | M + H (obs ion) |
|---|---|---|---|---|---|
| 178 | 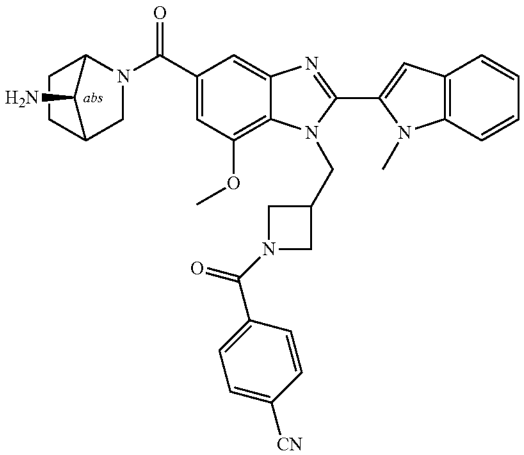 [SMILES: COc1cc(C(=O)N2CC3CCC2[C@@H]3N)cc2nc(-c3cc4ccccc4n3C)n(CC3CN(C(=O)c4ccc(C#N)cc4)C3)c12] | 4-[3-({5-[(7R)-7-amino-2-azabicyclo[2.2.1]heptane-2-carbonyl]-7-methoxy-2-(1-methyl-1H-indol-2-yl)-1H-1,3-benzodiazol-1-yl}methyl)azetidine-1-carbonyl]benzonitrile | 1.41 | 2 | 614 |
| 179 | 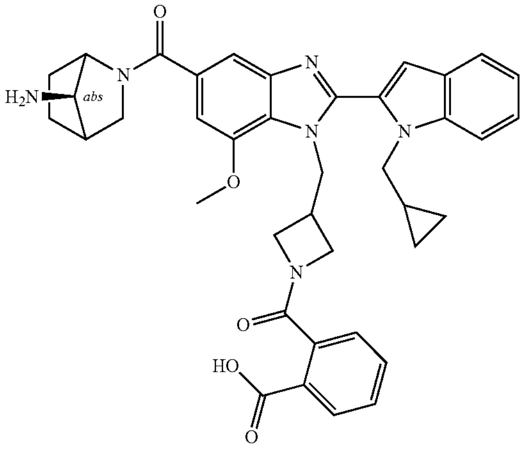 [SMILES: COc1cc(C(=O)N2CC3CCC2[C@@H]3N)cc2nc(-c3cc4ccccc4n3CC3CC3)n(CC3CN(C(=O)c4ccccc4C(=O)O)C3)c12] | 2-[3-({5-[(1R,4R,7R)-7-amino-2-azabicyclo[2.2.1]heptane-2-carobnyl]-2-[1-(cyclopropylmethyl)-1H-indol-2-yl]-7-methoxy-1H-1,3-benzodiazol-1-yl}methyl)azetidine-1-carbonyl]benzoic acid | 1.5 | 2 | 672 |
| 180 | 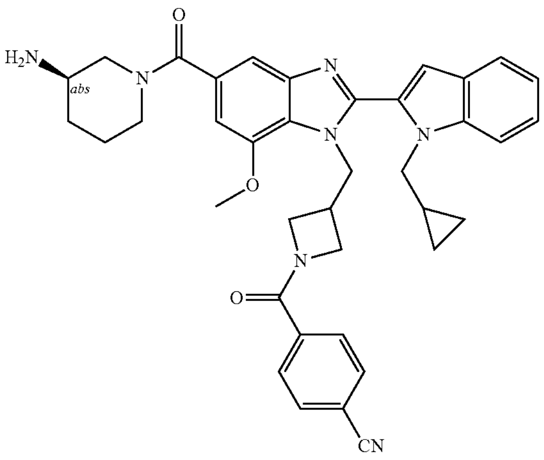 [SMILES: COc1cc(C(=O)N2CCC[C@@H](N)C2)cc2nc(-c3cc4ccccc4n3CC3CC3)n(CC3CN(C(=O)c4ccc(C#N)cc4)C3)c12] | 4-[3-({5-[(3R)-3-aminopiperidine-1-carbonyl]-2-[1-(cyclopropylmethyl)-1H-indol-2-yl]-7-methoxy-1H-1,3-benzodiazol-1-yl}methyl)azetidine-1-carbonyl]benzonitrile | 1.61 | 1 | 642 |

TABLE 2-continued

| Ex # | Structure | Name | LC/MS Rt (min) | LC/MS Method | M + H (obs ion) |
|---|---|---|---|---|---|
| 181 | 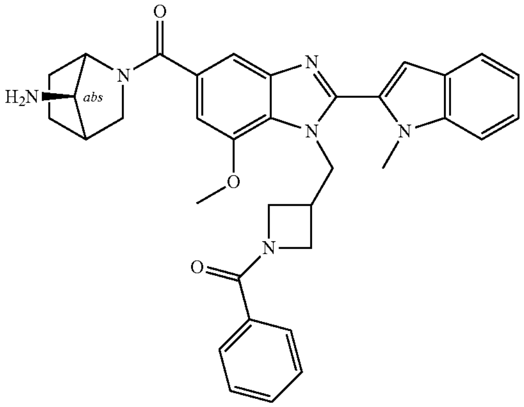 [SMILES: COc1cc(C(=O)N2CC3CCC2[C@@H]3N)cc2nc(-c3cc4ccccc4n3C)n(CC3CN(C(=O)c4ccccc4)C3)c12] | (1R,4R,7R)-2-{1-[(1-benzoylazetidin-3-yl)methyl]-7-methoxy-2-(1-methyl-1H-indol-2-yl)-1H-1,3-benzodiazole-5-carbonyl}-2-azabicyclo[2.2.1]heptan-7-amine | 1.45 | 2 | 589 |
| 182 | 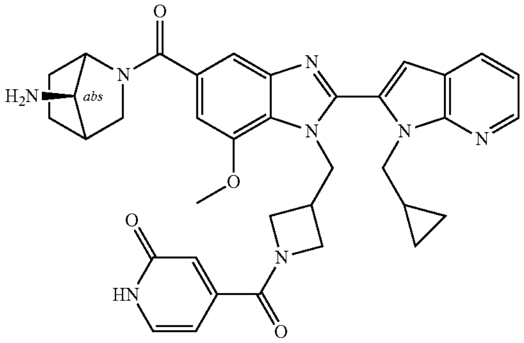 [SMILES: COc1cc(C(=O)N2CC3CCC2[C@@H]3N)cc2nc(-c3cc4cccnc4n3CC3CC3)n(CC3CN(C(=O)c4cc[nH]c(=O)c4)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]-1,2-dihydropyridin-2-one | 1.02 | 1 | 647 |
| 183 | 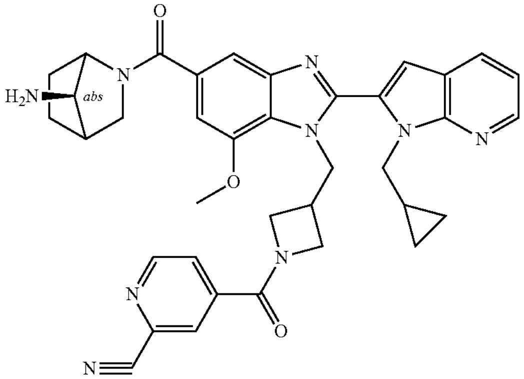 [SMILES: COc1cc(C(=O)N2CC3CCC2[C@@H]3N)cc2nc(-c3cc4cccnc4n3CC3CC3)n(CC3CN(C(=O)c4ccnc(C#N)c4)C3)c12] | 4-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]pyridine-2-carbonitrile | 1.13 | 2 | 656 |
| 184 | 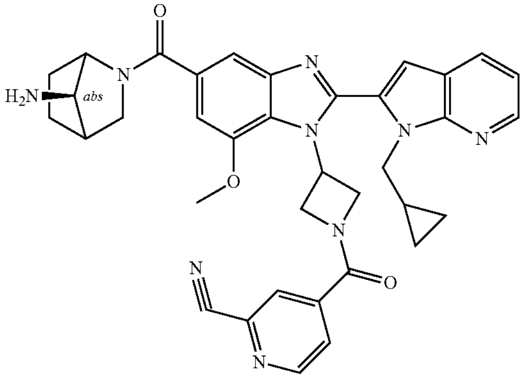 [SMILES: COc1cc(C(=O)N2CC3CCC2[C@@H]3N)cc2nc(-c3cc4cccnc4n3CC3CC3)n(C3CN(C(=O)c4ccnc(C#N)c4)C3)c12] | 4-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidine-1-carbonyl)pyridine-2-carbonitrile | 1.29 | 1 | 642 |

TABLE 2-continued

| Ex # | Structure | Name | LC/MS Rt (min) | LC/MS Method | M + H (obs ion) |
|---|---|---|---|---|---|
| 185 | 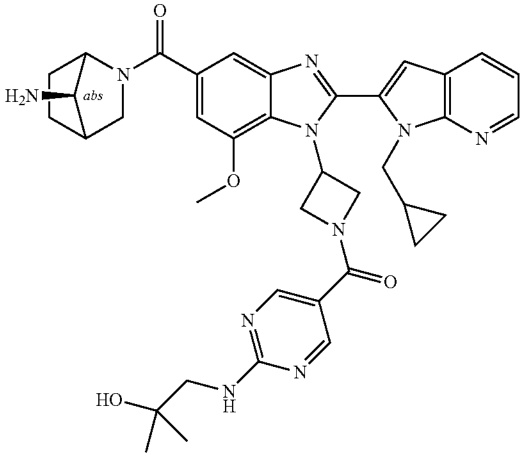 [SMILES: COc1cc(C(=O)N2CC3CCC2[C@@H]3N)cc2nc(-c3cc4cccnc4n3CC3CC3)n(C3CN(C(=O)c4cnc(NCC(C)(C)O)nc4)C3)c12] | 1-{[5-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidine-1-carbonyl)pyrimidin-2-yl]amino}-2-methylpropan-2-ol | 1.08 | 2 | 705 |
| 186 | 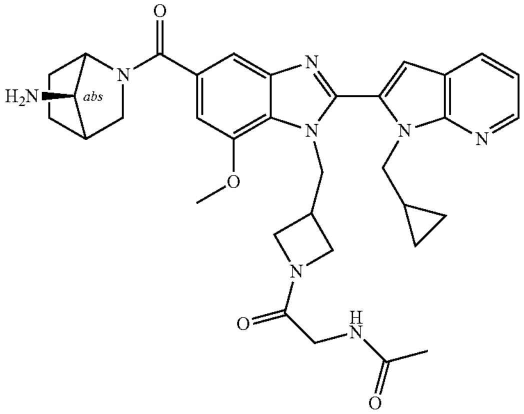 [SMILES: COc1cc(C(=O)N2CC3CCC2[C@@H]3N)cc2nc(-c3cc4cccnc4n3CC3CC3)n(CC3CN(C(=O)CNC(C)=O)C3)c12] | N-{2-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]-2-oxoethyl}acetamide | 1.05 | 2 | 625 |
| 187 | 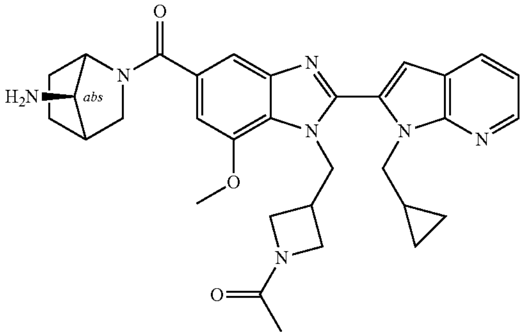 [SMILES: COc1cc(C(=O)N2CC3CCC2[C@@H]3N)cc2nc(-c3cc4cccnc4n3CC3CC3)n(CC3CN(C(C)=O)C3)c12] | 1-[3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidin-1-yl]ethan-1-one | 1.1 | 1 | 568 |
| 188 | 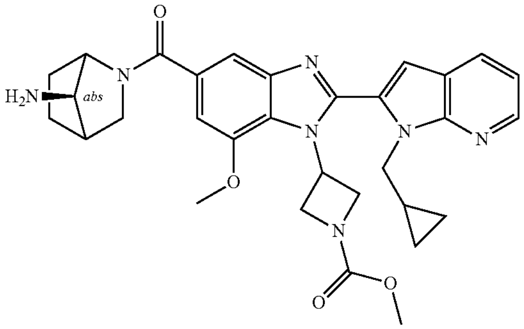 [SMILES: COC(=O)N1CC(n2c(-c3cc4cccnc4n3CC3CC3)nc3cc(C(=O)N4CC5CCC4[C@@H]5N)cc(OC)c32)C1] | methyl 3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidine-1-carboxylate | 1.19 | 2 | 570 |

TABLE 2-continued

| Ex # | Structure | Name | LC/MS Rt (min) | LC/MS Method | M + H (obs ion) |
|---|---|---|---|---|---|
| 189 | 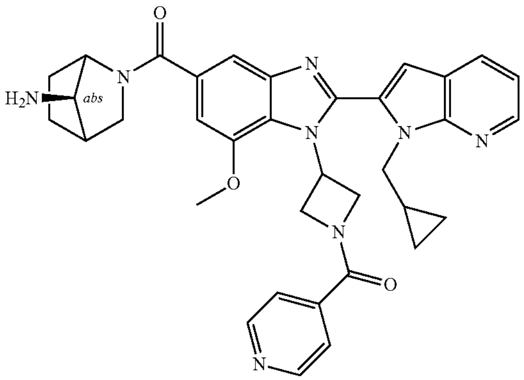 [SMILES: COc1cc(C(=O)N2CC3CCC2[C@@H]3N)cc2nc(-c3cc4cccnc4n3CC3CC3)n(C3CN(C(=O)c4ccncc4)C3)c12] | (1R,4R,7R)-2-{2-[1-(cyclopropylmethyl)-1H-pyrrolo[2,3-b]pyridin-2-yl]-7-methoxy-1-[1-(pyridine-4-carbonyl)azetidin-3-yl]-1H-1,3-benzodiazol-5-carbonyl}-2-azabicyclo[2.2.1]heptan-7-amine | 1.2 | 1 | 617 |
| 190 | 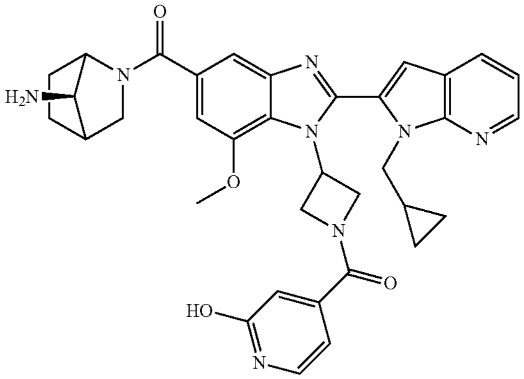 [SMILES: COc1cc(C(=O)N2CC3CCC2[C@@H]3N)cc2nc(-c3cc4cccnc4n3CC3CC3)n(C3CN(C(=O)c4ccnc(O)c4)C3)c12] | 4-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidine-1-carbonyl)pyridin-2-ol | 1.06 | 1 | 633 |
| 191 | 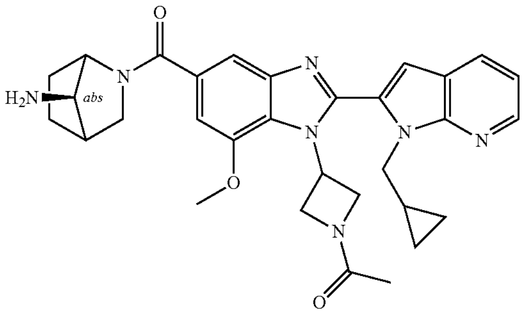 [SMILES: COc1cc(C(=O)N2CC3CCC2[C@@H]3N)cc2nc(-c3cc4cccnc4n3CC3CC3)n(C3CN(C(C)=O)C3)c12] | 1-(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}azetidin-1-yl)ethan-1-one | 1.08 | 1 | 554 |

TABLE 2-continued

| Ex # | Structure | Name | LC/MS Rt (min) | LC/MS Method | M + H (obs ion) |
|---|---|---|---|---|---|
| 192 | 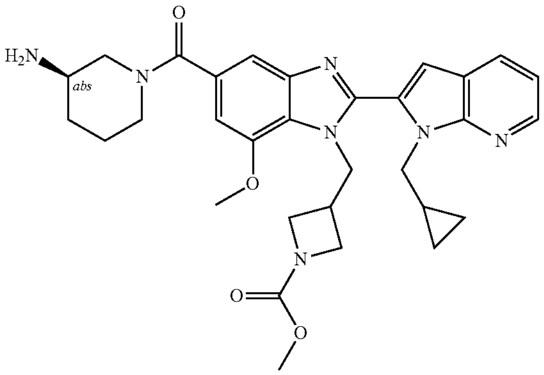 [SMILES: COC(=O)N1CC(Cn2c(-c3cc4cccnc4n3CC3CC3)nc3cc(C(=O)N4CCC[C@@H](N)C4)cc(OC)c32)C1] | methyl 3-({5-[(3R)-3-aminopiperidine-1-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carboxylate | 1.26 | 1 | 572 |
| 193 | 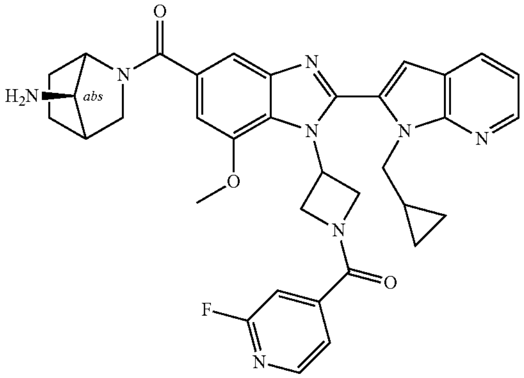 [SMILES: COc1cc(C(=O)N2CC3CCC2[C@@H]3N)cc2nc(-c3cc4cccnc4n3CC3CC3)n(C3CN(C(=O)c4ccnc(F)c4)C3)c12] | (1R,4R,7R)-2-{2-[1-(cyclopropylmethyl)-1H-pyrrolo[2,3-b]pyridin-2-yl]-1-[1-(2-fluoropyridine-4-carbonyl)azetidin-3-yl]-7-methoxy-1H-1,3-benzodiazole-5-carbonyl}-2-azabicyclo[2.2.1]heptan-7-amine | 1.2 | 2 | 635 |

Example 194

5-(4-((5-((1R,4R,7R)-7-amino-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)piperdine-1-carbonyl)pyrimidine-2-carbonitrile

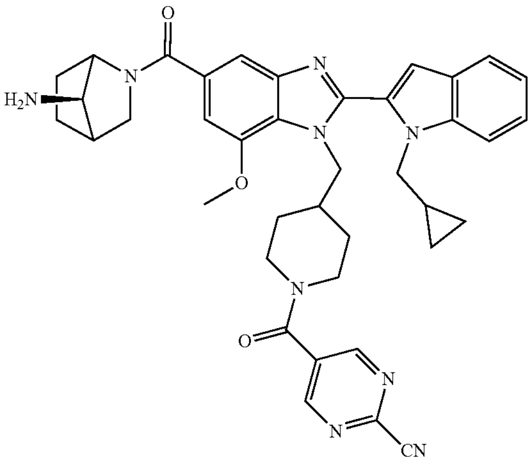 [SMILES: COc1cc(C(=O)N2CC3CCC2[C@@H]3N)cc2nc(-c3cc4ccccc4n3CC3CC3)n(CC3CCN(C(=O)c4cnc(C#N)nc4)CC3)c12]

Intermediate 194A: Tert-butyl 4-(((2-methoxy-4-(methoxycarbonyl)-6-nitrophenyl)amino)methyl)piperidine-1-carboxylate

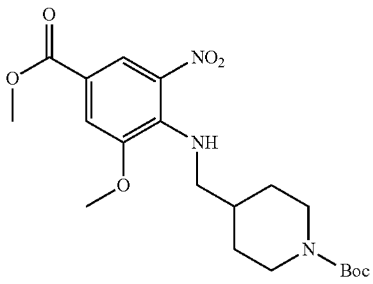

A mixture of tert-butyl 4-(aminomethyl)piperidine-1-carboxylate (2.0 g, 9.33 mmol), methyl 4-chloro-3-methoxy-5-nitrobenzoate (2.292 g, 9.33 mmol) and potassium carbonate (3.87 g, 28.0 mmol) in DMF (30 mL) was stirred at 80° C. for 18 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient) to yield tert-butyl 4-(((2-methoxy-4-(methoxycarbonyl)-6-nitrophenyl)amino)methyl)piperidine-1-carboxylate (3.42 g, 7.67 mmol, 82% yield) as orange gum. LC/MS (2M+Na): 869; LC retention time: 1.08 min (analytical HPLC Method 3).

Intermediate 194B: Tert-butyl 4-(((2-amino-6-methoxy-4-(methoxycarbonyl)phenyl)amino)methyl)piperidine-1-carboxylate

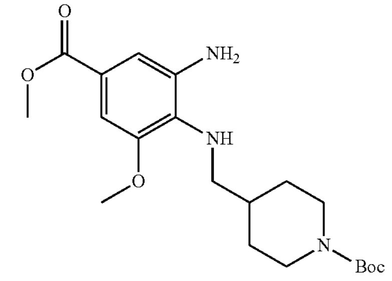 [SMILES: COC(=O)c1cc(OC)c(NCC2CCN(C(=O)OC(C)(C)C)CC2)c([N+](=O)[O-])c1]

A mixture of tert-butyl 4-(((2-methoxy-4-(methoxycarbonyl)-6-nitrophenyl)amino)methyl)piperidine-1-carboxylate (3.42 g, 8.08 mmol) and 10% palladium on carbon (0.859 g, 0.808 mmol) in MeOH (30 mL) was hydrogenated under 1 atm hydrogen for 18 hour. Pd/C was filtered off and the filtrate was concentrated to give crude tert-butyl 4-(((2-amino-6-methoxy-4-(methoxycarbonyl)phenyl)amino)methyl)piperidine-1-carboxylate (3.20 g, 6.51 mmol, 81% yield). The crude product was used in next step without further purification. LC/MS (M+H): 394; LC retention time: 0.80 min (analytical HPLC Method 3).

Intermediate 194C: Methyl 1-((1-((benzyloxy)carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylate

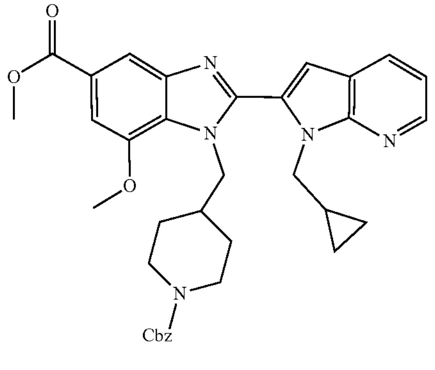 [SMILES: COC(=O)c1cc(OC)c2c(c1)nc(-c1cc3cccnc3n1CC1CC1)n2CC1CCN(C(=O)OCc2ccccc2)CC1]

To a solution of tert-butyl 4-(((2-amino-6-methoxy-4-(methoxycarbonyl)phenyl)amino)methyl)piperidine-1-carboxylate (1.61 g, 4.09 mmol), 1-(cyclopropylmethyl)-1H-pyrrolo[2,3-b]pyridine-2-carboxylic acid (0.885 g, 4.09 mmol) and TEA (1.711 mL, 12.27 mmol) in DMF (15 mL) at 0° C. was added HATU (1,556 g, 4.09 mmol), and the mixture was stirred at 0° C. for 30 min. then RT for 18 hr. The resulting mixture was diluted with EtOAc (25 mL) and was washed with a solution of aqueous saturated sodium bicarbonate (2×25 mL). The organic layer was dried over sodium sulfate and concentrated to give crude tert-butyl 4-(((2-(1-(cyclopropylmethyl)-1H-pyrrolo[2,3-b]pyridine-2-carboxamido)-6-methoxy-4-(methoxycarbonyl)phenyl)amino)methyl)piperidine-1-car boxy late (1.0 g, 1.690 mmol, 41.3% yield). Material was used as is in next reaction.

A solution of tert-butyl 4-(((2-(1-(cyclopropylmethyl)-1H-pyrrolo[2,3-b]pyridine-2-carboxamido)-6-methoxy-4-(methoxycarbonyl)phenyl)amino)methyl)piperidine-1-carboxylate (1.0 g, 1.690 mmol) in acetic acid (25 mL) was stirred at 70° C. for 18 hour. The mixture was concentrated. The resulting mixture was diluted with EtOAc (35 mL) and was washed with a solution of aqueous saturated sodium bicarbonate (2×35 mL). The organic layer was dried over sodium sulfate and concentrated to give a crude yield of methyl 1-((1-(tert-butoxycarbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylate (950 mg, 1,656 mmol, 40.5% yield). Material was used as is in next reaction.

A mixture of methyl 1-((1-(tert-butoxycarbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylate (950 mg, 1.656 mmol) in DCM (5.0 mL) and TFA (5.0 mL) was stirred at RT for 30 min, and the mixture was concentrated to give crude methyl 2-(1-(cyclopropylmethyl)-1H-pyrrolo[2,3-b]pyridin-2-yl)-7-methoxy-1-(piperidin-4-ylmethyl)-1H-benzo[d]imidazole-5-carboxylate, TFA salt. Material was used as is in next reaction.

To a solution of methyl 2-(1-(cyclopropylmethyl)-1H-pyrrolo[2,3-b]pyridin-2-yl)-7-methoxy-1-(piperidin-4-ylmethyl)-1H-benzo[d]imidazole-5-carboxylate, TFA salt and TEA (1.154 mL, 8.28 mmol) in DMF (20 mL) was added benzyl (2,5-dioxopyrrolidin-1-yl) carbonate (413 mg, 1.656 mmol), and the mixture was stirred at RT for 2 hour. The mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-EtOAc 100:0 to 0:100 gradient) to yield methyl 1-((1-((benzyloxy)carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylate (650 mg, 1.016 mmol, 61.4% yield). LC/MS (M+H): 608; LC retention time: 1.08 min (analytical HPLC Method 3).

Intermediate 194D: Benzyl 4-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)piperidine-1-carboxylate

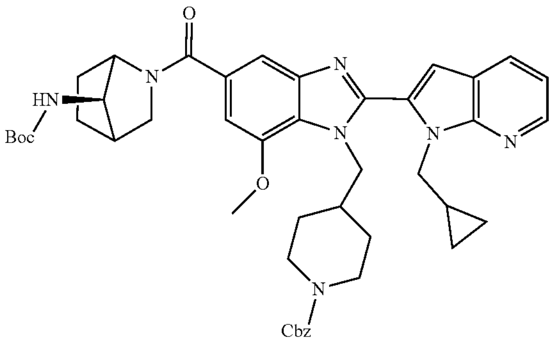 [SMILES: COc1cc(C(=O)N2CC3CCC2[C@@H]3NC(=O)OC(C)(C)C)cc2nc(-c3cc4cccnc4n3CC3CC3)n(CC3CCN(C(=O)OCc4ccccc4)CC3)c12]

A mixture of methyl 1-((1-((benzyloxy)carbonyl)piperidin-4-yl)methyl)-2-(1-(cyclopropylmethyl)-1H-pyrrolo[2,3- b]pyridin-2-yl)-7-methoxy-1H-benzo[d]imidazole-5-carboxylate (650 mg, 1.070 mmol) and 1.0 M aqueous sodium hydroxide (5.35 mL, 5.35 mmol) in THF (20 mL) was stirred at 50° C. for 18 hour. The mixture was cooled to RT. A solution of 1.0 M aqueous HCl (5.5 mL) was added to the mixture and the mixture was concentrated to give crude 1-((1-((benzyloxy)carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylic acid (635 mg, 0.963 mmol, 90% yield). LC/MS (M+H): 594; LC retention time: 0.97 min (analytical HPLC Method 3). Material was used as is in next reaction.

A mixture of 1-((1-((benzyloxy)carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carboxylic acid (635 mg, 0.963 mmol), tert-butyl ((1R,4R,7R)-2-azabicyclo[2.2.1]heptan-7-yl)carbamate (227 mg, 1.070 mmol), BOP (473 mg, 1.070 mmol) and TEA (0.745 mL, 5.35 mmol) in DMF (30 mL) was stirred at RT for 2 hour. The mixture was diluted with EtOAc (35 mL) and was washed with a solution of aqueous saturated sodium bicarbonate (2×35 mL) and aqueous 1.0 M HCl (15 mL). The organic layer was dried over sodium sulfate and concentrated. The crude product was subjected to ISCO flash chromatography (silica gel/hexane-10% MeOH/EtOAc-100:0 to 0:100 gradient) to yield benzyl 4-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)piperidine-1-carboxylate (800 mg, 0.965 mmol, 90% yield) as white foam. LC/MS (M+H): 788; LC retention time: 1.02 min (analytical HPLC Method 3).

Intermediate 194E: Tert-butyl ((1R,4R,7R)-2-(2-(1-(cyclopropylmethyl)-1H-pyrrolo[2,3-b]pyridin-2-yl)-7-methoxy-1-(piperidin-4-ylmethyl)-1H-benzo[d]imidazole-5-carbonyl)-2-azabicyclo[2.2.1]heptan-7-yl)carbamate

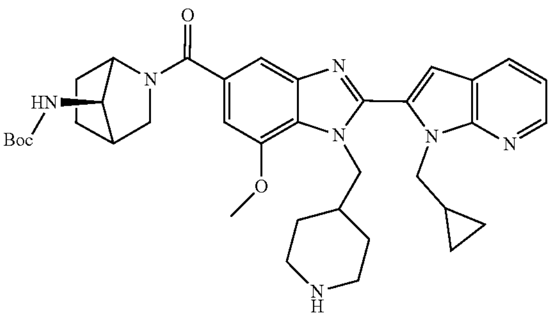 [SMILES: COc1cc(C(=O)N2CC3CCC2[C@@H]3NC(=O)OC(C)(C)C)cc2nc(-c3cc4cccnc4n3CC3CC3)n(CC3CCNCC3)c12]

A mixture of benzyl 4-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)piperidine-1-carboxylate (800 mg, 1.015 mmol) and 10% palladium on carbon (108 mg, 0.102 mmol) in MeOH (20 mL) was hydrogenated under 1 atm of hydrogen for 18 hour. Pd/C was filtered off and the filtrate was concentrated to give crude tert-butyl ((1R,4R,7R)-2-(2-(1-(cyclopropylmethyl)-1H-pyrrolo[2,3-b]pyridin-2-yl)-7-methoxy-1-(piperidin-4-ylmethyl)-1H-benzo[d]imidazole-5-carbonyl)-2-azabicyclo[2.2.1]heptan-7-yl)carbamate (651 mg, 0.946 mmol, 93% yield) LC/MS (M+H): 654; LC retention time: 0.73 min (analytical HPLC Method 3).

Example 194: 5-(4-((5-(1R,4R,7R)-7-amino-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)piperdine-1-carbonyl)pyrimidine-2-carbonitrile A mixture of 2-cyanopyrimidine-5-carboxylic acid (3.42 mg, 0.023 mmol), BOP (11.16 mg, 0.025 mmol) and TEA (0.011 mL, 0.080 mmol) in DMF (1.0 mL) was stirred at RT for 10 min. tert-Butyl ((1R,4R,7R)-2-(2-(1-(cyclopropylmethyl)-1H-pyrrolo[2,3-b]pyridin-2-yl)-7-methoxy-1-(piperidin-4-ylmethyl)-1H-benzo[d]imidazole-5-carbonyl)-2-azabicyclo[2.2.1]heptan-7-yl)carbamate (15 mg, 0.023 mmol) was then added to the reaction mixture and the resulting mixture was stirred at RT for 1 hour. The mixture was diluted with EtOAc (5 mL) and was washed with a solution of aqueous saturated sodium bicarbonate (2×5 mL). The organic layer was dried over sodium sulfate and concentrated to give crude tert-butyl ((1R,4R,7R)-2-(1-((1-(2-cyanopyrimidine-5-carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(2-cyanopyrimidine-5-carbonyl)piperidin-4-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 10% B, 10-50% B over 20 minutes, then a 4-minute hold at 100% B; Flow Rate: 20 mL/min: Column Temperature: 25 C. Fraction collection was triggered by MS and ITS/signals. Fractions containing the desired product were combined and dried via centrifugal evaporation, 5-[4-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)piperidine-1-carbonyl]pyrimidine-2-carbonitrile (13.3 mg, 19.4 μmol, 84.4%) was isolated. LC/MS (M+H): 685; LC retention time: 1.48 min (analytical HPLC Method 2). $^1$H NMR (500 MHz, DMSO-$d_6$) δ 8.29-8.23 (m, 3H), 7.50-7.31 (m, 1H), 7.23 (d, J=8.2 Hz, 1H), 7.13-7.06 (m, 2H), 6.96-6.85 (m, 1H), 4.51-4.00 (m, 6H), 3.92 (br s, 3H), 3.14-3.06 (m, 1H), 2.90-2.51 (m, 2H), 1.98-1.71 (m, 3H), 1.59 (br s, 1H), 1.28-0.90 (m, 3H), 0.23 (br d, J=7.3 Hz, 2H), 0.00 (br s, 2H).

Example 195

5-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-vi]-7-methoxy-1H-1,3-benzodiazol-1-yl}methyl)pyrrolidin-1-yl]pyridine-3-carbonitrile

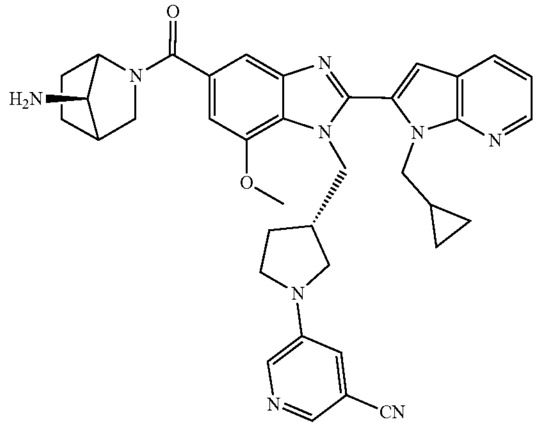 [SMILES: COc1cc(C(=O)N2CC3CCC2[C@@H]3N)cc2nc(-c3cc4cccnc4n3CC3CC3)n(C[C@H]3CCN(c4cncc(C#N)c4)C3)c12]

Intermediate 195A: Tert-butyl (R)-3-(((2-amino-6-methoxy-4-(methoxycarbonyl)phenyl)amino)methyl)pyrrolidine-1-carboxylate

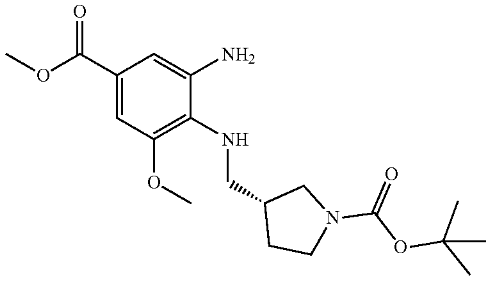 [SMILES: COC(=O)c1cc(N)c(NC[C@H]2CCN(C(=O)OC(C)(C)C)C2)c(OC)c1]

A mixture of tert-butyl (R)-3-(aminomethyl)pyrrolidine-1-carboxylate (0.815 g, 4.07 mmol), methyl 4-chloro-3-methoxy-5-nitrobenzoate (1.00 g, 4.07 mmol) and potassium carbonate (1.688 g, 12.21 mmol) in DMF (20 mL) was stirred at 80° C. for 18 hr. The mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-EtOAc 100:0 to 0:100 gradient) to yield tert-butyl (R)-3-(((2-methoxy-4-(methoxycarbonyl)-6-nitrophenyl)amino)methyl)pyrrolidine-1-carboxylate (1.0 g, 2.442 mmol, 60.0% yield). LC/MS (M+H): 410; LC retention time: 1.07 mm (analytical HPLC Method 3).

A mixture of tert-butyl (R)-3-(((2-methoxy-4-(methoxycarbonyl)-6-nitrophenyl)amino)methyl)pyrrolidine-1-carboxylate (1.0 g, 2.442 mmol) and 10% palladium on carbon (0.433 g, 0.407 mmol) in MeOH (80 mL) was hydrogenated at 1 atm of hydrogen for 5 hour. Pd/C was filtered off and the filtrate was concentrated to give a crude yield of tert-butyl (R)-3-(((2-amino-6-methoxy-4-(methoxycarbonyl)phenyl)amino)methyl)pyrrolidine-1-carboxylate (945 mg, 2.241 mmol, 55.1% yield) as white foam. LC/MS (M+H): 380; LC retention time: 0.79 min (analytical HPLC Method 3). Material was used as is in next reaction.

Intermediate 195B: Methyl (R)-1-((1-(tert-butoxycarbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate

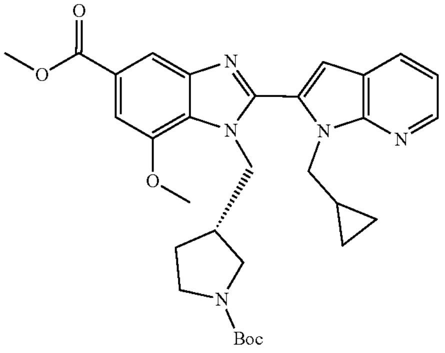 [SMILES: COC(=O)c1cc(OC)c2c(c1)nc(-c1cc3cccnc3n1CC1CC1)n2C[C@H]1CCN(C(=O)OC(C)(C)C)C1]

A mixture of 1-(cyclopropylmethyl)-1H-pyrrolo[2,3-b]pyridine-2-carboxylic acid (539 mg, 2.490 mmol), tert-butyl (R)-3-(((2-amino-6-methoxy-4-(methoxycarbonyl)phenyl)amino)methyl)pyrrolidine-1-carboxylate (945 mg, 2.490 mmol), HATU (947 mg, 2.490 mmol) and TEA (1.736 mL, 12.45 mmol) was stirred at RT for 18 hr. The mixture was diluted with EtOAc (35 mL) and was washed with a solution of aqueous saturated sodium bicarbonate (2×35 mL). The organic layer was dried over sodium sulfate and concentrated to give crude tert-butyl (R)-3-(((2-(1-(cyclopropylmethyl)-1H-pyrrolo[2,3-b]pyridine-2-carboxamido)-6-methoxy-4-(methoxycarbonyl)phenyl)amino)methyl)pyrrolidine-1-carboxylate. LC/MS (M+H): 578; LC retention time: 1.07 mm (analytical HPLC Method 3). Material was used as is in next reaction.

A mixture of tert-butyl (R)-3-(((2-(1-(cyclopropylmethyl)-1H-pyrrolo[2,3-b]pyridine-2-carboxamido)-6-methoxy-4-(methoxycarbonyl)phenyl)amino)methyl)pyrrolidine-1-carboxylate in acetic acid (20 mL) was stirred at 80° C. for 5 hour. The mixture was cooled to RT and was then concentrated. The resulting mixture was diluted with EtOAc (35 mL) and was washed with a solution of aqueous saturated sodium bicarbonate (2×35 mL). The organic layer was dried over sodium sulfate and concentrated. The crude product was subjected to ISCO flash chromatography (silica gel/hexane-EtOAc 100:0 to 0:100 gradient) to yield methyl (R)-1-((1-(tert-butoxycarbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate (440 mg, 0.747 mmol, 30.0% yield) as white foam. LC/MS (M+H): 560; LC retention time: 1.09 min (analytical HPLC Method 3).

Intermediate 195C: Methyl (R)-1-((1-((benzyloxy)carbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate

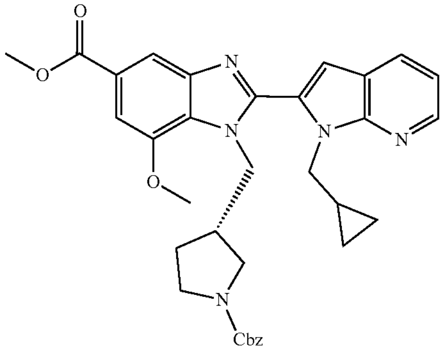 [SMILES: COC(=O)c1cc(OC)c2c(c1)nc(-c1cc3cccnc3n1CC1CC1)n2C[C@H]1CCN(C(=O)OCc2ccccc2)C1]

A mixture of methyl (R)-1-((1-(tert-butoxycarbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate (440 mg, 0.786 mmol) in DCM (2.0 mL) and TFA (2.0 mL) was stirred at RT for 30 min. The mixture was concentrated to give crude methyl (S)-2-(1-(cyclopropylmethyl)-1H-pyrrolo[2,3-b]pyridin-2-yl)-7-methoxy-1-(pyrolidin-3-ylmethyl)-1H-benzo[d]imidazole-5-carboxylate. Material was used as is in next reaction.

To a mixture of methyl (S)-2-(1-(cyclopropylmethyl)-1H-pyrrolo[2,3-b]pyridin-2-yl)-7-methoxy-1-(pyrrolidin-3-ylmethyl)-1H-benzo[d]imidazole-5-carboxylate and TEA (0.110 mL, 0,786 mmol) in THE (10 mL) was added TEA (0.110 mL, 0.786 mmol), and the resulting mixture was stirred at RT for 2 hour. The mixture was concentrated and the crude product was subjected to ISCO flash chromatography (silica gel/hexane-EtOAc 100:0 to 0:100 gradient) to yield methyl (R)-1-((1-((benzyloxy)carbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate (450 mg, 0.720 mmol, 92% yield). LC/MS (M+H): 594; LC retention time: 1.10 min (analytical HPLC Method 3).

Intermediate 195D: Benzyl (3R)-3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)pyrrolidine-1-carboxylate

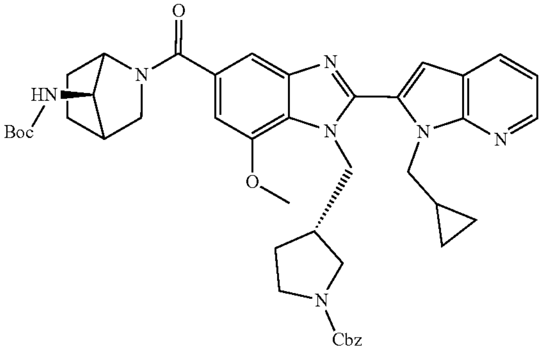 [SMILES: COc1cc(C(=O)N2CC3CCC2[C@@H]3NC(=O)OC(C)(C)C)cc2nc(-c3cc4cccnc4n3CC3CC3)n(C[C@H]3CCN(C(=O)OCc4ccccc4)C3)c12]

A mixture of methyl (R)-1-((1-((benzyloxy)carbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylate (450 mg, 0.758 mmol) and 1.0 M aqueous sodium hydroxide (3.79 mL, 3.79 mmol) in THF (15 mL) was stirred at 50° C. for 18 hour. LCMS indicated 50% converted to product. Another portion of 1.0M aqueous sodium hydroxide (3.79 mL, 3.79 mmol) was added and the mixture was stirred at RT for 18 hour. A solution of 1.0M aqueous HCl (8.0 mL) was then added and the mixture was extracted with EtOAc (2×35 mL). The organic layer was dried over sodium sulfate and concentrated to give crude (R)-1-((1-((benzyloxy)carbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylic acid. LC/MS (M+H): 580; LC retention time: 1.00 min (analytical HPLC Method 3). Material was used as is in next reaction.

A mixture of (R)-1-((1-((benzyloxy)carbonyl)pyrrolidin-3-yl)methyl)-2-(1-(cyclopropylmethyl)-1H-pyrrolo[2,3-b]pyridin-2-yl)-7-methoxy-1H-benzo[d]imidazole-5-carboxylic acid, tert-butyl ((1R,4R,7R)-2-azabicyclo[2.2.1]heptan-7-yl)carbamate (161 mg, 0.758 mmol), BOP (335 mg, 0,758 mmol) and TEA (0.528 mL, 3.79 mmol) in DMF (10 mL) was stirred at RT for 2 hour. The resulting mixture was diluted with EtOAc (25 mL) and was washed with a solution of aqueous saturated sodium bicarbonate (2×25 mL). The organic layer was dried over sodium sulfate and concentrated. The crude product was subjected to ISCO flash chromatography (silica gel/hexane-10% MeOH/EtOAc 100:0 to 0:100 gradient) to yield benzyl (3R)-3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)pyrrolidine-1-carboxylate (566 mg, 0.695 mmol, 92% yield) as white solid. LC/MS (M+H): 774; LC retention time: 1.02 min (analytical HPLC Method 3).

Intermediate 195E: Tert-butyl ((1R,4R,7R)-2-(2-(1-(cyclopropylmethyl)-1H-pyrrolo[2,3-b]pyridin-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate

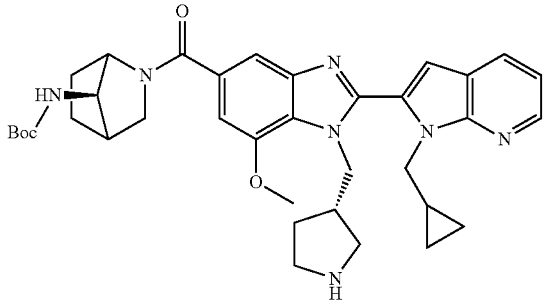 [SMILES: COc1cc(C(=O)N2CC3CCC2[C@@H]3NC(=O)OC(C)(C)C)cc2nc(-c3cc4cccnc4n3CC3CC3)n(C[C@H]3CCNC3)c12]

A mixture of benzyl (3R)-3-((5-((1R,4R,7R)-7-((tert-butoxycarbonyl)amino)-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)pyrrolidine-1-carboxylate (566 mg, 0.731 mmol) and 10% palladium on carbon (78 mg, 0.073 mmol) in MeOH (20 mL) was stirred under 1 atm of hydrogen for 18 hour. Pd/C was filtered and the filtrate was concentrated to give a crude yield of tert-butyl ((1R,4R,7R)-2-(2-(1-(cyclopropylmethyl)-1H-pyrrolo[2,3-b]pyridin-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate (448 mg, 0.665 mmol, 91% yield) as white solid. LC/MS (M+H): 640; LC retention time: 0.81 min (analytical HPLC Method 3). Material was used as is in next reaction.

Example 195: 5-((3S)-3-((5-((1R,4R,7R)-7-amino-2-azabicyclo[2.2.1]heptane-2-carbonyl)-2-(1-(cyclopropylmethyl)-1H-pyrrolo[2,3-b]pyridin-2-yl)-7-methoxy-1H-benzo[d]imidazol-1-yl)methyl)pyrrolidin-1-yl)nicotinonitrile A mixture of tert-butyl ((1R,4R,7R)-2-(2-(1-(cyclopropylmethyl)-1H-pyrrolo[2,3-b]pyridin-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate (15 mg, 0.023 mmol), 5-bromonicotinonitrile (4.29 mg, 0.023 mmol), cesium carbonate (15.28 mg, 0.047 mmol), BINAP (0.730 mg, 1.172 μmol) and $Pd_2(dba)_3$ (1.073 mg, 1.172 μmol) in degassed dioxane (1.0 mL) under nitrogen in a sealed vial was stirred at 80° C. for 18 hour. The resulting mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-(((S)-1-(5-cyanopyridin-3-yl)pyrrolidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-(((S)-1-(5-cyanopyridin-3-yl)pyrrolidin-3-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. 5-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyri din-2-yl]-7-methoxy-1H-1,3-benzodiazol-1-yl}methyl)pyrrolidin-1-yl]pyridine-3-carbonitrile (13.2 mg, 20.6 μmol, 89.4%) was isolated. LC/MS (M+H): 642; LC retention time: 1.35 min (analytical HPLC Method 2), $^1H$ NMR (500 MHz, DMSO-$d_6$) δ 8.26-8.07 (m, 1H), 7.90-7.66 (m, 3H), 7.42-7.11 (m, 1H), 7.02-6.67 (m, 4H), 4.58-4.41 (m, 2H), 4.30-4.15 (m, 2H), 3.65-2.42 (m, 9H), 2.12-1.92 (m, 1H), 1.87-0.58 (m, 9H), 0.23-0.26 (m, 4H).

Example 196

6-[(3S)-3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)pyrrolidin-1-yl]pyrazine-2-carbonitrile

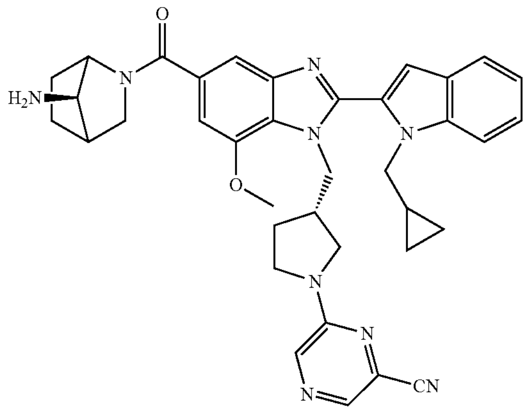 [SMILES: COc1cc(C(=O)N2CC3CCC2[C@@H]3N)cc2nc(-c3cc4ccccc4n3CC3CC3)n(C[C@H]3CCN(c4cncc(C#N)n4)C3)c12]

Intermediate 196A: Tert-butyl (R)-3-(((2-methoxy-4-(methoxycarbonyl)-6-nitrophenyl)amino)methyl)pyrrolidine-1-carboxylate

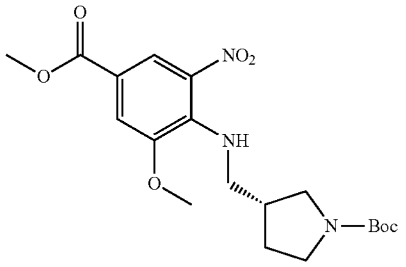 [SMILES: COC(=O)c1cc(OC)c(NC[C@H]2CCN(C(=O)OC(C)(C)C)C2)c([N+](=O)[O-])c1]

A mixture of tert-butyl (R)-3-(aminomethyl)pyrrolidine-1-carboxylate hydrochloride (335 mg, 1,415 mmol), methyl 4-chloro-3-methoxy-5-nitrobenzoate (348 mg, 1.415 mmol) and potassium carbonate (978 mg, 7.08 mmol) in DMF (10 mL) was stirred at 80° C. for 18 hour. The mixture was diluted with EtOAc (25 mL) and was washed with a solution of aqueous saturated sodium bicarbonate (2×25 mL). The organic layer was dried over sodium sulfate and concentrated. The crude product was subjected to ISCO flash chromatography (silica gel/hexane-EtOAc 100:0 to 0:100 gradient). Yield tert-butyl (R)-3-(((2-methoxy-4-(methoxycarbonyl)-6-nitrophenyl)amino)methyl)pyrrolidine-1-carboxylate (421 mg, 0.977 mmol, 69.0% yield) as orange gum, LC/MS (2M+Na): 841; LC retention time: 1.06 min (analytical HPLC Method 3). Material was used as is in next reaction.

Intermediate 196B: Benzyl (3R)-3-(((4-((1R,4R,7R)-7-((tert-butoxycarbonyl)amino)-2-azabicyclo[2.2.1]heptane-2-carbonyl)-2-methoxy-6-nitrophenyl)amino)methyl)pyrrolidin-1-carboxylate

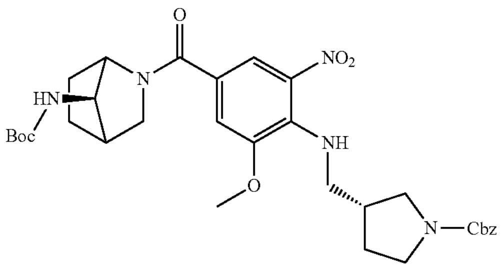 [SMILES: COc1cc(C(=O)N2CC3CCC2[C@@H]3NC(=O)OC(C)(C)C)cc([N+](=O)[O-])c1NC[C@H]1CCN(C(=O)OCc2ccccc2)C1]

A mixture of tert-butyl (R)-3-(((2-methoxy-4-(methoxycarbonyl)-6-nitrophenyl)amino)methyl)pyrrolidine-1-carboxylate (387 mg, 0.945 mmol) in DCM (5.0 mL) and TFA (5.0 mL) was stirred at RT for 30 min. The resulting mixture was concentrated to give crude methyl (S)-3-methoxy-5-nitro-4-((pyrrolidin-3-ylmethyl)amino)benzoate. Material was used as is in next reaction.

To a solution of methyl (S)-3-methoxy-5-nitro-4-((pyrrolidin-3-ylmethyl)amino)benzoate in THF (20 mL) was added TEA (0.659 mL, 4.73 mmol) and benzyl (2,5-dioxopyrrolidin-1-yl) carbonate (236 mg, 0.945 mmol), and the mixture was stirred at RT for 2 hour. The resulting mixture was concentrated to give crude benzyl (R)-3-(((2-methoxy-4-(methoxycarbonyl)-6-nitrophenyl)amino)methyl)pyrrolidine-1-carboxylate. Material was used as is in next reaction.

A mixture benzyl (R)-3-(((2-methoxy-4-(methoxycarbonyl)-6-nitrophenyl)amino)methyl)pyrrolidine-1-carboxylate and 1.0 M aqueous sodium hydroxide (9.45 mL, 9.45 mmol) in THF (20 mL) was stirred at 60° C. for 18 hour, THF was removed and a solution of aqueous 1.0 M HCl was added. The mixture was extracted with EtOAc (2×mL). The organic layer was dried over sodium sulfate and concentrated to give crude (R)-4-(((1-((benzyloxy)carbonyl)pyrrolidin-3-yl)methyl)amino)-3-methoxy-5-nitrobenzoic acid. Material was used as is in next reaction.

A mixture of (R)-4-(((1-((benzyloxy)carbonyl)pyrrolidin-3-yl)methyl)amino)-3~methoxy-5-nitrobenzoic acid, tert-butyl ((1R,4R,7R)-2-azabicyclo[2.2.1]heptan-7-yl)carbamate (201 mg, 0.945 mmol), BOP (418 mg, 0.945 mmol) and TEA (0.659 mL, 4.73 mmol) m DMF (10 mL) was stirred at RT for 18 hour. The resulting mixture was diluted with EtOAc (25 mL) and was washed with a solution of aqueous saturated sodium bicarbonate (2×25 mL). The organic layer was dried over sodium sulfate and concentrated. The crude product was subjected to ISCO flash chromatography (silica gel/hexane-10% MeOH/EtOAc 100:0 to 0:100 gradient). Yield benzyl (3R)-3-(((4-((1R,4R,7R)-7-((tert-butoxycarbonyl)amino)-2-azabicyclo[2.2.1]heptane-2-carbonyl)-2-methoxy-6-nitrophenyl)amino)methyl)pyrrolidine-1-carboxylate (517 mg, 0.829 mmol, 88% yield) as orange solid.

Intermediate 196C: Tert-butyl ((1R,4R,7R)-2-(2-(1-(cyclopropylmethyl)-1H-indol-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate

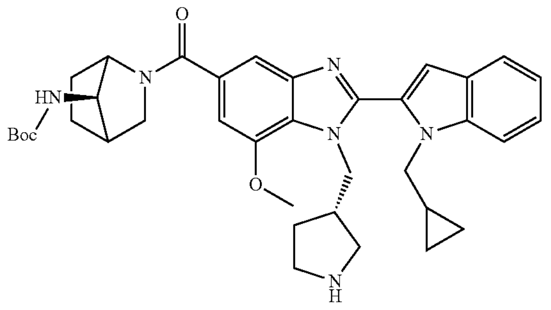 [SMILES: COc1cc(C(=O)N2CC3CCC2[C@@H]3NC(=O)OC(C)(C)C)cc2nc(-c3cc4ccccc4n3CC3CC3)n(C[C@H]3CCNC3)c12]

To a solution of benzyl (3R)-3-(((4-((1R,4R,7R)-7-((tert-butoxycarbonyl)amino)-2-azabicyclo[2.2.1]heptane-2-carbonyl)-2-methoxy-6-nitrophenyl)amino)methyl)pyrrolidine-1-carboxylate (150 mg, 0.240 mmol) and 1-(cyclopropylmethyl)-1H-indole-2-carbaldehyde (47.9 mg, 0.240 mmol) in EtOH (0.80 mL) was added a solution of sodium hydrosulfite (126 mg, 0.721 mmol) in water (0.40 mL) at RT under nitrogen. The mixture was stirred at 80° C. for 18 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield benzyl (3R)-3-((5-((1R,4R,7R)-7-((tert-butoxycarbonyl)amino)-2-azabicyclo[2.2.1]heptane-2-carbonyl)-2-(1-(cyclopropylmethyl)-1H-indol-2-yl)-7-methoxy-1H-benzo[d]imidazol-1-yl)methyl)pyrrolidine-1-carboxylate as white solid. LC/MS (M+H): 773; LC retention time: 1.04 min (analytical HPLC Method 3). Material was used as is in next reaction.

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrol-2-yl)-7-methoxy-1H-benzo[d]imidazol-1-yl)methyl)azetidine-1-carboxylate (133 mg, 0.188 mmol) and 10% palladium on carbon (25.6 mg, 0.024 mmol) in MeOH (10 mL) was hydrogenated under 1 atm of hydrogen for 18 hour. Pd/C was filtered off and the filtrate was concentrated to give a crude yield of tert-butyl ((1R,4R,7R)-2-(2-(1-(cyclopropylmethyl)-1H-indol-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate (108 mg, 0.161 mmol, 66.8% yield) as white solid. LC/MS (M+H): 639; LC retention time: 0.78 min (analytical HPLC Method 3). Material was used as is in next reaction.

Example 196: 6-[(3S)-3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)pyrrolidin-1-yl]pyrazine-2-carbonitrile A mixture of tert-butyl ((1R,4R,7R)-2-(2-(1-(cyclopropylmethyl)-1H-indol-2-yl)-7-methoxy-1-(((S)-pyrrolidin-3-yl)methyl)-1H-benzo[d]imidazole-5-carbonyl)-2-azabicyclo[2.2.1]heptan-7-yl)carbamate (15 mg, 0.023 mmol), 6-bromopyrazine-2-carbonitrile (4.32 mg, 0.023 mmol), cesium carbonate (15.30 mg, 0.047 mmol), BINAP (0.731 mg, 1.174 μmol) and $Pd_2(dba)_3$ (1.075 mg, 1.174 μmol) in degassed dioxane (1.0 mL) under nitrogen in a sealed vial was stirred at 80° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-(((S)-1-(6-cyanopyrazin-2-yl)pyrrolidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((7R)-2-(1-(((S)-1-(6-cyanopyrazin-2-yl)pyrrolidin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge CIS, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 20% B, 20-60% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. 6-[(3S)-3-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)pyrrolidin-1-yl]pyrazine-2-carbonitrile (14.2 mg, 22.1 μmol, 96.2%) was isolated. LC/MS (M+H): 642; LC retention tune: 1.62 mm (analytical HPLC Method 2). $^1$H NMR (500 MHz, DMSO-$d_6$) δ 8.00-7.81 (m, 2H), 7.48-7.26 (m, 3H), 7.17-7.06 (m, 1H), 7.00-6.75 (m, 3H), 4.62-2.43 (in, 15H), 1.97-0.86 (m, 7H), 0.30-0.16 (m, 2H), 0.12--0.06 (m, 2H).

Examples 197 to 241 in Table 3 were prepared as described in the general procedures given for Examples 194 to 196.

TABLE 3

| Ex # | Structure | Name | LC/MS Rt (min) | LC/MS Method | M + H (obs ion) |
|---|---|---|---|---|---|
| 197 | 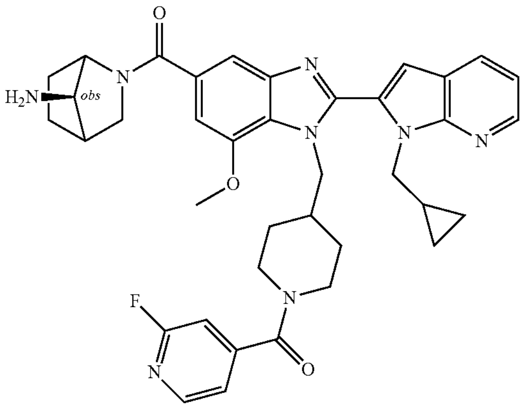 [SMILES: COc1cc(C(=O)N2CC3CCC2[C@@H]3N)cc2nc(-c3cc4cccnc4n3CC3CC3)n(CC3CCN(C(=O)c4ccnc(Cl)c4)CC3)c12] | (1R,4R,7R)-2-{2-[1-(cyclopropylmethyl)-1H-pyrrolo[2,3-b]pyridin-2-yl]-1-{[1-(2-fluoropyridine-4-carbonyl)piperidin-4-yl]methyl}-7-methoxy-1H-1,3-benzodiazole-5-carbonyl}-2-azabicyclo[2.2.1]heptan-7-amine | 1.26 | 1 | 677 |
| 198 | 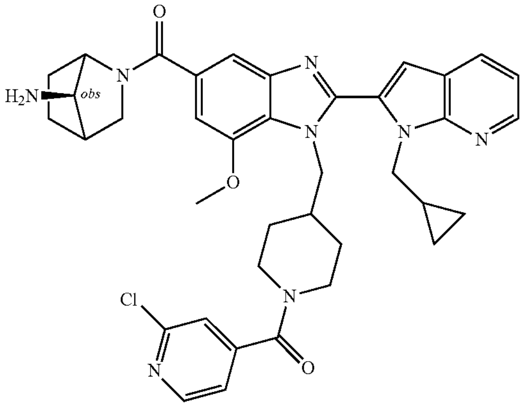 | (1R,4R,7R)-2-(1-{[1-(2-chloropyridine-4-carbonyl)piperidin-4-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.63 | 2 | 693 |

TABLE 3-continued

| Ex # | Structure | Name | LC/MS Rt (min) | LC/MS Method | M + H (obs ion) |
|---|---|---|---|---|---|
| 199 | 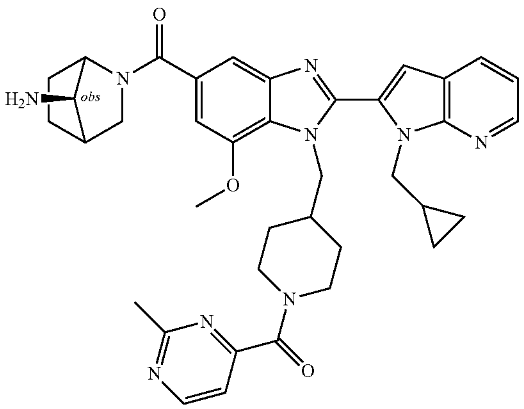 [SMILES: COc1cc(C(=O)N2CC3CCC2[C@@H]3N)cc2nc(-c3cc4cccnc4n3CC3CC3)n(CC3CCN(C(=O)c4ccnc(C)n4)CC3)c12] | (1R,4R,7R)-2-{2-[1-(cyclopropylmethyl)-1H-pyrrolo[2,3-b]pyridin-2-yl]-7-methoxy-1-{[1-(2-methylpyrimidine-4-carbonyl)piperidin-4-yl]methyl}-1H-1,3-benzodiazole-5-carbonyl}-2-azabicyclo[2.2.1]heptan-7-amine | 1.23 | 2 | 674 |
| 200 | 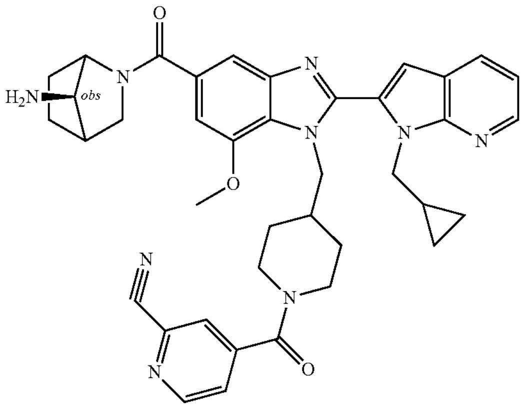 [SMILES: COc1cc(C(=O)N2CC3CCC2[C@@H]3N)cc2nc(-c3cc4cccnc4n3CC3CC3)n(CC3CCN(C(=O)c4ccnc(C#N)c4)CC3)c12] | 4-[4-({5-[(1R,4R,7R)-7-amino-2-azabicyclo[2.2.1]heptane-2-(cyclopropylmethyl)-1H-pyrrolo[2,3-b]pyridin-2-yl]-7-methoxy-1H-1,3-benzodiazol-1-yl}methyl)piperidine-1-carbonyl]pyridine-2-carbonitrile | 1.44 | 1 | 684 |
| 201 | 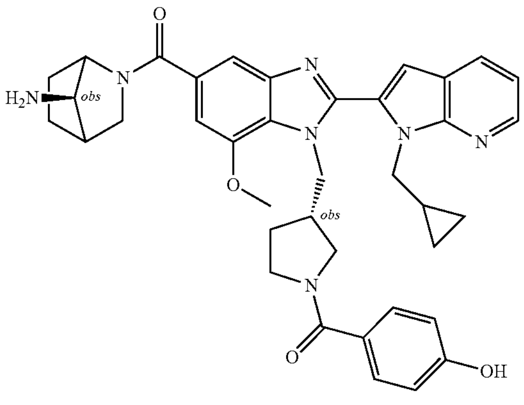 [SMILES: COc1cc(C(=O)N2CC3CCC2[C@@H]3N)cc2nc(-c3cc4cccnc4n3CC3CC3)n(C[C@H]3CCN(C(=O)c4ccc(O)cc4)C3)c12] | 4-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidine-1-carbonyl]benzonitrile | 1.31 | 2 | 669 |

TABLE 3-continued

| Ex # | Structure | Name | LC/MS Rt (min) | LC/MS Method | M + H (obs ion) |
|---|---|---|---|---|---|
| 202 | 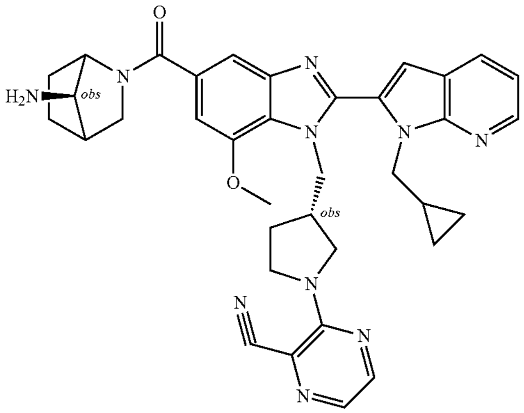 [SMILES: COc1cc(C(=O)N2CC3CCC2[C@@H]3N)cc2nc(-c3cc4cccnc4n3CC3CC3)n(C[C@H]3CCN(c4nccnc4C#N)C3)c12] | 3-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrazine-2-carbonitrile | 1.49 | 2 | 643 |
| 203 | 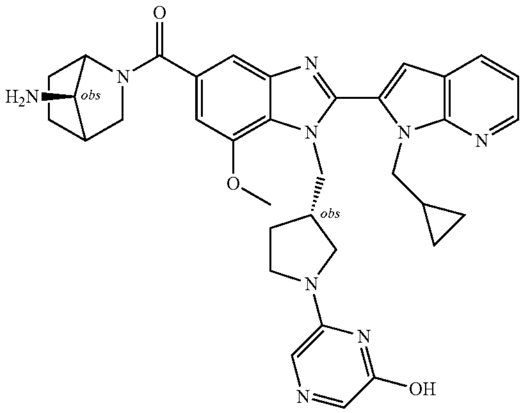 [SMILES: COc1cc(C(=O)N2CC3CCC2[C@@H]3N)cc2nc(-c3cc4cccnc4n3CC3CC3)n(C[C@H]3CCN(c4cncc(O)n4)C3)c12] | 6-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrazine-2-carbonitrile | 1.6 | 2 | 643 |
| 204 | 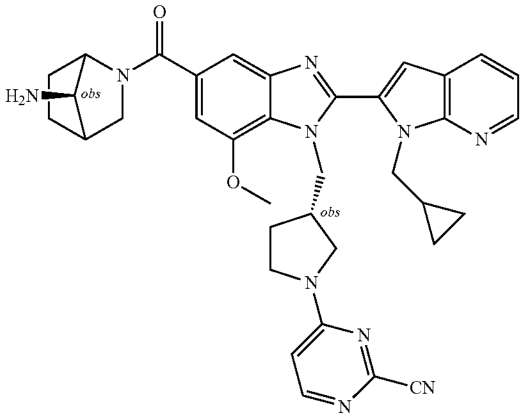 [SMILES: COc1cc(C(=O)N2CC3CCC2[C@@H]3N)cc2nc(-c3cc4cccnc4n3CC3CC3)n(C[C@H]3CCN(c4ccnc(C#N)n4)C3)c12] | 4-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrimidine-2-carbonitrile | 1.46 | 2 | 643 |

TABLE 3-continued

| Ex # | Structure | Name | LC/MS Rt (min) | LC/MS Method | M + H (obs ion) |
|---|---|---|---|---|---|
| 205 | 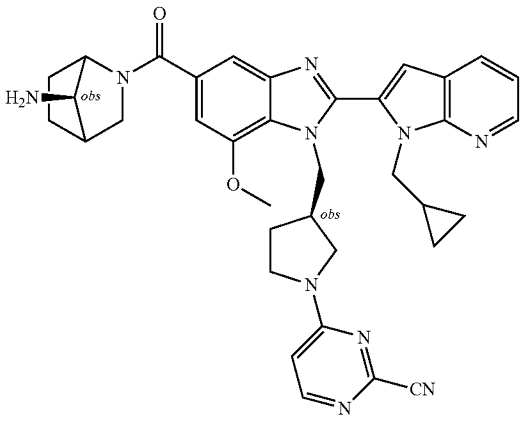 [SMILES: COc1cc(C(=O)N2CC3CCC2[C@@H]3N)cc2nc(-c3cc4cccnc4n3CC3CC3)n(C[C@@H]3CCN(c4ccnc(C#N)n4)C3)c12] | 4-[(3R)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-l-yl]pyrimidine-2-carbonitrile | 1.51 | 2 | 643 |
| 206 | 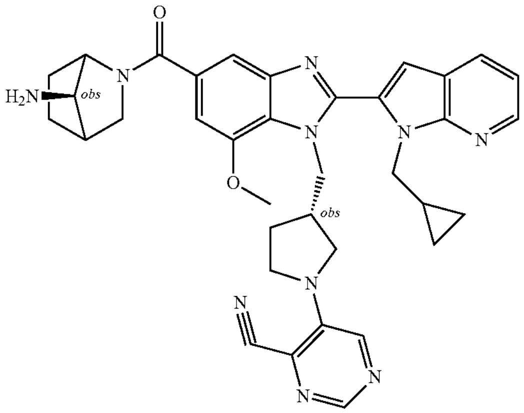 [SMILES: COc1cc(C(=O)N2CC3CCC2[C@@H]3N)cc2nc(-c3cc4cccnc4n3CC3CC3)n(C[C@H]3CCN(c4cncnc4C#N)C3)c12] | 5-[(3S)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrimidine-4-carbonitrile | 1.38 | 2 | 643 |
| 207 | 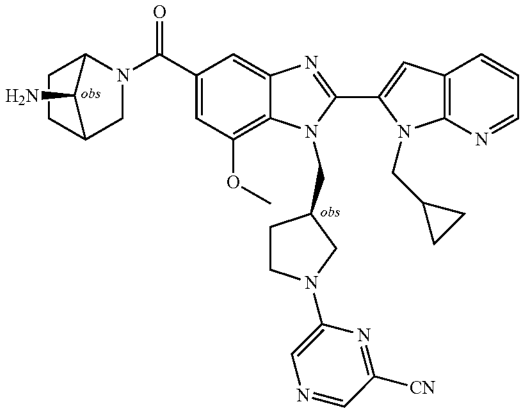 [SMILES: COc1cc(C(=O)N2CC3CCC2[C@@H]3N)cc2nc(-c3cc4cccnc4n3CC3CC3)n(C[C@@H]3CCN(c4cncc(C#N)n4)C3)c12] | 6-[(3R)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrazine-2-carbonitrile | 1.57 | 2 | 643 |

TABLE 3-continued

| Ex # | Structure | Name | LC/MS Rt (min) | LC/MS Method | M + H (obs ion) |
|---|---|---|---|---|---|
| 208 | 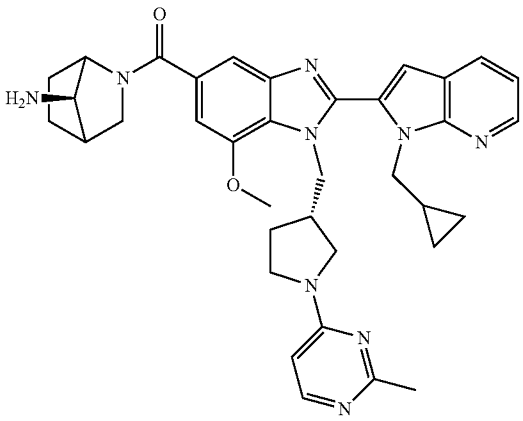 [SMILES: COc1cc(C(=O)N2CC3CCC2[C@@H]3N)cc2nc(-c3cc4cccnc4n3CC3CC3)n(C[C@H]3CCN(c4ccnc(C)n4)C3)c12] | ((1R,4R,7R)-7-amino-2-azabicyclo[2.2.1]heptan-2-yl)(2-(1-(cyclopropylmethyl)-1H-pyrrolo[2,3-b]pyridin-2-yl)-7-methoxy-1-(((S)-1-(2-methylpyrimidin-4-yl)pyrrolidin-3-yl)methyl)-1H-benzo[d]imidazol-5-yl)methanone | 1.27 | 1 | 632 |
| 209 | 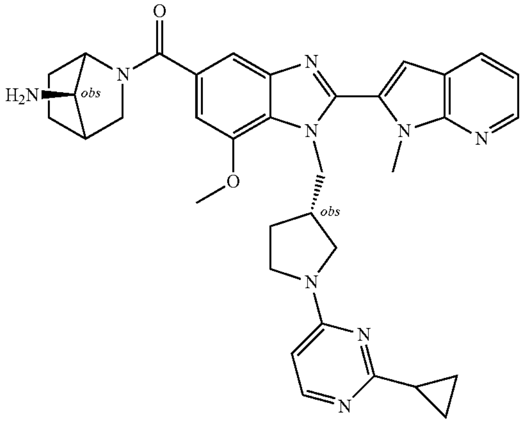 [SMILES: COc1cc(C(=O)N2CC3CCC2[C@@H]3N)cc2nc(-c3cc4cccnc4n3C)n(C[C@H]3CCN(c4ccnc(C5CC5)n4)C3)c12] | (1R,4R,7R)-2-(1-{[(3S)-1-(2-cyclopropylpyrimidin-4-yl)pyrrolidin-3-yl]methyl}-7-methoxy-2-{1-methyl-1H-pyrrolo[2,3-b]pyridin-2-yl}-1H-1,3-benzodiazole-5-carbonyl)-2-azabicyclo[2.2.1]heptan-7-amine | 1.42 | 2 | 618 |
| 210 | 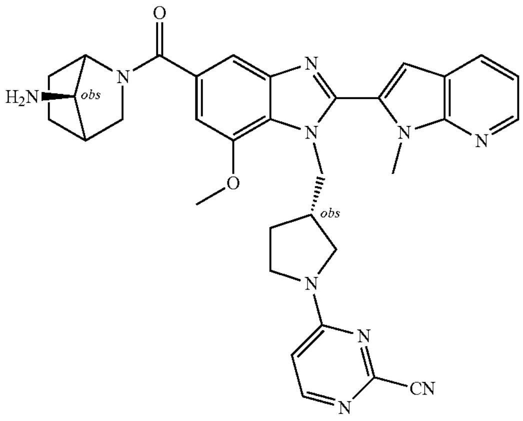 [SMILES: COc1cc(C(=O)N2CC3CCC2[C@@H]3N)cc2nc(-c3cc4cccnc4n3C)n(C[C@H]3CCN(c4ccnc(C#N)n4)C3)c12] | 4-[(3S)-3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)pyrrolidin-1-yl]pyrimidine-2-carbonitrile | 1.26 | 2 | 603 |

TABLE 3-continued

| Ex # | Structure | Name | LC/MS Rt (min) | LC/MS Method | M + H (obs ion) |
|---|---|---|---|---|---|
| 211 | 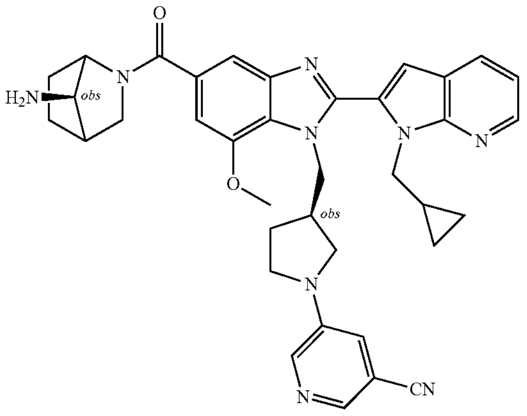 | 5-[(3R)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyridine-3-carbonitrile | 1.54 | 2 | 642 |
| 212 | 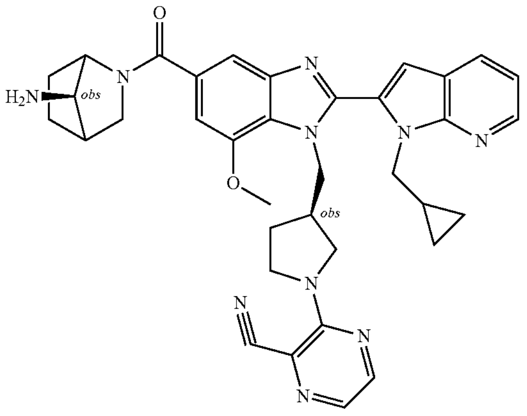 [SMILES: COc1cc(C(=O)N2CC3CCC2[C@@H]3N)cc2nc(-c3cc4cccnc4n3CC3CC3)n(C[C@@H]3CCN(c4nccnc4C#N)C3)c12] | 3-[(3R)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrazine-2-carbonitrite | 1.51 | 2 | 643 |
| 213 | 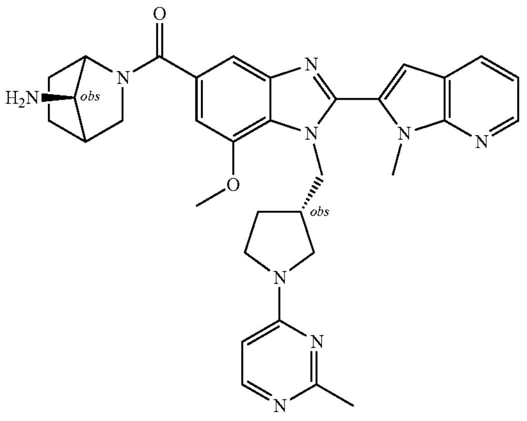 [SMILES: COc1cc(C(=O)N2CC3CCC2[C@@H]3N)cc2nc(-c3cc4cccnc4n3C)n(C[C@H]3CCN(c4ccnc(C)n4)C3)c12] | (1R,4R,7R)-2-(7-methoxy-2-{1-methyl-1H-pyrrolo[2,3-b]pyridin-2-yl}-1-{[(3S)-1-(2-methylpyrimidin-4-yl)pyrrolidin-3-yl]methyl}-1H-1,3-benzodiazole-5-carbonyl)-2-azabicyclo[2.2.1]heptan-7-amine | 1.27 | 2 | 591 |

TABLE 3-continued

| Ex # | Structure | Name | LC/MS Rt (min) | LC/MS Method | M + H (obs ion) |
|---|---|---|---|---|---|
| 214 | 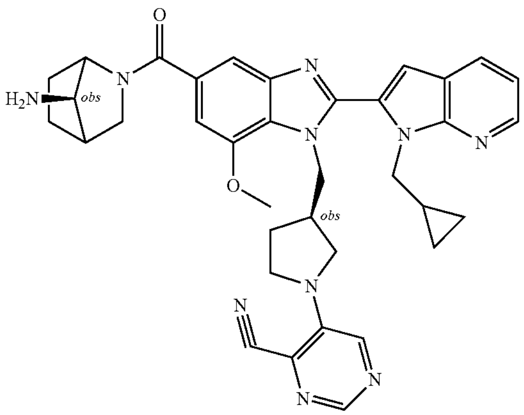 [SMILES: COc1cc(C(=O)N2CC3CCC2[C@@H]3N)cc2nc(-c3cc4cccnc4n3CC3CC3)n(C[C@@H]3CCN(c4cncnc4C#N)C3)c12] | 5-[(3R)-3-({5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)pyrrolidin-1-yl]pyrimidine-4-carbonitrile | 1.35 | 2 | 643 |
| 215 | 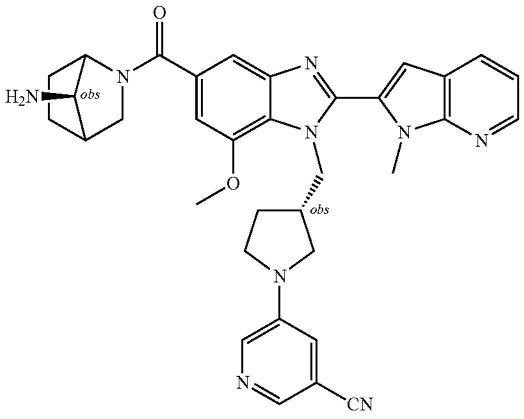 [SMILES: COc1cc(C(=O)N2CC3CCC2[C@@H]3N)cc2nc(-c3cc4cccnc4n3C)n(C[C@H]3CCN(c4cncc(C#N)c4)C3)c12] | 5[(3S)-3-({5-[(1R,4R,7R)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)pyrrolidin-1-yl]pyridine-3-carbonitrile | 1.25 | 1 | 602 |
| 216 | 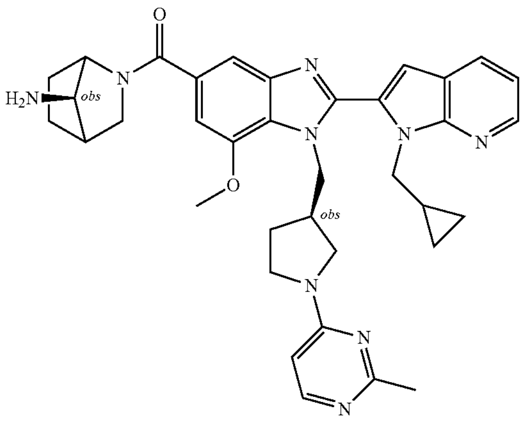 [SMILES: COc1cc(C(=O)N2CC3CCC2[C@@H]3N)cc2nc(-c3cc4cccnc4n3CC3CC3)n(C[C@@H]3CCN(c4ccnc(C)n4)C3)c12] | (1R,4R,7R)-2-{2-[1-(cyclopropylmethyl)-1H-pyrrolo[2,3-b]pyridin-2-yl]-7-methoxy-1-{[(3R)-1-(2-methylpyrimidin-4-yl)pyrrolidin-3-yl]methyl}-1H-1,3-benzodiazole-5-carbonyl}-2-azabicyclo[2.2.1]heptan-7-amine | 1.27 | 2 | 632 |

TABLE 3-continued

| Ex # | Structure | Name | LC/MS Rt (min) | LC/MS Method | M + H (obs ion) |
|---|---|---|---|---|---|
| 217 | 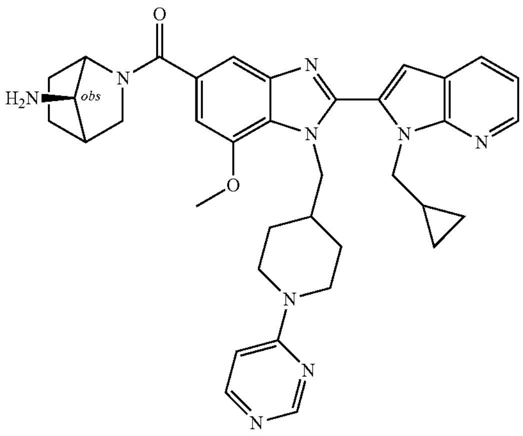 [SMILES: COc1cc(C(=O)N2CC3CCC2[C@@H]3N)cc2nc(-c3cc4cccnc4n3CC3CC3)n(CC3CCN(c4ccncn4)CC3)c12] | (1R,4R,7R)-2-{2-[1-(cyclopropylmethyl)-1H-pyrrolo[2,3-b]pyridin-2-yl]-7-methoxy-1-{[1-(pyrimidin-4-yl)piperidin-4-yl]methyl}-1H-1,3-benzodiazole-5-carbonyl}-2-azabicyclo[2.2.1]heptan-7-amine | 1.09 | 1 | 632 |
| 218 | 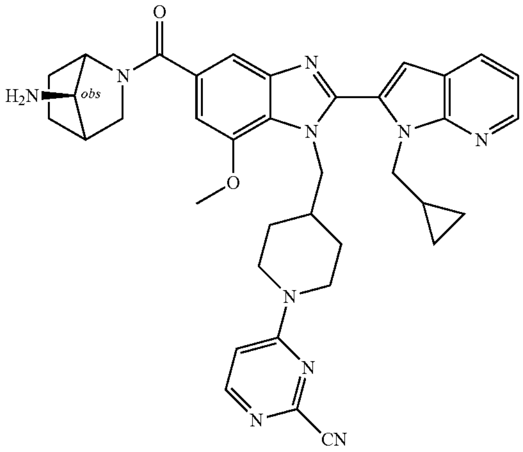 | 4-[4-({5-[(1R,4R.,7R)-7-amino-2-azabicyclo[2.2.1]heptane020 carbonyl]-2-[1-(cyclopropylmethyl)-1H-pyrrolo[2,3-b]pyridin-2-yl]-7-methoxy-1H-1,3-benzodiazol-1-yl}methyl)piperidin-1-yl]pyrimidin-2-carbonitrile | 1.7 | 2 | 657 |
| 219 | 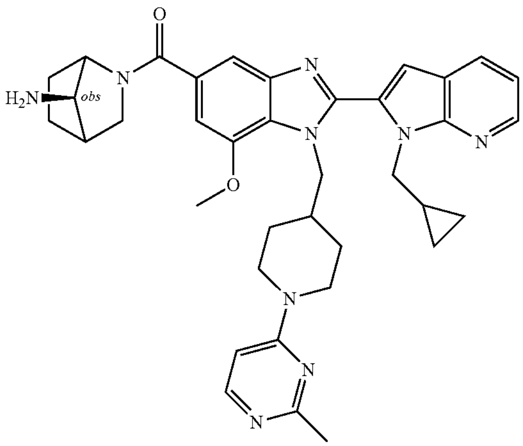 [SMILES: COc1cc(C(=O)N2CC3CCC2[C@@H]3N)cc2nc(-c3cc4cccnc4n3CC3CC3)n(CC3CCN(c4ccnc(C)n4)CC3)c12] | (1R,4R.,7R)-2-{2-[1-(cyclopropylmethyl)-1H-pyrrolo[2,3-b]pyridin-2-yl]-7-methoxy-1-{[1-[(2 methylpyrimidin-4-yl)piperidin-4-yl]methyl}-1H-1,3-benzodiazole-5-carbonyl}-2-azabicyclo[2.2.1]heptan-7-amine | 1.29 | 2 | 646 |

TABLE 3-continued

| Ex # | Structure | Name | LC/MS Rt (min) | LC/MS Method | M + H (obs ion) |
|---|---|---|---|---|---|
| 220 | 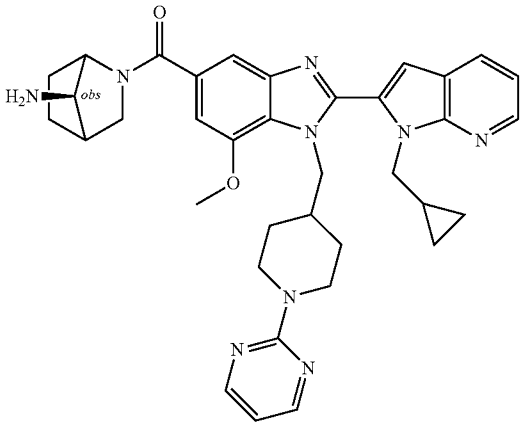 [SMILES: COc1cc(C(=O)N2CC3CCC2[C@@H]3N)cc2nc(-c3cc4cccnc4n3CC3CC3)n(CC3CCN(c4ncccn4)CC3)c12] | (1R,4R,7R)-2-{2-[1-(cyclopropylmethyl)-1H-pyrrolo[2,3-b]pyridin-2-yl]-7-methoxy-1-{[1-(pyrimidin-2-yl)piperidin-4-yl]methyl)-1H-1,3-benzodiazole-5-carbonyl}-2-azabicyc1o[2.2.1]heptan-7-amine | 1.71 | 2 | 632 |
| 221 | 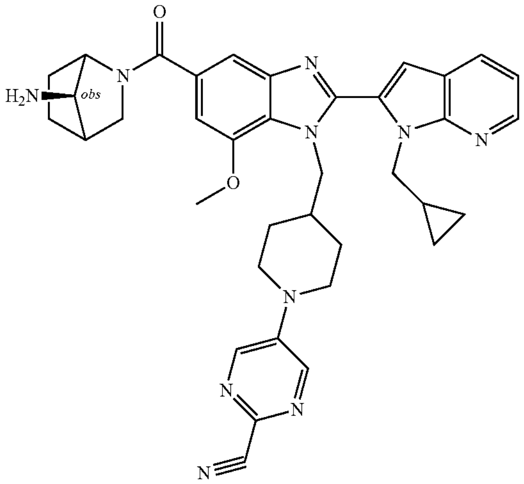 [SMILES: COc1cc(C(=O)N2CC3CCC2[C@@H]3N)cc2nc(-c3cc4cccnc4n3CC3CC3)n(CC3CCN(c4cnc(C#N)nc4)CC3)c12] | 5-[4-({5-[(1R,4R.,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)piperidin-1-yl]pyrimidine-2-carbonitrile | 1.62 | 2 | 657 |
| 222 | 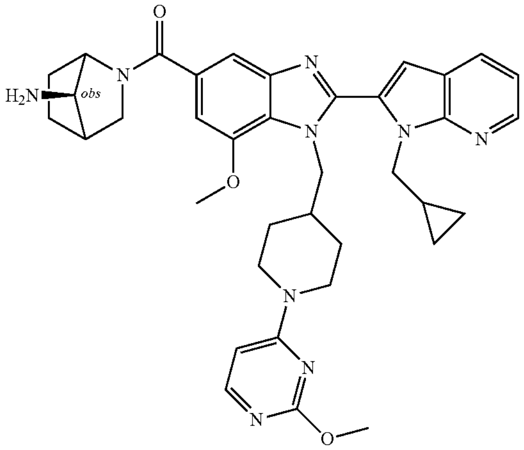 [SMILES: COc1nccc(N2CCC(Cn3c(-c4cc5cccnc5n4CC4CC4)nc4cc(C(=O)N5CC6CCC5[C@@H]6N)cc(OC)c43)CC2)n1] | (1R.,4R,7R)-2-{2-[1-(cyclopropylmethyl)-1H-pyrrolo[2,3-b]pyridin-2-yl]-7-methoxy-1-{[1-(2-methoxypyrimidin-4-yl)piperidin-4-yl]methyl}-1H-1,3-benzodiazole-5-carbonyl}-2-azabicyclo[2.2.1]heptan-7-amine | 1.8 | 2 | 662 |

TABLE 3-continued

| Ex # | Structure | Name | LC/MS Rt (min) | LC/MS Method | M + H (obs ion) |
|---|---|---|---|---|---|
| 223 | 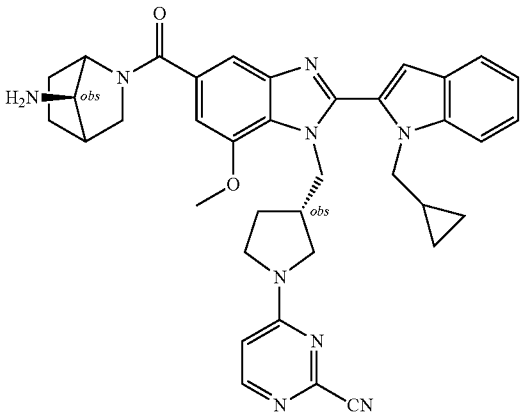 [SMILES: COc1cc(C(=O)N2CC3CCC2[C@@H]3N)cc2nc(-c3cc4ccccc4n3CC3CC3)n(C[C@H]3CCN(c4ccnc(C#N)n4)C3)c12] | 4-[(3S)-3-({5-[(1R,4R,7R)-7-amino-2-azabicyclo[2.2.1]heptane-2-carbonyl]-2-[1-(cyc1opropylmethyl)-1H-indo1-2-yl]-7-methoxy-1H-1,3-benzodiazo1-1-yl}methyl)pyrrolidin-1-yl]pyrimidine-2-carbonitrile | 1.56 | 1 | 642 |
| 224 | 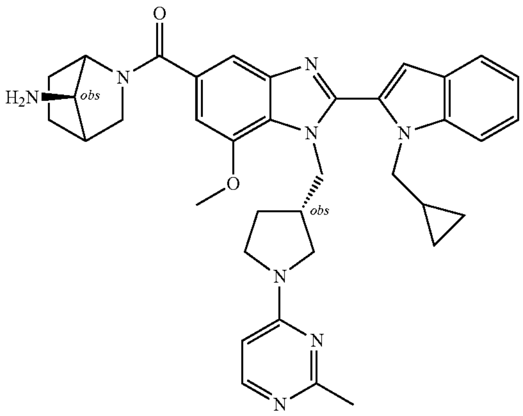 [SMILES: COc1cc(C(=O)N2CC3CCC2[C@@H]3N)cc2nc(-c3cc4ccccc4n3CC3CC3)n(C[C@H]3CCN(c4ccnc(C)n4)C3)c12] | (1R.,4R,7R)-2-{2-[1-(cyclopropylmethyl)-1H-indol-2-yl]-7-methoxy-1-{[(3S)-1-(2-methylpyrimidin-4-yl)pyrrolidin-3-yl]methyl}-1H-1,3-benzodiazole-5-carbonyl}-2-azabicyclo[2.2.1]heptan-7-amine | 1.13 | 1 | 631 |
| 225 | 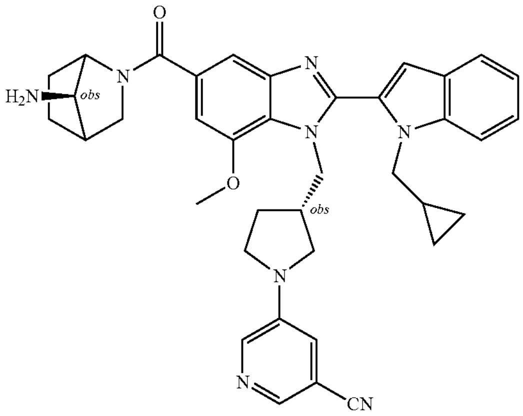 [SMILES: COc1cc(C(=O)N2CC3CCC2[C@@H]3N)cc2nc(-c3cc4ccccc4n3CC3CC3)n(C[C@H]3CCN(c4cncc(C#N)c4)C3)c12] | 5-[(3S)-3-({5-[(1R,4R,7R)-7-amino-2-azabicyclo[2.2.1]heptane-2-carbonyl]-2-[1-(cyclopropylmethyl)-1H-indo1-2-yl]-7-methoxy-1H-1,3-benzodiazol-1-yl}methyl)pyrrolidin-1-yl]pyridine-3-carbonitrile | 1.51 | 1 | 641 |

TABLE 3-continued

| Ex # | Structure | Name | LC/MS Rt (min) | LC/MS Method | M + H (obs ion) |
|---|---|---|---|---|---|
| 226 | 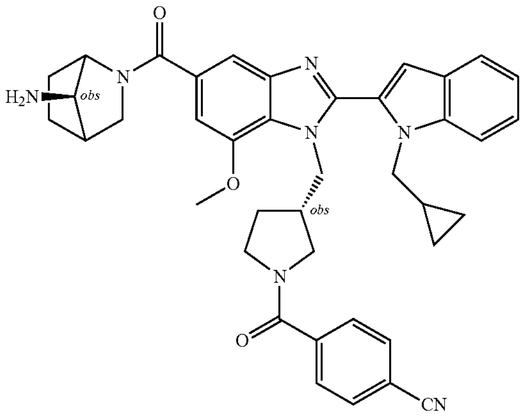 [SMILES: COc1cc(C(=O)N2CC3CCC2[C@@H]3N)cc2nc(-c3cc4ccccc4n3CC3CC3)n(C[C@H]3CCN(C(=O)c4ccc(C#N)cc4)C3)c12] | 4-[(3S)-3-({5-[(1R,4R,7R)-7-aminobicyclo[2.2.1]heptane-2-carbonyl]-2-[1-(cyc1opropylmethyl)-1H-indo1-2-yl]-7-methoxy-1H-1,3-benzodiazol-1-yl}methyl)pyrrolidine-1-carbonyl]benzonitrile | 1.48 | 1 | 668 |
| 227 | 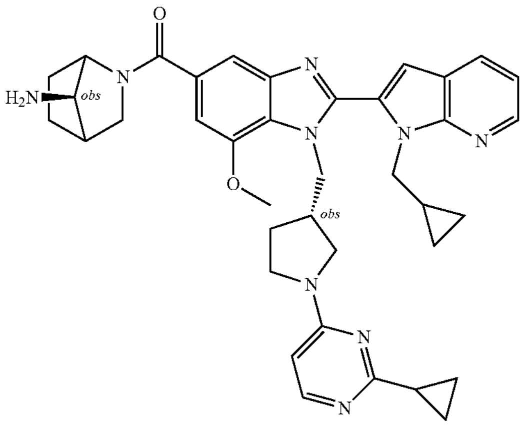 [SMILES: COc1cc(C(=O)N2CC3CCC2[C@@H]3N)cc2nc(-c3cc4cccnc4n3CC3CC3)n(C[C@H]3CCN(c4ccnc(C5CC5)n4)C3)c12] | (1R,4R,7R)-2-{2-[1-(cyclopropylmethyl)-1H-indo1-2-yl]-1-{[(3S)-1-(2-cyclopropylpyrimidin-4-yl)pyrrolidin-3-yl]methyl}-7-methoxy-1H-1,3-benzodiazole-5-carbonyl}-2-azabicyclo[2.2.1]heptan-7-amine | 1. 73 | 2 | 657 |
| 228 | 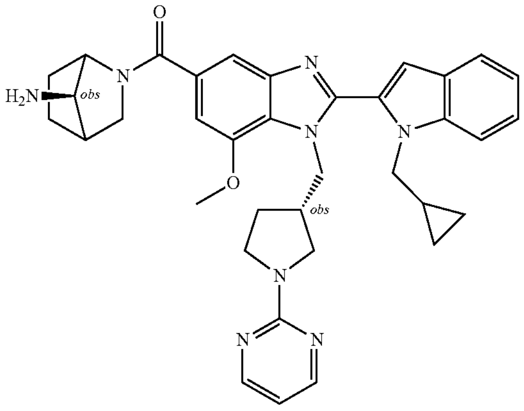 [SMILES: COc1cc(C(=O)N2CC3CCC2[C@@H]3N)cc2nc(-c3cc4ccccc4n3CC3CC3)n(C[C@H]3CCN(c4ncccn4)C3)c12] | (1R,4R,7R)-2-{2-[1-(cyclopropylmethyl)-1H-indol-2-yl]-7-methoxy-1-{[(3S)-1-(pyrimidin-2-yl)pyrrolidin-3-yl]methyl}-1H-1,3-benzodiazole-5-carbonyl}-2-azabicyclo[2.2.1]heptan-7-amine | 1.85 | 2 | 617 |

TABLE 3-continued

| Ex # | Structure | Name | LC/MS Rt (min) | LC/MS Method | M + H (obs ion) |
|---|---|---|---|---|---|
| 229 | 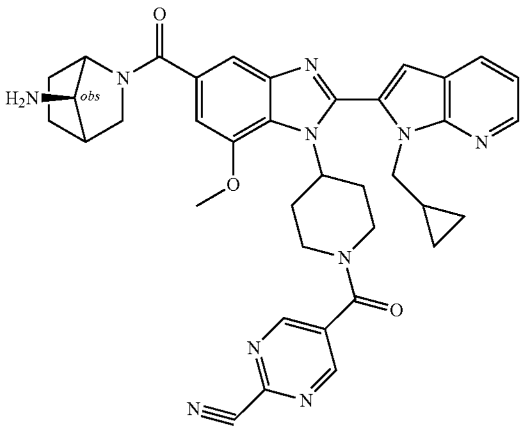 [SMILES: COc1cc(C(=O)N2CC3CCC2[C@@H]3N)cc2nc(-c3cc4cccnc4n3CC3CC3)n(C3CCN(C(=O)c4cnc(C#N)nc4)CC3)c12] | 5-(4-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}piperidine-1-carbonyl)pyrimidine-2-carbonitrile | 1.25 | 1 | 671 |
| 230 | 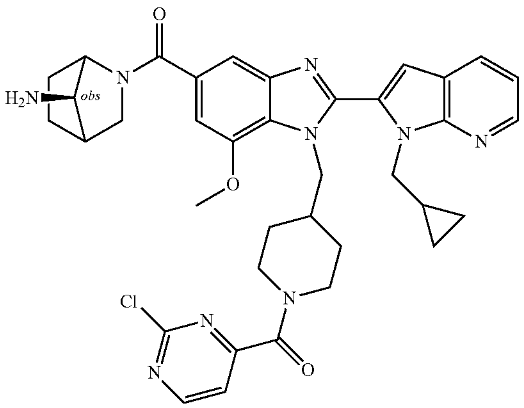 [SMILES: COc1cc(C(=O)N2CC3CCC2[C@@H]3N)cc2nc(-c3cc4cccnc4n3CC3CC3)n(CC3CCN(C(=O)c4ccnc(Cl)n4)CC3)c12] | (1R,4R,7R)-2-(1-{[1-(2-chloropyrimidine-4-carbonyl)piperidin-4-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.49 | 2 | 694 |
| 231 | 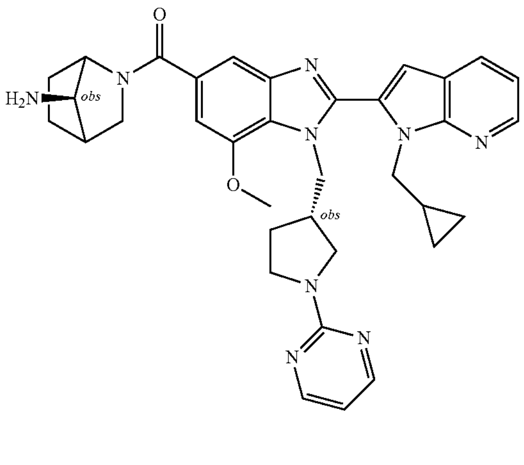 [SMILES: COc1cc(C(=O)N2CC3CCC2[C@@H]3N)cc2nc(-c3cc4cccnc4n3CC3CC3)n(C[C@H]3CCN(c4ncccn4)C3)c12] | (1R,4R,7R)-2-{2-[1-(cyclopropylmethyl)-1H-pyrrolo[2,3-b]pyridin-2-yl]-7-methoxy-1-{[(3S)-1-(pyrimidin-2-yl)pyrrolidin-3-yl]methyl}-1H-1,3-benzodiazole-5-carbonyl}-2-azabicyclo [2.2.1]heptan-7-amine | 1.43 | 1 | 618 |

TABLE 3-continued

| Ex # | Structure | Name | LC/MS Rt (min) | LC/MS Method | M + H (obs ion) |
|---|---|---|---|---|---|
| 232 | 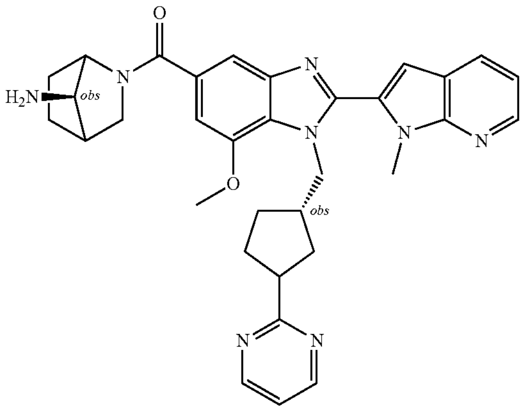 [SMILES: COc1cc(C(=O)N2CC3CCC2[C@@H]3N)cc2nc(-c3cc4cccnc4n3C)n(C[C@H]3CCC(c4ncccn4)C3)c12] | (1R,4R,7R)-2-(7-methoxy-2-{1-methyl-1H-pyrrolo[2,3-b]pyridin-2-yl}-1-{[(3S)-1-(pyrimidin-2-yl)pyrrolidin-3-yl]methyl}-1H-1,3-benzodiazole-5-carbonyl)-2-azabicyclo[2.2.1]heptan-7-amine | 1.13 | 1 | 578 |
| 233 | 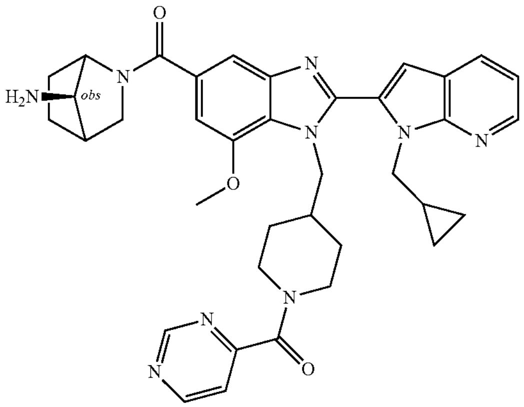 [SMILES: COc1cc(C(=O)N2CC3CCC2[C@@H]3N)cc2nc(-c3cc4cccnc4n3CC3CC3)n(CC3CCN(C(=O)c4ccncn4)CC3)c12] | (1R,4R,7R)-2-{2-[1-(cyclopropylmethyl)-1H-pyrrolo[2,3-b]pyridin-2-yl]-7-methoxy-1-{[1-(pyrimidine-4-carbonyl)piperidin-4-yl]methyl}-1H-1,3-benzodiazole-5-carbonyl}-2-azabicyclo[2.2.1]heptan-7-amine | 1.18 | 2 | 660 |
| 234 | 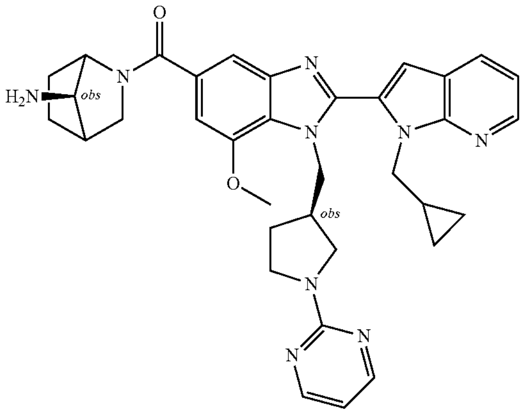 [SMILES: COc1cc(C(=O)N2CC3CCC2[C@@H]3N)cc2nc(-c3cc4cccnc4n3CC3CC3)n(C[C@@H]3CCN(c4ncccn4)C3)c12] | (1R,4R,7R)-2-{2-[1-(cyclopropylmethyl)-1H-pyrrolo[2,3-b]pyridin-2-yl]-7-methoxy-1-{[(3R)-1-(pyrimidin-2-yl)pyrrolidin-3-yl]methyl}-1H-1,3-benzodiazole-5-carbonyl}-2-azabicyclo[2.2.1]heptan-7-amine | 1.16 | 1 | 618 |

TABLE 3-continued

| Ex # | Structure | Name | LC/MS Rt (min) | LC/MS Method | M + H (obs ion) |
|---|---|---|---|---|---|
| 235 | 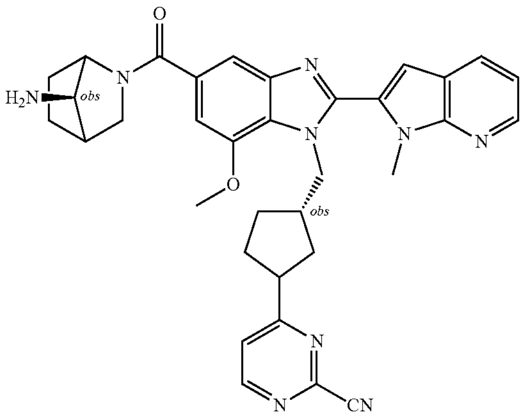 [SMILES: COc1cc(C(=O)N2CC3CCC2[C@@H]3N)cc2nc(-c3cc4cccnc4n3C)n(C[C@H]3CCC(c4ccnc(C#N)n4)C3)c12] | 6-[(3S)-3-({5-[(1R,4R,7R,)-7-amino-2-azabicyclo[2.2.1]heptane-2-carbonyl]-7-methoxy-2-{1-methyl-1H-pyrrolo[2,3-b]pyridin-2-yl}-1H-1,3-benzodiazol-1-yl}methyl)pyrrolidin-1-yl]pyrazine-2-carbonitrile | 1.31 | 2 | 603 |
| 236 | 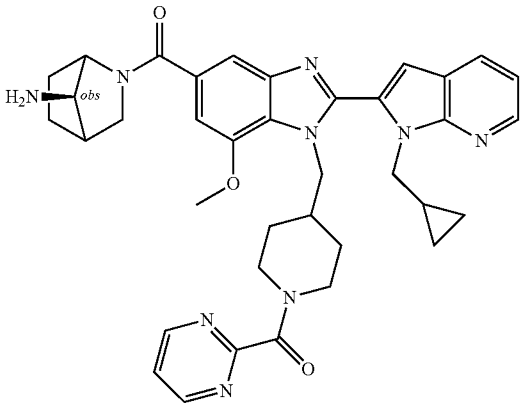 [SMILES: COc1cc(C(=O)N2CC3CCC2[C@@H]3N)cc2nc(-c3cc4cccnc4n3CC3CC3)n(CC3CCN(C(=O)c4ncccn4)CC3)c12] | (1R,4R.,7R)-2-{2-[1-(cyclopropylmethyl)-1H-pyrrolo[2,3-b]pyridin-2-yl]-7-methoxy-1-{[1-(pyrimidine-2-carbonyl)piperidin-4-yl]methyl}-1H-1,3-benzodiazole-5-carbonyl}-2-azabicyclo[2.2.1]heptan-7-amine | 1.06 | 1 | 660 |
| 237 | 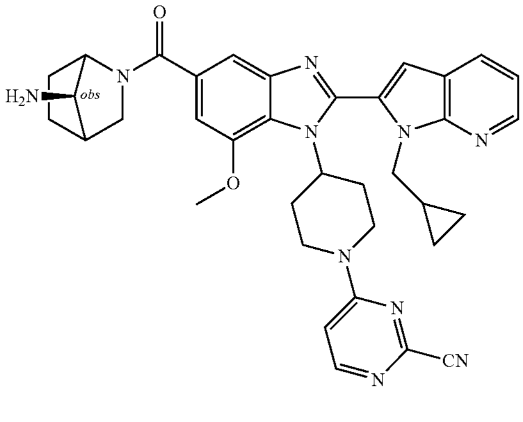 | 4-(4-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}piperidin-l-yl)pyrimidine-2-carbonitrile | 1.42 | 1 | 643 |

TABLE 3-continued

| Ex # | Structure | Name | LC/MS Rt (min) | LC/MS Method | M + H (obs ion) |
|---|---|---|---|---|---|
| 238 | 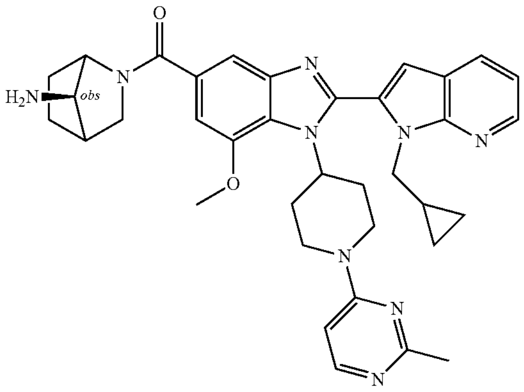 [SMILES: COc1cc(C(=O)N2CC3CCC2[C@@H]3N)cc2nc(-c3cc4cccnc4n3CC3CC3)n(C3CCN(c4ccnc(C)n4)CC3)c12] | (1R.,4R,7R)-2-{2-[1-(cyclopropylmethyl)-1H-pyrrolo[2,3-b]pyridin-2-yl]-7-methoxy-1-[1-(2-methylpyrimidin-4-yl)piperidin-4-yl]-1H-1,3-benzodiazole-5-carbonyl}-2-azabicyclo[2.2.1]heptan-7-amine | 1.01 | 1 | 632 |
| 239 | 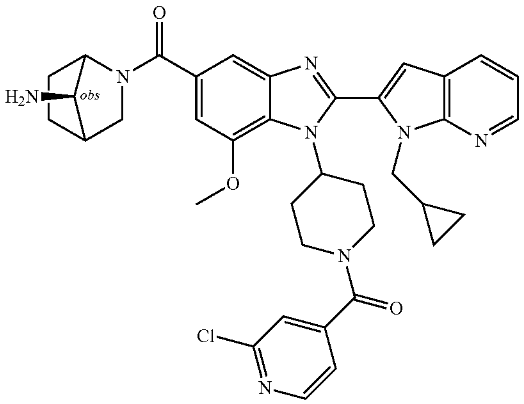 [SMILES: COc1cc(C(=O)N2CC3CCC2[C@@H]3N)cc2nc(-c3cc4cccnc4n3CC3CC3)n(C3CCN(C(=O)c4ccnc(Cl)c4)CC3)c12] | (1R,4R.,7R)-2-{1-[1-(2-chloropyridine-4-carbonyl)piperidin-4-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.48 | 2 | 679 |
| 240 | 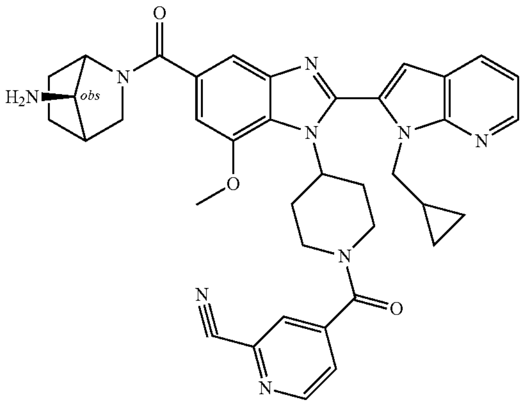 [SMILES: COc1cc(C(=O)N2CC3CCC2[C@@H]3N)cc2nc(-c3cc4cccnc4n3CC3CC3)n(C3CCN(C(=O)c4ccnc(C#N)c4)CC3)c12] | 4-(4-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}piperidine-1-carbonyl)pyridine-2-carbonitrile | 1.3 | 1 | 670 |

TABLE 3-continued

| Ex # | Structure | Name | LC/MS Rt (min) | LC/MS Method | M + H (obs ion) |
|---|---|---|---|---|---|
| 241 | 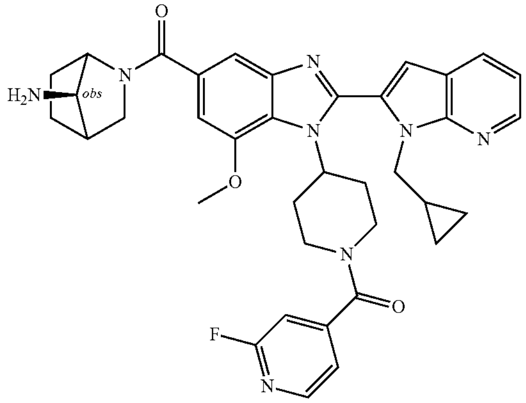 [SMILES: COc1cc(C(=O)N2CC3CCC2[C@@H]3N)cc2nc(-c3cc4cccnc4n3CC3CC3)n(C3CCN(C(=O)c4ccnc(F)c4)CC3)c12] | (1R,4R,7R)-2-{2-[1-(cyclopropylmethyl)-1H-pyrrolo[2,3-b]pyridin-2-yl]-1-[1-(2-fluoropyridine-4-carbonyl)piperidin-4-yl]-7-methoxy-1H-1,3-benzodiazole-5-carbonyl}-2-azabicyclo[2.2.1]heptan-7-amine | 1.42 | 2 | 663 |

Example 242

(1R,4R,7R)-2-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine

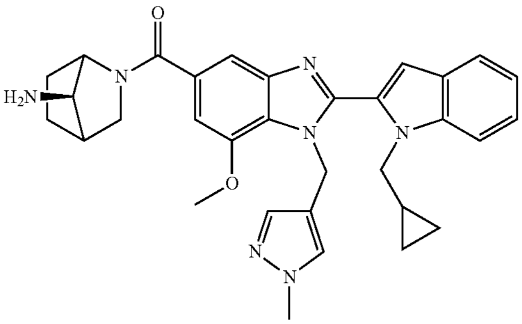 [SMILES: COc1cc(C(=O)N2CC3CCC2[C@@H]3N)cc2nc(-c3cc4ccccc4n3CC3CC3)n(Cc3cnn(C)c3)c12]

Intermediate 242A: Methyl 3-methoxy-4-(((1-methyl-1H-pyrazol-4-yl)methyl)amino)-5-nitrobenzoate

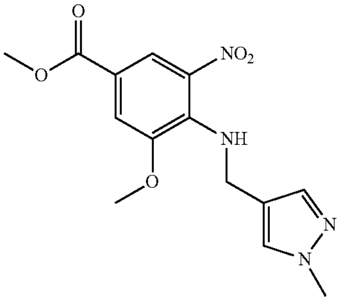 [SMILES: COC(=O)c1cc(OC)c(NCc2cnn(C)c2)c([N+](=O)[O-])c1]

A mixture of (1-methyl-1H-pyrazol-4-yl)methanamine (600 mg, 5.40 mmol), methyl 4-chloro-3-methoxy-5-nitrobenzoate (1326 mg, 5.40 mmol) and potassium carbonate (2238 mg, 16.19 mmol) in DMF (10 mL) was stirred at 80° C. for 18 hours. The mixture was diluted with EtOAc (35 mL) and was washed with a solution of aqueous saturated sodium bicarbonate (2×35 ml). The organic layer was dried over sodium sulfate and concentrated. The crude product was subjected to ISCO flash chromatography (silica gel/hexane-EtOAc 100:0 to 0:100 gradient) to yield methyl 3-methoxy-4-(((1-methyl-1H-pyrazol-4~yl)methyl)amino)-5-nitrobenzoate (395 mg, 1.172 mmol, 21.70% yield) as orange solid. LC/MS (M+H): 321; LC retention time: 0.81 min (analytical HPLC Method 3). Material was used as is in next reaction.

Intermediate 242B: Methyl 2-(1-(cyclopropylmethyl)-1H-indol-2-yl)-7-methoxy-1-((1-methyl-1H-pyrazol-4-yl)methyl)-1H-benzo[d]imidazole-5-carboxylate

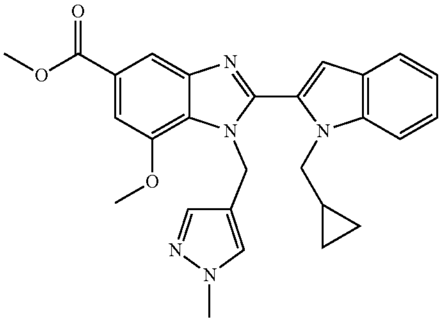 [SMILES: COC(=O)c1cc(OC)c2c(c1)nc(-c1cc3ccccc3n1CC1CC1)n2Cc1cnn(C)c1]

To a solution of methyl 3-methoxy-4-(((1-methyl-1H-pyrazol-4-yl)methyl)amino)-5-nitrobenzoate (100 mg, 0.312 mmol) and 1-(cyclopropylmethyl)-1H-indole-2-carbaldehyde (62.2 mg, 0.312 mmol) in EtOH (2.000 mL) was added a solution of sodium hydrosulfite (163 mg, 0.937 mmol) in water (1.000 mL) at RT under nitrogen. The mixture was stirred at 80° C. for 6 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient). Yield methyl 2-(1-(cyclopropylmethyl)-1H-indol-2-yl)-7-methoxy-1-((1-methyl-1H-pyrazol-4-yl)methyl)-1H-benzo[d]imidazole-5-carboxylate (108 mg, 0.219 mmol, 70.0% yield) as white foam. LC/MS (M+H): 470; LC retention time: 0.96 min (analytical HPLC Method 3).

Intermediate 242C: 2-(1-(cyclopropylmethyl)-1H-indol-2-yl)-7-methoxy-1-((1-methyl-1H-Pyrazol-4-yl)methyl)-1H-benzo[d]imidazole-5-carboxylic acid

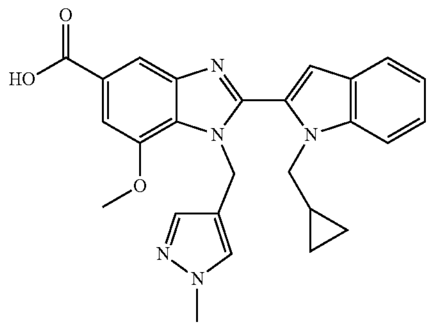 [SMILES: COc1cc(C(=O)O)cc2nc(-c3cc4ccccc4n3CC3CC3)n(Cc3cnn(C)c3)c12]

A mixture of methyl 2-(1-(cyclopropylmethyl)-1H-indol-2-yl)-7-methoxy-1-((1-methyl-1H-pyrazol-4-yl)methyl)-1H-benzo[d]imidazole-5-carboxylate (105 mg, 0.224 mmol) and 1.0 M aqueous sodium hydroxide (1.118 mL, 1.118 mmol) in THF (5.0 mL) was stirred at 60° C. for 18 hours. A solution of 1.0 M aqueous HCl (1.2 mL) was added and the mixture was extracted with EtOAc (2×10 mL). The combined organic layers were dried over sodium sulfate and concentrated to give a crude yield of 2-(1-(cyclopropylmethyl)-1H-indol-2-yl)-7-methoxy-1-((1-methyl-1H-pyrazol-4-yl)methyl)-1H-benzo[d]imidazole-5-carboxylic acid (109 mg, 0.215 mmol, 96% yield) as off-white solid. LC/MS (M+H): 456; LC retention time: 0.86 min (analytical HPLC Method 3). Material was used as is in next reaction.

Example 242: (1R,4R,7R)-2-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine

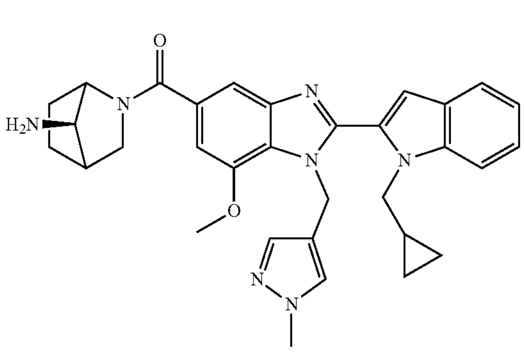 [SMILES: COc1cc(C(=O)N2CC3CCC2[C@@H]3N)cc2nc(-c3cc4ccccc4n3CC3CC3)n(Cc3cnn(C)c3)c12]

A mixture of 2-(1-(cyclopropylmethyl)-1H-indol-2-yl)-7-methoxy-1-((1-methyl-1H-pyrazol-4-yl)methyl)-1H-benzo[d]imidazole-5-carboxylic acid (15 mg, 0.033 mmol), tert-butyl ((1R,4R,7R)-2-azabicyclo[2.2.1]heptan-7-yl) carbamate (6.99 mg, 0.033 mmol), BOP (14.56 mg, 0.033 mmol) and TEA (0.023 mL, 0.165 mmol) in DMF (1.0 mL) was stirred at RT for 2 hour. The mixture was diluted with EtOAc (15 mL) and was washed with a solution of aqueous saturated sodium bicarbonate (2×15 mL). The organic layer was dried over sodium sulfate and concentrated to give crude tert-butyl ((1R,4R,7R)-2-(2-(1-(cyclopropylmethyl)-1H-indol-2-yl)-7-methoxy-1-((1-methyl-1H-pyrazol-4-yl)methyl)-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(2-(1-(cyclopropylmethyl)-1H-indol-2-yl)-7-methoxy-1-((1-methyl-1H-pyrazol-4-yl)methyl)-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over 20 minutes, then a 6-minute hold at 100% B; Flow Rate: 20 mL/min; Column Temperature: 25 C. Fraction collection was triggered by MS signals. Fractions containing the desired product were combined and dried via centrifugal evaporation. (1R,4R,7R)-2-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine (9.4 mg, 17.1 μmol, 51.8%) was isolated. LC/MS (M+H): 550; LC retention time: 1.34 min (analytical HPLC Method 2). $^1$H NMR (500 MHz, DMSO-$d_6$) δ 7.66 (br d, J=7.9 Hz, 1H), 7.62 (br d, J=8.2 Hz, 1H), 7.35-7.28 (m, 2H), 7.27-7.21 (m, 1H), 7.11 (br t, J=7.3 Hz, 1H), 7.02-6.88 (m, 3H), 5.56 (br s, 2H), 4.35-4.15 (m, 2H), 3.96 (s, 2H), 4.08 (br s, 1H), 3.76-3.58 (m, 3H), 3.42-3.22 (m, 1H), 3.16-2.95 (m, 2H), 2.21-2.03 (m, 1H), 2.01-1.86 (m, 2H), 1.80-1.58 (m, 1H), 1.48-1.26 (m, 1H), 1.23-1.11 (m, 1H), 0.81 (br s, 1H), 0.17-0.08 (m, 2H), 0.08–-0.09 (m, 2H).

Example 243

(1R,4R,7R)-2-{2-[1-(cyclopropylmethyl)-1H-pyrrolo[2,3-b]pyridin-2-yl]-7-methoxy-1-[(1-methyl-1H-pyrazol-4-yl)methyl]-1H-1,3-benzodiazole-5-carbonyl}-2-azabicyclo[2.2.1]heptan-7-amine

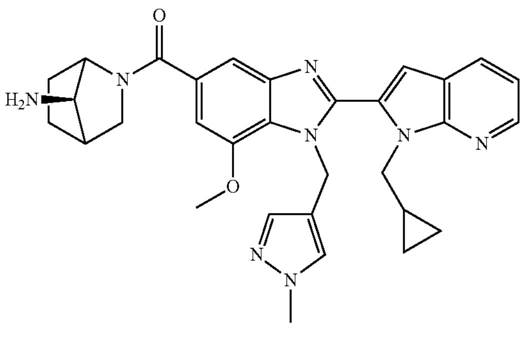 [SMILES: COc1cc(C(=O)N2CC3CCC2[C@@H]3N)cc2nc(-c3cc4cccnc4n3CC3CC3)n(Cc3cnn(C)c3)c12]

Intermediate 243A: 2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carboxylic acid

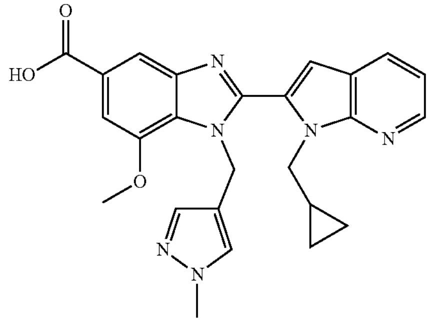 [SMILES: COc1cc(C(=O)O)cc2nc(-c3cc4cccnc4n3CC3CC3)n(Cc3cnn(C)c3)c12]

To a solution of methyl 3-methoxy-4-(((1-methyl-1H-pyrazol-4-yl)methyl)amino)-5-nitrobenzoate, intermediate 242A (50 mg, 0.156 mmol) and 1-(cyclopropylmethyl)-1H-pyrrolo[2,3-b]pyridine-2-carbaldehyde (31.3 mg, 0.156 mmol) in EtOH (3.0 mL) was added a solution of sodium dithionite (82 mg, 0.468 mmol) in water (1.500 mL), and the mixture was stirred at 80° C. for 8 hours. The resulting mixture was cooled to RT, diluted with EtOAc (10 mL) and was washed with a solution of aqueous saturated sodium bicarbonate (2×15 mL). The organic layer was dried over sodium sulfate and concentrated to yield methyl 2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carboxylate (58 mg, 0.123 mmol, 79% yield) as clear gum. LC/MS (M+H): 471; LC retention time: 0.88 min (analytical HPLC Method 3). Material was used as is in next reaction.

A mixture of methyl 2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carboxylate (58 mg, 0.123 mmol) and sodium hydroxide (0.781 mL, 0.781 mmol) in MeOH (5.0 mL) was stirred at 50° C. for 4 hours, then RT for 18 hours. A solution of aqueous 1.0 N HCl (0.80 mL) was added and the mixture was concentrated to give a crude yield of 2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carboxylic acid (56 mg, 0.117 mmol, 74.7% yield). LC/MS (M+H): 457; LC retention time: 0.75 min (analytical HPLC Method 3). Material was used as is in next reaction.

Example 243: (1R,4R,7R)-2-{2-[1-(cyclopropylmethyl)-1H-pyrrolo[2,3-b]pyridin-2-yl]-7-methoxy-1-[(1-methyl-1H-pyrazol-4-yl)methyl]-1H-1,3-benzodiazole-5-carbonyl}-2-azabicyclo[2.2.1]heptan-7-amine A mixture of 2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carboxylic acid (10 mg, 0.022 mmol), tert-butyl ((1R,4R,7R)-2-azabicyclo[2.2.1]heptan-7-yl)carbamate (4.65 mg, 0.022 mmol), BOP (9.69 mg, 0.022 mmol) and TEA (9.16 µl, 0.066 mmol) in DMF (1.0 mL) was stirred at RT for 60 min. The mixture was diluted with EtOAc (5 mL) and was washed with a solution of aqueous saturated sodium, bicarbonate (2×5 mL). The organic layer was dried over sodium sulfate and concentrated to give tert-butyl ((1R,4R,7R)-2-(2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazole-5-carbonyl)-2-azabicyclo[2.2.1]heptan-7-yl)carbamate in DCM (1.0 mL) and TEA (1.0 mL) was stirred at RT for 30 min. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 20 minutes, then a 4-minute hold at 100% B; Flow Rate: 20 mL/min; Column Temperature: 25 C, Fraction collection was triggered by MS signals. Fractions containing the desired product were combined and dried via centrifugal evaporation. (1R,4R,7R)-2-{2-[1-(cyclopropylmethyl)-1H-pyrrolo[2,3-b]pyridin-2-yl]-7-methoxy-1-[(1-methyl-1H-pyrazol-4-yl)methyl]-1H-1,3-benzodiazole-5-carbonyl}-2-azabicyclo[2.2.1]heptan-7-amino (5.9 mg, 10.7 µmol, 48.7%) was isolated. LC/MS (M+H): 551; LC retention time: 1.24 mm (analytical HPLC Method 2). $^1H$ NMR (499 MHz, methanol-$d_4$) δ 8.49-8.36 (m, 1H), 8.22-8.14 (m, 1H), 7.56-7.45 (m, 1H), 7.36-7.23 (m, 2H), 7.14-7.09 (m, 2H), 7.06-7.03 (m, 1H), 5.83-5.69 (m, 2H), 4.45-4.32 (m, 2H), 4.18-4.08 (m, 3H), 4.04-3.94 (m, 1H), 3.81-3.66 (m, 4H), 3.49-3.41 (m, 1H), 3.31-3.15 (m, 2H), 2.46-2.26 (m, 1H), 2.18-1.88 (m, 3H), 1.73-1.50 (m, 1H), 0.86-0.66 (m, 1H), 0.22-0.12 (m, 2H), 0.04--0.08 (m, 2H).

Example 244

(1R,4R,7R)-2-{1-[(6-aminopyridin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine

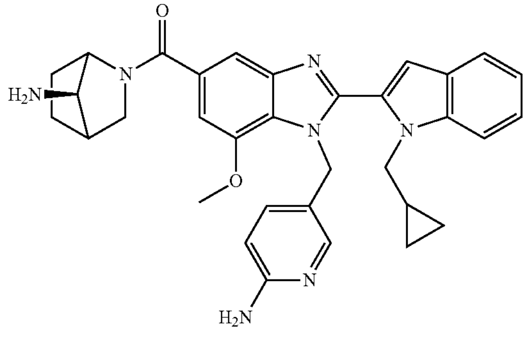 [SMILES: COc1cc(C(=O)N2CC3CCC2[C@@H]3N)cc2nc(-c3cc4ccccc4n3CC3CC3)n(Cc3ccc(N)nc3)c12]

Intermediate 244A: Methyl 4-(((6-((tert-butoxycarbonyl)amino)pyridin-3-yl)methyl)amino)-3-methoxy-5-nitrobenzoate

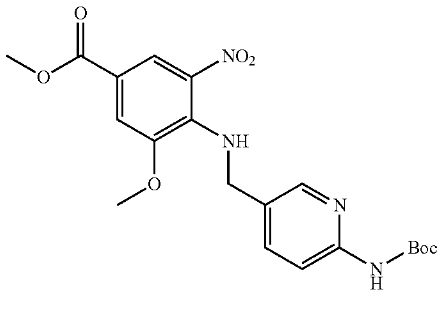 [SMILES: COC(=O)c1cc(OC)c(NCc2ccc(NC(=O)OC(C)(C)C)nc2)c([N+](=O)[O-])c1]

A mixture of methyl 4-chloro-3-methoxy-5-nitrobenzoate (500 mg, 2.036 mmol), 2-(Boc-amino)-5-(aminomethyl) pyridine (455 mg, 2.036 mmol) and potassium carbonate (844 mg, 6.11 mmol) in DMF (8.0 mL) was stirred at RT for 3 days. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient) to yield methyl 4-(((6-((tert-butoxycarbonyl)amino)pyridin-3-yl)methyl)amino)-3-methoxy-5-nitrobenzoate (307 mg, 0.674 mmol, 33.1% yield) as orange solid. LC/MS (M+H): 433; LC retention time: 0.85 min (analytical HPLC Method 3).

Intermediate 244B: 1-((6-((tert-butoxycarbonyl) amino)pyridin-3-yl)methyl)-2-(1-(cyclopropylmethyl)-1H-indol-2-yl)-7-methoxy-1H-benzo[d]imidazole-5-carboxylic acid

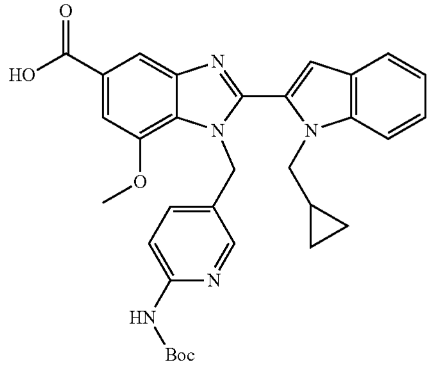 [SMILES: COc1cc(C(=O)O)cc2nc(-c3cc4ccccc4n3CC3CC3)n(Cc3ccc(NC(=O)OC(C)(C)C)nc3)c12]

To a solution of methyl 4-(((6-((tert-butoxycarbonyl) amino)pyridin-3-yl)methyl)amino)-3-methoxy-5-nitrobenzoate (60 mg, 0.139 mmol) and 1-(cyclopropylmethyl)-1H-indole-2-carbaldehyde (27.6 mg, 0.139 mmol) in EtOH (3.0 mL) was added a solution of sodium dithioate (72.5 mg, 0.416 mmol) in water (1.500 mL), and the mixture was stirred at 80° C. for 18 hours. The mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient). Yield methyl 1-((6-((tert-butoxycarbonyl)amino)pyridin-3-yl)methyl)-2-(1-(cyclopropylmethyl)-1H-indol-2-yl)-7-methoxy-1H-benzo[d]imidazole-5-carboxylate as white solid. LC/MS (M+H): 582; LC retention time: 1.65 min (analytical HPLC Method 4).

A mixture of methyl 1-((6-((tert-butoxycarbonyl)amino) pyridin-3-yl)methyl)-2-(1-(cyclopropylmethyl)-1H-indol-2-yl)-7-methoxy-1H-benzo[d]imidazole-5-carboxylate and 1.0 M aqueous sodium hydroxide (0.694 mL, 0.694 mmol) in MeOH (3.0 mL) was stirred at 60° C. for 4 hours. A solution of 1.0 N aqueous HCl (0.85 mL) was added and the mixture was concentrated. The mixture was extracted with EtOAc (15 mL) and the organic layer was dried over sodium sulfate and concentrated to give a crude yield of 1-((6-((tert-butoxycarbonyl)amino)pyridin-3-yl)methyl)-2-(1-(cyclopropylmethyl)-1H-indol-2-yl)-7-methoxy-1H-benzo[d]imidazole-5-carboxylic acid (20 mg, 0.032 mmol, 22.85% yield) as light brown solid. LC/MS (M+H): 568; LC retention time: 0.95 min (analytical HPLC Method 3). Material was used as is in next reaction.

Example 244: (1R,4R,7R)-2-{1-[(6-aminopyridin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine A mixture of 1-((6-((tert-butoxycarbonyl)amino)pyridin-3-yl)methyl)-2-(1-(cyclopropylmethyl)-1H-indol-2-yl)-7-methoxy-1H-benzo[d]imidazole-5-carboxylic acid (20 mg, 0,035 mmol), tert-butyl ((1R,4R,7R)-2-azabicyclo[2.2.1] heptan-7-yl)carbamate (7.48 mg, 0.035 mmol), BOP (15.58 mg, 0.035 mmol) and TEA (0.015 mL, 0.106 mmol) in DMF (1.0 mL) was stirred at RT for 18 hour. The mixture was diluted with EtOAc (5 mL) and was washed with a solution of aqueous saturated sodium bicarbonate (2×5 mL). The organic layer was dried over sodium sulfate and concentrated to give crude tert-butyl ((1R,4R,7R)-2-(1-((6-((tert-butoxycarbonyl)amino)pyridin-3-yl)methyl)-2-(1-(cyclopropylmethyl)-1H-indol-2-yl)-7-methoxy-1H-benzo[d] imidazole-5-carbonyl)-2-azabicyclo[2.2.1]heptan-7-yl) carbamate. Material was used as is in next reaction.

A mixture of tert-butyl ((1R,4R,7R)-2-(1-((6-((tert-butoxycarbonyl)amino)pyridin-3-yl)methyl)-2-(1-(cyclopropylmethyl)-1H-indol-2-yl)-7-methoxy-1H-benzo[d]imidazole-5-carbonyl)-2-azabicyclo[2.2.1]heptan-7-yl)carbamate in DCM (3.0 mL) and DMF (1.0 mL) was stirred at RT for 30 min. The mixture was concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over minutes, then a 4-minute hold at 100% B; Flow Rate: 20 mL/min; Column Temperature: 25 C. Fraction collection was triggered by MS signals. Fractions containing the desired product were combined and dried via centrifugal evaporation. (1R,4R,7R)-2-{1-[(6-aminopyridin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine (3.7 mg, 6.6 μmol, 18.8%) was isolated. LC/MS (M+H): 562; LC retention time: 1.36 min (analytical HPLC Method 1). $^1$H NMR (500 MHz, DMSO-$d_6$) δ 7.72-7.56 (m, 2H), 7.49-7.32 (m, 2H), 7.31-7.19 (m, 1H), 7.15-7.05 (m, 1H), 7.01-6.82 (m, 3H), 6.30-6.16 (m, 1H), 5.86-5.72 (m, 2H), 5.67-5.54 (m, 2H), 4.33-4.18 (m, 2H), 4.00-3.89 (m, 3H), 3.67-3.23 (m, 1H), 3.19-2.94 (m, 2H), 2.23-1.91 (m, 3H), 1.80-1.59 (m, 1H), 1.49-1.11 (m, 3H), 1.05-0.59 (m, 2H), 0.18-0.07 (m, 2H), 0.04--0.04 (m, 2H).

Example 245

((1R,4R,7R)-7-amino-2-azabicyclo[2.2.1]heptan-2-yl)(2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazol-5-yl)methanone

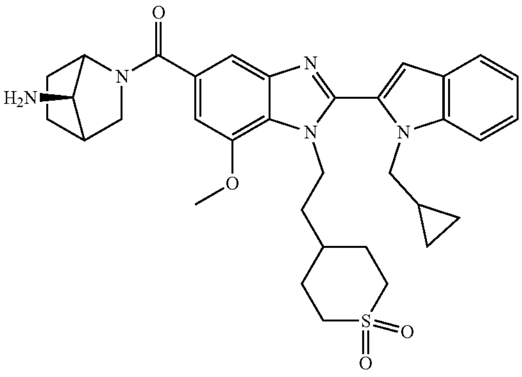 [SMILES: COc1cc(C(=O)N2CC3CCC2[C@@H]3N)cc2nc(-c3cc4ccccc4n3CC3CC3)n(CCC3CCS(=O)(=O)CC3)c12]

Intermediate 245A: Methyl 4-((2-(1,1-dioxidotetrahydro-2H-thiopyran-4-yl)ethyl)amino)-3-methoxy-5-nitrobenzoate

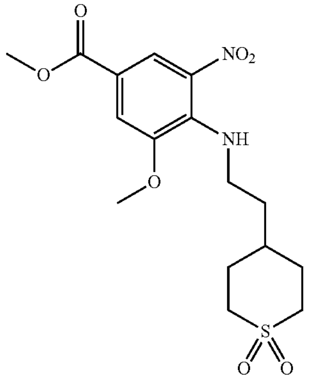 [SMILES: COC(=O)c1cc(OC)c(NCCC2CCS(=O)(=O)CC2)c([N+](=O)[O-])c1]

A mixture of methyl 4-chloro-3-methoxy-5-nitrobenzoate (350 mg, 1,425 mmol), 2-(1,1-dioxidotetrahydro-2H-thiopyran-4-yl)ethanamine (253 mg, 1.425 mmol) and potassium carbonate (591 mg, 4.27 mmol) in DMF (8.0 mL) was stirred at RT for 4 days. The mixture was diluted with EtOAc (15 ml) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient). Yield methyl 4-((2-(1,1-dioxidotetrahydro-2H-thiopyran-4-yl)ethyl)amino)-3-methoxy-5-nitrobenzoate (425 mg, 1.045 mmol, 73.3% yield) as orange foam. LC/MS (M+H): 387; LC retention time: 0.84 min (analytical HPLC Method 3).

Intermediate 245B: 2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazole-5-carboxylic acid

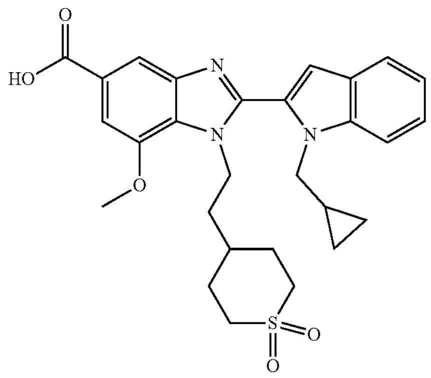 [SMILES: COc1cc(C(=O)O)cc2nc(-c3cc4ccccc4n3CC3CC3)n(CCC3CCS(=O)(=O)CC3)c12]

To a solution of methyl 4-((2-(1,1-dioxidotetrahydro-2H-thiopyran-4-yl)ethyl)amino)-3-methoxy-5-nitrobenzoate (50 mg, 0.129 mmol) and 1-(cyclopropylmethyl)-1H-indole-2-carbaldehyde (25.8 mg, 0.129 mmol) in EtOH (10 mL) was added a solution of sodium dithionite (67.6 mg, 0.388 mmol) in water (5.00 mL), and the mixture was stirred at 80° C. for 4 hours. The resulting mixture was diluted with EtOAc (10 mL) and was washed with a solution of aqueous saturated sodium chloride (2×10 mL). The organic layer was dried over sodium sulfate and concentrated. The crude product was subjected to ISCO flash chromatography (silica gel/hexane-EtOAc 100:0 to 0:100 gradient). Yield methyl 2-(1-(cyclopropylmethyl)-1H-indol-2-yl)-1-(2-(l, 1-dioxidotetrahydro-2H-thiopyran-4-yl)ethyl)-7-methoxy-1H-benzo[d]imidazole-5-carboxylate as white solid. LC/MS (M+H): 536; LC retention time: 0.93 min (analytical HPLC Method 3).

A mixture of methyl 2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazole-5-carboxylate and 1.0 M aqueous sodium hydroxide (0.647 mL, 0.647 mmol) in THE (10 mL) was stirred at RT for 3 days. A solution of 1.0 N aqueous HCl (0.65 mL) was added and the mixture was concentrated. The resulting mixture was extracted with EtOAc (15 mL) and the organic layer was dried over sodium sulfate and concentrated to give a crude yield of 2-(1-(cyclopropylmethyl)-1H-indol-2-yl)-1-(2-(l, 1-dioxidotetrahydro-2H-thiopyran-4-yl)ethyl)-7-methoxy-1H-benzo[d]imidazole-5-carboxylic acid (56 mg, 0.102 mmol, 79% yield) as white solid. LC/MS (M+H): 522; LC retention time: 0.83 min (analytical HPLC Method 3). Material was used as is in next reaction.

Example 245: ((1R,4R,7R)-7-amino-2-azabicyclo[2.2.1]heptan-2-yl)(2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazol-5-yl)methanone A mixture of 2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazole-5-carboxylic acid (10 mg, 0.019 mmol), tert-butyl ((7R)-2-azabicyclo[2.2.1]heptan-7-yl)carbamate (4.07 mg, 0.019 mmol), BOP (8.48 mg, 0.019 mmol) and TEA (8.02 μl, 0.058 mmol) in DMF (1.0 mL) was stirred at RT for 2 hour. The mixture was diluted with EtOAc (5 mL) and was washed with a solution of aqueous saturated sodium bicarbonate (2×5 mL). The organic layer was dried over sodium sulfate and concentrated to give crude tert-butyl ((7R)-2-(2-(1-(cyclopropylmethyl)-1H-indol-2-yl)-1-(2-(1,1-dioxidotetrahydro-2H-thiopyran-4-yl)ethyl)-7~methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazole-5-carbonyl)-2-azabicyclo[2.2.1]heptan-7-yl)carbamate in DCM (1.0 mL) and DMF (1.0 mL) was stirred at RT for 30 min. The mixture was then concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 22% B, 22-62% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. ((1R,4R,7R)-7-amino-2-azabicyclo[2.2.1]heptan-2-yl)(2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazol-5-yl)methanone (10.4 mg, 16.9 μmol, 88.9%) was isolated. LC/MS (M+H): 616; LC retention time: 1.47 mm (analytical HPLC Method 1). $^1$H NMR (500 MHz, DMSO-$d_6$) δ 7.72-7.57 (m, 2H), 7.44-7.30 (m, 1H), 7.28-7.22 (m, 1H), 7.14-7.07 (m, 1H), 7.01-6.86 (m, 2H), 4.49-4.37 (m, 2H), 4.34-4.24 (m, 2H), 4.01-3.92 (m, 3H), 3.51-3.24 (m, 2H), 3.15-2.87 (m, 5H), 2.21-1.87 (m, 5H), 1.76-1.47 (m, 6H), 1.44-1.13 (m, 3H), 1.00-0.76 (m, 2H), 0.29-0.17 (m, 2H), 0.06--0.08 (m, 2H).

Example 246

(1R,4R,7R)-2-{2-[1-(cyclopropylmethyl)-1H-indol-2-yl]-7-methoxy-1-[(pyridin-3-yl)methyl]-1H-1,3-benzodiazole-5-carbonyl}-2-azabicyclo[2.2.1]heptan-7-amine

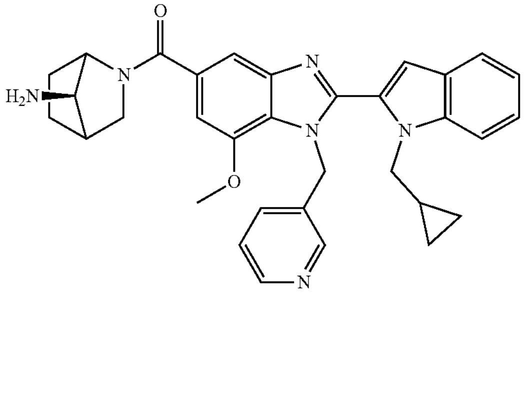 [SMILES: COc1cc(C(=O)N2CC3CCC2[C@@H]3N)cc2nc(-c3cc4ccccc4n3CC3CC3)n(Cc3cccnc3)c12]

Intermediate 246A: Methyl 3-methoxy-5-nitro-4-((pyridin-3-ylmethyl)amino)benzoate

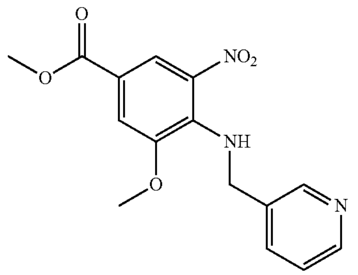 [SMILES: COC(=O)c1cc(OC)c(NCc2cccnc2)c([N+](=O)[O-])c1]

A mixture of methyl 4-chloro-3-methoxy-5-nitrobenzoate (500 mg, 2.036 mmol), 3-(aminomethyl)pyridine (220 mg, 2.036 mmol) and potassium carbonate (844 mg, 6.11 mmol) in DMF (10 mL) was stirred at RT for 18 hours. LCMS indicated 10% product. The mixture was stirred at RT for 4 days. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-EtOAc 100:0 to 0:100 gradient) to yield methyl 3-methoxy-5-nitro-4-((pyridin-3-ylmethyl)amino)benzoate (345 mg, 1.033 mmol, 50.7% yield) as orange solid. LC/MS (M+H): 318; LC retention time: 0.84 min (analytical HPLC Method 3).

Intermediate 246B: 2-(1-(cyclopropylmethyl)-1H-indol-2-yl)-7-methoxy-1-(pyridin-2-ylmethyl)-1H-benzo[d]imidazole-S-carboxylic acid

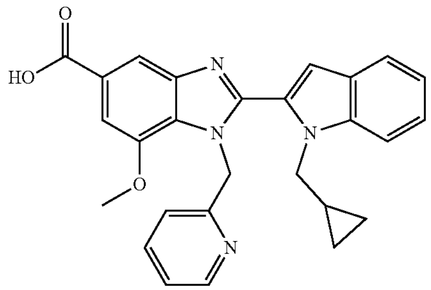 [SMILES: COc1cc(C(=O)O)cc2nc(-c3cc4ccccc4n3CC3CC3)n(Cc3ccccn3)c12]

To a solution of methyl 3-methoxy-5-nitro-4-((pyridin-3-ylmethyl)amino)benzoate (50 mg, 0.158 mmol) and 1-(cyclopropylmethyl)-1H-indole-2-carbaldehyde (31.4 mg, 0.158 mmol) in EtOH (3.0 mL) was added a solution of sodium dithionite (82 mg, 0.473 mmol) in water (1.500 mL), and the mixture was stirred at 80° C. for 18 hours. The mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient) to yield methyl 2-(1-(cyclopropylmethyl)-1H-indol-2-yl)-7-methoxy-1-(pyridin-3-ylmethyl)-1H-benzo[d]imidazole-5-carboxylate as white solid. LC/MS (M+H): 467; LC retention time: 0.84 min (analytical HPLC Method 3).

A mixture of methyl 2-(1-(cyclopropylmethyl)-1H-indol-2-yl)-7-methoxy-1-(pyridin-3-ylmethyl)-1H-benzo[d]imidazole-5-carboxylate and 1.0 M aqueous sodium hydroxide (0.788 mL, 0.788 mmol) in MeOH (3.0 mL) was stirred at RT for 3 days.

A solution of 1.0 N aqueous HCl (0.85 mL) was added and the mixture was concentrated. The resulting mixture was extracted with EtOAc (15 mL) and the organic layer was dried over sodium sulfate and concentrated to give a crude yield of 2-(1-(cyclopropylmethyl)-1H-indol-2-yl)-7-methoxy-1-(pyridin-3-ylmethyl)-1H-benzo[d]imidazole-5-carboxylic acid (42 mg, 0.084 mmol, 53.0% yield) as white solid. LC/MS (M+H): 453; LC retention time: 0.74 min (analytical HPLC Method 3). Material was used as is in next reaction.

Example 246: (1R,4R,7R)-2-{2-[1-(cyclopropylmethyl)-1H-indol-2-yl]-7-methoxy-1-[(pyridin-3-yl)methyl]-1H-1,3-benzodiazole-5-carbonyl}-2-azabicyclo[2.2.1]heptan-7-amine A mixture of 2-(1-(cyclopropylmethyl)-1H-indol-2-yl)-7-methoxy-1-(pyridin-3-ylmethyl)-1H-benzo[d]imidazole-5-carboxylic acid (10 mg, 0.022 mmol), tert-butyl ((7R)-2-azabicyclo[2.2.1]heptan-7-yl)carbamate (4.69 mg, 0.022 mmol), BOP (9.77 mg, 0.022 mmol) and TEA (9.24 µl, 0.066 mmol) in DMF (1.0 mL) was stirred at RT for 2 hours. The mixture was diluted with EtOAc (5 mL) and was washed with a solution of aqueous saturated sodium bicarbonate (2x5 mL). The ethyl acetate layer was dried over sodium sulfate and concentrated to give crude tert-butyl ((1R,4R,7R)-2-(2-(1-(cyclopropylmethyl)-1H-indol-2-yl)-7-methoxy-1-(pyridin-3-ylmethyl)-1H-benzo[d]imidazole-5-carbonyl)-2-azabicyclo[2.2.1]heptan-7-yl)carbamate. A mixture of tert-butyl ((1R,4R,7R)-2-(2-(1-(cyclopropylmethyl)-1H-indol-2-yl)-7-methoxy-1-(pyridin-3-ylmethyl)-1H-benzo[d]imidazole-5-carbonyl)-2-azabicyclo[2.2.1]heptan-7-yl)carbamate in DCM (1.0 mL) and TFA (1.0 mL) was stirred at RT for 30 min. The mixture was concentrated. The crude material was purified via preparative LC/MS with the following conditions: Column: XBridge CIS, 200 mmx19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 17% B, 17-57% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. (1R,4R,7R)-2-{2-[1-(cyclopropylmethyl)-1H-indol-2-yl]-7-methoxy-1-[(pyridin-3-yl)methyl]-1H-1,3-benzodiazole-5-carbonyl}-2-azabicyclo[2.2.1]heptan-7-amine (9.5 mg, 17.4 µmol, 79%) was isolated. LC/MS (M+H): 547; LC retention time: 1.69 mm (analytical HPLC Method 1) $^1$H NMR (500 MHz, DMSO-$d_6$) δ 8.31-8.19 (m, 1H), 8.08-7.91 (m, 1H), 7.55-7.43 (m, 2H), 7.37-7.06 (m, 4H), 7.03-6.91 (m, 1H), 6.87-6.65 (m, 2H), 5.79-5.55 (m, 2H), 4.24-4.08 (m, 2H), 3.83-3.66 (m, 3H), 3.65-3.43 (m, 1H), 3.43-3.09 (m, 1H), 3.07-2.80 (m, 2H), 2.10-1.76 (m, 3H), 1.65-1.43 (m, 1H), 1.35-0.95 (m, 2H), 0.74-0.55 (m, 1H), 0.07--0.06 (m, 2H), −0.08--0.20 (m, 2H).

Example 247

(1-((1H-pyrazol-4-yl)methyl)-2-(1-(cyclopropylmethyl)-1H-indol-2-yl)-7-methoxy-1H-benzo[d]imidazol-5-yl)((1R,4R,7R)-7-amino-2-azabicyclo[2.2.1]heptan-2-yl)methanone

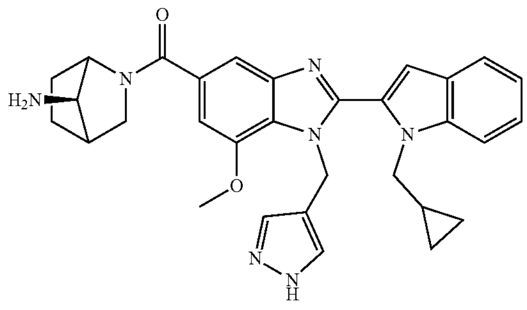 [SMILES: COc1cc(C(=O)N2CC3CCC2[C@@H]3N)cc2nc(-c3cc4ccccc4n3CC3CC3)n(Cc3cn[nH]c3)c12]

Intermediate 247A: Methyl 3-methoxy-5-nitro-4-(((1-((2-(trimethylsilyl)ethoxy)methyl)-1H-pyrazol-4-yl)methyl)amino)benzoate

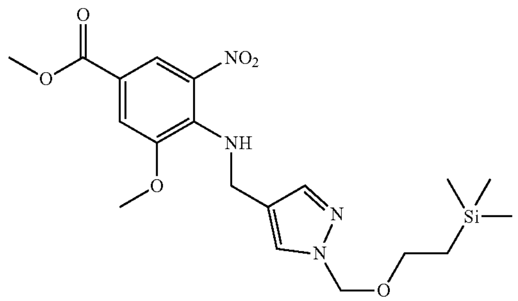

A mixture of methyl 4-chloro-3-methoxy-5-nitrobenzoate (700 mg, 2.85 mmol), (1-((2-(trimethylsilyl)ethoxy)methyl)-1H-pyrazol-4-yl)methanamine (648 mg, 2.85 mmol) and potassium carbonate (1182 mg, 8.55 mmol) in BASF (10 mL) was stirred at 80° C. for 4 hours. The mixture was cooled to RT, diluted with EtOAc (15 mL) and was washed with a solution of aqueous saturated sodium bicarbonate (2x15 mL). The organic layer was dried over sodium sulfate and concentrated. The crude product was subjected to ISCO flash chromatography (silica gel/hexane-EtOAc 100:0 to 0:100 gradient) to yield methyl 3-methoxy-5-nitro-4-(((1-((2-(trimethylsilyl)ethoxy)methyl)-1H-pyrazol-3-yl)methyl)amino)benzoate (630 mg, 1.371 mmol, 48.1% yield) as orange gum. LC/MS (M+H): 437; LC retention time: 1.07 min (analytical HPLC Method 3).

Intermediate 247B: 2-(1-(cyclopropylmethyl)-1H-indol-2-yl)-7-methoxy-1-((1-((2-(trimethylsilyl)ethoxy)methyl)-1H-pyrazol-4-yl)-1H-benzo[d]imidazole-5-carboxylic acid

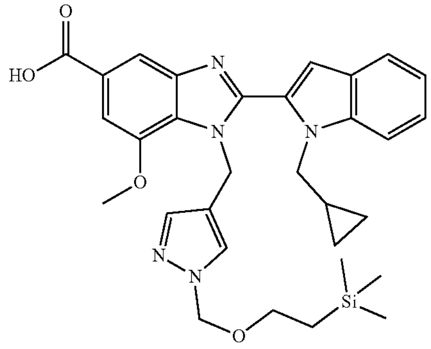 [SMILES: COc1cc(C(=O)O)cc2nc(-c3cc4ccccc4n3CC3CC3)n(Cc3cnn(COCC[Si](C)(C)C)c3)c12]

To a solution of methyl 3-methoxy-5-nitro-4-(((1-((2-(trimethylsilyl)ethoxy)methyl)-1H-pyrazol-3-yl)methyl)amino)benzoate (100 mg, 0.229 mmol) and 1-(cyclopropylmethyl)-1H-indole-2-carbaldehyde (45.6 mg, 0.229 mmol) in EtOH (3.0 mL) was added a solution of sodium dithionite (120 mg, 0.687 mmol) in water (1.500 mL), and the mixture was stirred at 80° C. for 6 hours. The resulting mixture was diluted with EtOAc (5 mL) and was washed with a solution of aqueous saturated sodium chloride (2×5 mL). The organic layer was dried over sodium sulfate and concentrated. The crude product was subjected to ISCO flash chromatography (silica gel/hexane-EtOAc 100:0 to 0:100 gradient) to yield methyl 2-(1-(cyclopropylmethyl)-1H-indol-2-yl)-7-methoxy-1-((1-((2-(trimethylsilyl)ethoxy)methyl)-1H-pyrazol-4-yl)methyl)-1H-benzo[d]imidazole-5-carboxylate as white foam. LC/MS (M+H): 586; LC retention time: 1.15 min (analytical HPLC Method 3). Material was used as is in next reaction.

A mixture of methyl 2-(1-(cyclopropylmethyl)-1H-indol-2-yl)-7-methoxy-1-((1-((2-(trimethylsilyl)ethoxy)methyl)-1H-pyrazol-4-yl)methyl)-1H-benzo[d]imidazole-5-carboxylate (104 mg, 0.169 mmol) and 1.0 M aqueous sodium hydroxide (1.145 mL, 1.145 mmol) in THE was stirred at 50° C. for 18 hours. The mixture was cooled to RT, a solution of aqueous HCl (1.20 mL) was added and the mixture was concentrated. The resulting mixture was extracted with EtOAc (2×15 mL), and the organic layer was dried over sodium sulfate and concentrated to give a crude yield of 2-(1-(cyclopropylmethyl)-1H-indol-2-yl)-7-methoxy-1-((1-((2-(trimethylsilyl)ethoxy)methyl)-1H-pyrazol-4-yl)methyl)-1H-benzo[d]imidazole-5-carboxylic acid (105 mg, 0.165 mmol, 72.2% yield). LC/MS (M+H): 572; LC retention time: 1.07 min (analytical HPLC Method 3). Material was used as is in next reaction.

Intermediate 247C: Tert-butyl ((1R,4R,7R)-2-(2-(1-(cyclopropylmethyl)-1H-indol-2-yl)-7-methoxy-1-((1-((2-(trimethylsilyl)ethoxy)meth yl)-1H-pyrazol-4-yl)methyl)-1H-benzo[d]imidazole-5-carbonyl)-2-azabicyclo[2.2.1]heptan-7-yl)carbamate

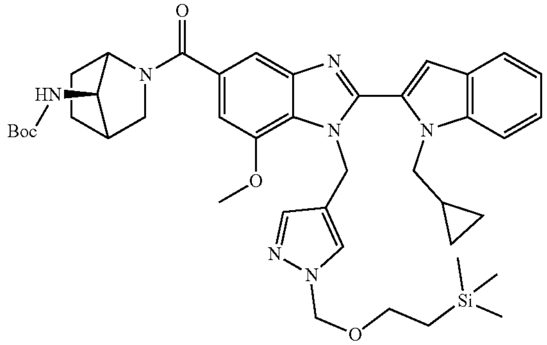 [SMILES: COc1cc(C(=O)N2CC3CCC2[C@@H]3NC(=O)OC(C)(C)C)cc2nc(-c3cc4ccccc4n3CC3CC3)n(Cc3cnn(COCC[Si](C)(C)C)c3)c12]

A mixture of 2-(1-(cyclopropylmethyl)-1H-indol-2-yl)-7-methoxy-1-((1-((2-(trimethylsilyl)ethoxy)methyl)-1H-pyrazol-4-yl)methyl)-1H-benzo[d]imidazole-5-carboxylic acid (53 mg, 0.093 mmol), tert-butyl ((1R,4R,7R)-2-azabicyclo[2.2.1]heptan-7-yl)carbamate (19.68 mg, 0.093 mmol), BOP (41.0 mg, 0.093 mmol) and TEA (0.039 mL, 0.278 mmol) in DMF (2.0 mL) was stirred at RT for 2 hours. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield tert-butyl ((1R,4R,7R)-2-(2-(1-(cyclopropylmethyl)-1H-indol-2-yl)-7-methoxy-1-((1-((2-(trimethylsilyl)ethoxy)methyl)-1H-pyrazol-4-yl)methyl)-1 IT-benzo[d]imidazole-5-carbonyl)-2-azabicyclo[2.2.1]heptan-7-yl)carbamate (43.4 mg, 0.054 mmol, 58% yield) as white solid. LC/MS (M+H): 766; LC retention time: 1.09 min (analytical HPLC Method 3).

Example 247: (1-((1H-pyrazol-4-yl)methyl)-2-(1-(cyclopropylmethyl)-1H-indol-2-yl)-7-methoxy-1H-benzo[d]imidazol-5-yl)((1R,4R,7R)-7-amino-2-azabicyclo[2.2.1]heptan-2-yl)methanone A mixture of tert-butyl ((1R,4R,7R)-2-(2-(1-(cyclopropylmethyl)-1H-indol-2-yl)-7-methoxy-1-((1-((2-(trimethylsilyl)ethoxy)methyl)-1H-pyrazol-4-yl)methyl)-1H-benzo[d]imidazole-5-carbonyl)-2-azabicyclo[2.2.1]heptan-7-yl)carbamate (15 mg, 0.020 mmol) in TEA (1.0 mL) was stirred at RT for 1 hour. The mixture was concentrated. The crude material was purified via preparative LC/MS with the following conditions: Column: XBridge 08, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 14% B, 14-54% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. (1R,4R,7R)-2-{2-[1-(cyclopropylmethyl)-1H-indol-2-yl]-7-methoxy-1-[(1H-pyrazol-4-yl)methyl]-1H-1,3-benzodiazole-5-carbonyl}-2-azabicyclo[2.2.1]heptan-7-amine (5.3 mg, 9.9 μmol, 49.5%) was isolated, LC/MS (M+H): 536; LC retention time: 1.49 min (analytical HPLC Method 1). $^1H$ NMR (500 MHz, DMSO-$d_6$) δ 7.60-7.45 (m, 2H), 7.34-7.12 (m, 2H), 7.10-6.96 (m, 3H), 6.92-6.78 (m, 2H), 5.59-5.43 (m, 2H), 4.22-4.06 (m, 2H), 3.91-3.81 (m, 3H), 3.69-3.38 (m, 1H), 3.06-2.86 (m, 2H), 2.12-1.95 (m, 1H), 1.91-1.79 (m, 2H), 1.66-1.48 (m, 1H), 1.33-1.18 (m, 1H), 1.13-1.02 (m, 1H), 0.72-0.58 (m, 1H), 0.06--0.08 (m, 2H), −0.12--0.20 (m, 2H).

Examples 248 to 310 in Table 4 were prepared as described in the general procedures given for Examples 242 to 247.

TABLE 4

| Ex # | Structure | Name | LC/MS Rt (min) | LC/MS Method | M + H (obs ion) |
|---|---|---|---|---|---|
| 248 | 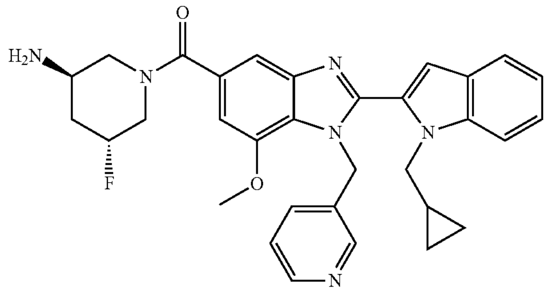 [SMILES: COc1cc(C(=O)N2C[C@H](N)C[C@@H](F)C2)cc2nc(-c3cc4ccccc4n3CC3CC3)n(Cc3cccnc3)c12] | ((3R,5R)-3-amino-5-fluoropiperidin-1-yl)(2-(1-(cyclopropylmethyl)-1H-indol-2-yl)-7-methoxy-1-(pyridin-3-ylmethyl)-1H-benzo[d]imidazol-5-yl)methanone | 1.67 | 1 | 553 |
| 249 | 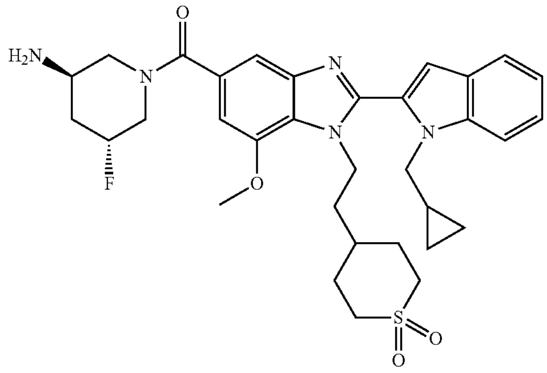 [SMILES: COc1cc(C(=O)N2C[C@H](N)C[C@@H](F)C2)cc2nc(-c3cc4ccccc4n3CC3CC3)n(CCC3CCS(=O)(=O)CC3)c12] | ((3R,5R)-3-amino-5-fluoropiperidin-1-yl)(2-(1-(cyclopropylmethyl)-1H-indol-2-yl)-1-(2-(1,1-dioxidotetrahydro-2H-thiopyran-4-yl)ethyl)-7-methoxy-1H-benzo[d]imidazol-5-yl)methanone | 1.45 | 1 | 622 |
| 250 | 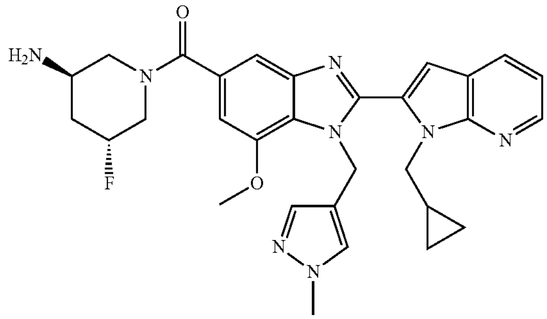 [SMILES: COc1cc(C(=O)N2C[C@H](N)C[C@@H](F)C2)cc2nc(-c3cc4cccnc4n3CC3CC3)n(Cc3cnn(C)c3)c12] | ((3R,5R)-3-amino-5-fluoropiperidin-1-yl)(2-(1-(cyclopropylmethyl)-1H-pyrrolo[2,3-b]pyridin-2-yl)-7-methoxy-1-((1-methyl-1H-pyrazol-4-yl)methyl)-1H-benzo[d]imidazol-5-yl)methanone | 1.26 | 1 | 557 |
| 251 | 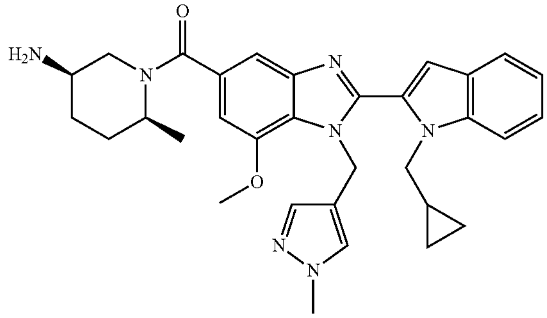 [SMILES: COc1cc(C(=O)N2C[C@H](N)CC[C@@H]2C)cc2nc(-c3cc4ccccc4n3CC3CC3)n(Cc3cnn(C)c3)c12] | ((2S,5R)-5-amino-2-methylpiperidin-1-yl)(2-(1-(cyclopropylmethyl)-1H-indol-2-yl)-7-methoxy-1-((1-methyl-1H-pyrazol-4-yl)methyl)-1H-benzo[d]imidazol-5-yl)methanone | 1.45 | 2 | 522 |

TABLE 4-continued

| Ex # | Structure | Name | LC/MS Rt (min) | LC/MS Method | M + H (obs ion) |
|---|---|---|---|---|---|
| 252 | 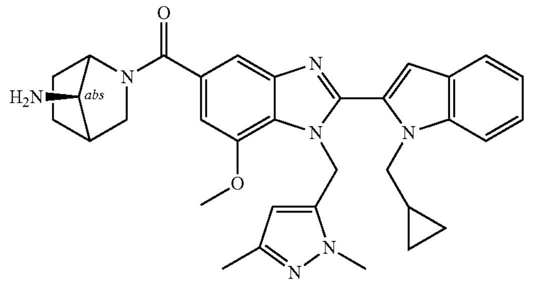 [SMILES: COc1cc(C(=O)N2CC3CCC2[C@@H]3N)cc2nc(-c3cc4ccccc4n3CC3CC3)n(Cc3cc(C)nn3C)c12] | (1R,4R,7R)-2-{2-[1-(cyclopropylmethyl)-1H-indol-2-yl]-1-[(1,3-dimethyl-1H-pyrazol-5-yl)methyl]-7-methoxy-1H-1,3-benzodiazole-5-carbonyl}-2-azabicyclo[2.2.1]heptan-7-amine | 1.74 | 1 | 564 |
| 253 | 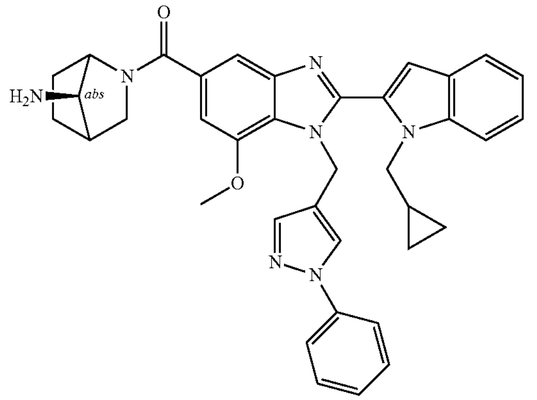 [SMILES: COc1cc(C(=O)N2CC3CCC2[C@@H]3N)cc2nc(-c3cc4ccccc4n3CC3CC3)n(Cc3cnn(-c4ccccc4)c3)c12] | (1R,4R,7R)-2-{2-[1-(cyclopropylmethyl)-1H-indol-2-yl]-7-methoxy-1-[(1-phenyl-1H-pyrazol-4-yl)methyl]-1H-1,3-benzodiazole-5-carbonyl}-2-azabicyclo[2.2.1]heptan-7-amine | 2.01 | 1 | 612 |
| 254 | 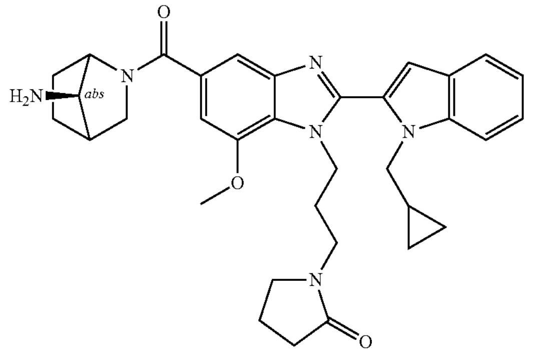 [SMILES: COc1cc(C(=O)N2CC3CCC2[C@@H]3N)cc2nc(-c3cc4ccccc4n3CC3CC3)n(CCCN3CCCC3=O)c12] | 1-(3-{5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}propyl)pyrrolidin-2-one | 1.59 | 1 | 581 |
| 255 | 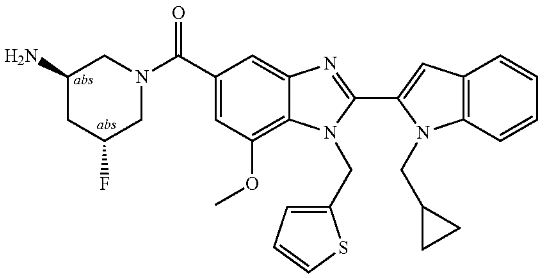 [SMILES: COc1cc(C(=O)N2C[C@H](N)C[C@@H](F)C2)cc2nc(-c3cc4ccccc4n3CC3CC3)n(Cc3cccs3)c12] | (3R,5R)-1-{2-[1-(cyclopropylmethyl)-1H-indol-2-yl]-7-methoxy-1-[(thiophen-2-yl)methyl]-1H-1,3-benzodiazole-5-carbonyl}-5-fluoropiperidin-3-amine | 1.98 | 1 | 558 |

TABLE 4-continued

| Ex # | Structure | Name | LC/MS Rt (min) | LC/MS Method | M + H (obs ion) |
|---|---|---|---|---|---|
| 256 | 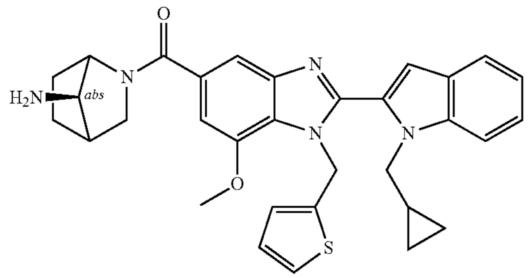 [SMILES: COc1cc(C(=O)N2CC3CCC2[C@@H]3N)cc2nc(-c3cc4ccccc4n3CC3CC3)n(Cc3cccs3)c12] | (1R,4R,7R)-2-{2-[1-(cyclopropylmethyl)-1H-indol-2-yl]-7-methoxy-1-[(thiophen-2-yl)methyl]-1H-1,3-benzodiazole-5-carbonyl}-2-azabicyclo[2.2.1]heptan-7-amine | 2.01 | 1 | 552 |
| 257 | 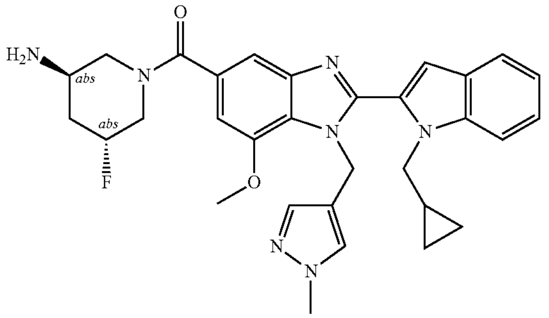 [SMILES: COc1cc(C(=O)N2C[C@H](N)C[C@@H](F)C2)cc2nc(-c3cc4ccccc4n3CC3CC3)n(Cc3cnn(C)c3)c12] | (3R,5R)-1-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}-5-fluoropiperidin-3-amine | 1.5 | 1 | 556 |
| 258 | 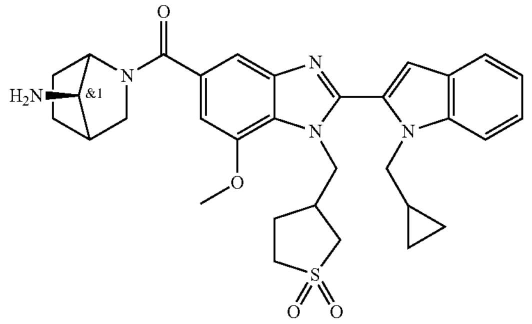 [SMILES: COc1cc(C(=O)N2CC3CCC2[C@@H]3N)cc2nc(-c3cc4ccccc4n3CC3CC3)n(CC3CCS(=O)(=O)C3)c12] | rac-((7R)-7-amino-2-azabicyclo[2.2.1]heptan-2-yl)(2-(1-(cyclopropylmethyl)-1H-indol-2-yl)-1-((1,1-dioxidotetrahydrothiophen-3-yl)methyl)-7-methoxy-1H-benzo[d]imidazol-5-yl)methanone | 1.58 | 1 | 588 |
| 259 | 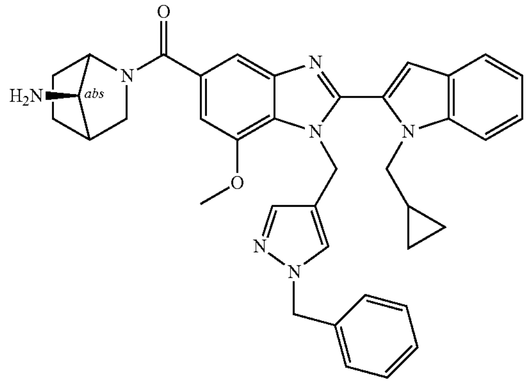 [SMILES: COc1cc(C(=O)N2CC3CCC2[C@@H]3N)cc2nc(-c3cc4ccccc4n3CC3CC3)n(Cc3cnn(Cc4ccccc4)c3)c12] | (1R,4R,7R)-2-{1-[(1-benzyl-1H-pyrazol-4-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine | 1.96 | 1 | 626 |

TABLE 4-continued

| Ex # | Structure | Name | LC/MS Rt (min) | LC/MS Method | M + H (obs ion) |
|---|---|---|---|---|---|
| 260 | 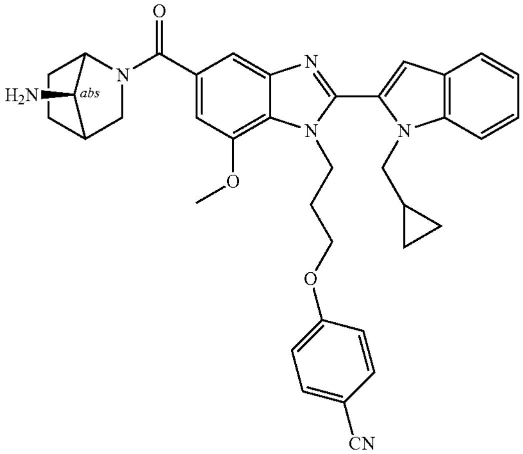 [SMILES: COc1cc(C(=O)N2CC3CCC2[C@@H]3N)cc2nc(-c3cc4ccccc4n3CC3CC3)n(CCCOc3ccc(C#N)cc3)c12] | 4-(3-{5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}propoxy)benzonitrile | 1.71 | 2 | 615 |
| 261 | 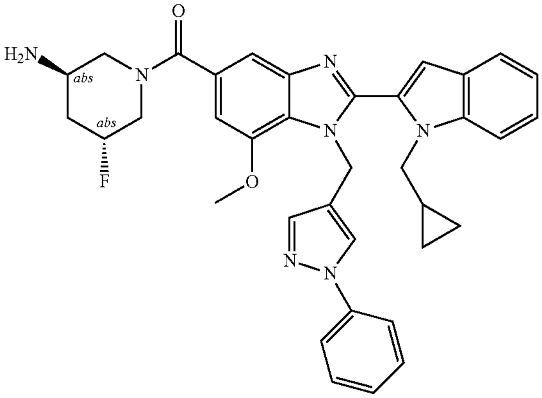 [SMILES: COc1cc(C(=O)N2C[C@H](N)C[C@@H](F)C2)cc2nc(-c3cc4ccccc4n3CC3CC3)n(Cc3cnn(-c4ccccc4)c3)c12] | (3R,5R)-1-{2-[1-(cyclopropylmethyl)-1H-indol-2-yl]-7-methoxy-1-[(1-phenyl-1H-pyrazol-4-yl)methyl]-1H-1,3-benzodiazole-5-carbonyl}-5-fluoropiperidin-3-amine | 2.07 | 1 | 618 |
| 262 | 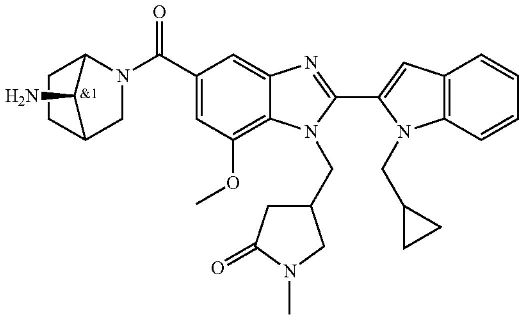 [SMILES: COc1cc(C(=O)N2CC3CCC2[C@@H]3N)cc2nc(-c3cc4ccccc4n3CC3CC3)n(CC3CC(=O)N(C)C3)c12] | 4-({5-[(1R,4R,7R)-7-amino-2-azabicyclo[2.2.1]heptane-2-carbonyl]-2-[1-(cyclopropylmethy!)-1H-indol-2-yl]-7-methoxy-1H-1,3-benzodiazol-1-yl}methyl)-1-methylpyrrolidin-2-one | 1.58 | 1 | 567 |
| 263 | 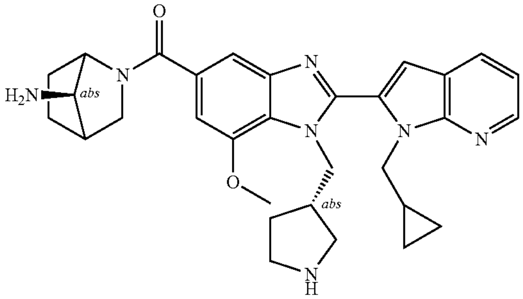 [SMILES: COc1cc(C(=O)N2CC3CCC2[C@@H]3N)cc2nc(-c3cc4cccnc4n3CC3CC3)n(C[C@H]3CCNC3)c12] | (1R,4R,7R)-2-{2-[1-(cyclopropylmethyl)-1H-pyrrolo[2,3-b]pyridin-2-yl]-7-methoxy-1-{[(3S)-pyrrolidin-3-yl]methyl}-1H-1,3-benzodiazole-5-carbonyl}-2-azabicyclo[2.2.1]heptan-7-amine | 1.08 | 1 | 540 |

TABLE 4-continued

| Ex # | Structure | Name | LC/MS Rt (min) | LC/MS Method | M + H (obs ion) |
|---|---|---|---|---|---|
| 264 | 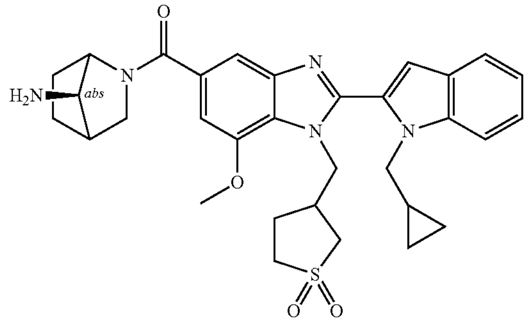 [SMILES: COc1cc(C(=O)N2CC3CCC2[C@@H]3N)cc2nc(-c3cc4ccccc4n3CC3CC3)n(CC3CCS(=O)(=O)C3)c12] | ((7R)-7-amino-2-azabicyclo[2.2.1]heptan-2-yl)(2-(1-(cyclopropylmethyl)-1H-indol-2-yl)-1-((1,1-dioxidotetrahydrothiophen-3-yl)methyl)-7-methoxy-1H-benzo[d]imidazol-5-yl)methanone | 1.42 | 1 | 588 |
| 265 | 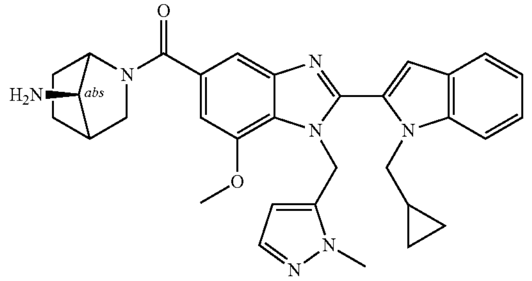 [SMILES: COc1cc(C(=O)N2CC3CCC2[C@@H]3N)cc2nc(-c3cc4ccccc4n3CC3CC3)n(Cc3ccnn3C)c12] | (1R,4R,7R)-2-{2-[1-(cyclopropylmethyl)-1H-indol-2-yl]-7-methoxy-1-[(1-methyl-1H-pyrazol-5-yl)methyl]-1H-1,3-benzodiazole-5-carbonyl}-2-azabicyclo[2.2.1]heptan-7-amine | 1.72 | 1 | 549 |
| 266 | 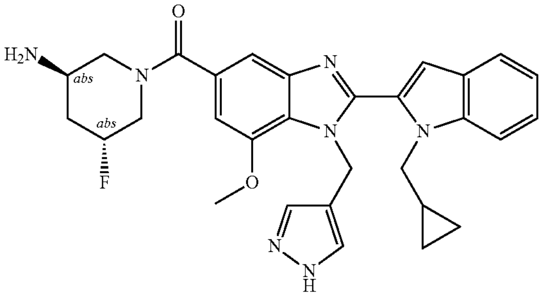 [SMILES: COc1cc(C(=O)N2C[C@H](N)C[C@@H](F)C2)cc2nc(-c3cc4ccccc4n3CC3CC3)n(Cc3cn[nH]c3)c12] | (3R,5R)-1-{2-[1-(cyclopropylmethyl)-1H-indol-2-yl]-7-methoxy-1-[(1H-pyrazol-4-yl)methyl]-1H-1,3-benzodiazole-5-carbonyl}-5-fluoropiperidin-3-amine | 1.48 | 1 | 542 |
| 267 | 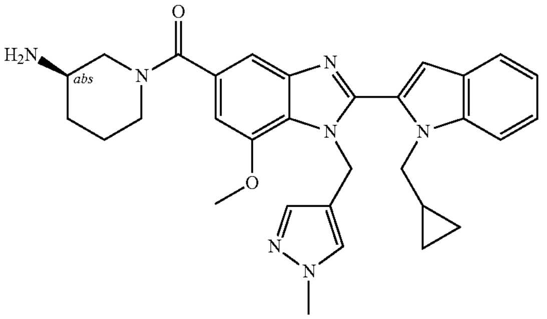 [SMILES: COc1cc(C(=O)N2CCC[C@@H](N)C2)cc2nc(-c3cc4ccccc4n3CC3CC3)n(Cc3cnn(C)c3)c12] | (3R)-1-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}piperidin-3-amine | 1.41 | 2 | 538 |
| 268 | 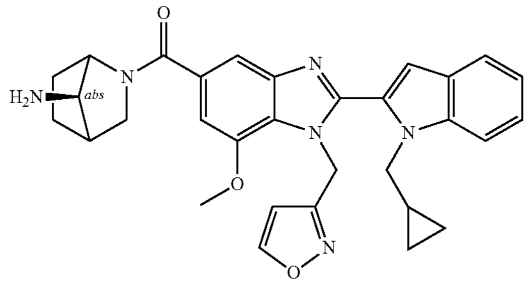 [SMILES: COc1cc(C(=O)N2CC3CCC2[C@@H]3N)cc2nc(-c3cc4ccccc4n3CC3CC3)n(Cc3ccon3)c12] | (1R,4R,7R)-2-{2-[1-(cyclopropylmethyl)-1H-indol-2-yl]-7-methoxy-1-[(1,2-oxazol-3-yl)methyl]-1H-1,3-benzodiazole-5-carbonyl}-2-azabicyclo[2.2.1]heptan-7-amine | 1.52 | 2 | 537 |

TABLE 4-continued

| Ex # | Structure | Name | LC/MS Rt (min) | LC/MS Method | M + H (obs ion) |
|---|---|---|---|---|---|
| 269 | 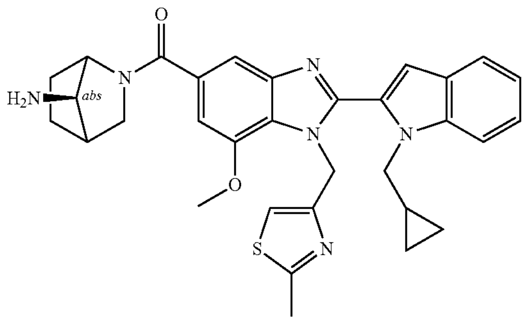 [SMILES: COc1cc(C(=O)N2CC3CCC2[C@@H]3N)cc2nc(-c3cc4ccccc4n3CC3CC3)n(Cc3csc(C)n3)c12] | (1R,4R,7R)-2-{2-[1-(cyclopropylmethyl)-1H-indol-2-yl]-7-methoxy-1-[(2-methyl-1,3-thiazol-4-yl)methyl]-1H-1,3-benzodiazole-5-carbonyl}-2-azabicyclo[2.2.1]heptan-7-amine | 1.59 | 2 | 567 |
| 270 | 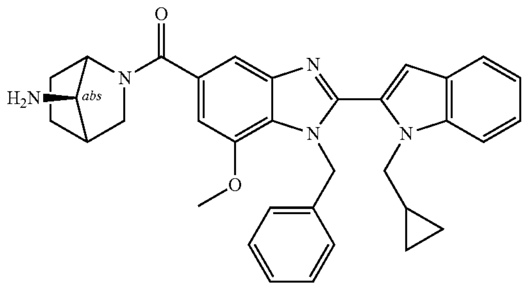 | (1R,4R,7R)-2-(1-benzyl-2-[1-(cyclopropylmethyl)-1H-indol-2-yl]-7-methoxy-1H-1,3-benzodiazole-5-carbony]}-2-azabicyclo[2.2.1]heptan-7-amine | 2.12 | 1 | 546 |
| 271 | 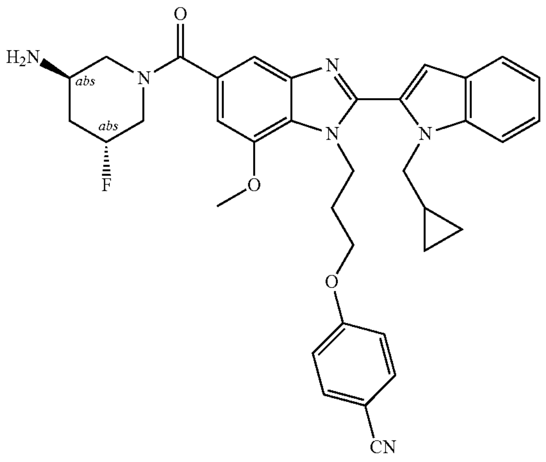 [SMILES: COc1cc(C(=O)N2C[C@H](N)C[C@@H](F)C2)cc2nc(-c3cc4ccccc4n3CC3CC3)n(CCCOc3ccc(C#N)cc3)c12] | 4-(3-{5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}propoxy)benzonitrile | 1.86 | 1 | 621 |
| 272 | 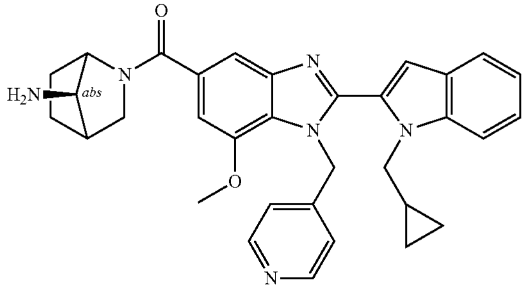 [SMILES: COc1cc(C(=O)N2CC3CCC2[C@@H]3N)cc2nc(-c3cc4ccccc4n3CC3CC3)n(Cc3ccncc3)c12] | (1R,4R,7R)-2-(2-[1-(cyclopropylmethyl)-1H-indol-2-yl]-7-methoxy-1-[(pyridin-4-yl)methyl]-1H-1,3-benzodiazole-5-carbonyl}-2-azabicyclo[2.2.1]heptan-7-amine | 1.68 | 1 | 547 |

TABLE 4-continued

| Ex # | Structure | Name | LC/MS Rt (min) | LC/MS Method | M + H (obs ion) |
|---|---|---|---|---|---|
| 273 | 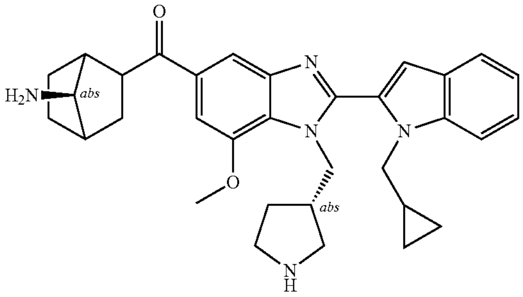 [SMILES: COc1cc(C(=O)C2CC3CCC2[C@@H]3N)cc2nc(-c3cc4ccccc4n3CC3CC3)n(C[C@H]3CCNC3)c12] | (1R,4R,7R)-2-{2-[1-(cyclopropylmethyl)-1H-indol-2-yl]-7-methoxy-1-{[(3S)-pyrrolidin-3-yl]methyl}-1H-1,3-benzodiazole-5-carbonyl}bicyclo[2.2.1]heptan-7-amine | 1.02 | 2 | 539 |
| 274 | 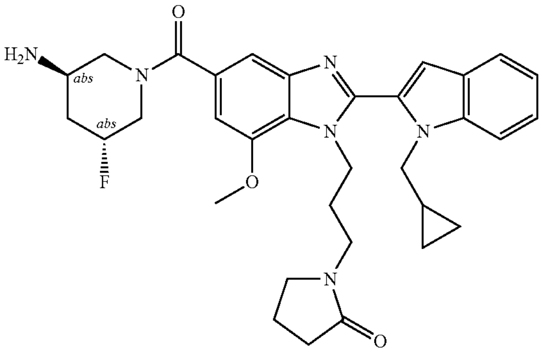 [SMILES: COc1cc(C(=O)N2C[C@H](N)C[C@@H](F)C2)cc2nc(-c3cc4ccccc4n3CC3CC3)n(CCCN3CCCC3=O)c12] | 1-(3-{5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}propyl)pyrrolidin-2-one | 1.38 | 1 | 587 |
| 275 | 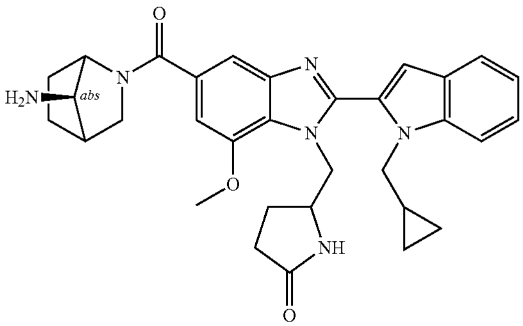 [SMILES: COc1cc(C(=O)N2CC3CCC2[C@@H]3N)cc2nc(-c3cc4ccccc4n3CC3CC3)n(CC3CCC(=O)N3)c12] | 5-({5-[(1R,4R,7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)pyrrolidin-2-one | 1.26 | 2 | 553 |
| 276 | 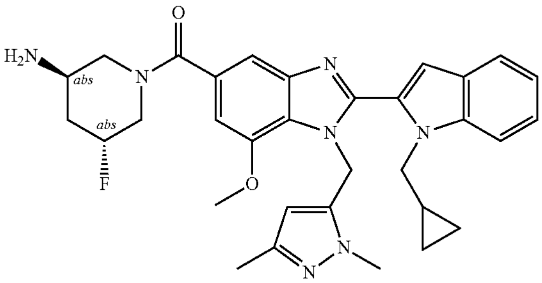 [SMILES: COc1cc(C(=O)N2C[C@H](N)C[C@@H](F)C2)cc2nc(-c3cc4ccccc4n3CC3CC3)n(Cc3cc(C)nn3C)c12] | (3R,5R)-1-{2-[1-(cyclopropylmethyl)-1H-indol-2-yl]-1-[(1,3-dimethyl-1H-pyrazol-5-yl)methyl]-7-methoxy-1H-1,3-benzodiazole-5-carbonyl}-5-fluoropiperidin-3-amine | 1.53 | 1 | 570 |
| 277 | 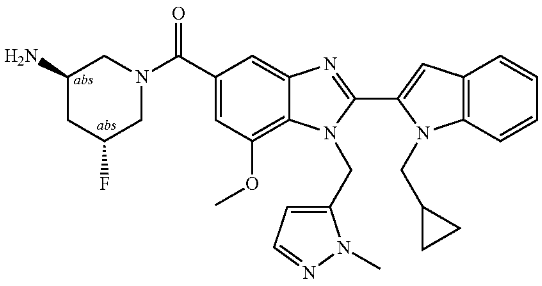 [SMILES: COc1cc(C(=O)N2C[C@H](N)C[C@@H](F)C2)cc2nc(-c3cc4ccccc4n3CC3CC3)n(Cc3ccnn3C)c12] | (3R,5R)-1-{2-[1-(cyclopropylmethyl)-1H-indol-2-yl]-7-methoxy-1-[(1-methyl-1H-pyrazol-5-yl)methyl]-1H-1,3-benzodiazole-5-carbonyl}-5-fluoropiperidin-3-amine | 1.48 | 2 | 556 |

TABLE 4-continued

| Ex # | Structure | Name | LC/MS Rt (min) | LC/MS Method | M + H (obs ion) |
|---|---|---|---|---|---|
| 278 | 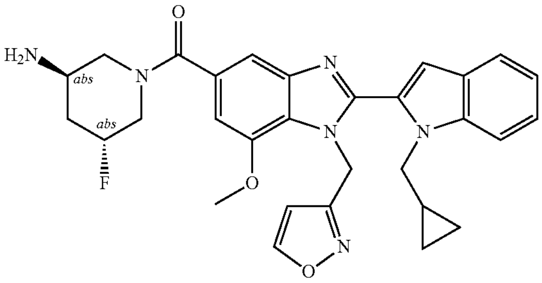 [SMILES: COc1cc(C(=O)N2C[C@H](N)C[C@@H](F)C2)cc2nc(-c3cc4ccccc4n3CC3CC3)n(Cc3ccon3)c12] | (3R,5R)-1-{2-[1-(cyclopropylmethyl)-1H-indol-2-yl]-7-methoxy-1-[(1,2-oxazol-3-yl)methyl]-1H-1,3-benzodiazole-5-carbonyl}-5-fluoropiperidin-3-amine | 1.51 | 1 | 543 |
| 279 | 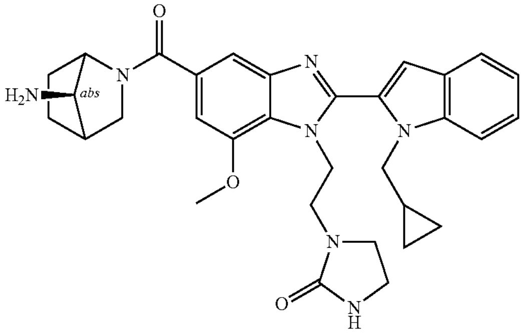 [SMILES: COc1cc(C(=O)N2CC3CCC2[C@@H]3N)cc2nc(-c3cc4ccccc4n3CC3CC3)n(CCN3CCNC3=O)c12] | 1-(2-{5-[(1R,4R,7R)-7-amino-2-azabicyclo[2.2.1]heptane-2-carbonyl]-2-[1-(cyclopropylmethyl)-1H-indol-2-yl]-7-methoxy-benzodiazol-1-yl}ethyl)imidazolidin-2-one | 1.47 | 1 | 567 |
| 280 | 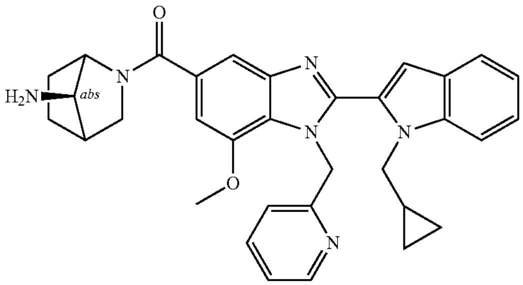 [SMILES: COc1cc(C(=O)N2CC3CCC2[C@@H]3N)cc2nc(-c3cc4ccccc4n3CC3CC3)n(Cc3ccccn3)c12] | (1R,4R,7R)-2-{2-[1-(cyclopropylmethyl)-1H-indol-2-yl]-7-methoxy-1-[(pyridin-2-yl)methyl]-1H-1,3-benzodiazole-5-carbonyl}-2-azabicyclo[2.2.1]heptan-7-amine | 1.82 | 1 | 547 |
| 281 | 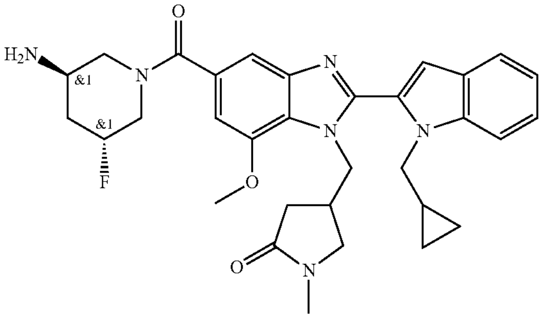 [SMILES: COc1cc(C(=O)N2C[C@H](N)C[C@@H](F)C2)cc2nc(-c3cc4ccccc4n3CC3CC3)n(CC3CC(=O)N(C)C3)c12] | 4-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)-1-methylpyrrolidin-2-one | 1.29 | 2 | 573 |
| 282 | 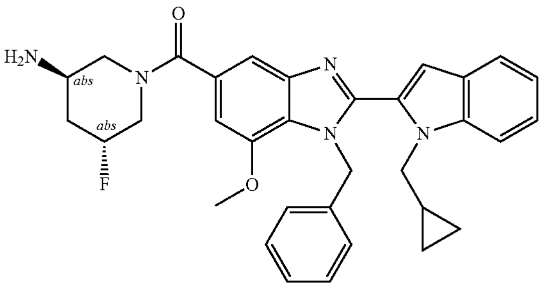 [SMILES: COc1cc(C(=O)N2C[C@H](N)C[C@@H](F)C2)cc2nc(-c3cc4ccccc4n3CC3CC3)n(Cc3ccccc3)c12] | (3R,5R)-1-{1-benzyl-2-[1-(cyclopropylmethyl)-1H-indol-2-yl]-7-methoxy-1H-1,3-benzodiazole-5-carbonyl}-5-fluoropiperidin-3-amine | 1.87 | 2 | 552 |

TABLE 4-continued

| Ex # | Structure | Name | LC/MS Rt (min) | LC/MS Method | M + H (obs ion) |
|---|---|---|---|---|---|
| 283 | 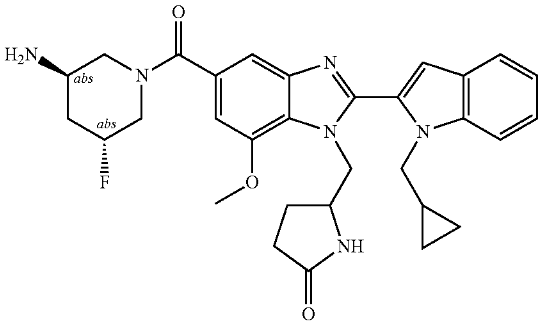 [SMILES: COc1cc(C(=O)N2C[C@H](N)C[C@@H](F)C2)cc2nc(-c3cc4ccccc4n3CC3CC3)n(CC3CCC(=O)N3)c12] | 5-({5-[(3R,5R)-3-amino-5-fluoropiperidine-1-carbonyl]-2-[1-(cyclopropylmethyl)-1H-indol-2-yl]-7-methoxy-1H-1,3-benzodiazol-1-yl}methyl)pyrrolidin-2-one | 1.3 | 1 | 559 |
| 284 | 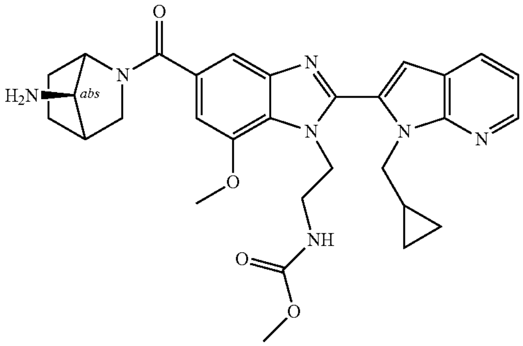 [SMILES: COC(=O)NCCn1c(-c2cc3cccnc3n2CC2CC2)nc2cc(C(=O)N3CC4CCC3[C@@H]4N)cc(OC)c21] | methyl N-(2-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}ethyl)carbamate | 1.17 | 1 | 558 |
| 285 | 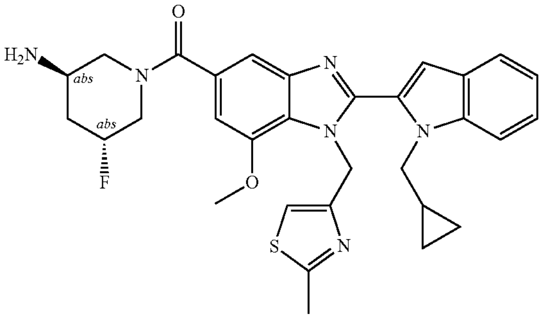 [SMILES: COc1cc(C(=O)N2C[C@H](N)C[C@@H](F)C2)cc2nc(-c3cc4ccccc4n3CC3CC3)n(Cc3csc(C)n3)c12] | (3R,5R)-1-{2-[1-(cyclopropylmethyl)-1H-indol-2-yl]-7-methoxy-1-[(2-methyl-1,3-thiazol-4-yl)methyl]-1H-1,3-benzodiazote-5-carbonyl}-5-fluoropiperidin-3-amine | 1.82 | 1 | 573 |
| 286 | 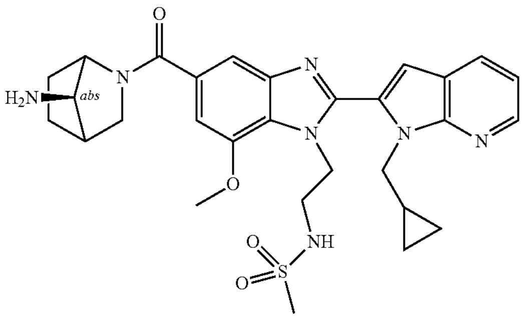 [SMILES: COc1cc(C(=O)N2CC3CCC2[C@@H]3N)cc2nc(-c3cc4cccnc4n3CC3CC3)n(CCNS(C)(=O)=O)c12] | N-(2-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}ethyl)methanesulfonamide | 1.09 | 1 | 578 |

TABLE 4-continued

| Ex # | Structure | Name | LC/MS Rt (min) | LC/MS Method | M + H (obs ion) |
|---|---|---|---|---|---|
| 287 | 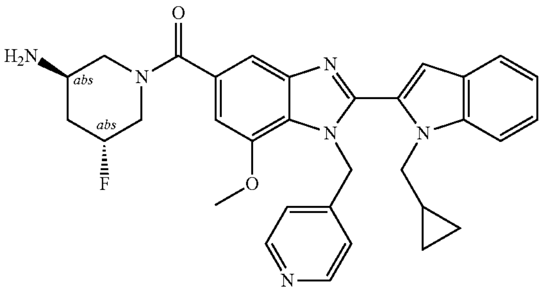 [SMILES: COc1cc(C(=O)N2C[C@H](N)C[C@@H](F)C2)cc2nc(-c3cc4ccccc4n3CC3CC3)n(Cc3ccncc3)c12] | (3R,5R)-1-{2-[1-(cyclopropylmethyl)-1H-indol-2-yl]-7-methoxy-1-[(pyridin-4-yl)methyl]-1H-1,3-benzodiazole-5-carbonyl}-5-fluoropiperidin-3-amine | 1.24 | 2 | 553 |
| 288 | 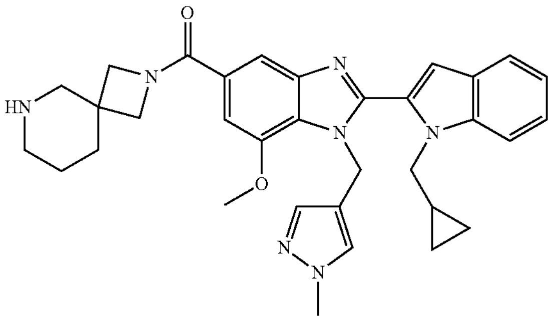 [SMILES: COc1cc(C(=O)N2CC3(CCCNC3)C2)cc2nc(-c3cc4ccccc4n3CC3CC3)n(Cc3cnn(C)c3)c12] | 2-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}-2,6-diazaspiro[3.5]nonane | 1.44 | 2 | 564 |
| 289 | 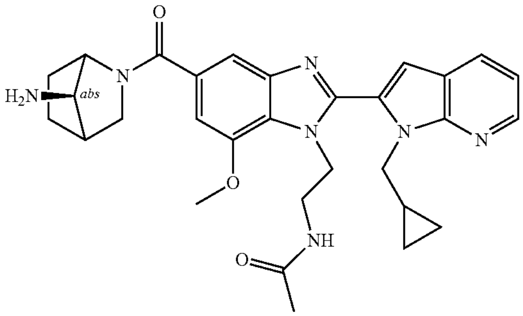 [SMILES: COc1cc(C(=O)N2CC3CCC2[C@@H]3N)cc2nc(-c3cc4cccnc4n3CC3CC3)n(CCNC(C)=O)c12] | N-(2-{5-[(1R,4R,7R)-7-amino-2-azabicyclo[2.2.1]heptane-2-carhonyl]-2-[1-(cyclopropylmethyl)-1H-pyrrolo[2,3-b]pyridin-2-yl]-7-methoxy-1H-1,3-benzodiazol-1-yl}ethyl)acetamide | 1.02 | 1 | 542 |
| 290 | 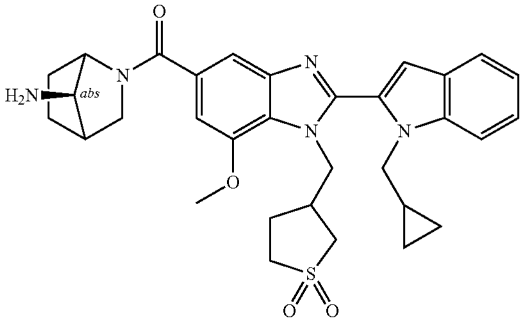 [SMILES: COc1cc(C(=O)N2CC3CCC2[C@@H]3N)cc2nc(-c3cc4ccccc4n3CC3CC3)n(CC3CCS(=O)(=O)C3)c12] | ((7R)-7-amino-2-azabicyclo[2.2.1]heptan-2-yl)(2-(1-(cyclopropylmethyl)-1H-indol-2-yl)-1-((1,1-dioxidotetrahydrothiophen-3-yl)methyl)-7-methoxy-1H-benzo[d]imidazol-5-yl)methanone | 1.42 | 1 | 588 |

TABLE 4-continued

| Ex # | Structure | Name | LC/MS Rt (min) | LC/MS Method | M + H (obs ion) |
|---|---|---|---|---|---|
| 291 | 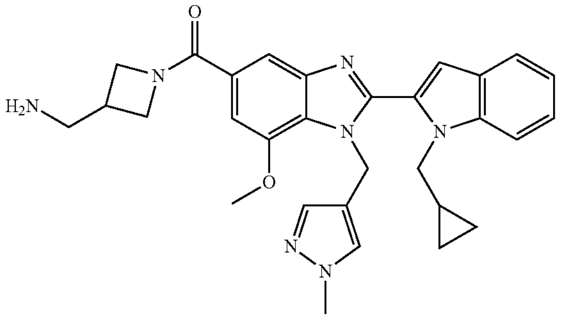 [SMILES: COc1cc(C(=O)N2CC(CN)C2)cc2nc(-c3cc4ccccc4n3CC3CC3)n(Cc3cnn(C)c3)c12] | (1-{2-[1-(cyclopropylmethyl)-1H-indol-2-yl]-7-methoxy-1-[(1-methyl-1H-pyrazol-4-yl)methyl]-1H-1,3-benzodiazole-5-carbonyl}azetidin-3 yl)methanamine | 1.42 | 1 | 524 |
| 292 | 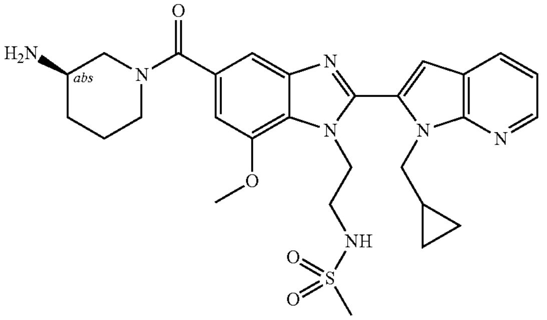 [SMILES: COc1cc(C(=O)N2CCC[C@@H](N)C2)cc2nc(-c3cc4cccnc4n3CC3CC3)n(CCNS(C)(=O)=O)c12] | N-(2-{5-[(3R)-3-aminopiperidine-1-carbonyl]-2-[1-(cyclopropylmethyl)-1H-pyrrolo[2,3-b]pyridin-2-yl]-7-methoxy-1H-1,3-benzodiazol-1-yl}ethyl)methanesulfonamide | 0.93 | 2 | 566 |
| 293 | 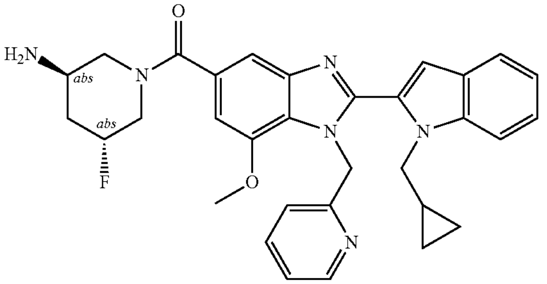 | (3R,5R)-1-{2-[1-(cyclopropylmethyl)-1H-indol-2-yl]-7-methoxy-1-[(pyridin-2-yl)methyl]-1H-1,3-benzodiazole-5-carbonyl}-5-fluoropiperidin-3-amine | 1.79 | 1 | 553 |
| 294 | 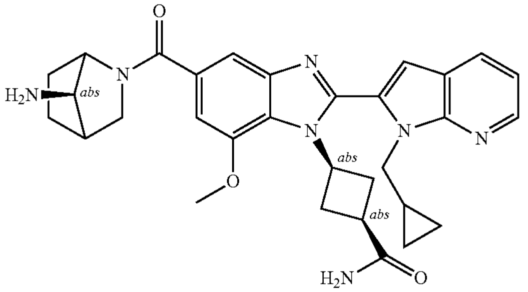 [SMILES: COc1cc(C(=O)N2CC3CCC2[C@@H]3N)cc2nc(-c3cc4cccnc4n3CC3CC3)n([C@H]3C[C@@H](C(N)=O)C3)c12] | (1s,3s)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutane-1-carboxamide | 0.96 | 1 | 554 |
| 295 | 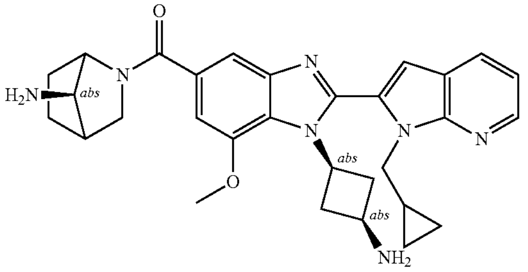 [SMILES: COc1cc(C(=O)N2CC3CCC2[C@@H]3N)cc2nc(-c3cc4cccnc4n3CC3CC3)n([C@H]3C[C@@H](N)C3)c12] | (1R,4R,7R)-2-{2-[1-(cyclopropylmethyl)-1H-pyrrolo[2,3-b]pyridin-2-yl]-7-methoxy-1-[(1s,3s)-3-aminocyclobutyl]-1H-1,3-benzodiazole-5-carbonyl}-2-azabicyclo[2.2.1]heptan-7-amine | 0.74 | 2 | 526 |

TABLE 4-continued

| Ex # | Structure | Name | LC/MS Rt (min) | LC/MS Method | M + H (obs ion) |
|---|---|---|---|---|---|
| 296 | 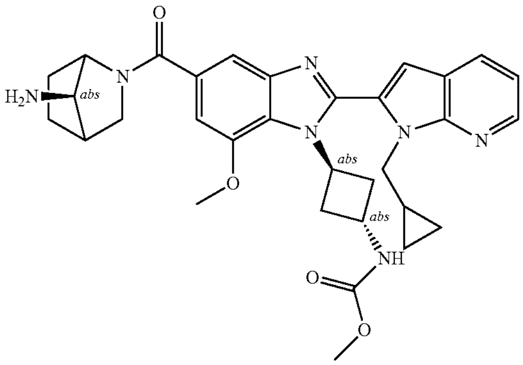 [SMILES: COC(=O)N[C@H]1C[C@H](n2c(-c3cc4cccnc4n3CC3CC3)nc3cc(C(=O)N4CC5CCC4[C@@H]5N)cc(OC)c32)C1] | methyl N-[(1r,3r)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]carbamate | 1.07 | 2 | 584 |
| 297 | 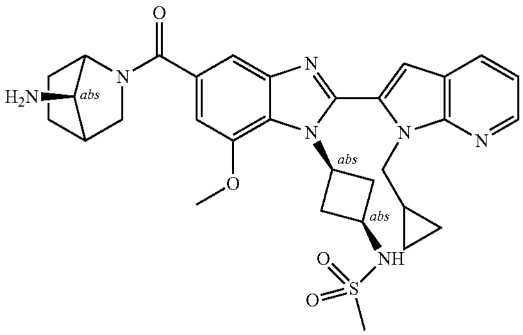 [SMILES: COc1cc(C(=O)N2CC3CCC2[C@@H]3N)cc2nc(-c3cc4cccnc4n3CC3CC3)n([C@H]3C[C@@H](NS(C)(=O)=O)C3)c12] | N-[(1s,3s)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]methanesulfonamide | 1.14 | 1 | 604 |
| 298 | 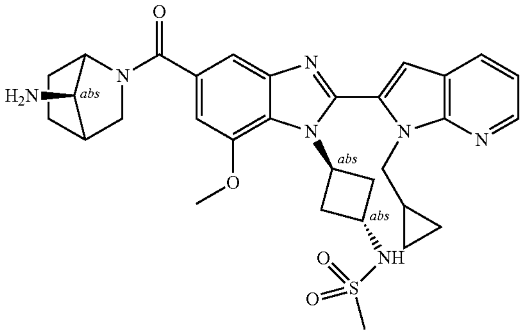 [SMILES: COc1cc(C(=O)N2CC3CCC2[C@@H]3N)cc2nc(-c3cc4cccnc4n3CC3CC3)n([C@H]3C[C@H](NS(C)(=O)=O)C3)c12] | N-[(1r,3r)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]methanesulfonamide | 1.15 | 1 | 604 |
| 299 | 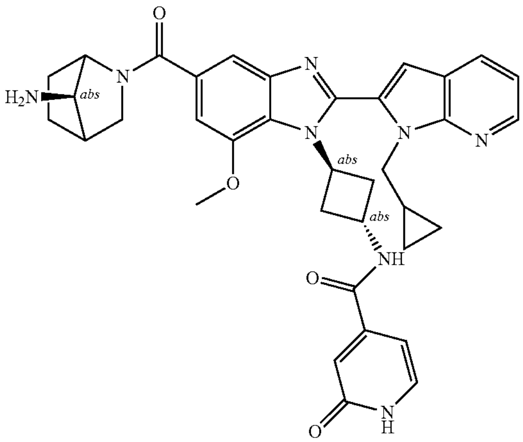 [SMILES: COc1cc(C(=O)N2CC3CCC2[C@@H]3N)cc2nc(-c3cc4cccnc4n3CC3CC3)n([C@H]3C[C@H](NC(=O)c4cc[nH]c(=O)c4)C3)c12] | 2-oxo-N-[(1r,3r)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]-1,2-dihydropyridine-4-carboxamide | 0.84 | 2 | 647 |

TABLE 4-continued

| Ex # | Structure | Name | LC/MS Rt (min) | LC/MS Method | M + H (obs ion) |
|---|---|---|---|---|---|
| 300 | 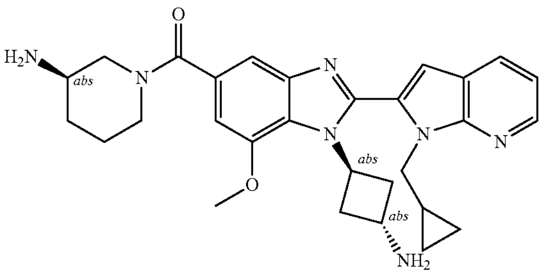 [SMILES: COc1cc(C(=O)N2CCC[C@@H](N)C2)cc2nc(-c3cc4cccnc4n3CC3CC3)n([C@H]3C[C@H](N)C3)c12] | (3R)-1-{2-[1-(cyclopropylmethyl)-1H-pyrrolo[2,3-b]pyridin-2-yl]-7-methoxy-1-[(1r,3r)-3-aminocyclobutyl]-1H-1,3-benzodiazole-5-carbonyl}piperidin-3-amine | 0.73 | 1 | 514 |
| 301 | 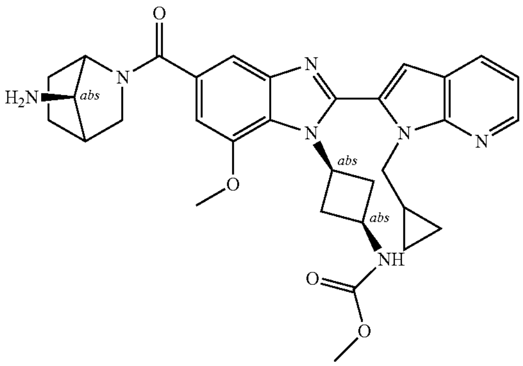 [SMILES: COC(=O)N[C@H]1C[C@@H](n2c(-c3cc4cccnc4n3CC3CC3)nc3cc(C(=O)N4CC5CCC4[C@@H]5N)cc(OC)c32)C1] | methyl N-[(1s,3s)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]carbamate | 1.09 | 2 | 584 |
| 302 | 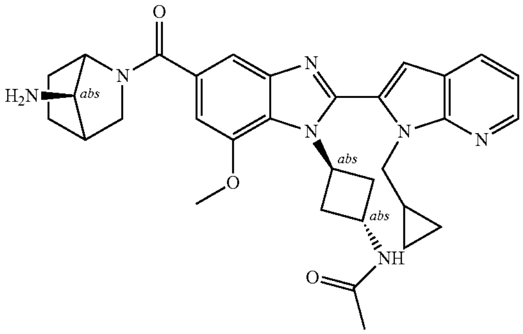 [SMILES: COc1cc(C(=O)N2CC3CCC2[C@@H]3N)cc2nc(-c3cc4cccnc4n3CC3CC3)n([C@H]3C[C@H](NC(C)=O)C3)c12] | N-[(1r,3r)-3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl)cyclobutyl]acetamide | 1.02 | 1 | 568 |
| 303 | 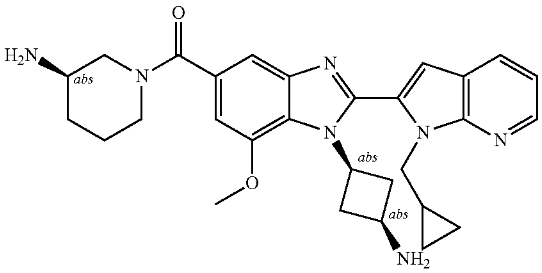 [SMILES: COc1cc(C(=O)N2CCC[C@@H](N)C2)cc2nc(-c3cc4cccnc4n3CC3CC3)n([C@H]3C[C@@H](N)C3)c12] | (3R)-1-{2-[1-(cyclopropylmethyl)-1H-pyrrolo[2,3-b]pyridin-2-yl]-7-methoxy-1-[(1s,3s)-3-aminocyclobutyl]-1H-1,3-benzodiazole-5-carbonyl}piperidin-3-amine | 0.76 | 1 | 514 |

TABLE 4-continued

| Ex # | Structure | Name | LC/MS Rt (min) | LC/MS Method | M + H (obs ion) |
|---|---|---|---|---|---|
| 304 | 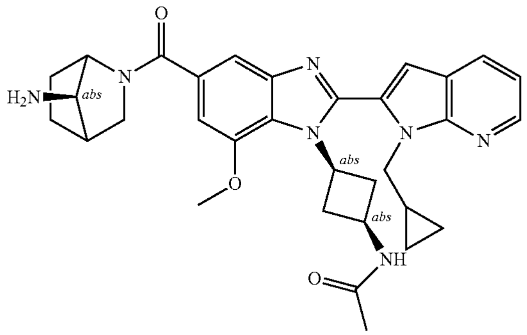 [SMILES: COc1cc(C(=O)N2CC3CCC2[C@@H]3N)cc2nc(-c3cc4cccnc4n3CC3CC3)n([C@H]3C[C@@H](NC(C)=O)C3)c12] | N-[(1s,3s)-3-{5-[(1R,4R,7R)-7-ammo-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}cyclobutyl]acetamide | 0.89 | 2 | 568 |
| 305 | 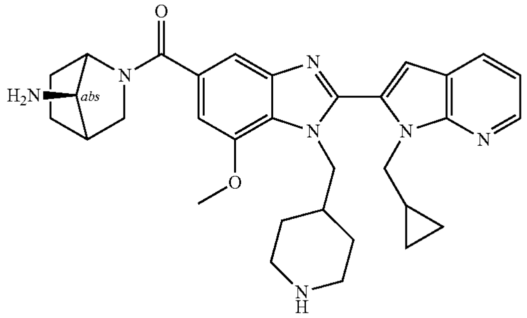 [SMILES: COc1cc(C(=O)N2CC3CCC2[C@@H]3N)cc2nc(-c3cc4cccnc4n3CC3CC3)n(CC3CCNCC3)c12] | (1R,4R,7R)-2-{2-[1-(cyclopropylmethyl)-1H-pyrrolo[2,3-b]pyridin-2-yl]-7-methoxy-1-[(piperidin-4-yl)methyl]-1H-1,3-benzodiazole-5-carbonyl)-2-azabicyclo[2.2.1]heptan-7-amine | 0.81 | 2 | 554 |
| 306 | 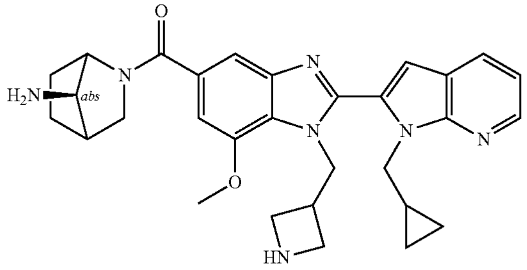 [SMILES: COc1cc(C(=O)N2CC3CCC2[C@@H]3N)cc2nc(-c3cc4cccnc4n3CC3CC3)n(CC3CNC3)c12] | (1R,4R,7R)-2-{1-[(azetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 0.86 | 1 | 526 |
| 307 | 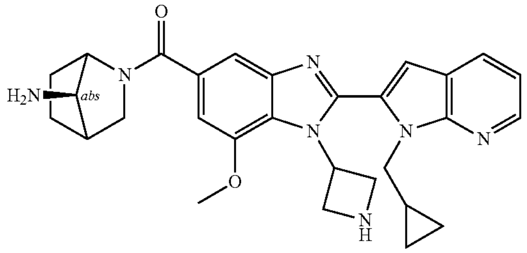 [SMILES: COc1cc(C(=O)N2CC3CCC2[C@@H]3N)cc2nc(-c3cc4cccnc4n3CC3CC3)n(C3CNC3)c12] | (1R,4R,7R)-2-[1-(azetidin-3-yl)-2-[1-(cyclopropylmethyl)-1H-pyrrolo[2,3-b]pyridin-2-yl]-7-methoxy-1H-1,3-benzodiazole-5-carbonyl]-2-azabicyclo[2.2.1]heptan-7-amine | 0.84 | 1 | 512 |
| 308 | 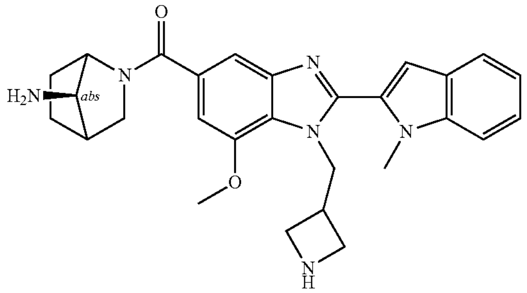 [SMILES: COc1cc(C(=O)N2CC3CCC2[C@@H]3N)cc2nc(-c3cc4ccccc4n3C)n(CC3CNC3)c12] | (1R,4R,7R)-2-{1-[(azetidin-3-yl)methyl]-7-methoxy-2-(1-methyl-1H-indol-2-yl)-1H-1,3-benzodiazole-5-carbonyl}-2-azabicyclo[2.2.1]heptan-7-amine | 0.93 | 1 | 485 |

TABLE 4-continued

| Ex # | Structure | Name | LC/MS Rt (min) | LC/MS Method | M + H (obs ion) |
|---|---|---|---|---|---|
| 309 | 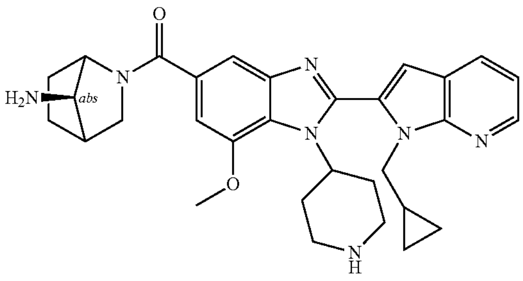 [SMILES: COc1cc(C(=O)N2CC3CCC2[C@@H]3N)cc2nc(-c3cc4cccnc4n3CC3CC3)n(C3CCNCC3)c12] | (1R,4R,7R)-2-{2-[1-(cyclopropylmethyl)-1H-pyrrolo[2,3-b]pyridin-2-yl]-7-methoxy-1-(piperidin-4-yl)-1H-1,3-benzodiazole-5-carbonyl}-2-azabicyclo[2.2.1]heptan-7-amine | 0.79 | 2 | 540 |
| 310 | 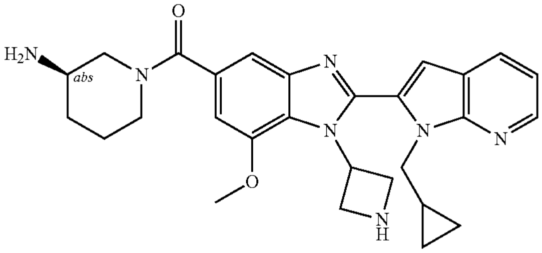 [SMILES: COc1cc(C(=O)N2CCC[C@@H](N)C2)cc2nc(-c3cc4cccnc4n3CC3CC3)n(C3CNC3)c12] | (3R)-1-[1-(azetidin-3-yl)-2-[1-(cyclopropylmethvl)-1H-pyrrolo[2,3-b]pyridin-2-yl]-7-methoxy-1H-1,3-benzodiazole-5-carbonyl]piperidin-3-amine | 0.99 | 1 | 500 |

Example 311

4-[3-({5-[(1R,4R,7R)-7-amino-2-azabicyclo[2.2.1]heptane-2-carbonyl]-2-[1-(cyclopropylmethyl)-1H-pyrrol-2-yl]-7-methoxy-1H-1,3-benzodiazol-1-yl}methylazetidin-1-yl]pyrimidine-2-carbonitrile

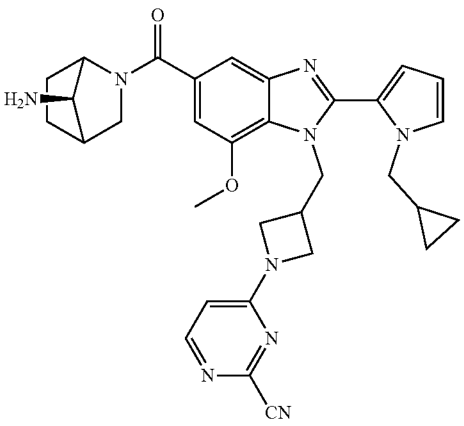 [SMILES: COc1cc(C(=O)N2CC3CCC2[C@@H]3N)cc2nc(-c3cccn3CC3CC3)n(CC3CN(c4ccnc(C#N)n4)C3)c12]

Intermediate 311 A: Benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrol-2-yl)-7-methoxy-1H-benzo[d]imidazol-1-yl)methyl)azetidine-1-carboxylate

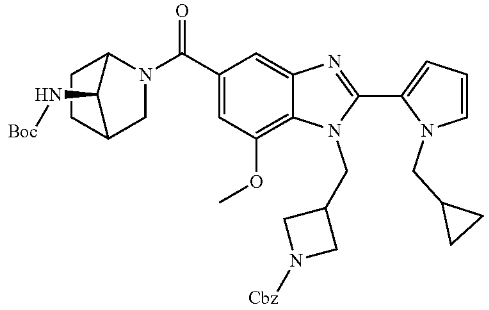 [SMILES: COc1cc(C(=O)N2CC3CCC2[C@@H]3NC(=O)OC(C)(C)C)cc2nc(-c3cccn3CC3CC3)n(CC3CN(C(=O)OCc4ccccc4)C3)c12]

To a solution of benzyl 3-(((4-((1R,4R,7R)-7-((tert-butoxycarbonyl)amino)-2-azabicyclo[2.2.1]heptane-2-carbonyl)-2-methoxy-6-nitrophenyl)amino)methyl)azetidine-1-carboxylate (150 mg, 0.246 mmol) and 1-(cyclopropylmethyl)-1H-pyrrole-2-carbaldehyde (36.7 mg, 0.246 mmol) in EtOH (0.80 mL) was added a solution of sodium dithionite (128 mg, 0.738 mmol) in water (0.40 mL) at RT under nitrogen. The mixture was stirred at 80° C. for 18 hour. The mixture was diluted with EtOAc (15 mL) and was washed with a solution of aqueous saturated sodium bicarbonate (2×15 mL). The organic layer was dried over sodium sulfate and concentrated. The crude product was subjected to ISCO flash chromatography (silica gel/hexane-10% MeOH/EtOAc 100:0 to 0:100 gradient) to yield benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrol-2-yl)-7-methoxy-1H-benzo[d]imidazol-1-yl)methyl)azetidine-1-carboxylate (133 mg, 0.188 mmol, 76% yield) as white solid. LC/MS (M+H): 709; LC retention time: 0.93 min (analytical HPLC Method 3). Material was used as is in next reaction.

A mixture of benzyl 3-((5-((1R,4R,7R)-7-((tert-butoxycarbonyl)amino)-2-azabicyclo[2.2.1]heptane-2-carbonyl)-2-(1-(cyclopropylmethyl)-1H-pyrrol-2-yl)-7-methoxy-1H-benzo[d]imidazol-1-yl)methyl)azetidine-1-carboxylate (133 mg, 0.188 mmol) and 10% palladium on carbon (26.2 mg, 0.025 mmol) in MeOH (10 mL) was hydrogenated under 1 atm of hydrogen for 18 hour. Pd/C was filtered off and the filtrate was concentrated to give a crude yield of tert-butyl ((1R,4R,7R)-2-(1-(azetidin-3-ylmethyl)-2-(1-(cyclopropylmethyl)-1H-pyrrol-2-yl)-7-methoxy-1H-benzo[d]imidazole-5-carbonyl)-2-azabicyclo[2.2.1]heptan-7-yl)carbamate (105 mg, 0,183 mmol, 74.3% yield) as white solid. Material was used as is in next reaction.

Example 311: 4-[3-({5-[(1R,4R,7R)-7-amino-2-azabicyclo[2.2.1]heptane-2-carbonyl]-2-[1-(cyclopropylmethyl)-1H-pyrrol-2-yl]-7-methoxy-1H-1,3-benzodiazol-1-yl}methyl)azetidin-1-yl]pyrimidine-2-carbonitrile A mixture of tert-butyl ((1R,4R,7R)-2-(1-(azetidin-3-ylmethyl)-2-(1-(cyclopropylmethyl)-1H-pyrrol-2-yl)-7-methoxy-1H-benzo[d]imidazole-5-carbonyl)-2-azabicyclo[2.2.1]heptan-7-yl)carbamate (15 mg, 0,026 mmol), 4-bromopyrimidine-2-carbonitrile (4.80 mg, 0.026 mmol), cesium carbonate (17.01 mg, 0.052 mmol), BINAP (0.813 mg, 1.305 μmol) and $Pd_2(dba)_3$ (1.195 mg, 1.305 μmol) in degassed dioxane (1.0 mL) under nitrogen in a sealed vial was stirred at 80° C. for 18 hour. The mixture was diluted with EtOAc (5 mL) and was washed with a solution of aqueous saturated sodium bicarbonate (5 mL). The organic layer was dried over sodium sulfate and concentrated to give crude tert-butyl ((1R,4R,7R)-2-(1-((1-(2-cyanopyrimidin-4-yl)azetidin-3-yl)methyl)-2-(1-(cyclopropylmethyl)-1H-pyrrol-2-yl)-7-methoxy-1H-benzo[d]imidazole-5-carbonyl)-2-azabicyclo[2.2.1]heptan-7-yl)carbamate. Material was used as is in next reaction.

A mixture of tert-butyl ((1R,4R,7R)-2-(1-((1-(2-cyanopyrimidin-4-yl)azetidin-3-yl)methyl)-2-(1-(cyclopropylmethyl)-1H-pyrrol-2-yl)-7-methoxy-1H-benzo[d]imidazole-5-carbonyl)-2-azabicyclo[2.2.1]heptan-7-yl)carbamate in DCM (1.0 mL) and IT A (1.0 mL) was stirred at RT for 30 min. The mixture was then concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 17% B, 17-57% B over 20 minutes, then a 5-minute hold at 100% B; Flow Rate: 20 mL/min; Column Temperature: 25 C. Fraction collection was triggered by MS signals. Fractions containing the desired product were combined and dried via centrifugal evaporation. 4-[3-({5-[(1R,4R,7R)-7-amino-2-azabicyclo[2.2.1]heptane-2-carbonyl]-2-[1-(cyclopropylmethyl)-1H-pyrrol-2-yl]-7-methoxy-1H-1,3-benzodiazol-1-yl}methyl)azetidin-1-yl]pyrimidine-2-carbonitrile (8.9 mg, 15.4 μmol, 59.3%) was isolated, LC/MS (M+H): 578; LC retention time: 1.20 min (analytical HPLC Method 2). $^1H$ NMR (500 MHz, DMSO-$d_6$) δ 8.07-7.89 (m, 1H), 7.29-7.11 (m, 1H), 7.04-6.89 (m, 1H), 6.86-6.66 (m, 1H), 6.50-6.27 (m, 2H), 6.12-5.94 (m, 1H), 4.72-4.58 (m, 2H), 3.91-3.71 (m, 5H), 3.61-3.41 (m, 5H), 3.09-2.46 (m, 4H), 2.14-1.74 (m, 3H), 1.65-1.44 (m, 1H), 1.36-0.93 (m, 2H), 0.89-0.63 (m, 2H), 0.30-0.14 (m, 2H), 0.04--0.09 (m, 2H).

Examples 312 to 324 in Table 5 were prepared as described in the general procedures given for Example 311.

TABLE 5

| Ex # | Structure | Name | LC/MS Rt (min) | LC/MS Method | M + H (obs ion) |
|---|---|---|---|---|---|
| 312 | 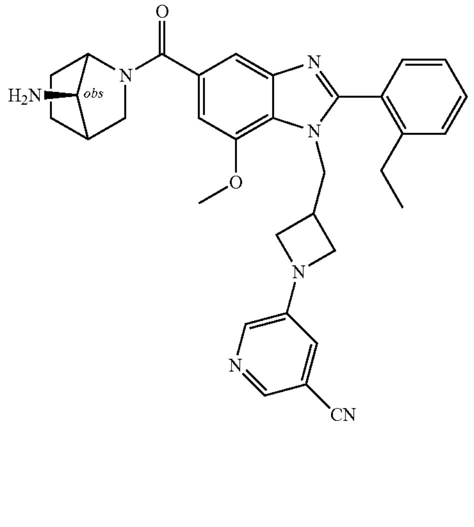 [SMILES: CCc1ccccc1-c1nc2cc(C(=O)N3CC4CCC3[C@@H]4N)cc(OC)c2n1CC1CN(c2cncc(C#N)c2)C1] | 5-[3-({5-[(1R,4R,7R)-7-amino-2-azabicyclo[2.2.1]heptane-2-carbonyl]-2-(2-ethylphenyl)-7-methoxy-1H-1,3-benzodiazol-1-yl}methyl)azetidin-1-yl]pyridine-3-carbonitrile | 1.55 | 1 | 562 |

TABLE 5-continued

| Ex # | Structure | Name | LC/MS Rt (min) | LC/MS Method | M + H (obs ion) |
|---|---|---|---|---|---|
| 313 | 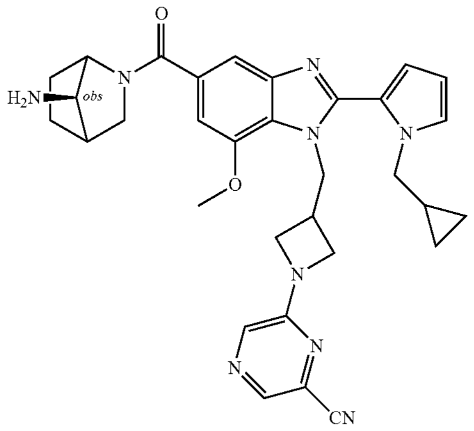 [SMILES: COc1cc(C(=O)N2CC3CCC2[C@@H]3N)cc2nc(-c3cccn3CC3CC3)n(CC3CN(c4cncc(C#N)n4)C3)c12] | 6-[3-({5-[(1R,4R,7R)-7-amino-2 azabicyclo[2.2.1]heptane-2-carbonyl]-2-[1-(cyclopropylmethyl)-1H-pyrrol-2-yl]-7-methoxy-1H-1,3-benzodiazol-1-yl}methyl)azetidin-1-yl]pyrazine-2-carbonitrile | 1.51 | 1 | 578 |
| 314 | 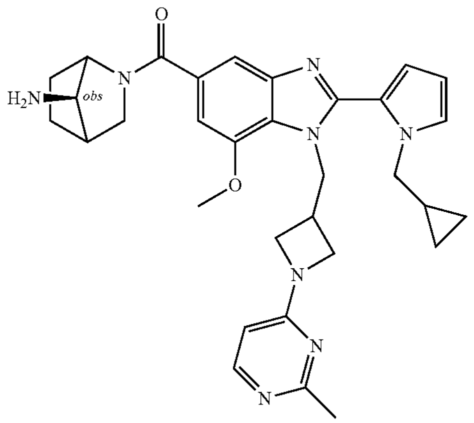 [SMILES: COc1cc(C(=O)N2CC3CCC2[C@@H]3N)cc2nc(-c3cccn3CC3CC3)n(CC3CN(c4ccnc(C)n4)C3)c12] | (1R,4R,7R)-2-{2-[1-(cyclopropylmethyl)-1H-pyrrol-2-yl]-7-methoxy-1-{[1-(2-methylpyrimidin-4-yl)azetidin-3-yl]methyl}-1H-1,3-benzodiazole-5-carbonyl}-2-azabicyclo[2.2.1]heptan-7-amine | 0.83 | 2 | 567 |
| 315 | 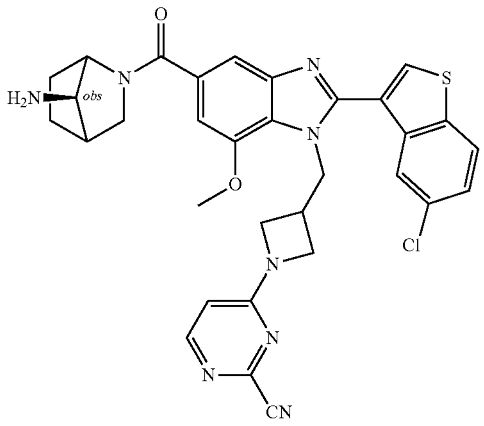 [SMILES: COc1cc(C(=O)N2CC3CCC2[C@@H]3N)cc2nc(-c3csc4ccc(Cl)cc34)n(CC3CN(c4ccnc(C#N)n4)C3)c12] | 4-[3-({5-[(1R,4R,7R)-7-amino-2-azabicyclo[2.2.1]heptane-2-carbonyl]-2-(5-chloro-1-benzothiophen-3-yl)-7-methoxy-1H-1,3-benzodiazol-1-yl}methyl)azetidin-1-yl]pyrimidine-2-carbonitrile | 1.62 | 1 | 625 |

TABLE 5-continued

| Ex # | Structure | Name | LC/MS Rt (min) | LC/MS Method | M + H (obs ion) |
|---|---|---|---|---|---|
| 316 | 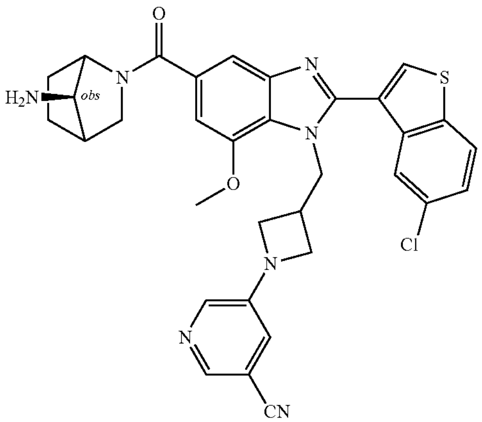 [SMILES: COc1cc(C(=O)N2CC3CCC2[C@@H]3N)cc2nc(-c3csc4ccc(Cl)cc34)n(CC3CN(c4cncc(C#N)c4)C3)c12] | 5-[3-({5-(1R,4R,7R)-7-amino-2-azabicyclo[2.2.1]heptane-2-carbonyl]-2-(5-chloro-1-benzothiophen-3-yl)-7-methoxy-1H-1,3-benzodiazol-1-yl)methyl)azetidin-1-yl]pyridine-3-carbonitrile | 1.69 | 1 | 624 |
| 317 | 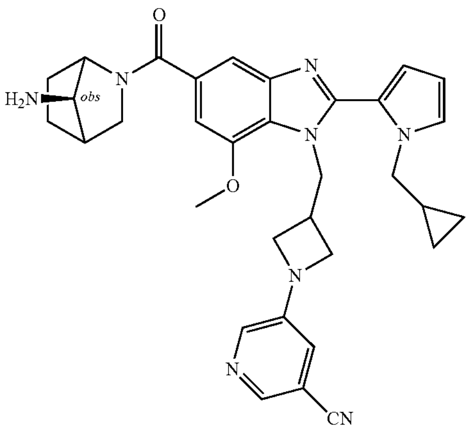 [SMILES: COc1cc(C(=O)N2CC3CCC2[C@@H]3N)cc2nc(-c3cccn3CC3CC3)n(CC3CN(c4cncc(C#N)c4)C3)c12] | 5-[3-({5-(1R,4R,7R)-7-amino-2-azabicyclo[2.2.1]heptane-2-carbonyl]-2-[1-(cyclopropylmethyl)-1H-pyrrol-2-yl]-7-methoxy-1H-1,3-benzodiazol-1-yl}methyl)azetidin-l-yl]pyridine-3-carbonitrile | 1.63 | 1 | 577 |
| 318 | 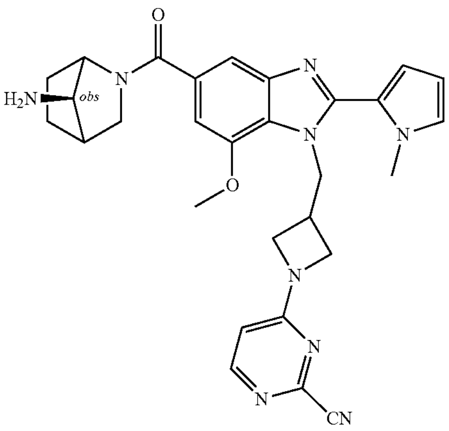 [SMILES: COc1cc(C(=O)N2CC3CCC2[C@@H]3N)cc2nc(-c3cccn3C)n(CC3CN(c4ccnc(C#N)n4)C3)c12] | 4-[3-({5-[(1R,4R,7R)-7-amino-2-azabicyclo[2.2.1]heptane-2-carbonyl]-7-methoxy-2-(1-methyl-1H-pyrrol-2-yl)-1H-1,3-benzodiazol-1-yl)methyl)azetidin-1-yl]pyrimidine-2-carbonitrile | 1.05 | 2 | 538 |

TABLE 5-continued

| Ex # | Structure | Name | LC/MS Rt (min) | LC/MS Method | M + H (obs ion) |
|---|---|---|---|---|---|
| 319 | 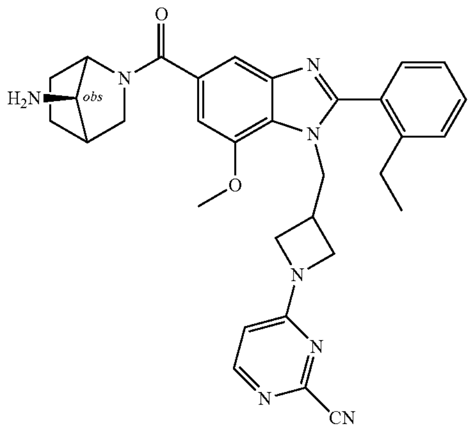 [SMILES: CCc1ccccc1-c1nc2cc(C(=O)N3CC4CCC3[C@@H]4N)cc(OC)c2n1CC1CN(c2ccnc(C#N)n2)C1] | 4-[3-({5-[(1R,4R,7R)-7-amino-2-azabicyclo[2.2.1]heptane-2-carbonyl]-2-(2-ethylphenyl)-7-methoxy-1H-1,3-benzodiazol-1-yl}methyl)azetidin-1-yl]pyrimidine-2-carbonitrile | 1.31 | 2 | 562 |
| 320 | 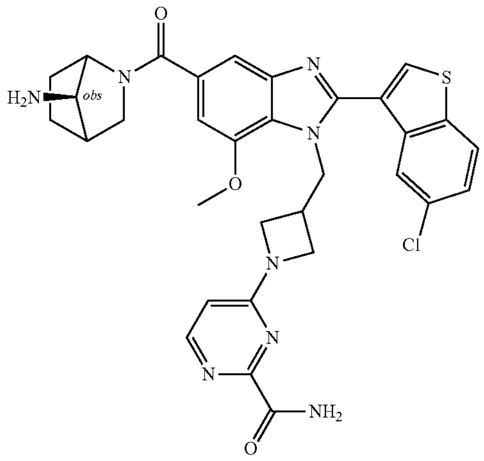 | 4-[3-({5-[(1R,4R,7R)-7-amino-2-azabicyclo[2.2.1]heptane-2-carbonyl]-2-(5-chloro-1-benzothiophen-3-yl)-7-methoxy-1H-1,3-benzodiazol-1-yl}methyl)azetidin-1-yl]pyrimidine-2-carboxamide | 1.38 | 1 | 643 |
| 321 | 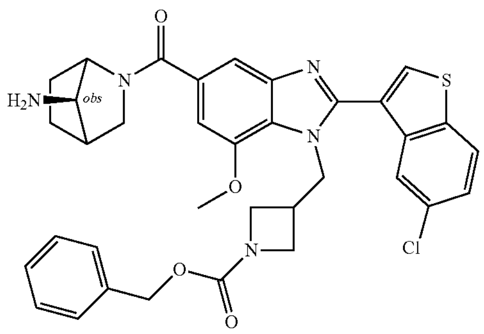 [SMILES: COc1cc(C(=O)N2CC3CCC2[C@@H]3N)cc2nc(-c3csc4ccc(Cl)cc34)n(CC3CN(C(=O)OCc4ccccc4)C3)c12] | benzyl 3-({5-[(1R,4R,7R)-7-amino-2-azabicyclo[2.2.1]heptane-2-carbonyl]-2-(5-chloro-1-benzothiophen-3-yl)-7-methoxy-1H-1,3-benzodiazol-1-yl}methyl)azetidine-1-carboxylate | 1.77 | 1 | 656 |

TABLE 5-continued

| Ex # | Structure | Name | LC/MS Rt (min) | LC/MS Method | M + H (obs ion) |
|---|---|---|---|---|---|
| 322 | 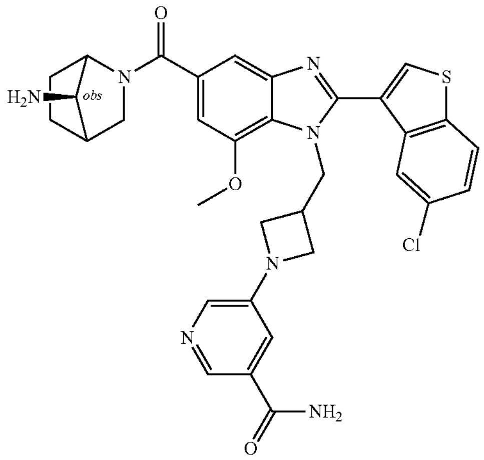 [SMILES: COc1cc(C(=O)N2CC3CCC2[C@@H]3N)cc2nc(-c3csc4ccc(Cl)cc34)n(CC3CN(c4cncc(C(N)=O)c4)C3)c12] | 5[3-({5-[(1R,4R,7R)-7-amino-2-azabicyclo[2.2.1]heptane-2-carbonyl]-2-(5-chloro-1-benzothiophen-3-yl)-7-methoxy-1H-1,3-benzodiazol-1-yl}methyl)azetidin-1-yl]pyridine-3-carboxamide | 1.39 | 1 | 642 |
| 323 | 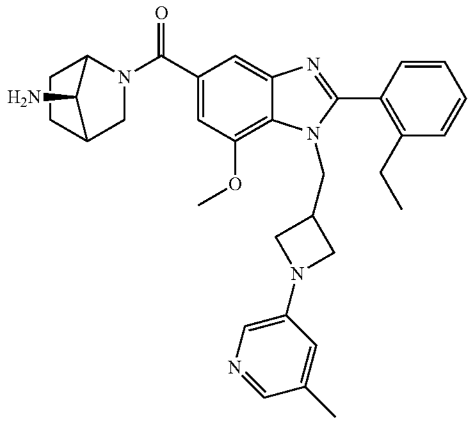 [SMILES: CCc1ccccc1-c1nc2cc(C(=O)N3CC4CCC3[C@@H]4N)cc(OC)c2n1CC1CN(c2cncc(C)c2)C1] | (1R,4R,7R)-2-[2-(2-ethytphenyl)-7-methoxy-1-{[1-(5-methylpyridin-3-yl)azetidin-3-yl]methyl}-1H-1,3-benzodiazole-5-carbonyl]-2-azabicyclo[2.2.1]heptan-7-amine | 1.61 | 1 | 551 |
| 324 | 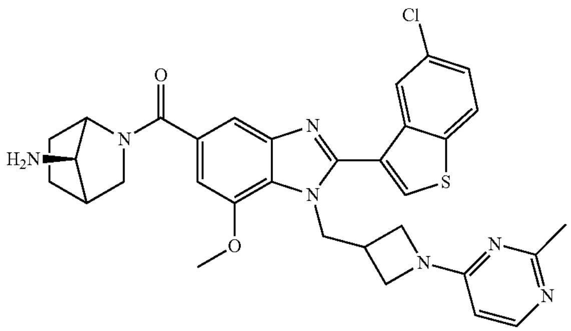 [SMILES: COc1cc(C(=O)N2CC3CCC2[C@@H]3N)cc2nc(-c3csc4ccc(Cl)cc34)n(CC3CN(c4ccnc(C)n4)C3)c12] | (1R,4R,7R)-2-[2-(5-chloro-1-benzothiophen-3-yl)-7-methoxy-1-{[1-(2-methylpyrimidin-4-yl)azetidin-3-yl]methyl}-1H-1,3-benzodiazole-5-carbonyl]-2-azabicyclo[2.2.1]heptan-7-amine | 1.42 | 1 | 614 |

Examples 325 to 341 in Table 6 were prepared as described in the general procedures given for Examples above and conditions known to those skilled in the art.

TABLE 6

| Ex # | Structure | Name | LC/MS Rt (min) | LC/MS Method | M + H (obs ion) |
|---|---|---|---|---|---|
| 325 | 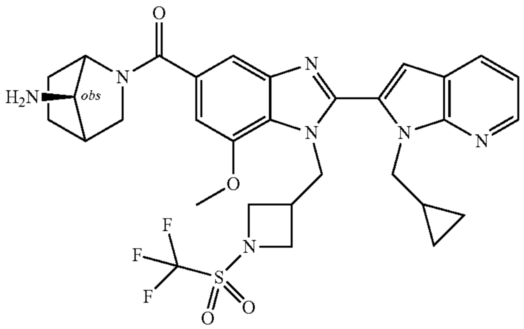 [SMILES: COc1cc(C(=O)N2CC3CCC2[C@@H]3N)cc2nc(-c3cc4cccnc4n3CC3CC3)n(CC3CN(S(=O)(=O)C(F)(F)F)C3)c12] | (1R,4R,7R)-2-{2-[1-(cyclopropylmethyl)-1H-pyrrolo[2,3-b]pyridin-2-yl]-7-methoxy-1-[(1-trifluoromethanesulfonylazetidin-3-yl)methyl]-1H-1,3-benzodiazole-5-carbonyl}-2-azabicyclo[2.2.1]heptan-7-amine | 1.73 | 1 | 658 |
| 326 | 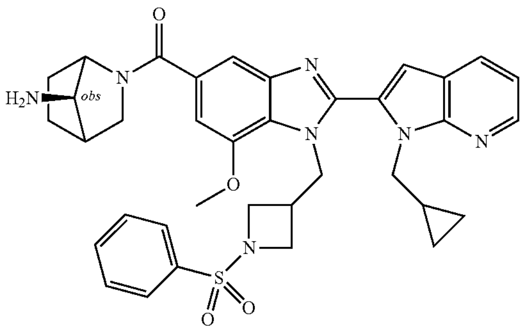 [SMILES: COc1cc(C(=O)N2CC3CCC2[C@@H]3N)cc2nc(-c3cc4cccnc4n3CC3CC3)n(CC3CN(S(=O)(=O)c4ccccc4)C3)c12] | (1R,4R,7R)-2-(1-{[1-(benzenesulfonyl)azetidin-3-yl]methyl}-2-[‖-(cyclopropylmethyl)-1H-pyrrolo[2,3-b1pyridin-2-yl]-7-methoxy-1H-1,3-benzodiazole-5-carbonyl)-2-azabicyclo[2.2.1]heptan-7-amine | 1.56 | 1 | 666 |
| 327 | 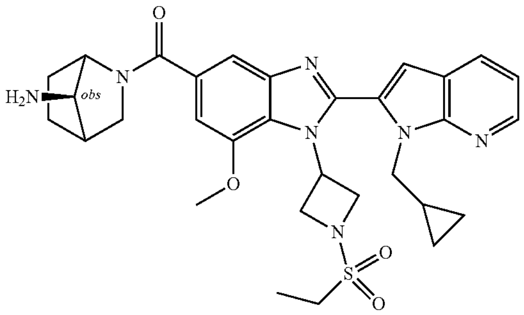 [SMILES: CCS(=O)(=O)N1CC(n2c(-c3cc4cccnc4n3CC3CC3)nc3cc(C(=O)N4CC5CCC4[C@@H]5N)cc(OC)c32)C1] | (1R,4R.,7R)-2-{2-[1-(cyclopropylmethyl)-1H-pyrrolo[2,3-b]pyridin-2-yl]-1-[1-(ethanesulfonyl)azetidin-3-yl]-7-methoy-1H-1,3-benzodiazole-5-carbonyl}-2-azabicyclo[2.2.1]heptan-7-amine | 1.39 | 1 | 604 |
| 328 | 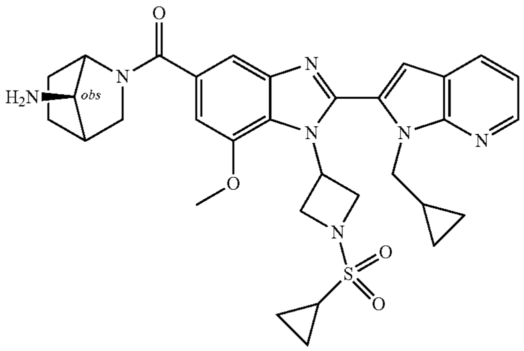 [SMILES: COc1cc(C(=O)N2CC3CCC2[C@@H]3N)cc2nc(-c3cc4cccnc4n3CC3CC3)n(C3CN(S(=O)(=O)C4CC4)C3)c12] | (1R,4R,7R)-2-{1-(cyclopropanesulfonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.28 | 2 | 616 |

TABLE 6-continued

| Ex # | Structure | Name | LC/MS Rt (min) | LC/MS Method | M + H (obs ion) |
| --- | --- | --- | --- | --- | --- |
| 329 | 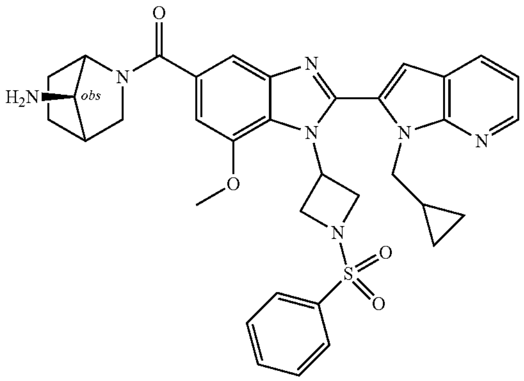 [SMILES: COc1cc(C(=O)N2CC3CCC2[C@@H]3N)cc2nc(-c3cc4cccnc4n3CC3CC3)n(C3CN(S(=O)(=O)c4ccccc4)C3)c12] | (1R,4R,7R)-2-{1-[1-(benzenesulfonyl)azetidin-3-yl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.56 | 1 | 652 |
| 330 | 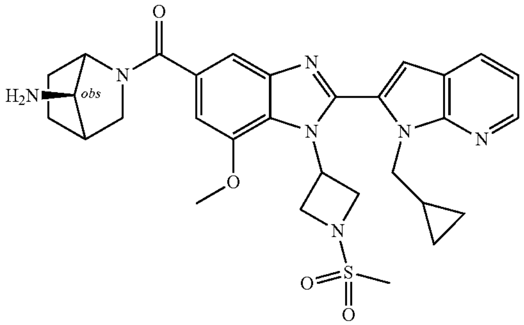 [SMILES: COc1cc(C(=O)N2CC3CCC2[C@@H]3N)cc2nc(-c3cc4cccnc4n3CC3CC3)n(C3CN(S(C)(=O)=O)C3)c12] | (1R,4R,7R)-2-{2-[1-(cyclopropylmethyl)-1H-pyrrolo[2,3-b]pyridin-2-yl]-1-(1-methanesulfonylazetidin-3-yl)-7-methoxy-1H-1,3-benzodiazole-5-carbonyl}-2-azabicyclo[2.2.1]heptan-7-amine | 1.3 | 1 | 590 |
| 331 | 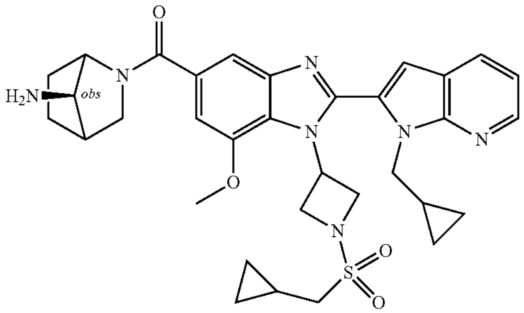 [SMILES: COc1cc(C(=O)N2CC3CCC2[C@@H]3N)cc2nc(-c3cc4cccnc4n3CC3CC3)n(C3CN(S(=O)(=O)CC4CC4)C3)c12] | (1R,4R,7R)-2-[1-(1-cyclopropylmethanesulfonyl azetidin-3-yl)-2-[1-(cyclopropylmethyl)-1H-pyrrolo[2,3-b]pyridin-2-yl]-7-methoxy-1H-1,3-benzodiazole-5-carbonyl]-2-azabicyclo[2.2.1]heptan-7-amine | 1.36 | 2 | 630 |
| 332 | 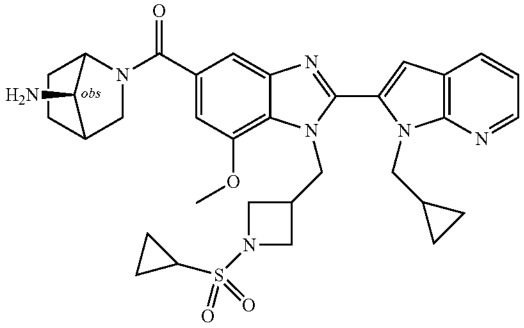 [SMILES: COc1cc(C(=O)N2CC3CCC2[C@@H]3N)cc2nc(-c3cc4cccnc4n3CC3CC3)n(CC3CN(S(=O)(=O)C4CC4)C3)c12] | (1R,4R,7R)-2-(1-{[1-(cyclopropanesulfonyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.18 | 2 | 630 |

TABLE 6-continued

| Ex # | Structure | Name | LC/MS Rt (min) | LC/MS Method | M + H (obs ion) |
|---|---|---|---|---|---|
| 333 | 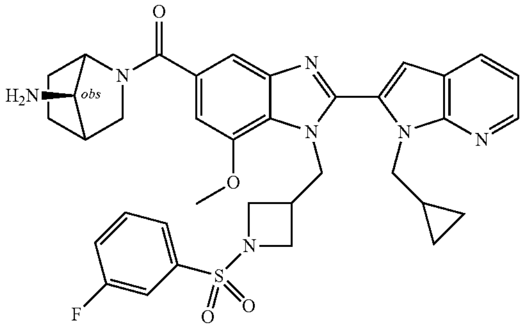 [SMILES: COc1cc(C(=O)N2CC3CCC2[C@@H]3N)cc2nc(-c3cc4cccnc4n3CC3CC3)n(CC3CN(S(=O)(=O)c4cccc(F)c4)C3)c12] | (1R,4R.,7R)-2-{2-{2-[1-(cyclopropylmethyl)-1H-pyrrolo[2,3-b]pyridin-2-yl]-1-{[1-(3-fluorobenzenesulfonyl)azetidin-3-yl]methyl}-7-methoxy-1H-1,3-benzodiazole-5-carbonyl}-2-azabicyclo[2.2.1]heptan-7-amine | 1.62 | 1 | 684 |
| 334 | 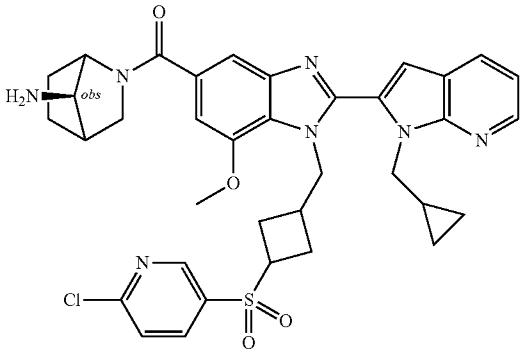 [SMILES: COc1cc(C(=O)N2CC3CCC2[C@@H]3N)cc2nc(-c3cc4cccnc4n3CC3CC3)n(CC3CC(S(=O)(=O)c4ccc(Cl)nc4)C3)c12] | (1R,4R,7R)-2-[1-({1-[(6-chloropyridin-3-yl)sulfonyl]azetidin-3-yl}methyl)-2-[1-(cyclopropylmethyl)-1H-pyrrolo[2,3-b]pyridin-2-yl]-7-methoxy-1H-1,3-benzodiazole-5-carbonyl]-2-azabicyclo[2.2.1]heptan-7-amine | 1.43 | 2 | 701 |
| 335 | 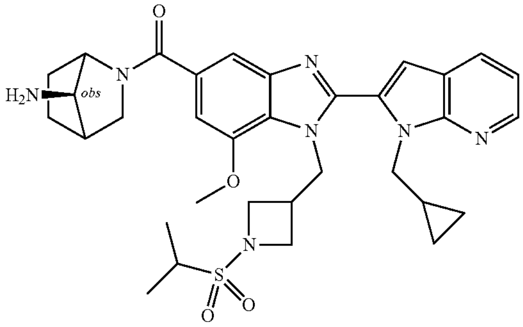 [SMILES: COc1cc(C(=O)N2CC3CCC2[C@@H]3N)cc2nc(-c3cc4cccnc4n3CC3CC3)n(CC3CN(S(=O)(=O)C(C)C)C3)c12] | (1R,4R,7R)-2-{2-[1-(cyclopropylmethyl)-1H-pyrrolo[2,3-b]pyridin-2-yl]-7-methoxy-1-{[1-(propane-2-sulfonyl)azetidin-3-yl)methyl}-1H-1,3-benzodiazole-5-carbonyl}-2-azabicyclo[2.2.1]heptan-7-amine | 1.45 | 1 | 632 |
| 336 | 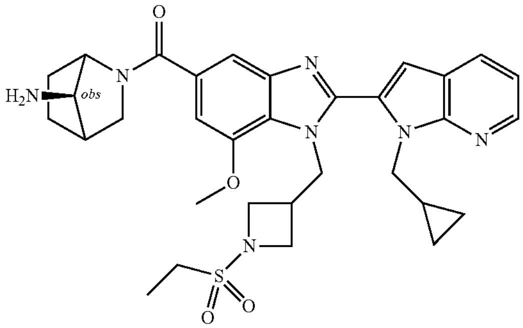 [SMILES: CCS(=O)(=O)N1CC(Cn2c(-c3cc4cccnc4n3CC3CC3)nc3cc(C(=O)N4CC5CCC4[C@@H]5N)cc(OC)c32)C1] | (1R,4R.,7R)-2-{2-[1-(cyclopropylmethyl)-1H-pyrrolo[2,3-b]pyridin-2-yl]-1-{[1-(ethanesulfonyl)azetidin-3-yl]methyl}-7-methoxy-1H-1,3-benzodiazole-5-carbonyl}-2-azabicyclo[2.2,1]heptan-7-amine | 1.14 | 2 | 618 |

TABLE 6-continued

| Ex # | Structure | Name | LC/MS Rt (min) | LC/MS Method | M + H (obs ion) |
|---|---|---|---|---|---|
| 337 | 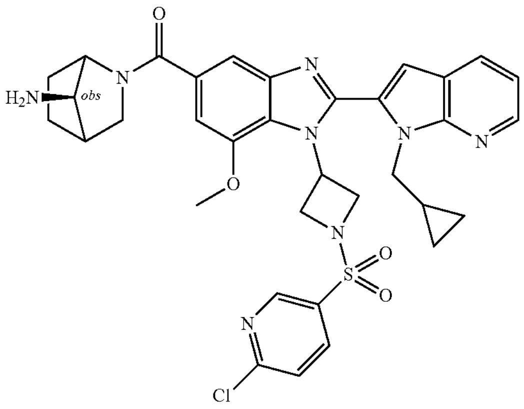 [SMILES: COc1cc(C(=O)N2CC3CCC2[C@@H]3N)cc2nc(-c3cc4cccnc4n3CC3CC3)n(C3CN(S(=O)(=O)c4ccc(Cl)nc4)C3)c12] | (1R,4R,7R)-2-{1-[(6-chloropyridin-3-yl)sulfonyl]azetidin-3-yl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.6 | 1 | 687 |
| 338 | 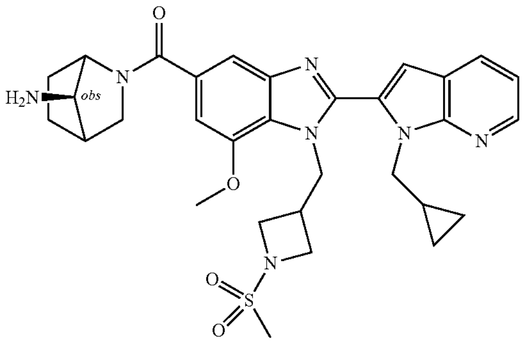 [SMILES: COc1cc(C(=O)N2CC3CCC2[C@@H]3N)cc2nc(-c3cc4cccnc4n3CC3CC3)n(CC3CN(S(C)(=O)=O)C3)c12] | (1R,4R,7R)-2-{2-[1-(cyclopropylmethyl)-1H-pyrrolo[2,3-b]pyridin-2-yl]-1-[(1-methanesulfonylazetidin-3-yl)methyl]-7-methoxy-1H-1,3-benzodiazole-5-carbonyl}-2-azabicyclo[2.2.1]heptan-7-amine | 1.19 | 2 | 604 |
| 339 | 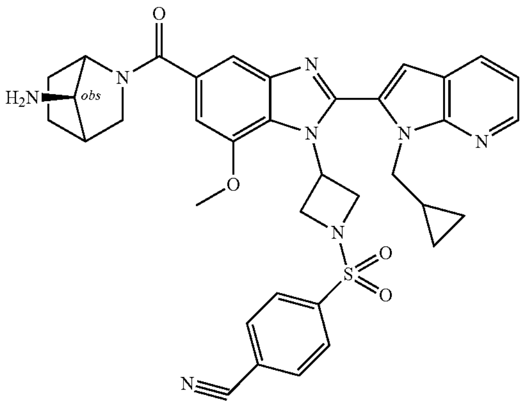 [SMILES: COc1cc(C(=O)N2CC3CCC2[C@@H]3N)cc2nc(-c3cc4cccnc4n3CC3CC3)n(C3CN(S(=O)(=O)c4ccc(C#N)cc4)C3)c12] | 4-[(3-{5-[(1R,4R,7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazo1-1-yl}azetidin-1-yl)sulfonyl]benzonitrile | 1.38 | 2 | 677 |

TABLE 6-continued

| Ex # | Structure | Name | LC/MS Rt (min) | LC/MS Method | M + H (obs ion) |
|---|---|---|---|---|---|
| 340 | 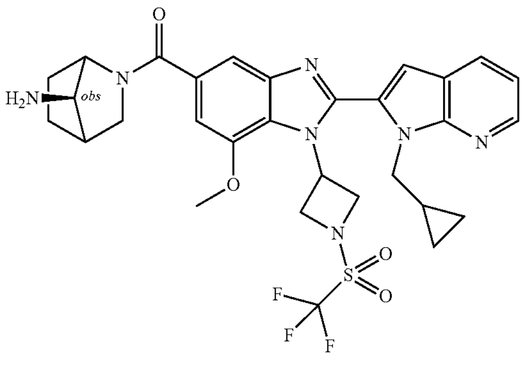 [SMILES: COc1cc(C(=O)N2CC3CCC2[C@@H]3N)cc2nc(-c3cc4cccnc4n3CC3CC3)n(C3CN(S(=O)(=O)C(F)(F)F)C3)c12] | (1R,,4R,7R)-2-{2-[1-(cyclopropylmethyl)-1H-pyrrolo[2,3-b]pyridin-2-yl]-7-methoxy-1-(1-trifluoromethanesulfonylazetidin-3-yl)-1H-1,3-benzodiazole-5-carbonyl}-2-azabicyclo[2.2.1]heptan-7-amine | 1.78 | 1 | 644 |
| 341 | 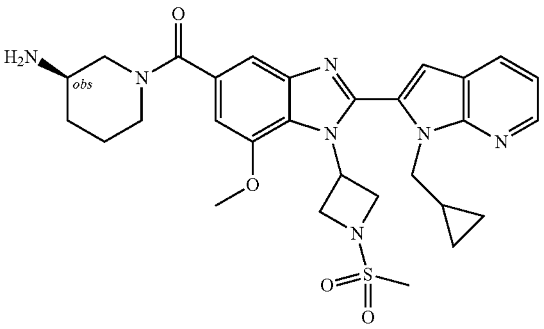 [SMILES: COc1cc(C(=O)N2CCC[C@@H](N)C2)cc2nc(-c3cc4cccnc4n3CC3CC3)n(C3CN(S(C)(=O)=O)C3)c12] | (3R)-1-{2-[1-(cyclopropylmethyl)-1H-pyrrolo[2,3-b]pyridin-2-yl]-1-(1-methanesulfonylazetidin-3-yl)-7-methoxy-IH-1,3-benzodiazole-5-carbonyl}piperidin-3-amine | 1.22 | 1 | 578 |

Example 342

((7R)-7-amino-2-azabicyclo[2.2.1]heptan-2-yl)(1-((1-(5-chloro-3-fluoropyridin-2-yl)-1H-pyrazol-4-yl)methyl)-2-(1-(cyclopropylmethyl)-1H-pyrrolo-[2,3-b]pyridin-2-yl)-7-methoxy-1H-benzo[d]imidazol-5-yl)methanone

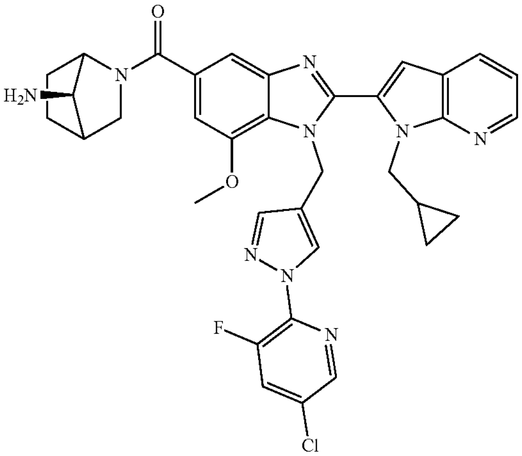 [SMILES: COc1cc(C(=O)N2CC3CCC2[C@@H]3N)cc2nc(-c3cc4cccnc4n3CC3CC3)n(Cc3cnn(-c4ncc(Cl)cc4F)c3)c12]

Intermediate 342A: tert-butyl ((7R)-2-(1-((1H-pyrazol-4-yl)methyl-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate

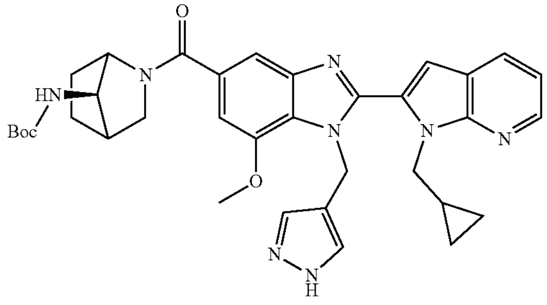 [SMILES: COc1cc(C(=O)N2CC3CCC2[C@@H]3NC(=O)OC(C)(C)C)cc2nc(-c3cc4cccnc4n3CC3CC3)n(Cc3cn[nH]c3)c12]

tert-butyl ((7R)-2-(1-((1H-pyrazol-4-yl)methyl)-2-(1-(cyclopropylmethyl)-1H-pyrrolo[2,3-b]pyridin-2-yl)-7-methoxy-1H-benzo[d]imidazole-5-carbonyl)-2-azabicyclo[2.2.1]heptan-7-yl)carbamate was prepared as the same procedure as in intermediate 247C. LC/MS (M+H): 643; LC retention time: 0.81 min (analytical HPLC Method 3).

Example 342: ((7R)-7-amino-2-azabicyclo[2.2.1]heptan-2-yl)(1-((1-(5-chloro-3-fluoropyridin-2-yl)-1H-pyrazol-4-yl)methyl)-2-(1-(cyclopropylmethyl)-1H-pyrrolo[2,3-b]pyridin-2-yl)-7-methoxy-1H-benzo[d]imidazol-5-yl)methanone

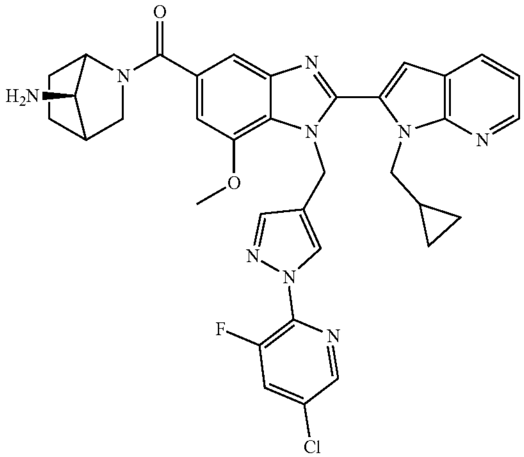 [SMILES: COc1cc(C(=O)N2CC3CCC2[C@@H]3N)cc2nc(-c3cc4cccnc4n3CC3CC3)n(Cc3cnn(-c4ncc(Cl)cc4F)c3)c12]

A mixture of tert-butyl ((3R,5R)-1-(1-((1H-pyrazol-4-yl)methyl)-2-(1-(cyclopropylmethyl)-1H-pyrrolo[2,3-b]pyridin-2-yl)-7-methoxy-1H-benzo[d]imidazole-5-carbonyl)-5-fluoropiperidin-3-yl)carbamate (10 mg, 0.016 mmol), 2-bromo-5-chloro-3-fluoropyridine (3.93 mg, 0.019 mmol), copper(I) iodide (0.889 mg, 4.67 μmol), potassium phosphate (9.91 mg, 0.047 mmol) and (1R,2R)—N1,N2-dimethylcyclohexane-1,2-diamine (2.213 mg, 0.016 mmol) in degassed dioxane (1.0 mL) under nitrogen in a sealed vial was stirred at 110° C. for 18 hours. The mixture was diluted with EtOAc (5 mL), the precipitate was filtered off and the filtrate was concentrated to give crude tert-butyl ((3R,5R)-1-(1-((1-(5-chloro-3-fluoropyridin-2-yl)-1H-pyrazol-4-yl)methyl)-2-(1-(cyclopropylmethyl)-1H-pyrrolo[2,3-b]pyridin-2-yl)-7-methoxy-1H-benzo[d]imidazole-5-carbonyl)-5-fluoropiperidin-3-yl)carbamate. LC/MS (M+H): 772; LC retention time: 0.95 mm (analytical HPLC Method 3).

A mixture of tert-butyl ((3R,5R)-1-(1-((1-(5-chloro-3-fluoropyridin-2-yl)-1H-pyrazol-4-yl)methyl)-2-(1-(cyclopropylmethyl)-1H-pyrrolo[2,3-b]pyridin-2-yl)-7-methoxy-1H-benzo[d]imidazole-5-carbonyl)-5-fluoropiperidin-3-yl)carbamate in DCM (1.0 mL) and TFA (1.0 mL) was stirred at RT for 30 min. The mixture was concentrated. The crude product was purified with XBridge CIS, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 24% B, 24-64% B over 20 minutes, then a 4-minute hold at 100% B; Flow Rate: 20 mL/min; Column Temperature: 25 C. Yield ((3R,5R)-3-amino-5-fluoropiperidin-1-yl)(1-((1-(5-chloro-3-fluoropyridin-2-yl)-1H-pyrazol-4-yl)methyl)-2-(1-(cyclopropylmethyl)-1H-pyrrolo[2,3-b]pyridin-2-yl)-7-methoxy-1H-benzo[d]imidazol-5-yl)methanone (7.90 mg, 0.012 mmol, 74.0% yield). LC/MS (M+H): 672; LC retention time: 1.67 min (analytical HPLC Method 1). $^1$H NMR (500 MHz, DMSO-$d_6$) δ 8.43-8.03 (m, 4H), 7.99-7.83 (m, 1H), 7.54-7.44 (m, 1H), 7.37-7.26 (m, 1H), 7.24-7.12 (m, 1H), 7.11-7.00 (m, 1H), 6.93-6.79 (m, 1H), 5.83-5.66 (m, 2H), 5.06-4.69 (m, 1H), 4.42-4.27 (m, 2H), 4.03-3.86 (m, 3H), 3.06-2.59 (m, 2H), 2.21-1.83 (m, 2H), 1.62-1.34 (m, 1H), 1.24-1.08 (m, 1H), 1.00-0.63 (m, 2H), 0.12--0.19 (m, 5H).

Examples 343 to Example 411 in Table 7 were prepared as described by the general procedure given for Example 342.

TABLE 7

| Ex# | Structure | Name | LC/MS Rt (min) | LC/MS Method | M + H (obs ion) |
|---|---|---|---|---|---|
| 343 | 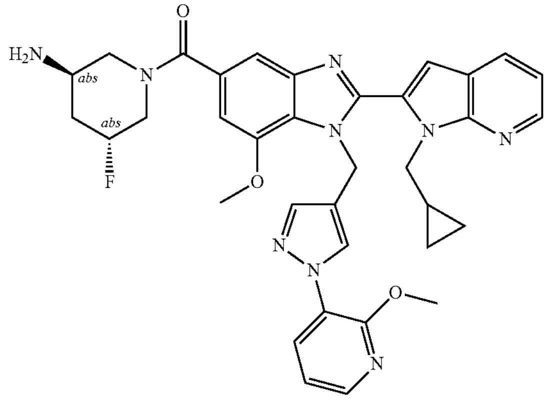 [SMILES: COc1ncccc1-n1cc(Cn2c(-c3cc4cccnc4n3CC3CC3)nc3cc(C(=O)N4C[C@H](N)C[C@@H](F)C4)cc(OC)c32)cn1] | (3R,5R)-1-{2-[1-(cyclopropylmethyl)-1H-pyrrolo[2,3-b]pyridin-2-yl]-7-methoxy-1-{[1-(2-methoxypyridin-3-yl)-1H-pyrazol-4-yl]methyl}-1H-1,3-benzodiazole-5-carbonyl}-5-fluoropiperidin-3-amine | 1.65 | 1 | 650.2 |

TABLE 7-continued

| Ex# | Structure | Name | LC/MS Rt (min) | LC/MS Method | M + H (obs ion) |
|---|---|---|---|---|---|
| 344 | 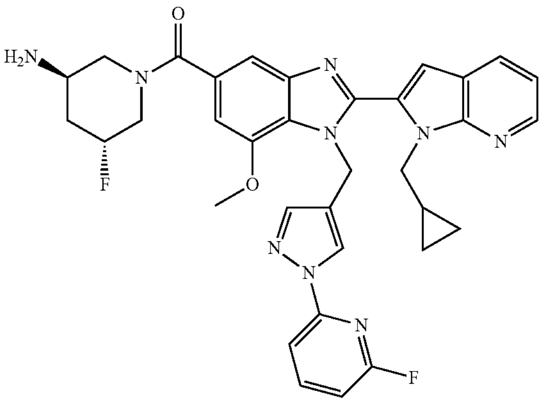 [SMILES: COc1cc(C(=O)N2C[C@H](N)C[C@@H](F)C2)cc2nc(-c3cc4cccnc4n3CC3CC3)n(Cc3cnn(-c4cccc(F)n4)c3)c12] | (3R,5R)-1-{2-[1-(cyclopropylmethyl)-1H-pyrrolo[2,3-b]pyridin-2-yl]-1-{[1-(6-fluoropyridin-2-yl)-1H-pyrazol-4-yl]methyl}-7-methoxy-1H-1,3-benzodiazole-5-carbonyl}-5-fluoropiperidin-3-amine | 1.66 | 2 | 638.2 |
| 345 | 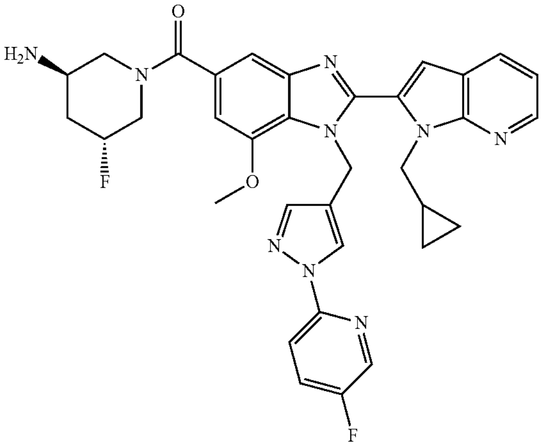 [SMILES: COc1cc(C(=O)N2C[C@H](N)C[C@@H](F)C2)cc2nc(-c3cc4cccnc4n3CC3CC3)n(Cc3cnn(-c4ccc(F)cn4)c3)c12] | (3R,5R)-1-{2-[1-(cyclopropylmethyl)-1H-pyrrolo[2,3-b]pyridin-2-yl]-1-{[1-(5-fluoropyridin-2-yl)-1H-pyrazol-4-yl]methyl}-7-methoxy-1H-1,3-benzodiazole-5-carbonyl}-5-fluoropiperidin-3-amine | 1.43 | 2 | 638.1 |
| 346 | 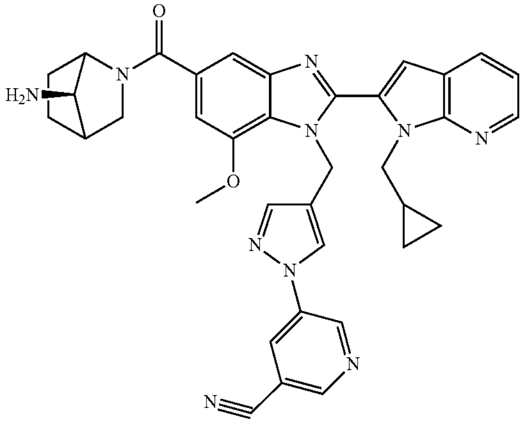 [SMILES: COc1cc(C(=O)N2CC3CCC2[C@@H]3N)cc2nc(-c3cc4cccnc4n3CC3CC3)n(Cc3cnn(-c4cncc(C#N)c4)c3)c12] | 5-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridine-3-carbonitrile | 1.62 | 1 | 639 |

TABLE 7-continued

| Ex# | Structure | Name | LC/MS Rt (min) | LC/MS Method | M + H (obs ion) |
|---|---|---|---|---|---|
| 347 | 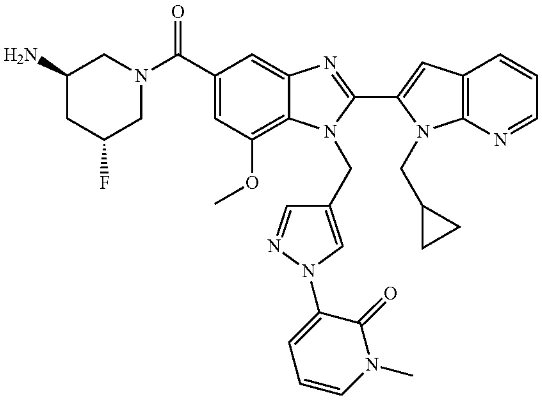 [SMILES: COc1cc(C(=O)N2C[C@H](N)C[C@@H](F)C2)cc2nc(-c3cc4cccnc4n3CC3CC3)n(Cc3cnn(-c4cccn(C)c4=O)c3)c12] | 3-[4-({5-[(3R,5R)-3-amino-5-fluoropiperidine-1-carbonyl]-2-[1-(cyclopropyimethyl)-1H-pyrrolo[2,3-b]pyridin-2-yl]-7-methoxy-1H-1,3-benzodiazol-1-yl}methyl)-1H-pyrazol-1-yl]-1-methyl-1,2-dihydropyridin-2-one | 1.35 | 2 | 650.2 |
| 348 | 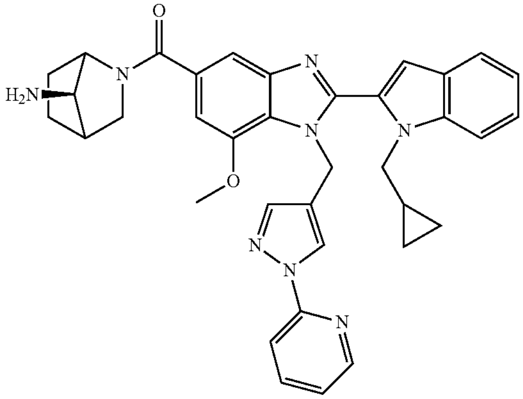 | (7R)-2-{2-[1-(cycl opropylmethyl)-1H-indol-2-yl]-7-methoxy-1-{[1-(pyridin-2-yl)-1H-pyrazol-4-yl]methyl}-1H-1,3-benzodiazoie-5-carbonyl}-2-azabicyclo[2.2.1]heptan-7-amine | 1.96 | 1 | 1225.3 [2M + H] |
| 349 | 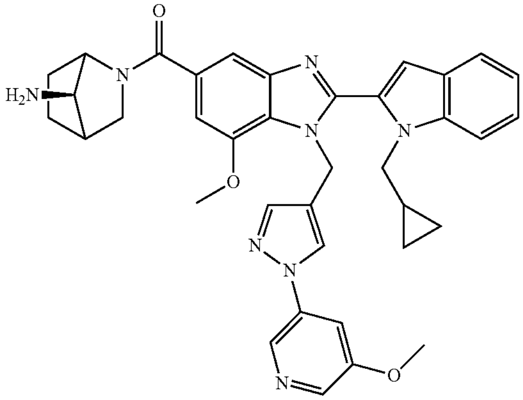 [SMILES: COc1cncc(-n2cc(Cn3c(-c4cc5ccccc5n4CC4CC4)nc4cc(C(=O)N5CC6CCC5[C@@H]6N)cc(OC)c43)cn2)c1] | (7R)-2-{2-[1-(cyclopropylmethyl)-1H-indol-2-yl]-7-methoxy-1-{[1-(5-methoxypyridin-3-yl)-1H-pyrazol-4-yl]methyl}-1H-1,3-benzodiazole-5-carbonyl)-2-azabicyclo[2.2.1]heptan-7-amine | 1.78 | 1 | 643.3 |

TABLE 7-continued

| Ex# | Structure | Name | LC/MS Rt (min) | LC/MS Method | M + H (obs ion) |
|---|---|---|---|---|---|
| 350 | 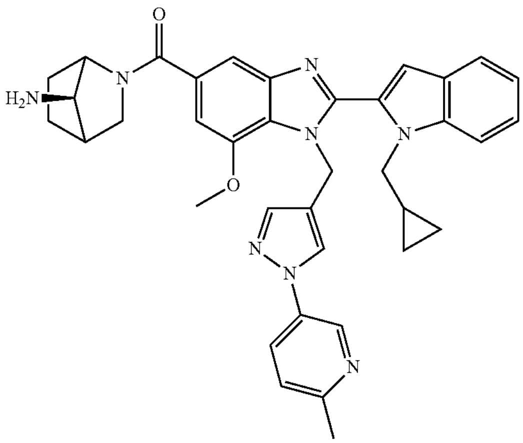 [SMILES: COc1cc(C(=O)N2CC3CCC2[C@@H]3N)cc2nc(-c3cc4ccccc4n3CC3CC3)n(Cc3cnn(-c4ccc(C)nc4)c3)c12] | (7R)-2-{2-[1-(cyclopropylmethyl)-1H-indol-2-yl]-7-methoxy-1-{[1-(6-methylpyridin-3-yl)-1H-pyrazol-4-yl]methyl}-1H-1,3-benzodiazole-5-carbonyl}-2-azabicyclo[2.2.1]heptan-7-amine | 1.79 | 1 | 627.3 |
| 351 | 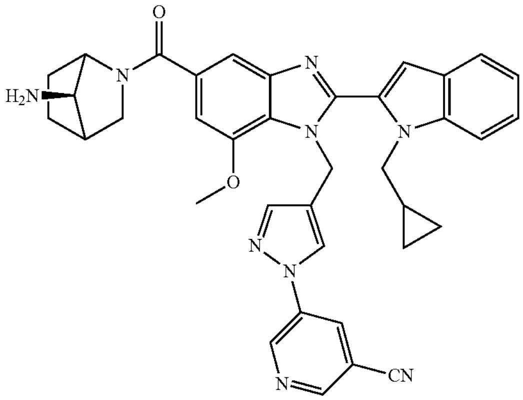 [SMILES: COc1cc(C(=O)N2CC3CCC2[C@@H]3N)cc2nc(-c3cc4ccccc4n3CC3CC3)n(Cc3cnn(-c4cncc(C#N)c4)c3)c12] | 5-[4-({5-[(7R)-7-amino~2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridine-3-carbonitrile | 1.54 | 2 | 638.2 |
| 352 | 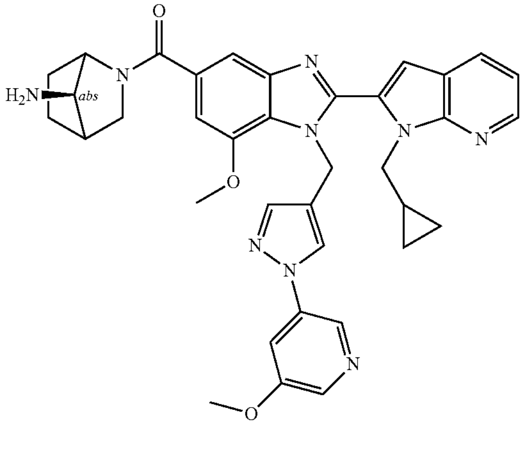 [SMILES: COc1cncc(-n2cc(Cn3c(-c4cc5cccnc5n4CC4CC4)nc4cc(C(=O)N5CC6CCC5[C@@H]6N)cc(OC)c43)cn2)c1] | (7R)-2-{2-[1-(cyclopropylmethyl)-1H-pyrrolo[2,3-b]pyridin-2-yl]-7-methoxy-1-{[1-(5-methoxypyridin-3-yl)-1H-pyrazol-4-yl]methyl}-1H-1,3-benzodiazole-5-carbonyl}-2-azabicyclo[2.2.1]heptan-7-amine | 1.54 | 1 | 644.2 |

TABLE 7-continued

| Ex# | Structure | Name | LC/MS Rt (min) | LC/MS Method | M + H (obs ion) |
|---|---|---|---|---|---|
| 353 | 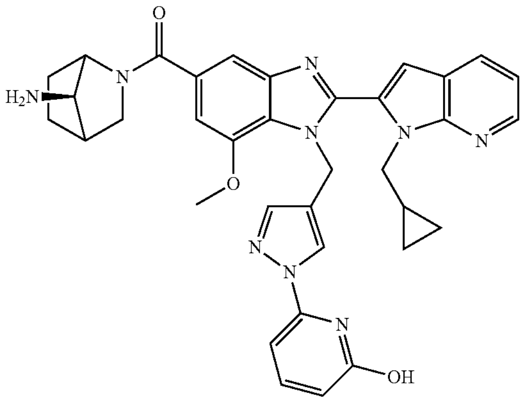 [SMILES: COc1cc(C(=O)N2CC3CCC2[C@@H]3N)cc2nc(-c3cc4cccnc4n3CC3CC3)n(Cc3cnn(-c4cccc(O)n4)c3)c12] | 6-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridin-2-ol | 1.42 | 2 | 629.9 |
| 354 | 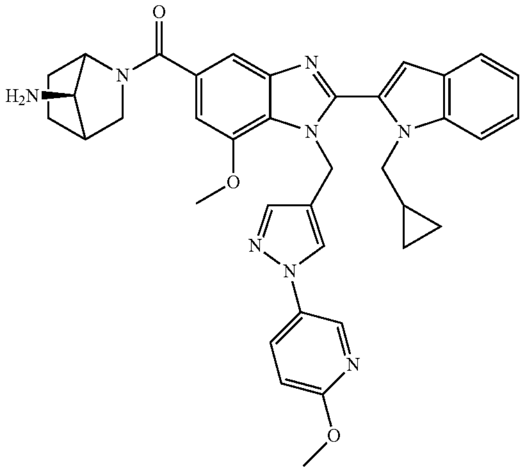 [SMILES: COc1ccc(-n2cc(Cn3c(-c4cc5ccccc5n4CC4CC4)nc4cc(C(=O)N5CC6CCC5[C@@H]6N)cc(OC)c43)cn2)cn1] | (7R)-2-{2-[1-(cyclopropylmethyl)-1H-indol-2-yl]-7-methoxy-1-{[1-(6-methoxypyridin-3-yl)-1H pyrazol-4-yl]methyl}-1H-1,3-benzodiazole-5-carbonyl}-2-azabicyclo[2.2.1]heptan-7-amine | 1.97 | 1 | 643.2 |
| 355 | 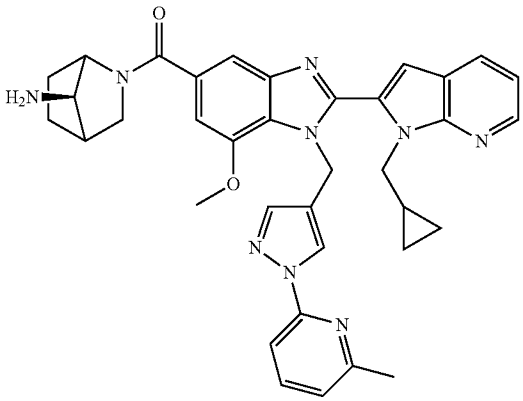 [SMILES: COc1cc(C(=O)N2CC3CCC2[C@@H]3N)cc2nc(-c3cc4cccnc4n3CC3CC3)n(Cc3cnn(-c4cccc(C)n4)c3)c12] | (7R)-2-{2-[1-(cyclopropylmethyl)-1H-pyrrolo[2,3-b]pyridin-2-yl]-7-methoxy-1-{[1-(6-methylpyridin-2-yl)-1H-pyrazol-4-yl]methyl}-1H-1,3-benzodiazole-5-carbonyl}-2-azabicyclo[2.2.1]heptan-7-amine | 1.83 | 1 | 628 |

TABLE 7-continued

| Ex# | Structure | Name | LC/MS Rt (min) | LC/MS Method | M + H (obs ion) |
|---|---|---|---|---|---|
| 356 | 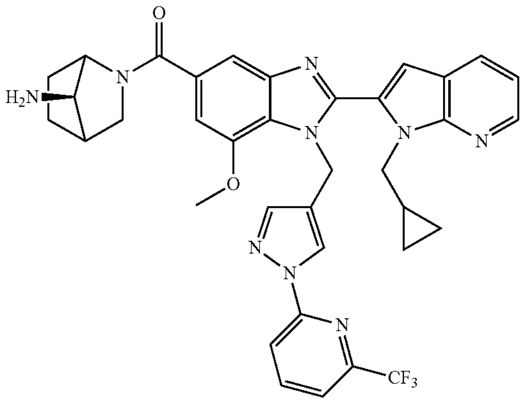 [SMILES: COc1cc(C(=O)N2CC3CCC2[C@@H]3N)cc2nc(-c3cc4cccnc4n3CC3CC3)n(Cc3cnn(-c4cccc(C(F)(F)F)n4)c3)c12] | (7R)-2-{2-[1-(cyclopropylmethyl)-1H-pyrrolo[2,3-b]pyridin-2-yl]-7-methoxy-1-({1-[6-(trifluoromethyl)pyridin-2-yl]-1H-pyrazol-4-yl}methyl)-1H-1,3-benzodiazole-5-carbonyl)-2-azabicyclo[2.2.1]heptan-7-amine | 1.78 | 2 | 682.1 |
| 357 | 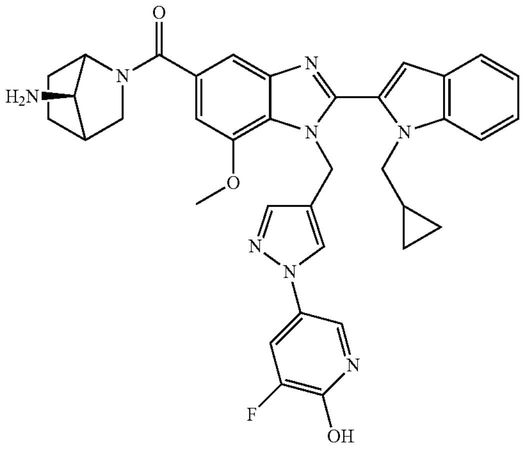 [SMILES: COc1cc(C(=O)N2CC3CCC2[C@@H]3N)cc2nc(-c3cc4ccccc4n3CC3CC3)n(Cc3cnn(-c4cnc(O)c(F)c4)c3)c12] | 5-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]-3-fluoropyridin-2-ol | 1.52 | 1 | 647.2 |
| 358 | 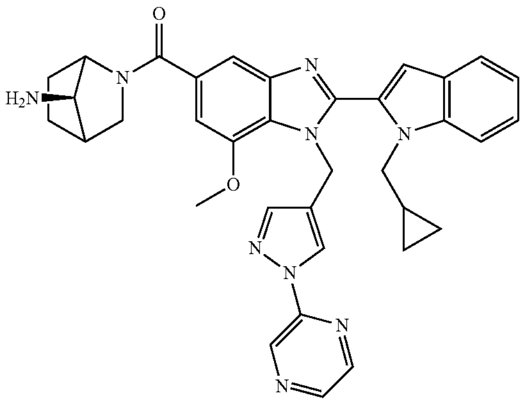 [SMILES: COc1cc(C(=O)N2CC3CCC2[C@@H]3N)cc2nc(-c3cc4ccccc4n3CC3CC3)n(Cc3cnn(-c4cnccn4)c3)c12] | (7R)-2-{2-[1-(cyclopropylmethyl)-1H-mdol-2-yl]-7-methoxy-1-{[1-(pyrazin-2-yl)-1H-pyrazol-4-yl]methyl}-1H-1,3-benzodiazole-5-carbonyl}-2-azabicyclo[2.2.1]heptan-7-amine | 1.53 | 2 | 614.5 |

TABLE 7-continued

| Ex# | Structure | Name | LC/MS Rt (min) | LC/MS Method | M + H (obs ion) |
|---|---|---|---|---|---|
| 359 | 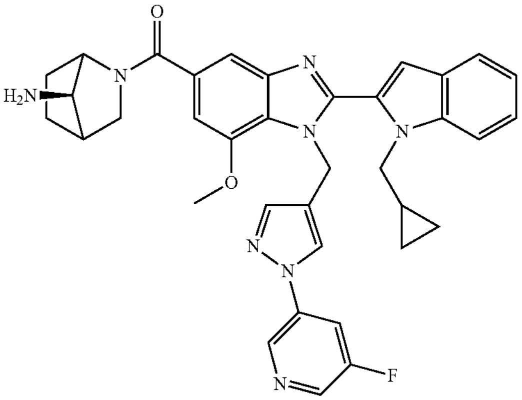 [SMILES: COc1cc(C(=O)N2CC3CCC2[C@@H]3N)cc2nc(-c3cc4ccccc4n3CC3CC3)n(Cc3cnn(-c4cncc(F)c4)c3)c12] | (7R)-2-{2-[1-(cyclopropylmethyl)-1H-indol-2-yl]-1-{[1-(5-fluoropyridin-3-yl)-1H-pyrazol-4-yl]methyl}-7-methoxy-1H-1,3-benzodiazole-5-carbonyl}-2-azabicyclo[2.2.1]heptan-7-amine | 1.88 | 1 | 631.2 |
| 360 | 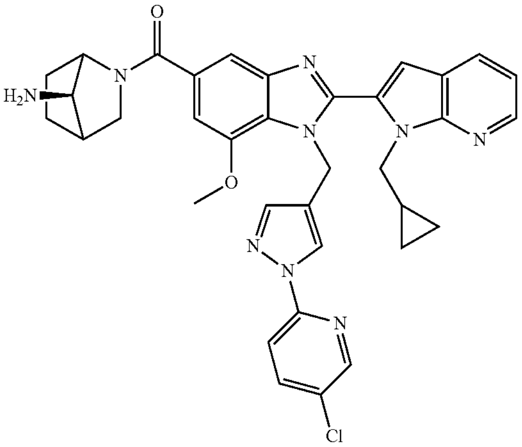 | (7R)-2-(1-{[1-(5-chloropyridin-2-yl)-1H-pyrazol-4-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.94 | 1 | 648 |
| 361 | 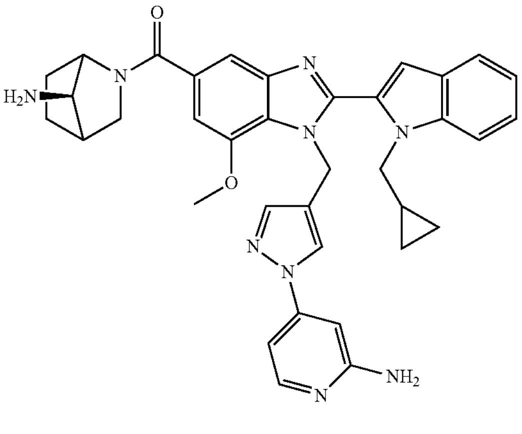 [SMILES: COc1cc(C(=O)N2CC3CCC2[C@@H]3N)cc2nc(-c3cc4ccccc4n3CC3CC3)n(Cc3cnn(-c4ccnc(N)c4)c3)c12] | (7R)-2-(1-{[1-(2-aminopyridin-4-yl)-1H-pyrazol-4-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.61 | 1 | 628.2 |

TABLE 7-continued

| Ex# | Structure | Name | LC/MS Rt (min) | LC/MS Method | M + H (obs ion) |
|---|---|---|---|---|---|
| 362 | 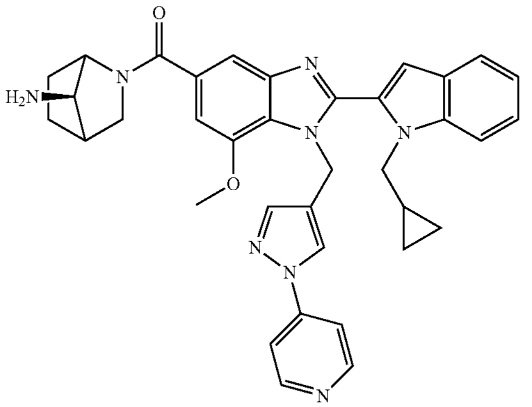 [SMILES: COc1cc(C(=O)N2CC3CCC2[C@@H]3N)cc2nc(-c3cc4ccccc4n3CC3CC3)n(Cc3cnn(-c4ccncc4)c3)c12] | (7R)-2-{2-[1-(cyclopropylmethyl)-1H-indol-2-yl]-7-methoxy-(pyridin-4-yl)-1H-pyrazol-4-yl]methyl}-1H-1,3-benzodiazole-5-carbonyl}-2-azabicyclo[2.2.1]heptan-7-amine | 1.16 | 2 | 613.3 |
| 363 | 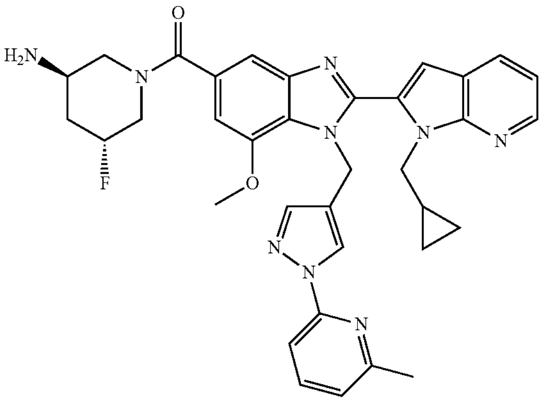 [SMILES: COc1cc(C(=O)N2C[C@H](N)C[C@@H](F)C2)cc2nc(-c3cc4cccnc4n3CC3CC3)n(Cc3cnn(-c4cccc(C)n4)c3)c12] | (3R,5R)-1-{2-[1-(cyclopropylmethyl)-1H-pyrrolo[2,3-b]pyridin-2-yl]-7-methoxy-1-{[1-(6-methylpyridin-2-yl)-1H-pyrazol-4-yl]methyl}-1H-1,3-benzodiazole-5-carbonyl}-5-fluoropiperidin-3-amine | 1.89 | 1 | 634.2 |
| 364 | 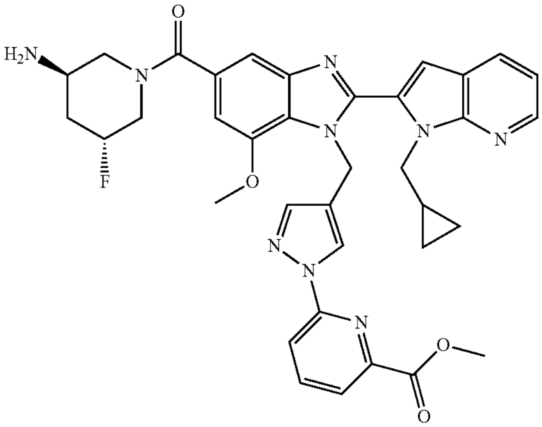 [SMILES: COC(=O)c1cccc(-n2cc(Cn3c(-c4cc5cccnc5n4CC4CC4)nc4cc(C(=O)N5C[C@H](N)C[C@@H](F)C5)cc(OC)c43)cn2)n1] | methyl 6-[4-({5-[(3R,5R)-3-amino-5-fluoropipendine-1-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridine-2-carboxylate | 1.7 | 1 | 678 |

TABLE 7-continued

| Ex# | Structure | Name | LC/MS Rt (min) | LC/MS Method | M + H (obs ion) |
| --- | --- | --- | --- | --- | --- |
| 365 | 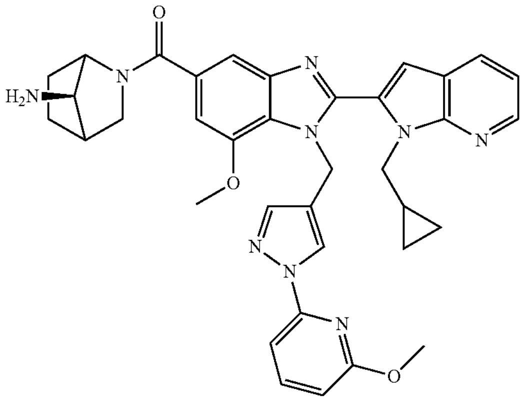 | (7R)-2-{2-[1-(cyclopropylmethyl)-1H-pyrrolo[2,3-b]pyridin-2-yl]-7-methoxy-1-{[1-(6-methoxypyridin-2-yl)-1H-pyrazol-4-yl]methyl}-1H-1,3-benzodiazole-5-carbonyl}-2-azabicyclo[2.2.1]heptan-7-amine | 1.81 | 1 | 644.4 |
| 366 | 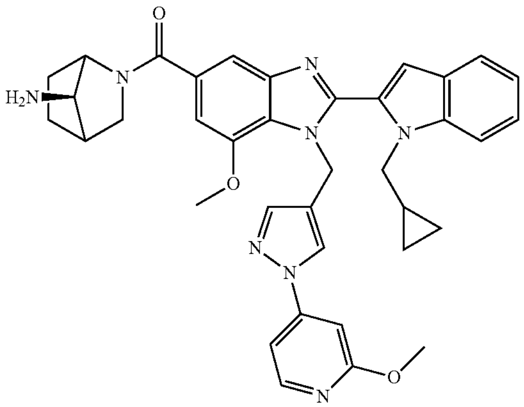 [SMILES: COc1cc(-n2cc(Cn3c(-c4cc5ccccc5n4CC4CC4)nc4cc(C(=O)N5CC6CCC5[C@@H]6N)cc(OC)c43)cn2)ccn1] | (7R)-2-{2-[1-(cyclopropylmethyl)-1H-indol-2-yl]-7-methoxy-1-{[1-(2-methoxypyridin-4-yl)-1H-pyrazol-4-yl]methyl}-1H-1,3-benzodiazole-5-carbonyl}-2-azabicyclo[2.2.1]heptan-7-amine | 1.85 | 1 | 643.5 |
| 367 | 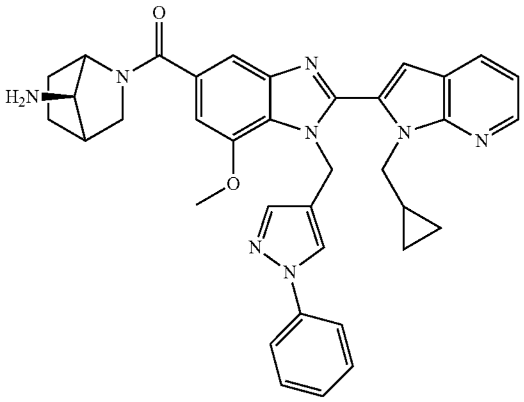 [SMILES: COc1cc(C(=O)N2CC3CCC2[C@@H]3N)cc2nc(-c3cc4ccccc4n3CC3CC3)n(Cc3cnn(-c4cccnc4)c3)c12] | (7R)-2-{2-[1-(cyclopropylmethyl)-1H-pyrrolo[2,3-b]pyridin-2-yl]-7-methoxy-1-[(1-phenyl-1H-pyrazol-4-yl)methyl]-1H-1,3-benzodiazole-5-carbonyl}-2-azabicyclo[2.2.1]heptan-7-amine | 1.47 | 2 | 613.2 |

TABLE 7-continued

| Ex# | Structure | Name | LC/MS Rt (min) | LC/MS Method | M + H (obs ion) |
|---|---|---|---|---|---|
| 368 | 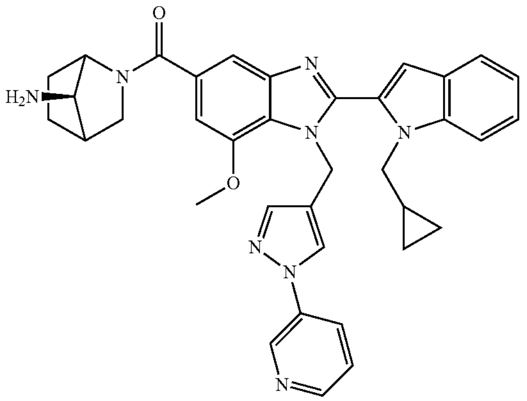 | (7R)-2-{2-[1-(cyclopropylmethyl)-1H-indol-2-yl]-7-methoxy-1-{[1-(pyridin-3-yl)-1H-pyrazol-4-yl]methyl}-1H-1,3-benzodiazole-5-carbonyl}-2-azabicyclo[2.2.1]heptan-7-amine | 1.78 | 1 | 613.3 |
| 369 | 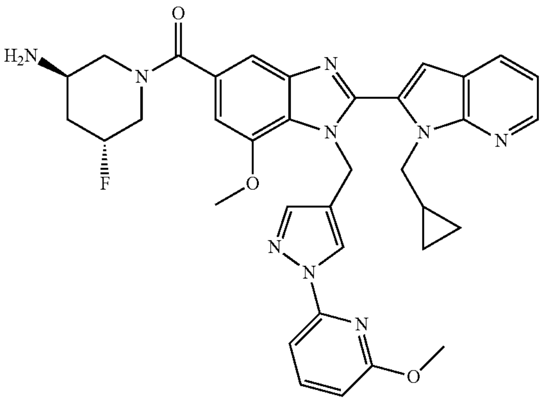 [SMILES: COc1cccc(-n2cc(Cn3c(-c4cc5cccnc5n4CC4CC4)nc4cc(C(=O)N5C[C@H](N)C[C@@H](F)C5)cc(OC)c43)cn2)n1] | (3R,5R)-1-{2-[1-(cyclopropylmethyl)-1H-pyrrolo[2,3-b]pyridin-2-yl]-7-methoxy-1-{[1-(6-methoxypyridin-2-yl)-1H-pyrazol-4-yl]methyl}-1H-1,3-benzodiazole-5-carbonyl}-5-fluoropiperidin-3-amine | 1.82 | 1 | 650.2 |
| 370 | 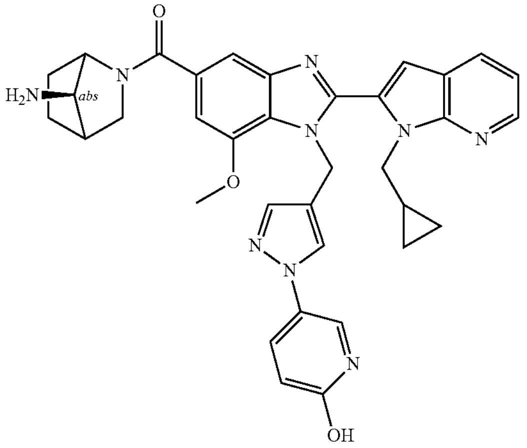 [SMILES: COc1cc(C(=O)N2CC3CCC2[C@@H]3N)cc2nc(-c3cc4cccnc4n3CC3CC3)n(Cc3cnn(-c4ccc(O)nc4)c3)c12] | 5-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridin-2-ol | 1.17 | 2 | 630.3 |

TABLE 7-continued

| Ex# | Structure | Name | LC/MS Rt (min) | LC/MS Method | M + H (obs ion) |
| --- | --- | --- | --- | --- | --- |
| 371 | 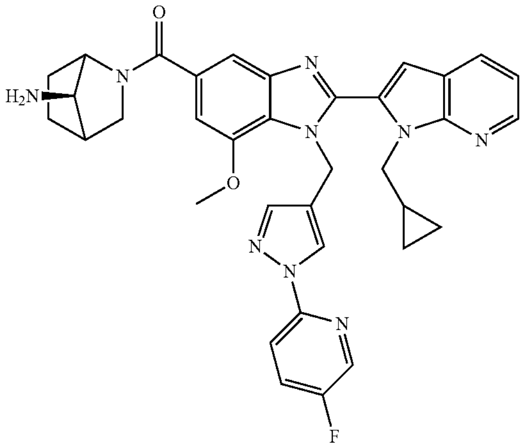 [SMILES: COc1cc(C(=O)N2CC3CCC2[C@@H]3N)cc2nc(-c3cc4cccnc4n3CC3CC3)n(Cc3cnn(-c4ccc(F)cn4)c3)c12] | (7R)-2-{2-[1-(cyclopropylmethyl)-1H-pyrrolo[2,3-b]pyridin-2-yl]-1-{[1-(5-fluoropyridin-2-yl)-1H-pyrazol-4-yl]methyl}-7-methoxy-1H-1,3-benzodiazole-5-carbonyl}-2-azabicyclo[2.2.1]heptan-7-amine | 1.71 | 1 | 632.4 |
| 372 | 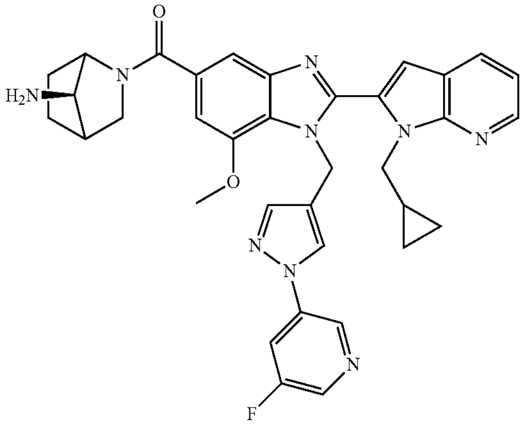 [SMILES: COc1cc(C(=O)N2CC3CCC2[C@@H]3N)cc2nc(-c3cc4cccnc4n3CC3CC3)n(Cc3cnn(-c4cncc(F)c4)c3)c12] | (7R)-2-{2-[1-(cyclopropylmethyl)-1H-pyrrolo[2,3-b]pyridin-2-yl]-1-{[1-(5-fluoropyridin-3-yl)-1H-pyrazol-4-yl]methyl}-7-methoxy-1H-1,3-benzodiazole-5-carbonyl}-2-azabicyclo[2.2.1]heptan-7-amine | 1.56 | 1 | 632.2 |
| 373 | 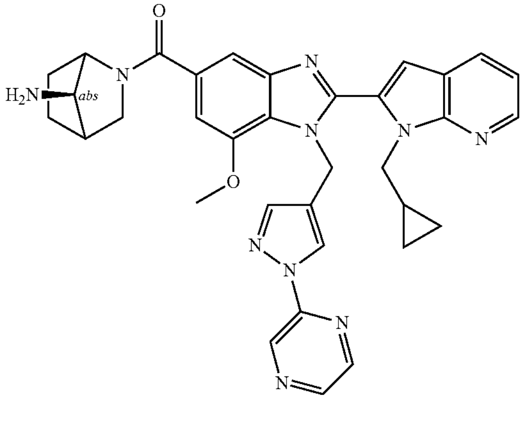 | (7R)-2-{2-[1-(cyclopropylmethyl)-1H-pyrrolo[2,3-b]pyridin-2-yl]-7-methoxy-1-{[1-(pyrazin-2-yl)-1H-pyrazol-4-yl]methyl}-1H-1,3-benzodiazole-5-carbonyl}-2-azabicyclo[2.2.1]heptan-7-amine | 1.58 | 1 | 615.2 |

TABLE 7-continued

| Ex# | Structure | Name | LC/MS Rt (min) | LC/MS Method | M + H (obs ion) |
|---|---|---|---|---|---|
| 374 | 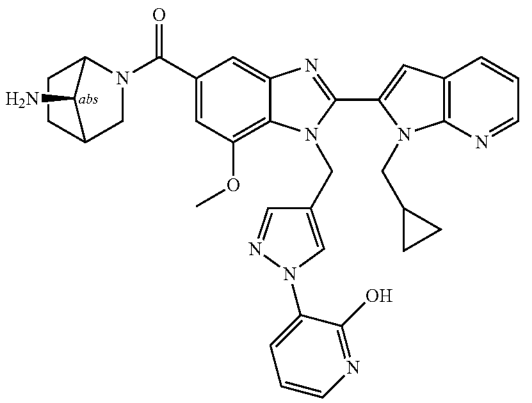 [SMILES: COc1cc(C(=O)N2CC3CCC2[C@@H]3N)cc2nc(-c3cc4cccnc4n3CC3CC3)n(Cc3cnn(-c4cccnc4O)c3)c12] | 3-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridin-2-ol | 1.22 | 2 | 630.4 |
| 375 | 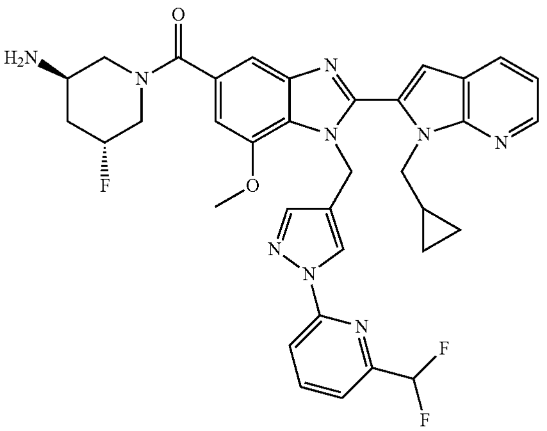 [SMILES: COc1cc(C(=O)N2C[C@H](N)C[C@@H](F)C2)cc2nc(-c3cc4cccnc4n3CC3CC3)n(Cc3cnn(-c4cccc(C(F)F)n4)c3)c12] | (3R,5R)-1-{2-[1-(cyclopropylmethyl)-1H-pyrrolo[2,3-b]pyridin-2-yl]-(difluoromethyl)pyridin-2-yl]-1H-pyrazol-4-yl}methyl)-7-methoxy-1H-1,3-benzodiazole-5-carbonyl}-5-fluoropiperidin-3-amine | 1.67 | 2 | 670.2 |
| 376 | 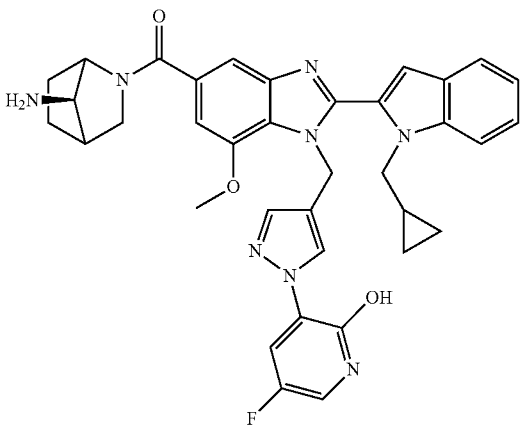 [SMILES: COc1cc(C(=O)N2CC3CCC2[C@@H]3N)cc2nc(-c3cc4ccccc4n3CC3CC3)n(Cc3cnn(-c4cc(F)cnc4O)c3)c12] | 3-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]-5-fluoropyridin-2-ol | 1.44 | 2 | 647.1 |

TABLE 7-continued

| Ex# | Structure | Name | LC/MS Rt (min) | LC/MS Method | M + H (obs ion) |
| --- | --- | --- | --- | --- | --- |
| 377 | 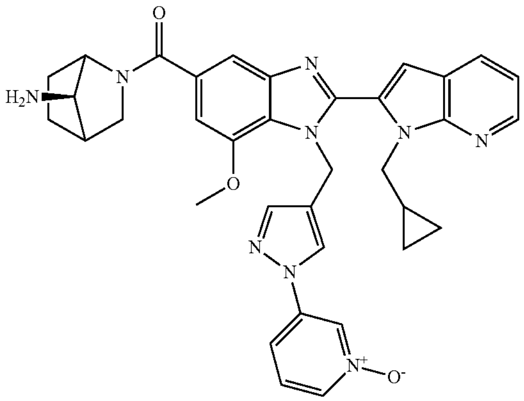 [SMILES: COc1cc(C(=O)N2CC3CCC2[C@@H]3N)cc2nc(-c3cc4cccnc4n3CC3CC3)n(Cc3cnn(-c4ccc[n+]([O-])c4)c3)c12] | 3-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridin-1-ium-1-olate | 1.26 | 1 | 630.2 |
| 378 | 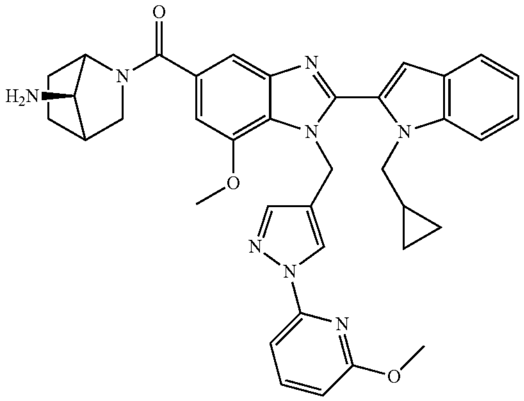 [SMILES: COc1cccc(-n2cc(Cn3c(-c4cc5ccccc5n4CC4CC4)nc4cc(C(=O)N5CC6CCC5[C@@H]6N)cc(OC)c43)cn2)n1] | (7R)-2-{2-[1-(cyclopropylmethyl)-1H-indol-2-yl]-7-methoxy-1-{[1-(6-methoxypyridin-2-yl)-1H-pyrazol-4-yl]methyl}-1H-1,3-benzodiazole-5-carbonyl}-2-azabicyclo[2.2.1]heptan-7-amine | 2.06 | 1 | 643.4 |
| 379 | 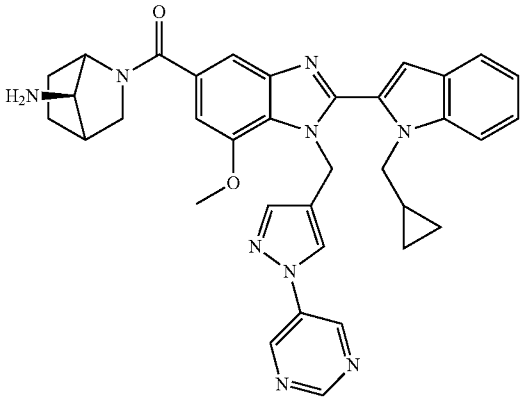 | (7R)-2-{2-[1-(cyclopropylmethyl)-1H-indol-2-yl]-7-methoxy-1-{[1-(pyrimidin-5-yl)-1H-pyrazol-4-yl]methyl}-1H-1,3-benzodiazole-5-carbonyl}-2-azabicyclo[2.2.1]heptan-7-amine | 1.48 | 2 | 614 |

TABLE 7-continued

| Ex# | Structure | Name | LC/MS Rt (min) | LC/MS Method | M + H (obs ion) |
| --- | --- | --- | --- | --- | --- |
| 380 | 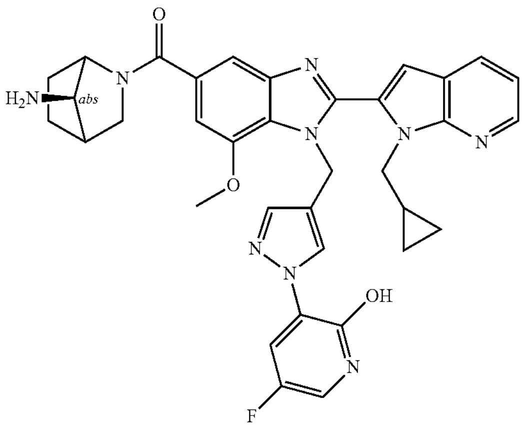 [SMILES: COc1cc(C(=O)N2CC3CCC2[C@@H]3N)cc2nc(-c3cc4cccnc4n3CC3CC3)n(Cc3cnn(-c4cc(F)cnc4O)c3)c12] | 3-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl)methyl}-1H-pyrazol-1-yl]-5-fluoropyridin-2-ol | 1.35 | 2 | 647.9 |
| 381 | 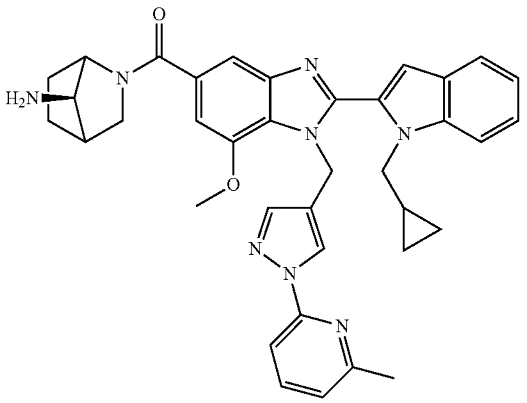 [SMILES: COc1cc(C(=O)N2CC3CCC2[C@@H]3N)cc2nc(-c3cc4ccccc4n3CC3CC3)n(Cc3cnn(-c4cccc(C)n4)c3)c12] | (7R)-2-{2-[1-(cyclopropylmethyl)-1H-indol-2-yl]-7-methoxy-1-{[1-(6-methylpyridin-2-yl)-1H-pyrazol-4-yl]methyl}-1H-1,3-benzodiazole-5-carbonyl}-2-azabicydo[2.2.1]heptan-7-amine | 2.01 | 1 | 627.5 |
| 382 | 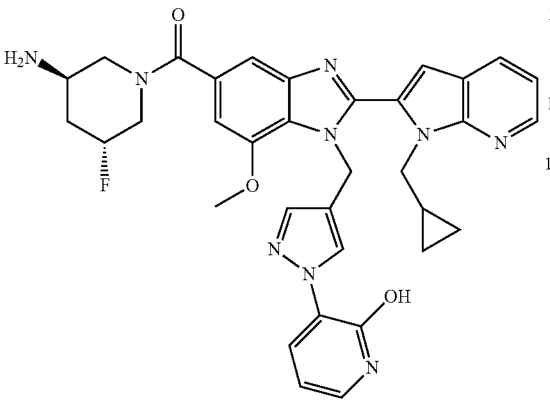 | 3-[4-({5-[(3R,5R)-3-amino-5-fluoropiperidine-1-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridin-2-ol | 1.41 | 1 | 636.2 |

TABLE 7-continued

| Ex# | Structure | Name | LC/MS Rt (min) | LC/MS Method | M + H (obs ion) |
| --- | --- | --- | --- | --- | --- |
| 383 | 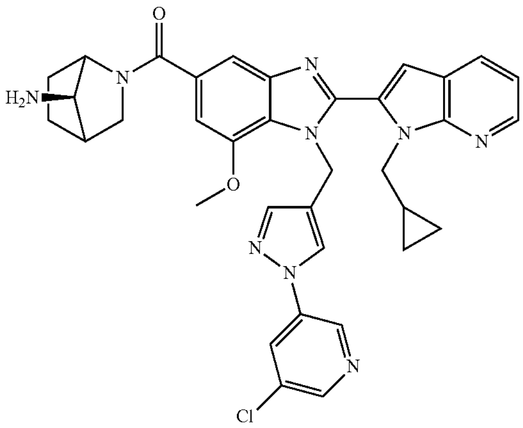 [SMILES: COc1cc(C(=O)N2CC3CCC2[C@@H]3N)cc2nc(-c3cc4cccnc4n3CC3CC3)n(Cc3cnn(-c4cncc(Cl)c4)c3)c12] | (7R)-2-(1-{[1-(5-chloropyridin-3-yl)-1H-pyrazol-4-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.78 | | 648.1 |
| 384 | 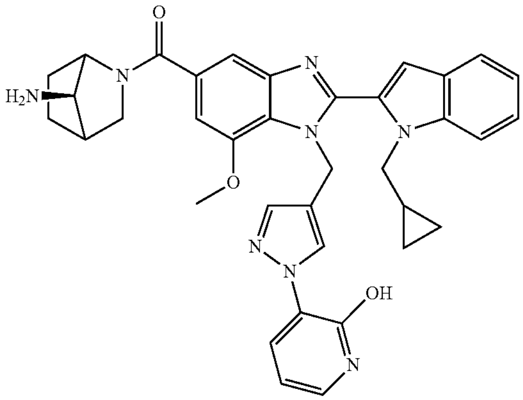 | 3-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridin-2-ol | 1.44 | 2 | 629 |
| 385 | 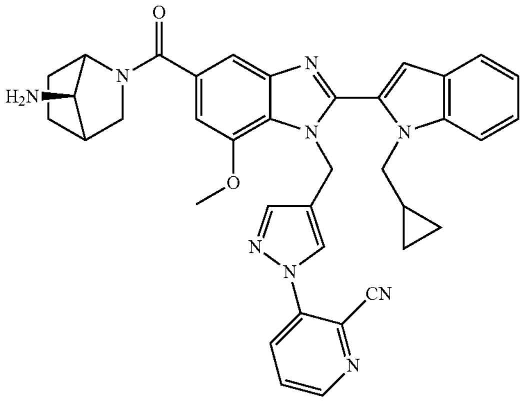 [SMILES: COc1cc(C(=O)N2CC3CCC2[C@@H]3N)cc2nc(-c3cc4ccccc4n3CC3CC3)n(Cc3cnn(-c4cccnc4O)c3)c12] | 3-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridine-2-carbonitrile | 1.48 | 2 | 638.3 |

TABLE 7-continued

| Ex# | Structure | Name | LC/MS Rt (min) | LC/MS Method | M + H (obs ion) |
|---|---|---|---|---|---|
| 386 | 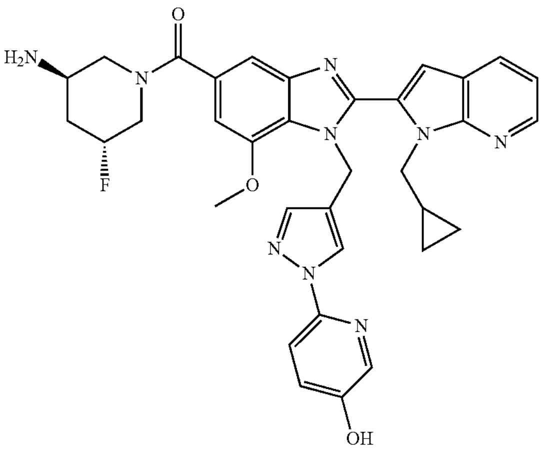 [SMILES: COc1cc(C(=O)N2C[C@H](N)C[C@@H](F)C2)cc2nc(-c3cc4cccnc4n3CC3CC3)n(Cc3cnn(-c4ccc(O)cn4)c3)c12] | 6-[4-({5-[(3R,5R)-3-amino-5-fluoropiperidine-1-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridine-3-carbonitrile | 1.55 | 2 | 645.2 |
| 387 | 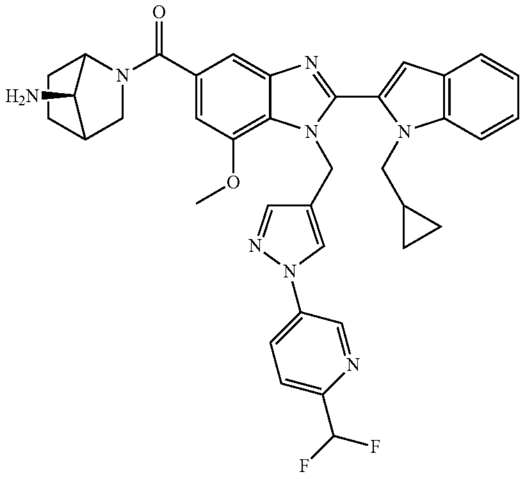 [SMILES: COc1cc(C(=O)N2CC3CCC2[C@@H]3N)cc2nc(-c3cc4ccccc4n3CC3CC3)n(Cc3cnn(-c4ccc(C(F)F)nc4)c3)c12] | (7R)-2-{2-[1-(cyclopropylmethyl)-1H-indol-2-yl]-1-({1-[6-(difluoromethyl)pyridin-3-yl]-1H-pyrazol-4-yl}methyl)-7-methoxy-1H-1,3-benzodiazole-5-carbonyl}-2-azabicyclo[2.2.1]heptan-7-amine | 1.94 | 1 | 663 |
| 388 | 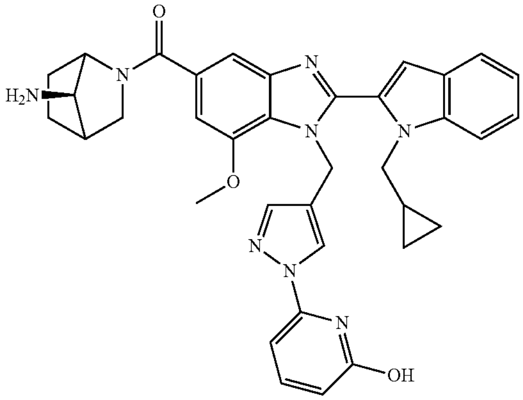 | 6-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridin-2-ol | 1.52 | 2 | 629.5 |

TABLE 7-continued

| Ex# | Structure | Name | LC/MS Rt (min) | LC/MS Method | M + H (obs ion) |
|---|---|---|---|---|---|
| 389 | 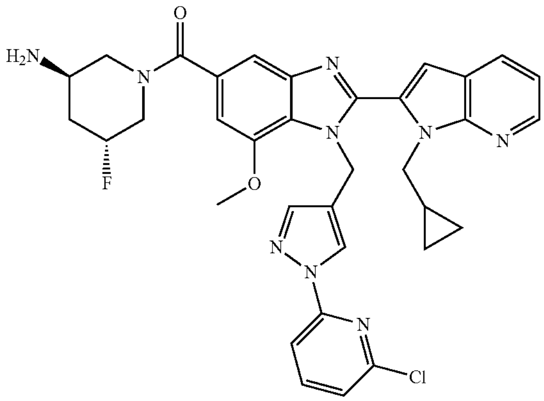 [SMILES: COc1cc(C(=O)N2C[C@H](N)C[C@@H](F)C2)cc2nc(-c3cc4cccnc4n3CC3CC3)n(Cc3cnn(-c4cccc(Cl)n4)c3)c12] | (3R,5R)-1-(1-{[1-(6-chloropyridin-2-yl)-1H-pyrazol-4-yl]methyl}-2-[1-(cyclopropylmethyl)-1H-pyrrolo[2,3-b]pyridin-2-yl]-7-methoxy-1H-1,3-benzodiazole-5-carbonyl)-5-fluoropiperidin-3-amine | 1.83 | 1 | 654.4 |
| 390 | 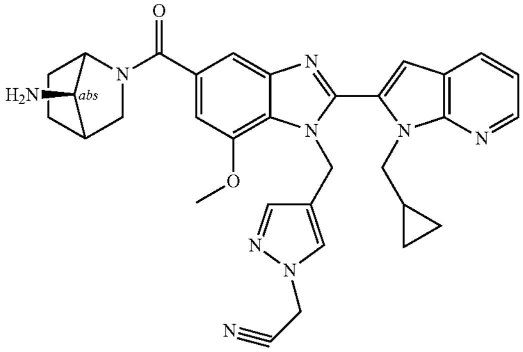 [SMILES: COc1cc(C(=O)N2CC3CCC2[C@@H]3N)cc2nc(-c3cc4cccnc4n3CC3CC3)n(Cc3cnn(CC#N)c3)c12] | 2-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]acetonitrile | 1.25 | 2 | 576.2 |
| 391 | 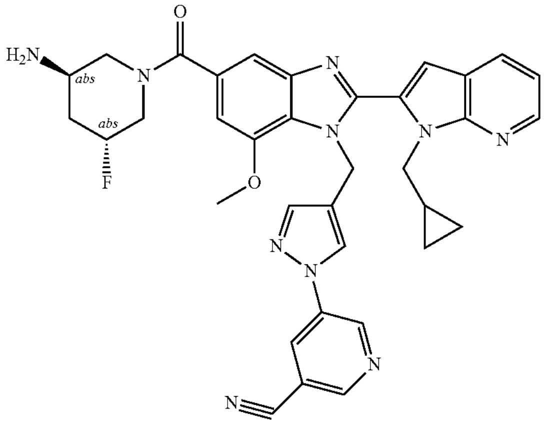 [SMILES: COc1cc(C(=O)N2C[C@H](N)C[C@@H](F)C2)cc2nc(-c3cc4cccnc4n3CC3CC3)n(Cc3cnn(-c4cncc(C#N)c4)c3)c12] | 5-[4-({5-[(3R,5R)-3-amino-5-fluoropiperidine-1-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]pyridine-3-carbonitrile | 1.59 | 1 | 645.1 |

TABLE 7-continued

| Ex# | Structure | Name | LC/MS Rt (min) | LC/MS Method | M + H (obs ion) |
|---|---|---|---|---|---|
| 392 | 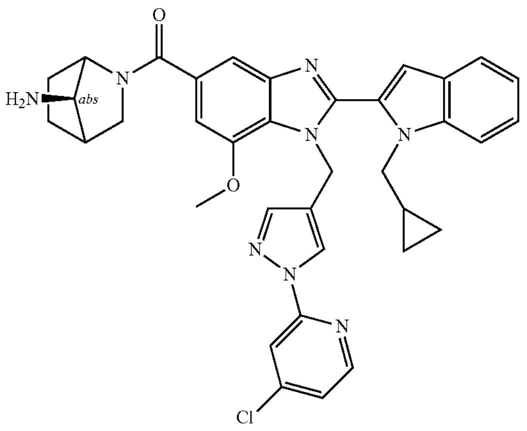 [SMILES: COc1cc(C(=O)N2CC3CCC2[C@@H]3N)cc2nc(-c3cc4ccccc4n3CC3CC3)n(Cc3cnn(-c4cc(Cl)ccn4)c3)c12] | (7R)-2-(1-{[1-(4-chloropyridin-2-yl)-1H-pyrazol-4-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.92 | 2 | 647.2 |
| 393 | 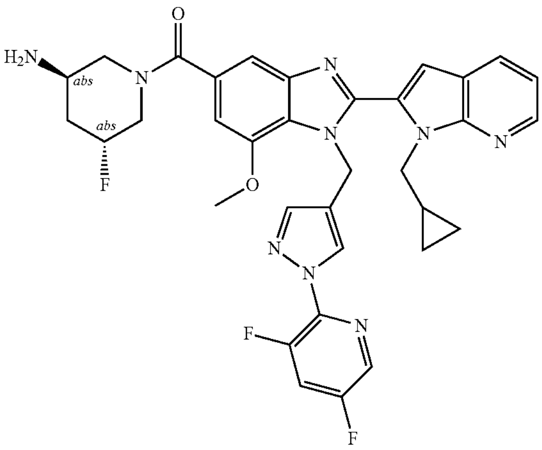 [SMILES: COc1cc(C(=O)N2C[C@H](N)C[C@@H](F)C2)cc2nc(-c3cc4cccnc4n3CC3CC3)n(Cc3cnn(-c4ncc(F)cc4F)c3)c12] | (3R,5R)-1-{2-[1-(cyclopropylmethyl)-1H-pyrrolo[2,3-b]pyridin-2-yl]-1-{[1-(3,5-difluoropyridin-2-yl)-1H-pyrazol-4-yl]methyl}-7-methoxy-1H-1,3-benzodiazole-5-carbonyl}-5-fluoropiperidin-3-amine | 1.53 | 1 | 656.2 |
| 394 | 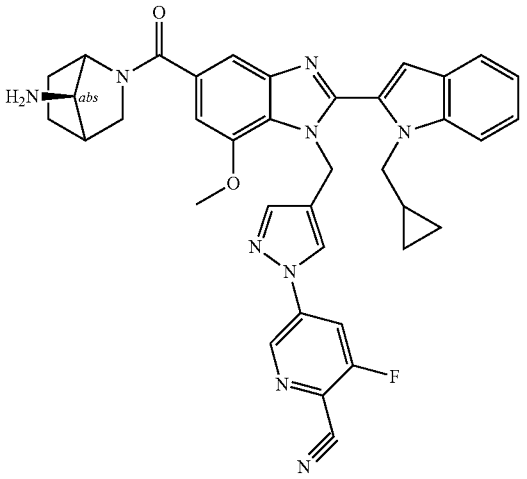 [SMILES: COc1cc(C(=O)N2CC3CCC2[C@@H]3N)cc2nc(-c3cc4ccccc4n3CC3CC3)n(Cc3cnn(-c4cnc(C#N)c(F)c4)c3)c12] | 5-[4-({5-[(7R)-7-amino-2-azabicyclo[2.2.1]heptane-2-carbonyl]-2-[1-(cyclopropyimethyl)-1H-indol-2-yl]-7-methoxy-1H-1,3-benzodiazol-1-yl}methyl)-1H-pyrazol-1-yl]-3-fluoropyridine-2-carbonitrile | 1.79 | 2 | 656.4 |

TABLE 7-continued

| Ex# | Structure | Name | LC/MS Rt (min) | LC/MS Method | M + H (obs ion) |
|---|---|---|---|---|---|
| 395 | 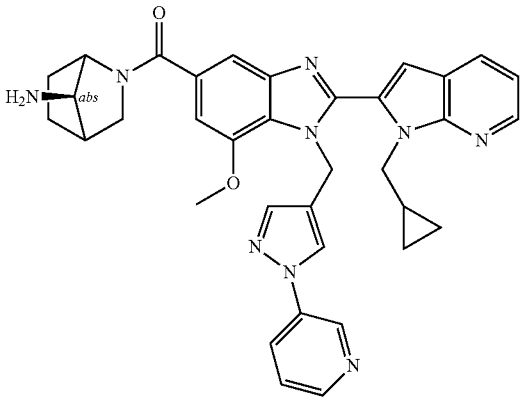 [SMILES: COc1cc(C(=O)N2CC3CCC2[C@@H]3N)cc2nc(-c3cc4cccnc4n3CC3CC3)n(Cc3cnn(-c4cccnc4)c3)c12] | (7R)-2-{2-[1-(cyclopropylmethyl)-1H-pyrrolo[2,3-b]pyridin-2-yl]-7-methoxy-1-{[1-(pyridin-3-yl)-1H-pyrazol-4-yl]methyl}-1H-1,3-benzodiazole-5-carbonyl}-2-azabicyclo[2.2.1]heptan-7-amine | 1.27 | 2 | 614.2 |
| 396 | 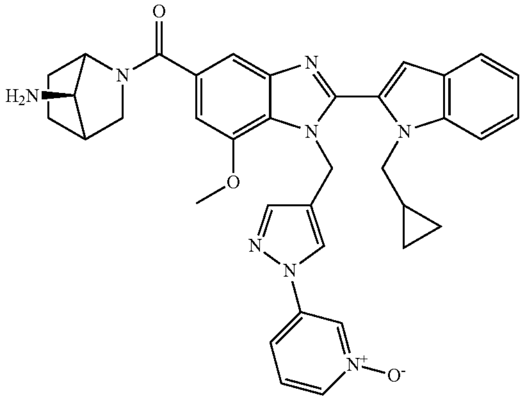 | 3-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridin-1-ium-1-olate | 1.45 | 1 | 629.4 |
| 397 | 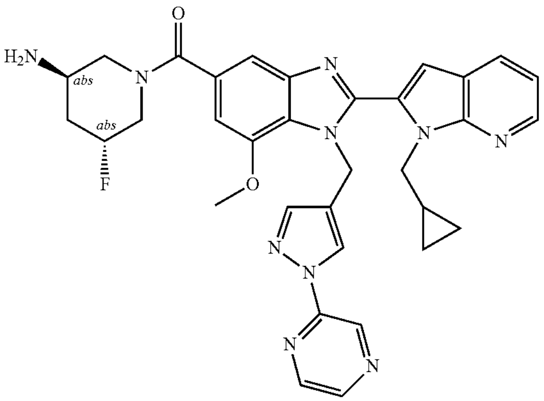 [SMILES: COc1cc(C(=O)N2C[C@H](N)C[C@@H](F)C2)cc2nc(-c3cc4cccnc4n3CC3CC3)n(Cc3cnn(-c4cnccn4)c3)c12] | (3R,5R)-1-{2-[1-(cyclopropylmethyl)-1H-pyrrolo[2,3-b]pyridin-2-yl]-7-methoxy-1-{[1-(pyrazin-2-yl)-1H-pyrazol-4-yl]methyl}-1H-1,3-benzodiazole-5-carbonyl}-5-fluoropiperidin-3-amine | 1.42 | 2 | 621.2 |

TABLE 7-continued

| Ex# | Structure | Name | LC/MS Rt (min) | LC/MS Method | M + H (obs ion) |
|---|---|---|---|---|---|
| 398 | 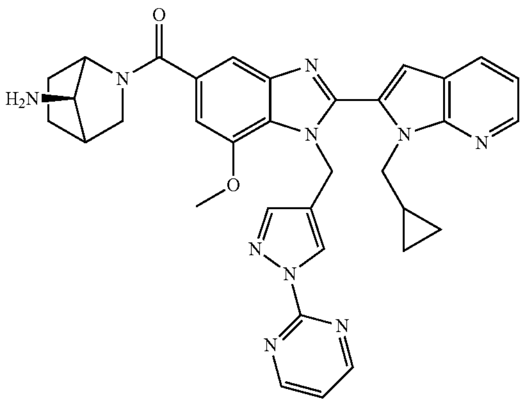 [SMILES: COc1cc(C(=O)N2CC3CCC2[C@@H]3N)cc2nc(-c3cc4cccnc4n3CC3CC3)n(Cc3cnn(-c4ncccn4)c3)c12] | (7R)-2-{2-[1-(cyclopropylmethyl)-1H-pyrrolo[2,3-b]pyridin-2-yl]-7-methoxy-1-{[1-(pyrimidin-2-yl)-1H-pyrazol-4-yl]methyl}-1H-1,3-benzodiazole-5-carbonyl}-2-azabicyclo[2.2.1]heptan-7-amine | 1.34 | 1 | 615.2 |
| 399 | 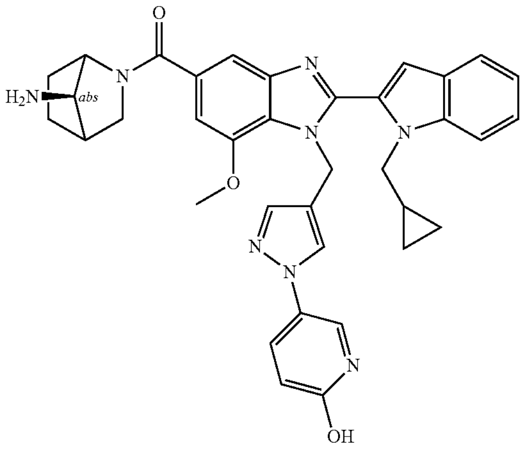 [SMILES: COc1cc(C(=O)N2CC3CCC2[C@@H]3N)cc2nc(-c3cc4ccccc4n3CC3CC3)n(Cc3cnn(-c4ccc(O)nc4)c3)c12] | 5-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]pyridin-2-ol | 1.38 | 1 | 629.5 |
| 400 | 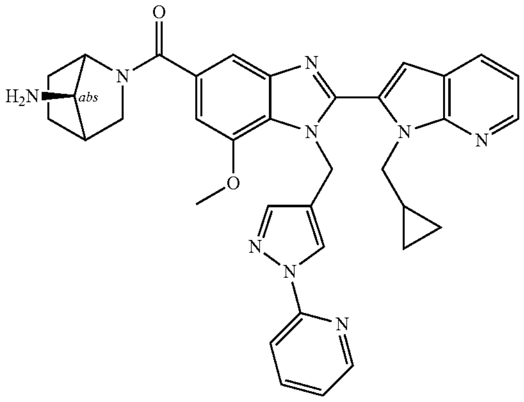 [SMILES: COc1cc(C(=O)N2CC3CCC2[C@@H]3N)cc2nc(-c3cc4cccnc4n3CC3CC3)n(Cc3cnn(-c4ccccn4)c3)c12] | (7R)-2-{2-[1-(cyclopropylmethyl)-1H-pyrrolo[2,3-b]pyridin-2-yl]-7-methoxy-1-{[1-(pyridin-2-yl)-1H-pyrazol-4-yl]methyl}-1H-1,3-benzodiazole-5-carbonyl)-2-azabicyclo[2.2.1]heptan-7-amine | 1.81 | 1 | 613.9 |

TABLE 7-continued

| Ex# | Structure | Name | LC/MS Rt (min) | LC/MS Method | M + H (obs ion) |
|---|---|---|---|---|---|
| 401 | 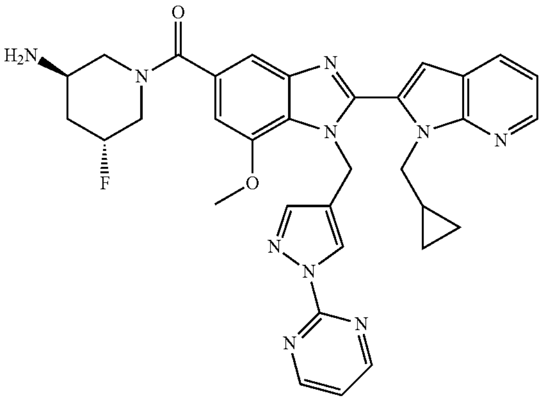 [SMILES: COc1cc(C(=O)N2C[C@H](N)C[C@@H](F)C2)cc2nc(-c3cc4cccnc4n3CC3CC3)n(Cc3cnn(-c4ncccn4)c3)c12] | (3R,5R)-1-{2-[1-(cyclopropylmethyl)-1H-pyrrolo[2,3-b]pyridin-2-yl]-7-methoxy-1-{[1-(pyrimidin-2-yl)-1H-pyrazol-4-yl]methyl}-1H-1,3-benzodiazole-5-carbonyl}-5-fluoropiperidin-3-amine | 1.32 | 1 | 621.4 |
| 402 | 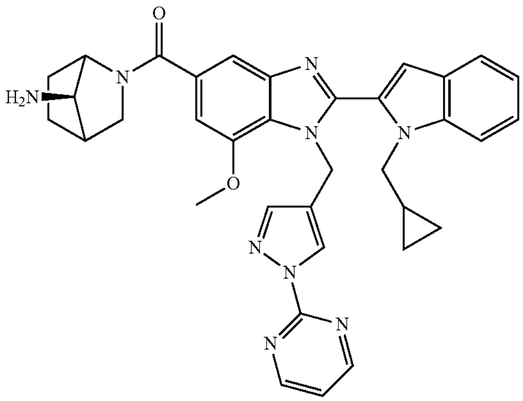 [SMILES: COc1cc(C(=O)N2CC3CCC2[C@@H]3N)cc2nc(-c3cc4ccccc4n3CC3CC3)n(Cc3cnn(-c4ncccn4)c3)c12] | (7R)-2-{2-[1-(cyclopropylmethyl)-1H-indol-2-yl]-7-methoxy-1-{[1-(pyrimidin-2-yl)-1H-pyrazol-4-yl]methyl}-1H-1,3-benzodiazole-5-carbonyl}-2-azabicyclo[2.2.1]heptan-7-amine | 1.63 | 1 | 614.2 |
| 403 | 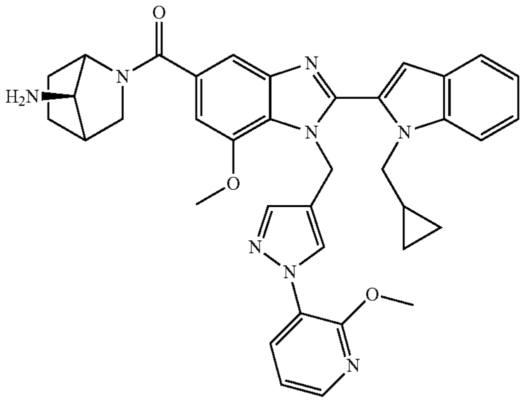 [SMILES: COc1ncccc1-n1cc(Cn2c(-c3cc4ccccc4n3CC3CC3)nc3cc(C(=O)N4CC5CCC4[C@@H]5N)cc(OC)c32)cn1] | (7R)-2-{2-[1-(cyclopropylmethyl)-1H-indol-2-yl]-7-methoxy-1-{[1-(2-methoxypyridin-3-yl)-1H-pyrazol-4-yl]methyl}-1H-1,3-benzodiazole-5-carbonyl)-2-azabicyclo[2.2.1]heptan-7-amine | 1.67 | 2 | 643.5 |

TABLE 7-continued

| Ex# | Structure | Name | LC/MS Rt (min) | LC/MS Method | M + H (obs ion) |
|---|---|---|---|---|---|
| 404 | 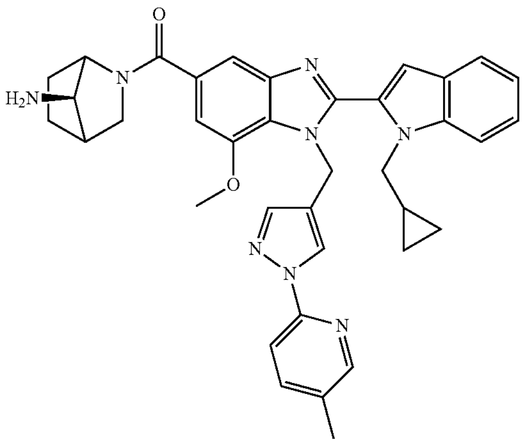 [SMILES: COc1cc(C(=O)N2CC3CCC2[C@@H]3N)cc2nc(-c3cc4ccccc4n3CC3CC3)n(Cc3cnn(-c4ccc(C)cn4)c3)c12] | (7R)-2-{2-[1-(cyclopropylmethyl)-1H-indol-2-yl]-7-methoxy-1-{[1-(5-methylpyridin-2-yl)-1H-pyrazol-4-yl]methyl}-1H-1,3-benzodiazole-5-carbonyl}-2-azabicyclo[2.2.1]heptan-7-amine | 1.83 | 2 | 627 |
| 405 | 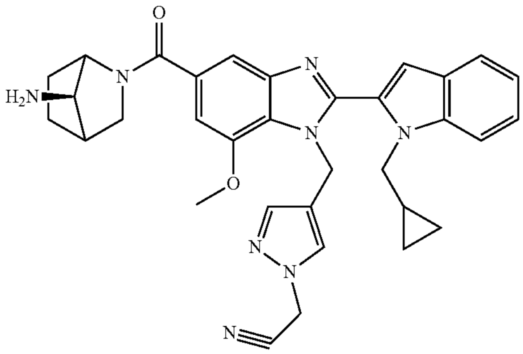 [SMILES: COc1cc(C(=O)N2CC3CCC2[C@@H]3N)cc2nc(-c3cc4ccccc4n3CC3CC3)n(Cc3cnn(CC#N)c3)c12] | 2-[4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1H-pyrazol-1-yl]acetonitrile | 1.59 | 1 | 574.9 |
| 406 | 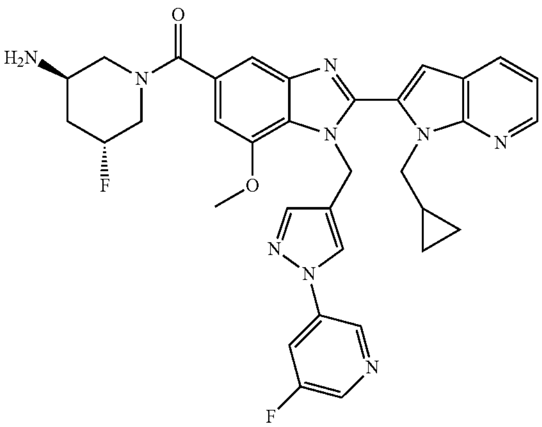 [SMILES: COc1cc(C(=O)N2C[C@H](N)C[C@@H](F)C2)cc2nc(-c3cc4cccnc4n3CC3CC3)n(Cc3cnn(-c4cncc(F)c4)c3)c12] | (3R,5R)-1-{2-[1-(cyclopropylmethyl)-1H-pyrrolo[2,3-b]pyridin-2-yl]-1-{[1-(5-fluoropyridin-3-yl)-1H-pyrazol-4-yl]methyl}-7-methoxy-1H-1,3-benzodiazole-5-carbonyl}-5-fluoropiperidin-3-amine | 2.1 | 2 | 638.2 |

TABLE 7-continued

| Ex# | Structure | Name | LC/MS Rt (min) | LC/MS Method | M + H (obs ion) |
|---|---|---|---|---|---|
| 407 | 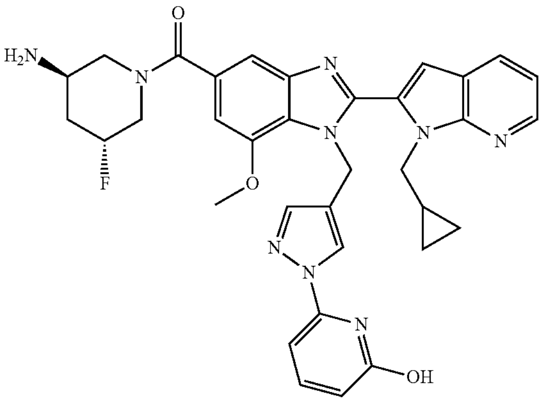 [SMILES: COc1cc(C(=O)N2C[C@H](N)C[C@@H](F)C2)cc2nc(-c3cc4cccnc4n3CC3CC3)n(Cc3cnn(-c4cccc(O)n4)c3)c12] | 6-[4-({5-[(3R,5R)-3-amino-5-fluoropipendine-1-carbonyl]-2-[1-(cyelopropylmethyl)-1H-pyrrolo[2,3-b]pyridin-2-yl]-7-methoxy-1H-1,3-benzodiazol-1-yl}methyl)-1H-pyrazol-1-yl]pyridin-2-ol | 1.38 | 2 | 636.2 |
| 408 | 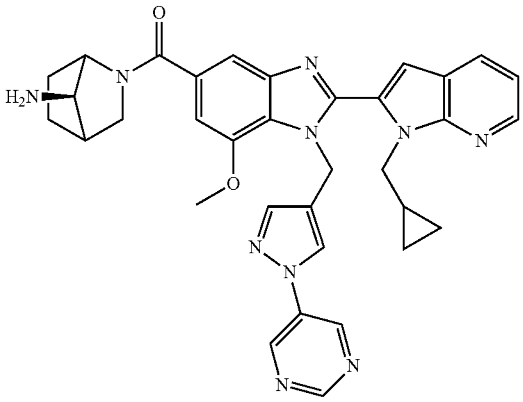 [SMILES: COc1cc(C(=O)N2CC3CCC2[C@@H]3N)cc2nc(-c3cc4cccnc4n3CC3CC3)n(Cc3cnn(-c4cncnc4)c3)c12] | (7R)-2-{2-[1-(cyclopropylmethyl)-1H-pyrrolo[2,3-b]pyridin-2-yl]-7-methoxy-1-{[1-(pyrimidin-5-yl)-1H-pyrazol-4-yl]methyl}-1H-1,3-benzodiazole-5-carbonyl}-2-azabicyclo[2.2.1]heptan-7-amine | 1.45 | 1 | 615.3 |
| 409 | 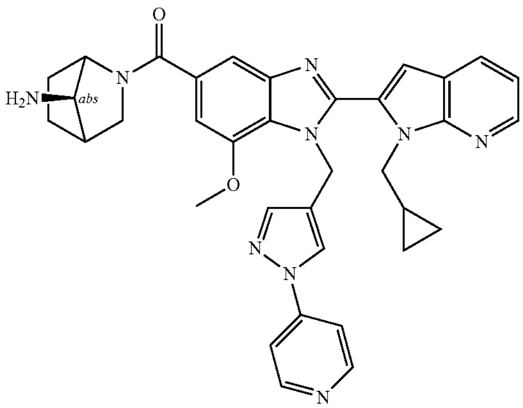 [SMILES: COc1cc(C(=O)N2CC3CCC2[C@@H]3N)cc2nc(-c3cc4cccnc4n3CC3CC3)n(Cc3cnn(-c4ccncc4)c3)c12] | (7R)-2-{2-[1-(cyclopropylmethyl)-1H-pyrrolo[2,3-b]pyridin-2-yl]-7-methoxy-1-{[1-(pyridin-4-yl)-1H-pyrazol-4-yl]methyl}-1H-1,3-benzodiazole-5-carbonyl)-2-azabicyclo[2.2.1]heptan-7-amine | 1.31 | 1 | 614.4 |

TABLE 7-continued

| Ex# | Structure | Name | LC/MS Rt (min) | LC/MS Method | M + H (obs ion) |
|---|---|---|---|---|---|
| 410 | 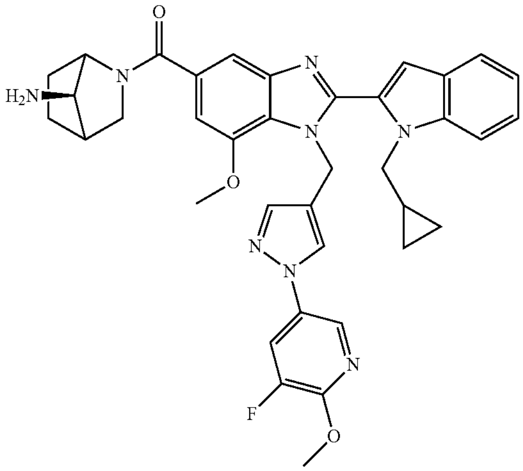 [SMILES: COc1ncc(-n2cc(Cn3c(-c4cc5ccccc5n4CC4CC4)nc4cc(C(=O)N5CC6CCC5[C@@H]6N)cc(OC)c43)cn2)cc1F] | (7R)-2-{2-[1-(cyclopropylmethyl)-1H-indol-2-yl]-1-{[1-(5-fluoro-6-methoxypyridin-3-yl)-1H-pyrazol-4-yl]methyl}-7-methoxy-1H-1,3-benzodiazole-5-carbonyl}-2-azabicyclo[2.2.1]heptan-7-amine | 1.7 | 2 | 661.1 |
| 411 | 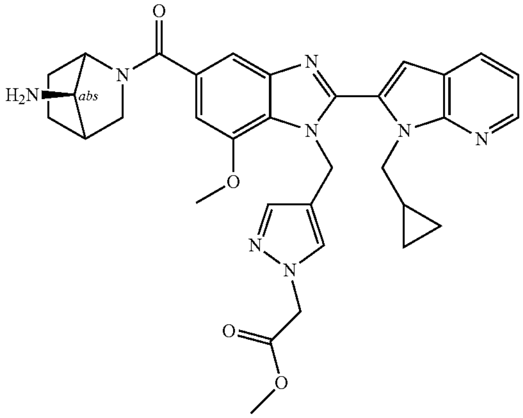 [SMILES: COC(=O)Cn1cc(Cn2c(-c3cc4cccnc4n3CC3CC3)nc3cc(C(=O)N4CC5CCC4[C@@H]5N)cc(OC)c32)cn1] | methyl 2-[4-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-1H-pyrazol-1-yl]acetate | 1.37 | 1 | 609.2 |

Example 412 to Example 472 in Table 8 were prepared as described in the general procedures given for Example 88 to

TABLE 8

| Ex# | Structure | Name | LC/MS Rt (min) | LC/MS Method | M + H (obs ion) |
|---|---|---|---|---|---|
| 412 | 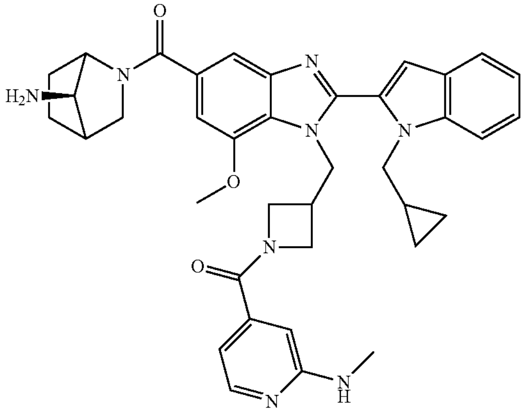 [SMILES: CNc1cc(C(=O)N2CC(Cn3c(-c4cc5ccccc5n4CC4CC4)nc4cc(C(=O)N5CC6CCC5[C@@H]6N)cc(OC)c43)C2)ccn1] | (7R)-2-{2-[1-(cyclopropylmethyl)-1H-indol-2-yl]-7-methoxy-1-({1-[2-(methylamino)pyridine-4-carbonyl]azetidin-3-yl}methyl)-1H-1,3-benzodiazole-5-carbonyl}-2-azabicyclo[2.2.1]heptan-7-amine | 1.42 | 1 | 659.4 |

TABLE 8-continued

| Ex# | Structure | Name | LC/MS Rt (min) | LC/MS Method | M + H (obs ion) |
|---|---|---|---|---|---|
| 413 | 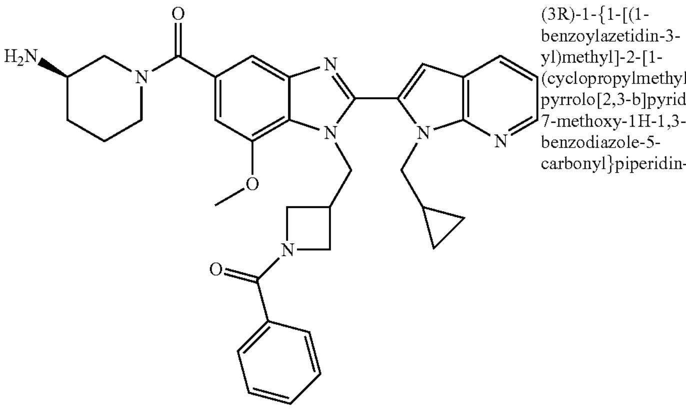 | (3R)-1-{1-[(1-benzoylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}piperidin-3-amine | 1.35 | 1 | 618.2 |
| 414 | 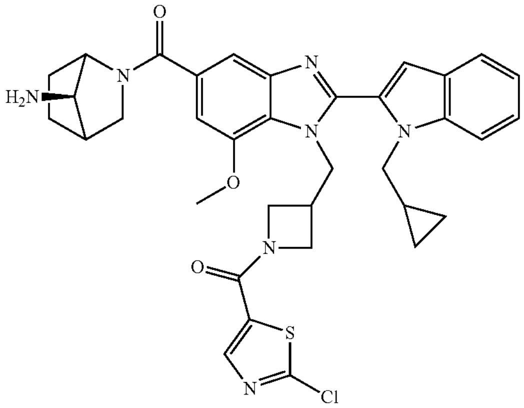 [SMILES: COc1cc(C(=O)N2CC3CCC2[C@@H]3N)cc2nc(-c3cc4ccccc4n3CC3CC3)n(CC3CN(C(=O)c4cnc(Cl)s4)C3)c12] | (7R)-2-(1-{[1-(2-chloro-1,3-thiazole-5-carbonyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.78 | 1 | 670.1 |
| 415 | 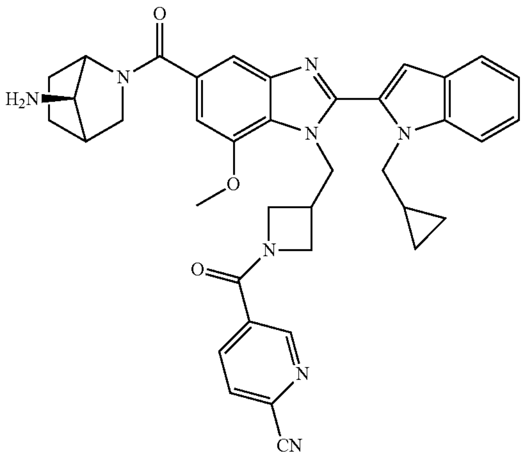 [SMILES: COc1cc(C(=O)N2CC3CCC2[C@@H]3N)cc2nc(-c3cc4ccccc4n3CC3CC3)n(CC3CN(C(=O)c4ccc(C#N)nc4)C3)c12] | 5-[3-({5-[(7R)-7-amino-2-azabicyclo[2.2.1]heptane-2-carbonyl]-2-{1-(cyclopropylmethyl)-1H-indol-2-yl]-7-methoxy-1H-1,3-benzodiazol-1-yl}methyl)azetidine-1-carbonyl]pyridine-2-carbonitrile | 1.51 | 1 | 655.4 |

TABLE 8-continued

| Ex# | Structure | Name | LC/MS Rt (min) | LC/MS Method | M + H (obs ion) |
|---|---|---|---|---|---|
| 416 | 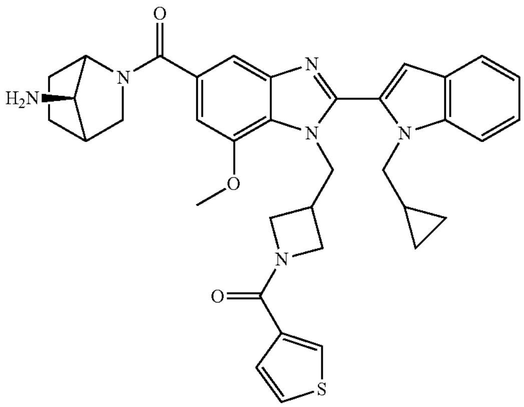 [SMILES: COc1cc(C(=O)N2CC3CCC2[C@@H]3N)cc2nc(-c3cc4ccccc4n3CC3CC3)n(CC3CN(C(=O)c4ccsc4)C3)c12] | (7R)-2-{2-[1-(cyclopropylmethyl)-1H-indol-2-yl]-7-methoxy-1-{[1-(thiophene-3-carbonyl)azetidin-3-yl]methyl}-1H-1,3-benzodiazole-5-carbonyl}-2-azabicyclo[2.2.1]heptan-7-amine | 1.74 | 1 | 635 |
| 417 | 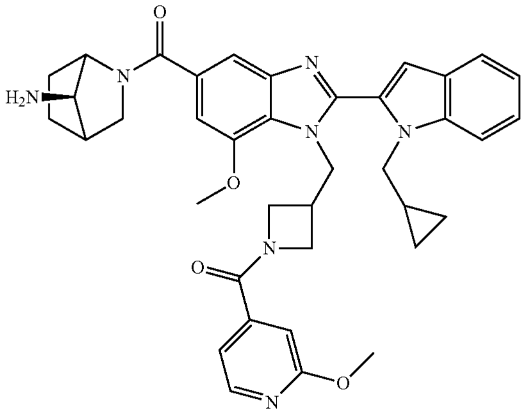 [SMILES: COc1cc(C(=O)N2CC(Cn3c(-c4cc5ccccc5n4CC4CC4)nc4cc(C(=O)N5CC6CCC5[C@@H]6N)cc(OC)c43)C2)ccn1] | (7R)-2-{2-[1-(cyclopropylmethyl)-1H-indol-2-yl]-7-methoxy-1-{[1-(2-methoxypyridine-4-carbonyl)azetidin-3-yl]methyl}-1H-1,3-benzodiazole-5-carbonyl}-2-azabicyclo[2.2.1]heptan-7-amine | 1.74 | 1 | 660 |
| 418 | 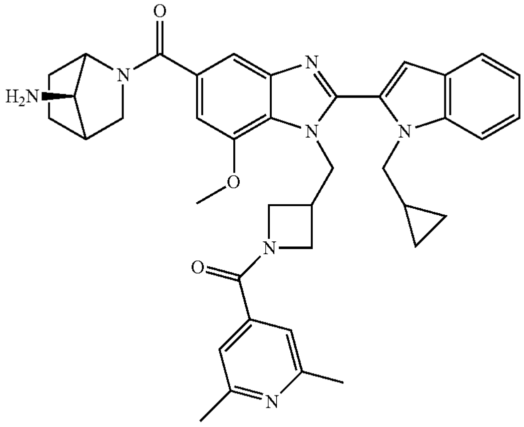 [SMILES: COc1cc(C(=O)N2CC3CCC2[C@@H]3N)cc2nc(-c3cc4ccccc4n3CC3CC3)n(CC3CN(C(=O)c4cc(C)nc(C)c4)C3)c12] | (7R)-2-{2-[1-(cyclopropylmethyl)-1H-indol-2-yl]-1-{[1-(2,6-dimethylpyridine-4-carbonyl)azetidin-3-yl]methyl}-7-methoxy-1H-1,3-benzodiazole-5-carbonyl}-2-azabicyclo[2.2.1]heptan-7-amine | 1.65 | 1 | 658 |

TABLE 8-continued

| Ex# | Structure | Name | LC/MS Rt (min) | LC/MS Method | M + H (obs ion) |
|---|---|---|---|---|---|
| 419 | 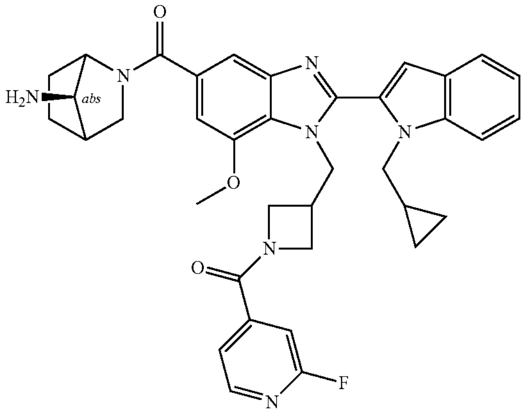 [SMILES: COc1cc(C(=O)N2CC3CCC2[C@@H]3N)cc2nc(-c3cc4ccccc4n3CC3CC3)n(CC3CN(C(=O)c4ccnc(F)c4)C3)c12] | (7R)-2-{2-[1-(cyclopropylmethyl)-1H-indol-2-yl]-1-{[1-(2-fluoropyridine-4-carbonyl)azetidin-3-yl]methyl}-7-methoxy-1H-1,3-benzodiazole-5-carbonyl}-2-azaticyclo[2.2.1]heptan-7-amine | 1.71 | 1 | 648.2 |
| 420 | 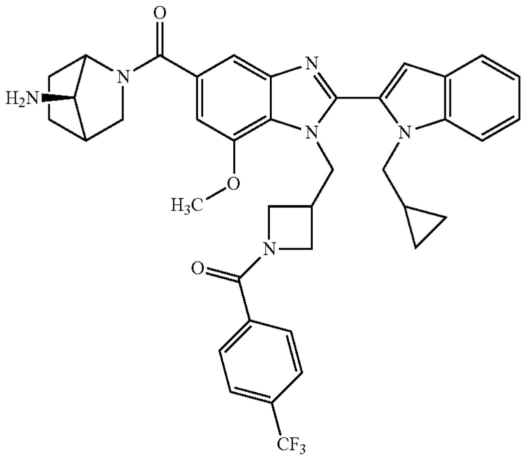 [SMILES: COc1cc(C(=O)N2CC3CCC2[C@@H]3N)cc2nc(-c3cc4ccccc4n3CC3CC3)n(CC3CN(C(=O)c4ccc(C(F)(F)F)cc4)C3)c12] | (7R)-2-{2-[1-(cyclopropylmethyl)-1H-indol-2-yl]-7-methoxy-1-({1-[4-(trifluoromethyl)benzoyl]azetidin-3-yl}methyl)-1H-1,3-benzodiazole-5-carbonyl}-2-azabicyclo[2.2.1]heptan-7-amine | 1.71 | 2 | 697.4 |
| 421 | 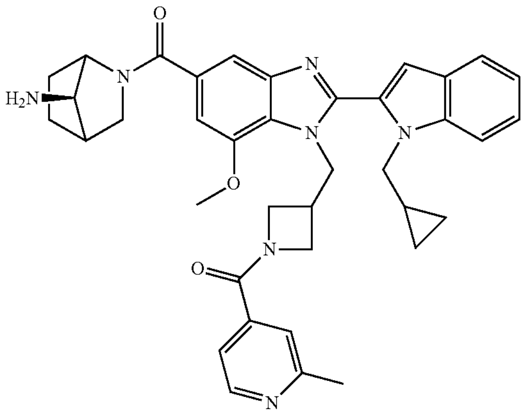 [SMILES: COc1cc(C(=O)N2CC3CCC2[C@@H]3N)cc2nc(-c3cc4ccccc4n3CC3CC3)n(CC3CN(C(=O)c4ccnc(C)c4)C3)c12] | (7R)-2-{2-[1-(cyclopropylmethyl)-1H-indol-2-yl]-7-methoxy-1-{[1-(2-methylpyridine-4-carbonyl)azetidin-3-yl]methyl}-1H-1,3-benzodiazole-5-carbonyl}-2-azabicyclo[2.2.1]heptan-7-amine | 1.06 | 2 | 644.3 |

TABLE 8-continued

| Ex# | Structure | Name | LC/MS Rt (min) | LC/MS Method | M + H (obs ion) |
|---|---|---|---|---|---|
| 422 | 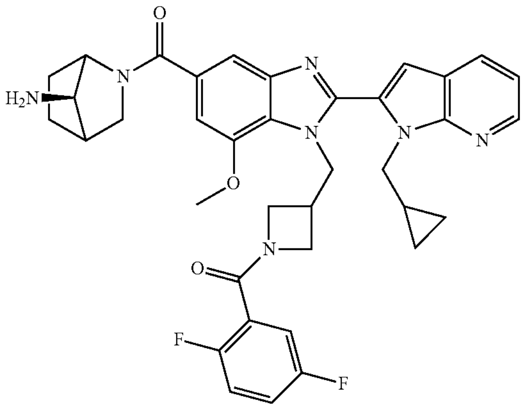 [SMILES: COc1cc(C(=O)N2CC3CCC2[C@@H]3N)cc2nc(-c3cc4cccnc4n3CC3CC3)n(CC3CN(C(=O)c4cc(F)ccc4F)C3)c12] | (7R)-2-{2-[1-(cyclopropylmethyl)-1H-pyrrolo[2,3-b]pyridin-2-yl]-1-{[1-(2,5-difluorobenzoyl)azetidin-3-yl]methyl}-7-methoxy-1H-1,3-benzodiazole-5-carbonyl}-2-azabicyclo[2.2.1]heptan-7-amine | 1.26 | 2 | 666.2 |
| 423 | 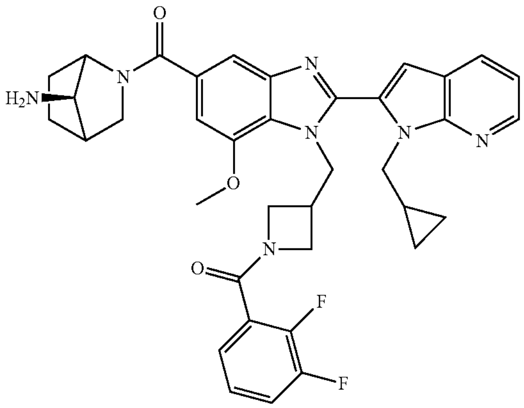 [SMILES: COc1cc(C(=O)N2CC3CCC2[C@@H]3N)cc2nc(-c3cc4cccnc4n3CC3CC3)n(CC3CN(C(=O)c4cccc(F)c4F)C3)c12] | (7R)-2-{2-[1-(cyclopropylmethyl)-1H-pyrrolo[2,3-b]pyridin-2-yl]-1-{[1-(2,3-difluorobenzoyl)azetidin-3-yl]methyl}-7-methoxy-1H-1,3-benzodiazole-5-carbonyl}-2-azabicyclo[2.2.1]heptan-7-amine | 1.46 | 1 | 666.2 |
| 424 | 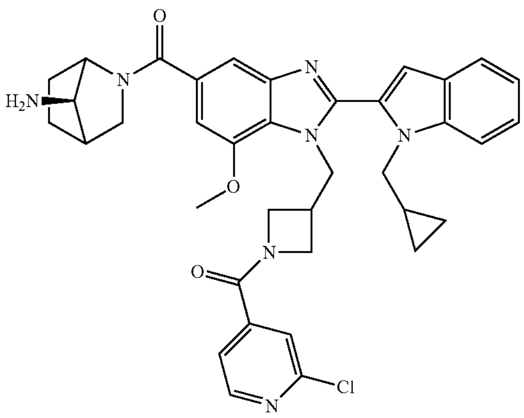 [SMILES: COc1cc(C(=O)N2CC3CCC2[C@@H]3N)cc2nc(-c3cc4ccccc4n3CC3CC3)n(CC3CN(C(=O)c4ccnc(Cl)c4)C3)c12] | (7R)-2-(1-{[1-(2-chloropyridine-4-carbonyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.54 | 1 | 664.3 |

TABLE 8-continued

| Ex# | Structure | Name | LC/MS Rt (min) | LC/MS Method | M + H (obs ion) |
|---|---|---|---|---|---|
| 425 | 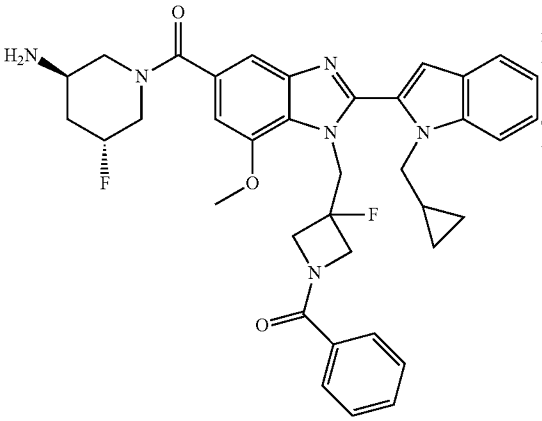 | (3R,5R)-1-{1-[(1-benzoyl-3-fluoroazetidin-3-yl)methyl]-2-[1-(cyclopropylmethyl)-1H-indol-2-yl]-7-methoxy-1H-1,3-benzodiazole-5-carbonyl}-5-fluoropiperidin-3-amine | 1.79 | 1 | 653.2 |
| 426 | 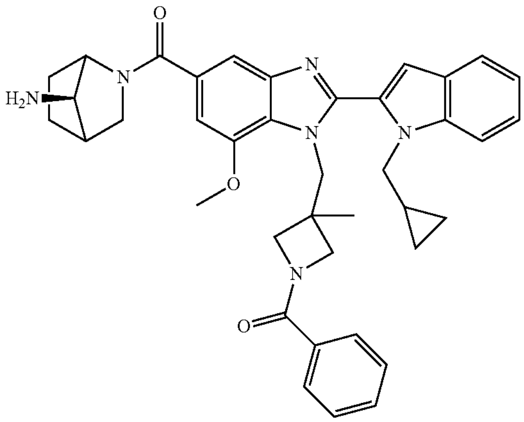 [SMILES: COc1cc(C(=O)N2CC3CCC2[C@@H]3N)cc2nc(-c3cc4ccccc4n3CC3CC3)n(CC3(C)CN(C(=O)c4ccccc4)C3)c12] | (7R)-2-{1-[(1-benzoyl-3-methylazetidin-3-yl)methyl]-2-[1-(cyclopropylmethyl)-1H-indol-2-yl]-7-methoxy-1H-1,3-benzodiazole-5-carobnyl}-2-azabicyclo[2.2.1]heptan-7-amine | 1.69 | 1 | 643.5 |
| 427 | 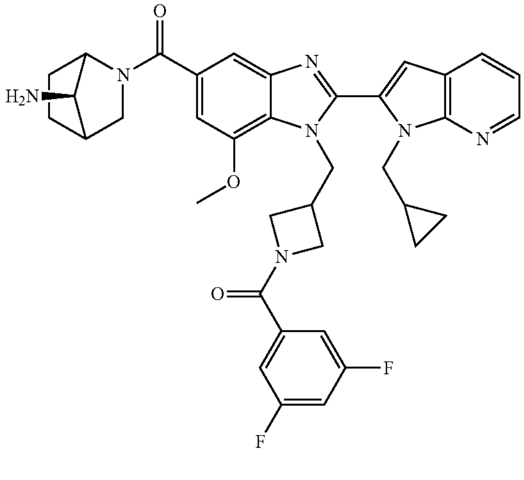 [SMILES: COc1cc(C(=O)N2CC3CCC2[C@@H]3N)cc2nc(-c3cc4cccnc4n3CC3CC3)n(CC3CN(C(=O)c4cc(F)cc(F)c4)C3)c12] | (7R)-2-{2-[1-(cyclopropylmethyl)-1H-pyrrolo[2,3-b]pyridin-2-yl]-1-{[1-(3,5-difluorobenzoyl)azetidin-3-yl]methyl}-7-methoxy-1H-1,3-benzodiazole-5-carbonyl}-2-azabicyclo[2.2.1]heptan-7-amine | 1.52 | 1 | 666.2 |

TABLE 8-continued

| Ex# | Structure | Name | LC/MS Rt (min) | LC/MS Method | M + H (obs ion) |
|---|---|---|---|---|---|
| 428 | 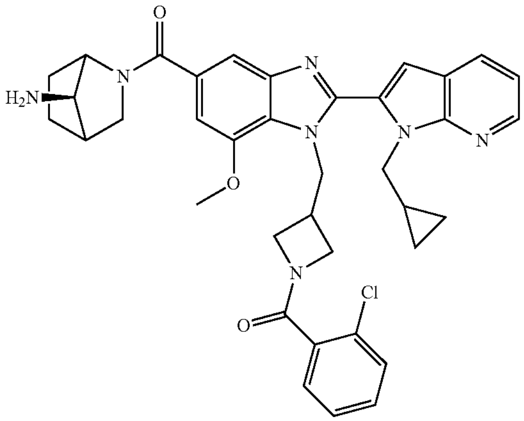 [SMILES: COc1cc(C(=O)N2CC3CCC2[C@@H]3N)cc2nc(-c3cc4cccnc4n3CC3CC3)n(CC3CN(C(=O)c4ccccc4Cl)C3)c12] | (7R)-2-(1-{[1-(2-chlorobenzoyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.41 | 2 | 664.2 |
| 429 | 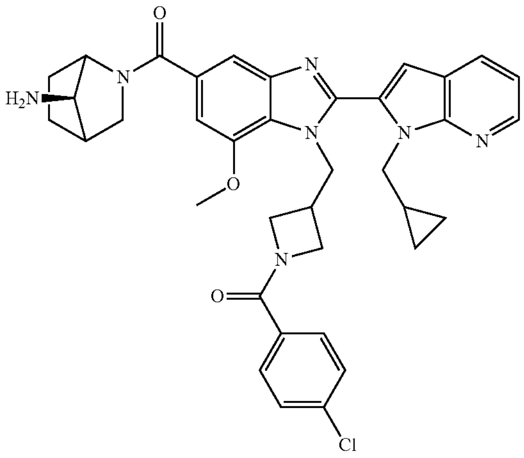 [SMILES: COc1cc(C(=O)N2CC3CCC2[C@@H]3N)cc2nc(-c3cc4cccnc4n3CC3CC3)n(CC3CN(C(=O)c4ccc(Cl)cc4)C3)c12] | (7R)-2-(1-{[1-(4-chlorobenzoyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.42 | 2 | 664.4 |
| 430 | 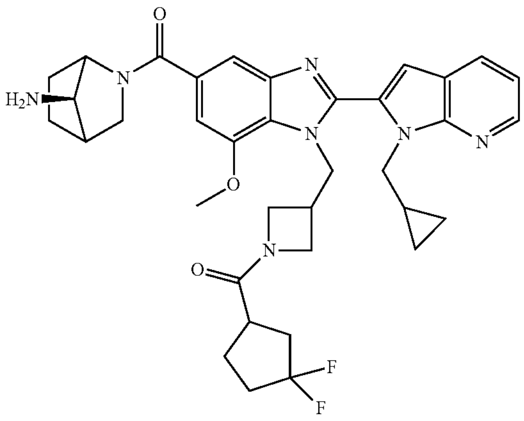 [SMILES: COc1cc(C(=O)N2CC3CCC2[C@@H]3N)cc2nc(-c3cc4cccnc4n3CC3CC3)n(CC3CN(C(=O)C4CCC(F)(F)C4)C3)c12] | (7R)-2-{2-[1-(cyclopropylmethyl)-1H-pyrrolo[2,3-b]pyridin-2-yl]-1-{[1-(3,3-difluorocyclopentanecarbonyl)azetidin-3-yl]methyl}-7-methoxy-1H-1,3-benzodiazole-5-carbonyl}-2-azabicyclo[2.2.1]heptan-7-amine | 1.44 | 1 | 658 |

TABLE 8-continued

| Ex# | Structure | Name | LC/MS Rt (min) | LC/MS Method | M + H (obs ion) |
| --- | --- | --- | --- | --- | --- |
| 431 | 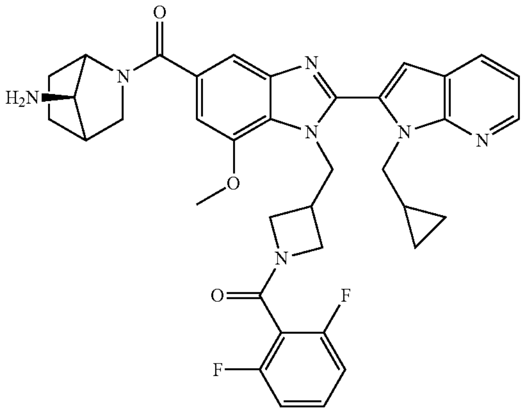 [SMILES: COc1cc(C(=O)N2CC3CCC2[C@@H]3N)cc2nc(-c3cc4cccnc4n3CC3CC3)n(CC3CN(C(=O)c4c(F)cccc4F)C3)c12] | (7R)-2-{2-[1-(cyclopropylmethyl)-1H-pyrrolo[2,3-b]pyridin-2-yl]-1-{[1-(2,6-difluorobenzoyl)azetidin-3-yl]methyl}-7-methoxy-1H-1,3-benzodiazole-5-carbonyl}-2-azabicyclo[2.2.1]heptan-7-amine | 1.41 | 1 | 666.5 |
| 432 | 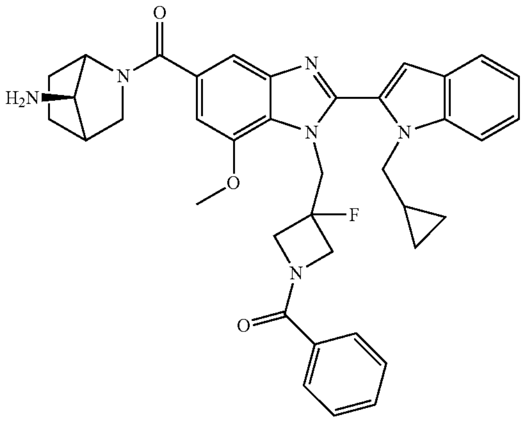 [SMILES: COc1cc(C(=O)N2CC3CCC2[C@@H]3N)cc2nc(-c3cc4ccccc4n3CC3CC3)n(CC3(F)CN(C(=O)c4ccccc4)C3)c12] | (7R)-2-{1-[(1-benzoyl-3-fluoroazetidin-3-yl)methyl]-2-[1-(cyclopropylmethyl)-1H-indol-2-yl]-7-methoxy-1H-1,3-benzodiazole-5-carbonyl}-2-azabicyclo[2.2.1]heptan-7-amine | 1.7 | 1 | 647.3 |
| 433 | 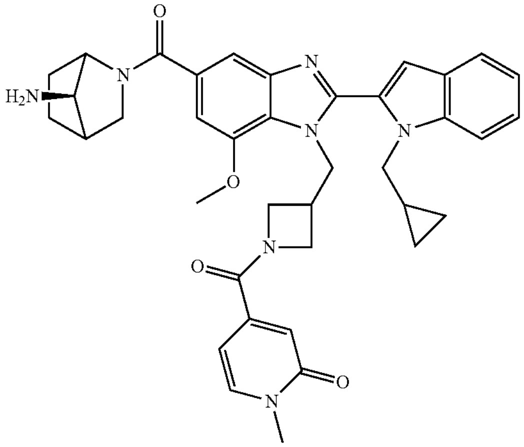 [SMILES: COc1cc(C(=O)N2CC3CCC2[C@@H]3N)cc2nc(-c3cc4ccccc4n3CC3CC3)n(CC3CN(C(=O)c4ccn(C)c(=O)c4)C3)c12] | 4-[3-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]-1-methyl-1,2-dihydropyridin-2-one | 1.12 | 2 | 660.3 |

TABLE 8-continued

| Ex# | Structure | Name | LC/MS Rt (min) | LC/MS Method | M + H (obs ion) |
| --- | --- | --- | --- | --- | --- |
| 434 | 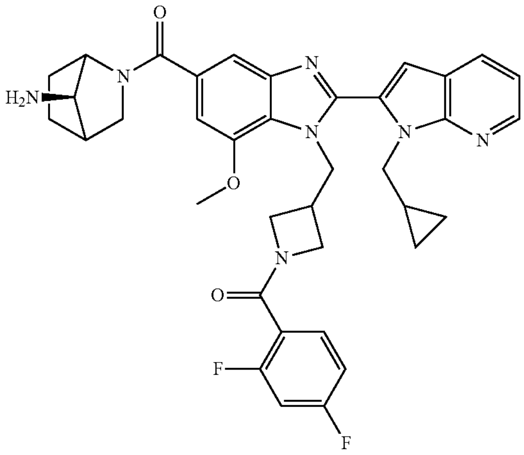 [SMILES: COc1cc(C(=O)N2CC3CCC2[C@@H]3N)cc2nc(-c3cc4cccnc4n3CC3CC3)n(CC3CN(C(=O)c4ccc(F)cc4F)C3)c12] | (7R)-2-{2-[1-(cyclopropylmethyl)-1H-pyrrolo[2,3-b]pyridin-2-yl]-1-{[1-(2,4-difluorobenzoyl)azetidin-3-yl]methyl}-7-methoxy-1H-1,3-benzodiazole-5-carbonyl}-2-azabicyclo[2.2.1]heptan-7-amine | 1.28 | 2 | 666.3 |
| 435 | 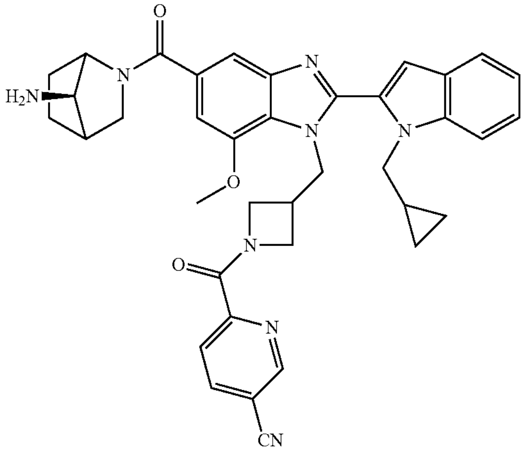 [SMILES: COc1cc(C(=O)N2CC3CCC2[C@@H]3N)cc2nc(-c3cc4ccccc4n3CC3CC3)n(CC3CN(C(=O)c4ccc(C#N)cn4)C3)c12] | 6-[3-({5-[(7R)-7-amino-2-azabicyclo[2.2.1]heptane-2-carobnyl]-2-[1-(cyclopropylmethyl)-1H-indol-2-yl]-7-methoxy-1H-1,3-benzodiazol-1-yl}methyl)azetidine-1-carobnyl]pyridine-3-carbonitrile | 1.59 | 1 | 655.2 |
| 436 | 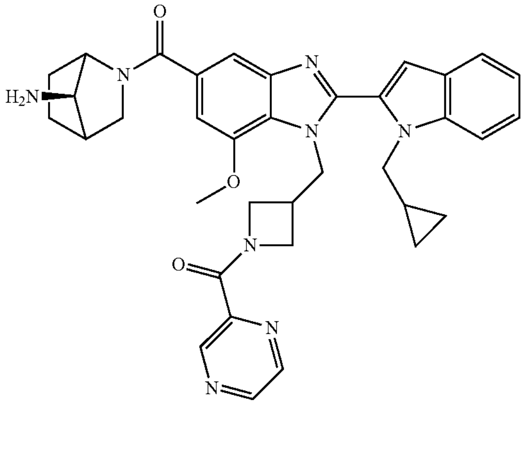 [SMILES: COc1cc(C(=O)N2CC3CCC2[C@@H]3N)cc2nc(-c3cc4ccccc4n3CC3CC3)n(CC3CN(C(=O)c4cnccn4)C3)c12] | (7R)-2-{2-[1-(cyclopropylmethyl)-1H-indol-2-yl]-7-methoxy-1-{[1-(pyrazine-2-carbonyl)azetidin-3-yl]methyl}-1H-1,3-benzodiazole-5-carbonyl}-2-azabicyclo[2.2.1]heptan-7-amine | 1.27 | 2 | 631.2 |

TABLE 8-continued

| Ex# | Structure | Name | LC/MS Rt (min) | LC/MS Method | M + H (obs ion) |
|---|---|---|---|---|---|
| 437 | 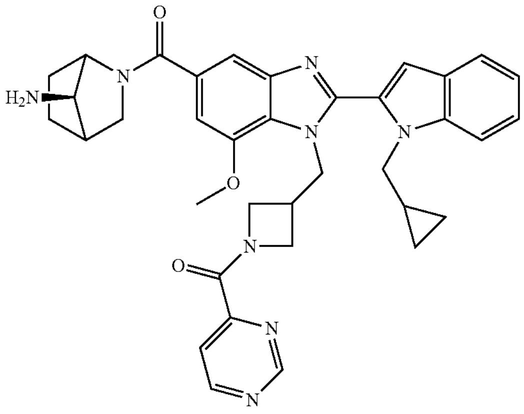 [SMILES: COc1cc(C(=O)N2CC3CCC2[C@@H]3N)cc2nc(-c3cc4ccccc4n3CC3CC3)n(CC3CN(C(=O)c4ccncn4)C3)c12] | (7R)-2-{2-[1-(cyclopropylmethyl)-1H-indol-2-yl]-7-methoxy-1-{[1-(pyrimidine-4-carbonyl)azetidin-3-yl]methyl}-1H-1,3-benzodiazole-5-carbonyl}-2-azabicyclo[2.2.1]heptan-7-amine | 1.46 | 1 | 631.1 |
| 438 | 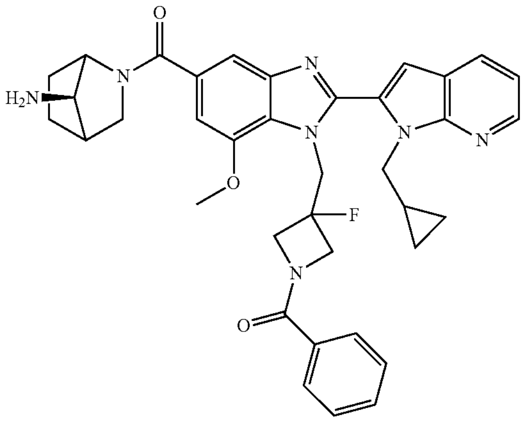 [SMILES: COc1cc(C(=O)N2CC3CCC2[C@@H]3N)cc2nc(-c3cc4cccnc4n3CC3CC3)n(CC3(F)CN(C(=O)c4ccccc4)C3)c12] | (7R)-2-{1-[(1-benzoyl-3-fluoroazetidin-3-yl)methyl]-2-[1-(cyclopropymethyl)-1H-pyrrolo[2,3-b]pyridin-2-yl]-7-methoxy-1H-1,3-benzodiazole-5-carbonyl}-2-azabicyclo[2.2.1]heptan-7-amine | 1.54 | 1 | 648.3 |
| 439 | 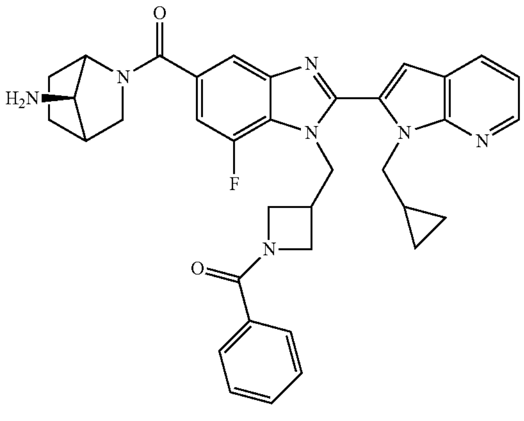 [SMILES: N[C@@H]1C2CCC1N(C(=O)c1cc(F)c3c(c1)nc(-c1cc4cccnc4n1CC1CC1)n3CC1CN(C(=O)c3ccccc3)C1)C2] | (7R)-2-{1-[(1-benozylazetidin-3-yl)methyl]-2-[1-(cyclopropylmethyl)-1H-pyrrolo[2,3-b]pyridin-2-yl]-7-fluoro-1H-1,3-benzodiazol-5-carbonyl}-2-azabicyclo[2.2.1]heptan-7-amine | 1.27 | 2 | 618.4 |

TABLE 8-continued

| Ex# | Structure | Name | LC/MS Rt (min) | LC/MS Method | M + H (obs ion) |
|---|---|---|---|---|---|
| 440 | 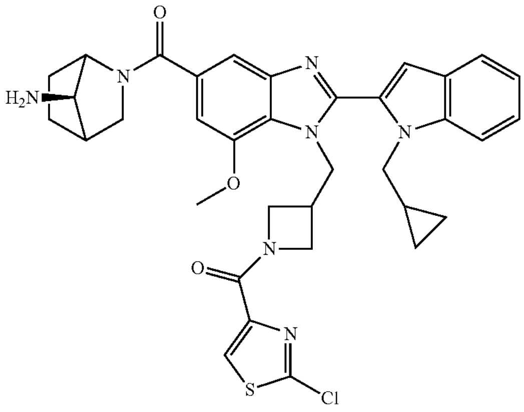 [SMILES: COc1cc(C(=O)N2CC3CCC2[C@@H]3N)cc2nc(-c3cc4ccccc4n3CC3CC3)n(CC3CN(C(=O)c4csc(Cl)n4)C3)c12] | (7R)-2-(1-{[1-(2-chloro-1,3-thiazole-4-carbonyl)azetidin-3-yl]methyl}-2-[1-(cyclopropylmethyl)-1H-indol-2-yl]-7-methoxy-1H-1,3-benzodiazole-4-carbonyl)-2-azabicyclo[2.2.1]heptan-7-amine | 1.86 | 1 | 669.9 |
| 441 | 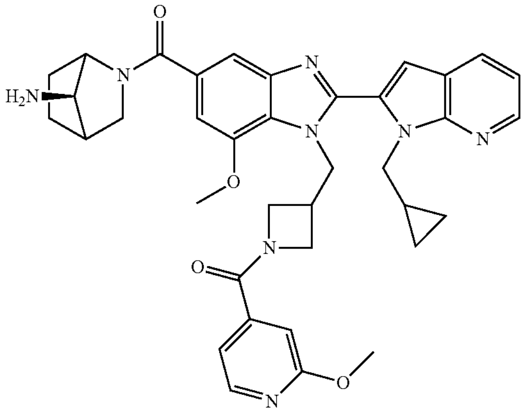 [SMILES: COc1cc(C(=O)N2CC(Cn3c(-c4cc5cccnc5n4CC4CC4)nc4cc(C(=O)N5CC6CCC5[C@@H]6N)cc(OC)c43)C2)ccn1] | (7R)-2-{2-[1-(cyclopropylmethyl)-1H-pyrrolo[2,3-b]pyridin-2-yl]-7-methoxy-1-{[1-(2-methoxypyridine-4-carbonyl)azetidin-3-yl]methyl}-1H-1,3-benzodiazole-5-carbonyl}-2-azabicyclo[2.2.1]heptan-7-amine | 1.18 | 2 | 661.4 |
| 442 | 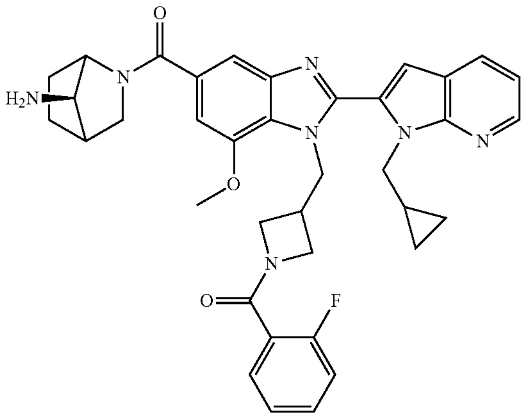 [SMILES: COc1cc(C(=O)N2CC3CCC2[C@@H]3N)cc2nc(-c3cc4cccnc4n3CC3CC3)n(CC3CN(C(=O)c4ccccc4F)C3)c12] | (7R)-2-{2-[1-(cyclopropylmethyl)-1H-pyrrolo[2,3-b]pyridin-2-yl]-1-{[1-(2-fluorobenzoyl)azetidin-3-yl]methyl}-7-methoxy-1H-1,3-benzodiazole-5-carbonyl}-2-azabicyclo[2.2.1]heptan-7-amine | 1.39 | 1 | 648.2 |

TABLE 8-continued

| Ex# | Structure | Name | LC/MS Rt (min) | LC/MS Method | M + H (obs ion) |
|---|---|---|---|---|---|
| 443 | 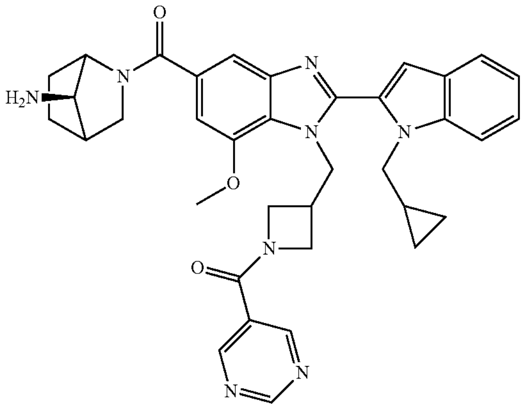 [SMILES: COc1cc(C(=O)N2CC3CCC2[C@@H]3N)cc2nc(-c3cc4ccccc4n3CC3CC3)n(CC3CN(C(=O)c4cncnc4)C3)c12] | (7R)-2-{2-[1-(cyclopropylmethyl)-1H-indol-2-yl]-7-methoxy-1-{[1-(pyrimidine-5-carbonyl)azetidin-3-yl]methyl}-1H-1,3-benzodiazole-5-carbonyl}-2-azabicyclo[2.2.1]heptan-7-amine | 1.33 | 1 | 631 |
| 444 | 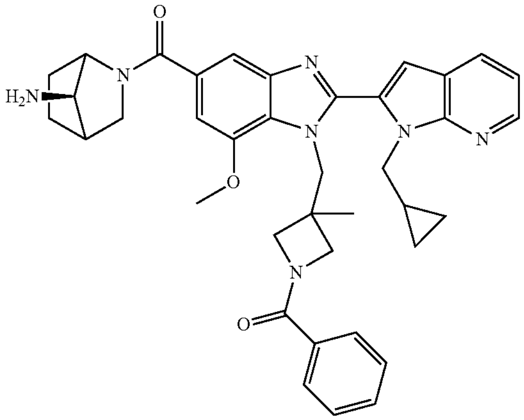 [SMILES: COc1cc(C(=O)N2CC3CCC2[C@@H]3N)cc2nc(-c3cc4cccnc4n3CC3CC3)n(CC3(C)CN(C(=O)c4ccccc4)C3)c12] | (7R)-2-{1-[(1-benzoyl-3-methylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-2-azabicyclo[2.2.1]heptan-7-amine | 1.39 | 1 | 644.5 |
| 445 | 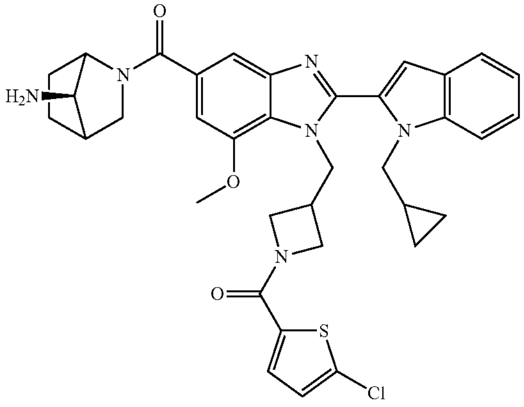 [SMILES: COc1cc(C(=O)N2CC3CCC2[C@@H]3N)cc2nc(-c3cc4ccccc4n3CC3CC3)n(CC3CN(C(=O)c4ccc(Cl)s4)C3)c12] | (7R)-2-(1-{[1-(5-chlorothiophene-2-carbonyl)azetidin-3-yl]methyl}-2-[1-(cyclopropylmethyl)-1H-indol-2-yl]-7-methoxy-1H-1,3-benzodiazole-5-carbonyl)-2-azabicyclo[2.2.1]heptan-7-amine | 1.78 | 1 | 669.2 |

TABLE 8-continued

| Ex# | Structure | Name | LC/MS Rt (min) | LC/MS Method | M + H (obs ion) |
|---|---|---|---|---|---|
| 446 | 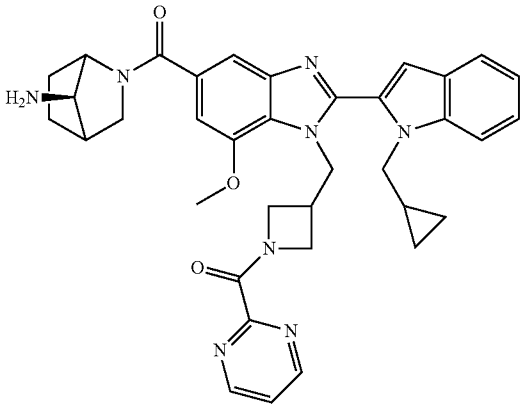 [SMILES: COc1cc(C(=O)N2CC3CCC2[C@@H]3N)cc2nc(-c3cc4ccccc4n3CC3CC3)n(CC3CN(C(=O)c4ncccn4)C3)c12] | (7R)-2-{2-[1-(cyclopropylmethyl)-1H-indol-2-yl]-7-methoxy-1-{[1-(pyrimidine-2-carbonyl)azetidin-3-yl]methyl}-1H-1,3-benzodiazole-5-carbonyl}-2-azabicyclo[2.2.1]heptan-7-amine | 1.22 | 2 | 631.4 |
| 447 | 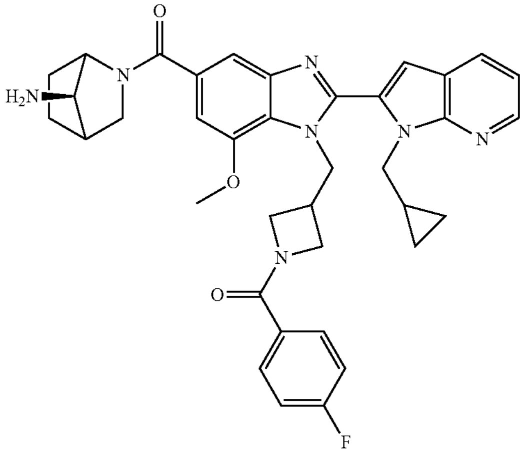 [SMILES: COc1cc(C(=O)N2CC3CCC2[C@@H]3N)cc2nc(-c3cc4cccnc4n3CC3CC3)n(CC3CN(C(=O)c4ccc(F)cc4)C3)c12] | (7R)-2-{2-[1-(cyclopropylmethyl)-1H-pyrrolo[2,3-b]pyridin-2-yl]-1-{[1-(4-fluorobenzoyl)azetidin-3-yl]methyl}-7-methoxy-1H-1,3-benzodiazole-5-carbonyl}-2-azabicyclo[2.2.1]heptan-7-amine | 1.48 | 1 | 648.3 |
| 448 | 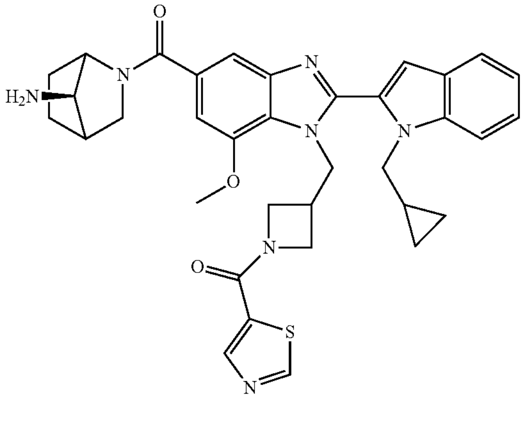 [SMILES: COc1cc(C(=O)N2CC3CCC2[C@@H]3N)cc2nc(-c3cc4ccccc4n3CC3CC3)n(CC3CN(C(=O)c4cncs4)C3)c12] | (7R)-2-{2-[1-(cyclopropylmethyl)-1H-indol-2-yl]-7-methoxy-1-{[1-(1,3-thiazole-5-carbonyl)azetidin-3-yl]methyl}-1H-1,3-benzodiazole-5-carbonyl}-2-azabicyclo[2.2.1]heptan-7-amine | 1.25 | 2 | 636.4 |

TABLE 8-continued

| Ex# | Structure | Name | LC/MS Rt (min) | LC/MS Method | M + H (obs ion) |
|---|---|---|---|---|---|
| 449 | 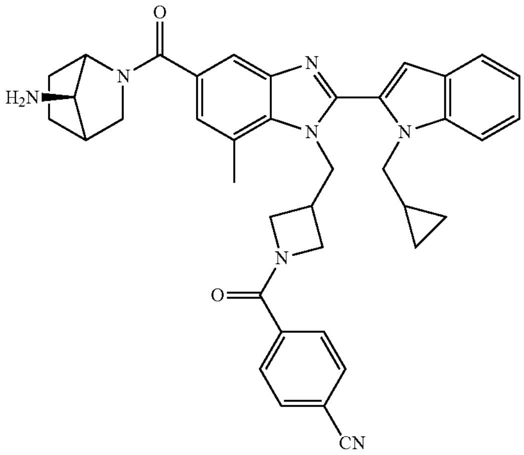 [SMILES: Cc1cc(C(=O)N2CC3CCC2[C@@H]3N)cc2nc(-c3cc4ccccc4n3CC3CC3)n(CC3CN(C(=O)c4ccc(C#N)cc4)C3)c12] | 4-[3-({5-[(7R)-7-amino-2-azabicyclo[2.2.1]heptane-2-carbonyl]-2-[1-(cyclopropylmethyl)-1H-indol-2-yl]-7-methyl-1H-1,3-benzodiazol-1-yl}methyl)azetidine-1-carbonyl]benzonitrile | 1.37 | 2 | 638.4 |
| 450 | 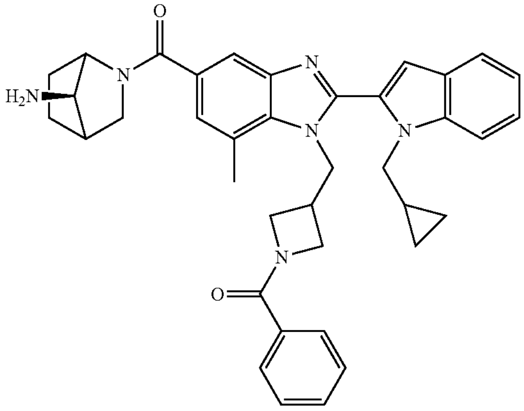 [SMILES: Cc1cc(C(=O)N2CC3CCC2[C@@H]3N)cc2nc(-c3cc4ccccc4n3CC3CC3)n(CC3CN(C(=O)c4ccccc4)C3)c12] | (7R)-2-{1-[(1-benzoylazetidin-3-yl)methyl]-2-[1-(cyclopropylmethyl)-1H-indol-2-yl]-7-methyl-1H-1,3-benzodiazole-5-carbonyl}-2-azabicyclo[2.2.1]heptan-7-amine | 1.55 | 1 | 613.4 |
| 451 | 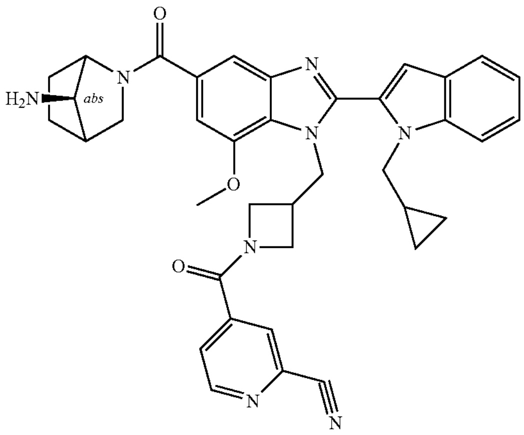 [SMILES: COc1cc(C(=O)N2CC3CCC2[C@@H]3N)cc2nc(-c3cc4ccccc4n3CC3CC3)n(CC3CN(C(=O)c4ccnc(C#N)c4)C3)c12] | 4-[3-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]pyridine-2-carbonitrile | 1.38 | 2 | 655.4 |

TABLE 8-continued

| Ex# | Structure | Name | LC/MS Rt (min) | LC/MS Method | M + H (obs ion) |
|---|---|---|---|---|---|
| 452 | 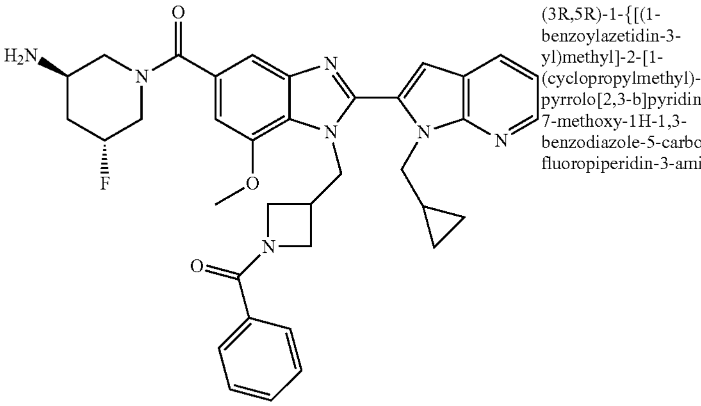 | (3R,5R)-1-{[(1-benzoylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-5-fluoropiperidin-3-amine | 1.37 | 2 | 636 |
| 453 | 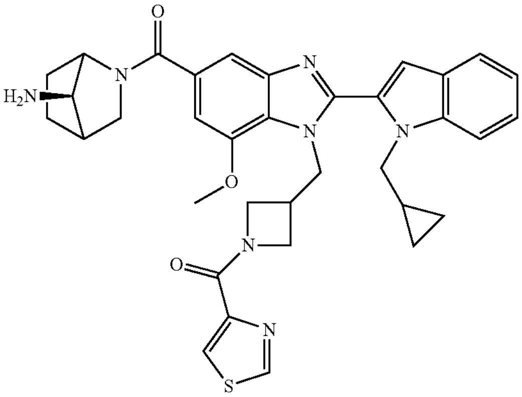 [SMILES: COc1cc(C(=O)N2CC3CCC2[C@@H]3N)cc2nc(-c3cc4ccccc4n3CC3CC3)n(CC3CN(C(=O)c4cscn4)C3)c12] | (7R)-2-{2-[1-(cyclopropylmethyl)-1H-indol-2-yl]-7-methoxy-1-{[1-(1,3-thiazole-4-carbonyl)azetidin-3-yl]methyl}-1H-1,3-benzodiazole-5-carbonyl}-2-azabicyclo[2.2.1]heptan-7-amine | 1.45 | 1 | 636.4 |
| 454 | 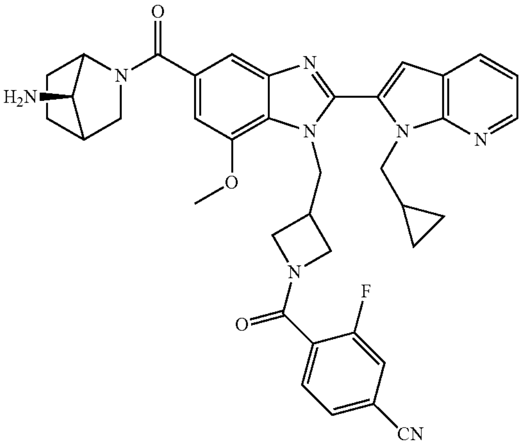 [SMILES: COc1cc(C(=O)N2CC3CCC2[C@@H]3N)cc2nc(-c3cc4cccnc4n3CC3CC3)n(CC3CN(C(=O)c4ccc(C#N)cc4F)C3)c12] | 4-[3-({5-[(7R)-7-amino-2-azabicyclo[2.2.1]heptane-2-carbonyl]-2-(1-(cyclopropylmethyl)-1H-pyrrolo[2,3-b]pyridin-2-yl]-7-methoxy-1H-1,3-benzodiazol-1-yl}methyl)azetidine-1-carbonyl]-3-fluorobenzointrile | 1.5 | 1 | 673.3 |

TABLE 8-continued

| Ex# | Structure | Name | LC/MS Rt (min) | LC/MS Method | M + H (obs ion) |
|---|---|---|---|---|---|
| 455 | 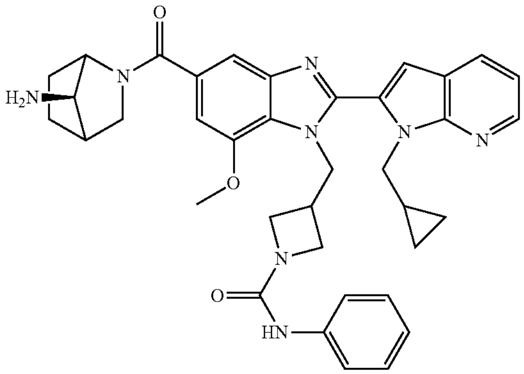 [SMILES: COc1cc(C(=O)N2CC3CCC2[C@@H]3N)cc2nc(-c3cc4cccnc4n3CC3CC3)n(CC3CN(C(=O)Nc4ccccc4)C3)c12] | 3-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)-N-phenylazetidine-1-carboxamide | 1.27 | 2 | 645.3 |
| 456 | 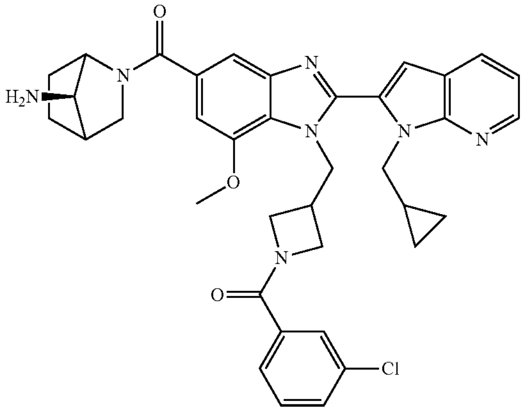 [SMILES: COc1cc(C(=O)N2CC3CCC2[C@@H]3N)cc2nc(-c3cc4cccnc4n3CC3CC3)n(CC3CN(C(=O)c4cccc(Cl)c4)C3)c12] | (7R)-2-(1-{[1-(3-chlorobenzoyl)azetidin-3-yl]methyl}-2-[1-(cyclopropylmethyl)-1H-pyrrolo[2,3-b]pyridin-2-yl]-7-methoxy-1H-1,3-benzodiazole-5-carbonyl)-2-azabicyclo[2.2.1]heptan-7-amine | 1.39 | 2 | 664 |
| 457 | 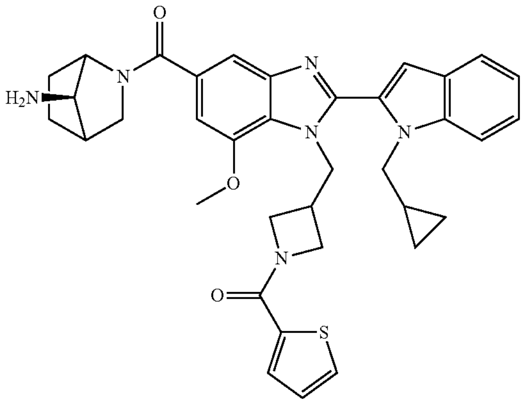 [SMILES: COc1cc(C(=O)N2CC3CCC2[C@@H]3N)cc2nc(-c3cc4ccccc4n3CC3CC3)n(CC3CN(C(=O)c4cccs4)C3)c12] | (7R)-2-{2-[1-(cyclopropylmethyl)-1H-indol-2-yl]-7-methoxy-1-{[1-(thiophene-2-carbonyl)azetidin-3-yl]methyl}-1H-1,3-benzodiazole-5-carbonyl}-2-azabicyclo[2.2.1]heptan-7-amine | 1.76 | 1 | 635.3 |

TABLE 8-continued

| Ex# | Structure | Name | LC/MS Rt (min) | LC/MS Method | M + H (obs ion) |
|---|---|---|---|---|---|
| 458 | 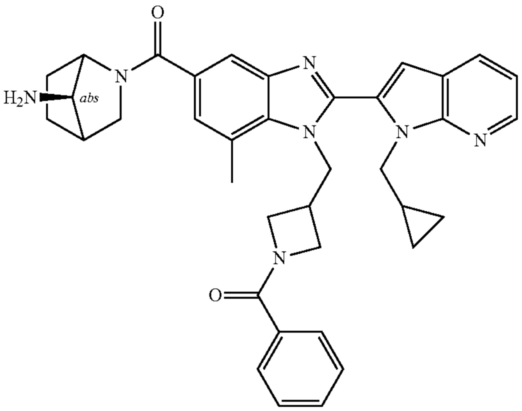 [SMILES: Cc1cc(C(=O)N2CC3CCC2[C@@H]3N)cc2nc(-c3cc4cccnc4n3CC3CC3)n(CC3CN(C(=O)c4ccccc4)C3)c12] | (7R)-2-{1-[(1-benozylazetidin-3-yl)methyl]-2-[1-(cyclopropylmethyl)-1H-pyrrolo[2,3-b]pyridin-2-yl]-7-methyl-1H-1,3-benzodiazole-5-carbonyl}-2-azabicyclo[2.2.1]heptan-7-amine | 1.41 | 1 | 614.4 |
| 459 | 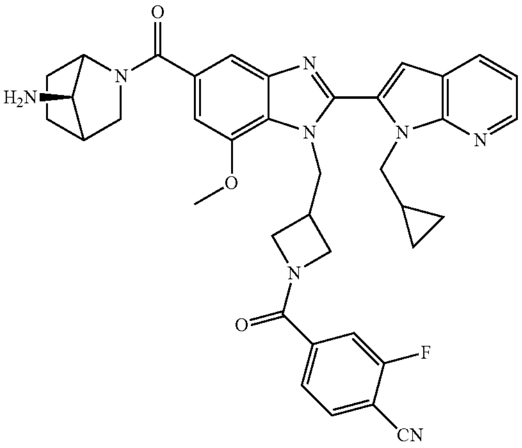 [SMILES: COc1cc(C(=O)N2CC3CCC2[C@@H]3N)cc2nc(-c3cc4cccnc4n3CC3CC3)n(CC3CN(C(=O)c4ccc(C#N)c(F)c4)C3)c12] | 4-[3-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)azetidine-1-carbonyl]-2-fluorobenzonitrile | 1.44 | 1 | 673.2 |
| 460 | 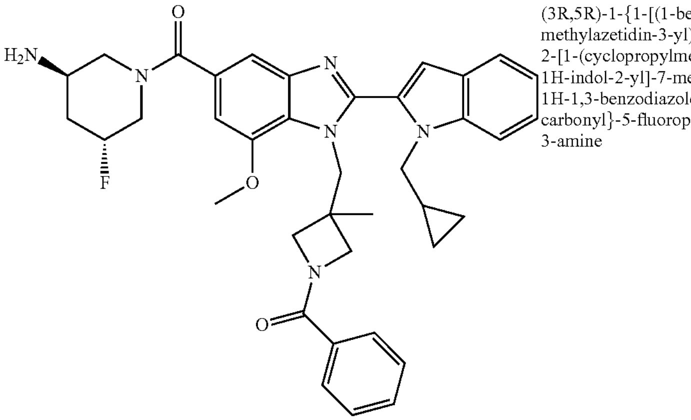 | (3R,5R)-1-{1-[(1-benzoyl-3-methylazetidin-3-yl)methyl]-2-[1-(cyclopropylmethyl)-1H-indol-2-yl]-7-methoxy-1H-1,3-benzodiazole-5-carbonyl}-5-fluoropiperidin-3-amine | 1.76 | 1 | 649.3 |

TABLE 8-continued

| Ex# | Structure | Name | LC/MS Rt (min) | LC/MS Method | M + H (obs ion) |
|---|---|---|---|---|---|
| 461 | 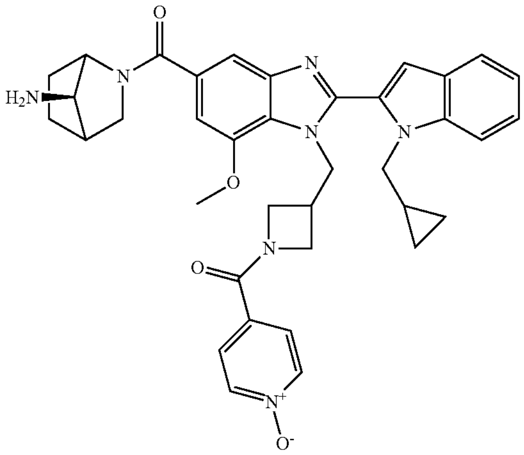 [SMILES: COc1cc(C(=O)N2CC3CCC2[C@@H]3N)cc2nc(-c3cc4ccccc4n3CC3CC3)n(CC3CN(C(=O)c4cc[n+]([O-])cc4)C3)c12] | 4-[3-({5-[(7R)-7-amino-2-azabicyclo[2.2.1]heptane-2-carobnyl]-2-[1-(cyclopropylmethyl)-1H-indol-2-yl]-7-methoxy-1H-1,3-benzodiazol-1-yl}methyl)azetidine-1-carbonyl]pyridin-1-ium-1-olate | 1.38 | 1 | 646.3 |
| 462 | 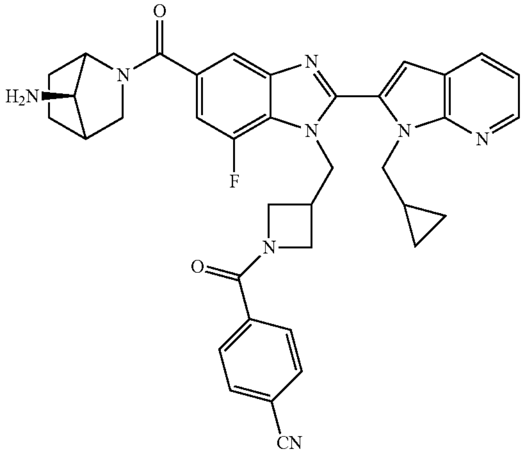 [SMILES: N#Cc1ccc(C(=O)N2CC(Cn3c(-c4cc5cccnc5n4CC4CC4)nc4cc(C(=O)N5CC6CCC5[C@@H]6N)cc(F)c43)C2)cc1] | 4-[3-({5-[(7R)-7-amino-2-azabicyclo[2.2.1]heptane-1-carbonyl]-2-[1-(cyclopropylmethyl)-1H-pyrrolo[2,3-b]pyridin-2-yl]-7-fluoro-1H-1,3-benzodiazol-1-yl}methyl)azetidine-1-carbonyl]benzonitrile | 1.24 | 2 | 643.4 |
| 463 | 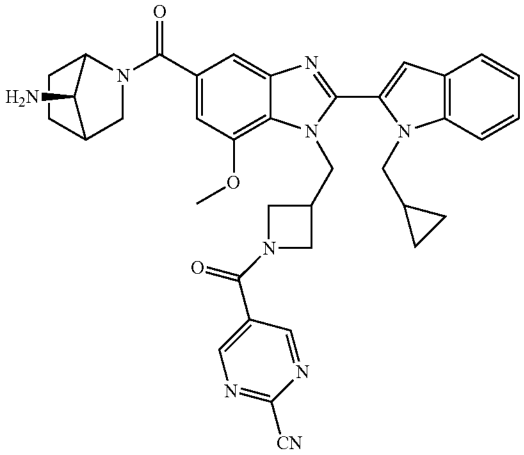 [SMILES: COc1cc(C(=O)N2CC3CCC2[C@@H]3N)cc2nc(-c3cc4ccccc4n3CC3CC3)n(CC3CN(C(=O)c4cnc(C#N)nc4)C3)c12] | 5-[3-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)azetidine-1-carbonyl]pyrimidine-2-carbonitrile | 1.58 | 1 | 656.2 |

TABLE 8-continued

| Ex# | Structure | Name | LC/MS Rt (min) | LC/MS Method | M + H (obs ion) |
|---|---|---|---|---|---|
| 464 | 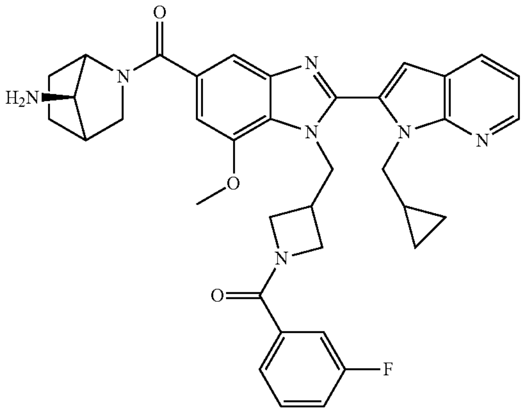 [SMILES: COc1cc(C(=O)N2CC3CCC2[C@@H]3N)cc2nc(-c3cc4cccnc4n3CC3CC3)n(CC3CN(C(=O)c4cccc(F)c4)C3)c12] | (7R)-2-{2-[1-(cyclopropylmethyl)-1H-pyrrolo[2,3-b]pyridin-2-yl]-1-{[1-(3-fluorobenzoyl)azetidin-3-yl]methyl}-7-methoxy-1H-1,3-benzodiazole-5-carbonyl}-2-azabicyclo[2.2.1]heptan-7-amine | 1.3 | 2 | 648.4 |
| 465 | 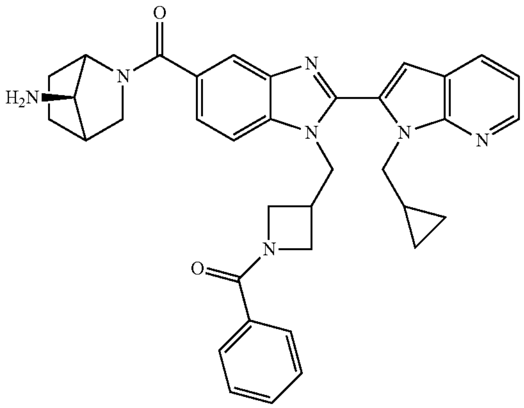 [SMILES: N[C@@H]1C2CCC1N(C(=O)c1ccc3c(c1)nc(-c1cc4cccnc4n1CC1CC1)n3CC1CN(C(=O)c3ccccc3)C1)C2] | (7R)-2-{1-[(1-benozylazetidin-3-yl)methyl]-2-[1-(cyclopropylmethyl)-1H-pyrrolo[2,3-b]pyridin-2-yl]-1H-1,3-benzodiazole-5-carbonyl}-2-azabicyclo[2.2.1]heptan-7-amine | 1.32 | 1 | 600.4 |
| 466 | 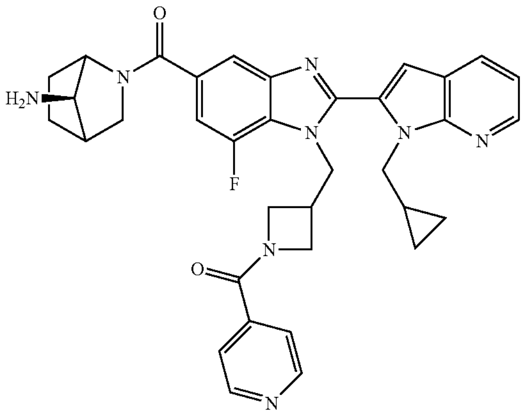 [SMILES: N[C@@H]1C2CCC1N(C(=O)c1cc(F)c3c(c1)nc(-c1cc4cccnc4n1CC1CC1)n3CC1CN(C(=O)c3ccncc3)C1)C2] | (7R)-2-{2-[1-(cyclopropylmethyl)-1H-pyrrolo[2,3-b]pyridin-2-yl]-7-fluoro-1-{[1-(pyridine-4-carbonyl)azetidin-3-yl]methyl}-1H-1,3-benzodiazole-5-carbonyl}-2-azabicyclo[2.2.1]heptan-7-amine | 1.12 | 1 | 619.2 |

TABLE 8-continued

| Ex# | Structure | Name | LC/MS Rt (min) | LC/MS Method | M + H (obs ion) |
|---|---|---|---|---|---|
| 467 | 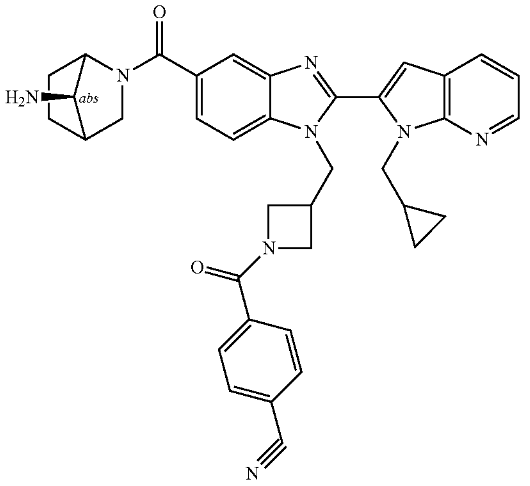 [SMILES: N#Cc1ccc(C(=O)N2CC(Cn3c(-c4cc5cccnc5n4CC4CC4)nc4cc(C(=O)N5CC6CCC5[C@@H]6N)ccc43)C2)cc1] | 4-[3-({5-[(7R)-7-amino-2-azabicyclo[2.2.1]heptane-2-carbonyl]-2-[1-(cyclopropylmethyl)-1H-pyrrolo[2,3-b]pyridin-2-yl]-1H-1,3-benzodiazol-1-yl}methyl)azetidine-1-carbonyl]benzonitrile | 1.27 | 1 | 625.2 |
| 468 | 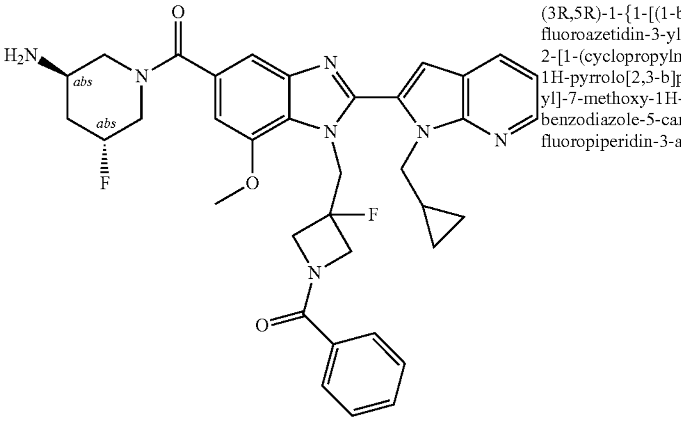 | (3R,5R)-1-{1-[(1-benzoyl-3-fluoroazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-5-fluoropiperidin-3-amine | 1.55 | 1 | 654.3 |
| 469 | 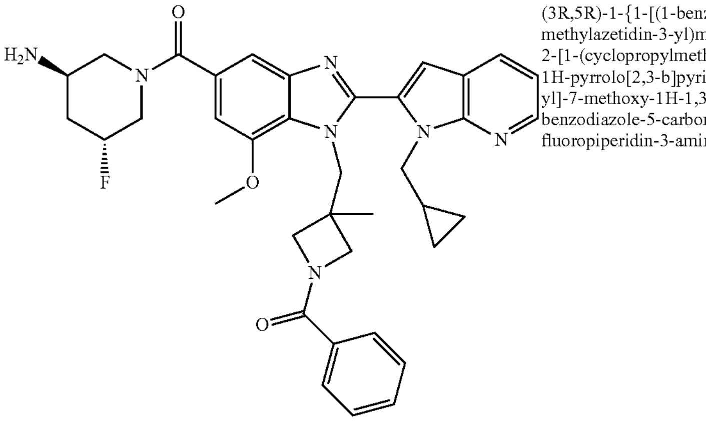 | (3R,5R)-1-{1-[(1-benzoyl-3-methylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-5-fluoropiperidin-3-amine | 1.43 | 1 | 650.5 |

TABLE 8-continued

| Ex# | Structure | Name | LC/MS Rt (min) | LC/MS Method | M + H (obs ion) |
|---|---|---|---|---|---|
| 470 | 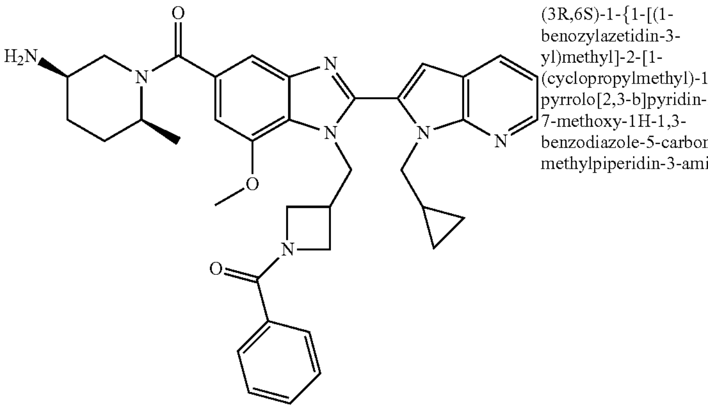 | (3R,6S)-1-{1-[(1-benozylazetidin-3-yl)methyl]-2-[1-(cyclopropylmethyl)-1H-pyrrolo[2,3-b]pyridin-2-yl]-7-methoxy-1H-1,3-benzodiazole-5-carbonyl}-6-methylpiperidin-3-amine | 1.51 | 1 | 632 |
| 471 | 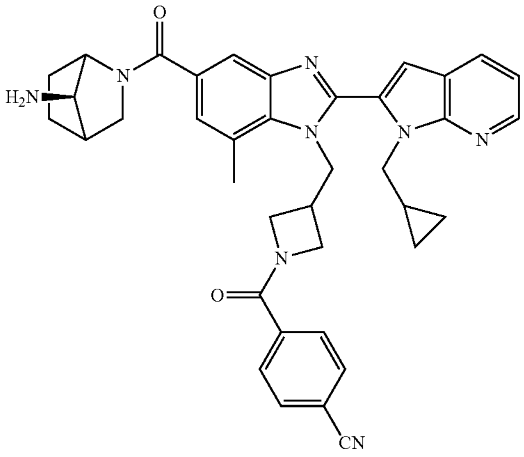 | 4-[3-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methyl-1H-1,3-benzodiazol-1-yl}methyl)azetidine-1-carbonyl]benzonitrile | 1.16 | 2 | 639.3 |
| 472 | 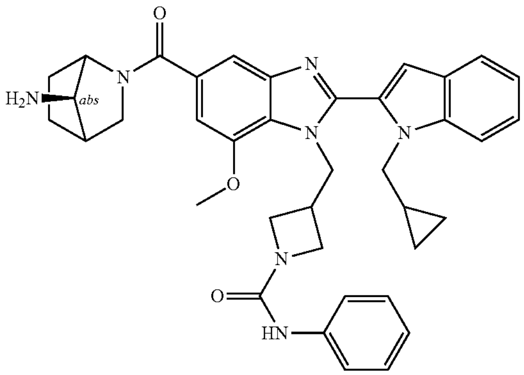 [SMILES: COc1cc(C(=O)N2CC3CCC2[C@@H]3N)cc2nc(-c3cc4ccccc4n3CC3CC3)n(CC3CN(C(=O)Nc4ccccc4)C3)c12] | 3-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-N-phenylazetidine-1-carboxamide | 1.51 | 2 | 644.3 |

Example 473 to Example 524 in Table 9 were prepared as described in the general procedures given for Examples 242 to 247 and other examples in Table 4.

TABLE 9

| Ex# | Structure | Name | LC/MS Rt (min) | LC/MS Method | M + H (obs ion) |
|---|---|---|---|---|---|
| 473 | 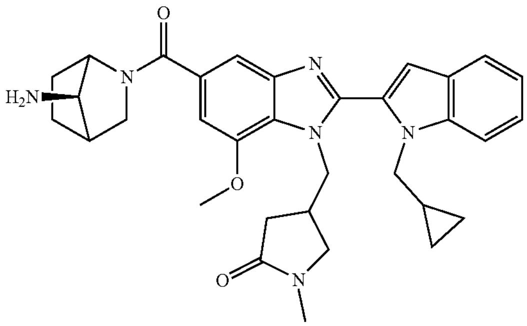 [SMILES: COc1cc(C(=O)N2CC3CCC2[C@@H]3N)cc2nc(-c3cc4ccccc4n3CC3CC3)n(CC3CC(=O)N(C)C3)c12] | 4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1-methylpyrrolidin-2-one | 1.36 | 1 | 567.3 |
| 474 | 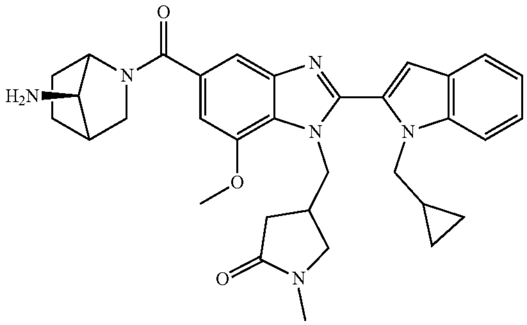 [SMILES: COc1cc(C(=O)N2CC3CCC2[C@@H]3N)cc2nc(-c3cc4ccccc4n3CC3CC3)n(CC3CC(=O)N(C)C3)c12] | 4-({5-[(7R)-7-amino-2-azabicyclo[2.2.1]heptane-2-carbonyl]-2-[1-(cyclopropylmethyl)-1H-indol-2-yl]-7-methoxy-1H-1,3-benzodiazol-1-yl}methyl)-1-methylpyrrolidin-2-one | 1.37 | 1 | 567.4 |
| 475 | 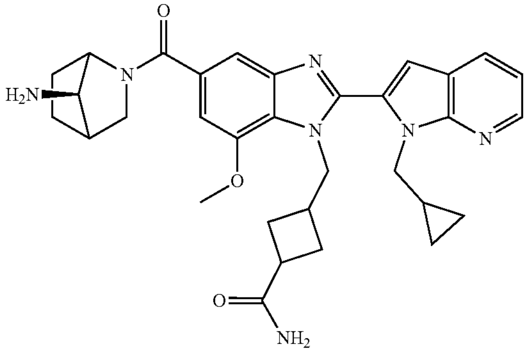 [SMILES: COc1cc(C(=O)N2CC3CCC2[C@@H]3N)cc2nc(-c3cc4cccnc4n3CC3CC3)n(CC3CC(C(N)=O)C3)c12] | 3-({5-[(7R)-7-amino-2-azabicyclo[2.2.1]heptane-2-carbonyl]-2-[1-(cyclopropylmethyl)-1H-pyrrolo[2,3-b]pyridin-2-yl]-7-methoxy-1H-1,3-benzodiazol-1-yl}methyl)cyclobutane-1-carboxamide | 1.28 | 1 | 568.2 |
| 476 | 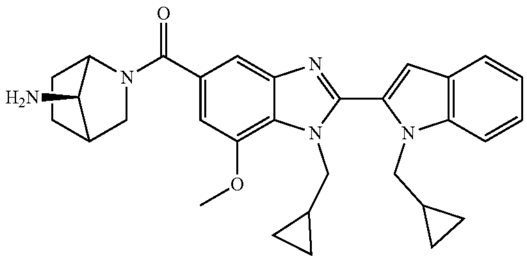 [SMILES: COc1cc(C(=O)N2CC3CCC2[C@@H]3N)cc2nc(-c3cc4ccccc4n3CC3CC3)n(CC3CC3)c12] | (7R)-2-[1-(cyclopropylmethyl)-2-[1-(cyclopropylmethyl)-1H-indol-2-yl]-7-methoxy-1H-1,3-benzodiazole-5-carbonyl]-2-azabicyclo[2.2.1]heptan-7-amine | 1.88 | 1 | 510.6 |

TABLE 9-continued

| Ex# | Structure | Name | LC/MS Rt (min) | LC/MS Method | M + H (obs ion) |
|---|---|---|---|---|---|
| 477 | 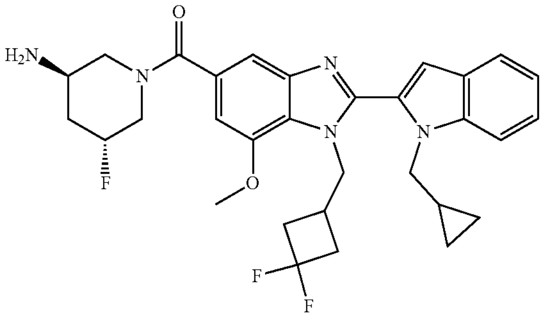 [SMILES: COc1cc(C(=O)N2C[C@H](N)C[C@@H](F)C2)cc2nc(-c3cc4ccccc4n3CC3CC3)n(CC3CC(F)(F)C3)c12] | (3R,5R)-1-{2-[1-(cyclopropylmethyl)-1H-indol-2-yl]-1-[(3,3-difluorocyclobutyl)methyl]-7-methoxy-1H-1,3-benzodiazole-5-carbonyl}-5-fluoropiperidin-3-amine | 1.72 | 2 | 566.3 |
| 478 | 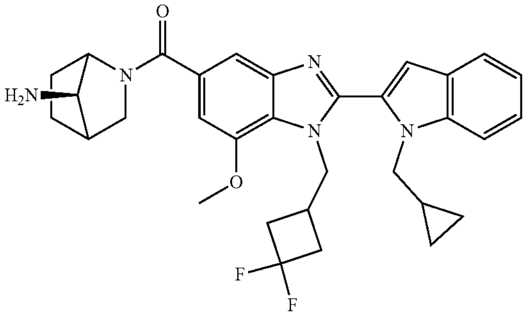 [SMILES: COc1cc(C(=O)N2CC3CCC2[C@@H]3N)cc2nc(-c3cc4ccccc4n3CC3CC3)n(CC3CC(F)(F)C3)c12] | (7R)-2-{2-[1-(cyclopropylmethyl)-1H-indol-2-yl]-1-[(3,3-difluorocyclobutyl)methyl]-7-methoxy-1H-1,3-benzodiazole-5-carbonyl}-2-azabicyclo[2.2.1]heptan-7-amine | 1.68 | 2 | 560.3 |
| 479 | 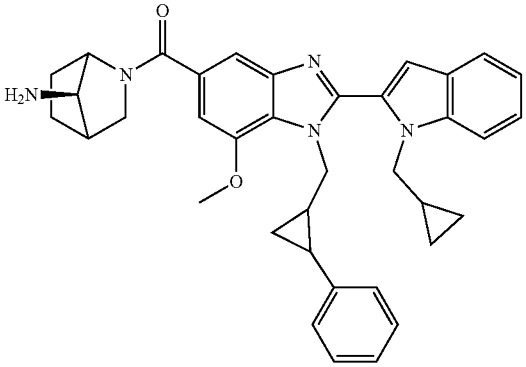 [SMILES: COc1cc(C(=O)N2CC3CCC2[C@@H]3N)cc2nc(-c3cc4ccccc4n3CC3CC3)n(CC3CC3c3ccccc3)c12] | (7R)-2-{2-[1-(cyclopropylmethyl)-1H-indol-2-yl]-7-methoxy-1-[(2-phenylcyclopropyl)methyl]-1H-1,3-benzodiazole-5-carbonyl}-2-azabicyclo[2.2.1]heptan-7-amine (diastereomeric mixture) | 2.05 | 2 | 586.2 |
| 480 | 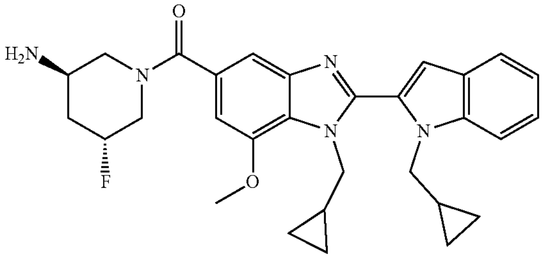 [SMILES: COc1cc(C(=O)N2C[C@H](N)C[C@@H](F)C2)cc2nc(-c3cc4ccccc4n3CC3CC3)n(CC3CC3)c12] | (3R,5R)-1-[1-(cyclopropylmethyl)-2-[1-(cyclopropylmethyl)-1H-indol-2-yl]-7-methoxy-1H-1,3-benzodiazole-5-carbonyl]-5-fluoropiperidin-3-amine | 1.77 | 2 | 516.6 |
| 481 | 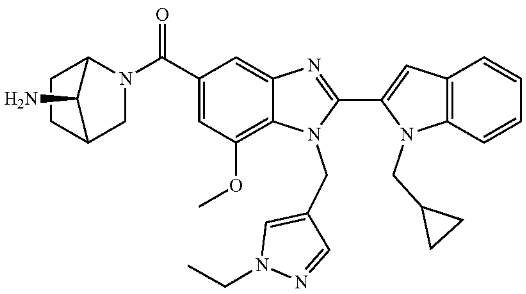 [SMILES: CCn1cc(Cn2c(-c3cc4ccccc4n3CC3CC3)nc3cc(C(=O)N4CC5CCC4[C@@H]5N)cc(OC)c32)cn1] | (7R)-2-{2-[1-(cyclopropylmethyl)-1H-indol-2-yl]-1-[(1-ethyl-1H-pyrazol-4-yl)methyl]-7-methoxy-1H-1,3-benzodiazole-5-carbonyl}-2-azabicyclo[2.2.1]heptan-7-amine | 1.62 | 1 | 564.4 |

TABLE 9-continued

| Ex# | Structure | Name | LC/MS Rt (min) | LC/MS Method | M + H (obs ion) |
|---|---|---|---|---|---|
| 482 | 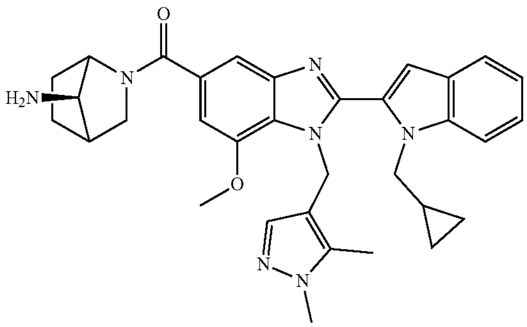 [SMILES: COc1cc(C(=O)N2CC3CCC2[C@@H]3N)cc2nc(-c3cc4ccccc4n3CC3CC3)n(Cc3cnn(C)c3C)c12] | (7R)-2-{2-[1-(cyclopropylmethyl)-1H-indol-2-yl]-1-[(1,5-dimethyl-1H-pyrazol-4-yl)methyl]-7-methoxy-1H-1,3-benzodiazole-5-carbonyl}-2-azabicyclo[2.2.1]heptan-7-amine | 1.57 | 1 | 564.3 |
| 483 | 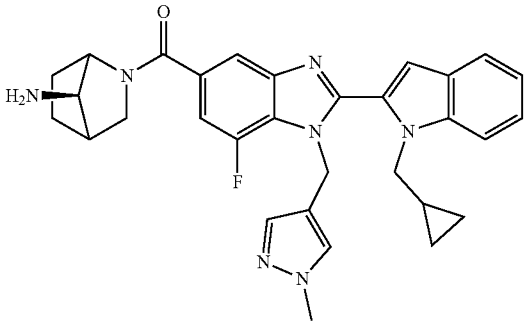 | (7R)-2-{2-[1-(cyclopropylmethyl)-1H-indol-2-yl]-7-fluoro-1-[(1-methyl-1H-pyrazol-4-yl)methyl]-1H-1,3-benzodiazole-5-carbonyl}-2-azabicyclo[2.2.1]heptan-7-amine | 1.63 | 1 | 537.9 |
| 484 | 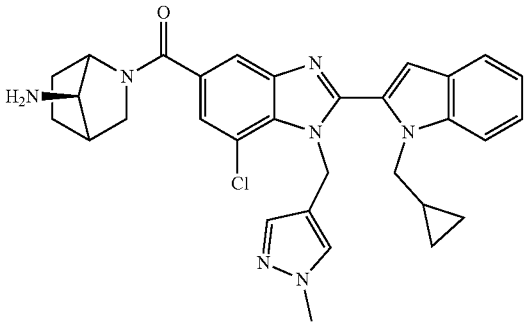 | (7R)-2-{7-chloro-2-[1-(cyclopropylmethyl)-1H-indol-2-yl]-1-[(1-methyl-1H-pyrazol-4-yl)methyl]-1H-1,3-benzodiazole-5-carbonyl}-2-azabicyclo[2.2.1]heptan-7-amine | 1.47 | 2 | 554.4 |
| 485 | 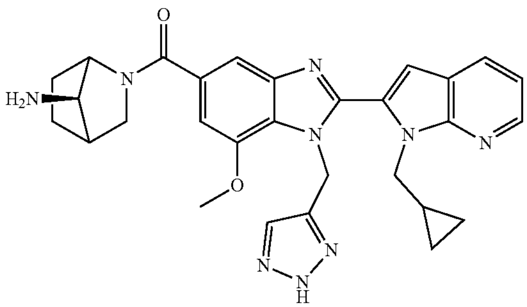 [SMILES: COc1cc(C(=O)N2CC3CCC2[C@@H]3N)cc2nc(-c3cc4cccnc4n3CC3CC3)n(Cc3cn[nH]n3)c12] | (7R)-2-{2-[1-(cyclopropylmethyl)-1H-pyrrolo[2,3-b]pyridin-2-yl]-7-methoxy-1-[(2H-1,2,3-triazol-4-yl)methyl]-1H-1,3-benzodiazole-5-carbonyl}-2-azabicyclo[2.2.1]heptan-7-amine | 1.17 | 2 | 537.9 |

TABLE 9-continued

| Ex# | Structure | Name | LC/MS Rt (min) | LC/MS Method | M + H (obs ion) |
|---|---|---|---|---|---|
| 486 | 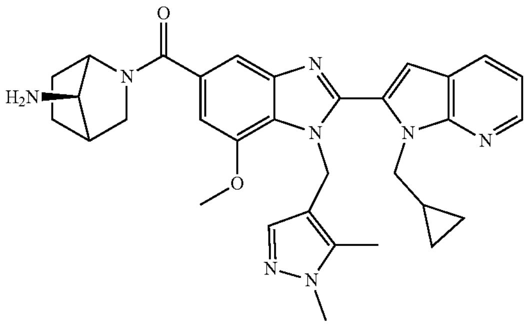 [SMILES: COc1cc(C(=O)N2CC3CCC2[C@@H]3N)cc2nc(-c3cc4cccnc4n3CC3CC3)n(Cc3cnn(C)c3C)c12] | (7R)-2-{2-[1-(cyclopropylmethyl)-1H-pyrrolo[2,3-b]pyridin-2-yl]-1-[(1,5-dimethyl-1H-pyrazol-4-yl)methyl]-7-methoxy-1H-1,3-benzodiazole-5-carbonyl}-2-azabicyclo[2.2.1]heptan-7-amine | 1.47 | 1 | 1129.4 |
| 487 | 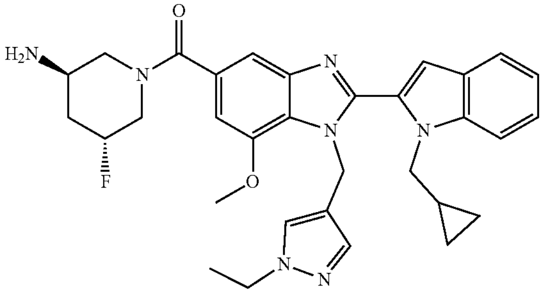 [SMILES: CCn1cc(Cn2c(-c3cc4ccccc4n3CC3CC3)nc3cc(C(=O)N4C[C@H](N)C[C@@H](F)C4)cc(OC)c32)cn1] | (3R,5R)-1-{2-[1-(cyclopropylmethyl)-1H-indol-2-yl]-1-[(1-ethyl-1H-pyrazol-4-yl)methyl]-7-methoxy-1H-1,3-benzodiazole-5-carbonyl}-5-fluoropiperidin-3-amine | 1.6 | 1 | 570.4 |
| 488 | 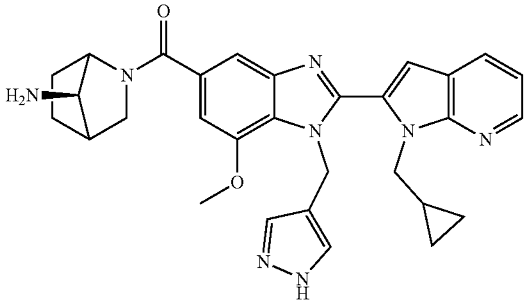 [SMILES: COc1cc(C(=O)N2CC3CCC2[C@@H]3N)cc2nc(-c3cc4cccnc4n3CC3CC3)n(Cc3cn[nH]c3)c12] | (7R)-2-{2-[1-(cyclopropylmethyl)-1H-pyrrolo[2,3-b]pyridin-2-yl]-7-methoxy-1-[(1H-pyrazol-4-yl)methyl]-1H-1,3-benzodiazole-5-carbonyl}-2-azabicyclo[2.2.1]heptan-7-amine | 1.19 | 1 | 537.2 |
| 489 | 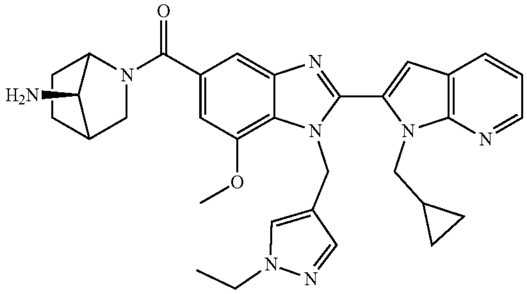 [SMILES: CCn1cc(Cn2c(-c3cc4cccnc4n3CC3CC3)nc3cc(C(=O)N4CC5CCC4[C@@H]5N)cc(OC)c32)cn1] | (7R)-2-{2-[1-(cyclopropylmethyl)-1H-pyrrolo[2,3-b]pyridin-2-yl]-1-[(1-ethyl-1H-pyrazol-4-yl)methyl]-7-methoxy-1H-1,3-benzodiazole-5-carbonyl}-2-azabicyclo[2.2.1]heptan-7-amine | 1.36 | 1 | 565.4 |
| 490 | 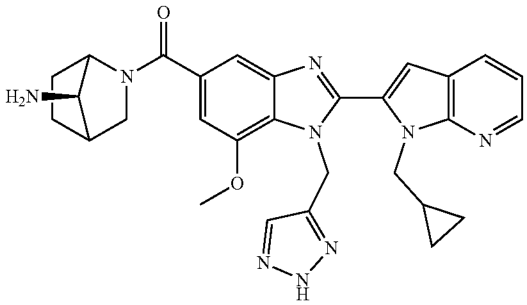 [SMILES: COc1cc(C(=O)N2CC3CCC2[C@@H]3N)cc2nc(-c3cc4cccnc4n3CC3CC3)n(Cc3cn[nH]n3)c12] | (7R)-2-{2-[1-(cyclopropylmethyl)-1H-indol-2-yl]-7-methoxy-1-[(2H-1,2,3-triazol-4-yl)methyl]-1H-1,3-benzodiazole-5-carbonyl}-2-azabicyclo[2.2.1]heptan-7-amine | 1.4 | 2 | 537.1 |

TABLE 9-continued

| Ex# | Structure | Name | LC/MS Rt (min) | LC/MS Method | M + H (obs ion) |
|---|---|---|---|---|---|
| 491 | 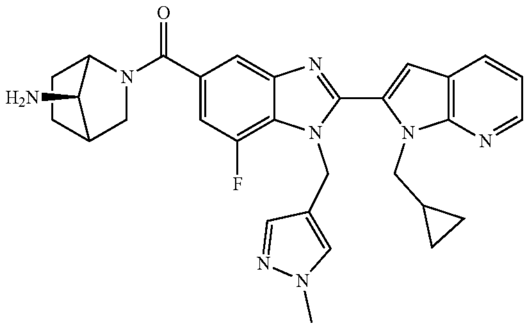 [SMILES: Cn1cc(Cn2c(-c3cc4cccnc4n3CC3CC3)nc3cc(C(=O)N4CC5CCC4[C@@H]5N)cc(F)c32)cn1] | (7R)-2-{2-[1-(cyclopropylmethyl)-1H-pyrrolo[2,3-b]pyridin-2-yl]-7-fluoro-1-[(1-methyl-1H-pyrazol-4-yl)methyl]-1H-1,3-benzodiazole-5-carbonyl}-2-azabicyclo[2.2.1]heptan-7-amine | 1.47 | 1 | 539.2 |
| 492 | 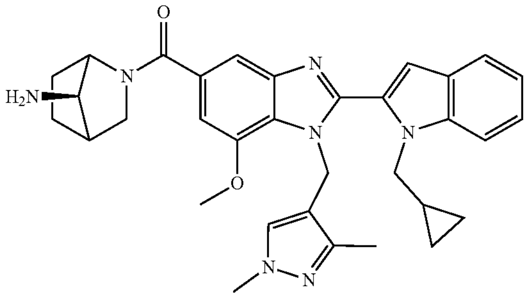 [SMILES: COc1cc(C(=O)N2CC3CCC2[C@@H]3N)cc2nc(-c3cc4ccccc4n3CC3CC3)n(Cc3cn(C)nc3C)c12] | (7R)-2-{2-[1-(cyclopropylmethyl)-1H-indol-2-yl]-1-[(1,3-dimethyl-1H-pyrazol-4-yl)methyl]-7-methoxy-1H-1,3-benzodiazole-5-carbonyl}-2-azabicyclo[2.2.1]heptan-7-amine | 1.54 | 1 | 564.5 |
| 493 | 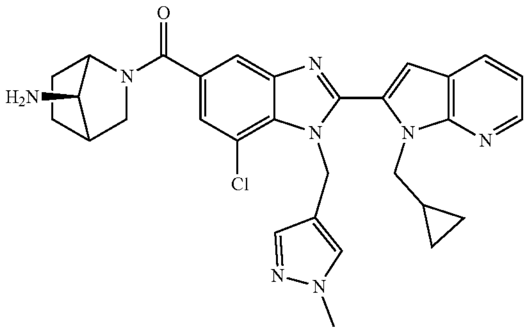 [SMILES: Cn1cc(Cn2c(-c3cc4cccnc4n3CC3CC3)nc3cc(C(=O)N4CC5CCC4[C@@H]5N)cc(Cl)c32)cn1] | (7R)-2-{7-chloro-2-[1-(cyclopropylmethyl)-1H-pyrrolo[2,3-b]pyridin-2-yl]-1-[(1-methyl-1H-pyrazol-4-yl)methyl]-1H-1,3-benzodiazole-5-carbonyl}-2-azabicyclo[2.2.1]heptan-7-amine | 1.34 | 1 | 555.2 |
| 494 | 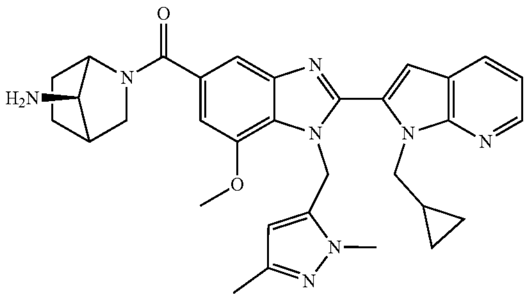 [SMILES: COc1cc(C(=O)N2CC3CCC2[C@@H]3N)cc2nc(-c3cc4cccnc4n3CC3CC3)n(Cc3cc(C)nn3C)c12] | (7R)-2-{2-[1-(cyclopropylmethyl)-1H-pyrrolo[2,3-b]pyridin-2-yl]-1-[(1,3-dimethyl-1H-pyrazol-5-yl)methyl]-7-methoxy-1H-1,3-benzodiazole-5-carbonyl}-2-azabicyclo[2.2.1]heptan-7-amine | 1.43 | 1 | 565.2 |

TABLE 9-continued

| Ex# | Structure | Name | LC/MS Rt (min) | LC/MS Method | M + H (obs ion) |
|---|---|---|---|---|---|
| 495 | 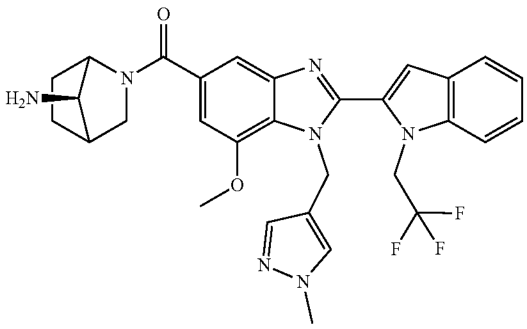 [SMILES: COc1cc(C(=O)N2CC3CCC2[C@@H]3N)cc2nc(-c3cc4ccccc4n3CC(F)(F)F)n(Cc3cnn(C)c3)c12] | (7R)-2-{7-methoxy-1-[(1-methyl-1H-pyrazol-4-yl)methyl]-2-[1-(2,2,2-trifluoroethyl)-1H-indol-2-yl]-1H-1,3-benzodiazole-5-carbonyl}-2-azabicyclo[2.2.1]heptan-7-amine | 1.51 | 1 | 578.2 |
| 496 | 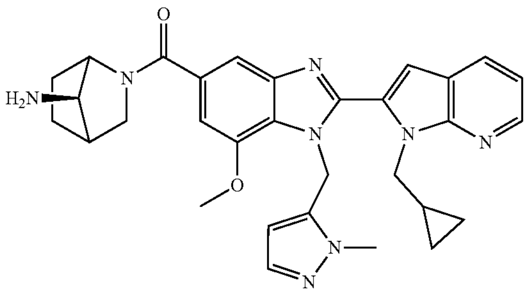 [SMILES: COc1cc(C(=O)N2CC3CCC2[C@@H]3N)cc2nc(-c3cc4cccnc4n3CC3CC3)n(Cc3ccnn3C)c12] | (7R)-2-{2-[1-(cyclopropylmethyl)-1H-pyrrolo[2,3-b]pyridin-2-yl]-7-methoxy-1-[(1-methyl-1H-pyrazol-5-yl)methyl]-1H-1,3-benzodiazole-5-carbonyl}-2-azabicyclo[2.2.1]heptan-7-amine | 1.25 | 1 | 551.2 |
| 497 | 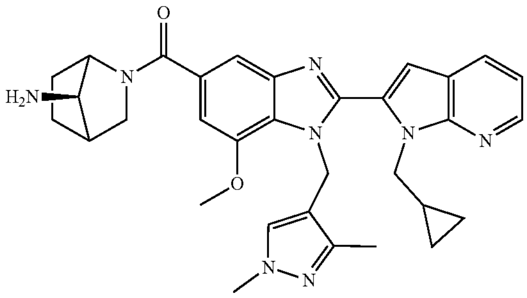 [SMILES: COc1cc(C(=O)N2CC3CCC2[C@@H]3N)cc2nc(-c3cc4cccnc4n3CC3CC3)n(Cc3cn(C)nc3C)c12] | (7R)-2-{2-[1-(cyclopropylmethyl)-1H-pyrrolo[2,3-b]pyridin-2-yl]-1-[(1,3-dimethyl-1H-pyrazol-4-yl)methyl]-7-methoxy-1H-1,3-benzodiazole-5-carbonyl}-2-azabicyclo[2.2.1]heptan-7-amine | 1.14 | 2 | 565.4 |
| 498 | 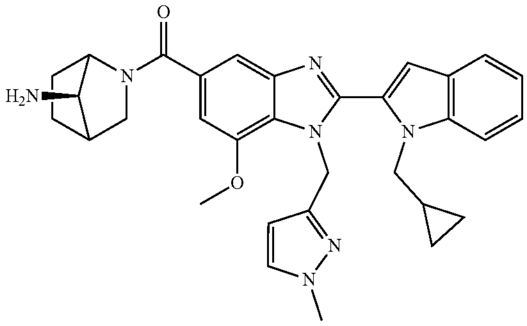 [SMILES: COc1cc(C(=O)N2CC3CCC2[C@@H]3N)cc2nc(-c3cc4ccccc4n3CC3CC3)n(Cc3ccn(C)n3)c12] | (7R)-2-{2-[1-(cyclopropylmethyl)-1H-indol-2-yl]-7-methoxy-1-[(1-methyl-1H-pyrazol-3-yl)methyl]-1H-1,3-benzodiazole-5-carbonyl}-2-azabicyclo[2.2.1]heptan-7-amine | 2.4 | 1 | 550.1 |

TABLE 9-continued

| Ex# | Structure | Name | LC/MS Rt (min) | LC/MS Method | M + H (obs ion) |
|---|---|---|---|---|---|
| 499 | 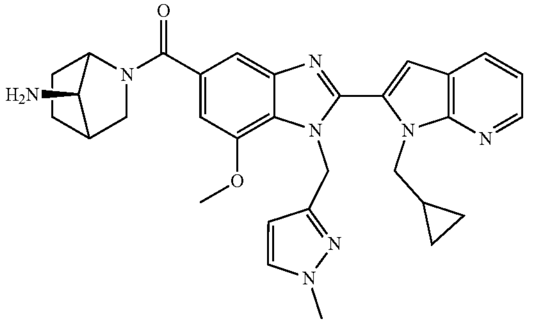 [SMILES: COc1cc(C(=O)N2CC3CCC2[C@@H]3N)cc2nc(-c3cc4cccnc4n3CC3CC3)n(Cc3ccn(C)n3)c12] | (7R)-2-{2-[1-(cyclopropylmethyl)-1H-pyrrolo[2,3-b]pyridin-2-yl]-7-methoxy-1-[(1-methyl-1H-pyrazol-3-yl)methyl]-1H-1,3-benzodiazole-5-carbonyl}-2-azabicyclo[2.2.1]heptan-7-amine | 1.2 | 2 | 551.4 |
| 500 | 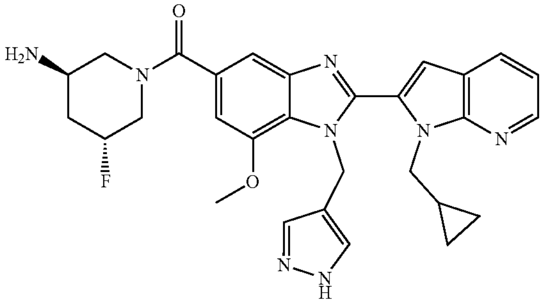 [SMILES: COc1cc(C(=O)N2C[C@H](N)C[C@@H](F)C2)cc2nc(-c3cc4cccnc4n3CC3CC3)n(Cc3cn[nH]c3)c12] | (3R,5R)-1-{2-[1-(cyclopropylmethyl)-1H-pyrrolo[2,3-b]pyridin-2-yl]-7-methoxy-1-[(1H-pyrazol-4-yl)methyl]-1H-1,3-benzodiazole-5-carbonyl}-5-fluoropiperidin-3-amine | 1.19 | 1 | 543.2 |
| 501 | 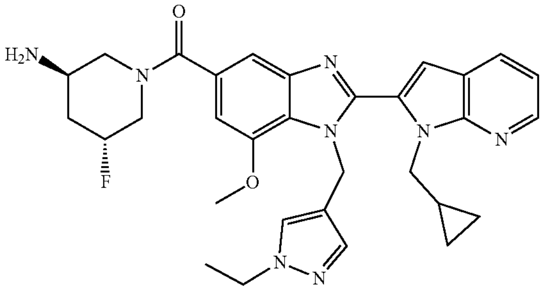 [SMILES: CCn1cc(Cn2c(-c3cc4cccnc4n3CC3CC3)nc3cc(C(=O)N4C[C@H](N)C[C@@H](F)C4)cc(OC)c32)cn1] | (3R,5R)-1-{2-[1-(cyclopropylmethyl)-1H-pyrrolo[2,3-b]pyridin-2-yl]-1-[(1-ethyl-1H-pyrazol-4-yl)methyl]-7-methoxy-1H-1,3-benzodiazole-5-carbonyl}-5-fluoropiperidin-3-amine | 1.35 | 1 | 571.4 |
| 502 | 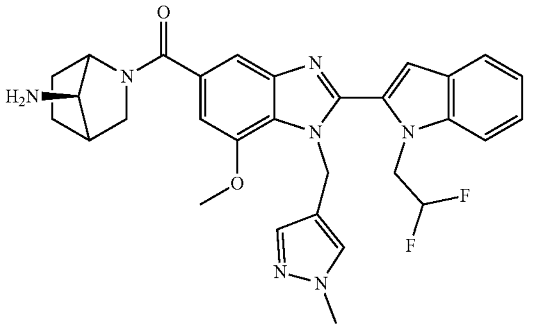 [SMILES: COc1cc(C(=O)N2CC3CCC2[C@@H]3N)cc2nc(-c3cc4ccccc4n3CC(F)F)n(Cc3cnn(C)c3)c12] | (7R)-2-{2-[1-(2,2-difluoroethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine | 1.55 | 1 | 560.2 |
| 503 | 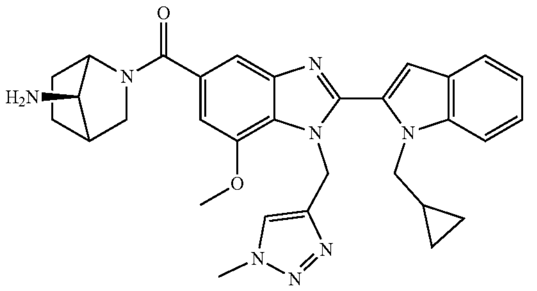 [SMILES: COc1cc(C(=O)N2CC3CCC2[C@@H]3N)cc2nc(-c3cc4ccccc4n3CC3CC3)n(Cc3cn(C)nn3)c12] | (7R)-2-{2-[1-(cyclopropylmethyl)-1H-indol-2-yl]-7-methoxy-1-[(1-methyl-1H-1,2,3-triazol-4-yl)methyl]-1H-1,3-benzodiazole-5-carbonyl}-2-azabicyclo[2.2.1]heptan-7-amine | 1.39 | 2 | 551.4 |

TABLE 9-continued

| Ex# | Structure | Name | LC/MS Rt (min) | LC/MS Method | M + H (obs ion) |
|---|---|---|---|---|---|
| 504 | 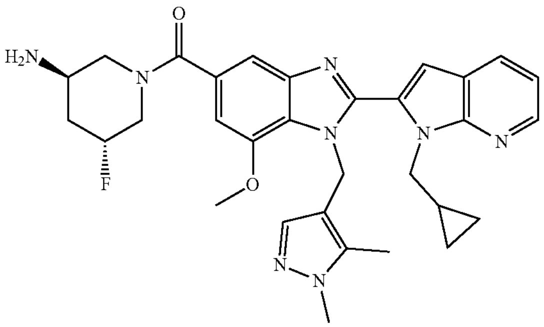 [SMILES: COc1cc(C(=O)N2C[C@H](N)C[C@@H](F)C2)cc2nc(-c3cc4cccnc4n3CC3CC3)n(Cc3cnn(C)c3C)c12] | (3R,5R)-1-{2-[1-(cyclopropylmethyl)-1H-pyrrolo[2,3-b]pyridin-2-yl]-1-[(1,5-dimethyl-1H-pyrazol-4-yl)methyl]-7-methoxy-1H-1,3-benzodiazole-5-carbonyl}-5-fluoropiperidin-3-amine | 1.29 | 2 | 571.3 |
| 505 | 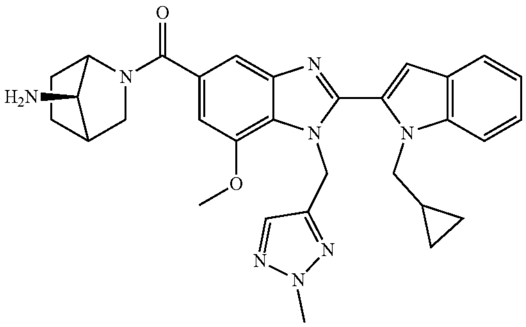 [SMILES: COc1cc(C(=O)N2CC3CCC2[C@@H]3N)cc2nc(-c3cc4ccccc4n3CC3CC3)n(Cc3cnn(C)n3)c12] | (7R)-2-{2-[1-(cyclopropylmethyl)-1H-indol-2-yl]-7-methoxy-1-[(2-methyl-2H-1,2,3-triazol-4-yl)methyl]-1H-1,3-benzodiazole-5-carbonyl}-2-azabicyclo[2.2.1]heptan-7-amine | 1.67 | 1 | 551.4 |
| 506 | 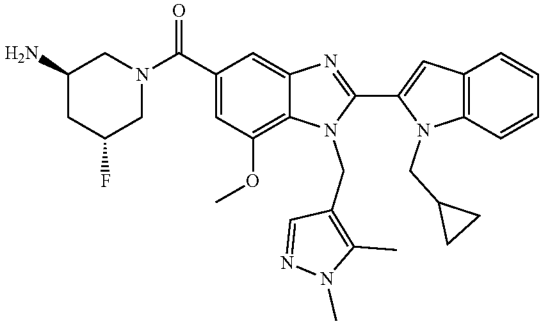 [SMILES: COc1cc(C(=O)N2C[C@H](N)C[C@@H](F)C2)cc2nc(-c3cc4ccccc4n3CC3CC3)n(Cc3cnn(C)c3C)c12] | (3R,5R)-1-{2-[1-(cyclopropylmethyl)-1H-indol-2-yl]-1-[(1,5-dimethyl-1H-pyrazol-4-yl)methyl]-7-methoxy-1H-1,3-benzodiazole-5-carbonyl}-5-fluoropiperidin-3-amine | 1.58 | 1 | 570.4 |
| 507 | 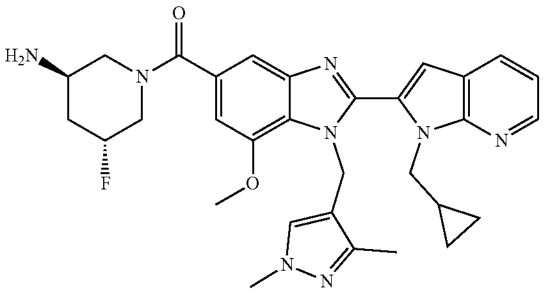 [SMILES: COc1cc(C(=O)N2C[C@H](N)C[C@@H](F)C2)cc2nc(-c3cc4cccnc4n3CC3CC3)n(Cc3cn(C)nc3C)c12] | (3R,5R)-1-{2-[1-(cyclopropylmethyl)-1H-pyrrolo[2,3-b]pyridin-2-yl]-1-[(1,3-dimethyl-1H-pyrazol-4-yl)methyl]-7-methoxy-1H-1,3-benzodiazole-5-carbonyl}-5-fluoropiperidin-3-amine | 1.13 | 2 | 571.2 |

TABLE 9-continued

| Ex# | Structure | Name | LC/MS Rt (min) | LC/MS Method | M + H (obs ion) |
|---|---|---|---|---|---|
| 508 | 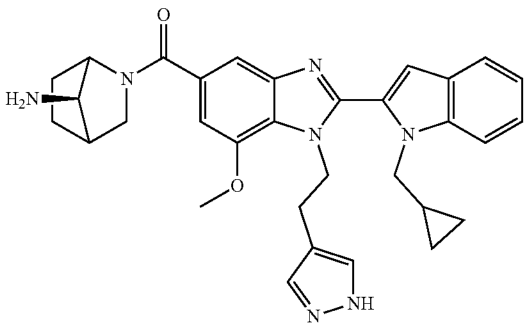 [SMILES: COc1cc(C(=O)N2CC3CCC2[C@@H]3N)cc2nc(-c3cc4ccccc4n3CC3CC3)n(CCc3cn[nH]c3)c12] | (7R)-2-{2-[1-(cyclopropylmethyl)-1H-indol-2-yl]-7-methoxy-1-[2-(1H-pyrazol-4-yl)ethyl]-1H-1,3-benzodiazole-5-carbonyl}-2-azabicyclo[2.2.1]heptan-7-amine | 1.57 | 1 | 550.2 |
| 509 | 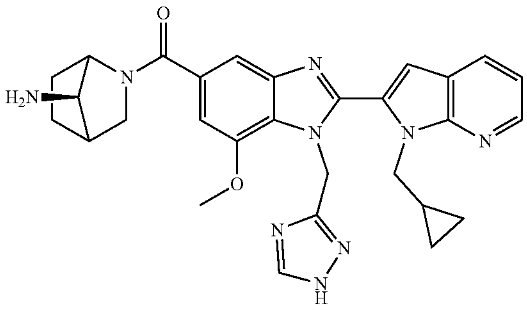 [SMILES: COc1cc(C(=O)N2CC3CCC2[C@@H]3N)cc2nc(-c3cc4cccnc4n3CC3CC3)n(Cc3nc[nH]n3)c12] | (7R)-2-{2-[1-(cyclopropylmethyl)-1H-pyrrolo[2,3-b]pyridin-2-yl]-7-methoxy-1-[(1H-1,2,4-triazol-3-yl)methyl]-1H-1,3-benzodiazole-5-carbonyl}-2-azabicyclo[2.2.1]heptan-7-amine | 1.25 | 1 | 538.1 |
| 510 | 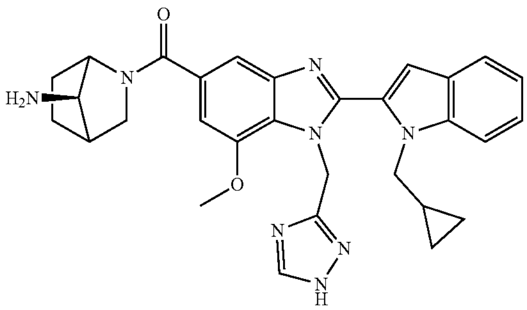 [SMILES: COc1cc(C(=O)N2CC3CCC2[C@@H]3N)cc2nc(-c3cc4ccccc4n3CC3CC3)n(Cc3nc[nH]n3)c12] | (7R)-2-{2-[1-(cyclopropylmethyl)-1H-indol-2-yl]-7-methoxy-1-[(1H-1,2,4-triazol-3-yl)methyl]-1H-1,3-benzodiazole-5-carbonyl}-2-azabicyclo[2.2.1]heptan-7-amine | 1.38 | 1 | 537.2 |
| 511 | 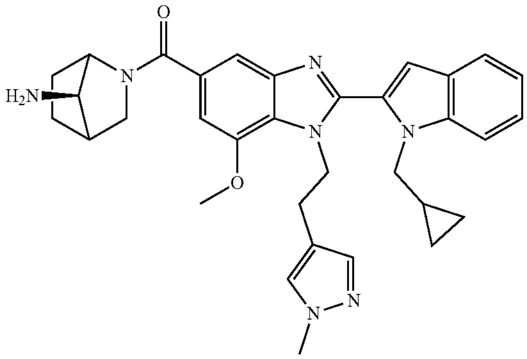 [SMILES: COc1cc(C(=O)N2CC3CCC2[C@@H]3N)cc2nc(-c3cc4ccccc4n3CC3CC3)n(CCc3cnn(C)c3)c12] | (7R)-2-{2-[1-(cyclopropylmethyl)-1H-indol-2-yl]-7-methoxy-1-[2-(1-methyl-1H-pyrazol-4-yl)ethyl]-1H-1,3-benzodiazole-5-carbonyl}-2-azabicyclo[2.2.1]heptan-7-amine | 1.55 | 1 | 564.4 |

TABLE 9-continued

| Ex# | Structure | Name | LC/MS Rt (min) | LC/MS Method | M + H (obs ion) |
|---|---|---|---|---|---|
| 512 | 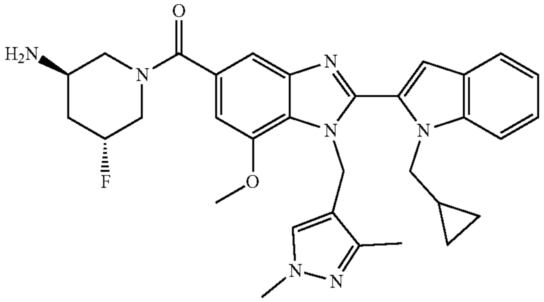 [SMILES: COc1cc(C(=O)N2C[C@H](N)C[C@@H](F)C2)cc2nc(-c3cc4ccccc4n3CC3CC3)n(Cc3cn(C)nc3C)c12] | (3R,5R)-1-{2-[1-(cyclopropylmethyl)-1H-indol-2-yl]-1-[(1,3-dimethyl-1H-pyrazol-4-yl)methyl]-7-methoxy-1H-1,3-benzodiazole-5-carbonyl}-5-fluoropiperidin-3-amine | 1.42 | 2 | 570.4 |
| 513 | 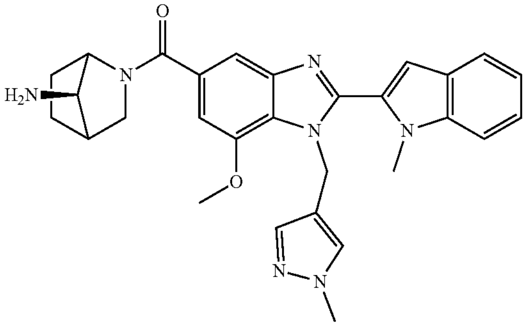 [SMILES: COc1cc(C(=O)N2CC3CCC2[C@@H]3N)cc2nc(-c3cc4ccccc4n3C)n(Cc3cnn(C)c3)c12] | (7R)-2-[7-methoxy-2-(1-methyl-1H-indol-2-yl)-1-[(1-methyl-1H-pyrazol-4-yl)methyl]-1H-1,3-benzodiazole-5-carbonyl]-2-azabicyclo[2.2.1]heptan-7-amine | 1.55 | 1 | 510.2 |
| 514 | 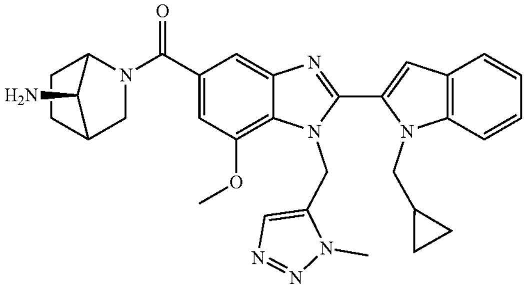 [SMILES: COc1cc(C(=O)N2CC3CCC2[C@@H]3N)cc2nc(-c3cc4ccccc4n3CC3CC3)n(Cc3cnnn3C)c12] | (7R)-2-{2-[1-(cyclopropylmethyl)-1H-indol-2-yl]-7-methoxy-1-[(1-methyl-1H-1,2,3-triazol-5-yl)methyl]-1H-1,3-benzodiazole-5-carbonyl}-2-azabicyclo[2.2.1]heptan-7-amine | 1.47 | 1 | 551.4 |
| 515 | 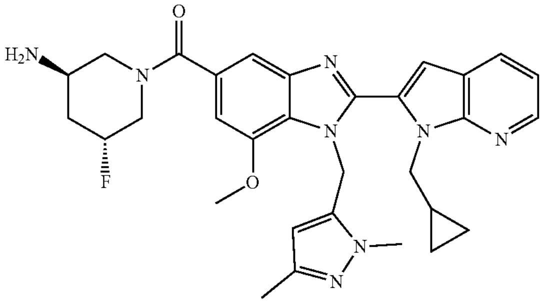 [SMILES: COc1cc(C(=O)N2C[C@H](N)C[C@@H](F)C2)cc2nc(-c3cc4cccnc4n3CC3CC3)n(Cc3cc(C)nn3C)c12] | (3R,5R)-1-{2-[1-(cyclopropylmethyl)-1H-pyrrolo[2,3-b]pyridin-2-yl]-1-[(1,3-dimethyl-1H-pyrazol-5-yl)methyl]-7-methoxy-1H-1,3-benzodiazole-5-carbonyl}-5-fluoropiperidin-3-amine | 1.4 | 1 | 570.9 |
| 516 | 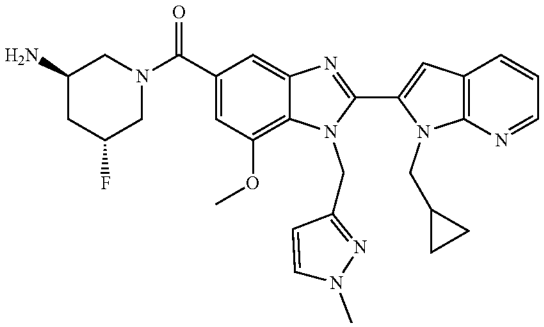 [SMILES: COc1cc(C(=O)N2C[C@H](N)C[C@@H](F)C2)cc2nc(-c3cc4cccnc4n3CC3CC3)n(Cc3ccn(C)n3)c12] | (3R,5R)-1-{2-[1-(cyclopropylmethyl)-1H-pyrrolo[2,3-b]pyridin-2-yl]-7-methoxy-1-[(1-methyl-1H-pyrazol-3-yl)methyl]-1H-1,3-benzodiazole-5-carbonyl}-5-fluoropiperidin-3-amine | 1.22 | 2 | 557.4 |

TABLE 9-continued

| Ex# | Structure | Name | LC/MS Rt (min) | LC/MS Method | M + H (obs ion) |
|---|---|---|---|---|---|
| 517 | 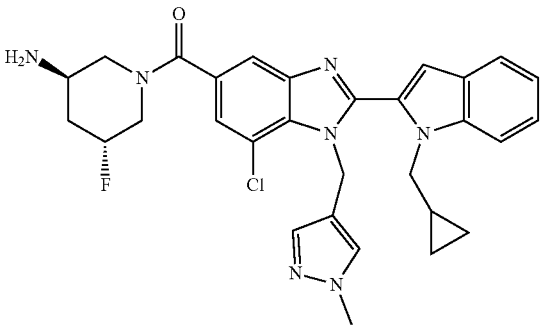 [SMILES: Cn1cc(Cn2c(-c3cc4ccccc4n3CC3CC3)nc3cc(C(=O)N4C[C@H](N)C[C@@H](F)C4)cc(Cl)c32)cn1] | (3R,5R)-1-{7-chloro-2-[1-(cyclopropylmethyl)-1H-indol-2-yl]-1-[(1-methyl-1H-pyrazol-4-yl)methyl]-1H-1,3-benzodiazole-5-carbonyl}-5-fluoropiperidin-3-amine | 1.56 | 1 | 560.2 |
| 518 | 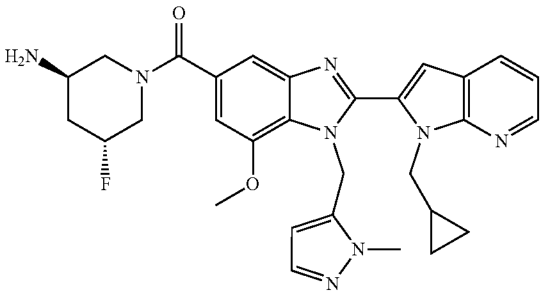 [SMILES: COc1cc(C(=O)N2C[C@H](N)C[C@@H](F)C2)cc2nc(-c3cc4cccnc4n3CC3CC3)n(Cc3ccnn3C)c12] | (3R,5R)-1-{2-[1-(cyclopropylmethyl)-1H-pyrrolo[2,3-b]pyridin-2-yl]-7-methoxy-1-[(1-methyl-1H-pyrazol-5-yl)methyl]-1H-1,3-benzodiazole-5-carbonyl}-5-fluoropiperidin-3-amine | 1.25 | 1 | 557.2 |
| 519 | 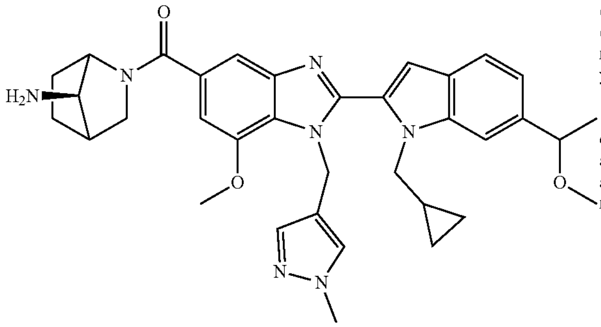 [SMILES: COc1cc(C(=O)N2CC3CCC2[C@@H]3N)cc2nc(-c3cc4ccc(C(C)OC)cc4n3CC3CC3)n(Cc3cnn(C)c3)c12] | (7R)-2-{2-[1-(cyclopropylmethyl)-6-(1-methoxyethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine (diastereomeric mixture) | 1.4 | 2 | 608.4 |
| 520 | 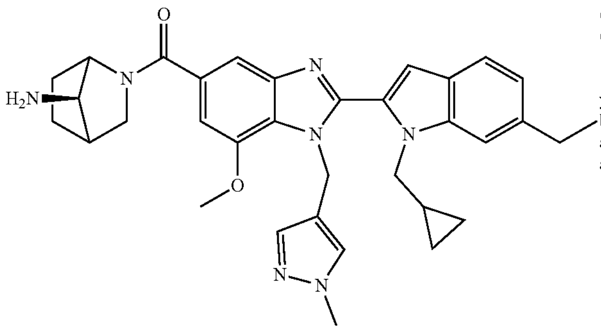 [SMILES: CCc1ccc2cc(-c3nc4cc(C(=O)N5CC6CCC5[C@@H]6N)cc(OC)c4n3Cc3cnn(C)c3)n(CC3CC3)c2c1] | (7R)-2-{2-[1-(cyclopropylmethyl)-6-ethyl-1H-indol-2-yl]-7-methoxy-1-[(1-methyl-1H-pyrazol-4-yl)methy]-1H-1,3-benzodiazole-5-carbonyl}-2-azabicyclo[2.2.1]heptan-7-amine | 1.63 | 2 | 578.1 |

TABLE 9-continued

| Ex# | Structure | Name | LC/MS Rt (min) | LC/MS Method | M + H (obs ion) |
|---|---|---|---|---|---|
| 521 | 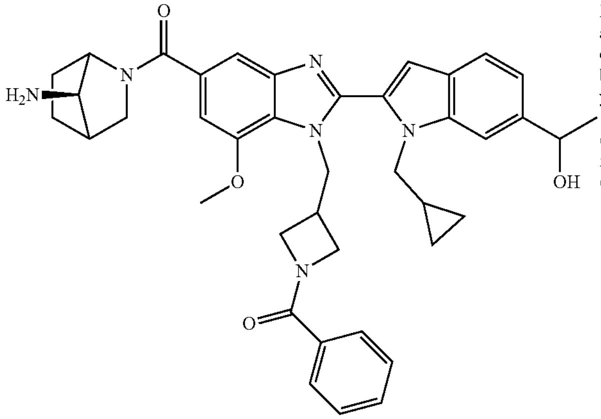 [SMILES: COc1cc(C(=O)N2CC3CCC2[C@@H]3N)cc2nc(-c3cc4ccc(C(C)O)cc4n3CC3CC3)n(CC3CN(C(=O)c4ccccc4)C3)c12] | l-(2-{5-[(7R)-7-amino-2-azabicyclo[2.2.1]heptane-2-carbonyl]-1-[(1-benzoylazetidin-3-yl)methyl]-7-methoxy-1H-1,3-benzodiazol-2-yl}-1-(cyclopropylmethyl)-1H-indol-6-yl)ethan-1-ol (diastereomeric mixture) | 1.21 | 2 | 673.2 |
| 522 | 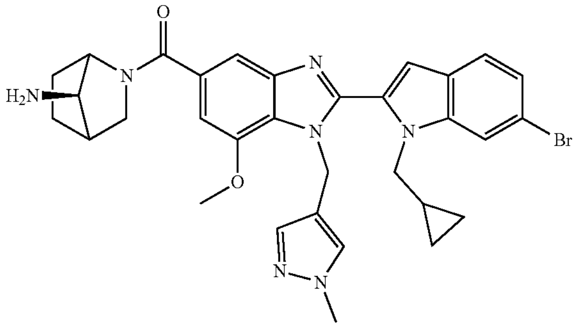 [SMILES: COc1cc(C(=O)N2CC3CCC2[C@@H]3N)cc2nc(-c3cc4ccc(Br)cc4n3CC3CC3)n(Cc3cnn(C)c3)c12] | (7R)-2-{2-[6-bromo-1-(cyclopropylmethyl)-1H-indol-2-yl]-7-methoxy-1-[(1-methyl-1H-pyrazol-4-yl)methyl]-1H-1,3-benzodiazole-5-carbonyl}-2-azabicyclo[2.2.1]heptan-7-amine | 1.52 | 2 | 628.1 |
| 523 | 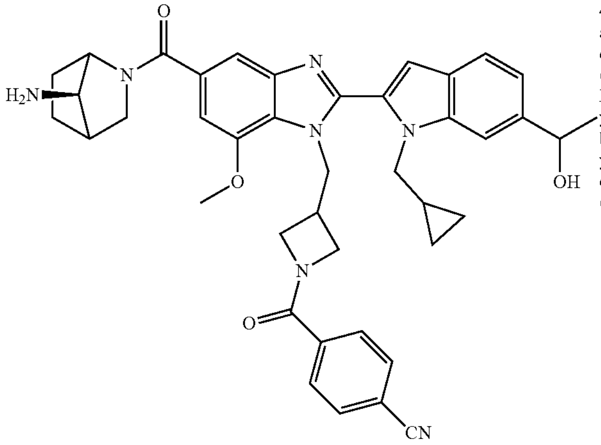 [SMILES: COc1cc(C(=O)N2CC3CCC2[C@@H]3N)cc2nc(-c3cc4ccc(C(C)O)cc4n3CC3CC3)n(CC3CN(C(=O)c4ccc(C#N)cc4)C3)c12] | 4-[3-({5-[(7R)-7-amino-2-azabicyclo[2.2.1]heptane-2-carbonyl]-2-[1-(cyclopropylmethyl)-6-(1-hydroxyethyl)-1H-indol-2-yl]-7-methoxy-1H-1,3-benzodiazol-1-yl}methyl)azetidine-1-carbonyl]benzonitrile (diastereomeric mixture) | 1.32 | 1 | 698.1 |
| 524 | 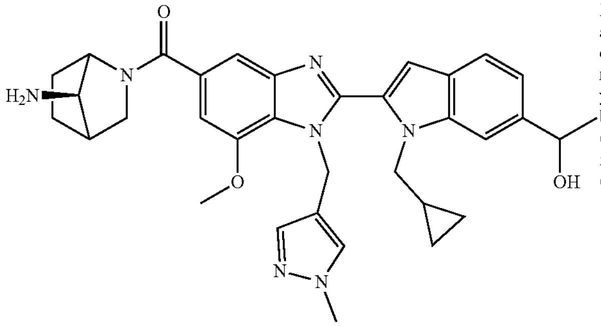 [SMILES: COc1cc(C(=O)N2CC3CCC2[C@@H]3N)cc2nc(-c3cc4ccc(C(C)O)cc4n3CC3CC3)n(Cc3cnn(C)c3)c12] | l-(2-{5-[(7R)-7-amino-2-azabicyclo[2.2.1]heptane-2-carbonyl]-7-methoxy-1-[(1-methyl-1H-pyrazol-4-yl)methyl]-1H-1,3-benzodiazol-2-yl}-1-(cyclopropylmethyl)-1H-indol-6-yl)ethan-1-ol (diastereomeric mixture) | 1.38 | 1 | 594.2 |

Biological Assays

Compounds of the present invention were assayed as inhibitors of PAD4 using the assay protocol described below.

RFMS tinman PAD4 Functional Assay:

Compounds were solubilized in 100% DMSO to achieve a 10 mM compound concentration. Compound stock solutions were stored at RT. A series of dilutions were prepared in DMSO and mixed 8 times with 20 µl, mixing volume. Final top concentration of compound in the assay is 50 µM. Final assay conditions were as follows:

- Reaction volume: 26 µl
- Assay buffer: 25 mM hepes, pH 7.5, 5 mM NaCl, 1 mM DTT, 0.2 mg/ml BSA, 0.01% CHAPS, 50 µM Calcium, and 5 µM TPEN
- Final concentrations: 5 nM hPAD4 enzyme, 250 µM BAEE, and 0.5% DMSO Total incubation time: 30 mins compound and enzyme preincubation at 37° C. 1-90 min enzyme/substrate reaction, 30 min reaction with phenyl glyoxal at 37° C.
- Stop solution: 40 µl 5% TCA in ACN 0.13 µL of compound solution was added to 13 µL of 10 nM PAD4 in assay buffer. After 30 min 13 µl of 500 µM of BAEE was added in 25 mM hepes, pH 7.5, 5 mM NaCl, 1 mM DTT, 0.2 mg/ml BS A, 0.01% CHAPS, 50 µM Calcium, 5 µM TPEN was added and the reaction incubated for 90 min at 37° C. The enzymatic reaction was quenched by addition of 15 µl of 6.1N TCA, 100% Final Concentration is 20%, 35 µl of 8.5 mM phenyl glyoxal (final concentration 4 mM) is then added and the reaction is incubated for 30 min at 37° C.

After 30 minutes the plates are spun down to remove all precipitate. The enzyme reaction was quenched with an equal volume of methanol containing internal standard (modified citrulline). Samples were loaded onto the Rapid Fire RF300 system (Agilent) wherein they were first sipped for 1000 ms and then directly loaded to a C18 separations cartridge using a mixture of acetonitrile containing 0.01% formic acid for 3000 ms desalting. The flow rate of the mobile phase was 1.5 ml/min. Once the samples were eluted from the cartridge, a mobile phase of acetonitrile containing 0.01% formic acid was used to move the samples into the mass spectrometer for 4000 ms at a flow rate of 1.25 ml/min/Sciex API5500 triple quadrupole mass spectrometer (Applied Biosystems) equipped with ESI was used to analyse the peptidyl citruline and internal standard ions.

MRM transition of product and internal standard were monitored at m/z 424.5 to 350.4 and m/z 293 to 247 respectively. The dwell time for each transition was set at 200 ms, and the ESI voltage was used at 5500 with a source temperature of 400° C. Extracted ion peaks for each transition were integrated using the Rapid Fire Integrator software. Peak area of analyte was normalized with internal standard).

For a given compound example, the Table below shows the human PAD4 (hPAD4) $IC_{50}$ in the rapid-fire mass spectrum (RFMS) assay.

TABLE 11

PAD4 Activity

| Example Number | hPAD4 RFMS $IC_{50}$ µM |
|---|---|
| 1 | 0.014 |
| 2 | 0.049 |
| 3 | 0.055 |
| 4 | 0.035 |
| 5 | 0.051 |
| 6 | 0.078 |
| 7 | 0.094 |
| 8 | 0.018 |
| 9 | 0.021 |
| 10 | 0.032 |
| 11 | 0.037 |
| 12 | 0.038 |
| 13 | 0.038 |
| 14 | 0.046 |
| 15 | 0.047 |
| 16 | 0.048 |
| 17 | 0.050 |
| 18 | 0.054 |
| 19 | 0.055 |
| 20 | 0.057 |
| 21 | 0.057 |
| 22 | 0.060 |
| 23 | 0.062 |
| 24 | 0.068 |
| 25 | 0.072 |
| 26 | 0.072 |
| 27 | 0.072 |
| 28 | 0.073 |
| 29 | 0.078 |
| 30 | 0.084 |
| 31 | 0.085 |
| 32 | 0.086 |
| 33 | 0.087 |
| 34 | 0.088 |
| 35 | 0.090 |
| 36 | 0.092 |
| 37 | 0.093 |
| 38 | 0.094 |
| 39 | 0.094 |
| 40 | 0.098 |
| 41 | 0.100 |
| 42 | 0.102 |
| 43 | 0.103 |
| 44 | 0.112 |
| 45 | 0.114 |
| 46 | 0.118 |
| 47 | 0.119 |
| 48 | 0.122 |
| 49 | 0.126 |
| 50 | 0.141 |
| 51 | 0.152 |
| 52 | 0.156 |
| 53 | 0.157 |
| 54 | 0.162 |
| 55 | 0.163 |
| 56 | 0.166 |
| 57 | 0.168 |
| 58 | 0.169 |
| 59 | 0.171 |
| 60 | 0.171 |
| 61 | 0.187 |
| 62 | 0.192 |
| 63 | 0.199 |
| 64 | 0.023 |
| 65 | 0.028 |
| 66 | 0.039 |
| 67 | 0.040 |
| 68 | 0.124 |
| 69 | 0.058 |
| 70 | 0.087 |
| 71 | 0.111 |
| 72 | 0.113 |
| 73 | 0.149 |
| 74 | 0.210 |
| 75 | 0.216 |
| 76 | 0.292 |
| 77 | 0.307 |
| 78 | 0.373 |
| 79 | 0.400 |

TABLE 11-continued

| PAD4 Activity | |
|---|---|
| Example Number | hPAD4 RFMS $IC_{50}$ μM |
| 80 | 0.403 |
| 81 | 0.403 |
| 82 | 0.424 |
| 83 | 0.440 |
| 84 | 0.511 |
| 85 | 0.638 |
| 86 | 1.682 |
| 87 | 2.280 |
| 88 | 0.021 |
| 89 | 0.041 |
| 90 | 0.028 |
| 91 | 0.009 |
| 92 | 0.012 |
| 93 | 0.016 |
| 94 | 0.034 |
| 95 | 0.016 |
| 96 | 0.083 |
| 97 | 0.063 |
| 98 | 0.071 |
| 99 | 0.111 |
| 100 | 0.117 |
| 101 | 0.125 |
| 102 | 0.141 |
| 103 | 0.014 |
| 104 | 0.027 |
| 105 | 0.031 |
| 106 | 0.032 |
| 107 | 0.033 |
| 108 | 0.040 |
| 109 | 0.041 |
| 110 | 0.046 |
| 111 | 0.051 |
| 112 | 0.051 |
| 113 | 0.052 |
| 114 | 0.054 |
| 115 | 0.059 |
| 116 | 0.059 |
| 117 | 0.066 |
| 118 | 0.068 |
| 119 | 0.069 |
| 120 | 0.073 |
| 121 | 0.095 |
| 122 | 0.098 |
| 123 | 0.100 |
| 124 | 0.102 |
| 125 | 0.102 |
| 126 | 0.108 |
| 127 | 0.109 |
| 128 | 0.109 |
| 129 | 0.116 |
| 130 | 0.128 |
| 131 | 0.138 |
| 132 | 0.148 |
| 133 | 0.165 |
| 134 | 0.193 |
| 135 | 0.008 |
| 136 | 0.011 |
| 137 | 0.011 |
| 138 | 0.011 |
| 139 | 0.012 |
| 140 | 0.014 |
| 141 | 0.014 |
| 142 | 0.014 |
| 143 | 0.023 |
| 144 | 0.017 |
| 145 | 0.018 |
| 146 | 0.018 |
| 147 | 0.019 |
| 148 | 0.019 |
| 149 | 0.019 |
| 150 | 0.020 |
| 151 | 0.020 |
| 152 | 0.021 |
| 153 | 0.021 |
| 154 | 0.021 |
| 155 | 0.022 |

TABLE 11-continued

| PAD4 Activity | |
|---|---|
| Example Number | hPAD4 RFMS $IC_{50}$ μM |
| 156 | 0.022 |
| 157 | 0.023 |
| 158 | 0.023 |
| 159 | 0.024 |
| 160 | 0.025 |
| 161 | 0.025 |
| 162 | 0.025 |
| 163 | 0.026 |
| 164 | 0.026 |
| 165 | 0.030 |
| 166 | 0.031 |
| 167 | 0.031 |
| 168 | 0.033 |
| 169 | 0.033 |
| 170 | 0.035 |
| 171 | 0.041 |
| 172 | 0.042 |
| 173 | 0.050 |
| 174 | 0.064 |
| 175 | 0.051 |
| 176 | 0.080 |
| 177 | 0.054 |
| 178 | 0.086 |
| 179 | 0.093 |
| 180 | 0.095 |
| 181 | 0.101 |
| 182 | 0.204 |
| 183 | 0.276 |
| 184 | 0.309 |
| 185 | 0.316 |
| 186 | 0.316 |
| 187 | 0.358 |
| 188 | 0.393 |
| 189 | 0.583 |
| 190 | 0.782 |
| 191 | 0.884 |
| 192 | 1.575 |
| 193 | 2.723 |
| 194 | 0.074 |
| 195 | 0.014 |
| 196 | 0.016 |
| 197 | 0.117 |
| 198 | 0.131 |
| 199 | 0.162 |
| 200 | 0.198 |
| 201 | 0.018 |
| 202 | 0.021 |
| 203 | 0.023 |
| 204 | 0.035 |
| 205 | 0.037 |
| 206 | 0.047 |
| 207 | 0.057 |
| 208 | 0.025 |
| 209 | 0.061 |
| 210 | 0.075 |
| 211 | 0.080 |
| 212 | 0.081 |
| 213 | 0.099 |
| 214 | 0.116 |
| 215 | 0.148 |
| 216 | 0.153 |
| 217 | 0.056 |
| 218 | 0.087 |
| 219 | 0.067 |
| 220 | 0.072 |
| 221 | 0.096 |
| 222 | 0.166 |
| 223 | 0.018 |
| 224 | 0.019 |
| 225 | 0.026 |
| 226 | 0.037 |
| 227 | 0.041 |
| 228 | 0.099 |
| 229 | 0.219 |
| 230 | 0.237 |
| 231 | 0.203 |

TABLE 11-continued

| PAD4 Activity | |
|---|---|
| Example Number | hPAD4 RFMS $IC_{50}$ μM |
| 232 | 0.310 |
| 233 | 0.315 |
| 234 | 0.332 |
| 235 | 0.366 |
| 236 | 0.402 |
| 237 | 0.540 |
| 238 | 0.922 |
| 239 | 0.927 |
| 240 | 1.443 |
| 241 | 2.545 |
| 242 | 0.041 |
| 243 | 0.033 |
| 244 | 0.011 |
| 245 | 0.020 |
| 246 | 0.025 |
| 247 | 0.027 |
| 248 | 0.116 |
| 249 | 0.035 |
| 250 | 0.089 |
| 251 | 0.048 |
| 252 | 0.022 |
| 253 | 0.027 |
| 254 | 0.031 |
| 255 | 0.037 |
| 256 | 0.041 |
| 257 | 0.041 |
| 258 | 0.043 |
| 259 | 0.044 |
| 260 | 0.048 |
| 261 | 0.049 |
| 262 | 0.055 |
| 263 | 0.020 |
| 264 | 0.057 |
| 265 | 0.065 |
| 266 | 0.082 |
| 267 | 0.098 |
| 268 | 0.114 |
| 269 | 0.127 |
| 270 | 0.140 |
| 271 | 0.145 |
| 272 | 0.179 |
| 273 | 0.033 |
| 274 | 0.261 |
| 275 | 0.298 |
| 276 | 0.298 |
| 277 | 0.319 |
| 278 | 0.460 |
| 279 | 0.491 |
| 280 | 0.555 |
| 281 | 0.649 |
| 282 | 0.780 |
| 283 | 0.895 |
| 284 | 0.925 |
| 285 | 1.025 |
| 286 | 1.187 |
| 287 | 1.233 |
| 288 | 1.283 |
| 289 | 1.292 |
| 290 | 1.588 |
| 291 | 1.913 |
| 292 | 2.059 |
| 293 | 2.663 |
| 294 | 0.456 |
| 295 | 0.282 |
| 296 | 0.582 |
| 297 | 2.101 |
| 298 | 0.331 |
| 299 | 0.603 |
| 300 | 0.912 |
| 301 | 1.000 |
| 302 | 1.210 |
| 303 | 1.647 |
| 304 | 2.878 |
| 305 | 0.303 |
| 306 | 0.243 |
| 307 | 0.297 |

TABLE 11-continued

| PAD4 Activity | |
|---|---|
| Example Number | hPAD4 RFMS $IC_{50}$ μM |
| 308 | 0.538 |
| 309 | 1.165 |
| 310 | 1.904 |
| 311 | 0.134 |
| 312 | 0.380 |
| 313 | 0.403 |
| 314 | 0.552 |
| 315 | 0.929 |
| 316 | 1.147 |
| 317 | 1.187 |
| 318 | 1.299 |
| 319 | 1.300 |
| 320 | 1.346 |
| 321 | 1.528 |
| 322 | 2.054 |
| 323 | 2.989 |
| 324 | 1.876 |
| 325 | 0.163 |
| 326 | 0.197 |
| 327 | 0.057 |
| 328 | 0.125 |
| 329 | 0.163 |
| 330 | 0.184 |
| 331 | 0.190 |
| 332 | 0.219 |
| 333 | 0.222 |
| 334 | 0.225 |
| 335 | 0.245 |
| 336 | 0.310 |
| 337 | 0.479 |
| 338 | 0.498 |
| 339 | 0.536 |
| 340 | 1.257 |
| 341 | 2.975 |
| 342 | 0.026 |
| 343 | 0.116 |
| 344 | 0.039 |
| 345 | 0.049 |
| 346 | 0.061 |
| 347 | 0.097 |
| 348 | 0.014 |
| 349 | 0.015 |
| 350 | 0.016 |
| 351 | 0.018 |
| 352 | 0.019 |
| 353 | 0.020 |
| 354 | 0.022 |
| 355 | 0.022 |
| 356 | 0.023 |
| 357 | 0.023 |
| 358 | 0.023 |
| 359 | 0.023 |
| 360 | 0.024 |
| 361 | 0.025 |
| 362 | 0.025 |
| 363 | 0.025 |
| 364 | 0.026 |
| 365 | 0.027 |
| 366 | 0.028 |
| 367 | 0.029 |
| 368 | 0.029 |
| 369 | 0.029 |
| 370 | 0.030 |
| 371 | 0.030 |
| 372 | 0.032 |
| 373 | 0.034 |
| 374 | 0.035 |
| 375 | 0.035 |
| 376 | 0.037 |
| 377 | 0.037 |
| 378 | 0.037 |
| 379 | 0.037 |
| 380 | 0.037 |
| 381 | 0.037 |
| 382 | 0.041 |
| 383 | 0.041 |

TABLE 11-continued

| PAD4 Activity | |
|---|---|
| Example Number | hPAD4 RFMS $IC_{50}$ μM |
| 384 | 0.041 |
| 385 | 0.042 |
| 386 | 0.042 |
| 387 | 0.042 |
| 388 | 0.043 |
| 389 | 0.043 |
| 390 | 0.045 |
| 391 | 0.047 |
| 392 | 0.048 |
| 393 | 0.049 |
| 394 | 0.050 |
| 395 | 0.050 |
| 396 | 0.051 |
| 397 | 0.053 |
| 398 | 0.054 |
| 399 | 0.057 |
| 400 | 0.057 |
| 401 | 0.059 |
| 402 | 0.066 |
| 403 | 0.066 |
| 404 | 0.066 |
| 405 | 0.066 |
| 406 | 0.069 |
| 407 | 0.072 |
| 408 | 0.074 |
| 409 | 0.082 |
| 410 | 0.087 |
| 411 | 0.055 |
| 412 | 0.018 |
| 413 | 0.263 |
| 414 | 0.035 |
| 415 | 0.041 |
| 416 | 0.010 |
| 417 | 0.011 |
| 418 | 0.014 |
| 419 | 0.016 |
| 420 | 0.020 |
| 421 | 0.021 |
| 422 | 0.022 |
| 423 | 0.023 |
| 424 | 0.025 |
| 425 | 0.027 |
| 426 | 0.024 |
| 427 | 0.024 |
| 428 | 0.028 |
| 429 | 0.029 |
| 430 | 0.030 |
| 431 | 0.030 |
| 432 | 0.031 |
| 433 | 0.031 |
| 434 | 0.033 |
| 435 | 0.034 |
| 436 | 0.034 |
| 437 | 0.034 |
| 438 | 0.035 |
| 439 | 0.036 |
| 440 | 0.037 |
| 441 | 0.038 |
| 442 | 0.039 |
| 443 | 0.042 |
| 444 | 0.043 |
| 445 | 0.043 |
| 446 | 0.043 |
| 447 | 0.043 |
| 448 | 0.044 |
| 449 | 0.044 |
| 450 | 0.046 |
| 451 | 0.047 |
| 452 | 0.048 |
| 453 | 0.053 |
| 454 | 0.053 |
| 455 | 0.059 |
| 456 | 0.059 |
| 457 | 0.063 |
| 458 | 0.065 |
| 459 | 0.066 |
| 460 | 0.067 |
| 461 | 0.068 |
| 462 | 0.070 |
| 463 | 0.073 |
| 464 | 0.076 |
| 465 | 0.083 |
| 466 | 0.084 |
| 467 | 0.091 |
| 468 | 0.099 |
| 469 | 0.129 |
| 470 | 0.177 |
| 471 | 0.228 |
| 472 | 0.075 |
| 473 | 0.129 |
| 474 | 0.149 |
| 475 | 0.180 |
| 476 | 0.100 |
| 477 | 0.142 |
| 478 | 0.048 |
| 479 | 0.212 |
| 480 | 0.301 |
| 481 | 0.020 |
| 482 | 0.023 |
| 483 | 0.030 |
| 484 | 0.030 |
| 485 | 0.047 |
| 486 | 0.045 |
| 487 | 0.046 |
| 488 | 0.055 |
| 489 | 0.055 |
| 490 | 0.058 |
| 491 | 0.057 |
| 492 | 0.078 |
| 493 | 0.083 |
| 494 | 0.086 |
| 495 | 0.088 |
| 496 | 0.102 |
| 497 | 0.109 |
| 498 | 0.092 |
| 499 | 0.125 |
| 500 | 0.127 |
| 501 | 0.136 |
| 502 | 0.146 |
| 503 | 0.149 |
| 504 | 0.158 |
| 505 | 0.163 |
| 506 | 0.225 |
| 507 | 0.256 |
| 508 | 0.289 |
| 509 | 0.300 |
| 510 | 0.326 |
| 511 | 0.338 |
| 512 | 0.373 |
| 513 | 0.391 |
| 514 | 0.409 |
| 515 | 0.501 |
| 516 | 0.574 |
| 517 | 0.590 |
| 518 | 0.606 |
| 519 | 0.107 |
| 520 | 0.034 |
| 521 | 0.086 |
| 522 | 0.023 |
| 523 | 0.034 |
| 524 | 0.048 |

What is claimed is:

1. A compound having Formula (III):

(III)

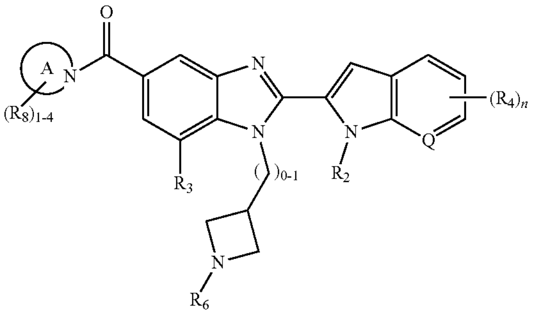

or a pharmaceutically acceptable salt thereof, wherein:

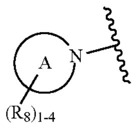

is selected from

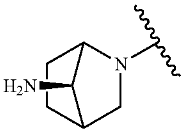
,
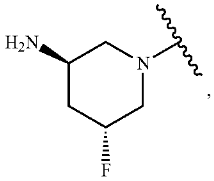
,
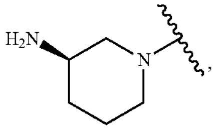
, and
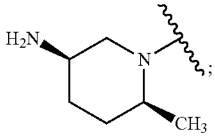
;

Q is selected from N and CH;

$R_2$ is selected from $CH_3$ and —$CH_2$-cyclopropyl;

$R_3$ is —$OC_{1-4}$ alkyl;

$R_4$, at each occurrence, is selected from Cl and —$OC_{1-3}$ alkyl;

$R_6$ is selected from

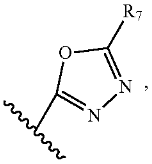
,
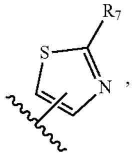
,
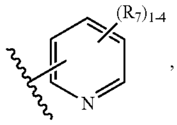
,
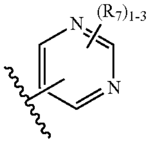
,
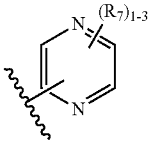
,
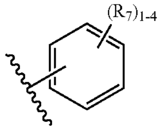
, and -continued

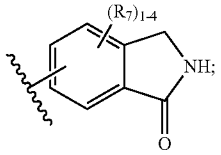

$R_7$, at each occurrence, is independently selected from H, F, Cl, Br, CN, $C_{1-4}$alkyl, —S(═O)$_p$$R_c$, C(═O)$R_b$, —C(═O)O$R_b$, C(═O)N$R_a$$R_a$, —O$R_b$, and $C_{3-6}$cycloalkyl;

$R_a$, at each occurrence, is independently selected from H and $C_{1-6}$ alkyl substituted with 0-5 $R_e$;

$R_b$, at each occurrence, is independently selected from H and $C_{1-6}$ alkyl substituted with 0-5 $R_e$;

$R_c$ is $C_{1-6}$ alkyl substituted with 0-5 $R_e$;

$R_e$, at each occurrence, is independently selected from F, Cl, Br, CN, and $C_{1-6}$ alkyl;

n, at each occurrence, is independently selected from zero and 1; and p, at each occurrence, is independently selected from zero, 1, and 2.

2. A pharmaceutically acceptable composition comprising the compound according to claim 1, and a pharmaceutically acceptable carrier, adjuvant, or vehicle.

3. The compound of claim 1 selected from

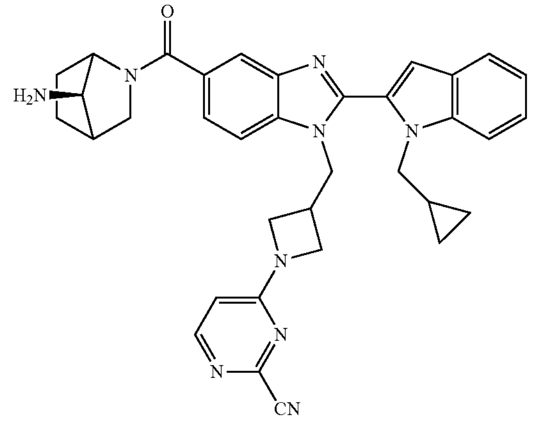
,

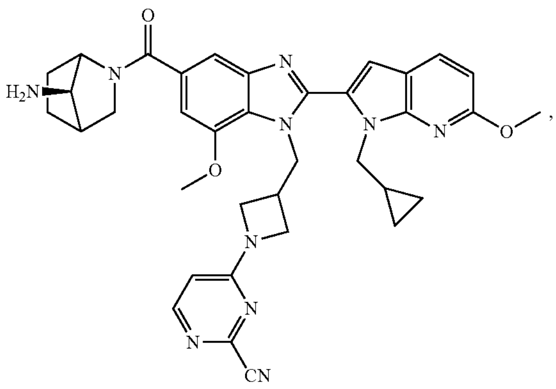
,

-continued
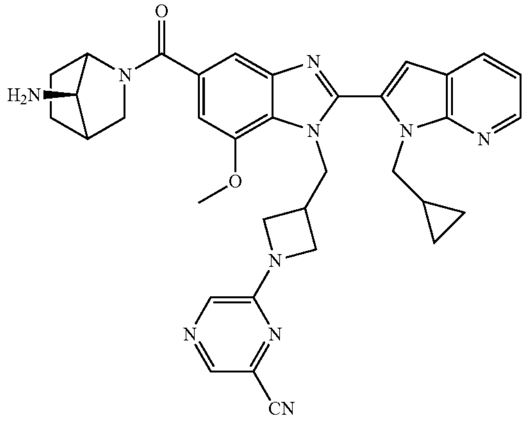
,
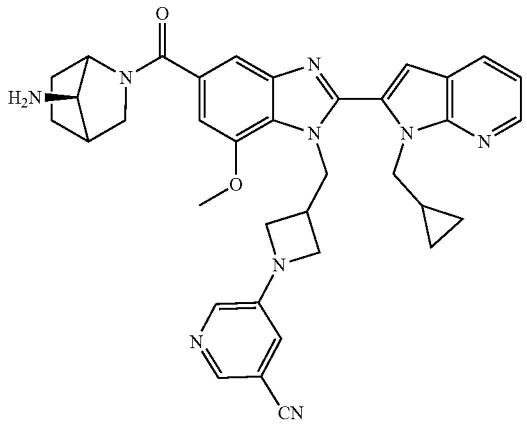
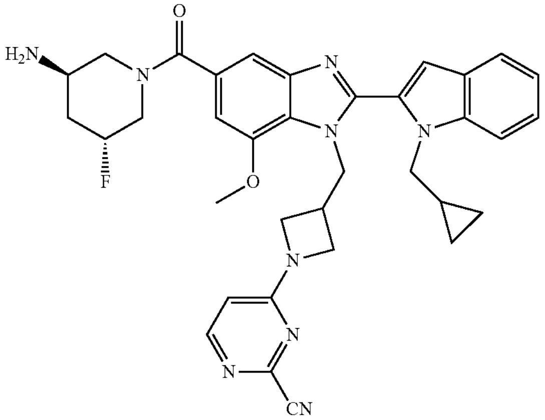
,
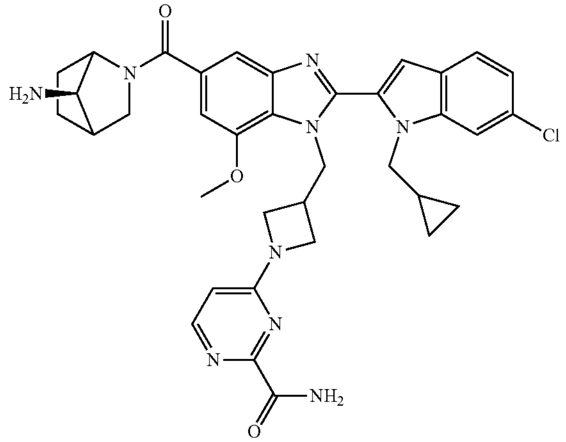
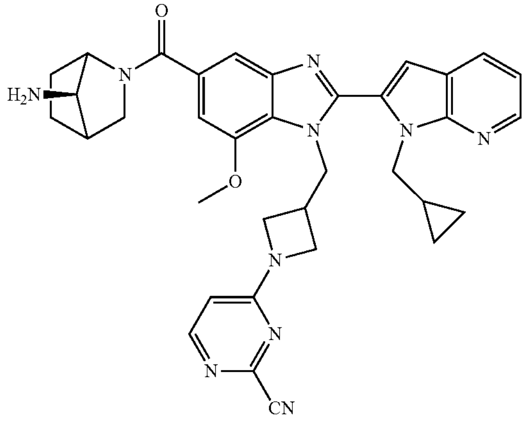
,
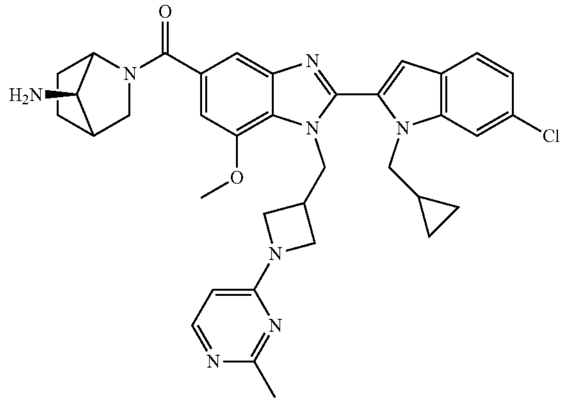
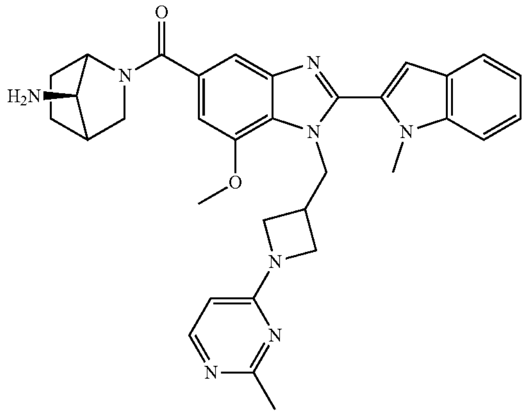
,
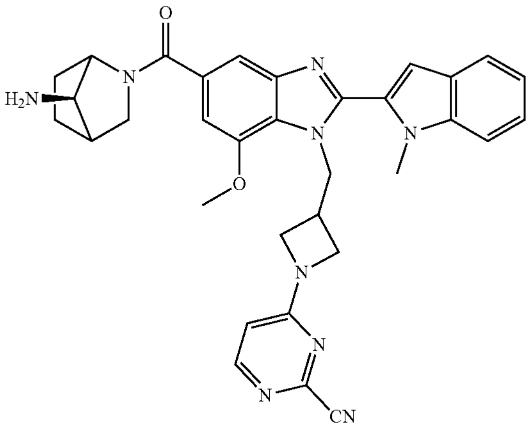

-continued
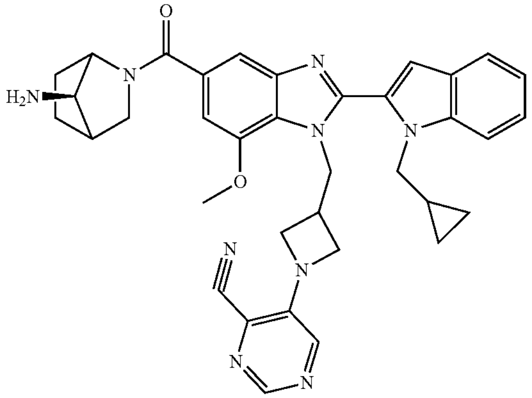
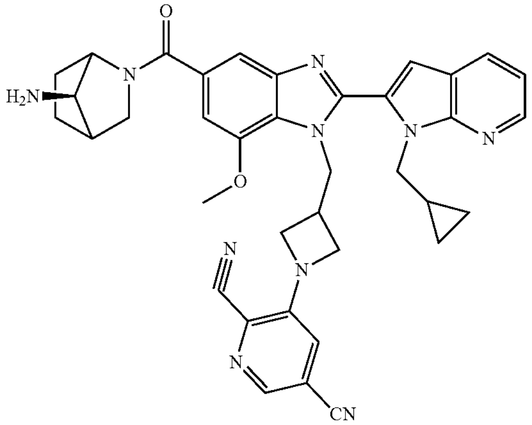
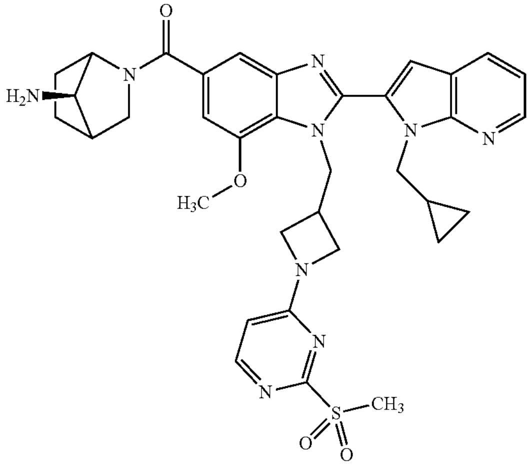
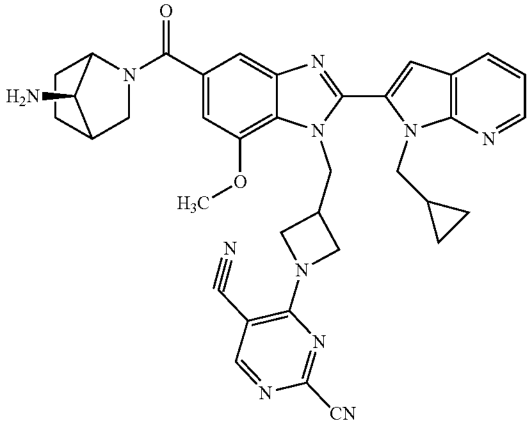
-continued
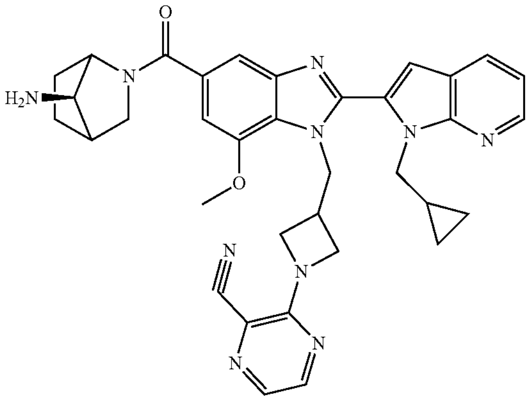
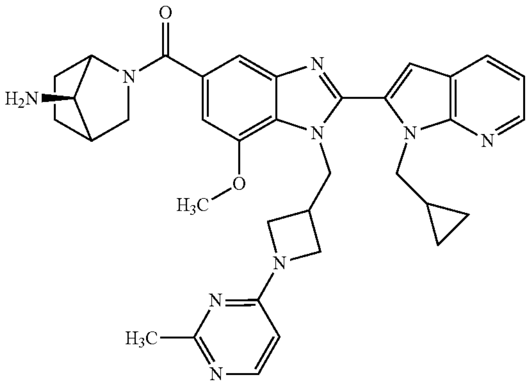
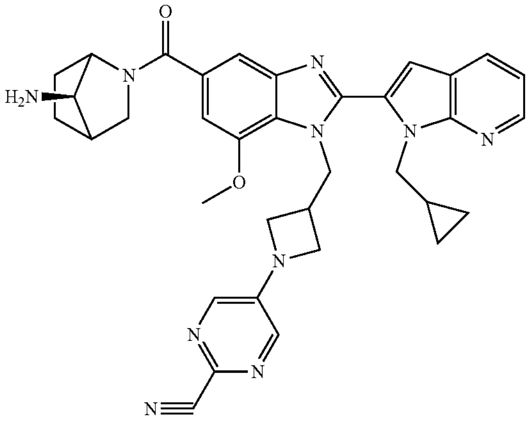
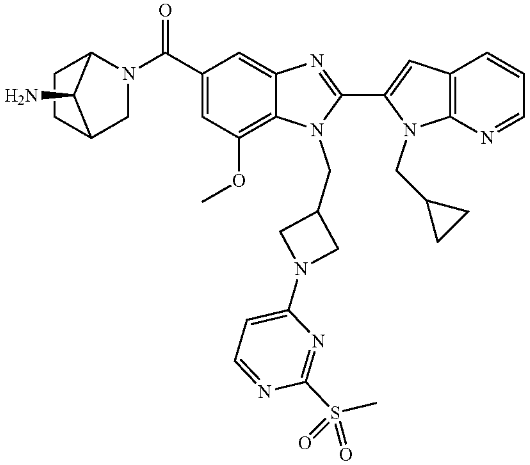

-continued
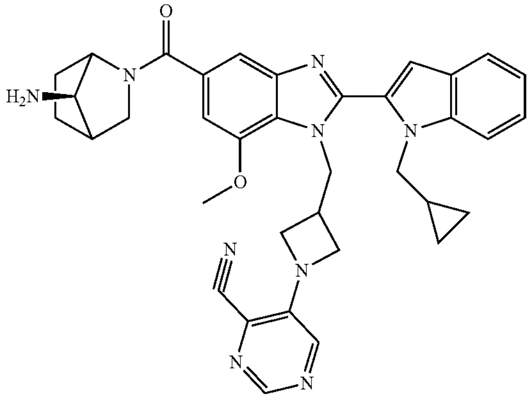
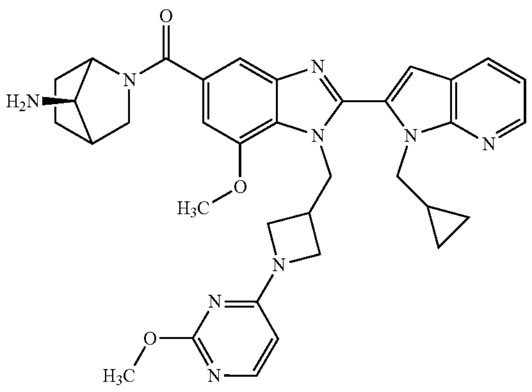
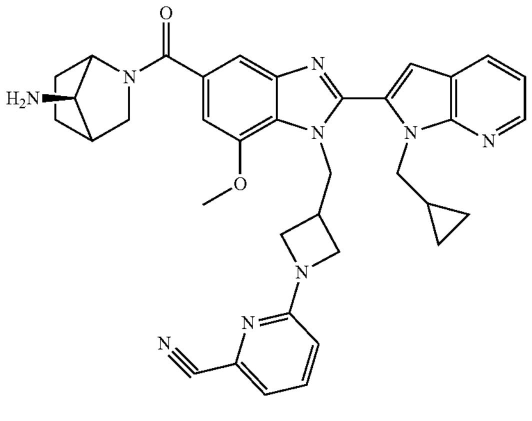
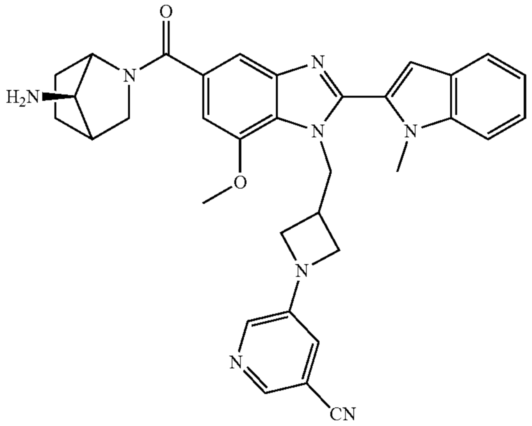
-continued
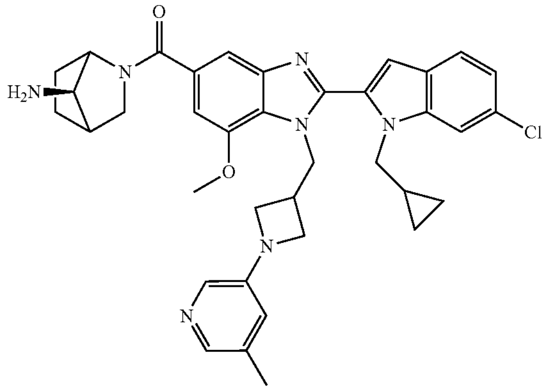
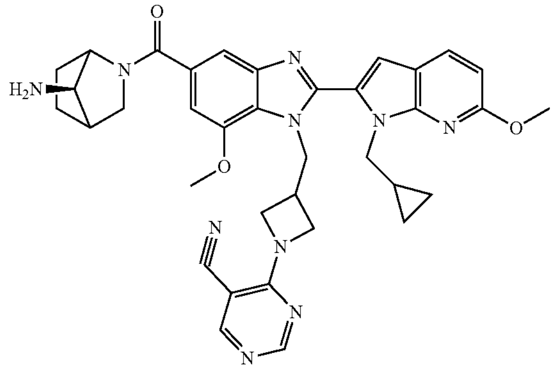
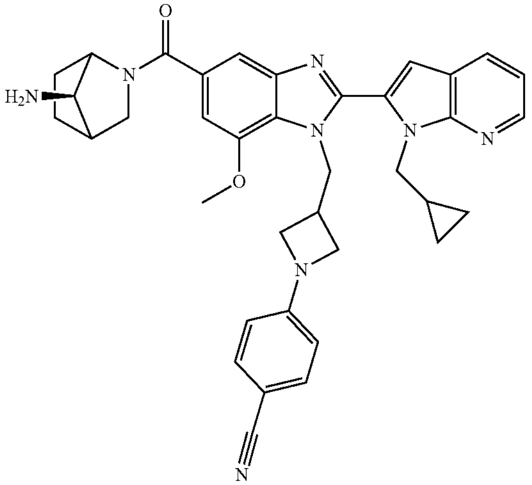
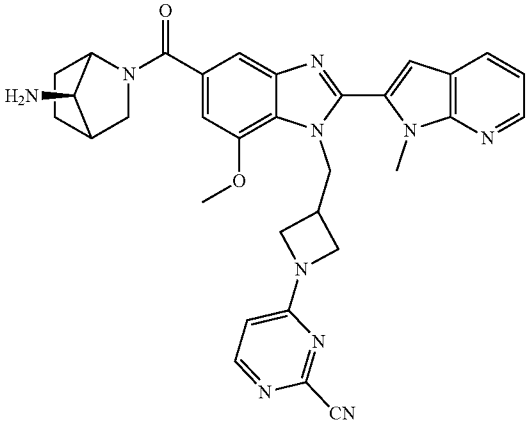

-continued
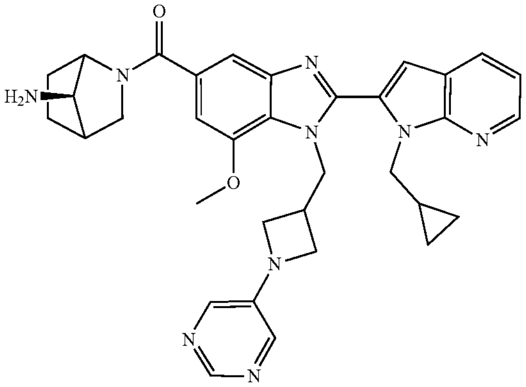
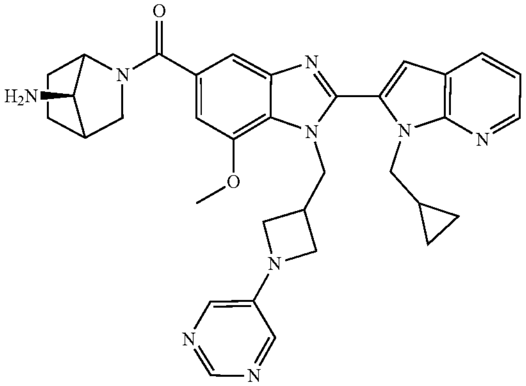
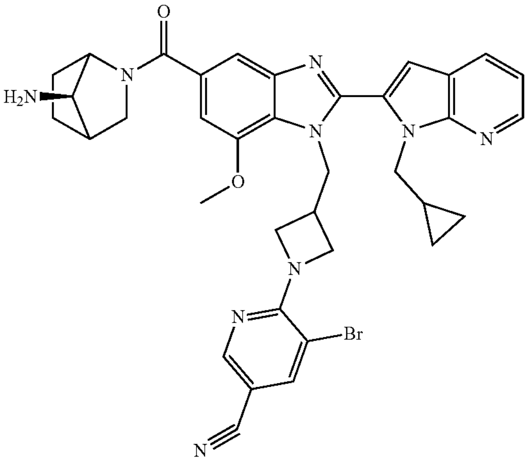
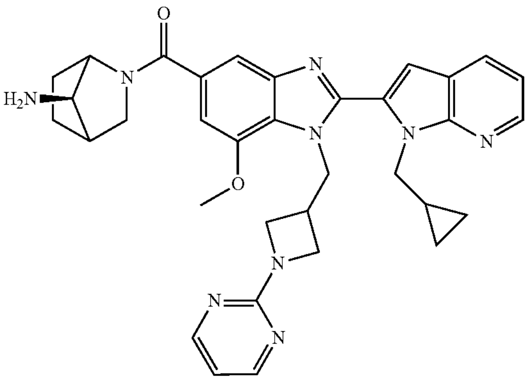
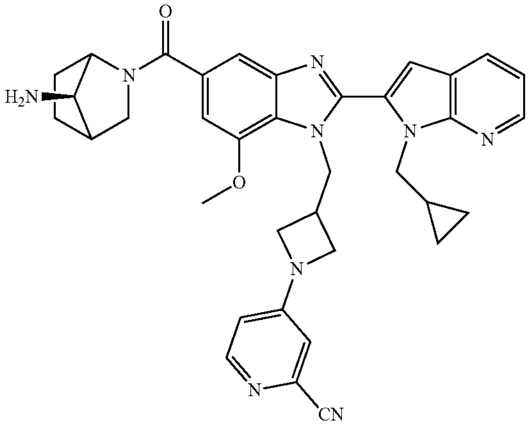
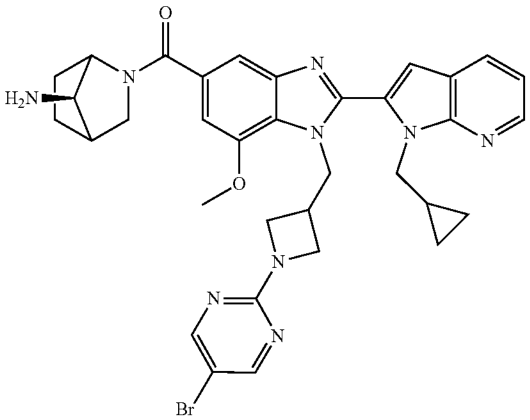
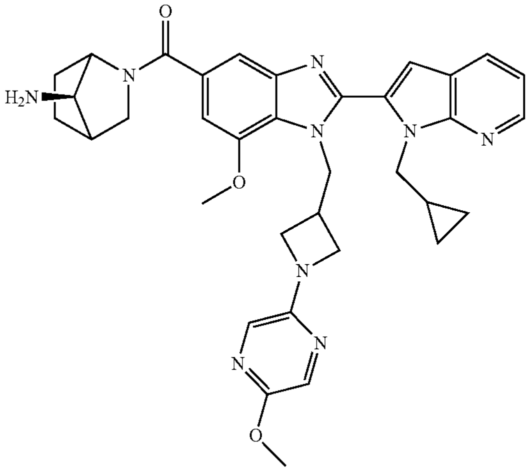

-continued
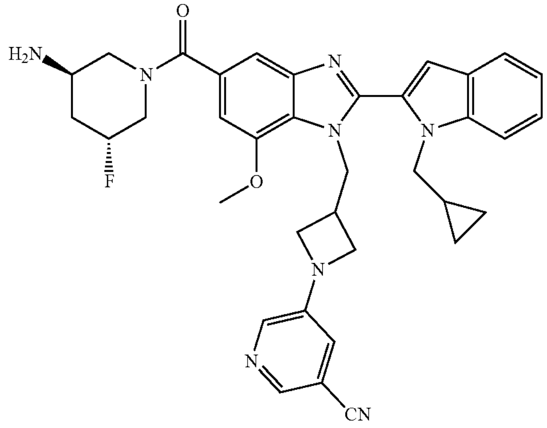
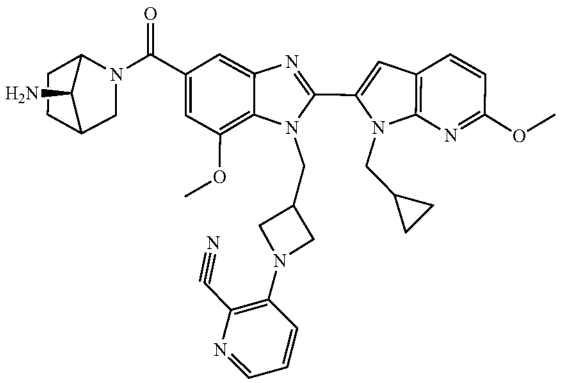
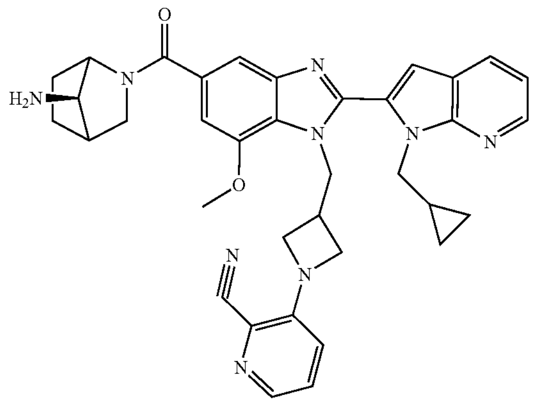
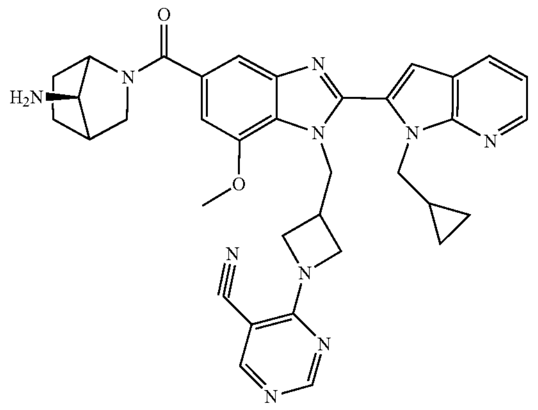
-continued
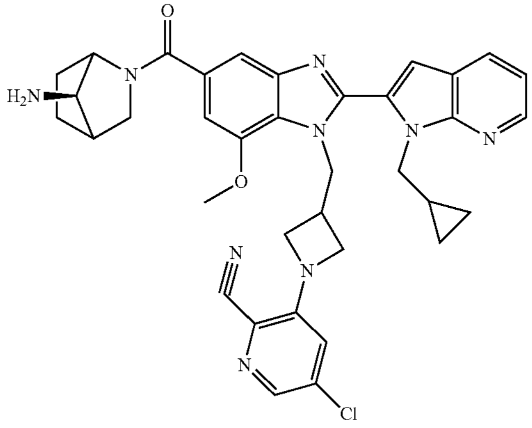
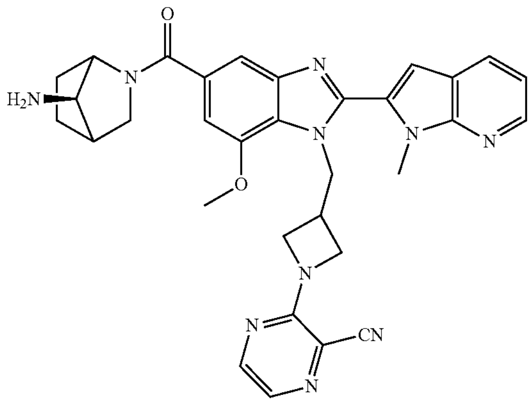
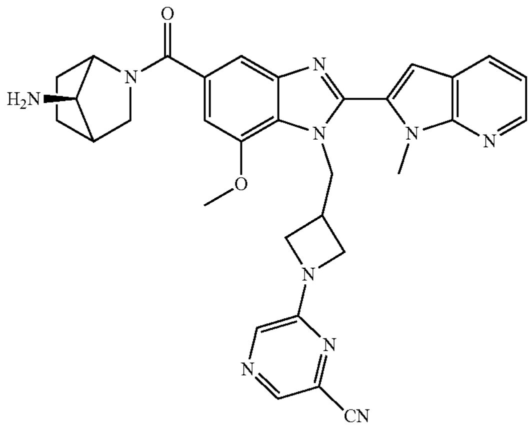
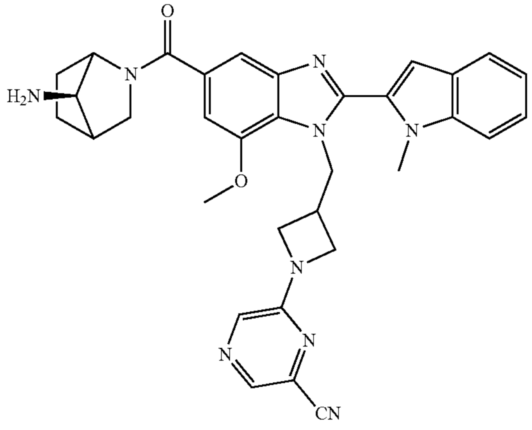

-continued
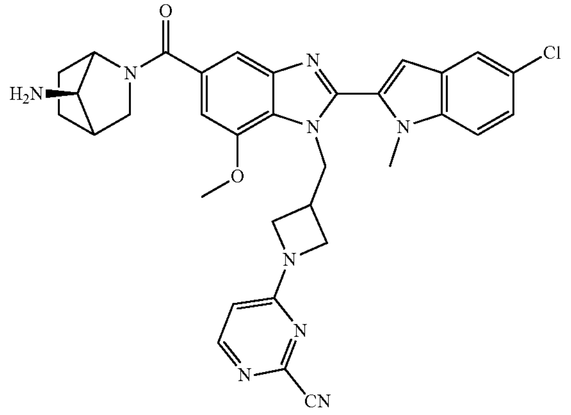
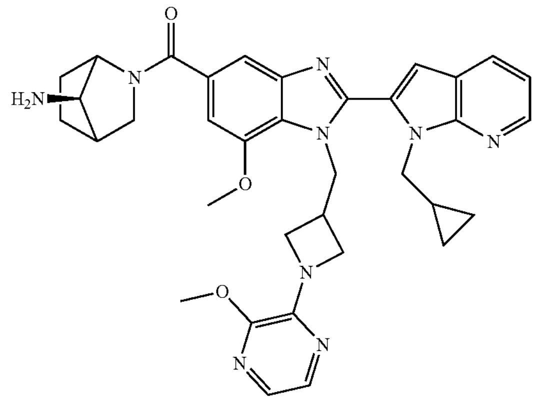
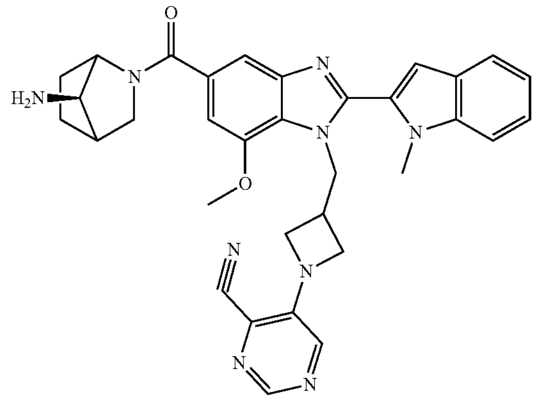
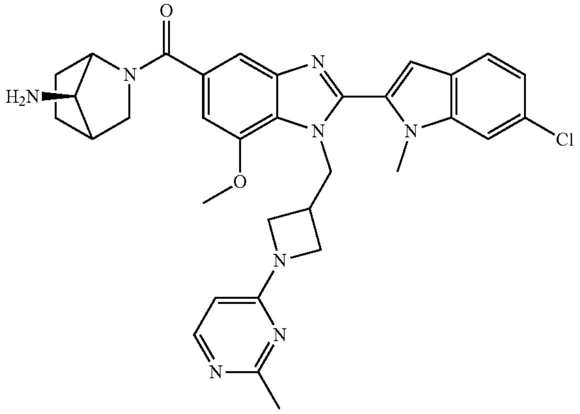
-continued
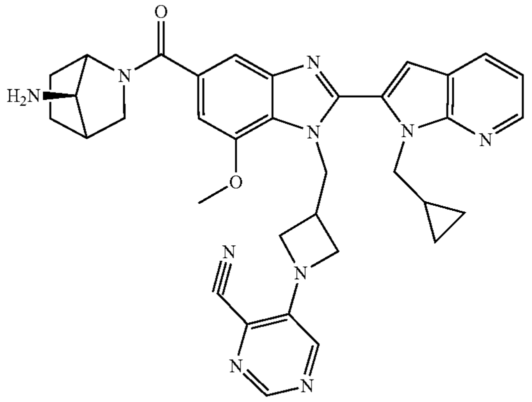
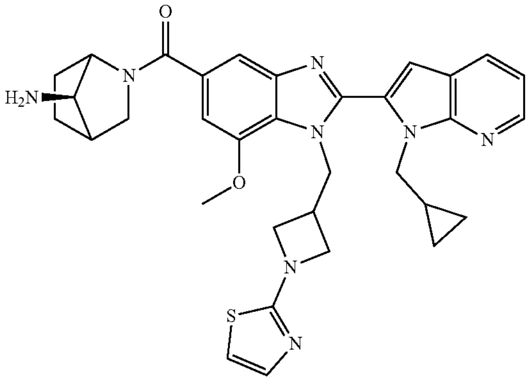
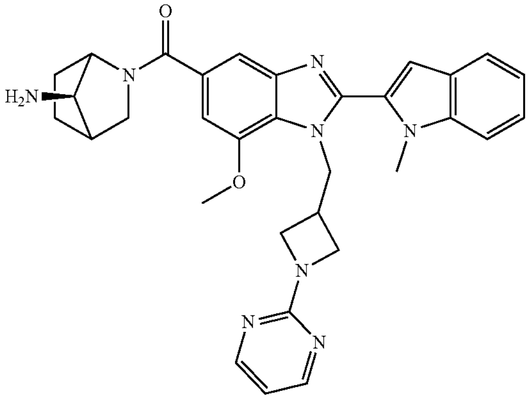
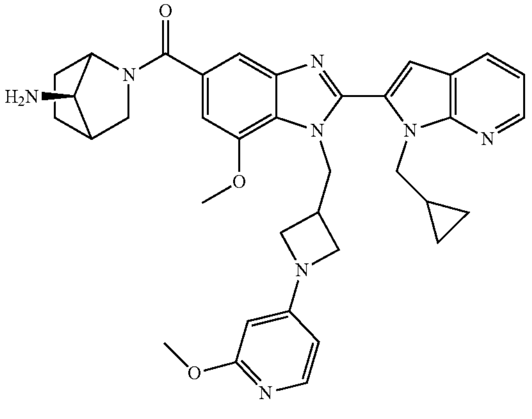

-continued
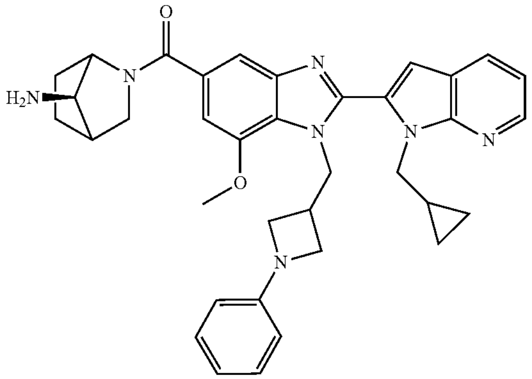
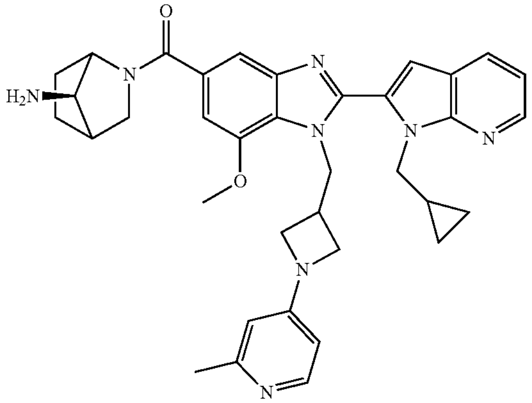
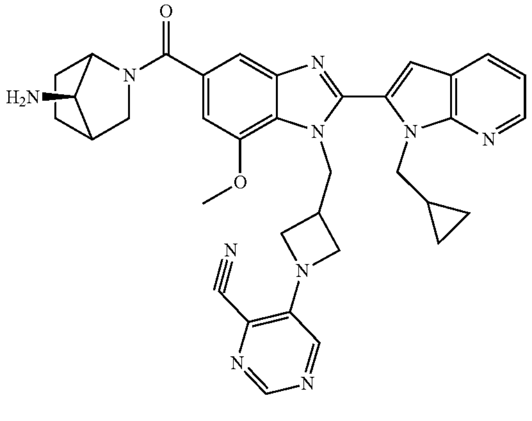
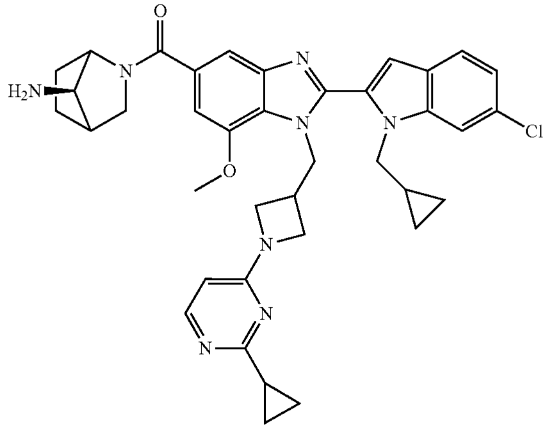
-continued
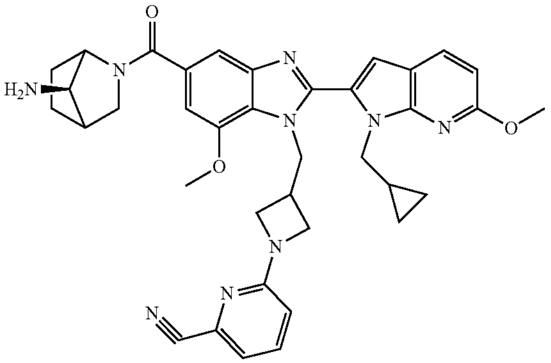
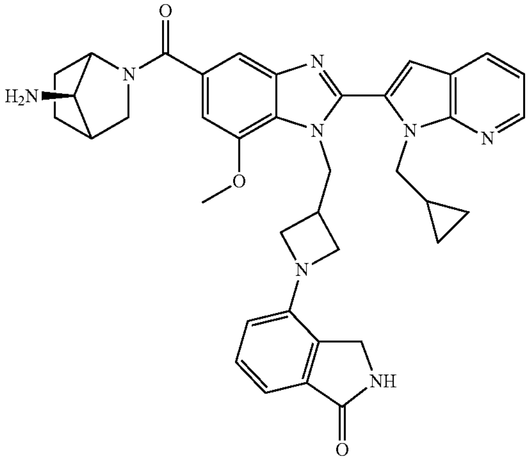
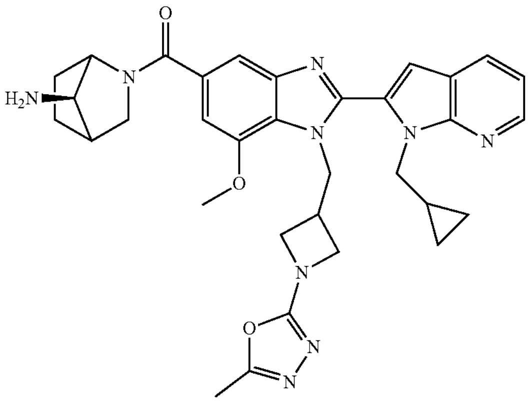
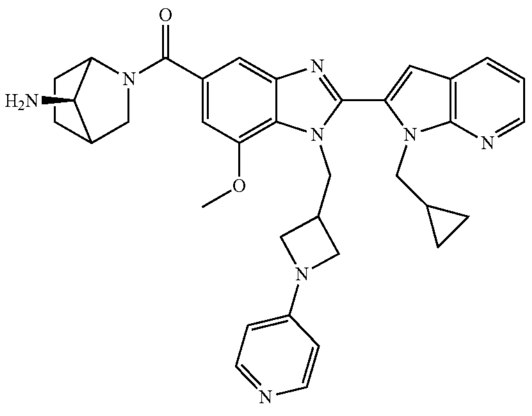

-continued
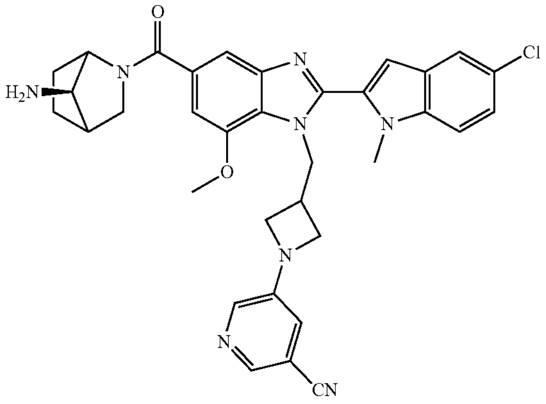
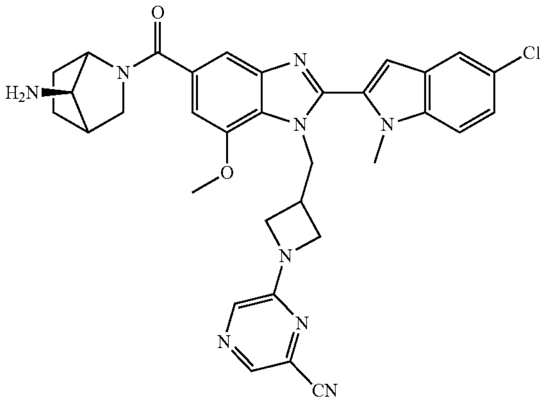
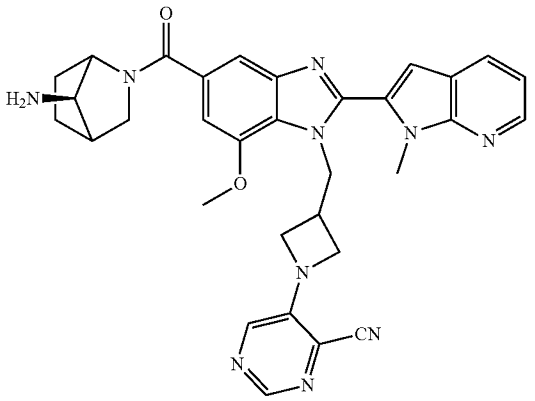
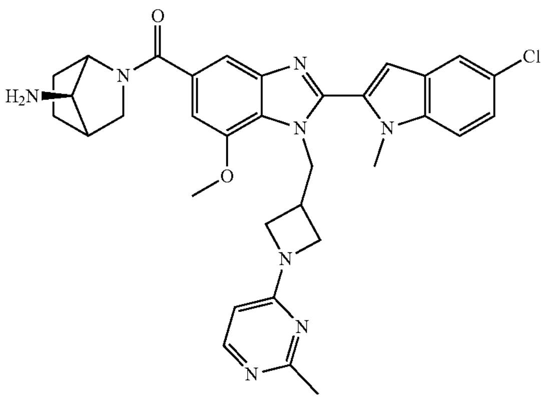
-continued
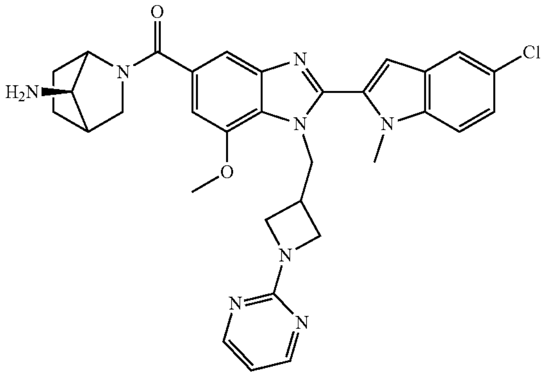
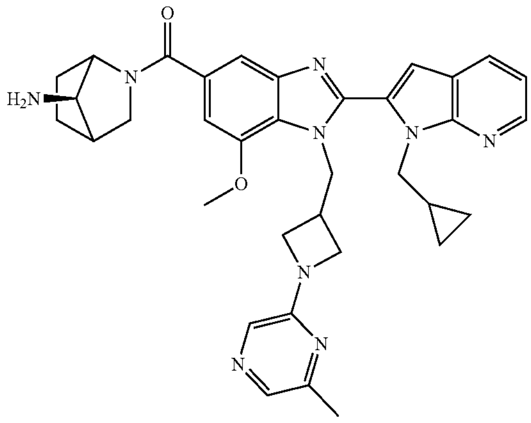
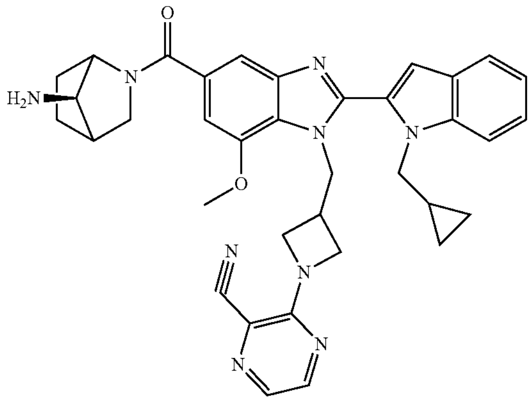
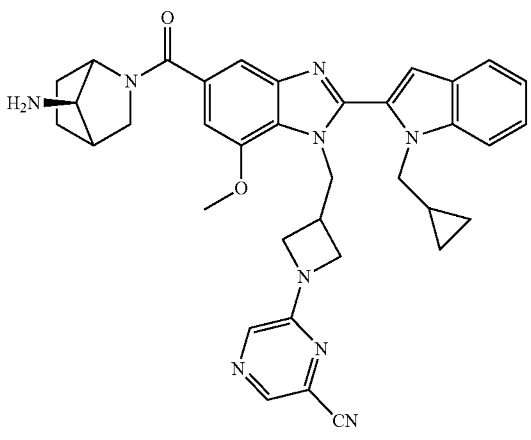

-continued
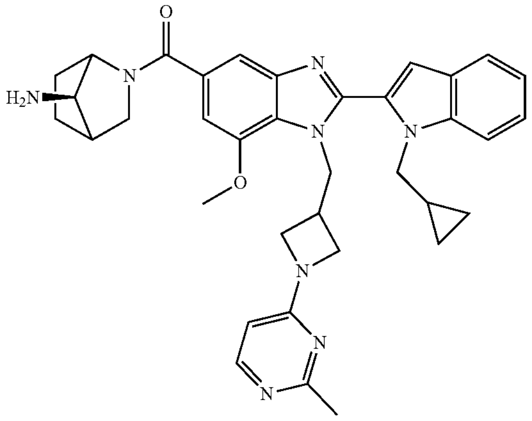
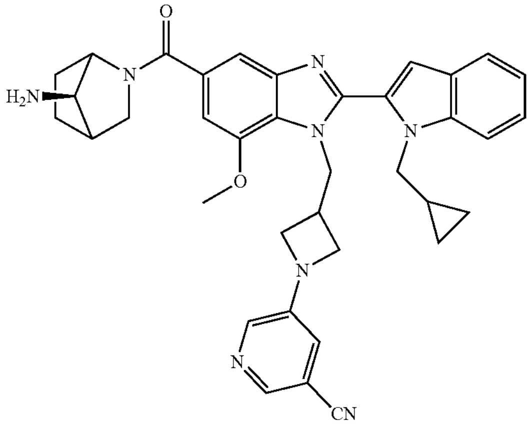
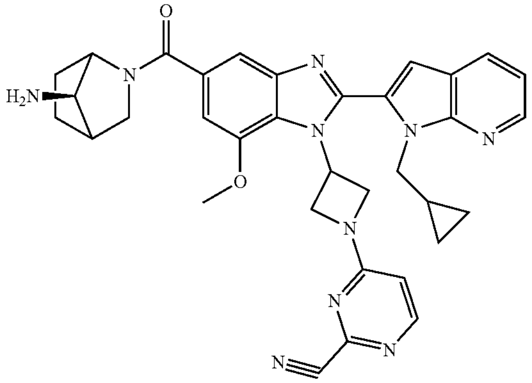
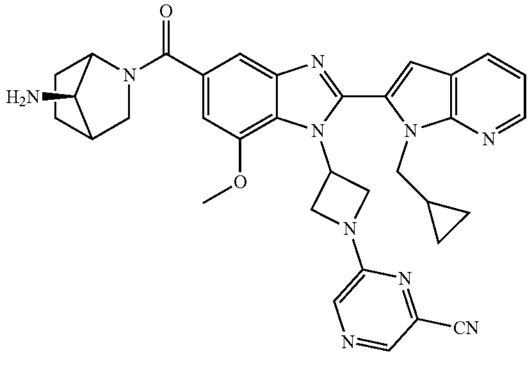
-continued
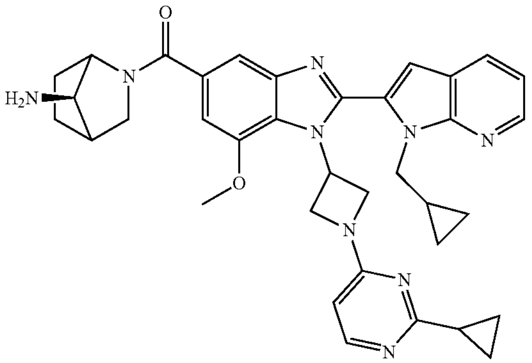
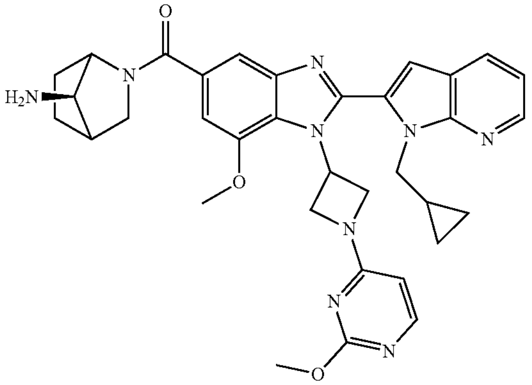
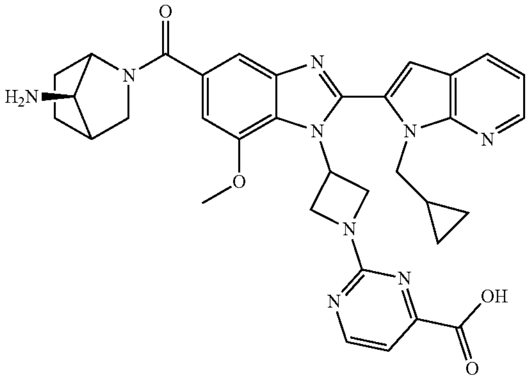
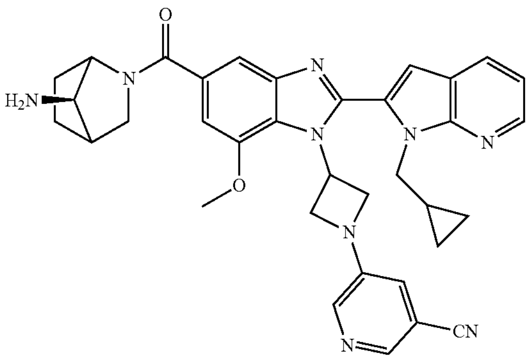

-continued
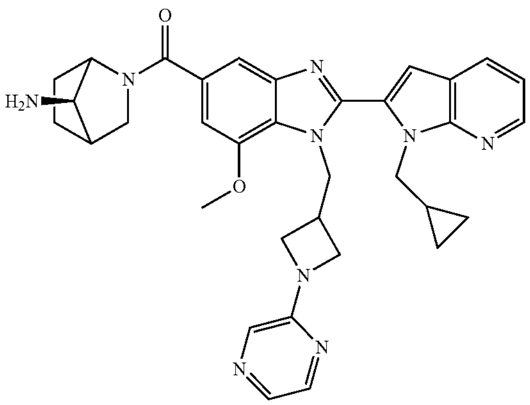
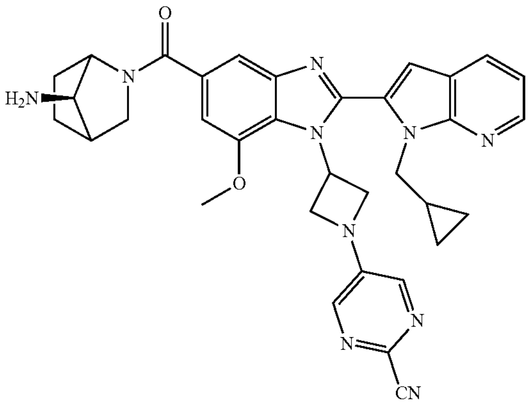
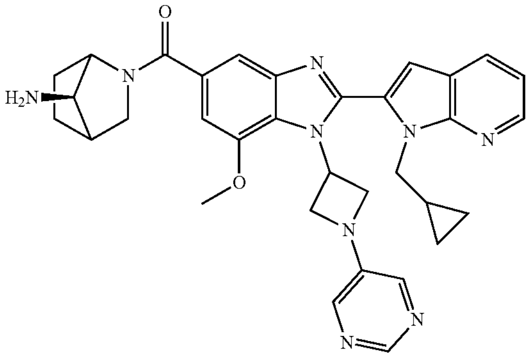
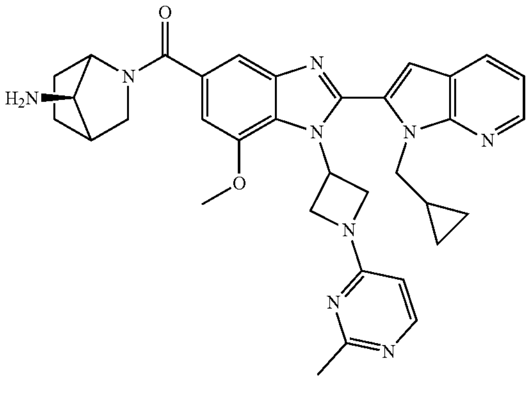
-continued
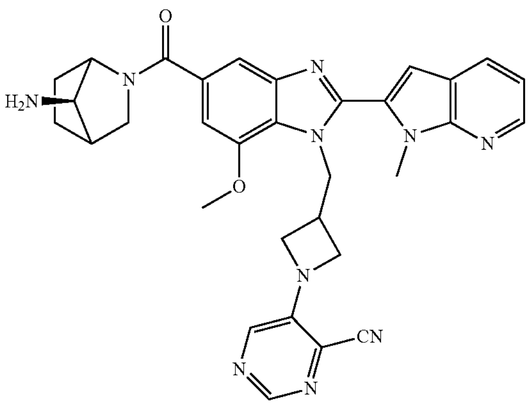
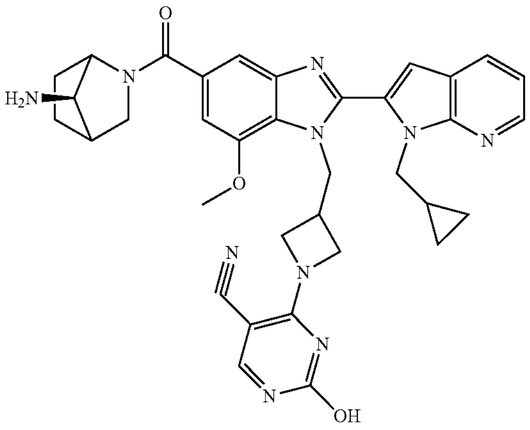
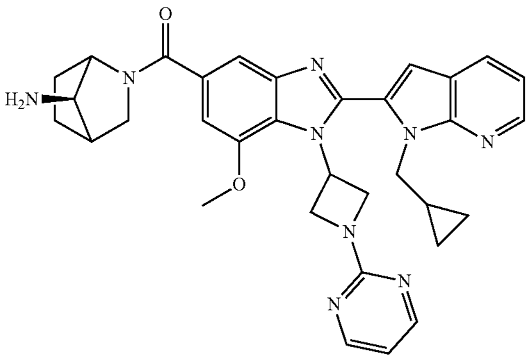
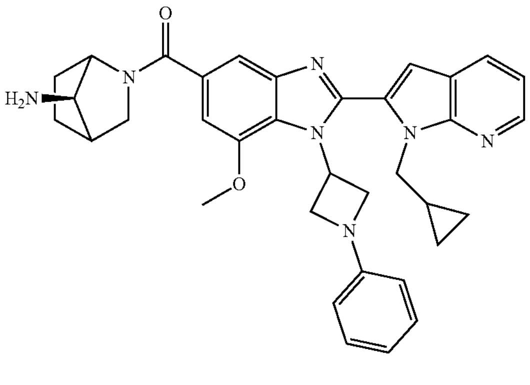

-continued
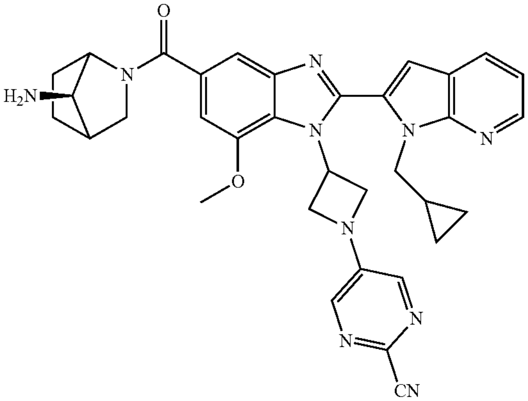
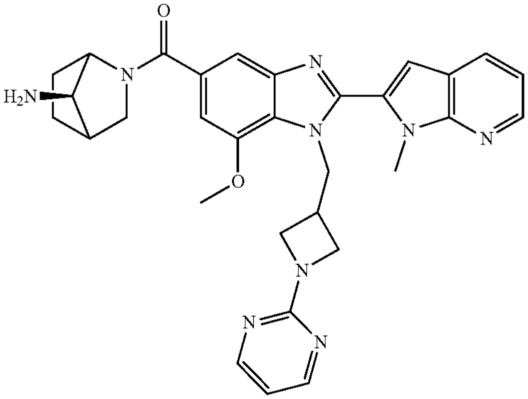
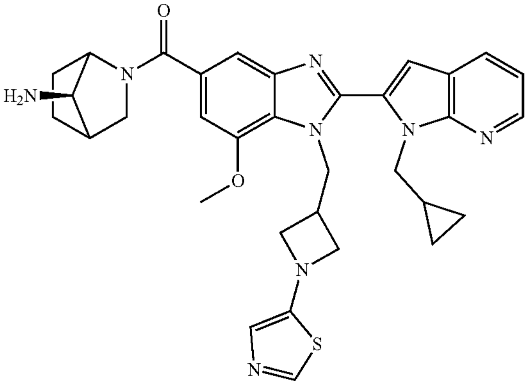
-continued
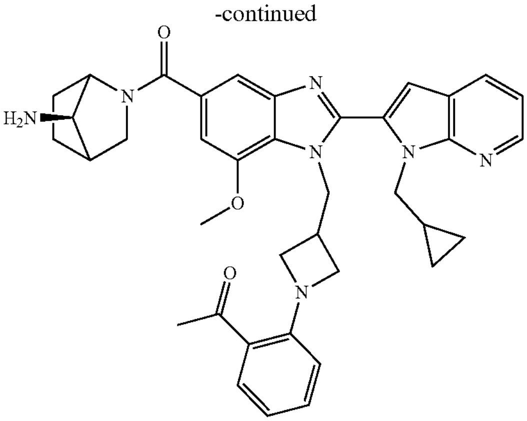
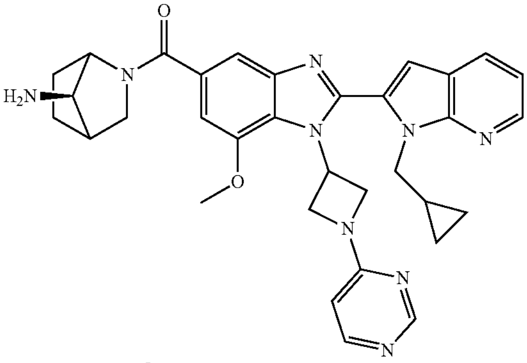
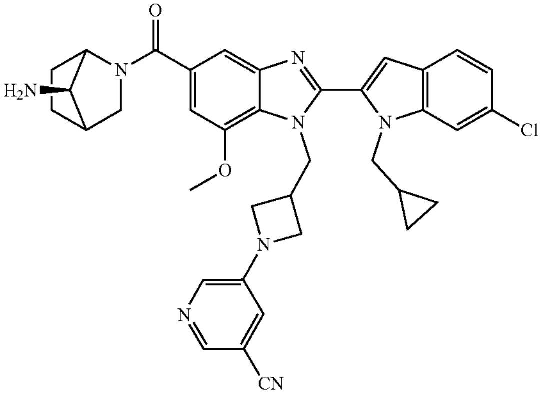
* * * * *